US010759767B2

(12) United States Patent
Lohmann et al.

(10) Patent No.: US 10,759,767 B2
(45) Date of Patent: *Sep. 1, 2020

(54) COMPOSITIONS COMPRISING A TRIAZOLE COMPOUND

(71) Applicant: BASF AGRO B.V., Arnhem (NL)

(72) Inventors: Jan Klaas Lohmann, Lambsheim (DE); Egon Haden, Speyer (DE); Dieter Strobel, Herxheim am Berg (DE); Siegfried Strathmann, Limburgerhof (DE); Martin Semar, Gleiszellen-Gleishorbach (DE); Frederik Menges, Schriesheim (DE); Nadege Boudet, Hemsbach (DE)

(73) Assignee: BASF AGRO B.V., Arnhem (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/653,578

(22) PCT Filed: Dec. 18, 2013

(86) PCT No.: PCT/EP2013/077081
§ 371 (c)(1),
(2) Date: Jun. 18, 2015

(87) PCT Pub. No.: WO2014/095994
PCT Pub. Date: Jun. 26, 2014

(65) Prior Publication Data
US 2015/0344445 A1   Dec. 3, 2015

Related U.S. Application Data

(60) Provisional application No. 61/739,814, filed on Dec. 20, 2012.

(30) Foreign Application Priority Data

Dec. 20, 2012   (EP) ..................................... 12198698
Jul. 3, 2013    (EP) ..................................... 13174975

(51) Int. Cl.
| A01N 25/00 | (2006.01) |
| C07D 249/08 | (2006.01) |
| A01N 43/653 | (2006.01) |
| A01N 47/24 | (2006.01) |
| A01N 37/42 | (2006.01) |
| A01N 43/56 | (2006.01) |
| A01N 43/54 | (2006.01) |
| A01N 43/36 | (2006.01) |

(52) U.S. Cl.
CPC ........... *C07D 249/08* (2013.01); *A01N 25/00* (2013.01); *A01N 37/42* (2013.01); *A01N 43/36* (2013.01); *A01N 43/54* (2013.01); *A01N 43/56* (2013.01); *A01N 43/653* (2013.01); *A01N 47/24* (2013.01); *A01N 2300/00* (2013.01)

(58) Field of Classification Search
None
See application file for complete search history.

(56) References Cited

U.S. PATENT DOCUMENTS

| 4,242,121 A | 12/1980 | Hawkins et al. |
| 4,599,362 A | 7/1986 | Nakatani et al. |
| 4,940,720 A | 7/1990 | Nevill et al. |
| 4,940,721 A | 7/1990 | Nevill et al. |
| 4,945,100 A | 7/1990 | Nyfeler et al. |
| 4,992,458 A | 2/1991 | Riebli et al. |
| 5,143,932 A | 9/1992 | Jautelat et al. |
| 5,162,358 A | 11/1992 | Jautelat et al. |
| 8,492,312 B2 | 7/2013 | Thomas et al. |
| 8,546,577 B2 | 10/2013 | Jeschke et al. |
| 2008/0108686 A1 | 5/2008 | Gewehr et al. |
| 2009/0036509 A1 | 2/2009 | Gewehr et al. |
| 2009/0286768 A1 | 11/2009 | Crew et al. |
| 2010/0240619 A1 | 9/2010 | Gregory et al. |
| 2014/0012855 A1 | 5/2014 | Dietz et al. |
| 2014/0127322 A1 | 5/2014 | Oberholzer et al. |
| 2015/0250173 A1* | 9/2015 | Korber .................. A01N 43/56 504/100 |

FOREIGN PATENT DOCUMENTS

| AU | 611315 | 6/1991 |
| CA | 1100976 | 5/1981 |
| CA | 1 187 084 | 5/1985 |
| CA | 1 210 404 | 8/1986 |
| CA | 1209152 | 8/1986 |
| CN | 101225074 | 7/2008 |

(Continued)

OTHER PUBLICATIONS

Yu, G-P.; Xu, L-Z.; Yi, X.; Bi, W-Z.; Zhu, Q.; Zhai, Z-W. "Synthesis and Fungicidal evaluation of 2-arylphenyl ether-3-(1H-1,2,4-triazol-1-yl)propan-2-ol derivatives" Journal of Agricultural and food chemistry, 2009, v. 57, 4854-4860. (Year: 2009).*

International Preliminary Report on Patentability dated Jun. 23, 2015, prepared in International Application No. PCT/EP2013/077081.

International Search Report dated Mar. 31, 2014, prepared in International Application No. PCT/EP2013/077081.

Akama, Tsutomu, et al. "Discovery and structure-activity study of a novel benzoxaborole anti-inflammatory agent (AN2728) for the potential topical treatment of psoriasis and atopic dermatitis", Bioorganic & Medicinal Chemistry Letters, 2009, p. 2129-2132, vol. 19.

(Continued)

*Primary Examiner* — Erin E Hirt
(74) *Attorney, Agent, or Firm* — Marshall, Gerstein & Borun LLP

(57) ABSTRACT

The present invention relates to compositions comprising, 1) as component I a compound of formula I, as defined in the claims and description, and 2) as component II an active ingredient, selected from the groups A) to O) defined in the claims and description.

11 Claims, No Drawings

(56) References Cited

FOREIGN PATENT DOCUMENTS

| | | | |
|---|---|---|---|
| CS | 247 200 | 12/1986 | |
| DE | 2 325 878 | 12/1974 | |
| DE | 38 01 233 | 8/1988 | |
| DE | 40 03 180 | 8/1991 | |
| EP | 0 000 017 | 12/1978 | |
| EP | 0 077 479 | 4/1983 | |
| EP | 0113640 | 7/1984 | |
| EP | 0 114 567 | 8/1984 | |
| EP | 0 126 430 | 11/1984 | |
| EP | 0 275 955 | 7/1988 | |
| EP | 0 354 183 | 2/1990 | |
| EP | 0354183 | 2/1990 | |
| EP | 0 440 950 | 8/1991 | |
| EP | 0 470 466 | 2/1992 | |
| EP | 1 431 275 | 6/2004 | |
| EP | 2559688 | 2/2013 | |
| EP | 2835052 | 11/2015 | |
| FR | 2 491 924 | 4/1982 | |
| GB | 2064520 A * | 6/1981 | ........... A01N 43/653 |
| GB | 2 132 195 | 7/1984 | |
| GB | 2 143 815 | 2/1985 | |
| JP | 59-222434 | 12/1984 | |
| JP | 2-83304 | 3/1990 | |
| NZ | 230176 | 1/1992 | |
| WO | WO 1996/041804 | 12/1996 | |
| WO | WO 03 064572 | 8/2003 | |
| WO | WO 2005/123689 | 12/2005 | |
| WO | WO 2005/123690 | 12/2005 | |
| WO | WO 2006/015866 | 2/2006 | |
| WO | WO 2006/087373 | 8/2006 | |
| WO | WO 2006/109933 | 10/2006 | |
| WO | WO 2006/119876 | 11/2006 | |
| WO | WO 2007/031308 | 3/2007 | |
| WO | WO 2007115644 | 10/2007 | |
| WO | WO 2008/082198 | 7/2008 | |
| WO | WO 2010/146114 | 12/2010 | |
| WO | WO-2010146114 A1 * | 12/2010 | ........... C07D 405/06 |
| WO | WO 2011/099804 | 8/2011 | |
| WO | WO 2012/037782 | 3/2012 | |
| WO | WO 2012035050 | 3/2012 | |
| WO | WO 2012090515 | 7/2012 | |
| WO | WO 2012092115 | 7/2012 | |
| WO | WO 2013/007767 | 1/2013 | |
| WO | WO 2013/010862 | 1/2013 | |
| WO | WO 2013/010885 | 1/2013 | |
| WO | WO 2013/010894 | 1/2013 | |
| WO | WO 2013/024082 | 1/2013 | |
| WO | WO 2013/024076 | 2/2013 | |
| WO | WO 2013/024077 | 2/2013 | |
| WO | WO 2013/024080 | 2/2013 | |
| WO | WO 2013/024081 | 2/2013 | |
| WO | WO 2013/024083 | 2/2013 | |
| WO | WO 2013/024075 | 12/2013 | |
| WO | WO 2014079719 | 5/2014 | |
| WO | WO 2014079724 | 5/2014 | |
| WO | WO 2014079728 | 5/2014 | |
| WO | WO 2014079730 | 5/2014 | |
| WO | WO 2014079752 | 5/2014 | |
| WO | WO 2014079754 | 5/2014 | |
| WO | WO 2014079764 | 5/2014 | |
| WO | WO 2014079766 | 5/2014 | |
| WO | WO 2014079769 | 5/2014 | |
| WO | WO 2014079770 | 5/2014 | |
| WO | WO 2014079771 | 5/2014 | |
| WO | WO 2014079772 | 5/2014 | |
| WO | WO 2014079773 | 5/2014 | |
| WO | WO 2014079774 | 5/2014 | |
| WO | WO 2014079804 | 5/2014 | |
| WO | WO 2014079813 | 5/2014 | |
| WO | WO 2014079814 | 5/2014 | |
| WO | WO 2014079841 | 5/2014 | |
| WO | WO 2014/095932 | 6/2014 | |
| WO | WO 2014095994 | 6/2014 | |
| WO | WO 2015003908 | 1/2015 | |
| WO | WO 2015113860 | 8/2015 | |
| WO | WO 2015135701 | 9/2015 | |
| WO | WO 2015169711 | 11/2015 | |
| WO | WO 2015/197393 | 12/2015 | |

OTHER PUBLICATIONS

Lima, Lidia Moreira et al., "Bioisosterism: A useful strategy for molecular Modification and drug design", Current Medicinal Chemistry, 2005, p. 23-49, vol. 12.

Yu et al., "Synthesis and Fungicidal Evaluation of 2-arylphenyl ether-3-(1H-1,2,4-triazol-1-yl)propan-2-ol Derivatives," Journal of Agricultural and Food Chemistry, vol. 57, No. 11, (2009), pp. 4854-4860.

Office Action dated Aug. 15, 2017 from U.S. Appl. No. 15/319,963, filed Dec. 19, 2016.

Office Action dated Mar. 8, 2018 from U.S. Appl. No. 15/319,963, filed Dec. 19, 2016.

Office Action dated Mar. 8, 2018 from U.S. Appl. No. 14/902,877, filed Jan. 5, 2016.

Final Office Action dated Aug. 6, 2018 from U.S. Appl. No. 14/902,877, filed Jan. 5, 2016.

Final Office Action dated May 22, 2019 from U.S. Appl. No. 15/739,876, filed Dec. 26, 2017.

\* cited by examiner

COMPOSITIONS COMPRISING A TRIAZOLE COMPOUND

This application is a National Stage application of International Application No. PCT/EP2013/077081, filed Dec. 18, 2013, which claims the benefit of U.S. Provisional Application No. 61/739,814, filed Dec. 20, 2012. This application also claims priority under 35 U.S.C. § 119 to European Patent Application No. 12198698.8, filed Dec. 20, 2012 and European Patent Application No. 13174975.6, filed Jul. 3, 2013.

The present invention relates to compositions comprising,
1) as component I a compound of formula I:

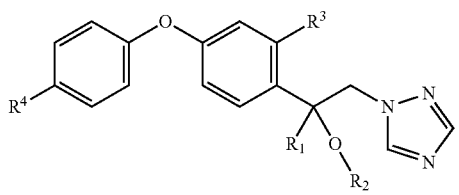

wherein
$R^1$ is $(C_1-C_4)$-alkyl, $(C_3-C_6)$-cycloalkyl, $(C_2-C_4)$-alkinyl or $CH_2OCH_3$, preferably $(C_1-C_4)$-alkyl, $(C_3-C_6)$-cycloalkyl or $(C_2-C_4)$-alkinyl; in particular $CH_3$, $C_2H_5$, n-$(C_3H_7)$, i-$(C_3H_7)$, $C(CH_3)_3$, cyclopropyl or $C\equiv C-CH_3$, more specifically $CH_3$, $C_2H_5$, n-$(C_3H_7)$, i-$(C_3H_7)$, cyclopropyl or $C\equiv C-CH_3$;
$R^2$ is hydrogen, $(C_1-C_3)$-alkyl, $(C_2-C_4)$-alkenyl or $(C_2-C_4)$-alkynyl, in particular hydrogen, $CH_3$, $C_2H_5$, n-$(C_3H_7)$, i-$(C_3H_7)$, $CH_2CH=CH_2$ (allyl), $CH_2C(CH_3)=CH_2$ or $CH_2C\equiv CH$;
$R^3$ is Cl or $CF_3$; and
$R^4$ is Cl;
and
2) as component II an active ingredient, selected from the following groups A) to O)

A) Respiration Inhibitors
Inhibitors of complex III at $Q_o$ site (e.g. strobilurins): azoxystrobin, coumethoxystrobin, coumoxystrobin, dimoxystrobin, enestroburin, fenaminstrobin, fenoxystrobin/flufenoxystrobin, fluoxastrobin, Isofetamid, kresoxim-methyl, metominostrobin, orysastrobin, picoxystrobin, pyraclostrobin, pyrametostrobin, pyraoxystrobin, trifloxystrobin, 2-[2-(2,5-dimethyl-phenoxymethyl)-phenyl]-3-methoxy-acrylic acid methyl ester and 2-(2-(3-(2,6-dichlorophenyl)-1-methyl-allylideneaminooxymethyl)-phenyl)-2-methoxyimino-N-methylacetamide, pyribencarb, triclopyricarb/chlorodincarb, famoxadone, fenamidone;
inhibitors of complex III at $Q_i$ site: cyazofamid, amisulbrom, [(3S,6S,7R,8R)-8-benzyl-3-[(3-acetoxy-4-methoxy-pyridine-2-carbonyl)amino]-6-methyl-4,9-dioxo-1,5-dioxonan-7-yl]2-methylpropanoate, [(3S,6S,7R,8R)-8-benzyl-3-[[3-(acetoxymethyl)-4-methoxy-pyridine-2-carbonyl]amino]-6-methyl-4,9-dioxo-1,5-dioxonan-7-yl]2-methylpropanoate, [(3S,6S,7R,8R)-8-benzyl-3-[(3-isobutoxycarbonyloxy-4-methoxy-pyridine-2-carbonyl)amino]-6-methyl-4,9-dioxo-1,5-dioxonan-7-yl]2-methylpropanoate, [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl]2-methylpropanoate; (3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate,
inhibitors of complex II (e.g. carboxamides): benodanil, benzovindiflupyr, bixafen, boscalid, carboxin, fenfuram, fluopyram, flutolanil, fluxapyroxad, furametpyr, isofetamid, isopyrazam, mepronil, oxycarboxin, penflufen, penthiopyrad, sedaxane, tecloftalam, thifluzamide, N-(4'-trifluoromethylthiobiphenyl-2-yl)-3-difluoromethyl-1-methyl-1H-pyrazole-4-carboxamide, N-(2-(1,3,3-trimethyl-butyl)-phenyl)-1,3-dimethyl-5-fluoro-1H-pyrazole-4-carboxamide, 3-(difluoromethyl)-1-methyl-N-(1,1,3-trimethylindan-4-yl)pyrazole-4-carboxamide, 3-(trifluoromethyl)-1-methyl-N-(1,1,3-trimethylindan-4-yl)pyrazole-4-carboxamide, 1,3-dimethyl-N-(1,1,3-trimethylindan-4-yl)pyrazole-4-carboxamide, 3-(trifluoromethyl)-1,5-dimethyl-N-(1,1,3-trimethylindan-4-yl)pyrazole-4-carboxamide, 1,3,5-trimethyl-N-(1,1,3-trimethylindan-4-yl)pyrazole-4-carboxamide, N-(7-fluoro-1,1,3-trimethyl-indan-4-yl)-1,3-dimethyl-pyrazole-4-carboxamide, N-[2-(2,4-dichlorophenyl)-2-methoxy-1-methyl-ethyl]-3-(difluoromethyl)-1-methyl-pyrazole-4-carboxamide;
other respiration inhibitors (e.g. complex I, uncouplers): diflumetorim, (5,8-difluoroquinazolin-4-yl)-{2-[2-fluoro-4-(4-trifluoromethylpyridin-2-yloxy)-phenyl]-ethyl}-amine; nitrophenyl derivates: binapacryl, dinobuton, dinocap, fluazinam; ferimzone; organometal compounds: fentin salts, such as fentin-acetate, fentin chloride or fentin hydroxide; ametoctradin; and silthiofam;

B) Sterol Biosynthesis Inhibitors (SBI Fungicides)
C14 demethylase inhibitors (DMI fungicides): triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole, 1-[rel-(2S,3R)-3-(2-chlorophenyl)-2-(2,4-difluorophenyl)-oxiranylmethyl]-5-thiocyanato-1H-[1,2,4]triazole, 2-[rel-(2S;3R)-3-(2-chlorophenyl)-2-(2,4-difluorophenyl)-oxiranylmethyl]-2H-[1,2,4]triazole-3-thiol; imidazoles: imazalil, pefurazoate, prochloraz, triflumizol; pyrimidines, pyridines and piperazines: fenarimol, nuarimol, pyrifenox, triforine; 3-(4-chloro-2-fluoro-phenyl)-5-(2,4-difluorophenyl)isoxazol-4-yl]-(3-pyridyl)methanol;
Delta14-reductase inhibitors: aldimorph, dodemorph, dodemorph-acetate, fenpropimorph, tridemorph, fenpropidin, piperalin, spiroxamine;
Inhibitors of 3-keto reductase: fenhexamid;

C) Nucleic Acid Synthesis Inhibitors
phenylamides or acyl amino acid fungicides: benalaxyl, benalaxyl-M, kiralaxyl, metalaxyl, metalaxyl-M (mefenoxam), ofurace, oxadixyl;
others: hymexazole, octhilinone, oxolinic acid, bupirimate, 5-fluorocytosine, 5-fluoro-2-(p-tolylmethoxy)pyrimidin-4-amine, 5-fluoro-2-(4-fluorophenylmethoxy)pyrimidin-4-amine;

D) Inhibitors of Cell Division and Cytoskeleton
tubulin inhibitors, such as benzimidazoles, thiophanates: benomyl, carbendazim, fuberidazole, thiabendazole, thiophanate-methyl; triazolopyrimidines: 5-chloro-7-

(4-methylpiperidin-1-yl)-6-(2,4,6-trifluorophenyl)-[1,2,4]triazolo[1,5-a]pyrimidine other cell division inhibitors: diethofencarb, ethaboxam, pencycuron, fluopicolide, zoxamide, metrafenone, pyriofenone;

E) Inhibitors of Amino Acid and Protein Synthesis methionine synthesis inhibitors (anilino-pyrimidines): cyprodinil, mepanipyrim, pyrimethanil;

protein synthesis inhibitors: blasticidin-S, kasugamycin, kasugamycin hydrochloride-hydrate, mildiomycin, streptomycin, oxytetracyclin, polyoxine, validamycin A;

F) Signal Transduction Inhibitors

MAP/histidine kinase inhibitors: fluoroimid, iprodione, procymidone, vinclozolin, fenpiclonil, fludioxonil;

G protein inhibitors: quinoxyfen;

G) Lipid and Membrane Synthesis Inhibitors

Phospholipid biosynthesis inhibitors: edifenphos, iprobenfos, pyrazophos, isoprothiolane;

lipid peroxidation: dicloran, quintozene, tecnazene, tolclofos-methyl, biphenyl, chloroneb, etridiazole;

phospholipid biosynthesis and cell wall deposition: dimethomorph, flumorph, mandipropamid, pyrimorph, benthiavalicarb, iprovalicarb, valifenalate and N-(1-(1-(4-cyano-phenyl)ethanesulfonyl)-but-2-yl) carbamic acid-(4-fluorophenyl) ester;

compounds affecting cell membrane permeability and fatty acides: propamocarb, propamocarb-hydrochlorid fatty acid amide hydrolase inhibitors: oxathiapiprolin, 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone, 2-{3-[2-(1-{[3,5-bis(difluoromethyl-1H-pyrazol-1-yl] acetyl}piperidin-4-yl)-1,3-thiazol-4-yl]-4,5-dihydro-1,2-oxazol-5-yl}phenyl methanesulfonate, 2-{3-[2-(1-{[3,5-bis(difluoromethyl)-1H-pyrazol-1-yl] acetyl}piperidin-4-yl) 1,3-thiazol-4-yl]-4,5-dihydro-1,2-oxazol-5-yl}-3-chlorophenyl methanesulfonate;

H) Inhibitors with Multi Site Action inorganic active substances: Bordeaux mixture, copper acetate, copper hydroxide, copper oxychloride, basic copper sulfate, sulfur;

thio- and dithiocarbamates: ferbam, mancozeb, maneb, metam, metiram, propineb, thiram, zineb, ziram;

organochlorine compounds (e.g. phthalimides, sulfamides, chloronitriles): anilazine, chlorothalonil, captafol, captan, folpet, dichlofluanid, dichlorophen, flusulfamide, hexachlorbenzene, pentachlorphenole and its salts, phthalide, tolylfluanid, N-(4-chloro-2-nitro-phenyl)-N-ethyl-4-methyl-benzenesulfonamide;

guanidines and others: guanidine, dodine, dodine free base, guazatine, guazatine-acetate, iminoctadine, iminoctadine-triacetate, iminoctadine-tris(albesilate), dithianon, 2,6-dimethyl-1H,5H-[1,4]dithiino[2,3-c:5,6-c']dipyrrole-1,3,5,7(2H,6H)-tetraone;

I) Cell Wall Synthesis Inhibitors inhibitors of glucan synthesis: validamycin, polyoxin B;

melanin synthesis inhibitors: pyroquilon, tricyclazole, carpropamid, dicyclomet, fenoxanil;

J) Plant Defence Inducers acibenzolar-S-methyl, probenazole, isotianil, tiadinil, prohexadione-calcium; phosphonates: fosetyl, fosetyl-aluminum, phosphorous acid and its salts;

K) Unknown Mode of Action bronopol, chinomethionat, cyflufenamid, cymoxanil, dazomet, debacarb, diclomezine, difenzoquat, difenzoquat-methylsulfate, diphenylamin, fenpyrazamine, flumetover, flusulfamide, flutianil, methasulfocarb, nitrapyrin, nitrothal-isopropyl, oxin-copper, proquinazid, tebufloquin, tecloftalam, oxathiapiprolin, 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone, 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone, tolprocarb, triazoxide, 2-butoxy-6-iodo-3-propylchromen-4-one, 2-[3,5-bis(difluoromethyl)-1H-pyrazol-1-yl]-1-[4-(4-{5-[2-(prop-2-yn-1-yloxy) phenyl]-4,5-dihydro-1,2-oxazol-3-yl}-1,3-thiazol-2-yl) piperidin-1-yl]ethanone, 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone, 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone, N-(cyclopropylmethoxyimino-(6-difluoro-methoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-prol)oxy)-phenyl)-N-ethyl-N-methyl formamidine, N'-(5-difluoromethyl-2-methyl-4-(3-trimethylsilanyl-prol)oxy)phenyl)-N-ethyl-N-methyl formamidine, 2methoxy-acetic acid 6-tert-butyl-8-fluoro-2,3-dimethyl-quinolin-4-yl ester, 3-[5-(4-methylphenyl)-2,3-dimethyl-isoxazolidin-3-yl]pyridine, 3-[5-(4-chloro-phenyl)-2,3-dimethyl-isoxazolidin-3-yl]pyridine (pyrisoxazole), N-(6-methoxypyridin-3-yl)cyclopropanecarboxylic acid amide, 5-chloro-1-(4,6-dimethoxy-pyrimidin-2-yl)-2-methyl-1H-benzoimidazole, 2-(4-chloro-phenyl)-N-[4-(3,4-dimethoxy-phenyl)-isoxazol-5-yl]-2-prop-2-ynyloxy-acetamide; ethyl(Z)-3-amino-2-cyano-3-phenyl-prop-2-enoate, tert-butyl N-[6-[[(Z)-[(1-methyltetrazol-5-yl)-phenyl-methylene]amino]oxymethyl]-2-pyridyl]carbamate, pentyl N-[6-[[(Z)-[(1-methyltetrazol-5-yl)-phenyl-methylene]amino]oxymethyl]-2-pyridyl]carbamate, 2-[2-[(7,8-difluoro-2-methyl-3-quinolyl)oxy]-6-fluoro-phenyl]propan-2-ol, 2-[2-fluoro-6-[(8-fluoro-2-methyl-3-quinolyl)oxy]phenyl]propan-2-ol, 3-(5-fluoro-3,3,4,4-tetramethyl-3,4-dihydroisoquinolin-1-yl)quinoline, 3-(4,4-difluoro-3,3-dimethyl-3,4-dihydroisoquinolin-1-yl)quinoline, 3-(4,4,5-trifluoro-3,3-dimethyl-3,4-dihydroisoquinolin-1-yl)quinolone; 9-fluoro-2,2-dimethyl-5-(3-quinolyl)-3H-1,4-benzoxazepine, ethyl(Z)-3-amino-2-cyano-3-phenyl-prop-2-enoate, picarbutrazox, pentyl N-[6-[[(Z)-[(1-methyltetrazol-5-yl)-phenyl-methylene]amino]oxymethyl]-2-pyridyl] carbamate, 2-[2-[(7,8-difluoro-2-methyl-3-quinolyl) oxy]-6-fluoro-phenyl]propan-2-ol, 2-[2-fluoro-6-[(8-fluoro-2-methyl-3-quinolyl)oxy]phen-yl]propan-2-ol, 3-(5-fluoro-3,3,4,4-tetramethyl-3,4-dihydroisoquino-lin-1-yl)quinoline, 3-(4,4-difluoro-3,3-dimethyl-3,4-dihydroisoquinolin-1-yl)quinoline, 3-(4,4,5-trifluoro-3,3-dimethyl-3,4-dihydroisoquinolin-1-yl)quinoline;

L) Biopesticides
- L1) Microbial pesticides with fungicidal, bactericidal, viricidal and/or plant defense activator activity: *Ampelomyces quisqualis, Aspergillus flavus, Aureobasidium pullulans, Bacillus amyloliquefaciens, B. mojavensis, B. pumilus, B. simplex, B. solisalsi, B. subtilis, B. subtilis* var. *amyloliquefaciens, Candida oleophila, C. saitoana, Clavibacter michiganensis* (bacteriophages), *Coniothyrium minitans, Cryphonectria parasitica, Cryptococcus albidus, Dilophosphora alopecuri, Fusarium oxysporum, Clonostachys rosea* f. *catenulate* (also named *Gliocladium catenulatum*), *Gliocladium roseum, Lysobacter antibioticus, L. enzymogenes, Metschnikowia fructicola, Microdochium dimerum, Microsphaeropsis ochracea, Muscodor albus, Paenibacillus polymyxa, Pantoea vagans, Phlebiopsis gigantea, Pseudomonas* sp., *Pseudomonas chloraphis, Pseudozyma flocculosa, Pichia anomala, Pythium oligandrum, Sphaerodes mycoparasitica, Streptomyces griseoviridis, S. lydicus, S. violaceusniger, Talaromyces flavus, Trichoderma asperellum, T. atroviride, T. fertile, T. gamsii, T. harmatum, T. harzianum*; mixture of *T. harzianum* and *T. viride*; mixture of *T. polysporum* and *T. harzianum*; *T. stromaticum, T. virens* (also named *Gliocladium virens*), *T. viride, Typhula phacorrhiza, Ulocladium oudemansii, Verticillium dahlia*, zucchini yellow mosaic virus (avirulent strain);
- L2) Biochemical pesticides with fungicidal, bactericidal, viricidal and/or plant defense activator activity: chitosan (hydrolysate), harpin protein, laminarin, Menhaden fish oil, natamycin, Plum pox virus coat protein, potassium or sodium bicarbonate, *Reynoutria sachlinensis* extract, salicylic acid, tea tree oil;
- L3) Microbial pesticides with insecticidal, acaricidal, molluscidal and/or nematicidal activity: *Agrobacterium radiobacter, Bacillus cereus, B. firmus, B. thuringiensis, B. thuringiensis* ssp. *aizawai, B. t.* ssp. *israelensis, B. t.* ssp. *galleriae, B. t.* ssp. *kurstaki, B. t.* ssp. *tenebrionis, Beauveria bassiana, B. brongniartii, Burkholderia* sp., *Chromobacterium subtsugae, Cydia pomonella* granulosis virus, *Cryptophlebia leucotreta* granulovirus (CrleGV), *Isaria fumosorosea, Heterorhabditis bacteriophora, Lecanicillium longisporum, L. muscarium* (formerly *Verticillium lecanii*), *Metarhizium anisopliae, M. anisopliae* var. acridum, *Nomuraea rileyi, Paecilomyces fumosoroseus, P. lilacinus, Paenibacillus popilliae, Pasteuria* spp., *P. nishizawae, P. penetrans, P. ramose, P. reneformis, P. thornea, P. usgae, Pseudomonas fluorescens, Steinernema carpocapsae, S. feltiae, S. kraussei*;
- L4) Biochemical pesticides with insecticidal, acaricidal, molluscidal, pheromone and/or nematicidal activity: L-carvone, citral, (E,Z)-7,9-dodecadien-1-ylacetate, ethyl formate, (E,Z)-2,4-ethyl decadienoate (pear ester), (Z,Z,E)-7,11,13-hexadecatrienal, heptyl butyrate, isopropyl myristate, lavanulyl senecioate, cis-jasmone, 2-methyl 1-butanol, methyl eugenol, methyl jasmonate, (E,Z)-2,13-octadecadien-1-ol, (E,Z)-2,13-octadecadien-1-ol acetate, (E,Z)-3,13-octadecadien-1-ol, R-1-octen-3-ol, pentatermanone, potassium silicate, sorbitol actanoate, (E,Z,Z)-3,8,11-tetradecatrienyl acetate, (Z,E)-9,12-tetradecadien-1-ylacetate, Z-7-tetradecen-2-one, Z-9-tetradecen-1-ylacetate, Z-11-tetradecenal, Z-11-tetradecen-1-ol, *Acacia negra* extract, extract of grapefruit seeds and pulp, extract of *Chenopodium ambrosiodae*, Catnip oil, Neem oil, Quillay extract, *Tagetes* oil;
- L5) Microbial pesticides with plant stress reducing, plant growth regulator, plant growth promoting and/or yield enhancing activity: *Azospirillum amazonense, A. brasilense, A. lipoferum, A. irakense, A. halopraeferens, Bradyrhizobium* sp., *B. elkanii, B. japonicum, B. liaoningense, B. lupini, Delftia acidovorans, Glomus intraradices, Mesorhizobium* sp., *Paenibacillus alvei, Penicillium bilaiae, Rhizobium leguminosarum* bv. *phaseoli, R. l. trifolii, R. l.* bv. *viciae, R. tropici, Sinorhizobium meliloti*;
- L6) Biochemical pesticides with plant stress reducing, plant growth regulator and/or plant yield enhancing activity: abscisic acid, aluminium silicate (kaolin), 3-decen-2-one, formononetin, genistein, hesperetin, homobrassinlide, humates, jasmonic acid or salts or derivatives thereof, lysophosphatidyl ethanolamine, naringenin, polymeric polyhydroxy acid, *Ascophyllum nodosum* (Norwegian kelp, Brown kelp) extract and *Ecklonia maxima* (kelp) extract; M) Growth regulators abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N-6-benzyladenine, paclobutrazol, prohexadione (prohexadione-calcium), prohydrojasmon, thidiazuron, triapenthenol, tributyl phosphorotrithioate, 2,3,5-tri-iodobenzoic acid, trinexapac-ethyl and uniconazole;
N) Herbicides
- acetamides: acetochlor, alachlor, butachlor, dimethachlor, dimethenamid, flufenacet, mefenacet, metolachlor, metazachlor, napropamide, naproanilide, pethoxamid, pretilachlor, propachlor, thenylchlor;
- amino acid derivatives: bilanafos, glyphosate, glufosinate, sulfosate;
- aryloxyphenoxypropionates: clodinafop, cyhalofop-butyl, fenoxaprop, fluazifop, haloxyfop, metamifop, propaquizafop, quizalofop, quizalofop-P-tefuryl;
- Bipyridyls: diquat, paraquat;
- (thio)carbamates: asulam, butylate, carbetamide, desmedipham, dimepiperate, eptam (EPTC), esprocarb, molinate, orbencarb, phenmedipham, prosulfocarb, pyributicarb, thiobencarb, triallate;
- cyclohexanediones: butroxydim, clethodim, cycloxydim, profoxydim, sethoxydim, tepraloxydim, tralkoxydim;
- dinitroanilines: benfluralin, ethalfluralin, oryzalin, pendimethalin, prodiamine, trifluralin;
- diphenyl ethers: acifluorfen, aclonifen, bifenox, diclofop, ethoxyfen, fomesafen, lactofen, oxyfluorfen;
- hydroxybenzonitriles: bomoxynil, dichlobenil, ioxynil;
- imidazolinones: imazamethabenz, imazamox, imazapic, imazapyr, imazaquin, imazethapyr;
- phenoxy acetic acids: clomeprop, 2,4-dichlorophenoxyacetic acid (2,4-D), 2,4-DB, dichlorprop, MCPA, MCPA-thioethyl, MCPB, Mecoprop;
- pyrazines: chloridazon, flufenpyr-ethyl, fluthiacet, norflurazon, pyridate;
- pyridines: aminopyralid, clopyralid, diflufenican, dithiopyr, fluridone, fluroxypyr, picloram, picolinafen, thiazopyr;
- sulfonyl ureas: amidosulfuron, azimsulfuron, bensulfuron, chlorimuron-ethyl, chlorsulfuron, cinosulfuron, cyclosulfamuron, ethoxysulfuron, flazasulfuron, flucetosulfuron, flupyrsulfuron, foramsulfuron, halosulfuron, imazosulfuron, iodosulfuron, mesosulfuron, metazosulfuron, metsulfuron-methyl, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, 1-((2-chloro-6-propyl-imidazo[1,2-b]pyridazin-3-yl)sulfonyl)-3-(4,6-dimethoxy-pyrimidin-2-yl)urea;

triazines: ametryn, atrazine, cyanazine, dimethametryn, ethiozin, hexazinone, metamitron, metribuzin, prometryn, simazine, terbuthylazine, terbutryn, triaziflam;

ureas: chlorotoluron, daimuron, diuron, fluometuron, isoproturon, linuron, methabenzthiazuron, tebuthiuron;

other acetolactate synthase inhibitors: bispyribac-sodium, cloransulam-methyl, diclosulam, florasulam, flucarbazone, flumetsulam, metosulam, ortho-sulfamuron, penoxsulam, prol)oxycarbazone, pyribambenz-propyl, pyribenzoxim, pyriftalid, pyriminobac-methyl, pyrimisulfan, pyrithiobac, pyroxasulfone, pyroxsulam;

others: amicarbazone, aminotriazole, anilofos, beflubutamid, benazolin, bencarbazone, benfluresate, benzofenap, bentazone, benzobicyclon, bicyclopyrone, bromacil, bromobutide, butafenacil, butamifos, cafenstrole, carfentrazone, cinidon-ethyl, chlorthal, cinmethylin, clomazone, cumyluron, cyprosulfamide, dicamba, difenzoquat, diflufenzopyr, *Drechslera monoceras*, endothal, ethofumesate, etobenzanid, fenoxasulfone, fentrazamide, flumiclorac-pentyl, flumioxazin, flupoxam, flurochloridone, flurtamone, indanofan, isoxaben, isoxaflutole, lenacil, propanil, propyzamide, quinclorac, quinmerac, mesotrione, methyl arsonic acid, naptalam, oxadiargyl, oxadiazon, oxaziclomefone, pentoxazone, pinoxaden, pyraclonil, pyraflufen-ethyl, pyrasulfotole, pyrazoxyfen, pyrazolynate, quinoclamine, saflufenacil, sulcotrione, sulfentrazone, terbacil, tefuryltrione, tembotrione, thiencarbazone, topramezone, (3-[2-chloro-4-fluoro-5-(3-methyl-2,6-dioxo-4-trifluoromethyl-3,6-dihydro-2H-pyrimidin-1-yl)-phenoxy]-pyridin-2-yloxy)-acetic acid ethyl ester, 6-amino-5-chloro-2-cyclopropyl-pyrimidine-4-carboxylic acid methyl ester, 6-chloro-3-(2-cyclopropyl-6-methyl-phenoxy)-pyridazin-4-ol, 4-amino-3-chloro-6-(4-chloro-phenyl)-5-fluoro-pyridine-2-carboxylic acid, 4-amino-3-chloro-6-(4-chloro-2-fluoro-3-methoxy-phenyl)-pyridine-2-carboxylic acid methyl ester, and 4-amino-3-chloro-6-(4-chloro-3-dimethylamino-2-fluoro-phenyl)-pyridine-2-carboxylic acid methyl ester.

O) Insecticides organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;

carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;

pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin;

insect growth regulators: a) chitin synthesis inhibitors: benzoylureas: chlorfluazuron, cyramazin, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramat;

nicotinic receptor agonists/antagonists compounds: clothianidin, dinotefuran, flupyradifurone, imidacloprid, thiamethoxam, nitenpyram, acetamiprid, thiacloprid, 1-2-chloro-thiazol-5-ylmethyl)-2-nitrimino-3,5-dimethyl-[1,3,5]triazinane;

GABA antagonist compounds: endosulfan, ethiprole, fipronil, vaniliprole, pyrafluprole, pyriprole, 5-amino-1-(2,6-dichloro-4-methyl-phenyl)-4-sulfinamoyl-1H-pyrazole-3-carbothioic acid amide;

macrocyclic lactone insecticides: abamectin, emamectin, milbemectin, lepimectin, spinosad, spinetoram;

mitochondrial electron transport inhibitor (METI) I acaricides: fenazaquin, pyridaben, tebufenpyrad, tolfenpyrad, flufenerim;

METI II and III compounds: acequinocyl, fluacyprim, hydramethylnon;

Uncouplers: chlorfenapyr;

oxidative phosphorylation inhibitors: cyhexatin, diafenthiuron, fenbutatin oxide, propargite;

moulting disruptor compounds: cryomazine;

mixed function oxidase inhibitors: piperonyl butoxide;

sodium channel blockers: indoxacarb, metaflumizone;

ryanodine receptor inhibitors: chlorantraniliprole, cyantraniliprole (former cyazypyr), flubendiamide, N-[4,6-dichloro-2-[(diethyl-lambda-4-sulfanylidene)carbamoyl]-phenyl]-2-(3-chloro-2-pyridyl)-5-(trifluoromethyl)pyrazole-3-carboxamide; N-[4-chloro-2-[(diethyl-lambda-4-sulfanylidene) carbamoyl]-6-methyl-phenyl]-2-(3-chloro-2-pyridyl)-5-(trifluoromethyl)pyrazole-3-carboxamide; N-[4-chloro-2-[(di-2-propyl-lambda-4-sulfanylidene) carbamoyl]-6-methyl-phenyl]-2-(3-chloro-2-pyridyl)-5-(trifluoromethyl)pyrazole-3-carboxamide; N-[4,6-dichloro-2-[(di-2-propyl-lambda-4-sulfanylidene) carbamoyl]-phenyl]-2-(3-chloro-2-pyridyl)-5-(trifluoromethyl)pyrazole-3-carboxamide; N-[4,6-dichloro-2-[(diethyl-lambda-4-sulfanylidene) carbamoyl]-phenyl]-2-(3-chloro-2-pyridyl)-5-(difluoromethyl)pyrazole-3-carboxamide; N-[4,6-dibromo-2-[(di-2-propyl-lambda-4-sulfanylidene) carbamoyl]-phenyl]-2-(3-chloro-2-pyridyl)-5-(trifluoromethyl)pyrazole-3-carboxamide; N-[4-chloro-2-[(di-2-propyl-lambda-4-sulfanylidene) carbamoyl]-6-cyano-phenyl]-2-(3-chloro-2-pyridyl)-5-(trifluoromethyl)pyrazole-3-carboxamide; N-[4,6-dibromo-2-[(diethyl-lambda-4-sulfanylidene) carbamoyl]-phenyl]-2-(3-chloro-2-pyridyl)-5-(trifluoromethyl)pyrazole-3-carboxamide;

others: benclothiaz, bifenazate, cartap, flonicamid, pyridalyl, pymetrozine, sulfur, thiocyclam, cyenopyrafen, flupyrazofos, cyflumetofen, amidoflumet, imicyafos, bistrifluron, pyrifluquinazon and 1,1'-[(3S,4R,4aR, 6S,6aS,12R,12aS,12bS)-4-[[(2-cyclopropylacetyl)oxy] methyl]-1,3,4,4a,5,6,6a,12,12a,12b-decahydro-12-hydroxy-4,6a,12b-trimethyl-11-oxo-9-(3-pyridinyl)-2H,11H-naphtho[2,1-b]pyrano[3,4-e]pyran-3,6-diyl] cyclopropaneacetic acid ester.

In particular, in compounds I, the substituents have the following preferred meanings. There, the specific meanings of the respective substituents are in each case on their own but also in any combination with one another, particular embodiments of the components I of the present invention.

$R^1$ is $(C_1-C_4)$-alkyl, $(C_3-C_6)$-cycloalkyl or $(C_2-C_4)$-alkinyl. Preferably, $R^1$ is $(C_1-C_4)$-alkyl, $(C_3)$-cycloalkyl or $(C_3)$-alkinyl.

In one embodiments, $R^1$ is $CH_3$. In a further embodiment $R^1$ is $C_2H_5$. In still a further embodiment $R^1$ is n-$(C_3H_7)$. In still a further embodiment $R^1$ is i-$(C_3H_7)$. In still a further embodiment $R^1$ is $C(CH_3)_3$.

In still a further embodiment $R^1$ is cyclopropyl.

In still a further embodiment $R^1$ is C≡C—$CH_3$.

$R^2$ is hydrogen, $(C_1-C_3)$-alkyl, $(C_2-C_4)$-alkenyl or $(C_2-C_4)$-alkynyl, in particular hydrogen, $(C_1-C_3)$-alkyl, $(C_2-C_3)$-alkenyl or $(C_2-C_4)$-alkynyl. Preferably, $R^2$ is hydrogen or $(C_1-C_3)$-alkyl.

In one embodiments, $R^2$ is hydrogen. In a further embodiment $R^2$ is $CH_3$. In still a further embodiment $R^2$ is $C_2H_5$. In still a further embodiment $R^2$ is n-$(C_3H_7)$. In still a further embodiment $R^2$ is i-$(C_3H_7)$.

In still a further embodiment $R^2$ is $CH_2CH=CH_2$ (allyl).

In still a further embodiment $R^2$ is $CH_2C(CH_3)=CH_2$.

In still a further embodiment $R^2$ is $CH_2C\equiv CH$.

$R^3$ is Cl or $CF_3$. In one embodiment $R^3$ is $C_1$. In the further embodiment, $R^3$ is $CF_3$.

$R^4$ is Cl or F. In one embodiment $R^4$ is $C_1$. In the further embodiment $R^4$ is F.

In particular, component I is a compound of formula IA or, more specifically IB:

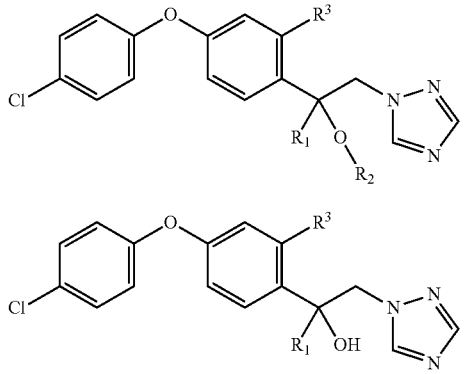

wherein
$R^1$ is $CH_3$, i-$(C_3H_7)$, cyclopropyl or C≡C—$CH_3$;
$R^2$ is hydrogen, $CH_3$, $C_2H_5$, n-$(C_3H_7)$, i-$(C_3H_7)$, $CH_2CH=CH_2$ (allyl), $CH_2C(CH_3)=CH_2$ or $CH_2C\equiv CH$, in particular hydrogen (compounds IB); and
$R^3$ is $C_1$ or $CF_3$.

Component I is particularly selected from the following compounds I-1 to I-16 according to the present invention:
compound I-1 2-[2-chloro-4-(4-chlorophenoxyl)phenyl]-1-(1,2,4-triazol-1-yl)pent-3-yn-2-ol;
compound I-2 1-[2-chloro-4-(4-chlorophenoxyl)phenyl]-1-cyclopropyl-2-(1,2,4-triazol-1-yl)ethanol;
compound I-3 2-[4-(4-chlorophenoxy)-2-(trifluoromethyl) phenyl]-1-(1,2,4-triazol-1-yl)propan-2-ol;
compound I-4 1-[4-(4-chlorophenoxy)-2-(trifluoromethyl) phenyl]-1-cyclopropyl-2-(1,2,4-triazol-1-yl)ethanol;
compound I-5 2-[4-(4-chlorophenoxy)-2-(trifluoromethyl) phenyl]-3-methyl-1-(1,2,4-triazol-1-yl)butan-2-ol;
compound I-6 1-[2-[2-chloro-4-(4-chlorophenoxyl)phenyl]-2-methoxy-pent-3-ynyl]-1,2,4-triazole;
compound I-7 2-[4-(4-chlorophenoxy)-2-(trifluoromethyl) phenyl]-1-(1,2,4-triazol-1-yl)butan-2-01;
compound I-8 1-[2-[2-chloro-4-(4-chlorophenoxyl)phenyl]-2-cyclopropyl-2-methoxy-ethyl]-1,2,4-triazole;
compound I-9 1-[2-[4-(4-chlorophenoxy)-2-(trifluoromethyl)phenyl]-2-methoxy-propyl]-1,2,4-triazole;
compound I-10 2-[2-chloro-4-(4-chlorophenoxyl)phenyl]-3,3-dimethyl-1-(1,2,4-triazol-1-yl)butan-2-ol,
compound I-11 1-[2-[4-(4-chlorophenoxy)-2-(trifluoromethyl)phenyl]-2-cyclopropyl-2-methoxy-ethyl]-1,2,4-triazole;
compound I-12 2-[2-trifluoromethyl-4-(4-chlorophenoxyl) phenyl]-1-methoxy-3-(1,2,4-triazol-1-yl)propan-2-ol;
compound I-13 1-[2-[4-(4-chlorophenoxy)-2-(trifluoromethyl)phenyl]-2-methoxy-butyl]1,2,4-triazole;
compound I-14 2-[4-(4-chlorophenoxy)-2-(trifluoromethyl) phenyl]-1-(1,2,4-triazol-1-yl)pent-3-yn-2-ol;
compound I-15 1-[2-[4-(4-chlorophenoxy)-2-(trifluoromethyl)phenyl]-2-methoxy-pent-3-ynyl]-1,2,4-triazole;
compound I-16 2-[4-(4-chlorophenoxy)-2-(trifluoromethyl) phenyl]-1-(1,2,4-triazol-1-yl)but-3-yn-2-ol.

Preferably I-1, I-2, I-3, I-4, I-5, I-6, I-7, I-8, I-9, I-11, I-12, I-13, I-14, I-15 and I-16. More specifically I-1, I-2, I-3, I-4, I-5, I-6, I-7, I-8, I-9, I-11, I-13, I-14, I-15 and I-16.

The weight ratio of component I to component II in the inventive compositions is preferably from 1000:1 to 1:1000, more specifically 500:1 to 1:500, particularly 100:1 to 1:100.

According to one embodiment, two-component compositions according to the invention may preferably have weight ratios of compound I versus compound II in the range of from 1000:1 to 1:1, often in the range of from 100:1 to 1:1, regularly in the range of from 50:1 to 1:1, preferably in the range of from 20:1 to 1:1, more preferably in the range of from 10:1 to 1:1, even more preferably in the range of from 4:1 to 1:1 and in particular in the range of from 2:1 to 1:1.

According to one embodiment, two-component compositions according to the invention may preferably have weight ratios of compound I versus compound II usually is in the range of from 1:1 to 1000, often in the range of from 1:1 to 1:100, regularly in the range of from 1:1 to 1:50, preferably in the range of from 1:1 to 1:20, more preferably in the range of from 1:1 to 1:10, even more preferably in the range of from 1:1 to 1:4 and in particular in the range of from 1:1 to 1:2.

The invention furthermore relates to the use of the inventive compositions for controlling phytopathogenic fungi as detailed herein and preparations or compositions comprising them. The invention furthermore also relates to seed comprising the compositions. The invention furthermore also relates to methods for controlling phytopathogenic fungi as detailed herein, wherein the fungi or the materials, plants, the soil or seed to be protected from fungal attack are treated with an effective amount of a compositions according to the invention. The invention furthermore also relates to processes for preparing the compositions according to the invention.

With a view to reducing the application rates and broadening the activity spectrum of the known compounds, it was an object of the present invention to provide compositions which, at a reduced total amount of active compounds applied, show improved activity against important harmful fungi, in particular for certain indications. It was a further object to provide for compositions that are useful for the control of specific pathogens in specific important crops that are often susceptible to the attack of pathogens.

Accordingly we have found the compositions and uses defined at the outset and in the following description. In particular, the present invention relates to compositions comprising component I and component II and to compositions comprising component I, component II and component III, wherein component III is selected from the compounds of groups A) to O) as defined herein, with the proviso that all components are different from one another. In addition to the components I, II and III mentioned, the compositions according to the invention may also comprise further components (for example component IV or components IV and V), wherein each of the additional components (for example component IV or components IV and V) is independently selected from the compounds of groups A) to O) defined herein, with the proviso that all components are different from one another.

The compounds I can be obtained by various routes in analogy to prior art processes known (cf. J. Agric. Food Chem. (2009) 57, 4854-4860; EP 0 275 955 A1; DE 40 03 180 A1; EP 0 113 640 A2; EP 0 126 430 A2). Furthermore, compounds of formula I, its preparation and use in crop protection are described in WO 2013/007767 (PCT/EP2012/063626), WO 2013/024076 (PCT/EP2012/065835), WO 2013/024075 (PCT/EP2012/065834,), WO 2013/024077 (PCT/EP2012/065836), WO 2013/024081 (PCT/EP2012/065848), WO 2013/024080 (PCT/EP2012/065847), WO 2013/024083 (PCT/EP2012/065852) WO 2013/010862 (PCT/EP2012/063526), WO 2013/010894 (PCT/EP2012/063635), WO 2013/010885 (PCT/EP2012/063620), WO 2013/024082 (PCT/EP2012/065850), which also disclose certain compositions with other active compounds. Owing to the basic character of their nitrogen atoms, the component I, i.e. in particular compound I-1, I-2, I-3, I-4, I-5, I-6, I-7, I-8, I-9, I-10, I-11, I-12, I-13, I-14, I-15 and I-16 or any group of compounds I detailed above, is capable of forming salts or adducts with inorganic or organic acids or with metal ions, in particular salts with inorganic acids.

Examples of inorganic acids are hydrohalic acids, such as hydrogen fluoride, hydrogen chloride, hydrogen bromide and hydrogen iodide, carbonic acid, sulfuric acid, phosphoric acid and nitric acid.

Suitable organic acids are, for example, formic acid and alkanoic acids, such as acetic acid, trifluoroacetic acid, trichloroacetic acid and propionic acid, and also glycolic acid, thiocyanic acid, lactic acid, succinic acid, citric acid, benzoic acid and other arylcarboxylic acids, cinnamic acid, oxalic acid, alkylsulfonic acids (sulfonic acids having straight-chain or branched alkyl radicals of 1 to 20 carbon atoms), arylsulfonic acids or aryldisulfonic acids (aromatic radicals, such as phenyl and naphthyl, which carry one or two sulfonic acid groups), alkylphosphonic acids (phosphonic acids having straight-chain or branched alkyl radicals with 1 to 20 carbon atoms), arylphosphonic acids or aryldiphosphonic acids (aromatic radicals, such as phenyl and naphthyl, which carry one or two phosphoric acid radicals), where the alkyl or aryl radicals may carry further substituents, for example p-toluenesulfonic acid, salicylic acid, p-aminosalicylic acid, 2-phenoxybenzoic acid, 2-acetoxybenzoic acid etc. Suitable metal ions are in particular the ions of the elements of the second main group, in particular calcium and magnesium, of the third and fourth main group, in particular aluminum, tin and lead, and also of the elements of transition groups one to eight, in particular chromium, manganese, iron, cobalt, nickel, copper, zinc, and others. Particular preference is given to the metal ions of the elements of transition groups of the fourth period. The metals can be present in the various valencies that they can assume.

Components I comprise chiral centers and they are generally obtained in the form of racemates. The R- and S-enantiomers of the compounds according to the invention can be separated and isolated in pure form with methods known by the skilled person, e.g. by using chiral HPLC. Suitable for use as antimicrobial agents are both the enantiomers and compositions thereof. This applies correspondingly to the compositions. Furthermore, components I can be present in different crystal modifications, which may differ in biological activity.

In particular, in each case, a racemic composition is present. Furthermore, any other proportions of the (R)-enantiomer and the (S)-enantiomer may be present according to the present invention. This applies to every composition detailed herein.

According to one embodiment of the present invention, component I is compound I-1. Compound I-1 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-1.

According to one specific embodiment, the compound I-1 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-1 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

Compound (R)-I-1: (R)-2-[2-chloro-4-(4-chlorophenoxy)phenyl]-1-(1,2,4-triazol-1-yl)pent-3-yn-2-ol; Compound (S)-I-1: (S)-2-[2-chloro-4-(4-chlorophenoxy)phenyl]-1-(1,2,4-triazol-1-yl)pent-3-yn-2-ol. According to a further embodiment of the present invention, component I is compound I-2. Compound I-2 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-2.

According to one specific embodiment, the compound I-2 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-2 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

Compound (R)-I-2: (R)-1-[2-chloro-4-(4-chlorophenoxyl)phenyl]-1-cyclopropyl-2-(1,2,4-triazol-1-yl)ethanol; compound (S)-I-2: (S)-1-[2-chloro-4-(4-chlorophenoxyl)phenyl]-1-cyclopropyl-2-(1,2,4-triazol-1-yl)ethanol.

According to still a further embodiment of the present invention, component I is compound I-3. Compound I-3 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-3.

According to one specific embodiment, the compound I-3 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-3 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

Compound (R)-I-3: (R)-2-[4-(4-chlorophenoxy)-2-(trifluoromethyl)phenyl]-1-(1,2,4-triazol-1-yl)propan-2-ol; compound (S)-I-3: (S)-2-[4-(4-chlorophenoxy)-2-(trifluoromethyl)phenyl]-1-(1,2,4-triazol-1-yl)propan-2-ol.

According to still a further embodiment of the present invention, component I is compound I-4. Compound I-4 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-4.

According to one specific embodiment, the compound I-4 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-4 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

Compound (R)-I-4: (R)-1-[4-(4-chlorophenoxy)-2-(trifluoromethyl)phenyl]-1-cyclopropyl-2-(1,2,4-triazol-1-yl)ethanol; compound (S)-I-4: (S)-1-[4-(4-chlorophenoxy)-2-(trifluoromethyl)phenyl]-1-cyclopropyl-2-(1,2,4-triazol-1-yl)ethanol.

According to still a further embodiment of the present invention, component I is compound I-5. Compound I-5 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-5.

According to one specific embodiment, the compound I-5 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-5 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

Compound (R)-I-5: (R)-2-[4-(4-chlorophenoxy)-2-(trifluoromethyl)phenyl]-3-methyl-1-(1,2,4-triazol-1-yl)butan-2-ol; compound (S)-I-5: (S)-2-[4-(4-chlorophenoxy)-2-(trifluoromethyl)phenyl]-3-methyl-1-(1,2,4-triazol-1-yl)butan-2-ol.

According to still a further embodiment of the present invention, component I is compound I-6. Compound I-6 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-6.

According to one specific embodiment, the compound I-6 is provided and used as (R)-enantiomer with an enantomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-6 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

Compound (S)-I-6: (S)-1-[2-[2-chloro-4-(4-chlorophenoxyl)phenyl]-2-methoxy-pent-3-ynyl]-1,2,4-triazole; compound (R)-I-6: (R)-1-[2-[2-chloro-4-(4-chlorophenoxyl)phenyl]-2-methoxy-pent-3-ynyl]-1,2,4-triazole.

According to still a further embodiment of the present invention, component I is compound I-7. Compound I-7 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-7.

According to one specific embodiment, the compound I-7 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-7 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

compound (S)-I-7: (S)-2-[4-(4-chlorophenoxy)-2-(trifluoromethyl)phenyl]-1-(1,2,4-triazol-1-yl)butan-2-ol; compound (R)-I-7: (R)-2-[4-(4-chlorophenoxy)-2-(trifluoromethyl)phenyl]-1-(1,2,4-triazol-1-yl)butan-2-ol.

According to still a further embodiment of the present invention, component I is compound I-8. Compound I-8 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-8.

According to one specific embodiment, the compound I-8 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-8 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

Compound (S)-I-8: (S)-1-[2-[2-chloro-4-(4-chlorophenoxyl)phenyl]-2-cyclopropyl-2-methoxy-ethyl]-1,2,4-triazole; Compound (R)-I-8: (R)-1-[2-[2-chloro-4-(4-chlorophenoxyl)phenyl]-2-cyclopropyl-2-methoxy-ethyl]-1,2,4-triazole.

According to still a further embodiment of the present invention, component I is compound I-9. Compound I-9 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-9.

According to one specific embodiment, the compound I-9 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-9 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

Compound (S)-I-9: (S)-1-[2-[4-(4-chlorophenoxy)-2-(trifluoromethyl)phenyl]-2-methoxy-propyl]-1,2,4-triazole; compound (R)-I-9: (R)-1-[2-[4-(4-chlorophenoxy)-2-(trifluoromethyl)phenyl]-2-methoxy-propyl]-1,2,4-triazole.

According to still a further embodiment of the present invention, component I is compound I-10. Compound I-10 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-10.

According to one specific embodiment, the compound I-10 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-10 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

Compound (S)-I-10: (S)-2-[2-chloro-4-(4-chlorophenoxyl)phenyl]-3,3-dimethyl-1-(1,2,4-triazol-1-yl)butan-2-ol; compound (R)-I-10: (R)-2-[2-chloro-4-(4-chlorophenoxyl)phenyl]-3,3-dimethyl-1-(1,2,4-triazol-1-yl)butan-2-ol.

According to still a further embodiment of the present invention, component I is compound I-11. Compound I-11 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-11.

According to one specific embodiment, the compound I-11 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-11 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

Compound (S)-I-11: (S)-1-[2-[4-(4-chlorophenoxy)-2-(trifluoromethyl)phenyl]-2-cyclopropyl-2-methoxy-ethyl]-1,2,4-triazole; compound (R)-I-11: (R)-1-[2-[4-(4-chlorophenoxy)-2-(trifluoromethyl)phenyl]-2-cyclopropyl-2-methoxy-ethyl]-1,2,4-triazole.

According to still a further embodiment of the present invention, component I is compound I-12. Compound I-12 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-12.

According to one specific embodiment, the compound I-12 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-12 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

Compound (S)-I-12: (S)-2-[2-trifluoromethyl-4-(4-chlorophenoxyl)phenyl]-1-methoxy-3-(1,2,4-triazol-1-yl)propan-2-ol; compound (R)-I-12: (R)-2-[2-trifluoromethyl-4-(4-chlorophenoxyl)phenyl]-1-methoxy-3-(1,2,4-triazol-1-yl)propan-2-ol.

According to still a further embodiment of the present invention, component I is compound I-13. Compound I-13 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-13.

According to one specific embodiment, the compound I-13 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-13 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

Compound (S)-I-13: (S)-1-[2-[4-(4-chlorophenoxy)-2-(trifluoromethyl)phenyl]-2-methoxy-butyl]1,2,4-triazole; Compound (R)-I-13: (R)-1-[2-[4-(4-chlorophenoxy)-2-(trifluoromethyl)phenyl]-2-methoxy-butyl]1,2,4-triazole.

According to still a further embodiment of the present invention, component I is compound I-14. Compound I-14 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-14.

According to one specific embodiment, the compound I-14 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-14 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

Compound (S)-I-14: (S)-2-[4-(4-chlorophenoxy)-2-(trifluoromethyl)phenyl]-1-(1,2,4-triazol-1-yl)pent-3-yn-2-ol; compound (R)-I-14: (R)-2-[4-(4-chlorophenoxy)-2-(trifluoromethyl)phenyl]-1-(1,2,4-triazol-1-yl)pent-3-yn-2-ol.

According to still a further embodiment of the present invention, component I is compound I-15. Compound I-15 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-15.

According to one specific embodiment, the compound I-15 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-15 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

Compound (S)-I-15: (S)-1-[2-[4-(4-chlorophenoxy)-2-(trifluoromethyl)phenyl]-2-methoxy-pent-3-ynyl]-1,2,4-triazole; Compound (R)-I-15: (R)-1-[2-[4-(4-chlorophenoxy)-2-(trifluoromethyl)phenyl]-2-methoxy-pent-3-ynyl]-1,2,4-triazole.

According to still a further embodiment of the present invention, component I is compound I-16. Compound I-16 may be present as racemic composition of the (R)-enantiomer and (S)-enantiomer, but the (R)-enantiomer and the (S)-enantiomer may also be present in any other proportion, for example the pure enantiomer (R) or the pure enantiomer (S) of I-16.

According to one specific embodiment, the compound I-16 is provided and used as (R)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

According to a further specific embodiment, the compound I-16 is provided and used as (S)-enantiomer with an enantiomeric excess (e.e.) of at least 40%, for example, at least 50%, 60%, 70% or 80%, preferably at least 90%, more preferably at least 95%, yet more preferably at least 98% and most preferably at least 99%.

Compound (S)-I-16: (S)-2-[4-(4-chlorophenoxy)-2-(trifluoromethyl)phenyl]-1-(1,2,4-triazol-1-yl)but-3-yn-2-ol; compound (R)-I-16: (R)-2-[4-(4-chlorophenoxy)-2-(trifluoromethyl)phenyl]-1-(1,2,4-triazol-1-yl)but-3-yn-2-ol.

According to one further embodiment of the present invention, component I is selected from compounds I-1, I-2, I-3, I-4, I-5, I-6, I-7, I-8, I-9, I-11, I-13, I-14, I-15 and I-16. According to a more particular embodiment of the present invention, component I is selected from compounds I-1, I-2, I-6 and I-8. According to another more particular embodiment of the present invention, component I is selected from compounds I-3, I-4, I-5, I-7, I-9, I-11, I-13, I-14, I-15 and I-16.

According to still a further embodiment of the present invention, component I is selected from compounds I-1, I-2, I-3, I-4 and I-5, more specifically selected from I-1, I-3, I-4 and I-5.

The active compounds of component II, component III and any further component, selected from the groups A) to O) as detailed herein, their preparation and their action against harmful fungi are known (cf.: http://www.alanwood.net/pesticides/). and mainly commercially available. Commercially available active compounds can be found, for example, in The Pesticide Manual, 14th Edition, British Crop Protection Council (2006) and other publications. Fluxapyroxad (N-(3',4',5'-trifluorobiphenyl-2-yl)-3-difluoromethyl-1-methyl-1H-pyrazole-4-carboxamide) and its preparation and use is described in WO 2006/087343.

In the following, references for the active compounds of component II, component III and any further component, selected from the groups A) to O) as detailed herein, are given: benalaxyl, methyl N-(phenylacetyl)-N-(2,6-xylyl)-DL-alaninate (DE 29 03 612); metalaxyl, methyl N-(methoxyacetyl)-N-(2,6-xylyl)-DL-alaninate (GB 15 00 581); ofurace, (RS)-α-(2-chloro-N-2,6-xylylacetamido)-γ-butyrolactone [CAS RN 58810-48-3]; oxadixyl; N-(2,6-dimethylphenyl)-2-methoxy-N-(2-oxo-3-oxazolidinyl)acetamide (GB 20 58 059); aldimorph, "4-alkyl-2,5(or 2,6)-dimethylmorpholine", comprising 65-75% of 2,6-dimethylmorpholine and 25-35% of 2,5-dimethylmorpholine, comprising more than 85% of 4-dodecyl-2,5(or 2,6)-dimethylmorpholine, where "alkyl" also includes octyl, decyl, tetradecyl and hexadecyl, with a cis/trans ratio of 1:1 [CAS RN 91315-15-0]; dodine, 1-dodecylguanidinium acetate (Plant Dis. Rep., Vol. 41, p. 1029 (1957)); dodemorph, 4-cyclododecyl-2,6-dimethylmorpholine (DE 1198125); fenpropimorph, (RS)-cis-4-[3-(4-tert-butylphenyl)-2-methylpropyl]-2,6-dimethylmorpholine (DE 27 52 096); fenpropidin, (RS)-1-[3-(4-tert-butylphenyl)-2-methylpropyl]piperidine (DE 27 52 096); guazatine, mixture of the reaction products from the amidation of technical grade iminodi(octamethylene)diamine, comprising various guanidines and polyamines [CAS RN 108173-90-6]; iminoctadine, 1,1'-iminodi(octamethylene)diguanidine (Congr. Plant Pathol. 1, p. 27 (1968); spiroxamine, (8-tert-butyl-1,4-dioxaspiro[4.5]dec-2-yl)diethylamine (EP-A 281 842); tridemorph, 2,6-dimethyl-4-tridecylmorpholine (DE 11 64 152); pyrimethanil, 4,6-dimethylpyrimidin-2-ylphenylamine (DD-A 151 404); mepanipyrim, (4-methyl-6-prop-1-ynylpyrimidin-2-yl)phenylamine (EP-A 224 339); cyprodinil, (4-cyclopropyl-6-methylpyrimidin-2-yl)phenylamine (EP-A 310 550); cycloheximid, 4-{(2R)-2-[(1S,3S,5S)-3,5-dimethyl-2-oxocyclohexyl]-2-hydroxyethyl}piperidine-2,6-dione [CAS RN 66-81-9]; griseofulvin, 7-chloro-2',4,6-trimethoxy-6'-methylspiro[benzofuran-2(3H),1'-cyclohex-2'-ene]-3,4'-dione [CAS RN 126-07-8]; kasugamycin, 3-O-[2-amino-4-[(carboxyiminomethyl)amino]-2,3,4,6-tetradeoxy-α-D-arabino-hexopyranosylyD-chiro-inositol [CAS RN 6980-18-3]; natamycin, (8E,14E,16E,18E,20E)-(1R,3S,5R,7R,12R,22R,24S,25R,26S)-22-(3-amino-3,6-dideoxy-β-D-mannopyranosyloxy)-

1,3,26-trihydroxy-12-methyl-10-oxo-6,11,28-trioxatricyclo[22.3.1.05,7]octacosa-8,14,16,18,20-pentaene-25-carboxylic acid [CAS RN 7681-93-8]; polyoxin, 5-(2-amino-5-O-carbamoyl-2-deoxy-L-xylonamido)-1-(5-carboxy-1,2,3,4-tetrahydro-2,4-dioxopyrimidin-1-yl)-1,5-dideoxy-β-D-allofuranuronic acid [CAS RN 22976-86-9]; streptomycin, 1,1'-{1-L-(1,3,5/2,4,6)-4-[5-deoxy-2-O-(2-deoxy-2-methylamino-α-L-glucopyranosyl)-3-C-formyl-α-L-lyxofuranosyloxy]-2,5,6-trihydroxycyclohex-1,3-ylene}diguanidine (J. Am. Chem. Soc. 69, p. 1234 (1947)); bitertanol, β-([1,1'-biphenyl]-4-yloxy)-α-(1,1-dimethylethyl)-1H-1,2,4-triazole-1-ethanol (DE 23 24 020); bromuconazole, 1-[[4-bromo-2-(2,4-dichlorophenyl)tetrahydro-2-furanyl]methyl]-1H-1,2,4-triazole (Proc. Br. Crop. Prot. Conf. 1990—Pests Dis. Vol. 1, p. 459); cyproconazole, 2-(4-chlorophenyl)-3-cyclopropyl-1-[1,2,4]triazol-1-ylbutan-2-ol (U.S. Pat. No. 4,664,696); difenoconazole, 1-{2-[2-chloro-4-(4-chlorophenoxyl)phenyl]-4-methyl-[1,3]dioxolan-2-ylmethyl}-1H-[1,2,4]triazole (GB-A 2 098 607); diniconazole, (βE)-β-[(2,4-dichlorophenyl)methylene]-α-(1,1-dimethylethyl)-1H-1,2,4-triazole-1-ethanol (Noyaku Kagaku, 1983, Vol. 8, p. 575); enilconazole (imazalil), 1-[2-(2,4-dichlorphenyl)-2-(2-propenyloxy)ethyl]-1H-imidazole (Fruits 28, p. 545, 1973); epoxiconazole, (2RS,3SR)-1-[3-(2-chlorophenyl)-2,3-el)oxy-2-(4-fluorophenyl)propyl]-1H-1,2,4-triazole (EP-A 196 038); fenbuconazole, α-[2-(4-chloro-phenyl)ethyl]-α-phenyl-1H-1,2,4-triazole-1-propanenitrile (Proc. Br. Crop Prot. Conf. 1988—Pests Dis. Vol. 1, p. 33); fluquinconazole, 3-(2,4-dichlorophenyl)-6-fluoro-2-[1,2,4]-triazol-1-yl-3H-quinazolin-4-one (Proc. Br. Crop Prot. Conf.-Pests Dis., 5-3, 411 (1992)); flusilazole, 1-{[bis-(4-fluorophenyl)methylsilanyl]methyl}-1H-[1,2,4]triazole (Proc. Br. Crop Prot. Conf.-Pests Dis., 1, 413 (1984)); flutriafol, α-(2-fluorophenyl)-α-(4-fluorophenyl)-1H-1,2,4-triazole-1-ethanol (EP 15 756); hexaconazole, 2-(2,4-dichlorophenyl)-1-[1,2,4]triazol-1-ylhexan-2-ol (CAS RN 79983-71-4); ipconazole, 2-[(4-chlorophenyl)methyl]-5-(1-methylethyl)-1-(1H-1,2,4-triazol-1-ylmethyl)cyclopentanol (EP 267 778), metconazole, 5-(4-chlorobenzyl)-2,2-dimethyl-1-(1,2,4]triazol-1-ylmethylcyclopentanol (GB 857 383); myclobutanil, 2-(4-chlorophenyl)-2-[1,2,4]triazol-1-ylmethylpentanenitrile (CAS RN 88671-89-0); penconazole, 1-[2-(2,4-dichlorophenyl)pentyl]-1H-[1,2,4]triazole (Pesticide Manual, 12th Ed. (2000), S. 712); propiconazole, 1-[[2-(2,4-dichlorophenyl)-4-propyl-1,3-dioxolan-2-yl]methyl]-1H-1,2,4-triazole (BE 835 579); prochloraz, N-(propyl-[2-(2,4,6-trichlorophenoxyl)ethyl]) imidazole-1-carboxamide (U.S. Pat. No. 3,991,071); prothioconazole, 2-[2-(1-chlorocyclopropyl)-3-(2-chlorophenyl)-2-hydroxypropyl]-2,4-dihydro-[1,2,4]triazole-3-thione (WO 96/16048); simeconazole, α-(4-fluorophenyl)-α-[(trimethylsilyl)methyl]-1H-1,2,4-triazole-1-ethanol [CAS RN 149508-90-7]; tebuconazole, 1-(4-chlorophenyl)-4,4-dimethyl-3-[1,2,4]triazol-1-ylmethylpentan-3-ol (EP-A 40 345); tetraconazole, 1-[2-(2,4-dichlorophenyl)-3-(1,1,2,2-tetrafluoroethoxyl)propyl]-1H-1,2,4-triazole (EP 234 242); triadimefon, 1-(4-chloro-phenoxy)-3,3-dimethyl-1-(1H-1,2,4-triazol-1-yl)-2-butanone (BE 793 867); triadimenol, β-(4-chlorophenoxy)-α-(1,1-dimethylethyl)-1H-1,2,4-triazole-1-ethanol (DE 23 24 010); triflumizol, (4-chloro-2-trifluoromethylphenyl)-(2-prol)oxy-1-[1,2,4]triazol-1-ylethyliden)-amine (JP-A 79/119 462); triticonazole, (5E)-5-[(4-chlorophenyl)methylene]-2,2-dimethyl-1-(1H-1,2,4-triazol-1-ylmethyl)cyclopentanol (FR 26 41 277); iprodione, N-isopropyl-3-(3,5-dichlorophenyl)-2,4-dioxoimidazolidine-1-carboxamide (GB 13 12 536); myclozolin, (RS)-3-(3,5-dichlorophenyl)-5-methoxymethyl-5-methyl-1,3-oxazolidine-2,4-dione [CAS RN 54864-61-8]; procymidone, N-(3,5-dichlorophenyl)-1,2-dimethylcyclopropane-1,2-dicarboximide (U.S. Pat. No. 3,903,090); vinclozolin, 3-(3,5-dichlorophenyl)-5-methyl-5-vinyloxazolidine-2,4-dione (DE-A 22 07 576); ferbam, iron(3+) dimethyldithiocarbamate (U.S. Pat. No. 1,972,961); nabam, disodium ethylenebis(dithiocarbamate) (U.S. Pat. No. 2,317,765); maneb, manganese ethylenebis(dithiocarbamate) (U.S. Pat. No. 2,504,404); mancozeb, manganese ethylenebis-(dithiocarbamate) polymer complex zinc salt (GB 996 264); metam, methyldithiocarbaminic acid (U.S. Pat. No. 2,791,605); metiram, zinc ammoniate ethylenebis(dithiocarbamate) (U.S. Pat. No. 3,248,400); propineb, zinc propylenebis(dithiocarbamate) polymer (BE 611 960); polycarbamate, bis(dimethylcarbamodithioato-S,S')[μ-[[1,2-ethanediylbis[carbamodithioato-S,S']](2-)]]di[zinc] [CAS RN 64440-88-6]; thiram, bis(dimethylthiocarbamoyl)disulfide (DE 642 532); ziram, dimethyldithiocarbamate [CAS RN 137-30-4]; zineb, zinc ethylenebis(dithiocarbamate) (U.S. Pat. No. 2,457,674); anilazine, 4,6-dichloro-N-(2-chlorophenyl)-1,3,5-triazine-2-amine (U.S. Pat. No. 2,720,480); benomyl, N-butyl-2-acetylaminobenzoimidazole-1-carboxamide (U.S. Pat. No. 3,631,176); boscalid, 2-chloro-N-(4'-chlorobiphenyl-2-yl) nicotinamide (EP-A 545 099); carbendazim, methyl(1H-benzoimidazol-2-yl)carbamate (U.S. Pat. No. 3,657,443); carboxin, 5,6-dihydro-2-methyl-N-phenyl-1,4-oxathiin-3-carboxamide (U.S. Pat. No. 3,249,499); oxycarboxin, 5,6-dihydro-2-methyl-1,4-oxathiin-3-carboxanilide 4,4-dioxide (U.S. Pat. No. 3,399,214); cyazofamid, 4-chloro-2-cyano-N,N-dimethyl-5-(4-methylphenyl)-1H-imidazole-1-sulfonamide (CAS RN 120116-88-3); dazomet, 3,5-dimethyl-1,3,5-thiadiazinane-2-thione (Bull. Soc. Chim. Fr. 15, p. 891 (1897)); dithianon, 5,10-dioxo-5,10-dihydronaphtho[2,3-b][1,4]dithiin-2,3-dicarbonitrile (GB 857 383); famoxadone, (RS)-3-anilino-5-methyl-5-(4-phenoxyphenyl)-1,3-oxazolidine-2,4-dione [CAS RN 131807-57-3]; fenamidone, (S)-1-anilino-4-methyl-2-methylthio-4-phenylimidazolin-5-one [CAS RN 161326-34-7]; fenarimol, α-(2-chlorophenyl)-α-(4-chlorophenyl)-5-pyrimidinemethanol (GB 12 18 623); fuberidazole, 2-(2-furanyl)-1H-benzimidazole (DE 12 09 799); flutolanil, α,α,α-trifluoro-3'-isoprol)oxy-o-toluanilide (JP 1104514); furametpyr, 5-chloro-N-(1,3-dihydro-1,1,3-trimethyl-4-isobenzofuranyl)-1,3-dimethyl-1H-pyrazole-4-carboxamide [CAS RN 123572-88-3]; isoprothiolane, diisopropyl 1,3-dithiolan-2-ylidenemalonate (Proc. Insectic. Fungic. Conf. 8. Vol. 2, p. 715 (1975)); mepronil, 3'-isoprol)oxy-o-toluanilide (U.S. Pat. No. 3,937,840); nuarimol, α-(2-chlorophenyl)-α-(4-fluorophenyl)-5-pyrimidinemethanol (GB 12 18 623); fluopicolide (picobenzamid), 2,6-dichloro-N-(3-chloro-5-trifluoromethylpyridin-2-ylmethyl)benzamide (WO 99/42447); probenazole, 3-allyloxy-1,2-benzothiazole 1,1-dioxide (Agric. Biol. Chem. 37, p. 737 (1973)); proquinazid, 6-iodo-2-prol)oxy-3-propylquinazolin-4(3H)-one (WO 97/48684); pyrifenox, 2',4'-dichloro-2-(3-pyridyl) acetophenone (EZ)-O-methyloxime (EP 49 854); pyroquilon, 1,2,5,6-tetrahydropyrrolo[3,2,1-ij]quinolin-4-one (GB 139 43 373) quinoxyfen, 5,7-dichloro-4-(4-fluorophenoxyl)quinoline (U.S. Pat. No. 5,240,940); silthiofam, N-allyl-4,5-dimethyl-2-(trimethylsilyl)thiophene-3-carboxamide [CAS RN 175217-20-6]; thiabendazole, 2-(1,3-thiazol-4-yl)benzimidazole (U.S. Pat. No. 3,017,415); thifluzamide, 2',6'-dibromo-2-methyl-4'-tri-fluormethoxy-4-trifluormethyl-1,3-thiazole-5-carboxanilide [CAS RN 130000-40-7]; thiophanate-methyl, 1,2-phenylenebis(iminocarbonothioyl) bis(dimethylcarbamate) (DE-A 19 30 540); tiadinil, 3'-chloro-4,4'-dimethyl-1,2,3-thiadiazole-5-carboxanilide [CAS RN 223580-51-6]; tricyclazole, 5-methyl-1,2,4-triazolo[3,4-b][1,3]benzothiazole [CAS RN 41814-78-2]; triforine, N,N'-{piperazine-1,4-diylbis[(trichloromethyl)methylene]}diformamide (DE 19 01 421); Bordeaux mixture, mixture of $CuSO_4 \times 3Cu(OH)_2 \times 3CaSO_4$ [CAS RN 8011-63-0]; copper acetate, $Cu(OCOCH_3)_2$ [CAS RN 8011-63-0]; copper oxychloride, $Cu_2Cl(OH)_3$ [CAS RN 1332-40-7]; basic copper sulfate, $CuSO_4$ [CAS RN 1344-73-6]; binapacryl, (RS)-2-sec-butyl-4,6-dinitrophenyl 3-methylcrotonate [CAS RN 485-31-4]; dinocap, mixture of 2,6-dinitro-4-octylphenylcrotonate and 2,4-dinitro-6-octylphenylcrotonate, where "octyl" is a mixture of 1-methylheptyl, 1-ethylhexyl and 1-propylpentyl (U.S. Pat. No. 2,526,660); dinobuton, (RS)-2-sec-butyl-4,6-dinitrophenyl isopropyl carbonate [CAS RN 973-21-7]; nitrothalisopropyl, diisopropyl 5-nitroisophthalate (Proc. Br. Insectic. Fungic. Conf. 7., Vol. 2, p. 673 (1973)); fenpiclonil, 4-(2,3-dichlorophenyl)-1H-pyrrole-3-carbonitrile (Proc. 1988 Br. Crop Prot. Conf.—Pests Dis., Vol. 1, p. 65); fludioxonil, 4-(2,2-difluorobenzo[1,3]dioxol-4-yl)-1H-pyrrole-3-carbonitrile (The Pesticide Manual, publ. The British Crop Protection Council, 10th ed. (1995), p. 482); acibenzolar-S-methyl, methyl 1,2,3-benzothiadiazol-7-carbothioate [CAS RN 135158-54-2]; flubenthiavalicarb (benthiavalicarb), isopropyl{(S)-1-[(1R)-1-(6-fluorobenzothiazol-2-yl)-ethylcarbamoyl]-2-methylpropyl}carbamate (JP-A 09/323 984); carpropamid, 2,2-dichloro-N-[1-(4-chlorophenyl) ethyl]-1-ethyl-3-methylcyclopropanecarboxamide [CAS RN 104030-54-8]; chlorothalonil, 2,4,5,6-tetrachloroisophthalonitrile (U.S. Pat. No. 3,290,353); cyflufenamid, (Z)—N-[α-(cyclopropylmethoxyimino)-2,3-difluoro-6-(trifluoromethyl)benzyl]-2-phenylacetamide (WO 96/19442); cymoxanil, 1-(2-cyano-2-methoxyiminoacetyl)-3-ethylurea (U.S. Pat. No. 3,957,847); diclomezine, 6-(3,5-dichlorophenyl-p-tolyl)pyridazin-3(2H)-one (U.S. Pat. No. 4,052,395) diclocymet, (RS)-2-cyano-N-[(R)-1-(2,4-dichlorophenyl) ethyl]-3,3-dimethylbutyramide [CAS RN 139920-32-4]; diethofencarb, isopropyl 3,4-diethoxycarbanilate (EP 78 663); edifenphos, O-ethyl S,S-diphenyl phosphorodithioate (DE 14 93 736) ethaboxam, N-(cyano-2-thienylmethyl)-4-ethyl-2-(ethylamino)-5-thiazolecarboxamide (EP-A 639 574); fenhexamid, N-(2,3-dichloro-4-hydroxyphenyl)-1-methylcyclohexanecarboxamide (Proc. Br. Crop Prot. Conf.—Pests Dis., 1998, Vol. 2, p. 327); fentin acetate, triphenyltin (U.S. Pat. No. 3,499,086); fenoxanil, N-(1-cyano-1,2-dimethylpropyl)-2-(2,4-dichlorophenoxy)propanamide (EP 262 393); ferimzone, mepanipyrim, (Z)-2'-methylacetophenone-4,6-dimethylpyrimidin-2-ylhydrazone [CAS RN 89269-64-7]; fluazinam, 3-chloro-N-[3-chloro-2,6-dinitro-4-(trifluoromethyl)phenyl]-5-(trifluoromethyl)-2-pyridinamine (The Pesticide Manual, publ. The British Crop Protection Council, 10th ed. (1995), p. 474); fosetyl, fosetyl-aluminum, ethylphosphonate (FR 22 54 276); iprovalicarb, isopropyl [(1S)-2-methyl-1-(1-p-tolylethylcarbamoyl)propyl]carbamate (EP-A 472 996); hexachlorbenzene (C. R. Seances Acad. Agric. Fr. 31, p. 24, 1945); metrafenon, 3'-bromo-2,3,4,6'-tetramethoxy-2',6-dimethylbenzophenone (U.S. Pat. No. 5,945,567); pencycuron, 1-(4-chlorobenzyl)-1-cyclopentyl-3-phenylurea (DE 27 32 257); penthiopyrad, (RS)—N-[2-(1,3-dimethylbutyl)-3-thienyl]-1-methyl-3-(trifluoromethyl)-1H-pyrazole-4-carboxamide (JP 10130268); propamocarb, propyl 3-(dimethylamino)propylcarbamate (DE 15 67 169); phthalide (DE 16 43 347); toloclofos-methyl, O-2,6-dichloro-p-tolyl O,O-dimethyl phosphorothioate (GB 14 67 561); quintozene, pentachlornitrobenzene (DE 682 048); zoxamide, (RS)-3,5-dichloro-N-(3-chloro-1-ethyl-1-methyl-2-oxopropyl)-p-toluamide [CAS RN 156052-68-5]; azoxystrobin, methyl 2-{2-[6-(2-cyano-1-vinylpenta-1,3-dienyloxy)pyrimidin-4-yloxy]phenyl}-3-methoxyacrylate (EP 382 375), dimoxystrobin, (E)-2-(methoxyimino)-N-methyl-2-[α-(2,5-xylyloxy)-o-tolyl] acetamide (EP 477 631); enestroburin, methyl 2-{2-[3-(4-chlorophenyl)-1-methylallylideneaminooxymethyl] phenyl}-3-methoxyacrylate (EP 936 213); fluoxastrobin, (E)-{2-[6-(2-chlorophenoxy)-5-fluoropyrimidin-4-yloxy] phenyl}(5,6-dihydro-1,4,2-dioxazin-3-yl)methanone O-methyloxime (WO 97/27189); kresoxim-methyl, methyl (E)-methoxyimino[α-(o-tolyloxy)-o-tolyl]acetate (EP 253 213); metominostrobin, (E)-2-(methoxyimino)-N-methyl-2-(2-phenoxyphenyl)acetamide (EP 398 692); orysastrobin, (2E)-2-(methoxyimino)-2-{2-[(3E,5E,6E)-5-(methoxyimino)-4,6-dimethyl-2,8-dioxa-3,7-diazanona-3,6-dien-1-yl]phenyl}-N-methylacetamide (WO 97/15552); picoxystrobin, methyl 3-methoxy-2-[2-(6-trifluoromethylpyridin-2-yloxymethyl)phenyl]acrylate (EP 278 595); pyraclostrobin, methyl N-{2-[1-(4-chlorophenyl)-1H-pyrazol-3-yloxymethyl]phenyl}(N-methoxy)carbamate (WO 96/01256); trifloxystrobin, methyl(E)-methoxyimino-{(E)-α-[1-(α,α,α-trifluoro-m-tolyl)ethylideneaminooxy]-o-tolyl}acetate (EP 460 575); captafol, N-(1,1,2,2-tetrachloroethylthio)cyclohex-4-ene-1,2-dicarboximide (Phytopathology, Vol. 52, p. 754 (1962)); captan, N-(trichloromethylthio)cyclohex-4-ene-1,2-dicarboximide (U.S. Pat. No. 2,553,770); dichlofluanid, N-dichlorofluoromethylthio-N',N'-dimethyl-N-phenylsulfamide (DE 11 93 498); folpet, N-(trichlormethylthio)phthalimide (U.S. Pat. No. 2,553, 770); tolylfluanid, N-dichlorofluoromethyl-thio-N',N'-dimethyl-N-p-tolylsulfamide (DE 11 93 498); dimethomorph, 3-(4-chlorophenyl)-3-(3,4-dimethoxyphenyl)-1-morpholin-4-yl-propenone (EP 120 321); flumetover, 2-(3,4-dimethoxyphenyl)-N-ethyl-α,α,α-trifluoro-N-methyl-p-toluamide [AGROW no. 243, 22 (1995)]; flumorph, 3-(4-fluorophenyl)-3-(3,4-dimethoxyphenyl)-1-morpholin-4-ylpropenone (EP 860 438); 5-Amino-2-isopropyl-3-oxo-4-o-tolyl-2,3-dihydro-pyrazole-1-carbothioic acid S-allyl ester (CN1939128).

The pesticides described by IUPAC nomenclature, their preparation and their fungicidal activity are also known (cf. Can. J. Plant Sci. 48(6), 587-94, 1968; EP-A 141 317; EP-A 152 031; EP-A 226 917; EP-A 243 970; EP-A 256 503; EP-A 428 941; EP-A 532 022; EP-A 1 028 125; EP-A 1 035 122; EP-A 1 201 648; EP-A 1 122 244, JP 2002316902; DE 19650197; DE 10021412; DE 102005009458; U.S. Pat. Nos. 3,296,272; 3,325,503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624, WO 11/028657, WO2012/168188, WO 2007/006670, WO 2011/77514; WO13/047749, WO 10/069882, WO 13/047441, WO 03/16303, WO 09/90181, WO 13/127704, WO 13/024009 and WO 13/024010).

The active compounds of group O) and their pesticidal action and processes for their preparation are known (see also http://www.hclrss.demon.co.uk/index.html). Commercially available active compounds can be found, for example, in The Pesticide Manual, 14th Edition, British Crop Protection Council (2006) and other publications. The compound BB) of group I)

BB)

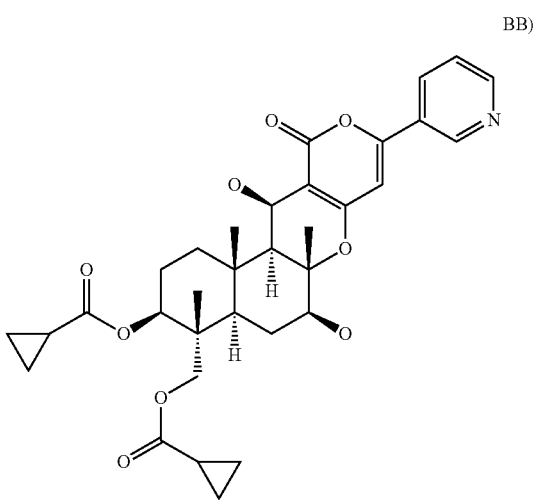

having the IUPAC name [(3S,4R,4aR,6S,6aS,12R,12aS,12bS)-3-(cyclopropanecarbonyloxy)-6,12-dihydroxy-4,6a,12b-trimethyl-11-oxo-9-(pyridin-3-yl)-1,2,3,4,4a,5,6,6a,12a,12b-decahydro-11H,12H-benzo[f]pyrano[4,3-b]chromen-4-yl]methyl cyclopropanecarboxylate and its pesticidal action are disclosed in WO2006/129714 and WO2009/081851.

The further component(s), i.e. component II, III, IV, V etc., according to the present invention, are selected from any one of groups A) to O) as given above, with the proviso that all of the components in one composition are different active ingredients.

In the following, the inventive compositions and their preferred uses are further described. In each case, according to the present invention, the use of the composition for controlling a particular phytopathogenic fungus is also meant to encompass the respective method for controlling the particular phytopathogenic fungi, wherein the fungi or the materials, plants, the soil or seed to be protected from fungal attack are treated with an effective amount of a composition as defined in that particular context.

According to one aspect, the present invention relates to two-component compositions, i.e. compositions comprising component I, i.e. in particular a compound selected from compounds I-1, I-2, I-3, I-4, I-5, I-6, I-7, I-8, I-9, I-10, I-11, I-12, I-13, I-14, I-15 and I-16 or any group of compounds I detailed above, and component II selected from groups A) to O). According to a specific embodiment thereof, only two active compounds as defined are present in these compositions (herein also called "binary compositions"). The composition may, of course, contain any kind of additive or the like as detailed below in order to provide a formulation suitable for use in agriculture.

The weight ratio of component I to component II depends from the properties of the active substances used and is usually in the range of from 1:1000 to 1000:1, more particularly 1:500 to 500:1. The weight ratio of component I to component II generally depends from the properties of the active substances used and is usually in the range of from 1:100 to 100:1, frequently in the range of from 1:50 to 50:1, preferably in the range of from 1:20 to 20:1, particularly preferably in the range of from 1:10 to 10:1, in particular in the range of from 1:3 to 3:1. It may also be preferable for the weight ratio to be in the range of from 1:2 to 2:1.

According to further embodiments of the two-component compositions according to the invention, the weight ratio of component I to component II usually is in the range of from 100:1 to 1:1, regularly in the range of from 50:1 to 1:1, preferably in the range of from 20:1 to 1:1, more preferably in the range of from 10:1 to 1:1, even more preferably in the range of from 4:1 to 1:1 and in particular in the range of from 2:1 to 1:1.

According to still further embodiments of the two-component compositions according to the invention, the weight ratio of component I to component II usually is in the range of from 1:1 to 1:100, regularly in the range of from 1:1 to 1:50, preferably in the range of from 1:1 to 1:20, more preferably in the range of from 1:1 to 1:10, even more preferably in the range of from 1:1 to 1:4 and in particular in the range of from 1:1 to 1:2.

According to one embodiment of the two-component compositions, component I is as defined above and component II is selected from any one of groups A) to K).

One specific embodiment relates to two-component compositions, wherein component I is as defined above, in particular selected from compounds I-1, I-2, I-3, I-4, I-5, I-6, I-7, I-8, I-9, I-11, I-13, I-14, I-15 and I-16 or any group of compounds I detailed above, and component II is selected from group A) of the respiration inhibitors. According to one embodiment thereof, component II is selected from the group of inhibitors of complex III at $Q_o$ site, in e.g. the strobilurins. Specifically, component II is selected from the group consisting of azoxystrobin, dimoxystrobin, fluoxastrobin, kresoxim-methyl, orysastrobin, picoxystrobin, pyraclostrobin, trifloxystrobin, famoxadone and fenamidone. According to a further specific embodiment, these are binary compositions which, as active compounds, comprise in each case only the mentioned two active components.

According to a further embodiment thereof, component II is selected from the group of inhibitors of complex II, e.g. carboxamides. Specifically, component II is selected from the group consisting of benzovindiflupyr, bixafen, boscalid, fluopyram, fluxapyroxad, isopyrazam, penflufen, penthiopyrad and sedaxane. According to a further embodiment, component II is selected from the group of ametotradin, cyazofamid, fluazinam, fentin salts such as fentin acetate. According to a further specific embodiment, these are binary compositions which, as active compounds, comprise in each case only the mentioned two active components.

According to a further embodiment of the two-component compositions, component I is as defined above, in particular selected from compounds I-1, I-2, I-3, I-4, I-5, I-6, I-7, I-8, I-9, I-10, I-11, I-12, I-13, I-14, I-15 and I-16 or any group of compounds I detailed above, and component II is selected from group B) of the sterol biosynthesis inhibitors (SBI fungicides). According to one embodiment thereof, component II is selected from the group of the C14 demethylase inhibitors (DMI fungicides), selected from cyproconazole, difenoconazole, epoxiconazole, fluquinconazole, flusilazole, flutriafol, metconazole, myclobutanil, penconazole, propiconazole, prothioconazole, triadimefon, triadimenol, tebuconazole, tetraconazole, triticonazole, prochloraz, fenarimol and triforine. According to a further embodiment thereof, component II is selected from the group of the delta14-reductase inhibitors, in particular dodemorph, fenpropimorph, tridemorph, fenpropidin and spiroxamine. According to a further embodiment thereof, component II is selected from the group of Inhibitors of 3-keto reductase such as fenhexamid.

According to a further embodiment of the two-component compositions, component I is as defined above, in particular selected from compounds I-1, I-2, I-3, I-4, I-5, I-6, I-7, I-8, I-9, I-10, I-11, I-12, I-13, I-14, I-15 and I-16 or any group of compounds I detailed above, and component II is selected from group C) of the Nucleic acid synthesis inhibitors and particularly selected from metalaxyl, (metalaxyl-M) mefenoxam, ofurace.

According to a further embodiment of the two-component compositions, component I is as defined above, in particular selected from compounds I-1, I-2, I-3, I-4, I-5, I-6, I-7, I-8, I-9, I-10, I-11, I-12, I-13, I-14, I-15 and I-16 or any group of compounds I detailed above, and component II is selected from group D) of the inhibitors of cell division and cytoskeleton, such as benomyl, carbendazim, thiophanate-methyl, ethaboxam, fluopicolide, zoxamide, metrafenone, pyriofenone, in particular ethaboxam, zoxamide and metrafenone.

According to a further embodiment of the two-component compositions, component I is as defined above, in particular selected from compounds I-1, I-2, I-3, I-4, I-5, I-6, I-7, I-8, I-9, I-10, I-11, I-12, I-13, I-14, I-15 and I-16 or any group of compounds I detailed above, and component II is selected from group E) of the inhibitors of amino acid and protein synthesis, in particular selected from cyprodinil, mepanipyrim and pyrimethanil.

According to a further embodiment of the two-component compositions, component I is as defined above, in particular selected from compounds I-1, I-2, I-3, I-4, I-5, I-6, I-7, I-8, I-9, I-10, I-11, I-12, I-13, I-14, I-15 and I-16 or any group of compounds I detailed above, and component II is selected from group F) of the signal transduction inhibitors, in particular selected from iprodione, fludioxonil, vinclozolin and quinoxyfen.

According to a further embodiment of the two-component compositions, component I is as defined above, in particular selected from compounds I-1, I-2, I-3, I-4, I-5, I-6, I-7, I-8, I-9, I-10, I-11, I-12, I-13, I-14, I-15 and I-16 or any group of compounds I detailed above, and component II is selected from group G) of the lipid and membrane synthesis inhibitors, such as dimethomorph, flumorph, iprovalicarb, benthiavalicarb, mandipropamid and propamocarb.

According to a further embodiment of the two-component compositions, component I is as defined above, in particular selected from compounds I-1, I-2, I-3, I-4, I-5, I-6, I-7, I-8, I-9, I-11, I-13, I-14, I-15 and I-16 or any group of compounds I detailed above, and component II is selected from group H) of the inhibitors with Multi Site Action, in particular selected from captan, Bordeaux mixture, copper acetate, copper hydroxide, copper oxychloride, copper sulfate, sulfur, (tri)basic copper sulfate, mancozeb, maneb, metiram, propineb, thiram, captafol, folpet, chlorothalonil, dichlofluanid, dithianon, dodine and 2,6-dimethyl-1H,5H-[1,4]dithiino[2,3-c:5,6-c']dipyrrole-1,3,5,7(2H,6H)-tetraone, more particularly selected from captan, Bordeaux mixture, copper hydroxide, copper oxychloride, copper sulfate, (tri)basic copper sulfate, mancozeb, maneb, metiramfolpet, chlorothalonil, dithianon, dodine and 2,6-dimethyl-1H,5H-[1,4]dithiino[2,3-c:5,6-c']dipyrrole-1,3,5,7(2H,6H)-tetraone.

According to a further embodiment of the two-component compositions, component I is as defined above, in particular selected from compounds I-1, I-2, I-3, I-4, I-5, I-6, I-7, I-8, I-9, I-11, I-13, I-14, I-15 and I-16 or any group of compounds I detailed above, and component II is selected from group I) of the cell wall synthesis inhibitors, in particular selected from carpropamid and fenoxanil.

According to a further embodiment of the two-component compositions, component I is as defined above, in particular selected from compounds I-1, I-2, I-3, I-4, I-5, I-6, I-7, I-8, I-9, I-11, I-13, I-14, I-15 and I-16 or any group of compounds I detailed above, and component II is selected from group J) of the plant defence inducers, in particular selected from acibenzolar-S-methyl, probenazole, tiadinil, fosetyl, fosetyl-aluminium, phosphorous acid and salts thereof such as potassium salt of phosphorous acid, sodium salt of phosphorous acid, calcium salt of phosphorous acid, lithium salt of phosphorous acid and aluminium salt of phosphorous acid.

According to a further embodiment of the two-component compositions, component I is as defined above, in particular selected from compounds I-1, I-2, I-3, I-4, I-5, I-6, I-7, I-8, I-9, I-11, I-13, I-14, I-15 and I-16 or any group of compounds I detailed above, and component II is selected from group K), in particular selected from cymoxanil, proquinazid and N-methyl-2-{1-[(5-methyl-3-trifluoromethyl-1H-pyrazol-1-yl)-acetyl]-piperidin-4-yl}-N-[(1R)-1,2,3,4-tetra-hydronaphthalen-1-yl]-4-thiazolecarboxamide.

According to a further embodiment of the two-component compositions, component I is as defined above, in particular selected from compounds I-1, I-2, I-3, I-4, I-5, I-6, I-7, I-8, I-9, I-11, I-13, I-14, I-15 and I-16 or any group of compounds I detailed above, and component II is selected from any one of group L) (antifungal biocontrol agents and plant bioactivators), in particular selected from *Bacillus subtilis* strain NRRL No. B-21661, *Bacillus pumilus* strain NRRL No. B-30087 and *Ulocladium oudemansii*.

According to a further embodiment of the two-component compositions, component I is as defined above, in particular selected from compounds I-1, I-2, I-3, I-4, I-5, I-6, I-7, I-8, I-9, I-11, I-13, I-14, I-15 and I-16 or any group of compounds I detailed above, and component II is selected from any one of group M) (growth regulators). According to one specific embodiment, the growth regulator is selected from chlormequat (chlormequat chloride), mepiquat (mepiquat chloride), paclobutrazole, prohexadione (prohexadione-calcium), trinexapac-ethyl and uniconazole.

According to a particular embodiment of the inventive two-component compositions comprising two fungicides, the composition comprises i.e in particular a compound selected from compounds I-1, I-2, I-3, I-4, I-5, I-6, I-7, I-8, I-9, I-11, I-13, I-14, I-15 and I-16 (component I), and a component II selected from pyraclostrobin, fluxapyroxad, fenpropimorph, prothioconazole and chlorothalonil in a weight ratio from 1:20 to 20:1, particularly preferably in the range of from 1:10 to 10:1, in particular in the range of from 1:3 to 3:1. It may also be preferable that the weight ratio is in the range of from 1:2 to 2:1. In a particular embodiments, these compositions are "binary composition" that is, in the sense of the present invention, a composition, wherein only the said two active compounds are present. The composition may, of course contain any kind of additive or the like as detailed below in order to provide a formulation suitable for use in agriculture. Said two-component compositions comprising two fungicides as components I and II are in particular suitable as fungicides as detailed below.

According to a specific embodiment thereof, said compositions are used for the control of cereal pathogens. In particular, said compositions are suitable for controlling wheat pathogens. When used in wheat, especially preferred weight ratios of the active ingredients are 20:1 to 1:20, in particular 2:1 to 1:2, wherein it may be especially preferred if component I to II is present 1:1 to 2:1. Said compositions are particularly suitable for controlling the wheat pathogens selected from *Septoria tritici, Stagonospora nodorum, Pyrenophora tritici repentis, Puccinia recondita, Puccinia striiformis* and *Blumeria graminis*. Furthermore, said composition is useful for the control of the pathogens selected from *Fusarium culmorum*, *Fusarium graminearum* and *Pseudocercosporella herpotrichoides*. According to a further specific embodiment, said compositions are used for controlling barley pathogens. When used in barley, especially preferred weight ratios of the active ingredients are 20:1 to 1:20, in particular 2:1 to 1:2, wherein it may be especially preferred if component I to II is present 1:1 to 2:1. Said compositions are particularly suitable for controlling the barley pathogens, selected from *Pyrenophera teres*, *Rhychosporium secalis*, *Puccinia hordei* and *Blumeria graminis*. Furthermore, said compositions are useful for controlling the barley pathogens, selected from *Ramularia collo-cygni* and *Pseudocercosporella herpotrichoides*.

According to a further specific embodiment, said compositions are used for the control of soy pathogens. When used in soy, especially preferred weight ratios of the active ingredients are 20:1 to 1:20, in particular 3:1 to 1:3, wherein it may be especially preferred if component I to II is present 3:1 to 2:1. In particular, said compositions are suitable for controlling soy pathogens selected from *phakopsora pachyrizi*, *P. meibomiae* and *Microsphaera diffusa*. In soy, said compositions may also be effectively used for the control of the so-called FDC (Foliar Disease Complex), e.g. against *Septoria glycines*, *Cercospora kikuchii*, *C. sojina*, *Corynespora cassiicola* and/or *Alternaria* spp.

According to a further specific embodiment, said compositions are used for the control of corn pathogens. When used in corn, especially preferred weight ratios of the active ingredients are 20:1 to 1:20, in particular 2:1 to 1:2, wherein it may be especially preferred if component I to II is present 2:1 to 1:1. In particular, said compositions are suitable for controlling corn pathogens selected from *Cercospora zeae-maydis*, *Puccinia sorghi* and *Helminthosporium maydis*.

According to still a further specific embodiment, said compositions are used for the control of sugar beet pathogens. When used in sugar beet, especially preferred weight ratios of the active ingredients are 20:1 to 1:20, in particular 2:1 to 1:2, wherein it may be especially preferred if component I to II is present 2:1 to 1:1. In particular, said compositions are suitable for controlling corn pathogens selected from *Cercospora beticola*, *Erysiphe betae*, *Ramularia betae* and *Uromyces betae*.

According to still a further specific embodiment, said compositions are used for the control of peanut pathogens, in particular selected from *Mycosphaerella arachidis* (=*Cercospora*) and *Puccinia arachidis*. When used in peanuts, especially preferred weight ratios of the active ingredients are 20:1 to 1:20, in particular 2:1 to 1:2, wherein it may be especially preferred if component I to II is present 2:1 to 1:1.

According to still a further specific embodiment, said compositions are used for the control of oil seed rape and canola pathogens, in particular selected from *Sclerotinia sclerotiorum*, *Leptosphearia maculans* and *Alternaria alternate*. When used in oil seed rape or canola, especially preferred weight ratios of the active ingredients are 20:1 to 1:20, in particular 2:1 to 1:2, wherein it may be especially preferred if component I to II is present 2:1 to 1:1.

According to still a further specific embodiment, said compositions are used for the control of rice pathogens, in particular selected from *Rhizoctonia solani* and *Pyricularia oryzae*. When used in rice, especially preferred weight ratios of the active ingredients are 20:1 to 1:20, in particular 2:1 to 1:2, wherein it may be especially preferred if component I to II is present 2:1 to 1:1.

Said compositions of component I and II is also suitable for the control of pathogens in specialty crops, such as turf, potato, tomato, cucurbits, grapes, apples, ornamentals and bananas. Turf pathogens that may be controlled according to the present invention are selected from *Sclerotinia homeocarpa* and *Rhizoctonia solani*. When used in turf, especially preferred weight ratios of the active ingredients are 20:1 bis 1:20, in particular 2:1 bis 1:2, wherein it may be especially preferred if component I to II is present 1:1 to 1:2. Potato and tomato pathogens that may be controlled according to the present invention are in particular selected from *Alternaria solani*, *A. alternata* and *Rhizoctonia solani*. A cucurbit pathogen that may be controlled according to the present invention is in particular *Sphaerotheca fuliginea*. A grape pathogen that may be controlled according to the present invention is in particular *Uncinula necator* and *Botrytis cinerea*. An apple pathogen that may be controlled according to the present invention is in particular *Podosphaera leucotricha* and *Venturia inaequalis*. Ornamental pathogens that may be controlled according to the present invention are in particular selected from *Sphaerotheca fuliginea*, *Diplocarpon* spp., *Alternaria* spp. and *Sclerotinia* spp. Banana pathogens that may be controlled according to the present invention are in particular selected from *Mycosphaerella fijiensis* and *Mycosphaerella musicola*.

A specific embodiment of the above embodiment relates to the composition, comprising component I and fluxapyroxad as component II in a weight ratio of 20:1 to 1:20, more specifically 5:1 to 1:5, in particular 3:1 to 1:3, more specifically 2:1 to 1:2. Surprisingly, this composition shows synergistical effects and the components are in particular used in synergistically effective amounts.

A further specific embodiment of the above two-component compositions relates to the composition, comprising component I and as component II pyraclostrobin in a weight ratio of 20:1 to 1:20, more specifically 5:1 to 1:5, in particular 3:1 to 1:3, more specifically 2:1 to 1:2. Surprisingly, this composition shows synergistical effects and the components are in particular used in synergistically effective amounts.

A further specific embodiment of the above two-component compositions relates to the composition, comprising component I and as component II fenpropimorph in a weight ratio of 20:1 to 1:20, more specifically 5:1 to 1:5, in particular 3:1 to 1:3, more specifically 2:1 to 1:2. Surprisingly, this composition shows synergistical effects and the components are in particular used in synergistically effective amounts.

A further specific embodiment of the above two-component compositions relates to the composition, comprising component I and as component II chlorothalonil in a weight ratio of 20:1 to 1:20, more specifically 5:1 to 1:5, in particular 3:1 to 1:3, more specifically 2:1 to 1:2. Surprisingly, this composition shows synergistical effects and the components are in particular used in synergistically effective amounts.

According to a further embodiment of the two-component compositions, component I is as defined above, in particular selected from compounds I-1, I-2, I-3, I-4, I-5, I-6, I-7, I-8, I-9, I-11, I-13, I-14, I-15 and I-16 or any group of compounds I detailed above, and component II is selected from any one of group N) (herbicides).

According to a further embodiment of the two-component compositions, component I is as defined above, in particular selected from compounds I-1, I-2, I-3, I-4, I-5, I-6, I-7, I-8, I-9, I-11, I-13, I-14, I-15 and I-16 or any group of compounds I detailed above, and component II is selected from any one of group O) (insecticides). According to one specific embodiment, the insecticide is selected from the group of the organo(thio)phosphates, in particular selected from the group consisting of acephate, chlorpyrifos, diazinon, dichlorvos, dimethoate, fenitrothion, methamidophos, methidathion, methyl-parathion, monocrotophos, phorate, profenofos and terbufos. According to a further specific embodiment, the insecticide is selected from the group of the carbamates, in particular selected from the group consisting of aldicarb, carbaryl, carbofuran, carbosulfan, methomyl and thiodicarb. According to a further specific embodiment, the insecticide is selected from the group of the pyrethroids, in particular selected from the group consisting of: bifenthrin, cyfluthrin, cypermethrin, alpha-cypermethrin, zeta-cypermethrin, deltamethrin, esfenvalerate, lambda-cyhalothrin and tefluthrin. According to still a further specific embodiment, the insecticide is selected from the group of insect growth regulators, in particular selected from the group consisting of lufenuron and spirotetramat. According to still a further specific embodiment, the insecticide is selected from the group of the nicotine receptor agonists/antagonists, in particular selected from the group consisting of: clothianidin, imidacloprid, thiamethoxam and thiacloprid. According to a further specific embodiment, the insecticide is selected from the group of the GABA antagonists, in particular selected from the group consisting of: endosulfan and fipronil. According to a further specific embodiment, the insecticide is selected from the group of the macrocyclic lactones, in particular selected from the group consisting of: abamectin, emamectin, spinosad and spinetoram. According to a further specific embodiment, the insecticide is hydramethylnon. According to a further specific embodiment, the insecticide is fenbutatin oxide. According to a further specific embodiment, the insecticide is selected from the group consisting of chlorfenapyr, indoxacarb, metaflumizone, flonicamid, flubendiamide, cyazypyr (HGW86) and cyflumetofen.

According to a preferred embodiment of the invention, component II is selected from the following fungicide compounds:

| | | |
|---|---|---|
| II-1 | ametoctradin | |
| II-2 | amisulbrom | |
| II-3 | azoxystrobin | |
| II-4 | benthiavalicarb | |
| II-5 | benzovindiflupyr | |
| II-6 | bixafen | |
| II-7 | boscalid | |
| II-8 | carbendazim | |
| II-9 | captan | |
| II-10 | carboxin | |
| II-11 | chlorothalonil | |
| II-12 | cyazofamid | |
| II-13 | cyflufenamid | |
| II-14 | cymoxanil | |
| II-15 | cyproconazole | |
| II-16 | cyprodinil | |
| II-17 | copper | |
| II-18 | copper hydroxide | |
| II-19 | dodemorph | |
| II-20 | dodine | |
| II-21 | difenoconazole | |
| II-22 | dimethomorph | |
| II-23 | dimoxystrobin | |
| II-24 | diniconazole | |
| II-25 | dithianon | |
| II-26 | epoxiconazole | |
| II-27 | ethaboxam | |
| II-28 | famoxadone | |
| II-29 | fenamidone | |
| II-30 | fenhexamid | |
| II-31 | fenpropidin | |
| II-32 | fenpropimorph | |
| II-33 | fluazinam | |

Consequently, particularly preferred two-component compositions are compiled in Table B, wherein each row corresponds to one embodiment of the compositions according to the invention, i.e. one specific individualized composition. According to one specific aspect, these are binary compositions which each only contain these two components as active compounds. Furthermore, also every combination of the compositions individualized in this table represent embodiments of the present invention.

TABLE B

Two-component compositions comprising one component I and one component II, in particular binary compositions containing the respective component I and II as only active ingredients.

| composition | I | II |
|---|---|---|
| B-1 | I-1 | II-1 |
| B-2 | I-2 | II-1 |
| B-3 | I-3 | II-1 |
| B-4 | I-4 | II-1 |
| B-5 | I-5 | II-1 |
| B-6 | I-6 | II-1 |
| B-7 | I-7 | II-1 |
| B-8 | I-8 | II-1 |
| B-9 | I-1 | II-2 |
| B-10 | I-2 | II-2 |
| B-11 | I-3 | II-2 |
| B-12 | I-4 | II-2 |
| B-13 | I-5 | II-2 |
| B-14 | I-6 | II-2 |
| B-15 | I-7 | II-2 |
| B-16 | I-8 | II-2 |
| B-17 | I-1 | II-3 |
| B-18 | I-2 | II-3 |
| B-19 | I-3 | II-3 |
| B-20 | I-4 | II-3 |
| B-21 | I-5 | II-3 |
| B-22 | I-6 | II-3 |
| B-23 | I-7 | II-3 |
| B-24 | I-8 | II-3 |
| B-25 | I-1 | II-4 |
| B-26 | I-2 | II-4 |
| B-27 | I-3 | II-4 |
| B-28 | I-4 | II-4 |
| B-29 | I-5 | II-4 |
| B-30 | I-6 | II-4 |
| B-31 | I-7 | II-4 |
| B-32 | I-8 | II-4 |
| B-33 | I-1 | II-5 |
| B-34 | I-2 | II-5 |
| B-35 | I-3 | II-5 |
| B-36 | I-4 | II-5 |
| B-37 | I-5 | II-5 |
| B-38 | I-6 | II-5 |
| B-39 | I-7 | II-5 |
| B-40 | I-8 | II-5 |
| B-41 | I-1 | II-6 |
| B-42 | I-2 | II-6 |
| B-43 | I-3 | II-6 |
| B-44 | I-4 | II-6 |
| B-45 | I-5 | II-6 |
| B-46 | I-6 | II-6 |
| B-47 | I-7 | II-6 |
| B-48 | I-8 | II-6 |
| B-49 | I-1 | II-7 |
| B-50 | I-2 | II-7 |
| B-51 | I-3 | II-7 |
| B-52 | I-4 | II-7 |
| B-53 | I-5 | II-7 |
| B-54 | I-6 | II-7 |
| B-55 | I-7 | II-7 |
| B-56 | I-8 | II-7 |
| B-57 | I-1 | II-8 |
| B-58 | I-2 | II-8 |
| B-59 | I-3 | II-8 |
| B-60 | I-4 | II-8 |
| B-61 | I-5 | II-8 |
| B-62 | I-6 | II-8 |
| B-63 | I-7 | II-8 |
| B-64 | I-8 | II-8 |

TABLE B-continued

| | | |
|---|---|---|
| B-65 | I-1 | II-9 |
| B-66 | I-2 | II-9 |
| B-67 | I-3 | II-9 |
| B-68 | I-4 | II-9 |
| B-69 | I-5 | II-9 |
| B-70 | I-6 | II-9 |
| B-71 | I-7 | II-9 |
| B-72 | I-8 | II-9 |
| B-73 | I-1 | II-10 |
| B-74 | I-2 | II-10 |
| B-75 | I-3 | II-10 |
| B-76 | I-4 | II-10 |
| B-77 | I-5 | II-10 |
| B-78 | I-6 | II-10 |
| B-79 | I-7 | II-10 |
| B-80 | I-8 | II-10 |
| B-81 | I-1 | II-11 |
| B-82 | I-2 | II-11 |
| B-83 | I-3 | II-11 |
| B-84 | I-4 | II-11 |
| B-85 | I-5 | II-11 |
| B-86 | I-6 | II-11 |
| B-87 | I-7 | II-11 |
| B-88 | I-8 | II-11 |
| B-89 | I-1 | II-12 |
| B-90 | I-2 | II-12 |
| B-91 | I-3 | II-12 |
| B-92 | I-4 | II-12 |
| B-93 | I-5 | II-12 |
| B-94 | I-6 | II-12 |
| B-95 | I-7 | II-12 |
| B-96 | I-8 | II-12 |
| B-97 | I-1 | II-13 |
| B-98 | I-2 | II-13 |
| B-99 | I-3 | II-13 |
| B-100 | I-4 | II-13 |
| B-101 | I-5 | II-13 |
| B-102 | I-6 | II-13 |
| B-103 | I-7 | II-13 |
| B-104 | I-8 | II-13 |
| B-105 | I-1 | II-14 |
| B-106 | I-2 | II-14 |
| B-107 | I-3 | II-14 |
| B-108 | I-4 | II-14 |
| B-109 | I-5 | II-14 |
| B-110 | I-6 | II-14 |
| B-111 | I-7 | II-14 |
| B-112 | I-8 | II-14 |
| B-113 | I-1 | II-15 |
| B-114 | I-2 | II-15 |
| B-115 | I-3 | II-15 |
| B-116 | I-4 | II-15 |
| B-117 | I-5 | II-15 |
| B-118 | I-6 | II-15 |
| B-119 | I-7 | II-15 |
| B-120 | I-8 | II-15 |
| B-121 | I-1 | II-16 |
| B-122 | I-2 | II-16 |
| B-123 | I-3 | II-16 |
| B-124 | I-4 | II-16 |
| B-125 | I-5 | II-16 |
| B-126 | I-6 | II-16 |
| B-127 | I-7 | II-16 |
| B-128 | I-8 | II-16 |
| B-129 | I-1 | II-17 |
| B-130 | I-2 | II-17 |
| B-131 | I-3 | II-17 |
| B-132 | I-4 | II-17 |
| B-133 | I-5 | II-17 |
| B-134 | I-6 | II-17 |
| B-135 | I-7 | II-17 |
| B-136 | I-8 | II-17 |
| B-137 | I-1 | II-18 |
| B-138 | I-2 | II-18 |
| B-139 | I-3 | II-18 |
| B-140 | I-4 | II-18 |
| B-141 | I-5 | II-18 |
| B-142 | I-6 | II-18 |
| B-143 | I-7 | II-18 |
| B-144 | I-8 | II-18 |
| B-145 | I-1 | II-19 |
| B-146 | I-2 | II-19 |
| B-147 | I-3 | II-19 |
| B-148 | I-4 | II-19 |
| B-149 | I-5 | II-19 |
| B-150 | I-6 | II-19 |
| B-151 | I-7 | II-19 |
| B-152 | I-8 | II-19 |
| B-153 | I-1 | II-20 |
| B-154 | I-2 | II-20 |
| B-155 | I-3 | II-20 |
| B-156 | I-4 | II-20 |
| B-157 | I-5 | II-20 |
| B-158 | I-6 | II-20 |
| B-159 | I-7 | II-20 |
| B-160 | I-8 | II-20 |
| B-161 | I-1 | II-21 |
| B-162 | I-2 | II-21 |
| B-163 | I-3 | II-21 |
| B-164 | I-4 | II-21 |
| B-165 | I-5 | II-21 |
| B-166 | I-6 | II-21 |
| B-167 | I-7 | II-21 |
| B-168 | I-8 | II-21 |
| B-169 | I-1 | II-22 |
| B-170 | I-2 | II-22 |
| B-171 | I-3 | II-22 |
| B-172 | I-4 | II-22 |
| B-173 | I-5 | II-22 |
| B-174 | I-6 | II-22 |
| B-175 | I-7 | II-22 |
| B-176 | I-8 | II-22 |
| B-177 | I-1 | II-23 |
| B-178 | I-2 | II-23 |
| B-179 | I-3 | II-23 |
| B-180 | I-4 | II-23 |
| B-181 | I-5 | II-23 |
| B-182 | I-6 | II-23 |
| B-183 | I-7 | II-23 |
| B-184 | I-8 | II-23 |
| B-185 | I-1 | II-24 |
| B-186 | I-2 | II-24 |
| B-187 | I-3 | II-24 |
| B-188 | I-4 | II-24 |
| B-189 | I-5 | II-24 |
| B-190 | I-6 | II-24 |
| B-191 | I-7 | II-24 |
| B-192 | I-8 | II-24 |
| B-193 | I-1 | II-25 |
| B-194 | I-2 | II-25 |
| B-195 | I-3 | II-25 |
| B-196 | I-4 | II-25 |
| B-197 | I-5 | II-25 |
| B-198 | I-6 | II-25 |
| B-199 | I-7 | II-25 |
| B-200 | I-8 | II-25 |
| B-201 | I-1 | II-26 |
| B-202 | I-2 | II-26 |
| B-203 | I-3 | II-26 |
| B-204 | I-4 | II-26 |
| B-205 | I-5 | II-26 |
| B-206 | I-6 | II-26 |
| B-207 | I-7 | II-26 |
| B-208 | I-8 | II-26 |
| B-209 | I-1 | II-27 |
| B-210 | I-2 | II-27 |
| B-211 | I-3 | II-27 |
| B-212 | I-4 | II-27 |
| B-213 | I-5 | II-27 |
| B-214 | I-6 | II-27 |
| B-215 | I-7 | II-27 |
| B-216 | I-8 | II-27 |
| B-217 | I-1 | II-28 |
| B-218 | I-2 | II-28 |
| B-219 | I-3 | II-28 |
| B-220 | I-4 | II-28 |
| B-221 | I-5 | II-28 |
| B-222 | I-6 | II-28 |
| B-223 | I-7 | II-28 |
| B-224 | I-8 | II-28 |

TABLE B-continued

| composition | I | II |
|---|---|---|
| B-225 | I-1 | II-29 |
| B-226 | I-2 | II-29 |
| B-227 | I-3 | II-29 |
| B-228 | I-4 | II-29 |
| B-229 | I-5 | II-29 |
| B-230 | I-6 | II-29 |
| B-231 | I-7 | II-29 |
| B-232 | I-8 | II-29 |
| B-233 | I-1 | II-30 |
| B-234 | I-2 | II-30 |
| B-235 | I-3 | II-30 |
| B-236 | I-4 | II-30 |
| B-237 | I-5 | II-30 |
| B-238 | I-6 | II-30 |
| B-239 | I-7 | II-30 |
| B-240 | I-8 | II-30 |
| B-241 | I-1 | II-31 |
| B-242 | I-2 | II-31 |
| B-243 | I-3 | II-31 |
| B-244 | I-4 | II-31 |
| B-245 | I-5 | II-31 |
| B-246 | I-6 | II-31 |
| B-247 | I-7 | II-31 |
| B-248 | I-8 | II-31 |
| B-249 | I-1 | II-32 |
| B-250 | I-2 | II-32 |
| B-251 | I-3 | II-32 |
| B-252 | I-4 | II-32 |
| B-253 | I-5 | II-32 |
| B-254 | I-6 | II-32 |
| B-255 | I-7 | II-32 |
| B-256 | I-8 | II-32 |
| B-257 | I-1 | II-33 |
| B-258 | I-2 | II-33 |
| B-259 | I-3 | II-33 |
| B-260 | I-4 | II-33 |
| B-261 | I-5 | II-33 |
| B-262 | I-6 | II-33 |
| B-263 | I-7 | II-33 |
| B-264 | I-8 | II-33 |

Continued Table B: Two-component compositions comprising other compounds I as component I and one component II, in particular binary compositions containing the respective component I and II as only active ingredients.

| composition | I | II |
|---|---|---|
| B-265 | I-9 | II-1 |
| B-266 | I-10 | II-1 |
| B-267 | I-11 | II-1 |
| B-268 | I-12 | II-1 |
| B-269 | I-13 | II-1 |
| B-270 | I-14 | II-1 |
| B-271 | I-15 | II-1 |
| B-272 | I-16 | II-1 |
| B-273 | I-9 | II-2 |
| B-274 | I-10 | II-2 |
| B-275 | I-11 | II-2 |
| B-276 | I-12 | II-2 |
| B-277 | I-13 | II-2 |
| B-278 | I-14 | II-2 |
| B-279 | I-15 | II-2 |
| B-280 | I-16 | II-2 |
| B-281 | I-9 | II-3 |
| B-282 | I-10 | II-3 |
| B-283 | I-11 | II-3 |
| B-284 | I-12 | II-3 |
| B-285 | I-13 | II-3 |
| B-286 | I-14 | II-3 |
| B-287 | I-15 | II-3 |
| B-288 | I-16 | II-3 |
| B-289 | I-9 | II-4 |
| B-290 | I-10 | II-4 |
| B-291 | I-11 | II-4 |
| B-292 | I-12 | II-4 |
| B-293 | I-13 | II-4 |
| B-294 | I-14 | II-4 |
| B-295 | I-15 | II-4 |
| B-296 | I-16 | II-4 |
| B-297 | I-9 | II-5 |
| B-298 | I-10 | II-5 |
| B-299 | I-11 | II-5 |
| B-300 | I-12 | II-5 |
| B-301 | I-13 | II-5 |
| B-302 | I-14 | II-5 |
| B-303 | I-15 | II-5 |
| B-304 | I-16 | II-5 |
| B-305 | I-9 | II-6 |
| B-306 | I-10 | II-6 |
| B-307 | I-11 | II-6 |
| B-308 | I-12 | II-6 |
| B-309 | I-13 | II-6 |
| B-310 | I-14 | II-6 |
| B-311 | I-15 | II-6 |
| B-312 | I-16 | II-6 |
| B-313 | I-9 | II-7 |
| B-314 | I-10 | II-7 |
| B-315 | I-11 | II-7 |
| B-316 | I-12 | II-7 |
| B-317 | I-13 | II-7 |
| B-318 | I-14 | II-7 |
| B-319 | I-15 | II-7 |
| B-320 | I-16 | II-7 |
| B-321 | I-9 | II-8 |
| B-322 | I-10 | II-8 |
| B-323 | I-11 | II-8 |
| B-324 | I-12 | II-8 |
| B-325 | I-13 | II-8 |
| B-326 | I-14 | II-8 |
| B-327 | I-15 | II-8 |
| B-328 | I-16 | II-8 |
| B-329 | I-9 | II-9 |
| B-330 | I-10 | II-9 |
| B-331 | I-11 | II-9 |
| B-332 | I-12 | II-9 |
| B-333 | I-13 | II-9 |
| B-334 | I-14 | II-9 |
| B-335 | I-15 | II-9 |
| B-336 | I-16 | II-9 |
| B-337 | I-9 | II-10 |
| B-338 | I-10 | II-10 |
| B-339 | I-11 | II-10 |
| B-340 | I-12 | II-10 |
| B-341 | I-13 | II-10 |
| B-342 | I-14 | II-10 |
| B-343 | I-15 | II-10 |
| B-344 | I-16 | II-10 |
| B-345 | I-9 | II-11 |
| B-346 | I-10 | II-11 |
| B-347 | I-11 | II-11 |
| B-348 | I-12 | II-11 |
| B-349 | I-13 | II-11 |
| B-350 | I-14 | II-11 |
| B-351 | I-15 | II-11 |
| B-352 | I-16 | II-11 |
| B-353 | I-9 | II-12 |
| B-354 | I-10 | II-12 |
| B-355 | I-11 | II-12 |
| B-356 | I-12 | II-12 |
| B-357 | I-13 | II-12 |
| B-358 | I-14 | II-12 |
| B-359 | I-15 | II-12 |
| B-360 | I-16 | II-12 |
| B-361 | I-9 | II-13 |
| B-362 | I-10 | II-13 |
| B-363 | I-11 | II-13 |
| B-364 | I-12 | II-13 |
| B-365 | I-13 | II-13 |
| B-366 | I-14 | II-13 |
| B-367 | I-15 | II-13 |
| B-368 | I-16 | II-13 |
| B-369 | I-9 | II-14 |
| B-370 | I-10 | II-14 |
| B-371 | I-11 | II-14 |
| B-372 | I-12 | II-14 |
| B-373 | I-13 | II-14 |
| B-374 | I-14 | II-14 |
| B-375 | I-15 | II-14 |
| B-376 | I-16 | II-14 |

TABLE B-continued

| | | |
|---|---|---|
| B-377 | I-9 | II-15 |
| B-378 | I-10 | II-15 |
| B-379 | I-11 | II-15 |
| B-380 | I-12 | II-15 |
| B-381 | I-13 | II-15 |
| B-382 | I-14 | II-15 |
| B-383 | I-15 | II-15 |
| B-384 | I-16 | II-15 |
| B-385 | I-9 | II-16 |
| B-386 | I-10 | II-16 |
| B-387 | I-11 | II-16 |
| B-388 | I-12 | II-16 |
| B-389 | I-13 | II-16 |
| B-390 | I-14 | II-16 |
| B-391 | I-15 | II-16 |
| B-392 | I-16 | II-16 |
| B-393 | I-9 | II-17 |
| B-394 | I-10 | II-17 |
| B-395 | I-11 | II-17 |
| B-396 | I-12 | II-17 |
| B-397 | I-13 | II-17 |
| B-398 | I-14 | II-17 |
| B-399 | I-15 | II-17 |
| B-400 | I-16 | II-17 |
| B-401 | I-9 | II-18 |
| B-402 | I-10 | II-18 |
| B-403 | I-11 | II-18 |
| B-404 | I-12 | II-18 |
| B-405 | I-13 | II-18 |
| B-406 | I-14 | II-18 |
| B-407 | I-15 | II-18 |
| B-408 | I-16 | II-18 |
| B-409 | I-9 | II-19 |
| B-410 | I-10 | II-19 |
| B-411 | I-11 | II-19 |
| B-412 | I-12 | II-19 |
| B-413 | I-13 | II-19 |
| B-414 | I-14 | II-19 |
| B-415 | I-15 | II-19 |
| B-416 | I-16 | II-19 |
| B-417 | I-9 | II-20 |
| B-418 | I-10 | II-20 |
| B-419 | I-11 | II-20 |
| B-420 | I-12 | II-20 |
| B-421 | I-13 | II-20 |
| B-422 | I-14 | II-20 |
| B-423 | I-15 | II-20 |
| B-424 | I-16 | II-20 |
| B-425 | I-9 | II-21 |
| B-426 | I-10 | II-21 |
| B-427 | I-11 | II-21 |
| B-428 | I-12 | II-21 |
| B-429 | I-13 | II-21 |
| B-430 | I-14 | II-21 |
| B-431 | I-15 | II-21 |
| B-432 | I-16 | II-21 |
| B-433 | I-9 | II-22 |
| B-434 | I-10 | II-22 |
| B-435 | I-11 | II-22 |
| B-436 | I-12 | II-22 |
| B-437 | I-13 | II-22 |
| B-438 | I-14 | II-22 |
| B-439 | I-15 | II-22 |
| B-440 | I-16 | II-22 |
| B-441 | I-9 | II-23 |
| B-442 | I-10 | II-23 |
| B-443 | I-11 | II-23 |
| B-444 | I-12 | II-23 |
| B-445 | I-13 | II-23 |
| B-446 | I-14 | II-23 |
| B-447 | I-15 | II-23 |
| B-448 | I-16 | II-23 |
| B-449 | I-9 | II-24 |
| B-450 | I-10 | II-24 |
| B-451 | I-11 | II-24 |
| B-452 | I-12 | II-24 |
| B-453 | I-13 | II-24 |
| B-454 | I-14 | II-24 |
| B-455 | I-15 | II-24 |
| B-456 | I-16 | II-24 |
| B-457 | I-9 | II-25 |
| B-458 | I-10 | II-25 |
| B-459 | I-11 | II-25 |
| B-460 | I-12 | II-25 |
| B-461 | I-13 | II-25 |
| B-462 | I-14 | II-25 |
| B-463 | I-15 | II-25 |
| B-464 | I-16 | II-25 |
| B-465 | I-9 | II-26 |
| B-466 | I-10 | II-26 |
| B-467 | I-11 | II-26 |
| B-468 | I-12 | II-26 |
| B-469 | I-13 | II-26 |
| B-470 | I-14 | II-26 |
| B-471 | I-15 | II-26 |
| B-472 | I-16 | II-26 |
| B-473 | I-9 | II-27 |
| B-474 | I-10 | II-27 |
| B-475 | I-11 | II-27 |
| B-476 | I-12 | II-27 |
| B-477 | I-13 | II-27 |
| B-478 | I-14 | II-27 |
| B-479 | I-15 | II-27 |
| B-480 | I-16 | II-27 |
| B-481 | I-9 | II-28 |
| B-482 | I-10 | II-28 |
| B-483 | I-11 | II-28 |
| B-484 | I-12 | II-28 |
| B-485 | I-13 | II-28 |
| B-486 | I-14 | II-28 |
| B-487 | I-15 | II-28 |
| B-488 | I-16 | II-28 |
| B-489 | I-9 | II-29 |
| B-490 | I-10 | II-29 |
| B-491 | I-11 | II-29 |
| B-492 | I-12 | II-29 |
| B-493 | I-13 | II-29 |
| B-494 | I-14 | II-29 |
| B-495 | I-15 | II-29 |
| B-496 | I-16 | II-29 |
| B-497 | I-9 | II-30 |
| B-498 | I-10 | II-30 |
| B-499 | I-11 | II-30 |
| B-500 | I-12 | II-30 |
| B-501 | I-13 | II-30 |
| B-502 | I-14 | II-30 |
| B-503 | I-15 | II-30 |
| B-504 | I-16 | II-30 |
| B-505 | I-9 | II-31 |
| B-506 | I-10 | II-31 |
| B-507 | I-11 | II-31 |
| B-508 | I-12 | II-31 |
| B-509 | I-13 | II-31 |
| B-510 | I-14 | II-31 |
| B-511 | I-15 | II-31 |
| B-512 | I-16 | II-31 |
| B-513 | I-9 | II-32 |
| B-514 | I-10 | II-32 |
| B-515 | I-11 | II-32 |
| B-516 | I-12 | II-32 |
| B-517 | I-13 | II-32 |
| B-518 | I-14 | II-32 |
| B-519 | I-15 | II-32 |
| B-520 | I-16 | II-32 |
| B-521 | I-9 | II-33 |
| B-522 | I-10 | II-33 |
| B-523 | I-11 | II-33 |
| B-524 | I-12 | II-33 |
| B-525 | I-13 | II-33 |
| B-526 | I-14 | II-33 |
| B-527 | I-15 | II-33 |
| B-528 | I-16 | II-33 |

According to a further preferred embodiment of the invention component II is selected from the following fungicide compounds:

| | | |
|---|---|---|
| II-34 | fludioxonil | |
| II-35 | fluopicolide | |
| II-36 | fluopyram | |
| II-37 | fluoxastrobin | |
| II-38 | fluquinconazole | |
| II-39 | flusilazole | |
| II-40 | flutolanil | |
| II-41 | flutriafol | |
| II-42 | fluxapyroxad | |
| II-43 | folpet | |
| II-44 | fosetyl-Al | |
| II-45 | guazatine | |
| II-46 | hymexazole | |
| II-47 | imazalil | |
| II-48 | ipconazole | |
| II-49 | iprodione | |
| II-50 | isopyrazam | |
| II-51 | iprovalicarb | |
| II-52 | kiralaxyl | |
| II-53 | kresoxim-methyl | |
| II-54 | mancozeb | |
| II-55 | mandipropamid | |
| II-56 | mefenoxam | |
| II-57 | mepanipyrim | |
| II-58 | meptyldinocap | |
| II-59 | metalaxyl | |
| II-60 | metconazole | |
| II-61 | metiram | |
| II-62 | metrafenone | |
| II-63 | myclobutanil | |
| II-64 | orysastrobin | |
| II-65 | proquinazid | |
| II-66 | pyraclostrobin | |

Consequently, further particularly preferred two-component compositions are compiled in Table B1, wherein each row corresponds to one embodiment of the compositions according to the invention, i.e. one specific individualized composition. According to one specific aspect, these are binary compositions which each only contain these two components as the active compounds. Furthermore, also every combination of the compositions individualized in this table represent embodiments of the present invention.

TABLE B1

Two-component compositions comprising one component I and one component II, in particular binary compositions containing the respective component I and II as only active ingredients.

| composition | I | II |
|---|---|---|
| B1-1 | I-1 | II-34 |
| B1-2 | I-2 | II-34 |
| B1-3 | I-3 | II-34 |
| B1-4 | I-4 | II-34 |
| B1-5 | I-5 | II-34 |
| B1-6 | I-6 | II-34 |
| B1-7 | I-7 | II-34 |
| B1-8 | I-8 | II-34 |
| B1-9 | I-1 | II-35 |
| B1-10 | I-2 | II-35 |
| B1-11 | I-3 | II-35 |
| B1-12 | I-4 | II-35 |
| B1-13 | I-5 | II-35 |
| B1-14 | I-6 | II-35 |
| B1-15 | I-7 | II-35 |
| B1-16 | I-8 | II-35 |
| B1-17 | I-1 | II-36 |
| B1-18 | I-2 | II-36 |
| B1-19 | I-3 | II-36 |
| B1-20 | I-4 | II-36 |
| B1-21 | I-5 | II-36 |
| B1-22 | I-6 | II-36 |
| B1-23 | I-7 | II-36 |
| B1-24 | I-8 | II-36 |
| B1-25 | I-1 | II-37 |
| B1-26 | I-2 | II-37 |
| B1-27 | I-3 | II-37 |
| B1-28 | I-4 | II-37 |
| B1-29 | I-5 | II-37 |
| B1-30 | I-6 | II-37 |
| B1-31 | I-7 | II-37 |
| B1-32 | I-8 | II-37 |
| B1-33 | I-1 | II-38 |
| B1-34 | I-2 | II-38 |
| B1-35 | I-3 | II-38 |
| B1-36 | I-4 | II-38 |
| B1-37 | I-5 | II-38 |
| B1-38 | I-6 | II-38 |
| B1-39 | I-7 | II-38 |
| B1-40 | I-8 | II-38 |
| B1-41 | I-1 | II-39 |
| B1-42 | I-2 | II-39 |
| B1-43 | I-3 | II-39 |
| B1-44 | I-4 | II-39 |
| B1-45 | I-5 | II-39 |
| B1-46 | I-6 | II-39 |
| B1-47 | I-7 | II-39 |
| B1-48 | I-8 | II-39 |
| B1-49 | I-1 | II-40 |
| B1-50 | I-2 | II-40 |
| B1-51 | I-3 | II-40 |
| B1-52 | I-4 | II-40 |
| B1-53 | I-5 | II-40 |
| B1-54 | I-6 | II-40 |
| B1-55 | I-7 | II-40 |
| B1-56 | I-8 | II-40 |
| B1-57 | I-1 | II-41 |
| B1-58 | I-2 | II-41 |
| B1-59 | I-3 | II-41 |
| B1-60 | I-4 | II-41 |
| B1-61 | I-5 | II-41 |
| B1-62 | I-6 | II-41 |
| B1-63 | I-7 | II-41 |
| B1-64 | I-8 | II-41 |
| B1-65 | I-1 | II-42 |
| B1-66 | I-2 | II-42 |
| B1-67 | I-3 | II-42 |
| B1-68 | I-4 | II-42 |
| B1-69 | I-5 | II-42 |
| B1-70 | I-6 | II-42 |
| B1-71 | I-7 | II-42 |
| B1-72 | I-8 | II-42 |
| B1-73 | I-1 | II-43 |
| B1-74 | I-2 | II-43 |
| B1-75 | I-3 | II-43 |
| B1-76 | I-4 | II-43 |
| B1-77 | I-5 | II-43 |
| B1-78 | I-6 | II-43 |
| B1-79 | I-7 | II-43 |
| B1-80 | I-8 | II-43 |
| B1-81 | I-1 | II-44 |
| B1-82 | I-2 | II-44 |
| B1-83 | I-3 | II-44 |
| B1-84 | I-4 | II-44 |
| B1-85 | I-5 | II-44 |
| B1-86 | I-6 | II-44 |
| B1-87 | I-7 | II-44 |
| B1-88 | I-8 | II-44 |
| B1-89 | I-1 | II-45 |
| B1-90 | I-2 | II-45 |
| B1-91 | I-3 | II-45 |
| B1-92 | I-4 | II-45 |
| B1-93 | I-5 | II-45 |
| B1-94 | I-6 | II-45 |
| B1-95 | I-7 | II-45 |
| B1-96 | I-8 | II-45 |
| B1-97 | I-1 | II-46 |
| B1-98 | I-2 | II-46 |
| B1-99 | I-3 | II-46 |
| B1-100 | I-4 | II-46 |
| B1-101 | I-5 | II-46 |
| B1-102 | I-6 | II-46 |
| B1-103 | I-7 | II-46 |
| B1-104 | I-8 | II-46 |
| B1-105 | I-1 | II-47 |
| B1-106 | I-2 | II-47 |

TABLE B1-continued

| | | |
|---|---|---|
| B1-107 | I-3 | II-47 |
| B1-108 | I-4 | II-47 |
| B1-109 | I-5 | II-47 |
| B1-110 | I-6 | II-47 |
| B1-111 | I-7 | II-47 |
| B1-112 | I-8 | II-47 |
| B1-113 | I-1 | II-48 |
| B1-114 | I-2 | II-48 |
| B1-115 | I-3 | II-48 |
| B1-116 | I-4 | II-48 |
| B1-117 | I-5 | II-48 |
| B1-118 | I-6 | II-48 |
| B1-119 | I-7 | II-48 |
| B1-120 | I-8 | II-48 |
| B1-121 | I-1 | II-49 |
| B1-122 | I-2 | II-49 |
| B1-123 | I-3 | II-49 |
| B1-124 | I-4 | II-49 |
| B1-125 | I-5 | II-49 |
| B1-126 | I-6 | II-49 |
| B1-127 | I-7 | II-49 |
| B1-128 | I-8 | II-49 |
| B1-129 | I-1 | II-50 |
| B1-130 | I-2 | II-50 |
| B1-131 | I-3 | II-50 |
| B1-132 | I-4 | II-50 |
| B1-133 | I-5 | II-50 |
| B1-134 | I-6 | II-50 |
| B1-135 | I-7 | II-50 |
| B1-136 | I-8 | II-50 |
| B1-137 | I-1 | II-51 |
| B1-138 | I-2 | II-51 |
| B1-139 | I-3 | II-51 |
| B1-140 | I-4 | II-51 |
| B1-141 | I-5 | II-51 |
| B1-142 | I-6 | II-51 |
| B1-143 | I-7 | II-51 |
| B1-144 | I-8 | II-51 |
| B1-145 | I-1 | II-52 |
| B1-146 | I-2 | II-52 |
| B1-147 | I-3 | II-52 |
| B1-148 | I-4 | II-52 |
| B1-149 | I-5 | II-52 |
| B1-150 | I-6 | II-52 |
| B1-151 | I-7 | II-52 |
| B1-152 | I-8 | II-52 |
| B1-153 | I-1 | II-53 |
| B1-154 | I-2 | II-53 |
| B1-155 | I-3 | II-53 |
| B1-156 | I-4 | II-53 |
| B1-157 | I-5 | II-53 |
| B1-158 | I-6 | II-53 |
| B1-159 | I-7 | II-53 |
| B1-160 | I-8 | II-53 |
| B1-161 | I-1 | II-54 |
| B1-162 | I-2 | II-54 |
| B1-163 | I-3 | II-54 |
| B1-164 | I-4 | II-54 |
| B1-165 | I-5 | II-54 |
| B1-166 | I-6 | II-54 |
| B1-167 | I-7 | II-54 |
| B1-168 | I-8 | II-54 |
| B1-169 | I-1 | II-55 |
| B1-170 | I-2 | II-55 |
| B1-171 | I-3 | II-55 |
| B1-172 | I-4 | II-55 |
| B1-173 | I-5 | II-55 |
| B1-174 | I-6 | II-55 |
| B1-175 | I-7 | II-55 |
| B1-176 | I-8 | II-55 |
| B1-177 | I-1 | II-56 |
| B1-178 | I-2 | II-56 |
| B1-179 | I-3 | II-56 |
| B1-180 | I-4 | II-56 |
| B1-181 | I-5 | II-56 |
| B1-182 | I-6 | II-56 |
| B1-183 | I-7 | II-56 |
| B1-184 | I-8 | II-56 |
| B1-185 | I-1 | II-57 |
| B1-186 | I-2 | II-57 |
| B1-187 | I-3 | II-57 |
| B1-188 | I-4 | II-57 |
| B1-189 | I-5 | II-57 |
| B1-190 | I-6 | II-57 |
| B1-191 | I-7 | II-57 |
| B1-192 | I-8 | II-57 |
| B1-193 | I-1 | II-58 |
| B1-194 | I-2 | II-58 |
| B1-195 | I-3 | II-58 |
| B1-196 | I-4 | II-58 |
| B1-197 | I-5 | II-58 |
| B1-198 | I-6 | II-58 |
| B1-199 | I-7 | II-58 |
| B1-200 | I-8 | II-58 |
| B1-201 | I-1 | II-59 |
| B1-202 | I-2 | II-59 |
| B1-203 | I-3 | II-59 |
| B1-204 | I-4 | II-59 |
| B1-205 | I-5 | II-59 |
| B1-206 | I-6 | II-59 |
| B1-207 | I-7 | II-59 |
| B1-208 | I-8 | II-59 |
| B1-209 | I-1 | II-60 |
| B1-210 | I-2 | II-60 |
| B1-211 | I-3 | II-60 |
| B1-212 | I-4 | II-60 |
| B1-213 | I-5 | II-60 |
| B1-214 | I-6 | II-60 |
| B1-215 | I-7 | II-60 |
| B1-216 | I-8 | II-60 |
| B1-217 | I-1 | II-61 |
| B1-218 | I-2 | II-61 |
| B1-219 | I-3 | II-61 |
| B1-220 | I-4 | II-61 |
| B1-221 | I-5 | II-61 |
| B1-222 | I-6 | II-61 |
| B1-223 | I-7 | II-61 |
| B1-224 | I-8 | II-61 |
| B1-225 | I-1 | II-62 |
| B1-226 | I-2 | II-62 |
| B1-227 | I-3 | II-62 |
| B1-228 | I-4 | II-62 |
| B1-229 | I-5 | II-62 |
| B1-230 | I-6 | II-62 |
| B1-231 | I-7 | II-62 |
| B1-232 | I-8 | II-62 |
| B1-233 | I-1 | II-63 |
| B1-234 | I-2 | II-63 |
| B1-235 | I-3 | II-63 |
| B1-236 | I-4 | II-63 |
| B1-237 | I-5 | II-63 |
| B1-238 | I-6 | II-63 |
| B1-239 | I-7 | II-63 |
| B1-240 | I-8 | II-63 |
| B1-241 | I-1 | II-64 |
| B1-242 | I-2 | II-64 |
| B1-243 | I-3 | II-64 |
| B1-244 | I-4 | II-64 |
| B1-245 | I-5 | II-64 |
| B1-246 | I-6 | II-64 |
| B1-247 | I-7 | II-64 |
| B1-248 | I-8 | II-64 |
| B1-249 | I-1 | II-65 |
| B1-250 | I-2 | II-65 |
| B1-251 | I-3 | II-65 |
| B1-252 | I-4 | II-65 |
| B1-253 | I-5 | II-65 |
| B1-254 | I-6 | II-65 |
| B1-255 | I-7 | II-65 |
| B1-256 | I-8 | II-65 |
| B1-257 | I-1 | II-66 |
| B1-258 | I-2 | II-66 |

TABLE B1-continued

| | | |
|---|---|---|
| B1-259 | I-3 | II-66 |
| B1-260 | I-4 | II-66 |
| B1-261 | I-5 | II-66 |
| B1-262 | I-6 | II-66 |
| B1-263 | I-7 | II-66 |
| B1-264 | I-8 | II-66 |

Continued Table B1: Two-component compositions comprising other compounds I as component I and one component II, in particular binary compositions containing the respective component I and II as only active ingredients.

| composition | I | II |
|---|---|---|
| B1-265 | I-9 | II-34 |
| B1-266 | I-10 | II-34 |
| B1-267 | I-11 | II-34 |
| B1-268 | I-12 | II-34 |
| B1-269 | I-13 | II-34 |
| B1-270 | I-14 | II-34 |
| B1-271 | I-15 | II-34 |
| B1-272 | I-16 | II-34 |
| B1-273 | I-9 | II-35 |
| B1-274 | I-10 | II-35 |
| B1-275 | I-11 | II-35 |
| B1-276 | I-12 | II-35 |
| B1-277 | I-13 | II-35 |
| B1-278 | I-14 | II-35 |
| B1-279 | I-15 | II-35 |
| B1-280 | I-16 | II-35 |
| B1-281 | I-9 | II-36 |
| B1-282 | I-10 | II-36 |
| B1-283 | I-11 | II-36 |
| B1-284 | I-12 | II-36 |
| B1-285 | I-13 | II-36 |
| B1-286 | I-14 | II-36 |
| B1-287 | I-15 | II-36 |
| B1-288 | I-16 | II-36 |
| B1-289 | I-9 | II-37 |
| B1-290 | I-10 | II-37 |
| B1-291 | I-11 | II-37 |
| B1-292 | I-12 | II-37 |
| B1-293 | I-13 | II-37 |
| B1-294 | I-14 | II-37 |
| B1-295 | I-15 | II-37 |
| B1-296 | I-16 | II-37 |
| B1-297 | I-9 | II-38 |
| B1-298 | I-10 | II-38 |
| B1-299 | I-11 | II-38 |
| B1-300 | I-12 | II-38 |
| B1-301 | I-13 | II-38 |
| B1-302 | I-14 | II-38 |
| B1-303 | I-15 | II-38 |
| B1-304 | I-16 | II-38 |
| B1-305 | I-9 | II-39 |
| B1-306 | I-10 | II-39 |
| B1-307 | I-11 | II-39 |
| B1-308 | I-12 | II-39 |
| B1-309 | I-13 | II-39 |
| B1-310 | I-14 | II-39 |
| B1-311 | I-15 | II-39 |
| B1-312 | I-16 | II-39 |
| B1-313 | I-9 | II-40 |
| B1-314 | I-10 | II-40 |
| B1-315 | I-11 | II-40 |
| B1-316 | I-12 | II-40 |
| B1-317 | I-13 | II-40 |
| B1-318 | I-14 | II-40 |
| B1-319 | I-15 | II-40 |
| B1-320 | I-16 | II-40 |
| B1-321 | I-9 | II-41 |
| B1-322 | I-10 | II-41 |
| B1-323 | I-11 | II-41 |
| B1-324 | I-12 | II-41 |
| B1-325 | I-13 | II-41 |
| B1-326 | I-14 | II-41 |
| B1-327 | I-15 | II-41 |
| B1-328 | I-16 | II-41 |
| B1-329 | I-9 | II-42 |
| B1-330 | I-10 | II-42 |
| B1-331 | I-11 | II-42 |
| B1-332 | I-12 | II-42 |
| B1-333 | I-13 | II-42 |
| B1-334 | I-14 | II-42 |
| B1-335 | I-15 | II-42 |
| B1-336 | I-16 | II-42 |
| B1-337 | I-9 | II-43 |
| B1-338 | I-10 | II-43 |
| B1-339 | I-11 | II-43 |
| B1-340 | I-12 | II-43 |
| B1-341 | I-13 | II-43 |
| B1-342 | I-14 | II-43 |
| B1-343 | I-15 | II-43 |
| B1-344 | I-16 | II-43 |
| B1-345 | I-9 | II-44 |
| B1-346 | I-10 | II-44 |
| B1-347 | I-11 | II-44 |
| B1-348 | I-12 | II-44 |
| B1-349 | I-13 | II-44 |
| B1-350 | I-14 | II-44 |
| B1-351 | I-15 | II-44 |
| B1-352 | I-16 | II-44 |
| B1-353 | I-9 | II-45 |
| B1-354 | I-10 | II-45 |
| B1-355 | I-11 | II-45 |
| B1-356 | I-12 | II-45 |
| B1-357 | I-13 | II-45 |
| B1-358 | I-14 | II-45 |
| B1-359 | I-15 | II-45 |
| B1-360 | I-16 | II-45 |
| B1-361 | I-9 | II-46 |
| B1-362 | I-10 | II-46 |
| B1-363 | I-11 | II-46 |
| B1-364 | I-12 | II-46 |
| B1-365 | I-13 | II-46 |
| B1-366 | I-14 | II-46 |
| B1-367 | I-15 | II-46 |
| B1-368 | I-16 | II-46 |
| B1-369 | I-9 | II-47 |
| B1-370 | I-10 | II-47 |
| B1-371 | I-11 | II-47 |
| B1-372 | I-12 | II-47 |
| B1-373 | I-13 | II-47 |
| B1-374 | I-14 | II-47 |
| B1-375 | I-15 | II-47 |
| B1-376 | I-16 | II-47 |
| B1-377 | I-9 | II-48 |
| B1-378 | I-10 | II-48 |
| B1-379 | I-11 | II-48 |
| B1-380 | I-12 | II-48 |
| B1-381 | I-13 | II-48 |
| B1-382 | I-14 | II-48 |
| B1-383 | I-15 | II-48 |
| B1-384 | I-16 | II-48 |
| B1-385 | I-9 | II-49 |
| B1-386 | I-10 | II-49 |
| B1-387 | I-11 | II-49 |
| B1-388 | I-12 | II-49 |
| B1-389 | I-13 | II-49 |
| B1-390 | I-14 | II-49 |
| B1-391 | I-15 | II-49 |
| B1-392 | I-16 | II-49 |
| B1-393 | I-9 | II-50 |
| B1-394 | I-10 | II-50 |
| B1-395 | I-11 | II-50 |
| B1-396 | I-12 | II-50 |
| B1-397 | I-13 | II-50 |
| B1-398 | I-14 | II-50 |
| B1-399 | I-15 | II-50 |
| B1-400 | I-16 | II-50 |
| B1-401 | I-9 | II-51 |
| B1-402 | I-10 | II-51 |
| B1-403 | I-11 | II-51 |
| B1-404 | I-12 | II-51 |
| B1-405 | I-13 | II-51 |
| B1-406 | I-14 | II-51 |
| B1-407 | I-15 | II-51 |
| B1-408 | I-16 | II-51 |
| B1-409 | I-9 | II-52 |
| B1-410 | I-10 | II-52 |

TABLE B1-continued

| | | |
|---|---|---|
| B1-411 | I-11 | II-52 |
| B1-412 | I-12 | II-52 |
| B1-413 | I-13 | II-52 |
| B1-414 | I-14 | II-52 |
| B1-415 | I-15 | II-52 |
| B1-416 | I-16 | II-52 |
| B1-417 | I-9 | II-53 |
| B1-418 | I-10 | II-53 |
| B1-419 | I-11 | II-53 |
| B1-420 | I-12 | II-53 |
| B1-421 | I-13 | II-53 |
| B1-422 | I-14 | II-53 |
| B1-423 | I-15 | II-53 |
| B1-424 | I-16 | II-53 |
| B1-425 | I-9 | II-54 |
| B1-426 | I-10 | II-54 |
| B1-427 | I-11 | II-54 |
| B1-428 | I-12 | II-54 |
| B1-429 | I-13 | II-54 |
| B1-430 | I-14 | II-54 |
| B1-431 | I-15 | II-54 |
| B1-432 | I-16 | II-54 |
| B1-433 | I-9 | II-55 |
| B1-434 | I-10 | II-55 |
| B1-435 | I-11 | II-55 |
| B1-436 | I-12 | II-55 |
| B1-437 | I-13 | II-55 |
| B1-438 | I-14 | II-55 |
| B1-439 | I-15 | II-55 |
| B1-440 | I-16 | II-55 |
| B1-441 | I-9 | II-56 |
| B1-442 | I-10 | II-56 |
| B1-443 | I-11 | II-56 |
| B1-444 | I-12 | II-56 |
| B1-445 | I-13 | II-56 |
| B1-446 | I-14 | II-56 |
| B1-447 | I-15 | II-56 |
| B1-448 | I-16 | II-56 |
| B1-449 | I-9 | II-57 |
| B1-450 | I-10 | II-57 |
| B1-451 | I-11 | II-57 |
| B1-452 | I-12 | II-57 |
| B1-453 | I-13 | II-57 |
| B1-454 | I-14 | II-57 |
| B1-455 | I-15 | II-57 |
| B1-456 | I-16 | II-57 |
| B1-457 | I-9 | II-58 |
| B1-458 | I-10 | II-58 |
| B1-459 | I-11 | II-58 |
| B1-460 | I-12 | II-58 |
| B1-461 | I-13 | II-58 |
| B1-462 | I-14 | II-58 |
| B1-463 | I-15 | II-58 |
| B1-464 | I-16 | II-58 |
| B1-465 | I-9 | II-59 |
| B1-466 | I-10 | II-59 |
| B1-467 | I-11 | II-59 |
| B1-468 | I-12 | II-59 |
| B1-469 | I-13 | II-59 |
| B1-470 | I-14 | II-59 |
| B1-471 | I-15 | II-59 |
| B1-472 | I-16 | II-59 |
| B1-473 | I-9 | II-60 |
| B1-474 | I-10 | II-60 |
| B1-475 | I-11 | II-60 |
| B1-476 | I-12 | II-60 |
| B1-477 | I-13 | II-60 |
| B1-478 | I-14 | II-60 |
| B1-479 | I-15 | II-60 |
| B1-480 | I-16 | II-60 |
| B1-481 | I-9 | II-61 |
| B1-482 | I-10 | II-61 |
| B1-483 | I-11 | II-61 |
| B1-484 | I-12 | II-61 |
| B1-485 | I-13 | II-61 |
| B1-486 | I-14 | II-61 |
| B1-487 | I-15 | II-61 |
| B1-488 | I-16 | II-61 |
| B1-489 | I-9 | II-62 |
| B1-490 | I-10 | II-62 |
| B1-491 | I-11 | II-62 |
| B1-492 | I-12 | II-62 |
| B1-493 | I-13 | II-62 |
| B1-494 | I-14 | II-62 |
| B1-495 | I-15 | II-62 |
| B1-496 | I-16 | II-62 |
| B1-497 | I-9 | II-63 |
| B1-498 | I-10 | II-63 |
| B1-499 | I-11 | II-63 |
| B1-500 | I-12 | II-63 |
| B1-501 | I-13 | II-63 |
| B1-502 | I-14 | II-63 |
| B1-503 | I-15 | II-63 |
| B1-504 | I-16 | II-63 |
| B1-505 | I-9 | II-64 |
| B1-506 | I-10 | II-64 |
| B1-507 | I-11 | II-64 |
| B1-508 | I-12 | II-64 |
| B1-509 | I-13 | II-64 |
| B1-510 | I-14 | II-64 |
| B1-511 | I-15 | II-64 |
| B1-512 | I-16 | II-64 |
| B1-513 | I-9 | II-65 |
| B1-514 | I-10 | II-65 |
| B1-515 | I-11 | II-65 |
| B1-516 | I-12 | II-65 |
| B1-517 | I-13 | II-65 |
| B1-518 | I-14 | II-65 |
| B1-519 | I-15 | II-65 |
| B1-520 | I-16 | II-65 |
| B1-521 | I-9 | II-66 |
| B1-522 | I-10 | II-66 |
| B1-523 | I-11 | II-66 |
| B1-524 | I-12 | II-66 |
| B1-525 | I-13 | II-66 |
| B1-526 | I-14 | II-66 |
| B1-527 | I-15 | II-66 |
| B1-528 | I-16 | II-66 |

According to a further preferred embodiment of the invention, component II is selected from the following fungicide compounds:

| | |
|---|---|
| II-67 | penconazole |
| II-68 | penflufen |
| II-69 | phosporous acid |
| II-70 | potassium salt of phosphorous acid |
| II-71 | sodium salt of phosphorous acid |
| II-72 | penthiopyrad |
| II-73 | picoxystrobin |
| II-74 | prochloraz |
| II-75 | propamocarb |
| II-76 | propiconazole |
| II-77 | propineb |
| II-78 | prothioconazole |
| II-79 | pyrimethanil |
| II-80 | pyriofenone |
| II-81 | quinoxyfen |
| II-82 | sedaxane |
| II-83 | silthiofam |
| II-84 | spiroxamine |
| II-85 | sulfur |
| II-86 | tebuconazole |
| II-87 | tetraconazole |
| II-88 | thiabendazole |
| II-89 | thiophanate-methyl |
| II-90 | thiram |
| II-91 | triazoxide |
| II-92 | trifloxystrobin |
| II-93 | triticonazole |
| II-94 | valifenalate |
| II-95 | vinclozolin |
| II-96 | ziram |
| II-97 | zoxamide |

Consequently, further particularly preferred two-component compositions are compiled in Table B2, wherein each row corresponds to one embodiment of the compositions according to the invention, i.e. one specific individualized composition. According to one specific aspect, these are binary compositions which each only contain these two components as the active compounds. Furthermore, also every combination of the compositions individualized in this table represent embodiments of the present invention.

TABLE B2

Two-component compositions comprising one component I and one component II, in particular binary compositions containing the respective component I and II as only active ingredients.

| composition | I | II |
| --- | --- | --- |
| B2-1 | I-1 | II-67 |
| B2-2 | I-2 | II-67 |
| B2-3 | I-3 | II-67 |
| B2-4 | I-4 | II-67 |
| B2-5 | I-5 | II-67 |
| B2-6 | I-6 | II-67 |
| B2-7 | I-7 | II-67 |
| B2-8 | I-8 | II-67 |
| B2-9 | I-1 | II-68 |
| B2-10 | I-2 | II-68 |
| B2-11 | I-3 | II-68 |
| B2-12 | I-4 | II-68 |
| B2-13 | I-5 | II-68 |
| B2-14 | I-6 | II-68 |
| B2-15 | I-7 | II-68 |
| B2-16 | I-8 | II-68 |
| B2-17 | I-1 | II-69 |
| B2-18 | I-2 | II-69 |
| B2-19 | I-3 | II-69 |
| B2-20 | I-4 | II-69 |
| B2-21 | I-5 | II-69 |
| B2-22 | I-6 | II-69 |
| B2-23 | I-7 | II-69 |
| B2-24 | I-8 | II-69 |
| B2-25 | I-1 | II-70 |
| B2-26 | I-2 | II-70 |
| B2-27 | I-3 | II-70 |
| B2-28 | I-4 | II-70 |
| B2-29 | I-5 | II-70 |
| B2-30 | I-6 | II-70 |
| B2-31 | I-7 | II-70 |
| B2-32 | I-8 | II-70 |
| B2-33 | I-1 | II-71 |
| B2-34 | I-2 | II-71 |
| B2-35 | I-3 | II-71 |
| B2-36 | I-4 | II-71 |
| B2-37 | I-5 | II-71 |
| B2-38 | I-6 | II-71 |
| B2-39 | I-7 | II-71 |
| B2-40 | I-8 | II-71 |
| B2-41 | I-1 | II-72 |
| B2-42 | I-2 | II-72 |
| B2-43 | I-3 | II-72 |
| B2-44 | I-4 | II-72 |
| B2-45 | I-5 | II-72 |
| B2-46 | I-6 | II-72 |
| B2-47 | I-7 | II-72 |
| B2-48 | I-8 | II-72 |
| B2-49 | I-1 | II-73 |
| B2-50 | I-2 | II-73 |
| B2-51 | I-3 | II-73 |
| B2-52 | I-4 | II-73 |
| B2-53 | I-5 | II-73 |
| B2-54 | I-6 | II-73 |
| B2-55 | I-7 | II-73 |
| B2-56 | I-8 | II-73 |
| B2-57 | I-1 | II-74 |
| B2-58 | I-2 | II-74 |
| B2-59 | I-3 | II-74 |
| B2-60 | I-4 | II-74 |
| B2-61 | I-5 | II-74 |
| B2-62 | I-6 | II-74 |
| B2-63 | I-7 | II-74 |
| B2-64 | I-8 | II-74 |
| B2-65 | I-1 | II-75 |
| B2-66 | I-2 | II-75 |
| B2-67 | I-3 | II-75 |
| B2-68 | I-4 | II-75 |
| B2-69 | I-5 | II-75 |
| B2-70 | I-6 | II-75 |
| B2-71 | I-7 | II-75 |
| B2-72 | I-8 | II-75 |
| B2-73 | I-1 | II-76 |
| B2-74 | I-2 | II-76 |
| B2-75 | I-3 | II-76 |
| B2-76 | I-4 | II-76 |
| B2-77 | I-5 | II-76 |
| B2-78 | I-6 | II-76 |
| B2-79 | I-7 | II-76 |
| B2-80 | I-8 | II-76 |
| B2-81 | I-1 | II-77 |
| B2-82 | I-2 | II-77 |
| B2-83 | I-3 | II-77 |
| B2-84 | I-4 | II-77 |
| B2-85 | I-5 | II-77 |
| B2-86 | I-6 | II-77 |
| B2-87 | I-7 | II-77 |
| B2-88 | I-8 | II-77 |
| B2-89 | I-1 | II-78 |
| B2-90 | I-2 | II-78 |
| B2-91 | I-3 | II-78 |
| B2-92 | I-4 | II-78 |
| B2-93 | I-5 | II-78 |
| B2-94 | I-6 | II-78 |
| B2-95 | I-7 | II-78 |
| B2-96 | I-8 | II-78 |
| B2-97 | I-1 | II-79 |
| B2-98 | I-2 | II-79 |
| B2-99 | I-3 | II-79 |
| B2-100 | I-4 | II-79 |
| B2-101 | I-5 | II-79 |
| B2-102 | I-6 | II-79 |
| B2-103 | I-7 | II-79 |
| B2-104 | I-8 | II-79 |
| B2-105 | I-1 | II-80 |
| B2-106 | I-2 | II-80 |
| B2-107 | I-3 | II-80 |
| B2-108 | I-4 | II-80 |
| B2-109 | I-5 | II-80 |
| B2-110 | I-6 | II-80 |
| B2-111 | I-7 | II-80 |
| B2-112 | I-8 | II-80 |
| B2-113 | I-1 | II-81 |
| B2-114 | I-2 | II-81 |
| B2-115 | I-3 | II-81 |
| B2-116 | I-4 | II-81 |
| B2-117 | I-5 | II-81 |
| B2-118 | I-6 | II-81 |
| B2-119 | I-7 | II-81 |
| B2-120 | I-8 | II-81 |
| B2-121 | I-1 | II-82 |
| B2-122 | I-2 | II-82 |
| B2-123 | I-3 | II-82 |
| B2-124 | I-4 | II-82 |
| B2-125 | I-5 | II-82 |
| B2-126 | I-6 | II-82 |
| B2-127 | I-7 | II-82 |
| B2-128 | I-8 | II-82 |
| B2-129 | I-1 | II-83 |
| B2-130 | I-2 | II-83 |
| B2-131 | I-3 | II-83 |
| B2-132 | I-4 | II-83 |
| B2-133 | I-5 | II-83 |
| B2-134 | I-6 | II-83 |
| B2-135 | I-7 | II-83 |
| B2-136 | I-8 | II-83 |
| B2-137 | I-1 | II-84 |
| B2-138 | I-2 | II-84 |
| B2-139 | I-3 | II-84 |
| B2-140 | I-4 | II-84 |
| B2-141 | I-5 | II-84 |
| B2-142 | I-6 | II-84 |

TABLE B2-continued

| | | |
|---|---|---|
| B2-143 | I-7 | II-84 |
| B2-144 | I-8 | II-84 |
| B2-145 | I-1 | II-85 |
| B2-146 | I-2 | II-85 |
| B2-147 | I-3 | II-85 |
| B2-148 | I-4 | II-85 |
| B2-149 | I-5 | II-85 |
| B2-150 | I-6 | II-85 |
| B2-151 | I-7 | II-85 |
| B2-152 | I-8 | II-85 |
| B2-153 | I-1 | II-86 |
| B2-154 | I-2 | II-86 |
| B2-155 | I-3 | II-86 |
| B2-156 | I-4 | II-86 |
| B2-157 | I-5 | II-86 |
| B2-158 | I-6 | II-86 |
| B2-159 | I-7 | II-86 |
| B2-160 | I-8 | II-86 |
| B2-161 | I-1 | II-87 |
| B2-162 | I-2 | II-87 |
| B2-163 | I-3 | II-87 |
| B2-164 | I-4 | II-87 |
| B2-165 | I-5 | II-87 |
| B2-166 | I-6 | II-87 |
| B2-167 | I-7 | II-87 |
| B2-168 | I-8 | II-87 |
| B2-169 | I-1 | II-88 |
| B2-170 | I-2 | II-88 |
| B2-171 | I-3 | II-88 |
| B2-172 | I-4 | II-88 |
| B2-173 | I-5 | II-88 |
| B2-174 | I-6 | II-88 |
| B2-175 | I-7 | II-88 |
| B2-176 | I-8 | II-88 |
| B2-177 | I-1 | II-89 |
| B2-178 | I-2 | II-89 |
| B2-179 | I-3 | II-89 |
| B2-180 | I-4 | II-89 |
| B2-181 | I-5 | II-89 |
| B2-182 | I-6 | II-89 |
| B2-183 | I-7 | II-89 |
| B2-184 | I-8 | II-89 |
| B2-185 | I-1 | II-90 |
| B2-186 | I-2 | II-90 |
| B2-187 | I-3 | II-90 |
| B2-188 | I-4 | II-90 |
| B2-189 | I-5 | II-90 |
| B2-190 | I-6 | II-90 |
| B2-191 | I-7 | II-90 |
| B2-192 | I-8 | II-90 |
| B2-193 | I-1 | II-91 |
| B2-194 | I-2 | II-91 |
| B2-195 | I-3 | II-91 |
| B2-196 | I-4 | II-91 |
| B2-197 | I-5 | II-91 |
| B2-198 | I-6 | II-91 |
| B2-199 | I-7 | II-91 |
| B2-200 | I-8 | II-91 |
| B2-201 | I-1 | II-92 |
| B2-202 | I-2 | II-92 |
| B2-203 | I-3 | II-92 |
| B2-204 | I-4 | II-92 |
| B2-205 | I-5 | II-92 |
| B2-206 | I-6 | II-92 |
| B2-207 | I-7 | II-92 |
| B2-208 | I-8 | II-92 |
| B2-209 | I-1 | II-93 |
| B2-210 | I-2 | II-93 |
| B2-211 | I-3 | II-93 |
| B2-212 | I-4 | II-93 |
| B2-213 | I-5 | II-93 |
| B2-214 | I-6 | II-93 |
| B2-215 | I-7 | II-93 |
| B2-216 | I-8 | II-93 |
| B2-217 | I-1 | II-94 |
| B2-218 | I-2 | II-94 |
| B2-219 | I-3 | II-94 |
| B2-220 | I-4 | II-94 |
| B2-221 | I-5 | II-94 |
| B2-222 | I-6 | II-94 |
| B2-223 | I-7 | II-94 |
| B2-224 | I-8 | II-94 |
| B2-225 | I-1 | II-95 |
| B2-226 | I-2 | II-95 |
| B2-227 | I-3 | II-95 |
| B2-228 | I-4 | II-95 |
| B2-229 | I-5 | II-95 |
| B2-230 | I-6 | II-95 |
| B2-231 | I-7 | II-95 |
| B2-232 | I-8 | II-95 |
| B2-233 | I-1 | II-96 |
| B2-234 | I-2 | II-96 |
| B2-235 | I-3 | II-96 |
| B2-236 | I-4 | II-96 |
| B2-237 | I-5 | II-96 |
| B2-238 | I-6 | II-96 |
| B2-239 | I-7 | II-96 |
| B2-240 | I-8 | II-96 |
| B2-241 | I-1 | II-97 |
| B2-242 | I-2 | II-97 |
| B2-243 | I-3 | II-97 |
| B2-244 | I-4 | II-97 |
| B2-245 | I-5 | II-97 |
| B2-246 | I-6 | II-97 |
| B2-247 | I-7 | II-97 |
| B2-248 | I-8 | II-97 |

Continued Table B2: Two-component compositions comprising other compounds I as component I and one component II, in particular binary compositions containing the respective component I and II as only active ingredients.

| composition | I | II |
|---|---|---|
| B2-249 | I-9 | II-67 |
| B2-250 | I-10 | II-67 |
| B2-251 | I-11 | II-67 |
| B2-252 | I-12 | II-67 |
| B2-253 | I-13 | II-67 |
| B2-254 | I-14 | II-67 |
| B2-255 | I-15 | II-67 |
| B2-256 | I-16 | II-67 |
| B2-257 | I-9 | II-68 |
| B2-258 | I-10 | II-68 |
| B2-259 | I-11 | II-68 |
| B2-260 | I-12 | II-68 |
| B2-261 | I-13 | II-68 |
| B2-262 | I-14 | II-68 |
| B2-263 | I-15 | II-68 |
| B2-264 | I-16 | II-68 |
| B2-265 | I-9 | II-69 |
| B2-266 | I-10 | II-69 |
| B2-267 | I-11 | II-69 |
| B2-268 | I-12 | II-69 |
| B2-269 | I-13 | II-69 |
| B2-270 | I-14 | II-69 |
| B2-271 | I-15 | II-69 |
| B2-272 | I-16 | II-69 |
| B2-273 | I-9 | II-70 |
| B2-274 | I-10 | II-70 |
| B2-275 | I-11 | II-70 |
| B2-276 | I-12 | II-70 |
| B2-277 | I-13 | II-70 |
| B2-278 | I-14 | II-70 |
| B2-279 | I-15 | II-70 |
| B2-280 | I-16 | II-70 |
| B2-281 | I-9 | II-71 |
| B2-282 | I-10 | II-71 |
| B2-283 | I-11 | II-71 |
| B2-284 | I-12 | II-71 |
| B2-285 | I-13 | II-71 |
| B2-286 | I-14 | II-71 |
| B2-287 | I-15 | II-71 |
| B2-288 | I-16 | II-71 |
| B2-289 | I-9 | II-72 |
| B2-290 | I-10 | II-72 |
| B2-291 | I-11 | II-72 |
| B2-292 | I-12 | II-72 |
| B2-293 | I-13 | II-72 |
| B2-294 | I-14 | II-72 |

TABLE B2-continued

| | | |
|---|---|---|
| B2-295 | I-15 | II-72 |
| B2-296 | I-16 | II-72 |
| B2-297 | I-9 | II-73 |
| B2-298 | I-10 | II-73 |
| B2-299 | I-11 | II-73 |
| B2-300 | I-12 | II-73 |
| B2-301 | I-13 | II-73 |
| B2-302 | I-14 | II-73 |
| B2-303 | I-15 | II-73 |
| B2-304 | I-16 | II-73 |
| B2-305 | I-9 | II-74 |
| B2-306 | I-10 | II-74 |
| B2-307 | I-11 | II-74 |
| B2-308 | I-12 | II-74 |
| B2-309 | I-13 | II-74 |
| B2-310 | I-14 | II-74 |
| B2-311 | I-15 | II-74 |
| B2-312 | I-16 | II-74 |
| B2-313 | I-9 | II-75 |
| B2-314 | I-10 | II-75 |
| B2-315 | I-11 | II-75 |
| B2-316 | I-12 | II-75 |
| B2-317 | I-13 | II-75 |
| B2-318 | I-14 | II-75 |
| B2-319 | I-15 | II-75 |
| B2-320 | I-16 | II-75 |
| B2-321 | I-9 | II-76 |
| B2-322 | I-10 | II-76 |
| B2-323 | I-11 | II-76 |
| B2-324 | I-12 | II-76 |
| B2-325 | I-13 | II-76 |
| B2-326 | I-14 | II-76 |
| B2-327 | I-15 | II-76 |
| B2-328 | I-16 | II-76 |
| B2-329 | I-9 | II-77 |
| B2-330 | I-10 | II-77 |
| B2-331 | I-11 | II-77 |
| B2-332 | I-12 | II-77 |
| B2-333 | I-13 | II-77 |
| B2-334 | I-14 | II-77 |
| B2-335 | I-15 | II-77 |
| B2-336 | I-16 | II-77 |
| B2-337 | I-9 | II-78 |
| B2-338 | I-10 | II-78 |
| B2-339 | I-11 | II-78 |
| B2-340 | I-12 | II-78 |
| B2-341 | I-13 | II-78 |
| B2-342 | I-14 | II-78 |
| B2-343 | I-15 | II-78 |
| B2-344 | I-16 | II-78 |
| B2-345 | I-9 | II-79 |
| B2-346 | I-10 | II-79 |
| B2-347 | I-11 | II-79 |
| B2-348 | I-12 | II-79 |
| B2-349 | I-13 | II-79 |
| B2-350 | I-14 | II-79 |
| B2-351 | I-15 | II-79 |
| B2-352 | I-16 | II-79 |
| B2-353 | I-9 | II-80 |
| B2-354 | I-10 | II-80 |
| B2-355 | I-11 | II-80 |
| B2-356 | I-12 | II-80 |
| B2-357 | I-13 | II-80 |
| B2-358 | I-14 | II-80 |
| B2-359 | I-15 | II-80 |
| B2-360 | I-16 | II-80 |
| B2-361 | I-9 | II-81 |
| B2-362 | I-10 | II-81 |
| B2-363 | I-11 | II-81 |
| B2-364 | I-12 | II-81 |
| B2-365 | I-13 | II-81 |
| B2-366 | I-14 | II-81 |
| B2-367 | I-15 | II-81 |
| B2-368 | I-16 | II-81 |
| B2-369 | I-9 | II-82 |
| B2-370 | I-10 | II-82 |
| B2-371 | I-11 | II-82 |
| B2-372 | I-12 | II-82 |
| B2-373 | I-13 | II-82 |
| B2-374 | I-14 | II-82 |
| B2-375 | I-15 | II-82 |
| B2-376 | I-16 | II-82 |
| B2-377 | I-9 | II-83 |
| B2-378 | I-10 | II-83 |
| B2-379 | I-11 | II-83 |
| B2-380 | I-12 | II-83 |
| B2-381 | I-13 | II-83 |
| B2-382 | I-14 | II-83 |
| B2-383 | I-15 | II-83 |
| B2-384 | I-16 | II-83 |
| B2-385 | I-9 | II-84 |
| B2-386 | I-10 | II-84 |
| B2-387 | I-11 | II-84 |
| B2-388 | I-12 | II-84 |
| B2-389 | I-13 | II-84 |
| B2-390 | I-14 | II-84 |
| B2-391 | I-15 | II-84 |
| B2-392 | I-16 | II-84 |
| B2-393 | I-9 | II-85 |
| B2-394 | I-10 | II-85 |
| B2-395 | I-11 | II-85 |
| B2-396 | I-12 | II-85 |
| B2-397 | I-13 | II-85 |
| B2-398 | I-14 | II-85 |
| B2-399 | I-15 | II-85 |
| B2-400 | I-16 | II-85 |
| B2-401 | I-9 | II-86 |
| B2-402 | I-10 | II-86 |
| B2-403 | I-11 | II-86 |
| B2-404 | I-12 | II-86 |
| B2-405 | I-13 | II-86 |
| B2-406 | I-14 | II-86 |
| B2-407 | I-15 | II-86 |
| B2-408 | I-16 | II-86 |
| B2-409 | I-9 | II-87 |
| B2-410 | I-10 | II-87 |
| B2-411 | I-11 | II-87 |
| B2-412 | I-12 | II-87 |
| B2-413 | I-13 | II-87 |
| B2-414 | I-14 | II-87 |
| B2-415 | I-15 | II-87 |
| B2-416 | I-16 | II-87 |
| B2-417 | I-9 | II-88 |
| B2-418 | I-10 | II-88 |
| B2-419 | I-11 | II-88 |
| B2-420 | I-12 | II-88 |
| B2-421 | I-13 | II-88 |
| B2-422 | I-14 | II-88 |
| B2-423 | I-15 | II-88 |
| B2-424 | I-16 | II-88 |
| B2-425 | I-9 | II-89 |
| B2-426 | I-10 | II-89 |
| B2-427 | I-11 | II-89 |
| B2-428 | I-12 | II-89 |
| B2-429 | I-13 | II-89 |
| B2-430 | I-14 | II-89 |
| B2-431 | I-15 | II-89 |
| B2-432 | I-16 | II-89 |
| B2-433 | I-9 | II-90 |
| B2-434 | I-10 | II-90 |
| B2-435 | I-11 | II-90 |
| B2-436 | I-12 | II-90 |
| B2-437 | I-13 | II-90 |
| B2-438 | I-14 | II-90 |
| B2-439 | I-15 | II-90 |
| B2-440 | I-16 | II-90 |
| B2-441 | I-9 | II-91 |
| B2-442 | I-10 | II-91 |
| B2-443 | I-11 | II-91 |
| B2-444 | I-12 | II-91 |
| B2-445 | I-13 | II-91 |
| B2-446 | I-14 | II-91 |
| B2-447 | I-15 | II-91 |
| B2-448 | I-16 | II-91 |
| B2-449 | I-9 | II-92 |
| B2-450 | I-10 | II-92 |
| B2-451 | I-11 | II-92 |
| B2-452 | I-12 | II-92 |
| B2-453 | I-13 | II-92 |
| B2-454 | I-14 | II-92 |

TABLE B2-continued

| composition | I | II |
|---|---|---|
| B2-455 | I-15 | II-92 |
| B2-456 | I-16 | II-92 |
| B2-457 | I-9 | II-93 |
| B2-458 | I-10 | II-93 |
| B2-459 | I-11 | II-93 |
| B2-460 | I-12 | II-93 |
| B2-461 | I-13 | II-93 |
| B2-462 | I-14 | II-93 |
| B2-463 | I-15 | II-93 |
| B2-464 | I-16 | II-93 |
| B2-465 | I-9 | II-94 |
| B2-466 | I-10 | II-94 |
| B2-467 | I-11 | II-94 |
| B2-468 | I-12 | II-94 |
| B2-469 | I-13 | II-94 |
| B2-470 | I-14 | II-94 |
| B2-471 | I-15 | II-94 |
| B2-472 | I-16 | II-94 |
| B2-473 | I-9 | II-95 |
| B2-474 | I-10 | II-95 |
| B2-475 | I-11 | II-95 |
| B2-476 | I-12 | II-95 |
| B2-477 | I-13 | II-95 |
| B2-478 | I-14 | II-95 |
| B2-479 | I-15 | II-95 |
| B2-480 | I-16 | II-95 |
| B2-481 | I-9 | II-96 |
| B2-482 | I-10 | II-96 |
| B2-483 | I-11 | II-96 |
| B2-484 | I-12 | II-96 |
| B2-485 | I-13 | II-96 |
| B2-486 | I-14 | II-96 |
| B2-487 | I-15 | II-96 |
| B2-488 | I-16 | II-96 |
| B2-489 | I-9 | II-97 |
| B2-490 | I-10 | II-97 |
| B2-491 | I-11 | II-97 |
| B2-492 | I-12 | II-97 |
| B2-493 | I-13 | II-97 |
| B2-494 | I-14 | II-97 |
| B2-495 | I-15 | II-97 |
| B2-496 | I-16 | II-97 |

According to still a further preferred embodiment of the invention, component II is selected from the following fungicide compounds:

| | |
|---|---|
| II-98 | 2,6-dimethyl-1H,5H-[1,4]dithiino[2,3-c:5,6-c']dipyrrole-1,3,5,7(2H,6H)-tetraone |
| II-99 | maneb |
| II-100 | Bordeaux mixture |
| II-101 | copper oxychloride |
| II-102 | basic copper sulfate |

Consequently, further particularly preferred two-component compositions are compiled in Table B2a, wherein each row corresponds to one embodiment of the compositions according to the invention, i.e. one specific individualized composition. According to one specific aspect, these are binary compositions which each only contain these two components as the active compounds. Furthermore, also every combination of the compositions individualized in this table represent embodiments of the present invention.

TABLE B2a

Two-component compositions comprising one component I and one component II, in particular binary compositions containing the respective component I and II as only active ingredients.

| composition | I | II |
|---|---|---|
| B2a-1 | I-1 | II-98 |
| B2a-2 | I-2 | II-98 |
| B2a-3 | I-3 | II-98 |
| B2a-4 | I-4 | II-98 |
| B2a-5 | I-5 | II-98 |
| B2a-6 | I-6 | II-98 |
| B2a-7 | I-7 | II-98 |
| B2a-8 | I-8 | II-98 |
| B2a-9 | I-1 | II-99 |
| B2a-10 | I-2 | II-99 |
| B2a-11 | I-3 | II-99 |
| B2a-12 | I-4 | II-99 |
| B2a-13 | I-5 | II-99 |
| B2a-14 | I-6 | II-99 |
| B2a-15 | I-7 | II-99 |
| B2a-16 | I-8 | II-99 |
| B2a-17 | I-1 | II-100 |
| B2a-18 | I-2 | II-100 |
| B2a-19 | I-3 | II-100 |
| B2a-20 | I-4 | II-100 |
| B2a-21 | I-5 | II-100 |
| B2a-22 | I-6 | II-100 |
| B2a-23 | I-7 | II-100 |
| B2a-24 | I-8 | II-100 |
| B2a-25 | I-1 | II-101 |
| B2a-26 | I-2 | II-101 |
| B2a-27 | I-3 | II-101 |
| B2a-28 | I-4 | II-101 |
| B2a-29 | I-5 | II-101 |
| B2a-30 | I-6 | II-101 |
| B2a-31 | I-7 | II-101 |
| B2a-32 | I-8 | II-101 |
| B2a-33 | I-1 | II-102 |
| B2a-34 | I-2 | II-102 |
| B2a-35 | I-3 | II-102 |
| B2a-36 | I-4 | II-102 |
| B2a-37 | I-5 | II-102 |
| B2a-38 | I-6 | II-102 |
| B2a-39 | I-7 | II-102 |
| B2a-40 | I-8 | II-102 |

Continued Table B2a: Two-component compositions comprising other compounds I as component I and one component II, in particular binary compositions containing the respective component I and II as only active ingredients.

| composition | I | II |
|---|---|---|
| B2a-41 | I-9 | II-98 |
| B2a-42 | I-10 | II-98 |
| B2a-43 | I-11 | II-98 |
| B2a-44 | I-12 | II-98 |
| B2a-45 | I-13 | II-98 |
| B2a-46 | I-14 | II-98 |
| B2a-47 | I-15 | II-98 |
| B2a-48 | I-16 | II-98 |
| B2a-49 | I-9 | II-99 |
| B2a-50 | I-10 | II-99 |
| B2a-51 | I-11 | II-99 |
| B2a-52 | I-12 | II-99 |
| B2a-53 | I-13 | II-99 |
| B2a-54 | I-14 | II-99 |
| B2a-55 | I-15 | II-99 |
| B2a-56 | I-16 | II-99 |
| B2a-57 | I-9 | II-100 |
| B2a-58 | I-10 | II-100 |
| B2a-59 | I-11 | II-100 |
| B2a-60 | I-12 | II-100 |
| B2a-61 | I-13 | II-100 |
| B2a-62 | I-14 | II-100 |
| B2a-63 | I-15 | II-100 |
| B2a-64 | I-16 | II-100 |
| B2a-65 | I-9 | II-101 |
| B2a-66 | I-10 | II-101 |
| B2a-67 | I-11 | II-101 |
| B2a-68 | I-12 | II-101 |
| B2a-69 | I-13 | II-101 |
| B2a-70 | I-14 | II-101 |
| B2a-71 | I-15 | II-101 |
| B2a-72 | I-16 | II-101 |
| B2a-73 | I-9 | II-102 |

TABLE B2a-continued

| | | |
|---|---|---|
| B2a-74 | I-10 | II-102 |
| B2a-75 | I-11 | II-102 |
| B2a-76 | I-12 | II-102 |
| B2a-77 | I-13 | II-102 |
| B2a-78 | I-14 | II-102 |
| B2a-79 | I-15 | II-102 |
| B2a-80 | I-16 | II-102 |

As detailed above, the components I contain chirality centers and may, therefore, be present as racemic mixtures, as pure enantiomers or in the two enantiomers of one component I may be present in any ration (S):(R).

According to particular embodiments of the invention, the respective component I is present as (S) enantiomer. Specific two-component compositions comprising the (S) enantiomer of the respective component I are compiled in Table Bs, wherein each row corresponds to one embodiment of the compositions according to the invention, i.e. one specific individualized composition. According to one specific aspect, these are binary compositions which each only contain these two components as active compounds. Furthermore, also every combination of the compositions individualized in this table represent embodiments of the present invention.

TABLE Bs

Two-component compositions comprising one component I as (S) enantiomer (appreviated as (S)-I, e.g. (S)-I-1 for the (S)-enantiomer of I-1) and one component II, in particular binary compositions containing the respective component I as (S) enantiomer and II as only active ingredients.

| composition | (S)-I | II |
|---|---|---|
| Bs-1 | (S)-I-1 | II-1 |
| Bs-2 | (S)-I-3 | II-1 |
| Bs-3 | (S)-I-4 | II-1 |
| Bs-4 | (S)-I-5 | II-1 |
| Bs-5 | (S)-I-1 | II-2 |
| Bs-6 | (S)-I-3 | II-2 |
| Bs-7 | (S)-I-4 | II-2 |
| Bs-8 | (S)-I-5 | II-2 |
| Bs-9 | (S)-I-1 | II-3 |
| Bs-10 | (S)-I-3 | II-3 |
| Bs-11 | (S)-I-4 | II-3 |
| Bs-12 | (S)-I-5 | II-3 |
| Bs-13 | (S)-I-1 | II-4 |
| Bs-14 | (S)-I-3 | II-4 |
| Bs-15 | (S)-I-4 | II-4 |
| Bs-16 | (S)-I-5 | II-4 |
| Bs-17 | (S)-I-1 | II-5 |
| Bs-18 | (S)-I-3 | II-5 |
| Bs-19 | (S)-I-4 | II-5 |
| Bs-20 | (S)-I-5 | II-5 |
| Bs-21 | (S)-I-1 | II-6 |
| Bs-22 | (S)-I-3 | II-6 |
| Bs-23 | (S)-I-4 | II-6 |
| Bs-24 | (S)-I-5 | II-6 |
| Bs-25 | (S)-I-1 | II-7 |
| Bs-26 | (S)-I-3 | II-7 |
| Bs-27 | (S)-I-4 | II-7 |
| Bs-28 | (S)-I-5 | II-7 |
| Bs-29 | (S)-I-1 | II-8 |
| Bs-30 | (S)-I-3 | II-8 |
| Bs-31 | (S)-I-4 | II-8 |
| Bs-32 | (S)-I-5 | II-8 |
| Bs-33 | (S)-I-1 | II-9 |
| Bs-34 | (S)-I-3 | II-9 |
| Bs-35 | (S)-I-4 | II-9 |
| Bs-36 | (S)-I-5 | II-9 |
| Bs-37 | (S)-I-1 | II-10 |
| Bs-38 | (S)-I-3 | II-10 |
| Bs-39 | (S)-I-4 | II-10 |
| Bs-40 | (S)-I-5 | II-10 |
| Bs-41 | (S)-I-1 | II-11 |
| Bs-42 | (S)-I-3 | II-11 |
| Bs-43 | (S)-I-4 | II-11 |
| Bs-44 | (S)-I-5 | II-11 |
| Bs-45 | (S)-I-1 | II-12 |
| Bs-46 | (S)-I-3 | II-12 |
| Bs-47 | (S)-I-4 | II-12 |
| Bs-48 | (S)-I-5 | II-12 |
| Bs-49 | (S)-I-1 | II-13 |
| Bs-50 | (S)-I-3 | II-13 |
| Bs-51 | (S)-I-4 | II-13 |
| Bs-52 | (S)-I-5 | II-13 |
| Bs-53 | (S)-I-1 | II-14 |
| Bs-54 | (S)-I-3 | II-14 |
| Bs-55 | (S)-I-4 | II-14 |
| Bs-56 | (S)-I-5 | II-14 |
| Bs-57 | (S)-I-1 | II-15 |
| Bs-58 | (S)-I-3 | II-15 |
| Bs-59 | (S)-I-4 | II-15 |
| Bs-60 | (S)-I-5 | II-15 |
| Bs-61 | (S)-I-1 | II-16 |
| Bs-62 | (S)-I-3 | II-16 |
| Bs-63 | (S)-I-4 | II-16 |
| Bs-64 | (S)-I-5 | II-16 |
| Bs-65 | (S)-I-1 | II-17 |
| Bs-66 | (S)-I-3 | II-17 |
| Bs-67 | (S)-I-4 | II-17 |
| Bs-68 | (S)-I-5 | II-17 |
| Bs-69 | (S)-I-1 | II-18 |
| Bs-70 | (S)-I-3 | II-18 |
| Bs-71 | (S)-I-4 | II-18 |
| Bs-72 | (S)-I-5 | II-18 |
| Bs-73 | (S)-I-1 | II-19 |
| Bs-74 | (S)-I-3 | II-19 |
| Bs-75 | (S)-I-4 | II-19 |
| Bs-76 | (S)-I-5 | II-19 |
| Bs-77 | (S)-I-1 | II-20 |
| Bs-78 | (S)-I-3 | II-20 |
| Bs-79 | (S)-I-4 | II-20 |
| Bs-80 | (S)-I-5 | II-20 |
| Bs-81 | (S)-I-1 | II-21 |
| Bs-82 | (S)-I-3 | II-21 |
| Bs-83 | (S)-I-4 | II-21 |
| Bs-84 | (S)-I-5 | II-21 |
| Bs-85 | (S)-I-1 | II-22 |
| Bs-86 | (S)-I-3 | II-22 |
| Bs-87 | (S)-I-4 | II-22 |
| Bs-88 | (S)-I-5 | II-22 |
| Bs-89 | (S)-I-1 | II-23 |
| Bs-90 | (S)-I-3 | II-23 |
| Bs-91 | (S)-I-4 | II-23 |
| Bs-92 | (S)-I-5 | II-23 |
| Bs-93 | (S)-I-1 | II-24 |
| Bs-94 | (S)-I-3 | II-24 |
| Bs-95 | (S)-I-4 | II-24 |
| Bs-96 | (S)-I-5 | II-24 |
| Bs-97 | (S)-I-1 | II-25 |
| Bs-98 | (S)-I-3 | II-25 |
| Bs-99 | (S)-I-4 | II-25 |
| Bs-100 | (S)-I-5 | II-25 |
| Bs-101 | (S)-I-1 | II-26 |
| Bs-102 | (S)-I-3 | II-26 |
| Bs-103 | (S)-I-4 | II-26 |
| Bs-104 | (S)-I-5 | II-26 |
| Bs-105 | (S)-I-1 | II-27 |
| Bs-106 | (S)-I-3 | II-27 |
| Bs-107 | (S)-I-4 | II-27 |
| Bs-108 | (S)-I-5 | II-27 |
| Bs-109 | (S)-I-1 | II-28 |

TABLE Bs-continued

Two-component compositions comprising one component I as (S) enantiomer (appreviated as (S)-I, e.g. (S)-I-1 for the (S)-enantiomer of I-1) and one component II, in particular binary compositions containing the respective component I as (S) enantiomer and II as only active ingredients.

| composition | (S)-I | II |
| --- | --- | --- |
| Bs-110 | (S)-I-3 | II-28 |
| Bs-111 | (S)-I-4 | II-28 |
| Bs-112 | (S)-I-5 | II-28 |
| Bs-113 | (S)-I-1 | II-29 |
| Bs-114 | (S)-I-3 | II-29 |
| Bs-115 | (S)-I-4 | II-29 |
| Bs-116 | (S)-I-5 | II-29 |
| Bs-117 | (S)-I-1 | II-30 |
| Bs-118 | (S)-I-3 | II-30 |
| Bs-119 | (S)-I-4 | II-30 |
| Bs-120 | (S)-I-5 | II-30 |
| Bs-121 | (S)-I-1 | II-31 |
| Bs-122 | (S)-I-3 | II-31 |
| Bs-123 | (S)-I-4 | II-31 |
| Bs-124 | (S)-I-5 | II-31 |
| Bs-125 | (S)-I-1 | II-32 |
| Bs-126 | (S)-I-3 | II-32 |
| Bs-127 | (S)-I-4 | II-32 |
| Bs-128 | (S)-I-5 | II-32 |
| Bs-129 | (S)-I-1 | II-33 |
| Bs-130 | (S)-I-3 | II-33 |
| Bs-131 | (S)-I-4 | II-33 |
| Bs-132 | (S)-I-5 | II-33 |
| Bs-133 | (S)-I-1 | II-34 |
| Bs-134 | (S)-I-3 | II-34 |
| Bs-135 | (S)-I-4 | II-34 |
| Bs-136 | (S)-I-5 | II-34 |
| Bs-137 | (S)-I-1 | II-35 |
| Bs-138 | (S)-I-3 | II-35 |
| Bs-139 | (S)-I-4 | II-35 |
| Bs-140 | (S)-I-5 | II-35 |
| Bs-141 | (S)-I-1 | II-36 |
| Bs-142 | (S)-I-3 | II-36 |
| Bs-143 | (S)-I-4 | II-36 |
| Bs-144 | (S)-I-5 | II-36 |
| Bs-145 | (S)-I-1 | II-37 |
| Bs-146 | (S)-I-3 | II-37 |
| Bs-147 | (S)-I-4 | II-37 |
| Bs-148 | (S)-I-5 | II-37 |
| Bs-149 | (S)-I-1 | II-38 |
| Bs-150 | (S)-I-3 | II-38 |
| Bs-151 | (S)-I-4 | II-38 |
| Bs-152 | (S)-I-5 | II-38 |
| Bs-153 | (S)-I-1 | II-39 |
| Bs-154 | (S)-I-3 | II-39 |
| Bs-155 | (S)-I-4 | II-39 |
| Bs-156 | (S)-I-5 | II-39 |
| Bs-157 | (S)-I-1 | II-40 |
| Bs-158 | (S)-I-3 | II-40 |
| Bs-159 | (S)-I-4 | II-40 |
| Bs-160 | (S)-I-5 | II-40 |
| Bs-161 | (S)-I-1 | II-41 |
| Bs-162 | (S)-I-3 | II-41 |
| Bs-163 | (S)-I-4 | II-41 |
| Bs-164 | (S)-I-5 | II-41 |
| Bs-165 | (S)-I-1 | II-42 |
| Bs-166 | (S)-I-3 | II-42 |
| Bs-167 | (S)-I-4 | II-42 |
| Bs-168 | (S)-I-5 | II-42 |
| Bs-169 | (S)-I-1 | II-43 |
| Bs-170 | (S)-I-3 | II-43 |
| Bs-171 | (S)-I-4 | II-43 |
| Bs-172 | (S)-I-5 | II-43 |
| Bs-173 | (S)-I-1 | II-44 |
| Bs-174 | (S)-I-3 | II-44 |
| Bs-175 | (S)-I-4 | II-44 |
| Bs-176 | (S)-I-5 | II-44 |
| Bs-177 | (S)-I-1 | II-45 |
| Bs-178 | (S)-I-3 | II-45 |
| Bs-179 | (S)-I-4 | II-45 |
| Bs-180 | (S)-I-5 | II-45 |
| Bs-181 | (S)-I-1 | II-46 |
| Bs-182 | (S)-I-3 | II-46 |
| Bs-183 | (S)-I-4 | II-46 |
| Bs-184 | (S)-I-5 | II-46 |
| Bs-185 | (S)-I-1 | II-47 |
| Bs-186 | (S)-I-3 | II-47 |
| Bs-187 | (S)-I-4 | II-47 |
| Bs-188 | (S)-I-5 | II-47 |
| Bs-189 | (S)-I-1 | II-48 |
| Bs-190 | (S)-I-3 | II-48 |
| Bs-191 | (S)-I-4 | II-48 |
| Bs-192 | (S)-I-5 | II-48 |
| Bs-193 | (S)-I-1 | II-49 |
| Bs-194 | (S)-I-3 | II-49 |
| Bs-195 | (S)-I-4 | II-49 |
| Bs-196 | (S)-I-5 | II-49 |
| Bs-197 | (S)-I-1 | II-50 |
| Bs-198 | (S)-I-3 | II-50 |
| Bs-199 | (S)-I-4 | II-50 |
| Bs-200 | (S)-I-5 | II-50 |
| Bs-201 | (S)-I-1 | II-51 |
| Bs-202 | (S)-I-3 | II-51 |
| Bs-203 | (S)-I-4 | II-51 |
| Bs-204 | (S)-I-5 | II-51 |
| Bs-205 | (S)-I-1 | II-52 |
| Bs-206 | (S)-I-3 | II-52 |
| Bs-207 | (S)-I-4 | II-52 |
| Bs-208 | (S)-I-5 | II-52 |
| Bs-209 | (S)-I-1 | II-53 |
| Bs-210 | (S)-I-3 | II-53 |
| Bs-211 | (S)-I-4 | II-53 |
| Bs-212 | (S)-I-5 | II-53 |
| Bs-213 | (S)-I-1 | II-54 |
| Bs-214 | (S)-I-3 | II-54 |
| Bs-215 | (S)-I-4 | II-54 |
| Bs-216 | (S)-I-5 | II-54 |
| Bs-217 | (S)-I-1 | II-55 |
| Bs-218 | (S)-I-3 | II-55 |
| Bs-219 | (S)-I-4 | II-55 |
| Bs-220 | (S)-I-5 | II-55 |
| Bs-221 | (S)-I-1 | II-56 |
| Bs-222 | (S)-I-3 | II-56 |
| Bs-223 | (S)-I-4 | II-56 |
| Bs-224 | (S)-I-5 | II-56 |
| Bs-225 | (S)-I-1 | II-57 |
| Bs-226 | (S)-I-3 | II-57 |
| Bs-227 | (S)-I-4 | II-57 |
| Bs-228 | (S)-I-5 | II-57 |
| Bs-229 | (S)-I-1 | II-58 |
| Bs-230 | (S)-I-3 | II-58 |
| Bs-231 | (S)-I-4 | II-58 |
| Bs-232 | (S)-I-5 | II-58 |
| Bs-233 | (S)-I-1 | II-59 |
| Bs-234 | (S)-I-3 | II-59 |
| Bs-235 | (S)-I-4 | II-59 |
| Bs-236 | (S)-I-5 | II-59 |
| Bs-237 | (S)-I-1 | II-60 |
| Bs-238 | (S)-I-3 | II-60 |
| Bs-239 | (S)-I-4 | II-60 |
| Bs-240 | (S)-I-5 | II-60 |
| Bs-241 | (S)-I-1 | II-61 |
| Bs-242 | (S)-I-3 | II-61 |
| Bs-243 | (S)-I-4 | II-61 |
| Bs-244 | (S)-I-5 | II-61 |
| Bs-245 | (S)-I-1 | II-62 |
| Bs-246 | (S)-I-3 | II-62 |
| Bs-247 | (S)-I-4 | II-62 |
| Bs-248 | (S)-I-5 | II-62 |
| Bs-249 | (S)-I-1 | II-63 |
| Bs-250 | (S)-I-3 | II-63 |
| Bs-251 | (S)-I-4 | II-63 |

TABLE Bs-continued

Two-component compositions comprising one component I as (S) enantiomer (appreviated as (S)-I, e.g. (S)-I-1 for the (S)-enantiomer of I-1) and one component II, in particular binary compositions containing the respective component I as (S) enantiomer and II as only active ingredients.

| composition | (S)-I | II |
|---|---|---|
| Bs-252 | (S)-I-5 | II-63 |
| Bs-253 | (S)-I-1 | II-64 |
| Bs-254 | (S)-I-3 | II-64 |
| Bs-255 | (S)-I-4 | II-64 |
| Bs-256 | (S)-I-5 | II-64 |
| Bs-257 | (S)-I-1 | II-65 |
| Bs-258 | (S)-I-3 | II-65 |
| Bs-259 | (S)-I-4 | II-65 |
| Bs-260 | (S)-I-5 | II-65 |
| Bs-261 | (S)-I-1 | II-66 |
| Bs-262 | (S)-I-3 | II-66 |
| Bs-263 | (S)-I-4 | II-66 |
| Bs-264 | (S)-I-5 | II-66 |
| Bs-265 | (S)-I-1 | II-67 |
| Bs-266 | (S)-I-3 | II-67 |
| Bs-267 | (S)-I-4 | II-67 |
| Bs-268 | (S)-I-5 | II-67 |
| Bs-269 | (S)-I-1 | II-68 |
| Bs-270 | (S)-I-3 | II-68 |
| Bs-271 | (S)-I-4 | II-68 |
| Bs-272 | (S)-I-5 | II-68 |
| Bs-273 | (S)-I-1 | II-69 |
| Bs-274 | (S)-I-3 | II-69 |
| Bs-275 | (S)-I-4 | II-69 |
| Bs-276 | (S)-I-5 | II-69 |
| Bs-277 | (S)-I-1 | II-70 |
| Bs-278 | (S)-I-3 | II-70 |
| Bs-279 | (S)-I-4 | II-70 |
| Bs-280 | (S)-I-5 | II-70 |
| Bs-281 | (S)-I-1 | II-71 |
| Bs-282 | (S)-I-3 | II-71 |
| Bs-283 | (S)-I-4 | II-71 |
| Bs-284 | (S)-I-5 | II-71 |
| Bs-285 | (S)-I-1 | II-72 |
| Bs-286 | (S)-I-3 | II-72 |
| Bs-287 | (S)-I-4 | II-72 |
| Bs-288 | (S)-I-5 | II-72 |
| Bs-289 | (S)-I-1 | II-73 |
| Bs-290 | (S)-I-3 | II-73 |
| Bs-291 | (S)-I-4 | II-73 |
| Bs-292 | (S)-I-5 | II-73 |
| Bs-293 | (S)-I-1 | II-74 |
| Bs-294 | (S)-I-3 | II-74 |
| Bs-295 | (S)-I-4 | II-74 |
| Bs-296 | (S)-I-5 | II-74 |
| Bs-297 | (S)-I-1 | II-75 |
| Bs-298 | (S)-I-3 | II-75 |
| Bs-299 | (S)-I-4 | II-75 |
| Bs-300 | (S)-I-5 | II-75 |
| Bs-301 | (S)-I-1 | II-76 |
| Bs-302 | (S)-I-3 | II-76 |
| Bs-303 | (S)-I-4 | II-76 |
| Bs-304 | (S)-I-5 | II-76 |
| Bs-305 | (S)-I-1 | II-77 |
| Bs-306 | (S)-I-3 | II-77 |
| Bs-307 | (S)-I-4 | II-77 |
| Bs-308 | (S)-I-5 | II-77 |
| Bs-309 | (S)-I-1 | II-78 |
| Bs-310 | (S)-I-3 | II-78 |
| Bs-311 | (S)-I-4 | II-78 |
| Bs-312 | (S)-I-5 | II-78 |
| Bs-313 | (S)-I-1 | II-79 |
| Bs-314 | (S)-I-3 | II-79 |
| Bs-315 | (S)-I-4 | II-79 |
| Bs-316 | (S)-I-5 | II-79 |
| Bs-317 | (S)-I-1 | II-80 |
| Bs-318 | (S)-I-3 | II-80 |
| Bs-319 | (S)-I-4 | II-80 |
| Bs-320 | (S)-I-5 | II-80 |
| Bs-321 | (S)-I-1 | II-81 |
| Bs-322 | (S)-I-3 | II-81 |
| Bs-323 | (S)-I-4 | II-81 |
| Bs-324 | (S)-I-5 | II-81 |
| Bs-325 | (S)-I-1 | II-82 |
| Bs-326 | (S)-I-3 | II-82 |
| Bs-327 | (S)-I-4 | II-82 |
| Bs-328 | (S)-I-5 | II-82 |
| Bs-329 | (S)-I-1 | II-83 |
| Bs-330 | (S)-I-3 | II-83 |
| Bs-331 | (S)-I-4 | II-83 |
| Bs-332 | (S)-I-5 | II-83 |
| Bs-333 | (S)-I-1 | II-84 |
| Bs-334 | (S)-I-3 | II-84 |
| Bs-335 | (S)-I-4 | II-84 |
| Bs-336 | (S)-I-5 | II-84 |
| Bs-337 | (S)-I-1 | II-85 |
| Bs-338 | (S)-I-3 | II-85 |
| Bs-339 | (S)-I-4 | II-85 |
| Bs-340 | (S)-I-5 | II-85 |
| Bs-341 | (S)-I-1 | II-86 |
| Bs-342 | (S)-I-3 | II-86 |
| Bs-343 | (S)-I-4 | II-86 |
| Bs-344 | (S)-I-5 | II-86 |
| Bs-345 | (S)-I-1 | II-87 |
| Bs-346 | (S)-I-3 | II-87 |
| Bs-347 | (S)-I-4 | II-87 |
| Bs-348 | (S)-I-5 | II-87 |
| Bs-349 | (S)-I-1 | II-88 |
| Bs-350 | (S)-I-3 | II-88 |
| Bs-351 | (S)-I-4 | II-88 |
| Bs-352 | (S)-I-5 | II-88 |
| Bs-353 | (S)-I-1 | II-89 |
| Bs-354 | (S)-I-3 | II-89 |
| Bs-355 | (S)-I-4 | II-89 |
| Bs-356 | (S)-I-5 | II-89 |
| Bs-357 | (S)-I-1 | II-90 |
| Bs-358 | (S)-I-3 | II-90 |
| Bs-359 | (S)-I-4 | II-90 |
| Bs-360 | (S)-I-5 | II-90 |
| Bs-361 | (S)-I-1 | II-91 |
| Bs-362 | (S)-I-3 | II-91 |
| Bs-363 | (S)-I-4 | II-91 |
| Bs-364 | (S)-I-5 | II-91 |
| Bs-365 | (S)-I-1 | II-92 |
| Bs-366 | (S)-I-3 | II-92 |
| Bs-367 | (S)-I-4 | II-92 |
| Bs-368 | (S)-I-5 | II-92 |
| Bs-369 | (S)-I-1 | II-93 |
| Bs-370 | (S)-I-3 | II-93 |
| Bs-371 | (S)-I-4 | II-93 |
| Bs-372 | (S)-I-5 | II-93 |
| Bs-373 | (S)-I-1 | II-94 |
| Bs-374 | (S)-I-3 | II-94 |
| Bs-375 | (S)-I-4 | II-94 |
| Bs-376 | (S)-I-5 | II-94 |
| Bs-377 | (S)-I-1 | II-95 |
| Bs-378 | (S)-I-3 | II-95 |
| Bs-379 | (S)-I-4 | II-95 |
| Bs-380 | (S)-I-5 | II-95 |
| Bs-381 | (S)-I-1 | II-96 |
| Bs-382 | (S)-I-3 | II-96 |
| Bs-383 | (S)-I-4 | II-96 |
| Bs-384 | (S)-I-5 | II-96 |
| Bs-385 | (S)-I-1 | II-97 |
| Bs-386 | (S)-I-3 | II-97 |
| Bs-387 | (S)-I-4 | II-97 |
| Bs-388 | (S)-I-5 | II-97 |
| Bs-389 | (S)-I-1 | II-98 |
| Bs-390 | (S)-I-3 | II-98 |
| Bs-391 | (S)-I-4 | II-98 |
| Bs-392 | (S)-I-5 | II-98 |
| Bs-393 | (S)-I-1 | II-99 |

TABLE Bs-continued

Two-component compositions comprising one component I as (S) enantiomer (appreviated as (S)-I, e.g. (S)-I-1 for the (S)-enantiomer of I-1) and one component II, in particular binary compositions containing the respective component I as (S) enantiomer and II as only active ingredients.

| composition | (S)-I | II |
| --- | --- | --- |
| Bs-394 | (S)-I-3 | II-99 |
| Bs-395 | (S)-I-4 | II-99 |
| Bs-396 | (S)-I-5 | II-99 |
| Bs-397 | (S)-I-1 | II-100 |
| Bs-398 | (S)-I-3 | II-100 |
| Bs-399 | (S)-I-4 | II-100 |
| Bs-400 | (S)-I-5 | II-100 |
| Bs-401 | (S)-I-1 | II-101 |
| Bs-402 | (S)-I-3 | II-101 |
| Bs-403 | (S)-I-4 | II-101 |
| Bs-404 | (S)-I-5 | II-101 |
| Bs-405 | (S)-I-1 | II-102 |
| Bs-406 | (S)-I-3 | II-102 |
| Bs-407 | (S)-I-4 | II-102 |
| Bs-408 | (S)-I-5 | II-102 |
| Bs-409 | (S)-I-13 | II-1 |
| Bs-410 | (S)-I-13 | II-2 |
| Bs-411 | (S)-I-13 | II-3 |
| Bs-412 | (S)-I-13 | II-4 |
| Bs-413 | (S)-I-13 | II-5 |
| Bs-414 | (S)-I-13 | II-6 |
| Bs-415 | (S)-I-13 | II-7 |
| Bs-416 | (S)-I-13 | II-8 |
| Bs-417 | (S)-I-13 | II-9 |
| Bs-418 | (S)-I-13 | II-10 |
| Bs-419 | (S)-I-13 | II-11 |
| Bs-420 | (S)-I-13 | II-12 |
| Bs-421 | (S)-I-13 | II-13 |
| Bs-422 | (S)-I-13 | II-14 |
| Bs-423 | (S)-I-13 | II-15 |
| Bs-424 | (S)-I-13 | II-16 |
| Bs-425 | (S)-I-13 | II-17 |
| Bs-426 | (S)-I-13 | II-18 |
| Bs-427 | (S)-I-13 | II-19 |
| Bs-428 | (S)-I-13 | II-20 |
| Bs-429 | (S)-I-13 | II-21 |
| Bs-430 | (S)-I-13 | II-22 |
| Bs-431 | (S)-I-13 | II-23 |
| Bs-432 | (S)-I-13 | II-24 |
| Bs-433 | (S)-I-13 | II-25 |
| Bs-434 | (S)-I-13 | II-26 |
| Bs-435 | (S)-I-13 | II-27 |
| Bs-436 | (S)-I-13 | II-28 |
| Bs-437 | (S)-I-13 | II-29 |
| Bs-438 | (S)-I-13 | II-30 |
| Bs-439 | (S)-I-13 | II-31 |
| Bs-440 | (S)-I-13 | II-32 |
| Bs-441 | (S)-I-13 | II-33 |
| Bs-442 | (S)-I-13 | II-34 |
| Bs-443 | (S)-I-13 | II-35 |
| Bs-444 | (S)-I-13 | II-36 |
| Bs-445 | (S)-I-13 | II-37 |
| Bs-446 | (S)-I-13 | II-38 |
| Bs-447 | (S)-I-13 | II-39 |
| Bs-448 | (S)-I-13 | II-40 |
| Bs-449 | (S)-I-13 | II-41 |
| Bs-450 | (S)-I-13 | II-42 |
| Bs-451 | (S)-I-13 | II-43 |
| Bs-452 | (S)-I-13 | II-44 |
| Bs-453 | (S)-I-13 | II-45 |
| Bs-454 | (S)-I-13 | II-46 |
| Bs-455 | (S)-I-13 | II-47 |
| Bs-456 | (S)-I-13 | II-48 |
| Bs-457 | (S)-I-13 | II-49 |
| Bs-458 | (S)-I-13 | II-50 |
| Bs-459 | (S)-I-13 | II-51 |
| Bs-460 | (S)-I-13 | II-52 |
| Bs-461 | (S)-I-13 | II-53 |
| Bs-462 | (S)-I-13 | II-54 |
| Bs-463 | (S)-I-13 | II-55 |
| Bs-464 | (S)-I-13 | II-56 |
| Bs-465 | (S)-I-13 | II-57 |
| Bs-466 | (S)-I-13 | II-58 |
| Bs-467 | (S)-I-13 | II-59 |
| Bs-468 | (S)-I-13 | II-60 |
| Bs-469 | (S)-I-13 | II-61 |
| Bs-470 | (S)-I-13 | II-62 |
| Bs-471 | (S)-I-13 | II-63 |
| Bs-472 | (S)-I-13 | II-64 |
| Bs-473 | (S)-I-13 | II-65 |
| Bs-474 | (S)-I-13 | II-66 |
| Bs-475 | (S)-I-13 | II-67 |
| Bs-476 | (S)-I-13 | II-68 |
| Bs-477 | (S)-I-13 | II-69 |
| Bs-478 | (S)-I-13 | II-70 |
| Bs-479 | (S)-I-13 | II-71 |
| Bs-480 | (S)-I-13 | II-72 |
| Bs-481 | (S)-I-13 | II-73 |
| Bs-482 | (S)-I-13 | II-74 |
| Bs-483 | (S)-I-13 | II-75 |
| Bs-484 | (S)-I-13 | II-76 |
| Bs-485 | (S)-I-13 | II-77 |
| Bs-486 | (S)-I-13 | II-78 |
| Bs-487 | (S)-I-13 | II-79 |
| Bs-488 | (S)-I-13 | II-80 |
| Bs-489 | (S)-I-13 | II-81 |
| Bs-490 | (S)-I-13 | II-82 |
| Bs-491 | (S)-I-13 | II-83 |
| Bs-492 | (S)-I-13 | II-84 |
| Bs-493 | (S)-I-13 | II-85 |
| Bs-494 | (S)-I-13 | II-86 |
| Bs-495 | (S)-I-13 | II-87 |
| Bs-496 | (S)-I-13 | II-88 |
| Bs-497 | (S)-I-13 | II-89 |
| Bs-498 | (S)-I-13 | II-90 |
| Bs-499 | (S)-I-13 | II-91 |
| Bs-500 | (S)-I-13 | II-92 |
| Bs-501 | (S)-I-13 | II-93 |
| Bs-502 | (S)-I-13 | II-94 |
| Bs-503 | (S)-I-13 | II-95 |
| Bs-504 | (S)-I-13 | II-96 |
| Bs-505 | (S)-I-13 | II-97 |
| Bs-506 | (S)-I-13 | II-98 |
| Bs-507 | (S)-I-13 | II-99 |
| Bs-508 | (S)-I-13 | II-100 |
| Bs-509 | (S)-I-13 | II-101 |
| Bs-510 | (S)-I-13 | II-102 |

According to particular embodiments of the invention, the respective component I is present as (R) enantiomer. Specific two-component compositions comprising the (R) enantiomer of the respective component I are compiled in Table Br, wherein each row corresponds to one embodiment of the compositions according to the invention, i.e. one specific individualized composition. According to one specific aspect, these are binary compositions which each only contain these two components as active compounds. Furthermore, also every combination of the compositions individualized in this table represent embodiments of the present invention.

TABLE Br

Two-component compositions comprising one component I as (R) enantiomer (appreviated as (R)-I, e.g. (R)-I-1 for the (R)-enantiomer of I-1) and one component II, in particular binary compositions containing the respective component I as (R) enantiomer and as only active ingredients.

| composition | (R)-I | II |
|---|---|---|
| Br-1 | (R)-I-1 | II-1 |
| Br-2 | (R)-I-3 | II-1 |
| Br-3 | (R)-I-4 | II-1 |
| Br-4 | (R)-I-5 | II-1 |
| Br-5 | (R)-I-1 | II-2 |
| Br-6 | (R)-I-3 | II-2 |
| Br-7 | (R)-I-4 | II-2 |
| Br-8 | (R)-I-5 | II-2 |
| Br-9 | (R)-I-1 | II-3 |
| Br-10 | (R)-I-3 | II-3 |
| Br-11 | (R)-I-4 | II-3 |
| Br-12 | (R)-I-5 | II-3 |
| Br-13 | (R)-I-1 | II-4 |
| Br-14 | (R)-I-3 | II-4 |
| Br-15 | (R)-I-4 | II-4 |
| Br-16 | (R)-I-5 | II-4 |
| Br-17 | (R)-I-1 | II-5 |
| Br-18 | (R)-I-3 | II-5 |
| Br-19 | (R)-I-4 | II-5 |
| Br-20 | (R)-I-5 | II-5 |
| Br-21 | (R)-I-1 | II-6 |
| Br-22 | (R)-I-3 | II-6 |
| Br-23 | (R)-I-4 | II-6 |
| Br-24 | (R)-I-5 | II-6 |
| Br-25 | (R)-I-1 | II-7 |
| Br-26 | (R)-I-3 | II-7 |
| Br-27 | (R)-I-4 | II-7 |
| Br-28 | (R)-I-5 | II-7 |
| Br-29 | (R)-I-1 | II-8 |
| Br-30 | (R)-I-3 | II-8 |
| Br-31 | (R)-I-4 | II-8 |
| Br-32 | (R)-I-5 | II-8 |
| Br-33 | (R)-I-1 | II-9 |
| Br-34 | (R)-I-3 | II-9 |
| Br-35 | (R)-I-4 | II-9 |
| Br-36 | (R)-I-5 | II-9 |
| Br-37 | (R)-I-1 | II-10 |
| Br-38 | (R)-I-3 | II-10 |
| Br-39 | (R)-I-4 | II-10 |
| Br-40 | (R)-I-5 | II-10 |
| Br-41 | (R)-I-1 | II-11 |
| Br-42 | (R)-I-3 | II-11 |
| Br-43 | (R)-I-4 | II-11 |
| Br-44 | (R)-I-5 | II-11 |
| Br-45 | (R)-I-1 | II-12 |
| Br-46 | (R)-I-3 | II-12 |
| Br-47 | (R)-I-4 | II-12 |
| Br-48 | (R)-I-5 | II-12 |
| Br-49 | (R)-I-1 | II-13 |
| Br-50 | (R)-I-3 | II-13 |
| Br-51 | (R)-I-4 | II-13 |
| Br-52 | (R)-I-5 | II-13 |
| Br-53 | (R)-I-1 | II-14 |
| Br-54 | (R)-I-3 | II-14 |
| Br-55 | (R)-I-4 | II-14 |
| Br-56 | (R)-I-5 | II-14 |
| Br-57 | (R)-I-1 | II-15 |
| Br-58 | (R)-I-3 | II-15 |
| Br-59 | (R)-I-4 | II-15 |
| Br-60 | (R)-I-5 | II-15 |
| Br-61 | (R)-I-1 | II-16 |
| Br-62 | (R)-I-3 | II-16 |
| Br-63 | (R)-I-4 | II-16 |
| Br-64 | (R)-I-5 | II-16 |
| Br-65 | (R)-I-1 | II-17 |
| Br-66 | (R)-I-3 | II-17 |
| Br-67 | (R)-I-4 | II-17 |
| Br-68 | (R)-I-5 | II-17 |
| Br-69 | (R)-I-1 | II-18 |
| Br-70 | (R)-I-3 | II-18 |
| Br-71 | (R)-I-4 | II-18 |
| Br-72 | (R)-I-5 | II-18 |
| Br-73 | (R)-I-1 | II-19 |
| Br-74 | (R)-I-3 | II-19 |
| Br-75 | (R)-I-4 | II-19 |
| Br-76 | (R)-I-5 | II-19 |
| Br-77 | (R)-I-1 | II-20 |
| Br-78 | (R)-I-3 | II-20 |
| Br-79 | (R)-I-4 | II-20 |
| Br-80 | (R)-I-5 | II-20 |
| Br-81 | (R)-I-1 | II-21 |
| Br-82 | (R)-I-3 | II-21 |
| Br-83 | (R)-I-4 | II-21 |
| Br-84 | (R)-I-5 | II-21 |
| Br-85 | (R)-I-1 | II-22 |
| Br-86 | (R)-I-3 | II-22 |
| Br-87 | (R)-I-4 | II-22 |
| Br-88 | (R)-I-5 | II-22 |
| Br-89 | (R)-I-1 | II-23 |
| Br-90 | (R)-I-3 | II-23 |
| Br-91 | (R)-I-4 | II-23 |
| Br-92 | (R)-I-5 | II-23 |
| Br-93 | (R)-I-1 | II-24 |
| Br-94 | (R)-I-3 | II-24 |
| Br-95 | (R)-I-4 | II-24 |
| Br-96 | (R)-I-5 | II-24 |
| Br-97 | (R)-I-1 | II-25 |
| Br-98 | (R)-I-3 | II-25 |
| Br-99 | (R)-I-4 | II-25 |
| Br-100 | (R)-I-5 | II-25 |
| Br-101 | (R)-I-1 | II-26 |
| Br-102 | (R)-I-3 | II-26 |
| Br-103 | (R)-I-4 | II-26 |
| Br-104 | (R)-I-5 | II-26 |
| Br-105 | (R)-I-1 | II-27 |
| Br-106 | (R)-I-3 | II-27 |
| Br-107 | (R)-I-4 | II-27 |
| Br-108 | (R)-I-5 | II-27 |
| Br-109 | (R)-I-1 | II-28 |
| Br-110 | (R)-I-3 | II-28 |
| Br-111 | (R)-I-4 | II-28 |
| Br-112 | (R)-I-5 | II-28 |
| Br-113 | (R)-I-1 | II-29 |
| Br-114 | (R)-I-3 | II-29 |
| Br-115 | (R)-I-4 | II-29 |
| Br-116 | (R)-I-5 | II-29 |
| Br-117 | (R)-I-1 | II-30 |
| Br-118 | (R)-I-3 | II-30 |
| Br-119 | (R)-I-4 | II-30 |
| Br-120 | (R)-I-5 | II-30 |
| Br-121 | (R)-I-1 | II-31 |
| Br-122 | (R)-I-3 | II-31 |
| Br-123 | (R)-I-4 | II-31 |
| Br-124 | (R)-I-5 | II-31 |
| Br-125 | (R)-I-1 | II-32 |
| Br-126 | (R)-I-3 | II-32 |
| Br-127 | (R)-I-4 | II-32 |
| Br-128 | (R)-I-5 | II-32 |
| Br-129 | (R)-I-1 | II-33 |
| Br-130 | (R)-I-3 | II-33 |
| Br-131 | (R)-I-4 | II-33 |
| Br-132 | (R)-I-5 | II-33 |
| Br-133 | (R)-I-1 | II-34 |
| Br-134 | (R)-I-3 | II-34 |
| Br-135 | (R)-I-4 | II-34 |
| Br-136 | (R)-I-5 | II-34 |
| Br-137 | (R)-I-1 | II-35 |
| Br-138 | (R)-I-3 | II-35 |
| Br-139 | (R)-I-4 | II-35 |
| Br-140 | (R)-I-5 | II-35 |
| Br-141 | (R)-I-1 | II-36 |
| Br-142 | (R)-I-3 | II-36 |

TABLE Br-continued

Two-component compositions comprising one component I as (R) enantiomer (appreviated as (R)-I, e.g. (R)-I-1 for the (R)-enantiomer of I-1) and one component II, in particular binary compositions containing the respective component I as (R) enantiomer and as only active ingredients.

| composition | (R)-I | II |
|---|---|---|
| Br-143 | (R)-I-4 | II-36 |
| Br-144 | (R)-I-5 | II-36 |
| Br-145 | (R)-I-1 | II-37 |
| Br-146 | (R)-I-3 | II-37 |
| Br-147 | (R)-I-4 | II-37 |
| Br-148 | (R)-I-5 | II-37 |
| Br-149 | (R)-I-1 | II-38 |
| Br-150 | (R)-I-3 | II-38 |
| Br-151 | (R)-I-4 | II-38 |
| Br-152 | (R)-I-5 | II-38 |
| Br-153 | (R)-I-1 | II-39 |
| Br-154 | (R)-I-3 | II-39 |
| Br-155 | (R)-I-4 | II-39 |
| Br-156 | (R)-I-5 | II-39 |
| Br-157 | (R)-I-1 | II-40 |
| Br-158 | (R)-I-3 | II-40 |
| Br-159 | (R)-I-4 | II-40 |
| Br-160 | (R)-I-5 | II-40 |
| Br-161 | (R)-I-1 | II-41 |
| Br-162 | (R)-I-3 | II-41 |
| Br-163 | (R)-I-4 | II-41 |
| Br-164 | (R)-I-5 | II-41 |
| Br-165 | (R)-I-1 | II-42 |
| Br-166 | (R)-I-3 | II-42 |
| Br-167 | (R)-I-4 | II-42 |
| Br-168 | (R)-I-5 | II-42 |
| Br-169 | (R)-I-1 | II-43 |
| Br-170 | (R)-I-3 | II-43 |
| Br-171 | (R)-I-4 | II-43 |
| Br-172 | (R)-I-5 | II-43 |
| Br-173 | (R)-I-1 | II-44 |
| Br-174 | (R)-I-3 | II-44 |
| Br-175 | (R)-I-4 | II-44 |
| Br-176 | (R)-I-5 | II-44 |
| Br-177 | (R)-I-1 | II-45 |
| Br-178 | (R)-I-3 | II-45 |
| Br-179 | (R)-I-4 | II-45 |
| Br-180 | (R)-I-5 | II-45 |
| Br-181 | (R)-I-1 | II-46 |
| Br-182 | (R)-I-3 | II-46 |
| Br-183 | (R)-I-4 | II-46 |
| Br-184 | (R)-I-5 | II-46 |
| Br-185 | (R)-I-1 | II-47 |
| Br-186 | (R)-I-3 | II-47 |
| Br-187 | (R)-I-4 | II-47 |
| Br-188 | (R)-I-5 | II-47 |
| Br-189 | (R)-I-1 | II-48 |
| Br-190 | (R)-I-3 | II-48 |
| Br-191 | (R)-I-4 | II-48 |
| Br-192 | (R)-I-5 | II-48 |
| Br-193 | (R)-I-1 | II-49 |
| Br-194 | (R)-I-3 | II-49 |
| Br-195 | (R)-I-4 | II-49 |
| Br-196 | (R)-I-5 | II-49 |
| Br-197 | (R)-I-1 | II-50 |
| Br-198 | (R)-I-3 | II-50 |
| Br-199 | (R)-I-4 | II-50 |
| Br-200 | (R)-I-5 | II-50 |
| Br-201 | (R)-I-1 | II-51 |
| Br-202 | (R)-I-3 | II-51 |
| Br-203 | (R)-I-4 | II-51 |
| Br-204 | (R)-I-5 | II-51 |
| Br-205 | (R)-I-1 | II-52 |
| Br-206 | (R)-I-3 | II-52 |
| Br-207 | (R)-I-4 | II-52 |
| Br-208 | (R)-I-5 | II-52 |
| Br-209 | (R)-I-1 | II-53 |
| Br-210 | (R)-I-3 | II-53 |
| Br-211 | (R)-I-4 | II-53 |
| Br-212 | (R)-I-5 | II-53 |
| Br-213 | (R)-I-1 | II-54 |
| Br-214 | (R)-I-3 | II-54 |
| Br-215 | (R)-I-4 | II-54 |
| Br-216 | (R)-I-5 | II-54 |
| Br-217 | (R)-I-1 | II-55 |
| Br-218 | (R)-I-3 | II-55 |
| Br-219 | (R)-I-4 | II-55 |
| Br-220 | (R)-I-5 | II-55 |
| Br-221 | (R)-I-1 | II-56 |
| Br-222 | (R)-I-3 | II-56 |
| Br-223 | (R)-I-4 | II-56 |
| Br-224 | (R)-I-5 | II-56 |
| Br-225 | (R)-I-1 | II-57 |
| Br-226 | (R)-I-3 | II-57 |
| Br-227 | (R)-I-4 | II-57 |
| Br-228 | (R)-I-5 | II-57 |
| Br-229 | (R)-I-1 | II-58 |
| Br-230 | (R)-I-3 | II-58 |
| Br-231 | (R)-I-4 | II-58 |
| Br-232 | (R)-I-5 | II-58 |
| Br-233 | (R)-I-1 | II-59 |
| Br-234 | (R)-I-3 | II-59 |
| Br-235 | (R)-I-4 | II-59 |
| Br-236 | (R)-I-5 | II-59 |
| Br-237 | (R)-I-1 | II-60 |
| Br-238 | (R)-I-3 | II-60 |
| Br-239 | (R)-I-4 | II-60 |
| Br-240 | (R)-I-5 | II-60 |
| Br-241 | (R)-I-1 | II-61 |
| Br-242 | (R)-I-3 | II-61 |
| Br-243 | (R)-I-4 | II-61 |
| Br-244 | (R)-I-5 | II-61 |
| Br-245 | (R)-I-1 | II-62 |
| Br-246 | (R)-I-3 | II-62 |
| Br-247 | (R)-I-4 | II-62 |
| Br-248 | (R)-I-5 | II-62 |
| Br-249 | (R)-I-1 | II-63 |
| Br-250 | (R)-I-3 | II-63 |
| Br-251 | (R)-I-4 | II-63 |
| Br-252 | (R)-I-5 | II-63 |
| Br-253 | (R)-I-1 | II-64 |
| Br-254 | (R)-I-3 | II-64 |
| Br-255 | (R)-I-4 | II-64 |
| Br-256 | (R)-I-5 | II-64 |
| Br-257 | (R)-I-1 | II-65 |
| Br-258 | (R)-I-3 | II-65 |
| Br-259 | (R)-I-4 | II-65 |
| Br-260 | (R)-I-5 | II-65 |
| Br-261 | (R)-I-1 | II-66 |
| Br-262 | (R)-I-3 | II-66 |
| Br-263 | (R)-I-4 | II-66 |
| Br-264 | (R)-I-5 | II-66 |
| Br-265 | (R)-I-1 | II-67 |
| Br-266 | (R)-I-3 | II-67 |
| Br-267 | (R)-I-4 | II-67 |
| Br-268 | (R)-I-5 | II-67 |
| Br-269 | (R)-I-1 | II-68 |
| Br-270 | (R)-I-3 | II-68 |
| Br-271 | (R)-I-4 | II-68 |
| Br-272 | (R)-I-5 | II-68 |
| Br-273 | (R)-I-1 | II-69 |
| Br-274 | (R)-I-3 | II-69 |
| Br-275 | (R)-I-4 | II-69 |
| Br-276 | (R)-I-5 | II-69 |
| Br-277 | (R)-I-1 | II-70 |
| Br-278 | (R)-I-3 | II-70 |
| Br-279 | (R)-I-4 | II-70 |
| Br-280 | (R)-I-5 | II-70 |
| Br-281 | (R)-I-1 | II-71 |
| Br-282 | (R)-I-3 | II-71 |
| Br-283 | (R)-I-4 | II-71 |
| Br-284 | (R)-I-5 | II-71 |

TABLE Br-continued

Two-component compositions comprising one component I as (R) enantiomer (appreviated as (R)-I, e.g. (R)-I-1 for the (R)-enantiomer of I-1) and one component II, in particular binary compositions containing the respective component I as (R) enantiomer and as only active ingredients.

| composition | (R)-I | II |
|---|---|---|
| Br-285 | (R)-I-1 | II-72 |
| Br-286 | (R)-I-3 | II-72 |
| Br-287 | (R)-I-4 | II-72 |
| Br-288 | (R)-I-5 | II-72 |
| Br-289 | (R)-I-1 | II-73 |
| Br-290 | (R)-I-3 | II-73 |
| Br-291 | (R)-I-4 | II-73 |
| Br-292 | (R)-I-5 | II-73 |
| Br-293 | (R)-I-1 | II-74 |
| Br-294 | (R)-I-3 | II-74 |
| Br-295 | (R)-I-4 | II-74 |
| Br-296 | (R)-I-5 | II-74 |
| Br-297 | (R)-I-1 | II-75 |
| Br-298 | (R)-I-3 | II-75 |
| Br-299 | (R)-I-4 | II-75 |
| Br-300 | (R)-I-5 | II-75 |
| Br-301 | (R)-I-1 | II-76 |
| Br-302 | (R)-I-3 | II-76 |
| Br-303 | (R)-I-4 | II-76 |
| Br-304 | (R)-I-5 | II-76 |
| Br-305 | (R)-I-1 | II-77 |
| Br-306 | (R)-I-3 | II-77 |
| Br-307 | (R)-I-4 | II-77 |
| Br-308 | (R)-I-5 | II-77 |
| Br-309 | (R)-I-1 | II-78 |
| Br-310 | (R)-I-3 | II-78 |
| Br-311 | (R)-I-4 | II-78 |
| Br-312 | (R)-I-5 | II-78 |
| Br-313 | (R)-I-1 | II-79 |
| Br-314 | (R)-I-3 | II-79 |
| Br-315 | (R)-I-4 | II-79 |
| Br-316 | (R)-I-5 | II-79 |
| Br-317 | (R)-I-1 | II-80 |
| Br-318 | (R)-I-3 | II-80 |
| Br-319 | (R)-I-4 | II-80 |
| Br-320 | (R)-I-5 | II-80 |
| Br-321 | (R)-I-1 | II-81 |
| Br-322 | (R)-I-3 | II-81 |
| Br-323 | (R)-I-4 | II-81 |
| Br-324 | (R)-I-5 | II-81 |
| Br-325 | (R)-I-1 | II-82 |
| Br-326 | (R)-I-3 | II-82 |
| Br-327 | (R)-I-4 | II-82 |
| Br-328 | (R)-I-5 | II-82 |
| Br-329 | (R)-I-1 | II-83 |
| Br-330 | (R)-I-3 | II-83 |
| Br-331 | (R)-I-4 | II-83 |
| Br-332 | (R)-I-5 | II-83 |
| Br-333 | (R)-I-1 | II-84 |
| Br-334 | (R)-I-3 | II-84 |
| Br-335 | (R)-I-4 | II-84 |
| Br-336 | (R)-I-5 | II-84 |
| Br-337 | (R)-I-1 | II-85 |
| Br-338 | (R)-I-3 | II-85 |
| Br-339 | (R)-I-4 | II-85 |
| Br-340 | (R)-I-5 | II-85 |
| Br-341 | (R)-I-1 | II-86 |
| Br-342 | (R)-I-3 | II-86 |
| Br-343 | (R)-I-4 | II-86 |
| Br-344 | (R)-I-5 | II-86 |
| Br-345 | (R)-I-1 | II-87 |
| Br-346 | (R)-I-3 | II-87 |
| Br-347 | (R)-I-4 | II-87 |
| Br-348 | (R)-I-5 | II-87 |
| Br-349 | (R)-I-1 | II-88 |
| Br-350 | (R)-I-3 | II-88 |
| Br-351 | (R)-I-4 | II-88 |
| Br-352 | (R)-I-5 | II-88 |
| Br-353 | (R)-I-1 | II-89 |
| Br-354 | (R)-I-3 | II-89 |
| Br-355 | (R)-I-4 | II-89 |
| Br-356 | (R)-I-5 | II-89 |
| Br-357 | (R)-I-1 | II-90 |
| Br-358 | (R)-I-3 | II-90 |
| Br-359 | (R)-I-4 | II-90 |
| Br-360 | (R)-I-5 | II-90 |
| Br-361 | (R)-I-1 | II-91 |
| Br-362 | (R)-I-3 | II-91 |
| Br-363 | (R)-I-4 | II-91 |
| Br-364 | (R)-I-5 | II-91 |
| Br-365 | (R)-I-1 | II-92 |
| Br-366 | (R)-I-3 | II-92 |
| Br-367 | (R)-I-4 | II-92 |
| Br-368 | (R)-I-5 | II-92 |
| Br-369 | (R)-I-1 | II-93 |
| Br-370 | (R)-I-3 | II-93 |
| Br-371 | (R)-I-4 | II-93 |
| Br-372 | (R)-I-5 | II-93 |
| Br-373 | (R)-I-1 | II-94 |
| Br-374 | (R)-I-3 | II-94 |
| Br-375 | (R)-I-4 | II-94 |
| Br-376 | (R)-I-5 | II-94 |
| Br-377 | (R)-I-1 | II-95 |
| Br-378 | (R)-I-3 | II-95 |
| Br-379 | (R)-I-4 | II-95 |
| Br-380 | (R)-I-5 | II-95 |
| Br-381 | (R)-I-1 | II-96 |
| Br-382 | (R)-I-3 | II-96 |
| Br-383 | (R)-I-4 | II-96 |
| Br-384 | (R)-I-5 | II-96 |
| Br-385 | (R)-I-1 | II-97 |
| Br-386 | (R)-I-3 | II-97 |
| Br-387 | (R)-I-4 | II-97 |
| Br-388 | (R)-I-5 | II-97 |
| Br-389 | (R)-I-1 | II-98 |
| Br-390 | (R)-I-3 | II-98 |
| Br-391 | (R)-I-4 | II-98 |
| Br-392 | (R)-I-5 | II-98 |
| Br-393 | (R)-I-1 | II-99 |
| Br-394 | (R)-I-3 | II-99 |
| Br-395 | (R)-I-4 | II-99 |
| Br-396 | (R)-I-5 | II-99 |
| Br-397 | (R)-I-1 | II-100 |
| Br-398 | (R)-I-3 | II-100 |
| Br-399 | (R)-I-4 | II-100 |
| Br-400 | (R)-I-5 | II-100 |
| Br-401 | (R)-I-1 | II-101 |
| Br-402 | (R)-I-3 | II-101 |
| Br-403 | (R)-I-4 | II-101 |
| Br-404 | (R)-I-5 | II-101 |
| Br-405 | (R)-I-1 | II-102 |
| Br-406 | (R)-I-3 | II-102 |
| Br-407 | (R)-I-4 | II-102 |
| Br-408 | (R)-I-5 | II-102 |
| Br-409 | (R)-I-13 | II-1 |
| Br-410 | (R)-I-13 | II-2 |
| Br-411 | (R)-I-13 | II-3 |
| Br-412 | (R)-I-13 | II-4 |
| Br-413 | (R)-I-13 | II-5 |
| Br-414 | (R)-I-13 | II-6 |
| Br-415 | (R)-I-13 | II-7 |
| Br-416 | (R)-I-13 | II-8 |
| Br-417 | (R)-I-13 | II-9 |
| Br-418 | (R)-I-13 | II-10 |
| Br-419 | (R)-I-13 | II-11 |
| Br-420 | (R)-I-13 | II-12 |
| Br-421 | (R)-I-13 | II-13 |
| Br-422 | (R)-I-13 | II-14 |
| Br-423 | (R)-I-13 | II-15 |
| Br-424 | (R)-I-13 | II-16 |
| Br-425 | (R)-I-13 | II-17 |
| Br-426 | (R)-I-13 | II-18 |

TABLE Br-continued

Two-component compositions comprising one component I as (R) enantiomer (appreviated as (R)-I, e.g. (R)-I-1 for the (R)-enantiomer of I-1) and one component II, in particular binary compositions containing the respective component I as (R) enantiomer and as only active ingredients.

| composition | (R)-I | II |
| --- | --- | --- |
| Br-427 | (R)-I-13 | II-19 |
| Br-428 | (R)-I-13 | II-20 |
| Br-429 | (R)-I-13 | II-21 |
| Br-430 | (R)-I-13 | II-22 |
| Br-431 | (R)-I-13 | II-23 |
| Br-432 | (R)-I-13 | II-24 |
| Br-433 | (R)-I-13 | II-25 |
| Br-434 | (R)-I-13 | II-26 |
| Br-435 | (R)-I-13 | II-27 |
| Br-436 | (R)-I-13 | II-28 |
| Br-437 | (R)-I-13 | II-29 |
| Br-438 | (R)-I-13 | II-30 |
| Br-439 | (R)-I-13 | II-31 |
| Br-440 | (R)-I-13 | II-32 |
| Br-441 | (R)-I-13 | II-33 |
| Br-442 | (R)-I-13 | II-34 |
| Br-443 | (R)-I-13 | II-35 |
| Br-444 | (R)-I-13 | II-36 |
| Br-445 | (R)-I-13 | II-37 |
| Br-446 | (R)-I-13 | II-38 |
| Br-447 | (R)-I-13 | II-39 |
| Br-448 | (R)-I-13 | II-40 |
| Br-449 | (R)-I-13 | II-41 |
| Br-450 | (R)-I-13 | II-42 |
| Br-451 | (R)-I-13 | II-43 |
| Br-452 | (R)-I-13 | II-44 |
| Br-453 | (R)-I-13 | II-45 |
| Br-454 | (R)-I-13 | II-46 |
| Br-455 | (R)-I-13 | II-47 |
| Br-456 | (R)-I-13 | II-48 |
| Br-457 | (R)-I-13 | II-49 |
| Br-458 | (R)-I-13 | II-50 |
| Br-459 | (R)-I-13 | II-51 |
| Br-460 | (R)-I-13 | II-52 |
| Br-461 | (R)-I-13 | II-53 |
| Br-462 | (R)-I-13 | II-54 |
| Br-463 | (R)-I-13 | II-55 |
| Br-464 | (R)-I-13 | II-56 |
| Br-465 | (R)-I-13 | II-57 |
| Br-466 | (R)-I-13 | II-58 |
| Br-467 | (R)-I-13 | II-59 |
| Br-468 | (R)-I-13 | II-60 |
| Br-469 | (R)-I-13 | II-61 |
| Br-470 | (R)-I-13 | II-62 |
| Br-471 | (R)-I-13 | II-63 |
| Br-472 | (R)-I-13 | II-64 |
| Br-473 | (R)-I-13 | II-65 |
| Br-474 | (R)-I-13 | II-66 |
| Br-475 | (R)-I-13 | II-67 |
| Br-476 | (R)-I-13 | II-68 |
| Br-477 | (R)-I-13 | II-69 |
| Br-478 | (R)-I-13 | II-70 |
| Br-479 | (R)-I-13 | II-71 |
| Br-480 | (R)-I-13 | II-72 |
| Br-481 | (R)-I-13 | II-73 |
| Br-482 | (R)-I-13 | II-74 |
| Br-483 | (R)-I-13 | II-75 |
| Br-484 | (R)-I-13 | II-76 |
| Br-485 | (R)-I-13 | II-77 |
| Br-486 | (R)-I-13 | II-78 |
| Br-487 | (R)-I-13 | II-79 |
| Br-488 | (R)-I-13 | II-80 |
| Br-489 | (R)-I-13 | II-81 |
| Br-490 | (R)-I-13 | II-82 |
| Br-491 | (R)-I-13 | II-83 |
| Br-492 | (R)-I-13 | II-84 |
| Br-493 | (R)-I-13 | II-85 |
| Br-494 | (R)-I-13 | II-86 |
| Br-495 | (R)-I-13 | II-87 |
| Br-496 | (R)-I-13 | II-88 |
| Br-497 | (R)-I-13 | II-89 |
| Br-498 | (R)-I-13 | II-90 |
| Br-499 | (R)-I-13 | II-91 |
| Br-500 | (R)-I-13 | II-92 |
| Br-501 | (R)-I-13 | II-93 |
| Br-502 | (R)-I-13 | II-94 |
| Br-503 | (R)-I-13 | II-95 |
| Br-504 | (R)-I-13 | II-96 |
| Br-505 | (R)-I-13 | II-97 |
| Br-506 | (R)-I-13 | II-98 |
| Br-507 | (R)-I-13 | II-99 |
| Br-508 | (R)-I-13 | II-100 |
| Br-509 | (R)-I-13 | II-101 |
| Br-510 | (R)-I-13 | II-102 |

According to a further embodiment, component II is selected from the following fungicides:

| | |
| --- | --- |
| II-3 | azoxystrobin |
| II-5 | benzovindiflupyr |
| II-6 | bixafen |
| II-7 | boscalid |
| II-8 | carbendazim |
| II-11 | chlorothalonil |
| II-16 | cyprodinil |
| II-21 | difenoconazole |
| II-26 | epoxiconazole |
| II-32 | fenpropimorph |
| II-33 | fluazinam |
| II-37 | fluoxastrobin |
| II-39 | flusilazole |
| II-42 | fluxapyroxad |
| II-44 | fosetyl-Al |
| II-50 | isopyrazam |
| II-53 | kresoxim-methyl |
| II-60 | metconazole |
| II-62 | metrafenone |
| II-66 | pyraclostrobin |
| II-69 | phosporous acid |
| II-70 | potassium salt of phosphorous acid |
| II-71 | sodium salt of phosphorous acid |
| II-72 | penthiopyrad |
| II-74 | prochloraz |
| II-76 | propiconazole |
| II-78 | prothioconazole |
| II-84 | spiroxamine |
| II-85 | sulfur |
| II-86 | tebuconazole |
| II-92 | trifloxystrobin |
| II-98 | 2,6-dimethyl-1H,5H-[1,4]dithiino[2,3-c:5,6-c']dipyrrole-1,3,5,7(2H,6H)-tetraone |

According to still a further embodiment, component II is selected from the following fungicides:

| | |
| --- | --- |
| II-5 | benzovindiflupyr |
| II-6 | bixafen |
| II-7 | boscalid |
| II-8 | carbendazim |
| II-11 | chlorothalonil |
| II-16 | cyprodinil |
| II-21 | difenoconazole |

-continued

| | |
|---|---|
| II-26 | epoxiconazole |
| II-32 | fenpropimorph |
| II-33 | fluazinam |
| II-37 | fluoxastrobin |
| II-42 | fluxapyroxad |
| II-44 | fosetyl-Al |
| II-53 | kresoxim-methyl |
| II-60 | metconazole |
| II-62 | metrafenone |
| II-72 | penthiopyrad |
| II-74 | prochloraz |
| II-76 | propiconazole |
| II-78 | prothioconazole |
| II-69 | phosporous acid |
| II-70 | potassium salt of phosphorous acid |
| II-71 | sodium salt of phosphorous acid |
| II-66 | pyraclostrobin |
| II-84 | spiroxamine |
| II-85 | sulfur |
| II-86 | tebuconazole |
| II-92 | trifloxystrobin |
| II-98 | 2,6-dimethyl-1H,5H-[1,4]dithiino[2,3-c:5,6-c']dipyrrole-1,3,5,7(2H,6H)-tetraone |

According to a further preferred embodiment of the invention, component II is selected from the following growth regulators:

| | |
|---|---|
| II-1a | mepiquat chloride |
| II-2a | chlormequat chloride |
| II-3a | trinexapac-ethyl |
| II-4a | prohexadione-calcium |
| II-5a | ethophon |

Consequently, particularly preferred two-component compositions are compiled in Table B3, wherein each row corresponds to one embodiment of the compositions according to the invention. According to one specific aspect, these are binary compositions which each only contain these two components as the active compounds. Furthermore, also every combination of the compositions individualized in this table represent embodiments of the present invention.

TABLE B3

Two-component compositions comprising one component I and one growth regulator as component II, in particular binary compositions containing the respective component I and II as only active ingredients.

| composition | I | II |
|---|---|---|
| B3-1 | I-1 | II-1a |
| B3-2 | I-2 | II-1a |
| B3-3 | I-3 | II-1a |
| B3-4 | I-4 | II-1a |
| B3-5 | I-5 | II-1a |
| B3-6 | I-6 | II-1a |
| B3-7 | I-7 | II-1a |
| B3-8 | I-8 | II-1a |
| B3-9 | I-9 | II-1a |
| B3-10 | I-10 | II-1a |
| B3-11 | I-11 | II-1a |
| B3-12 | I-12 | II-1a |
| B3-13 | I-13 | II-1a |
| B3-14 | I-14 | II-1a |
| B3-15 | I-15 | II-1a |
| B3-16 | I-16 | II-1a |
| B3-17 | | |
| B3-18 | | |
| B3-19 | I-1 | II-2a |
| B3-20 | I-2 | II-2a |
| B3-21 | I-3 | II-2a |
| B3-22 | I-4 | II-2a |
| B3-23 | I-5 | II-2a |
| B3-24 | I-6 | II-2a |
| B3-25 | I-7 | II-2a |
| B3-26 | I-8 | II-2a |
| B3-27 | I-9 | II-2a |
| B3-28 | I-10 | II-2a |
| B3-29 | I-11 | II-2a |
| B3-30 | I-12 | II-2a |
| B3-31 | I-13 | II-2a |
| B3-32 | I-14 | II-2a |
| B3-33 | I-15 | II-2a |
| B3-34 | I-16 | II-2a |
| B3-35 | | |
| B3-36 | | |
| B3-37 | I-1 | II-3a |
| B3-38 | I-2 | II-3a |
| B3-39 | I-3 | II-3a |
| B3-40 | I-4 | II-3a |
| B3-41 | I-5 | II-3a |
| B3-42 | I-6 | II-3a |
| B3-43 | I-7 | II-3a |
| B3-44 | I-8 | II-3a |
| B3-45 | I-9 | II-3a |
| B3-46 | I-10 | II-3a |
| B3-47 | I-11 | II-3a |
| B3-48 | I-12 | II-3a |
| B3-49 | I-13 | II-3a |
| B3-50 | I-14 | II-3a |
| B3-51 | I-15 | II-3a |
| B3-52 | I-16 | II-3a |
| B3-53 | | |
| B3-54 | | |
| B3-55 | I-1 | II-4a |
| B3-56 | I-2 | II-4a |
| B3-57 | I-3 | II-4a |
| B3-58 | I-4 | II-4a |
| B3-59 | I-5 | II-4a |
| B3-60 | I-6 | II-4a |
| B3-61 | I-7 | II-4a |
| B3-62 | I-8 | II-4a |
| B3-63 | I-9 | II-4a |
| B3-64 | I-10 | II-4a |
| B3-65 | I-11 | II-4a |
| B3-66 | I-12 | II-4a |
| B3-67 | I-13 | II-4a |
| B3-68 | I-14 | II-4a |
| B3-69 | I-15 | II-4a |
| B3-70 | I-16 | II-4a |
| B3-71 | | |
| B3-72 | | |
| B3-73 | I-1 | II-5a |
| B3-74 | I-2 | II-5a |
| B3-75 | I-3 | II-5a |
| B3-76 | I-4 | II-5a |
| B3-77 | I-5 | II-5a |
| B3-78 | I-6 | II-5a |
| B3-79 | I-7 | II-5a |
| B3-80 | I-8 | II-5a |
| B3-81 | I-9 | II-5a |
| B3-82 | I-10 | II-5a |
| B3-83 | I-11 | II-5a |
| B3-84 | I-12 | II-5a |

TABLE B3-continued

Two-component compositions comprising one component
I and one growth regulator as component II, in particular
binary compositions containing the respective component
I and II as only active ingredients.

| composition | I | II |
|---|---|---|
| B3-85 | I-13 | II-5a |
| B3-86 | I-14 | II-5a |
| B3-87 | I-15 | II-5a |
| B3-88 | I-16 | II-5a |
| B3-89 | | |
| B3-90 | | |

As detailed above, the components I contain chirality centers and may, therefore, be present as racemic mixtures, as pure enantiomers or in the two enantiomers of one component I may be present in any ratio (S):(R).

According to particular embodiments of the invention, the respective component I is present as (S) enantiomer. Specific two-component compositions comprising the (S) enantiomer of the respective component I are compiled in Table B3s, wherein each row corresponds to one embodiment of the compositions according to the invention, i.e. one specific individualized composition. According to one specific aspect, these are binary compositions which each only contain these two components as active compounds. Furthermore, also every combination of the compositions individualized in this table represent embodiments of the present invention.

TABLE B3s

Two-component compositions comprising one component I as
(S) enantiomer (apprevriated as (S)-I, e.g. (S)-I-1 for the
(S)-enantiomer of I-1) and one component II, in particular
binary compositions containing the respective component I
as (S) enantiomer and II as only active ingredients.

| composition | (S)-I | II |
|---|---|---|
| B3s-1 | (S)-I-1 | II-1a |
| B3s-2 | (S)-I-3 | II-1a |
| B3s-3 | (S)-I-4 | II-1a |
| B3s-4 | (S)-I-5 | II-1a |
| B3s-5 | (S)-I-13 | II-1a |
| B3s-6 | (S)-I-1 | II-2a |
| B3s-7 | (S)-I-3 | II-2a |
| B3s-8 | (S)-I-4 | II-2a |
| B3s-9 | (S)-I-5 | II-2a |
| B3s-10 | (S)-I-13 | II-2a |
| B3s-11 | (S)-I-1 | II-3a |
| B3s-12 | (S)-I-3 | II-3a |
| B3s-13 | (S)-I-4 | II-3a |
| B3s-14 | (S)-I-5 | II-3a |
| B3s-15 | (S)-I-13 | II-3a |
| B3s-16 | (S)-I-1 | II-4a |
| B3s-17 | (S)-I-3 | II-4a |
| B3s-18 | (S)-I-4 | II-4a |
| B3s-19 | (S)-I-5 | II-4a |
| B3s-20 | (S)-I-13 | II-4a |
| B3s-21 | (S)-I-1 | II-5a |
| B3s-22 | (S)-I-3 | II-5a |
| B3s-23 | (S)-I-4 | II-5a |
| B3s-24 | (S)-I-5 | II-5a |
| B3s-25 | (S)-I-13 | II-5a |

According to particular embodiments of the invention, the respective component I is present as (R) enantiomer. Specific two-component compositions comprising the (R) enantiomer of the respective component I are compiled in Table B3r, wherein each row corresponds to one embodiment of the compositions according to the invention, i.e. one specific individualized composition. According to one specific aspect, these are binary compositions which each only contain these two components as active compounds. Furthermore, also every combination of the compositions individualized in this table represent embodiments of the present invention.

TABLE B3r

Two-component compositions comprising one component I as
(R) enantiomer (appreviated as (R)-I, e.g. (R)-I-1 for the
(R)-enantiomer of I-1) and one component II, in particular
binary compositions containing the respective component I
as (R) enantiomer and II as only active ingredients.

| composition | (R)-I | II |
|---|---|---|
| B3s-26 | (R)-I-1 | II-1a |
| B3s-27 | (R)-I-3 | II-1a |
| B3s-28 | (R)-I-4 | II-1a |
| B3s-29 | (R)-I-5 | II-1a |
| B3s-30 | (R)-I-13 | II-1a |
| B3s-31 | (R)-I-1 | II-2a |
| B3s-32 | (R)-I-3 | II-2a |
| B3s-33 | (R)-I-4 | II-2a |
| B3s-34 | (R)-I-5 | II-2a |
| B3s-35 | (R)-I-13 | II-2a |
| B3s-36 | (R)-I-1 | II-3a |
| B3s-37 | (R)-I-3 | II-3a |
| B3s-38 | (R)-I-4 | II-3a |
| B3s-39 | (R)-I-5 | II-3a |
| B3s-40 | (R)-I-13 | II-3a |
| B3s-41 | (R)-I-1 | II-4a |
| B3s-42 | (R)-I-3 | II-4a |
| B3s-43 | (R)-I-4 | II-4a |
| B3s-44 | (R)-I-5 | II-4a |
| B3s-45 | (R)-I-13 | II-4a |
| B3s-46 | (R)-I-1 | II-5a |
| B3s-47 | (R)-I-3 | II-5a |
| B3s-48 | (R)-I-4 | II-5a |
| B3s-49 | (R)-I-5 | II-5a |
| B3s-50 | (R)-I-13 | II-5a |

According to a further preferred embodiment of the invention, component II is selected from the following herbicides:

| | |
|---|---|
| II-1b | glyphosate |
| II-2b | imazamox |
| II-3b | dicamba |
| II-4b | glufosinate |
| II-5b | imazapic |
| II-6b | imazapyr |
| II-7b | imazethapyr |

Consequently, particularly preferred two-component compositions are compiled in Table B4, wherein each row corresponds to one embodiment of the compositions according to the invention, i.e. one specific individualized composition. According to one specific aspect, these are binary compositions which each only contain these two components as the active compounds. Furthermore, also every combination of the compositions individualized in this table represent embodiments of the present invention.

TABLE B4

Two-component compositions comprising one component I and one herbicide as component II, in particular binary compositions containing the respective component I and II as only active ingredients.

| composition | I | II |
|---|---|---|
| B4-1 | I-1 | II-1b |
| B4-2 | I-2 | II-1b |
| B4-3 | I-3 | II-1b |
| B4-4 | I-4 | II-1b |
| B4-5 | I-5 | II-1b |
| B4-6 | I-6 | II-1b |
| B4-7 | I-7 | II-1b |
| B4-8 | I-8 | II-1b |
| B4-9 | I-9 | II-1b |
| B4-10 | I-10 | II-1b |
| B4-11 | I-11 | II-1b |
| B4-12 | I-12 | II-1b |
| B4-13 | I-13 | II-1b |
| B4-14 | I-14 | II-1b |
| B4-15 | I-15 | II-1b |
| B4-16 | I-16 | II-1b |
| B4-17 | | |
| B4-18 | | |
| B4-19 | I-1 | II-2b |
| B4-20 | I-2 | II-2b |
| B4-21 | I-3 | II-2b |
| B4-22 | I-4 | II-2b |
| B4-23 | I-5 | II-2b |
| B4-24 | I-6 | II-2b |
| B4-25 | I-7 | II-2b |
| B4-26 | I-8 | II-2b |
| B4-27 | I-9 | II-2b |
| B4-28 | I-10 | II-2b |
| B4-29 | I-11 | II-2b |
| B4-30 | I-12 | II-2b |
| B4-31 | I-13 | II-2b |
| B4-32 | I-14 | II-2b |
| B4-33 | I-15 | II-2b |
| B4-34 | I-16 | II-2b |
| B4-35 | | |
| B4-36 | | |
| B4-37 | I-1 | II-3b |
| B4-38 | I-2 | II-3b |
| B4-39 | I-3 | II-3b |
| B4-40 | I-4 | II-3b |
| B4-41 | I-5 | II-3b |
| B4-42 | I-6 | II-3b |
| B4-43 | I-7 | II-3b |
| B4-44 | I-8 | II-3b |
| B4-45 | I-9 | II-3b |
| B4-46 | I-10 | II-3b |
| B4-47 | I-11 | II-3b |
| B4-48 | I-12 | II-3b |
| B4-49 | I-13 | II-3b |
| B4-50 | I-14 | II-3b |
| B4-51 | I-15 | II-3b |
| B4-52 | I-16 | II-3b |
| B4-53 | | |
| B4-54 | | |
| B4-55 | I-1 | II-4b |
| B4-56 | I-2 | II-4b |
| B4-57 | I-3 | II-4b |
| B4-58 | I-4 | II-4b |
| B4-59 | I-5 | II-4b |
| B4-60 | I-6 | II-4b |
| B4-61 | I-7 | II-4b |
| B4-62 | I-8 | II-4b |
| B4-63 | I-9 | II-4b |
| B4-64 | I-10 | II-4b |
| B4-65 | I-11 | II-4b |
| B4-66 | I-12 | II-4b |
| B4-67 | I-13 | II-4b |
| B4-68 | I-14 | II-4b |
| B4-69 | I-15 | II-4b |
| B4-70 | I-16 | II-4b |
| B4-71 | | |
| B4-72 | | |
| B4-73 | I-1 | II-5b |
| B4-74 | I-2 | II-5b |
| B4-75 | I-3 | II-5b |
| B4-76 | I-4 | II-5b |
| B4-77 | I-5 | II-5b |
| B4-78 | I-6 | II-5b |
| B4-79 | I-7 | II-5b |
| B4-80 | I-8 | II-5b |
| B4-81 | I-9 | II-5b |
| B4-82 | I-10 | II-5b |
| B4-83 | I-11 | II-5b |
| B4-84 | I-12 | II-5b |
| B4-85 | I-13 | II-5b |
| B4-86 | I-14 | II-5b |
| B4-87 | I-15 | II-5b |
| B4-88 | I-16 | II-5b |
| B4-89 | | |
| B4-90 | | |
| B4-91 | I-1 | II-6b |
| B4-92 | I-2 | II-6b |
| B4-93 | I-3 | II-6b |
| B4-94 | I-4 | II-6b |
| B4-95 | I-5 | II-6b |
| B4-96 | I-6 | II-6b |
| B4-97 | I-7 | II-6b |
| B4-98 | I-8 | II-6b |
| B4-99 | I-9 | II-6b |
| B4-100 | I-10 | II-6b |
| B4-101 | I-11 | II-6b |
| B4-102 | I-12 | II-6b |
| B4-103 | I-13 | II-6b |
| B4-104 | I-14 | II-6b |
| B4-105 | I-15 | II-6b |
| B4-106 | I-16 | II-6b |
| B4-107 | | |
| B4-108 | | |
| B4-109 | I-1 | II-7b |
| B4-110 | I-2 | II-7b |
| B4-111 | I-3 | II-7b |
| B4-112 | I-4 | II-7b |
| B4-113 | I-5 | II-7b |
| B4-114 | I-6 | II-7b |
| B4-115 | I-7 | II-7b |
| B4-116 | I-8 | II-7b |
| B4-117 | I-9 | II-7b |
| B4-118 | I-10 | II-7b |
| B4-119 | I-11 | II-7b |
| B4-120 | I-12 | II-7b |
| B4-121 | I-13 | II-7b |
| B4-122 | I-14 | II-7b |
| B4-123 | I-15 | II-7b |
| B4-124 | I-16 | II-7b |
| B4-125 | | |
| B4-126 | | |

As detailed above, the components I contain chirality centers and may, therefore, be present as racemic mixtures, as pure enantiomers or in the two enantiomers of one component I may be present in any ratio (S):(R).

According to particular embodiments of the invention, the respective component I is present as (S) enantiomer. Specific two-component compositions comprising the (S) enantiomer of the respective component I are compiled in Table B4s, wherein each row corresponds to one embodiment of the compositions according to the invention, i.e. one specific individualized composition. According to one specific aspect, these are binary compositions which each only contain these two components as active compounds. Furthermore, also every combination of the compositions individualized in this table represent embodiments of the present invention.

TABLE B4s

Two-component compositions comprising one component I as (S) enantiomer (appreviated as (S)-I, e.g. (S)-I-1 for the (S)-enantiomer of I-1) and one component II, in particular binary compositions containing the respective component I as (S) enantiomer and II as only active ingredients.

| composition | (S)-I | II |
|---|---|---|
| B3s-1 | (S)-I-1 | II-1b |
| B3s-2 | (S)-I-3 | II-1b |
| B3s-3 | (S)-I-4 | II-1b |
| B3s-4 | (S)-I-5 | II-1b |
| B3s-5 | (S)-I-13 | II-1b |
| B3s-6 | (S)-I-1 | II-2b |
| B3s-7 | (S)-I-3 | II-2b |
| B3s-8 | (S)-I-4 | II-2b |
| B3s-9 | (S)-I-5 | II-2b |
| B3s-10 | (S)-I-13 | II-2b |
| B3s-11 | (S)-I-1 | II-3b |
| B3s-12 | (S)-I-3 | II-3b |
| B3s-13 | (S)-I-4 | II-3b |
| B3s-14 | (S)-I-5 | II-3b |
| B3s-15 | (S)-I-13 | II-3b |
| B3s-16 | (S)-I-1 | II-4b |
| B3s-17 | (S)-I-3 | II-4b |
| B3s-18 | (S)-I-4 | II-4b |
| B3s-19 | (S)-I-5 | II-4b |
| B3s-20 | (S)-I-13 | II-4b |
| B3s-21 | (S)-I-1 | II-5b |
| B3s-22 | (S)-I-3 | II-5b |
| B3s-23 | (S)-I-4 | II-5b |
| B3s-24 | (S)-I-5 | II-5b |
| B3s-25 | (S)-I-13 | II-5b |
| B3s-26 | (S)-I-1 | II-6b |
| B3s-27 | (S)-I-3 | II-6b |
| B3s-28 | (S)-I-4 | II-6b |
| B3s-29 | (S)-I-5 | II-6b |
| B3s-30 | (S)-I-13 | II-6b |
| B3s-31 | (S)-I-1 | II-7b |
| B3s-32 | (S)-I-3 | II-7b |
| B3s-33 | (S)-I-4 | II-7b |
| B3s-34 | (S)-I-5 | II-7b |
| B3s-35 | (S)-I-13 | II-7b |

According to particular embodiments of the invention, the respective component I is present as (R) enantiomer. Specific two-component compositions comprising the (R) enantiomer of the respective component I are compiled in Table B4r, wherein each row corresponds to one embodiment of the compositions according to the invention, i.e. one specific individualized composition. According to one specific aspect, these are binary compositions which each only contain these two components as active compounds. Furthermore, also every combination of the compositions individualized in this table represent embodiments of the present invention.

TABLE B4r

Two-component compositions comprising one component I as (R) enantiomer (appreviated as (R)-I, e.g. (R)-I-1 for the (R)-enantiomer of I-1) and one component II, in particular binary compositions containing the respective component I as (R) enantiomer and II as only active ingredients.

| composition | (R)-I | II |
|---|---|---|
| B3s-36 | (R)-I-1 | II-1b |
| B3s-37 | (R)-I-3 | II-1b |
| B3s-38 | (R)-I-4 | II-1b |
| B3s-39 | (R)-I-5 | II-1b |
| B3s-40 | (R)-I-13 | II-1b |
| B3s-41 | (R)-I-1 | II-2b |
| B3s-42 | (R)-I-3 | II-2b |
| B3s-43 | (R)-I-4 | II-2b |
| B3s-44 | (R)-I-5 | II-2b |
| B3s-45 | (R)-I-13 | II-2b |
| B3s-46 | (R)-I-1 | II-3b |
| B3s-47 | (R)-I-3 | II-3b |
| B3s-48 | (R)-I-4 | II-3b |
| B3s-49 | (R)-I-5 | II-3b |
| B3s-50 | (R)-I-13 | II-3b |
| B3s-51 | (R)-I-1 | II-4b |
| B3s-52 | (R)-I-3 | II-4b |
| B3s-53 | (R)-I-4 | II-4b |
| B3s-54 | (R)-I-5 | II-4b |
| B3s-55 | (R)-I-13 | II-4b |
| B3s-56 | (R)-I-1 | II-5b |
| B3s-57 | (R)-I-3 | II-5b |
| B3s-58 | (R)-I-4 | II-5b |
| B3s-59 | (R)-I-5 | II-5b |
| B3s-60 | (R)-I-13 | II-5b |
| B3s-61 | (R)-I-1 | II-6b |
| B3s-62 | (R)-I-3 | II-6b |
| B3s-63 | (R)-I-4 | II-6b |
| B3s-64 | (R)-I-5 | II-6b |
| B3s-65 | (R)-I-13 | II-6b |
| B3s-66 | (R)-I-1 | II-7b |
| B3s-67 | (R)-I-3 | II-7b |
| B3s-68 | (R)-I-4 | II-7b |
| B3s-69 | (R)-I-5 | II-7b |
| B3s-70 | (R)-I-13 | II-7b |

According to a further preferred embodiment of the invention, component II is selected from the following insecticides:

| | |
|---|---|
| II-1c | abamectin |
| II-2c | acephate |
| II-3c | acetamiprid |
| II-4c | aldicarb |
| II-5c | alpha-cypermethrin |
| II-6c | betacyfluthrin |
| II-7c | bifenthrin |
| II-8c | carbofuran |
| II-9c | chlorfenapyr |
| II-10c | chlorpyrifos |
| II-11c | clothianidin |
| II-12c | cyazypyr |
| II-13c | cyflumetofen |
| II-14c | deltamethrin |
| II-15c | dimethoate |
| II-16c | dinotefuran |
| II-17c | endosulfan |
| II-18c | esfenvalerate |
| II-19c | fenbutatin oxide |
| II-20c | fipronil |
| II-21c | flonicamid |
| II-22c | flubendiamide |
| II-23c | hydramethylnon |
| II-24c | imidacloprid |
| II-25c | indoxacarb |
| II-26c | lambda-cyhalothrin |
| II-27c | metaflumizon |
| II-28c | methamidophos |
| II-29c | metoxyfenozide |
| II-30c | nitenpyram |
| II-31c | pirimicarb |
| II-32c | pymetrozine |
| II-33c | pyridabene |
| II-34c | rynaxapyr |
| II-35c | spirotetramat |
| II-36c | spinosad |
| II-37c | spinetoram |
| II-38c | tebufernpyrad |

-continued

| | |
|---|---|
| II-39c | tefluthrin |
| II-40c | terbufos |
| II-41c | thiacloprid |
| II-42c | thiamethoxam |
| II-43c | zetacypermethrin |
| II-44c | [(3S,4R,4aR,6S,6aS,12R,12aS,12bS)-3-(cyclopropanecarbonyloxy)-6,12-dihydroxy-4,6a,12b-trimethyl-11-oxo-9-(pyridin-3-yl)-1,2,3,4,4a,5,6,6a,12a,12b-decahydro-11H,12H-benzo[f]pyrano[4,3-b]chromen-4-yl]methyl cyclopropanecarboxylate. |

According to a more specific embodiment thereof, component II is selected from the following insecticides:

| | |
|---|---|
| II-1c | abamectin |
| II-3c | acetamiprid |
| II-5c | alpha-cypermethrin |
| II-6c | betacyfluthrin |
| II-7c | bifenthrin |
| II-9c | chlorfenapyr |
| II-10c | chlorpyrifos |
| II-11c | clothianidin |
| II-12c | cyazypyr |
| II-13c | cyflumetofen |
| II-14c | deltamethrin |
| II-16c | dinotefuran |
| II-18c | esfenvalerate |
| II-20c | fipronil |
| II-21c | flonicamid |
| II-22c | flubendiamide |
| II-24c | imidacloprid |
| II-25c | indoxacarb |
| II-26c | lambda-cyhalothrin |
| II-27c | metaflumizon |
| II-29c | metoxyfenozide |
| II-30c | nitenpyram |
| II-31c | pirimicarb |
| II-32c | pymetrozine |
| II-33c | pyridaben |
| II-34c | rynaxapyr |
| II-35c | spirotetramat |
| II-36c | spinosad |
| II-37c | spinetoram |
| II-38c | tebufenpyrad |
| II-39c | tefluthrin |
| II-41c | thiacloprid |
| II-42c | thiamethoxam |
| II-43c | zetacypermethrin, and |
| II-44c | [(3S,4R,4aR,6S,6aS,12R,12aS,12bS)-3-(cyclopropanecarbonyloxy)-6,12-dihydroxy-4,6a,12b-trimethyl-11-oxo-9-(pyridin-3-yl)-1,2,3,4,4a,5,6,6a,12a,12b-decahydro-11H,12H-benzo[f]pyrano[4,3-b]chromen-4-yl]methyl cyclopropanecarboxylate. |

Consequently, particularly preferred two-component compositions are compiled in Table B5, wherein each row corresponds to one embodiment of the compositions according to the invention, i.e. one specific individualized composition. According to one specific aspect, these are binary compositions which each only contain these two components as the active compounds. Furthermore, also every combination of the compositions individualized in this table represent embodiments of the present invention.

TABLE B5

Two-component compositions comprising one component I and one insecticide as component II, in particular binary compositions containing the respective component I and II as only active ingredients.

| composition | I | II |
|---|---|---|
| B5-1 | I-1 | II-1c |
| B5-2 | I-2 | II-1c |
| B5-3 | I-3 | II-1c |
| B5-4 | I-4 | II-1c |
| B5-5 | I-5 | II-1c |
| B5-6 | I-6 | II-1c |
| B5-7 | I-7 | II-1c |
| B5-8 | I-8 | II-1c |
| B5-9 | I-9 | II-1c |
| B5-10 | I-10 | II-1c |
| B5-11 | I-11 | II-1c |
| B5-12 | I-12 | II-1c |
| B5-13 | I-13 | II-1c |
| B5-14 | I-14 | II-1c |
| B5-15 | I-15 | II-1c |
| B5-16 | I-16 | II-1c |
| B5-17 | I-1 | II-2c |
| B5-18 | I-2 | II-2c |
| B5-19 | I-3 | II-2c |
| B5-20 | I-4 | II-2c |
| B5-21 | I-5 | II-2c |
| B5-22 | I-6 | II-2c |
| B5-23 | I-7 | II-2c |
| B5-24 | I-8 | II-2c |
| B5-25 | I-9 | II-2c |
| B5-26 | I-10 | II-2c |
| B5-27 | I-11 | II-2c |
| B5-28 | I-12 | II-2c |
| B5-29 | I-13 | II-2c |
| B5-30 | I-14 | II-2c |
| B5-31 | I-15 | II-2c |
| B5-32 | I-16 | II-2c |
| B5-33 | I-1 | II-3c |
| B5-34 | I-2 | II-3c |
| B5-35 | I-3 | II-3c |
| B5-36 | I-4 | II-3c |
| B5-37 | I-5 | II-3c |
| B5-38 | I-6 | II-3c |
| B5-39 | I-7 | II-3c |
| B5-40 | I-8 | II-3c |
| B5-41 | I-9 | II-3c |
| B5-42 | I-10 | II-3c |
| B5-43 | I-11 | II-3c |
| B5-44 | I-12 | II-3c |
| B5-45 | I-13 | II-3c |
| B5-46 | I-14 | II-3c |
| B5-47 | I-15 | II-3c |
| B5-48 | I-16 | II-3c |
| B5-49 | I-1 | II-4c |
| B5-50 | I-2 | II-4c |
| B5-51 | I-3 | II-4c |
| B5-52 | I-4 | II-4c |
| B5-53 | I-5 | II-4c |
| B5-54 | I-6 | II-4c |
| B5-55 | I-7 | II-4c |
| B5-56 | I-8 | II-4c |
| B5-57 | I-9 | II-4c |
| B5-58 | I-10 | II-4c |
| B5-59 | I-11 | II-4c |
| B5-60 | I-12 | II-4c |
| B5-61 | I-13 | II-4c |
| B5-62 | I-14 | II-4c |
| B5-63 | I-15 | II-4c |
| B5-64 | I-16 | II-4c |
| B5-65 | I-1 | II-5c |
| B5-66 | I-2 | II-5c |
| B5-67 | I-3 | II-5c |
| B5-68 | I-4 | II-5c |
| B5-69 | I-5 | II-5c |
| B5-70 | I-6 | II-5c |
| B5-71 | I-7 | II-5c |
| B5-72 | I-8 | II-5c |
| B5-73 | I-9 | II-5c |

TABLE B5-continued

Two-component compositions comprising one component I and one insecticide as component II, in particular binary compositions containing the respective component I and II as only active ingredients.

| composition | I | II |
| --- | --- | --- |
| B5-74 | I-10 | II-5c |
| B5-75 | I-11 | II-5c |
| B5-76 | I-12 | II-5c |
| B5-77 | I-13 | II-5c |
| B5-78 | I-14 | II-5c |
| B5-79 | I-15 | II-5c |
| B5-80 | I-16 | II-5c |
| B5-81 | I-1 | II-6c |
| B5-82 | I-2 | II-6c |
| B5-83 | I-3 | II-6c |
| B5-84 | I-4 | II-6c |
| B5-85 | I-5 | II-6c |
| B5-86 | I-6 | II-6c |
| B5-87 | I-7 | II-6c |
| B5-88 | I-8 | II-6c |
| B5-89 | I-9 | II-6c |
| B5-90 | I-10 | II-6c |
| B5-91 | I-11 | II-6c |
| B5-92 | I-12 | II-6c |
| B5-93 | I-13 | II-6c |
| B5-94 | I-14 | II-6c |
| B5-95 | I-15 | II-6c |
| B5-96 | I-16 | II-6c |
| B5-97 | I-1 | II-7c |
| B5-98 | I-2 | II-7c |
| B5-99 | I-3 | II-7c |
| B5-100 | I-4 | II-7c |
| B5-101 | I-5 | II-7c |
| B5-102 | I-6 | II-7c |
| B5-103 | I-7 | II-7c |
| B5-104 | I-8 | II-7c |
| B5-105 | I-9 | II-7c |
| B5-106 | I-10 | II-7c |
| B5-107 | I-11 | II-7c |
| B5-108 | I-12 | II-7c |
| B5-109 | I-13 | II-7c |
| B5-110 | I-14 | II-7c |
| B5-111 | I-15 | II-7c |
| B5-112 | I-16 | II-7c |
| B5-113 | I-1 | II-8c |
| B5-114 | I-2 | II-8c |
| B5-115 | I-3 | II-8c |
| B5-116 | I-4 | II-8c |
| B5-117 | I-5 | II-8c |
| B5-118 | I-6 | II-8c |
| B5-119 | I-7 | II-8c |
| B5-120 | I-8 | II-8c |
| B5-121 | I-9 | II-8c |
| B5-122 | I-10 | II-8c |
| B5-123 | I-11 | II-8c |
| B5-124 | I-12 | II-8c |
| B5-125 | I-13 | II-8c |
| B5-126 | I-14 | II-8c |
| B5-127 | I-15 | II-8c |
| B5-128 | I-16 | II-8c |
| B5-129 | I-1 | II-9c |
| B5-130 | I-2 | II-9c |
| B5-131 | I-3 | II-9c |
| B5-132 | I-4 | II-9c |
| B5-133 | I-5 | II-9c |
| B5-134 | I-6 | II-9c |
| B5-135 | I-7 | II-9c |
| B5-136 | I-8 | II-9c |
| B5-137 | I-9 | II-9c |
| B5-138 | I-10 | II-9c |
| B5-139 | I-11 | II-9c |
| B5-140 | I-12 | II-9c |
| B5-141 | I-13 | II-9c |
| B5-142 | I-14 | II-9c |
| B5-143 | I-15 | II-9c |
| B5-144 | I-16 | II-9c |
| B5-145 | I-1 | II-10c |
| B5-146 | I-2 | II-10c |
| B5-147 | I-3 | II-10c |
| B5-148 | I-4 | II-10c |
| B5-149 | I-5 | II-10c |
| B5-150 | I-6 | II-10c |
| B5-151 | I-7 | II-10c |
| B5-152 | I-8 | II-10c |
| B5-153 | I-9 | II-10c |
| B5-154 | I-10 | II-10c |
| B5-155 | I-11 | II-10c |
| B5-156 | I-12 | II-10c |
| B5-157 | I-13 | II-10c |
| B5-158 | I-14 | II-10c |
| B5-159 | I-15 | II-10c |
| B5-160 | I-16 | II-10c |
| B5-161 | I-1 | II-11c |
| B5-162 | I-2 | II-11c |
| B5-163 | I-3 | II-11c |
| B5-164 | I-4 | II-11c |
| B5-165 | I-5 | II-11c |
| B5-166 | I-6 | II-11c |
| B5-167 | I-7 | II-11c |
| B5-168 | I-8 | II-11c |
| B5-169 | I-9 | II-11c |
| B5-170 | I-10 | II-11c |
| B5-171 | I-11 | II-11c |
| B5-172 | I-12 | II-11c |
| B5-173 | I-13 | II-11c |
| B5-174 | I-14 | II-11c |
| B5-175 | I-15 | II-11c |
| B5-176 | I-16 | II-11c |
| B5-177 | I-1 | II-12c |
| B5-178 | I-2 | II-12c |
| B5-179 | I-3 | II-12c |
| B5-180 | I-4 | II-12c |
| B5-181 | I-5 | II-12c |
| B5-182 | I-6 | II-12c |
| B5-183 | I-7 | II-12c |
| B5-184 | I-8 | II-12c |
| B5-185 | I-9 | II-12c |
| B5-186 | I-10 | II-12c |
| B5-187 | I-11 | II-12c |
| B5-188 | I-12 | II-12c |
| B5-189 | I-13 | II-12c |
| B5-190 | I-14 | II-12c |
| B5-191 | I-15 | II-12c |
| B5-192 | I-16 | II-12c |
| B5-193 | I-1 | II-13c |
| B5-194 | I-2 | II-13c |
| B5-195 | I-3 | II-13c |
| B5-196 | I-4 | II-13c |
| B5-197 | I-5 | II-13c |
| B5-198 | I-6 | II-13c |
| B5-199 | I-7 | II-13c |
| B5-200 | I-8 | II-13c |
| B5-201 | I-9 | II-13c |
| B5-202 | I-10 | II-13c |
| B5-203 | I-11 | II-13c |
| B5-204 | I-12 | II-13c |
| B5-205 | I-13 | II-13c |
| B5-206 | I-14 | II-13c |
| B5-207 | I-15 | II-13c |
| B5-208 | I-16 | II-13c |
| B5-209 | | |
| B5-210 | | |
| B5-211 | I-1 | II-14c |
| B5-212 | I-2 | II-14c |
| B5-213 | I-3 | II-14c |
| B5-214 | I-4 | II-14c |
| B5-215 | I-5 | II-14c |
| B5-216 | I-6 | II-14c |
| B5-217 | I-7 | II-14c |
| B5-218 | I-8 | II-14c |
| B5-219 | I-9 | II-14c |

TABLE B5-continued

Two-component compositions comprising one component I and one insecticide as component II, in particular binary compositions containing the respective component I and II as only active ingredients.

| composition | I | II |
|---|---|---|
| B5-220 | I-10 | II-14c |
| B5-221 | I-11 | II-14c |
| B5-222 | I-12 | II-14c |
| B5-223 | I-13 | II-14c |
| B5-224 | I-14 | II-14c |
| B5-225 | I-15 | II-14c |
| B5-226 | I-16 | II-14c |
| B5-227 | I-1 | II-15c |
| B5-228 | I-2 | II-15c |
| B5-229 | I-3 | II-15c |
| B5-230 | I-4 | II-15c |
| B5-231 | I-5 | II-15c |
| B5-232 | I-6 | II-15c |
| B5-233 | I-7 | II-15c |
| B5-234 | I-8 | II-15c |
| B5-235 | I-9 | II-15c |
| B5-236 | I-10 | II-15c |
| B5-237 | I-11 | II-15c |
| B5-238 | I-12 | II-15c |
| B5-239 | I-13 | II-15c |
| B5-240 | I-14 | II-15c |
| B5-241 | I-15 | II-15c |
| B5-242 | I-16 | II-15c |
| B5-243 | | |
| B5-244 | | |
| B5-245 | I-1 | II-16c |
| B5-246 | I-2 | II-16c |
| B5-247 | I-3 | II-16c |
| B5-248 | I-4 | II-16c |
| B5-249 | I-5 | II-16c |
| B5-250 | I-6 | II-16c |
| B5-251 | I-7 | II-16c |
| B5-252 | I-8 | II-16c |
| B5-253 | I-9 | II-16c |
| B5-254 | I-10 | II-16c |
| B5-255 | I-11 | II-16c |
| B5-256 | I-12 | II-16c |
| B5-257 | I-13 | II-16c |
| B5-258 | I-14 | II-16c |
| B5-259 | I-15 | II-16c |
| B5-260 | I-16 | II-16c |
| B5-261 | I-1 | II-17c |
| B5-262 | I-2 | II-17c |
| B5-263 | I-3 | II-17c |
| B5-264 | I-4 | II-17c |
| B5-265 | I-5 | II-17c |
| B5-266 | I-6 | II-17c |
| B5-267 | I-7 | II-17c |
| B5-268 | I-8 | II-17c |
| B5-269 | I-9 | II-17c |
| B5-270 | I-10 | II-17c |
| B5-271 | I-11 | II-17c |
| B5-272 | I-12 | II-17c |
| B5-273 | I-13 | II-17c |
| B5-274 | I-14 | II-17c |
| B5-275 | I-15 | II-17c |
| B5-276 | I-16 | II-17c |
| B5-277 | I-1 | II-18c |
| B5-278 | I-2 | II-18c |
| B5-279 | I-3 | II-18c |
| B5-280 | I-4 | II-18c |
| B5-281 | I-5 | II-18c |
| B5-282 | I-6 | II-18c |
| B5-283 | I-7 | II-18c |
| B5-284 | I-8 | II-18c |
| B5-285 | I-9 | II-18c |
| B5-286 | I-10 | II-18c |
| B5-287 | I-11 | II-18c |
| B5-288 | I-12 | II-18c |
| B5-289 | I-13 | II-18c |
| B5-290 | I-14 | II-18c |
| B5-291 | I-15 | II-18c |
| B5-292 | I-16 | II-18c |
| B5-293 | I-1 | II-19c |
| B5-294 | I-2 | II-19c |
| B5-295 | I-3 | II-19c |
| B5-296 | I-4 | II-19c |
| B5-297 | I-5 | II-19c |
| B5-298 | I-6 | II-19c |
| B5-299 | I-7 | II-19c |
| B5-300 | I-8 | II-19c |
| B5-301 | I-9 | II-19c |
| B5-302 | I-10 | II-19c |
| B5-303 | I-11 | II-19c |
| B5-304 | I-12 | II-19c |
| B5-305 | I-13 | II-19c |
| B5-306 | I-14 | II-19c |
| B5-307 | I-15 | II-19c |
| B5-308 | I-16 | II-19c |
| B5-309 | I-1 | II-20c |
| B5-310 | I-2 | II-20c |
| B5-311 | I-3 | II-20c |
| B5-312 | I-4 | II-20c |
| B5-313 | I-5 | II-20c |
| B5-314 | I-6 | II-20c |
| B5-315 | I-7 | II-20c |
| B5-316 | I-8 | II-20c |
| B5-317 | I-9 | II-20c |
| B5-318 | I-10 | II-20c |
| B5-319 | I-11 | II-20c |
| B5-320 | I-12 | II-20c |
| B5-321 | I-13 | II-20c |
| B5-322 | I-14 | II-20c |
| B5-323 | I-15 | II-20c |
| B5-324 | I-16 | II-20c |
| B5-325 | I-1 | II-21c |
| B5-326 | I-2 | II-21c |
| B5-327 | I-3 | II-21c |
| B5-328 | I-4 | II-21c |
| B5-329 | I-5 | II-21c |
| B5-330 | I-6 | II-21c |
| B5-331 | I-7 | II-21c |
| B5-332 | I-8 | II-21c |
| B5-333 | I-9 | II-21c |
| B5-334 | I-10 | II-21c |
| B5-335 | I-11 | II-21c |
| B5-336 | I-12 | II-21c |
| B5-337 | I-13 | II-21c |
| B5-338 | I-14 | II-21c |
| B5-339 | I-15 | II-21c |
| B5-340 | I-16 | II-21c |
| B5-341 | I-1 | II-22c |
| B5-342 | I-2 | II-22c |
| B5-343 | I-3 | II-22c |
| B5-344 | I-4 | II-22c |
| B5-345 | I-5 | II-22c |
| B5-346 | I-6 | II-22c |
| B5-347 | I-7 | II-22c |
| B5-348 | I-8 | II-22c |
| B5-349 | I-9 | II-22c |
| B5-350 | I-10 | II-22c |
| B5-351 | I-11 | II-22c |
| B5-352 | I-12 | II-22c |
| B5-353 | I-13 | II-22c |
| B5-354 | I-14 | II-22c |
| B5-355 | I-15 | II-22c |
| B5-356 | I-16 | II-22c |
| B5-357 | I-1 | II-23c |
| B5-358 | I-2 | II-23c |
| B5-359 | I-3 | II-23c |
| B5-360 | I-4 | II-23c |
| B5-361 | I-5 | II-23c |
| B5-362 | I-6 | II-23c |
| B5-363 | I-7 | II-23c |
| B5-364 | I-8 | II-23c |
| B5-365 | I-9 | II-23c |

TABLE B5-continued

Two-component compositions comprising one component I and one insecticide as component II, in particular binary compositions containing the respective component I and II as only active ingredients.

| composition | I | II |
|---|---|---|
| B5-366 | I-10 | II-23c |
| B5-367 | I-11 | II-23c |
| B5-368 | I-12 | II-23c |
| B5-369 | I-13 | II-23c |
| B5-370 | I-14 | II-23c |
| B5-371 | I-15 | II-23c |
| B5-372 | I-16 | II-23c |
| B5-373 | I-1 | II-24c |
| B5-374 | I-2 | II-24c |
| B5-375 | I-3 | II-24c |
| B5-376 | I-4 | II-24c |
| B5-377 | I-5 | II-24c |
| B5-378 | I-6 | II-24c |
| B5-379 | I-7 | II-24c |
| B5-380 | I-8 | II-24c |
| B5-381 | I-9 | II-24c |
| B5-382 | I-10 | II-24c |
| B5-383 | I-11 | II-24c |
| B5-384 | I-12 | II-24c |
| B5-385 | I-13 | II-24c |
| B5-386 | I-14 | II-24c |
| B5-387 | I-15 | II-24c |
| B5-388 | I-16 | II-24c |
| B5-389 | I-1 | II-25c |
| B5-390 | I-2 | II-25c |
| B5-391 | I-3 | II-25c |
| B5-392 | I-4 | II-25c |
| B5-393 | I-5 | II-25c |
| B5-394 | I-6 | II-25c |
| B5-395 | I-7 | II-25c |
| B5-396 | I-8 | II-25c |
| B5-397 | I-9 | II-25c |
| B5-398 | I-10 | II-25c |
| B5-399 | I-11 | II-25c |
| B5-400 | I-12 | II-25c |
| B5-401 | I-13 | II-25c |
| B5-402 | I-14 | II-25c |
| B5-403 | I-15 | II-25c |
| B5-404 | I-16 | II-25c |
| B5-405 | I-1 | II-26c |
| B5-406 | I-2 | II-26c |
| B5-407 | I-3 | II-26c |
| B5-408 | I-4 | II-26c |
| B5-409 | I-5 | II-26c |
| B5-410 | I-6 | II-26c |
| B5-411 | I-7 | II-26c |
| B5-412 | I-8 | II-26c |
| B5-413 | I-9 | II-26c |
| B5-414 | I-10 | II-26c |
| B5-415 | I-11 | II-26c |
| B5-416 | I-12 | II-26c |
| B5-417 | I-13 | II-26c |
| B5-418 | I-14 | II-26c |
| B5-419 | I-15 | II-26c |
| B5-420 | I-16 | II-26c |
| B5-421 | I-1 | II-27c |
| B5-422 | I-2 | II-27c |
| B5-423 | I-3 | II-27c |
| B5-424 | I-4 | II-27c |
| B5-425 | I-5 | II-27c |
| B5-426 | I-6 | II-27c |
| B5-427 | I-7 | II-27c |
| B5-428 | I-8 | II-27c |
| B5-429 | I-9 | II-27c |
| B5-430 | I-10 | II-27c |
| B5-431 | I-11 | II-27c |
| B5-432 | I-12 | II-27c |
| B5-433 | I-13 | II-27c |
| B5-434 | I-14 | II-27c |
| B5-435 | I-15 | II-27c |
| B5-436 | I-16 | II-27c |
| B5-437 | I-1 | II-28c |
| B5-438 | I-2 | II-28c |
| B5-439 | I-3 | II-28c |
| B5-440 | I-4 | II-28c |
| B5-441 | I-5 | II-28c |
| B5-442 | I-6 | II-28c |
| B5-443 | I-7 | II-28c |
| B5-444 | I-8 | II-28c |
| B5-445 | I-9 | II-28c |
| B5-446 | I-10 | II-28c |
| B5-447 | I-11 | II-28c |
| B5-448 | I-12 | II-28c |
| B5-449 | I-13 | II-28c |
| B5-450 | I-14 | II-28c |
| B5-451 | I-15 | II-28c |
| B5-452 | I-16 | II-28c |
| B5-453 | I-1 | II-29c |
| B5-454 | I-2 | II-29c |
| B5-455 | I-3 | II-29c |
| B5-456 | I-4 | II-29c |
| B5-457 | I-5 | II-29c |
| B5-458 | I-6 | II-29c |
| B5-459 | I-7 | II-29c |
| B5-460 | I-8 | II-29c |
| B5-461 | I-9 | II-29c |
| B5-462 | I-10 | II-29c |
| B5-463 | I-11 | II-29c |
| B5-464 | I-12 | II-29c |
| B5-465 | I-13 | II-29c |
| B5-466 | I-14 | II-29c |
| B5-467 | I-15 | II-29c |
| B5-468 | I-16 | II-29c |
| B5-469 | I-1 | II-30c |
| B5-470 | I-2 | II-30c |
| B5-471 | I-3 | II-30c |
| B5-472 | I-4 | II-30c |
| B5-473 | I-5 | II-30c |
| B5-474 | I-6 | II-30c |
| B5-475 | I-7 | II-30c |
| B5-476 | I-8 | II-30c |
| B5-477 | I-9 | II-30c |
| B5-478 | I-10 | II-30c |
| B5-479 | I-11 | II-30c |
| B5-480 | I-12 | II-30c |
| B5-481 | I-13 | II-30c |
| B5-482 | I-14 | II-30c |
| B5-483 | I-15 | II-30c |
| B5-484 | I-16 | II-30c |
| B5-485 | I-1 | II-31c |
| B5-486 | I-2 | II-31c |
| B5-487 | I-3 | II-31c |
| B5-488 | I-4 | II-31c |
| B5-489 | I-5 | II-31c |
| B5-490 | I-6 | II-31c |
| B5-491 | I-7 | II-31c |
| B5-492 | I-8 | II-31c |
| B5-493 | I-9 | II-31c |
| B5-494 | I-10 | II-31c |
| B5-495 | I-11 | II-31c |
| B5-496 | I-12 | II-31c |
| B5-497 | I-13 | II-31c |
| B5-498 | I-14 | II-31c |
| B5-499 | I-15 | II-31c |
| B5-500 | I-16 | II-31c |
| B5-501 | I-1 | II-32c |
| B5-502 | I-2 | II-32c |
| B5-503 | I-3 | II-32c |
| B5-504 | I-4 | II-32c |
| B5-505 | I-5 | II-32c |
| B5-506 | I-6 | II-32c |
| B5-507 | I-7 | II-32c |
| B5-508 | I-8 | II-32c |
| B5-509 | I-9 | II-32c |
| B5-510 | I-10 | II-32c |
| B5-511 | I-11 | II-32c |

TABLE B5-continued

Two-component compositions comprising one component I and one insecticide as component II, in particular binary compositions containing the respective component I and II as only active ingredients.

| composition | I | II |
|---|---|---|
| B5-512 | I-12 | II-32c |
| B5-513 | I-13 | II-32c |
| B5-514 | I-14 | II-32c |
| B5-515 | I-15 | II-32c |
| B5-516 | I-16 | II-32c |
| B5-517 | I-1 | II-33c |
| B5-518 | I-2 | II-33c |
| B5-519 | I-3 | II-33c |
| B5-520 | I-4 | II-33c |
| B5-521 | I-5 | II-33c |
| B5-522 | I-6 | II-33c |
| B5-523 | I-7 | II-33c |
| B5-524 | I-8 | II-33c |
| B5-525 | I-9 | II-33c |
| B5-526 | I-10 | II-33c |
| B5-527 | I-11 | II-33c |
| B5-528 | I-12 | II-33c |
| B5-529 | I-13 | II-33c |
| B5-530 | I-14 | II-33c |
| B5-531 | I-15 | II-33c |
| B5-532 | I-16 | II-33c |
| B5-533 | I-1 | II-34c |
| B5-534 | I-2 | II-34c |
| B5-535 | I-3 | II-34c |
| B5-536 | I-4 | II-34c |
| B5-537 | I-5 | II-34c |
| B5-538 | I-6 | II-34c |
| B5-539 | I-7 | II-34c |
| B5-540 | I-8 | II-34c |
| B5-541 | I-9 | II-34c |
| B5-542 | I-10 | II-34c |
| B5-543 | I-11 | II-34c |
| B5-544 | I-12 | II-34c |
| B5-545 | I-13 | II-34c |
| B5-546 | I-14 | II-34c |
| B5-547 | I-15 | II-34c |
| B5-548 | I-16 | II-34c |
| B5-549 | I-1 | II-35c |
| B5-550 | I-2 | II-35c |
| B5-551 | I-3 | II-35c |
| B5-552 | I-4 | II-35c |
| B5-553 | I-5 | II-35c |
| B5-554 | I-6 | II-35c |
| B5-555 | I-7 | II-35c |
| B5-556 | I-8 | II-35c |
| B5-557 | I-9 | II-35c |
| B5-558 | I-10 | II-35c |
| B5-559 | I-11 | II-35c |
| B5-560 | I-12 | II-35c |
| B5-561 | I-13 | II-35c |
| B5-562 | I-14 | II-35c |
| B5-563 | I-15 | II-35c |
| B5-564 | I-16 | II-35c |
| B5-565 | I-1 | II-36c |
| B5-566 | I-2 | II-36c |
| B5-567 | I-3 | II-36c |
| B5-568 | I-4 | II-36c |
| B5-569 | I-5 | II-36c |
| B5-570 | I-6 | II-36c |
| B5-571 | I-7 | II-36c |
| B5-572 | I-8 | II-36c |
| B5-573 | I-9 | II-36c |
| B5-574 | I-10 | II-36c |
| B5-575 | I-11 | II-36c |
| B5-576 | I-12 | II-36c |
| B5-577 | I-13 | II-36c |
| B5-578 | I-14 | II-36c |
| B5-579 | I-15 | II-36c |
| B5-580 | I-16 | II-36c |
| B5-581 | I-1 | II-37c |
| B5-582 | I-2 | II-37c |
| B5-583 | I-3 | II-37c |
| B5-584 | I-4 | II-37c |
| B5-585 | I-5 | II-37c |
| B5-586 | I-6 | II-37c |
| B5-587 | I-7 | II-37c |
| B5-588 | I-8 | II-37c |
| B5-589 | I-9 | II-37c |
| B5-590 | I-10 | II-37c |
| B5-591 | I-11 | II-37c |
| B5-592 | I-12 | II-37c |
| B5-593 | I-13 | II-37c |
| B5-594 | I-14 | II-37c |
| B5-595 | I-15 | II-37c |
| B5-596 | I-16 | II-37c |
| B5-597 | I-1 | II-38c |
| B5-598 | I-2 | II-38c |
| B5-599 | I-3 | II-38c |
| B5-600 | I-4 | II-38c |
| B5-601 | I-5 | II-38c |
| B5-602 | I-6 | II-38c |
| B5-603 | I-7 | II-38c |
| B5-604 | I-8 | II-38c |
| B5-605 | I-9 | II-38c |
| B5-606 | I-10 | II-38c |
| B5-607 | I-11 | II-38c |
| B5-608 | I-12 | II-38c |
| B5-609 | I-13 | II-38c |
| B5-610 | I-14 | II-38c |
| B5-611 | I-15 | II-38c |
| B5-612 | I-16 | II-38c |
| B5-613 | I-1 | II-39c |
| B5-614 | I-2 | II-39c |
| B5-615 | I-3 | II-39c |
| B5-616 | I-4 | II-39c |
| B5-617 | I-5 | II-39c |
| B5-618 | I-6 | II-39c |
| B5-619 | I-7 | II-39c |
| B5-620 | I-8 | II-39c |
| B5-621 | I-9 | II-39c |
| B5-622 | I-10 | II-39c |
| B5-623 | I-11 | II-39c |
| B5-624 | I-12 | II-39c |
| B5-625 | I-13 | II-39c |
| B5-626 | I-14 | II-39c |
| B5-627 | I-15 | II-39c |
| B5-628 | I-16 | II-39c |
| B5-629 | I-1 | II-40c |
| B5-630 | I-2 | II-40c |
| B5-631 | I-3 | II-40c |
| B5-632 | I-4 | II-40c |
| B5-633 | I-5 | II-40c |
| B5-634 | I-6 | II-40c |
| B5-635 | I-7 | II-40c |
| B5-636 | I-8 | II-40c |
| B5-637 | I-9 | II-40c |
| B5-638 | I-10 | II-40c |
| B5-639 | I-11 | II-40c |
| B5-640 | I-12 | II-40c |
| B5-641 | I-13 | II-40c |
| B5-642 | I-14 | II-40c |
| B5-643 | I-15 | II-40c |
| B5-644 | I-16 | II-40c |
| B5-645 | I-1 | II-41c |
| B5-646 | I-2 | II-41c |
| B5-647 | I-3 | II-41c |
| B5-648 | I-4 | II-41c |
| B5-649 | I-5 | II-41c |
| B5-650 | I-6 | II-41c |
| B5-651 | I-7 | II-41c |
| B5-652 | I-8 | II-41c |
| B5-653 | I-9 | II-41c |
| B5-654 | I-10 | II-41c |
| B5-655 | I-11 | II-41c |
| B5-656 | I-12 | II-41c |
| B5-657 | I-13 | II-41c |

TABLE B5-continued

Two-component compositions comprising one component I and one insecticide as component II, in particular binary compositions containing the respective component I and II as only active ingredients.

| composition | I | II |
|---|---|---|
| B5-658 | I-14 | II-41c |
| B5-659 | I-15 | II-41c |
| B5-660 | I-16 | II-41c |
| B5-661 | I-1 | II-42c |
| B5-662 | I-2 | II-42c |
| B5-663 | I-3 | II-42c |
| B5-664 | I-4 | II-42c |
| B5-665 | I-5 | II-42c |
| B5-666 | I-6 | II-42c |
| B5-667 | I-7 | II-42c |
| B5-668 | I-8 | II-42c |
| B5-669 | I-9 | II-42c |
| B5-670 | I-10 | II-42c |
| B5-671 | I-11 | II-42c |
| B5-672 | I-12 | II-42c |
| B5-673 | I-13 | II-42c |
| B5-674 | I-14 | II-42c |
| B5-675 | I-15 | II-42c |
| B5-676 | I-16 | II-42c |
| B5-677 | I-1 | II-43c |
| B5-678 | I-2 | II-43c |
| B5-679 | I-3 | II-43c |
| B5-680 | I-4 | II-43c |
| B5-681 | I-5 | II-43c |
| B5-682 | I-6 | II-43c |
| B5-683 | I-7 | II-43c |
| B5-684 | I-8 | II-43c |
| B5-685 | I-9 | II-43c |
| B5-686 | I-10 | II-43c |
| B5-687 | I-11 | II-43c |
| B5-688 | I-12 | II-43c |
| B5-689 | I-13 | II-43c |
| B5-690 | I-14 | II-43c |
| B5-691 | I-15 | II-43c |
| B5-692 | I-16 | II-43c |
| B5-693 | I-1 | II-44c |
| B5-694 | I-2 | II-44c |
| B5-695 | I-3 | II-44c |
| B5-696 | I-4 | II-44c |
| B5-697 | I-5 | II-44c |
| B5-698 | I-6 | II-44c |
| B5-699 | I-7 | II-44c |
| B5-700 | I-8 | II-44c |
| B5-701 | I-9 | II-44c |
| B5-702 | I-10 | II-44c |
| B5-703 | I-11 | II-44c |
| B5-704 | I-12 | II-44c |
| B5-705 | I-13 | II-44c |
| B5-706 | I-14 | II-44c |
| B5-707 | I-15 | II-44c |
| B5-708 | I-16 | II-44c |

As detailed above, the components I contain chirality centers and may, therefore, be present as racemic mixtures, as pure enantiomers or in the two enantiomers of one component I may be present in any ratio (S):(R).

According to particular embodiments of the invention, the respective component I is present as (S) enantiomer. Specific two-component compositions comprising the (S) enantiomer of the respective component I are compiled in Table B5s, wherein each row corresponds to one embodiment of the compositions according to the invention, i.e. one specific individualized composition. According to one specific aspect, these are binary compositions which each only contain these two components as active compounds. Furthermore, also every combination of the compositions individualized in this table represent embodiments of the present invention.

TABLE 5s

Two-component compositions comprising one component I as (S) enantiomer (appreviated as (S)-I, e.g. (S)-I-1 for the (S)-enantiomer of I-1) and one component II, in particular binary compositions containing the respective component I as (S) enantiomer and II as only active ingredients.

| composition | (S)-I | II |
|---|---|---|
| B5s-1 | (S)-I-1 | II-1c |
| B5s-2 | (S)-I-3 | II-1c |
| B5s-3 | (S)-I-4 | II-1c |
| B5s-4 | (S)-I-5 | II-1c |
| B5s-5 | (S)-I-13 | II-1c |
| B5s-6 | (S)-I-1 | II-2c |
| B5s-7 | (S)-I-3 | II-2c |
| B5s-8 | (S)-I-4 | II-2c |
| B5s-9 | (S)-I-5 | II-2c |
| B5s-10 | (S)-I-13 | II-2c |
| B5s-11 | (S)-I-1 | II-3c |
| B5s-12 | (S)-I-3 | II-3c |
| B5s-13 | (S)-I-4 | II-3c |
| B5s-14 | (S)-I-5 | II-3c |
| B5s-15 | (S)-I-13 | II-3c |
| B5s-16 | (S)-I-1 | II-4c |
| B5s-17 | (S)-I-3 | II-4c |
| B5s-18 | (S)-I-4 | II-4c |
| B5s-19 | (S)-I-5 | II-4c |
| B5s-20 | (S)-I-13 | II-4c |
| B5s-21 | (S)-I-1 | II-5c |
| B5s-22 | (S)-I-3 | II-5c |
| B5s-23 | (S)-I-4 | II-5c |
| B5s-24 | (S)-I-5 | II-5c |
| B5s-25 | (S)-I-13 | II-5c |
| B5s-26 | (S)-I-1 | II-6c |
| B5s-27 | (S)-I-3 | II-6c |
| B5s-28 | (S)-I-4 | II-6c |
| B5s-29 | (S)-I-5 | II-6c |
| B5s-30 | (S)-I-13 | II-6c |
| B5s-31 | (S)-I-1 | II-7c |
| B5s-32 | (S)-I-3 | II-7c |
| B5s-33 | (S)-I-4 | II-7c |
| B5s-34 | (S)-I-5 | II-7c |
| B5s-35 | (S)-I-13 | II-7c |
| B5s-36 | (S)-I-1 | II-8c |
| B5s-37 | (S)-I-3 | II-8c |
| B5s-38 | (S)-I-4 | II-8c |
| B5s-39 | (S)-I-5 | II-8c |
| B5s-40 | (S)-I-13 | II-8c |
| B5s-41 | (S)-I-1 | II-9c |
| B5s-42 | (S)-I-3 | II-9c |
| B5s-43 | (S)-I-4 | II-9c |
| B5s-44 | (S)-I-5 | II-9c |
| B5s-45 | (S)-I-13 | II-9c |
| B5s-46 | (S)-I-1 | II-10c |
| B5s-47 | (S)-I-3 | II-10c |
| B5s-48 | (S)-I-4 | II-10c |
| B5s-49 | (S)-I-5 | II-10c |
| B5s-50 | (S)-I-13 | II-10c |
| B5s-51 | (S)-I-1 | II-11c |
| B5s-52 | (S)-I-3 | II-11c |
| B5s-53 | (S)-I-4 | II-11c |
| B5s-54 | (S)-I-5 | II-11c |
| B5s-55 | (S)-I-13 | II-11c |
| B5s-56 | (S)-I-1 | II-12c |
| B5s-57 | (S)-I-3 | II-12c |
| B5s-58 | (S)-I-4 | II-12c |
| B5s-59 | (S)-I-5 | II-12c |
| B3s-60 | (S)-I-13 | II-12c |
| B3s-61 | (S)-I-1 | II-13c |
| B3s-62 | (S)-I-3 | II-13c |
| B3s-63 | (S)-I-4 | II-13c |
| B3s-64 | (S)-I-5 | II-13c |
| B3s-65 | (S)-I-13 | II-13c |
| B3s-66 | (S)-I-1 | II-14c |
| B3s-67 | (S)-I-3 | II-14c |
| B3s-68 | (S)-I-4 | II-14c |
| B3s-69 | (S)-I-5 | II-14c |
| B3s-70 | (S)-I-13 | II-14c |
| B3s-71 | (S)-I-1 | II-15c |
| B5s-72 | (S)-I-3 | II-15c |

TABLE 5s-continued

Two-component compositions comprising one component I as (S) enantiomer (appreviated as (S)-I, e.g. (S)-I-1 for the (S)-enantiomer of I-1) and one component II, in particular binary compositions containing the respective component I as (S) enantiomer and II as only active ingredients.

| composition | (S)-I | II |
| --- | --- | --- |
| B3s-73 | (S)-I-4 | II-15c |
| B5s-74 | (S)-I-5 | II-15c |
| B5s-75 | (S)-I-13 | II-15c |
| B5s-76 | (S)-I-1 | II-16c |
| B5s-77 | (S)-I-3 | II-16c |
| B5s-78 | (S)-I-4 | II-16c |
| B5s-79 | (S)-I-5 | II-16c |
| B3s-80 | (S)-I-13 | II-16c |
| B3s-81 | (S)-I-1 | II-17c |
| B3s-82 | (S)-I-3 | II-17c |
| B3s-83 | (S)-I-4 | II-17c |
| B3s-84 | (S)-I-5 | II-17c |
| B3s-85 | (S)-I-13 | II-17c |
| B3s-86 | (S)-I-1 | II-18c |
| B3s-87 | (S)-I-3 | II-18c |
| B3s-88 | (S)-I-4 | II-18c |
| B3s-89 | (S)-I-5 | II-18c |
| B3s-90 | (S)-I-13 | II-18c |
| B3s-91 | (S)-I-1 | II-19c |
| B3s-92 | (S)-I-3 | II-19c |
| B3s-93 | (S)-I-4 | II-19c |
| B3s-94 | (S)-I-5 | II-19c |
| B3s-95 | (S)-I-13 | II-19c |
| B3s-96 | (S)-I-1 | II-20c |
| B3s-97 | (S)-I-3 | II-20c |
| B3s-98 | (S)-I-4 | II-20c |
| B3s-99 | (S)-I-5 | II-20c |
| B3s-100 | (S)-I-13 | II-20c |
| B3s-101 | (S)-I-1 | II-21c |
| B3s-102 | (S)-I-3 | II-21c |
| B5s-103 | (S)-I-4 | II-21c |
| B3s-104 | (S)-I-5 | II-21c |
| B3s-105 | (S)-I-13 | II-21c |
| B3s-106 | (S)-I-1 | II-22c |
| B3s-107 | (S)-I-3 | II-22c |
| B5s-108 | (S)-I-4 | II-22c |
| B3s-109 | (S)-I-5 | II-22c |
| B3s-110 | (S)-I-13 | II-22c |
| B5s-111 | (S)-I-1 | II-23c |
| B3s-112 | (S)-I-3 | II-23c |
| B3s-113 | (S)-I-4 | II-23c |
| B3s-114 | (S)-I-5 | II-23c |
| B3s-115 | (S)-I-13 | II-23c |
| B3s-116 | (S)-I-1 | II-24c |
| B3s-117 | (S)-I-3 | II-24c |
| B3s-118 | (S)-I-4 | II-24c |
| B3s-119 | (S)-I-5 | II-24c |
| B3s-120 | (S)-I-13 | II-24c |
| B3s-121 | (S)-I-1 | II-25c |
| B5s-122 | (S)-I-3 | II-25c |
| B5s-123 | (S)-I-4 | II-25c |
| B5s-124 | (S)-I-5 | II-25c |
| B5s-125 | (S)-I-13 | II-25c |
| B5s-126 | (S)-I-1 | II-26c |
| B5s-127 | (S)-I-3 | II-26c |
| B5s-128 | (S)-I-4 | II-26c |
| B5s-129 | (S)-I-5 | II-26c |
| B3s-130 | (S)-I-13 | II-26c |
| B3s-131 | (S)-I-1 | II-27c |
| B3s-132 | (S)-I-3 | II-27c |
| B3s-133 | (S)-I-4 | II-27c |
| B3s-134 | (S)-I-5 | II-27c |
| B3s-135 | (S)-I-13 | II-27c |
| B3s-136 | (S)-I-1 | II-28c |
| B3s-137 | (S)-I-3 | II-28c |
| B3s-138 | (S)-I-4 | II-28c |
| B3s-139 | (S)-I-5 | II-28c |
| B3s-140 | (S)-I-13 | II-28c |
| B3s-141 | (S)-I-1 | II-29c |
| B5s-142 | (S)-I-3 | II-29c |
| B3s-143 | (S)-I-4 | II-29c |
| B5s-144 | (S)-I-5 | II-29c |
| B5s-145 | (S)-I-13 | II-29c |
| B5s-146 | (S)-I-1 | II-30c |
| B5s-147 | (S)-I-3 | II-30c |
| B5s-148 | (S)-I-4 | II-30c |
| B5s-149 | (S)-I-5 | II-30c |
| B3s-150 | (S)-I-13 | II-30c |
| B5s-151 | (S)-I-1 | II-31c |
| B5s-152 | (S)-I-3 | II-31c |
| B5s-153 | (S)-I-4 | II-31c |
| B5s-154 | (S)-I-5 | II-31c |
| B5s-155 | (S)-I-13 | II-31c |
| B5s-156 | (S)-I-1 | II-32c |
| B5s-157 | (S)-I-3 | II-32c |
| B5s-158 | (S)-I-4 | II-32c |
| B5s-159 | (S)-I-5 | II-32c |
| B3s-160 | (S)-I-13 | II-32c |
| B3s-161 | (S)-I-1 | II-33c |
| B3s-162 | (S)-I-3 | II-33c |
| B3s-163 | (S)-I-4 | II-33c |
| B3s-164 | (S)-I-5 | II-33c |
| B3s-165 | (S)-I-13 | II-33c |
| B3s-166 | (S)-I-1 | II-34c |
| B3s-167 | (S)-I-3 | II-34c |
| B3s-168 | (S)-I-4 | II-34c |
| B3s-169 | (S)-I-5 | II-34c |
| B3s-170 | (S)-I-13 | II-34c |
| B3s-171 | (S)-I-1 | II-35c |
| B5s-172 | (S)-I-3 | II-35c |
| B3s-173 | (S)-I-4 | II-35c |
| B5s-174 | (S)-I-5 | II-35c |
| B5s-175 | (S)-I-13 | II-35c |
| B5s-176 | (S)-I-1 | II-36c |
| B5s-177 | (S)-I-3 | II-36c |
| B5s-178 | (S)-I-4 | II-36c |
| B5s-179 | (S)-I-5 | II-36c |
| B3s-180 | (S)-I-13 | II-36c |
| B3s-181 | (S)-I-1 | II-37c |
| B3s-182 | (S)-I-3 | II-37c |
| B3s-183 | (S)-I-4 | II-37c |
| B3s-184 | (S)-I-5 | II-37c |
| B3s-185 | (S)-I-13 | II-37c |
| B3s-186 | (S)-I-1 | II-38c |
| B3s-187 | (S)-I-3 | II-38c |
| B3s-188 | (S)-I-4 | II-38c |
| B3s-189 | (S)-I-5 | II-38c |
| B3s-190 | (S)-I-13 | II-38c |
| B3s-191 | (S)-I-1 | II-39c |
| B3s-192 | (S)-I-3 | II-39c |
| B3s-193 | (S)-I-4 | II-39c |
| B3s-194 | (S)-I-5 | II-39c |
| B3s-195 | (S)-I-13 | II-39c |
| B3s-196 | (S)-I-1 | II-40c |
| B3s-197 | (S)-I-3 | II-40c |
| B3s-198 | (S)-I-4 | II-40c |
| B3s-199 | (S)-I-5 | II-40c |
| B5s-200 | (S)-I-13 | II-40c |
| B3s-201 | (S)-I-1 | II-41c |
| B3s-202 | (S)-I-3 | II-41c |
| B3s-203 | (S)-I-4 | II-41c |
| B5s-204 | (S)-I-5 | II-41c |
| B5s-205 | (S)-I-13 | II-41c |
| B3s-206 | (S)-I-1 | II-42c |
| B3s-207 | (S)-I-3 | II-42c |
| B5s-208 | (S)-I-4 | II-42c |
| B3s-209 | (S)-I-5 | II-42c |
| B3s-210 | (S)-I-13 | II-42c |
| B3s-211 | (S)-I-1 | II-43c |
| B5s-212 | (S)-I-3 | II-43c |
| B5s-213 | (S)-I-4 | II-43c |
| B5s-214 | (S)-I-5 | II-43c |
| B5s-215 | (S)-I-13 | II-43c |
| B5s-216 | (S)-I-1 | II-44c |

TABLE 5s-continued

Two-component compositions comprising one component I as (S) enantiomer (appreviated as (S)-I, e.g. (S)-I-1 for the (S)-enantiomer of I-1) and one component II, in particular binary compositions containing the respective component I as (S) enantiomer and II as only active ingredients.

| composition | (S)-I | II |
|---|---|---|
| B5s-217 | (S)-I-3 | II-44c |
| B5s-218 | (S)-I-4 | II-44c |
| B5s-219 | (S)-I-5 | II-44c |
| B5s-220 | (S)-I-13 | II-44c |

According to particular embodiments of the invention, the respective component I is present as (R) enantiomer. Specific two-component compositions comprising the (R) enantiomer of the respective component I are compiled in Table B5r, wherein each row corresponds to one embodiment of the compositions according to the invention, i.e. one specific individualized composition. According to one specific aspect, these are binary compositions which each only contain these two components as active compounds. Furthermore, also every combination of the compositions individualized in this table represent embodiments of the present invention.

TABLE 5r

Two-component compositions comprising one component I as (S) enantiomer (appreviated as (R)-I, e.g. (R)-I-1 for the (R)-enantiomer of I-1) and one component II, in particular binary compositions containing the respective component I as (R) enantiomer and II as only active ingredients.

| composition | (R)-I | II |
|---|---|---|
| B5r-1 | (R)-I-1 | II-1c |
| B5r-2 | (R)-I-3 | II-1c |
| B5r-3 | (R)-I-4 | II-1c |
| B5r-4 | (R)-I-5 | II-1c |
| B5r-5 | (R)-I-13 | II-1c |
| B5r-6 | (R)-I-1 | II-2c |
| B5r-7 | (R)-I-3 | II-2c |
| B5r-8 | (R)-I-4 | II-2c |
| B5r-9 | (R)-I-5 | II-2c |
| B5r-10 | (R)-I-13 | II-2c |
| B5r-11 | (R)-I-1 | II-3c |
| B5r-12 | (R)-I-3 | II-3c |
| B5r-13 | (R)-I-4 | II-3c |
| B5r-14 | (R)-I-5 | II-3c |
| B5r-15 | (R)-I-13 | II-3c |
| B5r-16 | (R)-I-1 | II-4c |
| B5r-17 | (R)-I-3 | II-4c |
| B5r-18 | (R)-I-4 | II-4c |
| B5r-19 | (R)-I-5 | II-4c |
| B5r-20 | (R)-I-13 | II-4c |
| B5r-21 | (R)-I-1 | II-5c |
| B5r-22 | (R)-I-3 | II-5c |
| B5r-23 | (R)-I-4 | II-5c |
| B5r-24 | (R)-I-5 | II-5c |
| B5r-25 | (R)-I-13 | II-5c |
| B5r-26 | (R)-I-1 | II-6c |
| B5r-27 | (R)-I-3 | II-6c |
| B5r-28 | (R)-I-4 | II-6c |
| B5r-29 | (R)-I-5 | II-6c |
| B5r-30 | (R)-I-13 | II-6c |
| B5r-31 | (R)-I-1 | II-7c |
| B5r-32 | (R)-I-3 | II-7c |
| B5r-33 | (R)-I-4 | II-7c |
| B5r-34 | (R)-I-5 | II-7c |
| B5r-35 | (R)-I-13 | II-7c |
| B5r-36 | (R)-I-1 | II-8c |
| B5r-37 | (R)-I-3 | II-8c |
| B5r-38 | (R)-I-4 | II-8c |
| B5r-39 | (R)-I-5 | II-8c |
| B5r-40 | (R)-I-13 | II-8c |
| B5r-41 | (R)-I-1 | II-9c |
| B5r-42 | (R)-I-3 | II-9c |
| B5r-43 | (R)-I-4 | II-9c |
| B5r-44 | (R)-I-5 | II-9c |
| B5r-45 | (R)-I-13 | II-9c |
| B5r-46 | (R)-I-1 | II-10c |
| B5r-47 | (R)-I-3 | II-10c |
| B5r-48 | (R)-I-4 | II-10c |
| B5r-49 | (R)-I-5 | II-10c |
| B5r-50 | (R)-I-13 | II-10c |
| B5r-51 | (R)-I-1 | II-11c |
| B5r-52 | (R)-I-3 | II-11c |
| B5r-53 | (R)-I-4 | II-11c |
| B5r-54 | (R)-I-5 | II-11c |
| B5r-55 | (R)-I-13 | II-11c |
| B5r-56 | (R)-I-1 | II-12c |
| B5r-57 | (R)-I-3 | II-12c |
| B5r-58 | (R)-I-4 | II-12c |
| B5r-59 | (R)-I-5 | II-12c |
| B5r-60 | (R)-I-13 | II-12c |
| B5r-61 | (R)-I-1 | II-13c |
| B5r-62 | (R)-I-3 | II-13c |
| B5r-63 | (R)-I-4 | II-13c |
| B5r-64 | (R)-I-5 | II-13c |
| B5r-65 | (R)-I-13 | II-13c |
| B5r-66 | (R)-I-1 | II-14c |
| B5r-67 | (R)-I-3 | II-14c |
| B5r-68 | (R)-I-4 | II-14c |
| B5r-69 | (R)-I-5 | II-14c |
| B5r-70 | (R)-I-13 | II-14c |
| B5r-71 | (R)-I-1 | II-15c |
| B5r-72 | (R)-I-3 | II-15c |
| B5r-73 | (R)-I-4 | II-15c |
| B5r-74 | (R)-I-5 | II-15c |
| B5r-75 | (R)-I-13 | II-15c |
| B5r-76 | (R)-I-1 | II-16c |
| B5r-77 | (R)-I-3 | II-16c |
| B5r-78 | (R)-I-4 | II-16c |
| B5r-79 | (R)-I-5 | II-16c |
| B5r-80 | (R)-I-13 | II-16c |
| B5r-81 | (R)-I-1 | II-17c |
| B5r-82 | (R)-I-3 | II-17c |
| B5r-83 | (R)-I-4 | II-17c |
| B5r-84 | (R)-I-5 | II-17c |
| B5r-85 | (R)-I-13 | II-17c |
| B5r-86 | (R)-I-1 | II-18c |
| B5r-87 | (R)-I-3 | II-18c |
| B5r-88 | (R)-I-4 | II-18c |
| B5r-89 | (R)-I-5 | II-18c |
| B5r-90 | (R)-I-13 | II-18c |
| B5r-91 | (R)-I-1 | II-19c |
| B5r-92 | (R)-I-3 | II-19c |
| B5r-93 | (R)-I-4 | II-19c |
| B5r-94 | (R)-I-5 | II-19c |
| B5r-95 | (R)-I-13 | II-19c |
| B5r-96 | (R)-I-1 | II-20c |
| B5r-97 | (R)-I-3 | II-20c |
| B5r-98 | (R)-I-4 | II-20c |
| B5r-99 | (R)-I-5 | II-20c |
| B5r-100 | (R)-I-13 | II-20c |
| B5r-101 | (R)-I-1 | II-21c |
| B5r-102 | (R)-I-3 | II-21c |
| B5r-103 | (R)-I-4 | II-21c |
| B5r-104 | (R)-I-5 | II-21c |
| B5r-105 | (R)-I-13 | II-21c |
| B5r-106 | (R)-I-1 | II-22c |
| B5r-107 | (R)-I-3 | II-22c |
| B5r-108 | (R)-I-4 | II-22c |
| B5r-109 | (R)-I-5 | II-22c |
| B5r-110 | (R)-I-13 | II-22c |
| B5r-111 | (R)-I-1 | II-23c |
| B5r-112 | (R)-I-3 | II-23c |

TABLE 5r-continued

Two-component compositions comprising one component I as (S) enantiomer (appreviated as (R)-I, e.g. (R)-I-1 for the (R)-enantiomer of I-1) and one component II, in particular binary compositions containing the respective component I as (R) enantiomer and II as only active ingredients.

| composition | (R)-I | II |
|---|---|---|
| B5r-113 | (R)-I-4 | II-23c |
| B5r-114 | (R)-I-5 | II-23c |
| B5r-115 | (R)-I-13 | II-23c |
| B5r-116 | (R)-I-1 | II-24c |
| B5r-117 | (R)-I-3 | II-24c |
| B5r-118 | (R)-I-4 | II-24c |
| B5r-119 | (R)-I-5 | II-24c |
| B5r-120 | (R)-I-13 | II-24c |
| B5r-121 | (R)-I-1 | II-25c |
| B5r-122 | (R)-I-3 | II-25c |
| B5r-123 | (R)-I-4 | II-25c |
| B5r-124 | (R)-I-5 | II-25c |
| B5r-125 | (R)-I-13 | II-25c |
| B5r-126 | (R)-I-1 | II-26c |
| B5r-127 | (R)-I-3 | II-26c |
| B5r-128 | (R)-I-4 | II-26c |
| B5r-129 | (R)-I-5 | II-26c |
| B5r-130 | (R)-I-13 | II-26c |
| B5r-131 | (R)-I-1 | II-27c |
| B5r-132 | (R)-I-3 | II-27c |
| B5r-133 | (R)-I-4 | II-27c |
| B5r-134 | (R)-I-5 | II-27c |
| B5r-135 | (R)-I-13 | II-27c |
| B5r-136 | (R)-I-1 | II-28c |
| B5r-137 | (R)-I-3 | II-28c |
| B5r-138 | (R)-I-4 | II-28c |
| B5r-139 | (R)-I-5 | II-28c |
| B5r-140 | (R)-I-13 | II-28c |
| B5r-141 | (R)-I-1 | II-29c |
| B5r-142 | (R)-I-3 | II-29c |
| B5r-143 | (R)-I-4 | II-29c |
| B5r-144 | (R)-I-5 | II-29c |
| B5r-145 | (R)-I-13 | II-29c |
| B5r-146 | (R)-I-1 | II-30c |
| B5r-147 | (R)-I-3 | II-30c |
| B5r-148 | (R)-I-4 | II-30c |
| B5r-149 | (R)-I-5 | II-30c |
| B5r-150 | (R)-I-13 | II-30c |
| B5r-151 | (R)-I-1 | II-31c |
| B5r-152 | (R)-I-3 | II-31c |
| B5r-153 | (R)-I-4 | II-31c |
| B5r-154 | (R)-I-5 | II-31c |
| B5r-155 | (R)-I-13 | II-31c |
| B5r-156 | (R)-I-1 | II-32c |
| B5r-157 | (R)-I-3 | II-32c |
| B5r-158 | (R)-I-4 | II-32c |
| B5r-159 | (R)-I-5 | II-32c |
| B5r-160 | (R)-I-13 | II-32c |
| B5r-161 | (R)-I-1 | II-33c |
| B5r-162 | (R)-I-3 | II-33c |
| B5r-163 | (R)-I-4 | II-33c |
| B5r-164 | (R)-I-5 | II-33c |
| B5r-165 | (R)-I-13 | II-33c |
| B5r-166 | (R)-I-1 | II-34c |
| B5r-167 | (R)-I-3 | II-34c |
| B5r-168 | (R)-I-4 | II-34c |
| B5r-169 | (R)-I-5 | II-34c |
| B5r-170 | (R)-I-13 | II-34c |
| B5r-171 | (R)-I-1 | II-35c |
| B5r-172 | (R)-I-3 | II-35c |
| B5r-173 | (R)-I-4 | II-35c |
| B5r-174 | (R)-I-5 | II-35c |
| B5r-175 | (R)-I-13 | II-35c |
| B5r-176 | (R)-I-1 | II-36c |
| B5r-177 | (R)-I-3 | II-36c |
| B5r-178 | (R)-I-4 | II-36c |
| B5r-179 | (R)-I-5 | II-36c |
| B5r-180 | (R)-I-13 | II-36c |
| B5r-181 | (R)-I-1 | II-37c |
| B5r-182 | (R)-I-3 | II-37c |
| B5r-183 | (R)-I-4 | II-37c |
| B5r-184 | (R)-I-5 | II-37c |
| B5r-185 | (R)-I-13 | II-37c |
| B5r-186 | (R)-I-1 | II-38c |
| B5r-187 | (R)-I-3 | II-38c |
| B5r-188 | (R)-I-4 | II-38c |
| B5r-189 | (R)-I-5 | II-38c |
| B5r-190 | (R)-I-13 | II-38c |
| B5r-191 | (R)-I-1 | II-39c |
| B5r-192 | (R)-I-3 | II-39c |
| B5r-193 | (R)-I-4 | II-39c |
| B5r-194 | (R)-I-5 | II-39c |
| B5r-195 | (R)-I-13 | II-39c |
| B5r-196 | (R)-I-1 | II-40c |
| B5r-197 | (R)-I-3 | II-40c |
| B5r-198 | (R)-I-4 | II-40c |
| B5r-199 | (R)-I-5 | II-40c |
| B5r-200 | (R)-I-13 | II-40c |
| B5r-201 | (R)-I-1 | II-41c |
| B5r-202 | (R)-I-3 | II-41c |
| B5r-203 | (R)-I-4 | II-41c |
| B5r-204 | (R)-I-5 | II-41c |
| B5r-205 | (R)-I-13 | II-41c |
| B5r-206 | (R)-I-1 | II-42c |
| B5r-207 | (R)-I-3 | II-42c |
| B5r-208 | (R)-I-4 | II-42c |
| B5r-209 | (R)-I-5 | II-42c |
| B5r-210 | (R)-I-13 | II-42c |
| B5r-211 | (R)-I-1 | II-43c |
| B5r-212 | (R)-I-3 | II-43c |
| B5r-213 | (R)-I-4 | II-43c |
| B5r-214 | (R)-I-5 | II-43c |
| B5r-215 | (R)-I-13 | II-43c |
| B5r-216 | (R)-I-1 | II-44c |
| B5r-217 | (R)-I-3 | II-44c |
| B5r-218 | (R)-I-4 | II-44c |
| B5r-219 | (R)-I-5 | II-44c |
| B5r-220 | (R)-I-13 | II-44c |

According to a further aspect, the present invention relates to three-component compositions, i.e. compositions comprising component I, i.e a compound I, in particular a compound selected from compounds I-1, I-2, I-3, I-4, I-5, I-6, I-7, I-8, I-9, I-11, I-13, I-14, I-15 and I-16 or any group of compounds I detailed above, a component II selected from groups A) to O) and a component III also selected from groups A) to O), wherein component II and III are not identical. In particular, the component II in each case is selected from the preferred groups or preferred active compounds as given above for component II and component III is selected from groups A) to O), in particular from the preferred active compounds used as component III as defined in the following.

According to a specific embodiment thereof, exactly three active compounds as defined are present in these compositions (herein also called "ternary compositions"). The composition may, of course, contain any kind of additive or the like as detailed below in order to provide a formulation suitable for use in agriculture.

In the inventive three-component-compositions, the weight ratio of component I to the $1^{st}$ further active compound (component II) depends on the properties of the active compounds in question and may particularly be 1000:1 to 1:1000, specifically 500:1 to 1:500. Preferably, it is in the range of from 1:100 to 100:1, preferably in the range of from 1:50 to 50:1 and in particular in the range of from 1:20 to 20:1. It may be preferable for the weight ratio to be in the region of from 1:10 to 10:1, preferably from 1:3 to 3:1, in particular from 1:2 to 2:1. The weight ratio of component I to the $2^{nd}$ further active compound (component III) may particularly be 1000:1 to 1:1000, specifically 500:1 to 1:500. It is preferably in the range of from 1:100 to 100:1, preferably in the range of from 1:50 to 50:1 and in particular in the range of from 1:20 to 20:1. It may be preferable for the weight ratio to be in the region of from 1:10 to 10:1, preferably from 1:3 to 3:1, in particular from 1:2 to 2:1. The weight ratio of $1^{st}$ further active compound (component II) to $2^{nd}$ further active compound (component III) is preferably in the range of from 1:100 to 100:1, frequently in the range of from 1:50 to 50:1, preferably in the range of from 1:20 to 20:1, and in particular in the range of from 1:10 to 10:1. It may be preferable for the weight to be in the range of from 1:3 to 3:1, in particular from 1:2 to 2:1.

According to one embodiment, the present invention relates to three-component compositions, comprising a component I, i.e a compound I, in particular a compound selected from compounds I-1, I-2, I-3, I-4, I-5, I-6, I-7, I-8, I-9, I-11, I-13, I-14, I-15 and I-16 or any group of compounds I detailed above, a component II selected from groups groups A) to K) and a component III selected from groups A) to K).

One specific embodiment relates to three-component compositions, wherein component I is as defined above and component II is selected from group A) of the respiration inhibitors of complex III at $Q_o$ site and component III is selected from the group of B) of the sterol biosynthesis inhibitors (SBI fungicides). According to one specific embodiment thereof, component II is selected from the group of strobilurins. Specifically, component II is selected from the group consisting of azoxystrobin, dimoxystrobin, fluoxastrobin, kresoxim-methyl, orysastrobin, picoxystrobin, pyraclostrobin and trifloxystrobin. According to a further specific embodiment thereof, component III is selected from the group of the C14 demethylase inhibitors (DMI fungicides), in particular selected from cyproconazole, difenoconazole, epoxiconazole, fluquinconazole, flusilazole, flutriafol, metconazole, myclobutanil, penconazole, propiconazole, prothioconazole, triadimefon, triadimenol, tebuconazole, tetraconazole, triticonazole and prochloraz. According to a further specific embodiment, these are ternary compositions which, as active compounds, comprise in each case only the mentioned three active components I, II and III.

A further specific embodiment relates to three-component compositions, wherein component I is as defined above and component II and component III are selected from the respiration inhibitors of complex III at $Q_o$ site, wherein component II and III are not the same. In particular, component II and III are selected from the group of the strobilurins. Specifically, component II and III are selected from the group consisting of azoxystrobin, dimoxystrobin, fluoxastrobin, kresoxim-methyl, orysastrobin, picoxystrobin, pyraclostrobin and trifloxystrobin. According to a specific embodiment, these are ternary compositions which, as active compounds, comprise in each case only the mentioned three active components I, II and III.

Still a further specific embodiment relates to three-component compositions, wherein component I is as defined above, component II is selected from the sterol biosynthesis inhibitors (SBI fungicides) and component III is selected from the respiration inhibitors of complex II. According to one specific embodiment thereof, component II is selected from is selected from the group of the C14 demethylase inhibitors (DMI fungicides), in particular selected from cyproconazole, difenoconazole, epoxiconazole, fluquinconazole, flusilazole, flutriafol, metconazole, myclobutanil, penconazole, propiconazole, prothioconazole, triadimefon, triadimenol, tebuconazole, tetraconazole, triticonazole and prochloraz. According to a further specific embodiment, component III is selected from the group of the carboxamides, in particular selected from benodanil, benzovindiflupyr, bixafen, boscalid, carboxin, fenfuram, fluopyram, flutolanil, fluxapyroxad, furametpyr, isopyrazam, mepronil, oxycarboxin, penflufen, penthiopyrad, sedaxane, tecloftalam, thifluzamide, N-(4'-trifluoromethylthiobiphenyl-2-yl)-3-difluoromethyl-1-methyl-1H-pyrazole-4-carboxamide, N-(2-(1,3,3-trimethyl-butyl)-phenyl)-1,3-dimethyl-5-fluoro-1H-pyrazole-4-carboxamide, 3-(difluoromethyl)-1-methyl-N-(1,1,3-trimethylindan-4-yl)pyrazole-4-carboxamide, 3-(trifluoromethyl)-1-methyl-N-(1,1,3-trimethyl-indan-4-yl)pyrazole-4-carboxamide, 1,3-dimethyl-N-(1,1,3-trimethylindan-4-yl)pyrazole-4-carboxamide, 3-(trifluoromethyl)-1,5-dimethyl-N-(1,1,3-trimethylindan-4-yl)pyrazole-4-carboxamide, 3-(difluoromethyl)-1,5-dimethyl-N-(1,1,3-trimethylindan-4-yl)pyrazole-4-carboxamide and 1,3,5-trimethyl-N-(1,1,3-trimethylindan-4-yl)pyrazole-4-carboxamide, in particular selected from benzovindiflupyr, bixafen, boscalid, fluopyram, fluxapyroxad, isopyrazam, penflufen, penthiopyrad and sedaxane. According to a further specific embodiment, these are ternary compositions which, as active compounds, comprise in each case only the mentioned three active components I, II and III.

Still a further specific embodiment relates to three-component compositions, wherein component I is as defined above, component II is selected the respiration inhibitors of complex III at $Q_o$ site and component III is selected from the respiration inhibitors of complex II. In particular, component II is selected from the group of the strobilurins. Specifically, component II is selected from the group consisting of azoxystrobin, dimoxystrobin, fluoxastrobin, kresoxim-methyl, orysastrobin, picoxystrobin, pyraclostrobin and trifloxystrobin. According to a further specific embodiment, component III is selected from the group of the carboxamides, in particular selected from benodanil, benzovindiflupyr, bixafen, boscalid, carboxin, fenfuram, fluopyram, flutolanil, fluxapyroxad, furametpyr, isopyrazam, mepronil, oxycarboxin, penflufen, penthiopyrad, sedaxane, tecloftalam, thifluzamide, N-(4'-trifluoromethylthiobiphenyl-2-yl)-3-difluoromethyl-1-methyl-1H-pyrazole-4-carboxamide, N-(2-(1,3,3-trimethyl-butyl)-phenyl)-1,3-dimethyl-5-fluoro-1H-pyrazole-4-carboxamide, 3-(difluoromethyl)-1-methyl-N-(1,1,3-trimethylindan-4-yl)pyrazole-4-carboxamide, 3-(trifluoromethyl)-1-methyl-N-(1,1,3-trimethylindan-4-yl)pyrazole-4-carboxamide, 1,3-dimethyl-N-(1,1,3-trimethylindan-4-yl)pyrazole-4-carboxamide, 3-(trifluoromethyl)-1,5-dimethyl-N-(1,1,3-trimethylindan-4-yl)pyrazole-4-carboxamide, 3-(difluoromethyl)-1,5-dimethyl-N-(1,1,3-trimethylindan-4-yl)pyrazole-4-carboxamide and 1,3,5-trimethyl-N-(1,1,3-trimethylindan-4-yl)pyrazole-4-carboxamide, in particular selected from benzovindiflupyr, bixafen, boscalid, fluopyram, fluxapyroxad, isopyrazam, penflufen, penthiopyrad and sedaxane. According to a further specific embodiment, these are ternary compositions which, as active compounds, comprise in each case only the mentioned three active components I, II and III.

Still a further specific embodiment relates to three-component compositions, wherein component I is as defined above, component II is selected the respiration inhibitors of complex III at $Q_o$ site and component III is selected from the Sterol biosynthesis inhibitors (SBI fungicides), in particular Delta14-reductase inhibitors. In a specific embodiment, component II is selected from the group of the strobilurins. Specifically, component II is selected from the group consisting of azoxystrobin, dimoxystrobin, fluoxastrobin, kresoxim-methyl, orysastrobin, picoxystrobin, pyraclostrobin and trifloxystrobin. In a further specific embodiment, component III is fenpropimorph. According to a further specific embodiment, these are ternary compositions which, as active compounds, comprise in each case only the mentioned three active components I, II and III.

Still a further specific embodiment relates to three-component compositions, wherein component I is as defined above, component II is selected the respiration inhibitors of complex III at $Q_o$ site and component III is selected from the Inhibitors of cell division and cytoskeleton. In a specific embodiment, component II is selected from the group of the strobilurins. Specifically, component II is selected from the group consisting of azoxystrobin, dimoxystrobin, fluoxastrobin, kresoxim-methyl, orysastrobin, picoxystrobin, pyraclostrobin and trifloxystrobin. In a further specific embodiment, component III is selected from tubulin inhibitors such as carbendazim. In a further specific embodiment, component III is selected from sell division inhibitors such as tubulin inhibitors such as metrafenone. According to a further specific embodiment, these are ternary compositions which, as active compounds, comprise in each case only the mentioned three active components I, II and III.

Still a further specific embodiment relates to three-component compositions, wherein component I is as defined above, component II is selected from the respiration inhibitors of complex III at $Q_o$ site and component III is selected from the Inhibitors with Multi Site Action. In a specific embodiment, component II is selected from the group of the strobilurins. Specifically, component II is selected from the group consisting of azoxystrobin, dimoxystrobin, fluoxastrobin, kresoxim-methyl, orysastrobin, picoxystrobin, pyraclostrobin and trifloxystrobin. In a further specific embodiment, component III is selected from captan, Bordeaux mixture, copper acetate, copper hydroxide, copper oxychloride, copper sulfate, sulfur, (tri)basic copper sulfate, mancozeb, maneb, metiram, propineb, thiram, captafol, folpet, chlorothalonil, dichlofluanid, dithianon, dodine and 2,6-dimethyl-1H,5H-[1,4]dithiino[2,3-c:5,6-c']dipyrrole-1,3,5,7 (2H,6H)-tetraone, in particular captan, Bordeaux mixture, copper hydroxide, copper oxychloride, copper sulfate, (tri) basic copper sulfate, mancozeb, maneb, metiram, folpet, chlorothalonil, dithianon, dodine and 2,6-dimethyl-1H,5H-[1,4]dithiino[2,3-c:5,6-c']dipyrrole-1,3,5,7(2H,6H)-tetraone. In one particular embodiment, component III in said compositions is chlorothalonil. According to a further specific embodiment, these are ternary compositions which, as active compounds, comprise in each case only the mentioned three active components I, II and III.

Still a further specific embodiment relates to three-component compositions, wherein component I is as defined above, component II is selected from the sterol biosynthesis inhibitors (SBI fungicides), in particular from the C14 demethylase inhibitors (DMI fungicides), and component III is selected from the Inhibitors with Multi Site Action. In a specific embodiment, component II is selected from cyproconazole, fluquinconazole, metconazole, propiconazole and prothioconazole. One particularly suitable component II is fluquinconazole. Component III is specifically selected from captan, Bordeaux mixture, copper acetate, copper hydroxide, copper oxychloride, copper sulfate, sulfur, (tri)basic copper sulfate, mancozeb, maneb, metiram, propineb, thiram, captafol, folpet, chlorothalonil, dichlofluanid, dithi-anon, dodine and 2,6-dimethyl-1H,5H-[1,4]dithiino[2,3-c:5, 6-c']dipyrrole-1,3,5,7(2H,6H)-tetraone, in particular captan, Bordeaux mixture, copper hydroxide, copper oxychloride, copper sulfate, (tri)basic copper sulfate, mancozeb, maneb, metiram, folpet, chlorothalonil, dithianon, dodine and 2,6-dimethyl-1H,5H-[1,4]dithiino[2,3-c:5,6-c']dipyrrole-1,3,5,7 (2H,6H)-tetraone.

Still a further specific embodiment relates to three-component compositions, wherein component I is as defined above, component II is selected from the sterol biosynthesis inhibitors (SBI fungicides), in particular from the C14 demethylase inhibitors (DMI fungicides), and component III is selected from the Signal transduction inhibitors. In a specific embodiment, component II is triticonazole and component III is fludioxonil.

According to one embodiment, the present invention relates to three-component compositions, comprising a component I, i.e a compound I, in particular a compound selected from compounds I-1, I-2, I-3, I-4, I-5, I-6, I-7, I-8, I-9, I-11, I-13, I-14, I-15 and I-16 or any group of compounds I detailed above, a component II selected from groups groups A) to K) and a component III selected from groups A) to K).

According to a particular embodiment of the inventive three-component compositions comprising three fungicides, the composition comprises compound I, in particular a compound selected from compounds I-1, I-2, I-3, I-4, I-5, I-6, I-7, I-8, I-9, I-11, I-13, I-14, I-15 and I-16 as component I, fluxapyroxad as component II and pyraclostrobin or fenpropimorph as component III. In a further specific embodiment of the present invention, the inventive three-component compositions comprise compound I, in particular a compound selected from compounds I-1, I-2, I-3, I-4, I-5, I-6, I-7, I-8, I-9, I-11, I-13, I-14, I-15 and I-16 or any group of compounds I detailed above, as component I, prothioconazole as component II and fluxapyroxad, bixafen, pyraclostrobin, dimoxystrobin, picoxystrobin, fluoxastrobin, fluopyram or penflufen as component III. In said three-component compositions the weight ratio of component I to component II is 1:20 to 20:1. It may be preferable for the weight ratio to be in the region of from 1:10 to 10:1, preferably from 1:3 to 3:1, in particular from 1:2 to 2:1. The weight ratio of component I to the component III is in the range of from 1:20 to 20:1. It may be preferable for the weight ratio to be in the region of from 1:10 to 10:1, preferably from 1:3 to 3:1, in particular from 1:2 to 2:1. The weight ratio of component I component III is in the range of from 1:20 to 20:1, and in particular in the range of from 1:10 to 10:1. It may be preferable for the weight to be in the range of from 1:3 to 3:1, in particular from 1:2 to 2:1. Said three-component compositions comprising two fungicides as components I and II are in particular suitable as fungicides as detailed below.

According to another embodiment the present invention relates to the use of said compositions for the control of cereal pathogens, wherein the components are used in the above mentioned weight ratios. According to one specific embodiment, said compositions are used for controlling wheat pathogens, wherein the wheat pathogens are in particular selected from *Septoria tritici, Stagonospora nodorum, Pyrenophora tritici repentis, Puccinia recondita, Puccinia striiformis* and *Blumeria graminis*. Furthermore, said compositions are useful for the control of the wheat pathogens selected from *Fusarium culmorum, Fusarium graminearum* and *Pseudocercosporella herpotrichoides*. According to another specific embodiment, said compositions are used for controlling barley pathogens, selected from *Pyrenophera teres, Rhychosporium secalis, Puccinia hordei* and *Blumeria graminis*. Furthermore, said compositions are suitable for the control of barley pathogens selected from *Ramularia collo-cygni* and *Pseudocercosporella herpotrichoides*.

According to still another specific embodiment, said compositions are used for controlling soy pathogens, in particular selected from *phakopsora pachyrizi, P. meibomiae* and *Microsphaera diffusa*. In soy, said compositions may also be effectively used for the control of the so-called FDC (Foliar Disease Complex), e.g. against *Septoria glycines, Cercospora kikuchii, C. sojina, Corynespora cassiicola* and/or *Alternaria* spp.

According to still another specific embodiment, said compositions are used for controlling corn pathogens, in particular selected from *Cercospora zeae-maydis, Puccinia sorghi* and *Helminthosporium maydis*.

According to still another specific embodiment, said compositions are used for controlling sugar beet pathogens, in particular selected from *Cercospora beticola, Erysiphe betae, Ramularia betae* and *Uromyces betae*.

According to still another specific embodiment, said compositions are used for the control of peanut pathogens, in particular selected from *Mycosphaerella arachidis* (=*Cercospora*) and *Puccinia arachidis*.

According to still another specific embodiment, said compositions are used for the control of oil seed rape and canola pathogens, in particular selected from *Sclerotinia sclerotiorum, Leptosphearia maculans* and *Alternaria alternate*.

According to still another specific embodiment, said compositions are used for the control of rice pathogens, in particular selected from *Rhizoctonia solani* and *Pyricularia oryzae*.

According to still another specific embodiment, said compositions are used for the control of pathogens in specialty crops, such as for example in turf, potato, tomato, cucurbits, grapes, apples, ornamentals and bananas. Turf pathogens that may be controlled using said compositions according to the present invention are in particular selected from *Sclerotinia homeocarpon* and *Rhizoctonia solani*. Potato and tomato pathogens that may be controlled according to the present invention are in particular selected from *Alternaria solani, A. alternata* and *Rhizoctonia solani*. A cucurbit pathogen that may be controlled using said compositions according to the present invention is in particular *Sphaerotheca fuliginea*. A grape pathogen that may be controlled using said compositions according to the present invention is in particular *Uncinula necator* and *Botrytis cinerea*. An apple pathogen that may be controlled using said compositions according to the present invention is in particular *Podosphaera leucotricha* and *Venturia inaequalis*. Ornamental pathogens that may be controlled using said compositions according to the present invention are in particular selected from *Sphaerotheca fuliginea*, *Diplocarpon* spp., *Alternaria* spp. and *Sclerotinia* spp. Banana pathogens that may be controlled using said compositions according to the present invention are in particular selected from *Mycosphaerella fijiensis* and *Mycosphaerella musicola*.

According to one embodiment thereof, the present invention relates to the composition of component I, fluxapyroxad and pyraclostrobin, wherein two of the components are present in a weight ratio of 20:1 to 1:20, more specifically 5:1 to 1:5, in particular 2:1 to 1:2. In particular, the weight ratios for the three components are component I to component 111 1:1 to 2:1; component I to component III 1:1 to 2:1 and component II to component III 1:1 to 1:2. It may be preferred if the components are present in a weight ratio of 1:1:1 to 2:1:2 or 2:1:2 to 2:1:1. The components are in particular used in synergistically effective amounts.

According to another embodiment, the present invention relates to the composition comprising component I, fluxapyroxad and fenpropimorph, wherein two of the components are present in a weight ratio of 20:1 to 1:20, more specifically 5:1 to 1:5, in particular 2:1 to 1:2. In particular, the weight ratios for the three components are component I to component II 1:1 to 2:1; component I to component III 1:3 to 1:6 and component II to component III 1:3 to 1:6. It may be preferred if the components are present in a weight ratio of 1:1:3 to 1:1:6. The components are in particular used in synergistically effective amounts.

A further embodiment of the invention relates to three-component compositions, comprising a component I, i.e a compound I, in particular a compound selected from compounds I-1, I-2, I-3, I-4, I-5, I-6, I-7, I-8, I-9, I-11, I-13, I-14, I-15 and I-16 or any group of compounds I detailed above, and components II and III, wherein at least one of components II and III selected from Group M), the growth regulators, in particular selected from chlormequat (chlormequat chloride), mepiquat (mepiquat chloride), paclobutrazole, prohexadione (prohexadione-calcium), trinexapac-ethyl and uniconazole. According to one specific embodiment thereof, components II is selected from groups A) to K) or any of the preferred embodiment thereof given herein, and component III is selected from Group M), the growth regulators, in particular selected from chlormequat (chlormequat chloride), mepiquat (mepiquat chloride), paclobutrazole, prohexadione (prohexadione-calcium), trinexapac-ethyl and uniconazole. According to another specific embodiment thereof, both components II and III are selected from Group M), the growth regulators, in particular selected from chlormequat (chlormequat chloride), mepiquat (mepiquat chloride), paclobutrazole, prohexadione (prohexadione-calcium), trinexapac-ethyl and uniconazole.

A further embodiment of the invention relates to three-component compositions, comprising a component I, i.e a compound I, in particular a compound selected from compounds I-1, I-2, I-3, I-4, I-5, I-6, I-7, I-8, I-9, I-11, I-13, I-14, I-15 and I-16 or any group of compounds I detailed above, component II selected from any one of groups A) to K) or any preferred embodiment thereof, and component III selected from the insecticides of group O).

According to one more specific embodiment, component I is as defined above, component II is selected from the respiration inhibitors of complex III at $Q_o$, in particular selected from the group of the strobilurins, and component III is an insecticide, in particular one of the insecticides as defined below. Specifically, component II is selected from the group consisting of azoxystrobin, dimoxystrobin, fluoxastrobin, kresoxim-methyl, orysastrobin, picoxystrobin, pyraclostrobin and trifloxystrobin.

Still a further specific embodiment relates to three-component compositions, wherein component I is as defined above, component II is selected from the sterol biosynthesis inhibitors (SBI fungicides) and component III is an insecticide, in particular one of the insecticides as defined below. Specifically, component II is selected from is selected from the group of the C14 demethylase inhibitors (DMI fungicides), in particular selected from cyproconazole, difenoconazole, epoxiconazole, fluquinconazole, flusilazole, flutriafol, metconazole, myclobutanil, penconazole, propiconazole, prothioconazole, triadimefon, triadimenol, tebuconazole, tetraconazole, triticonazole and prochloraz.

A further embodiment of the invention relates to three-component compositions, comprising a component I, i.e a compound I, in particular a compound selected from compounds I-1, I-2, I-3, I-4, I-5, I-6, I-7, I-8, I-9, I-11, I-13, I-14, I-15 and I-16 or any group of compounds I detailed above, and components II and III that are selected from the insecticides of group O).

In the three-component compositions of the inventions comprising an insecticide, the insecticide is, according to one embodiment, selected from the group of the organo (thio)phosphates, in particular selected from the group consisting of acephate, chlorpyrifos, diazinon, dichlorvos, dimethoate, fenitrothion, methamidophos, methidathion, methyl-parathion, monocrotophos, phorate, profenofos and terbufos. According to a further specific embodiment, the insecticide in the three-component compositions is selected from the group of the carbamates, in particular selected from the group consisting of aldicarb, carbaryl, carbofuran, carbosulfan, methomyl and thiodicarb. According to a further specific embodiment, the insecticide in the three-component compositions is selected from the group of the pyrethroids, in particular selected from the group consisting of: bifenthrin, cyfluthrin, cypermethrin, alpha-cypermethrin, zeta-cypermethrin, deltamethrin, esfenvalerate, lambda-cyhalothrin and tefluthrin. According to still a further specific embodiment, the insecticide in the three-component compositions is selected from the group of insect growth regulators, in particular selected from the group consisting of lufenuron and spirotetramat. According to still a further specific embodiment, the insecticide in the three-component compositions is selected from the group of the nicotine receptor agonists/antagonists, in particular selected from the group consisting of: clothianidin, imidacloprid, thiamethoxam and thiacloprid. According to a further specific embodiment, the insecticide in the three-component compositions is selected from the group of the GABA antagonists, in particular selected from the group consisting of: endosulfan and fipronil. According to a further specific embodiment, the insecticide in the three-component compositions is selected from the group of the macrocyclic lactones, in particular selected from the group consisting of: abamectin, emamectin, spinosad and spinetoram. According to a further specific embodiment, the insecticide in the three-component compositions is hydramethylnon. According to a further specific embodiment, the insecticide in the three-component compositions is fenbutatin oxide. According to a further specific embodiment, the insecticide in the three-component compositions is selected from the group consisting of chlorfenapyr, indoxacarb, metaflumizone, flonicamid, flubendiamide, cyazypyr (HGW86) and cyflumetofen.

Particularly preferred fungicidal components III used in the inventive compositions, are compounds selected from the group of the following compounds:

| | |
|---|---|
| II-1 | ametoctradin |
| II-2 | amisulbrom |
| II-3 | azoxystrobin |
| II-4 | benthiavalicarb |
| II-5 | benzovindiflupyr |
| II-6 | bixafen |
| II-7 | boscalid |
| II-8 | carbendazim |
| II-11 | chlorothalonil |
| II-12 | cyazofamid |
| II-13 | cyflufenamid |
| II-15 | cyproconazole |

-continued

| | |
|---|---|
| II-16 | cyprodinil |
| II-21 | difenoconazole |
| II-23 | dimoxystrobin |
| II-25 | dithianon |
| II-26 | epoxiconazole |
| II-27 | ethaboxam |
| II-31 | fenpropidin |
| II-32 | fenpropimorph |
| II-33 | fluazinam |
| II-34 | fludioxonil |
| II-35 | fluopicolide |
| II-36 | fluopyram |
| II-37 | fluoxastrobin |
| II-38 | fluquinconazole |
| II-39 | flusilazole |
| II-42 | fluxapyroxad |
| II-43 | folpet |
| II-44 | fosetyl-Al |
| II-50 | isopyrazam |
| II-51 | iprovalicarb |
| II-53 | kresoxim-methyl |
| II-54 | mancozeb |
| II-60 | metconazole |
| II-61 | metiram |
| II-62 | metrafenone |
| II-65 | proquinazid |
| II-66 | pyraclostrobin |
| II-68 | penflufen |
| II-69 | phosporous acid |
| II-70 | potassium salt of phosphorous acid |
| II-71 | sodium salt of phosphorous acid |
| II-72 | penthiopyrad |
| II-73 | picoxystrobin |
| II-74 | prochloraz |
| II-76 | propiconazole |
| II-78 | prothioconazole |
| II-83 | silthiofam |
| II-84 | spiroxamine |
| II-85 | sulfur |
| II-86 | tebuconazole |
| II-89 | thiophanate-methyl |
| II-92 | trifloxystrobin |
| II-93 | triticonazole |
| II-97 | zoxamide |

Particularly preferred fungicidal components III are compounds selected from the group of the following compounds:

| | |
|---|---|
| II-3 | azoxystrobin |
| II-5 | benzovindiflupyr |
| II-6 | bixafen |
| II-7 | boscalid |
| II-8 | carbendazim |
| II-11 | chlorothalonil |
| II-15 | cyproconazole |
| II-16 | cyprodinil |
| II-21 | difenoconazole |
| II-26 | epoxiconazole |
| II-32 | fenpropimorph |
| II-33 | fluazinam |
| II-34 | fludioxonil |
| II-37 | fluoxastrobin |
| II-38 | fluquinconazole |
| II-39 | flusilazole |
| II-42 | fluxapyroxad |
| II-44 | fosetyl-Al |
| II-50 | isopyrazam |
| II-53 | kresoxim-methyl |
| II-60 | metconazole |
| II-62 | metrafenone |
| II-66 | pyraclostrobin |
| II-69 | phosporous acid |
| II-70 | potassium salt of phosphorous acid |
| II-71 | sodium salt of phosphorous acid |

| | |
|---|---|
| II-72 | penthiopyrad |
| II-74 | prochloraz |
| II-76 | propiconazole |
| II-78 | prothioconazole |
| II-84 | spiroxamine |
| II-85 | sulfur |
| II-86 | tebuconazole |
| II-92 | trifloxystrobin |
| II-93 | triticonazole |

Particularly preferred compositions are the three-component compositions, wherein component I is as defined above, i.e a compound I, in particular a compound selected from compounds I-1, I-2, I-3, I-4, I-5, I-6, I-7, I-8, I-9, I-11, I-13, I-14, I-15 and I-16 or any group of compounds I detailed above, and components II and III are selected from

| | |
|---|---|
| II-3 | azoxystrobin |
| II-5 | benzovindiflupyr |
| II-6 | bixafen |
| II-7 | boscalid |
| II-8 | carbendazim |
| II-11 | chlorothalonil |
| II-16 | cyprodinil |
| II-21 | difenoconazole |
| II-26 | epoxiconazole |
| II-32 | fenpropimorph |
| II-33 | fluazinam |
| II-37 | fluoxastrobin |
| II-39 | flusilazole |
| II-42 | fluxapyroxad |
| II-44 | fosetyl-Al |
| II-50 | isopyrazam |
| II-53 | kresoxim-methyl |
| II-60 | metconazole |
| II-62 | metrafenone |
| II-66 | pyraclostrobin |
| II-69 | phosporous acid |
| II-70 | potassium salt of phosphorous acid |
| II-71 | sodium salt of phosphorous acid |
| II-72 | penthiopyrad |
| II-74 | prochloraz |
| II-76 | propiconazole |
| II-78 | prothioconazole |
| II-84 | spiroxamine |
| II-85 | sulfur |
| II-86 | tebuconazole |
| II-92 | trifloxystrobin | wherein components II and III are different from each other. Particularly preferred compositions of these compositions are compiled in Table T1, where each row corresponds to one embodiment of the compositions according to the invention, i.e. one specific individualized three-component composition. According to one specific aspect, these are ternary compositions which each only contain these three components as the active compound. Furthermore, also every combination of the compositions individualized in this table represent embodiments of the present invention.

TABLE T1

| composition | I | II | III |
|---|---|---|---|
| Three-component compositions comprising a component I, a component II a component III, wherein component II and III are selected from the preferred fungicides detained above, wherein components II and III are different from each other. | | | |
| T1-1 | I-1 | II-3 | II-5 |
| T1-2 | I-1 | II-3 | II-6 |
| T1-3 | I-1 | II-3 | II-7 |
| T1-4 | I-1 | II-3 | II-8 |
| T1-5 | I-1 | II-3 | II-11 |
| T1-6 | I-1 | II-3 | II-16 |
| T1-7 | I-1 | II-3 | II-21 |
| T1-8 | I-1 | II-3 | II-26 |
| T1-9 | I-1 | II-3 | II-32 |
| T1-10 | I-1 | II-3 | II-33 |
| T1-11 | I-1 | II-3 | II-37 |
| T1-12 | I-1 | II-3 | II-39 |
| T1-13 | I-1 | II-3 | II-42 |
| T1-14 | I-1 | II-3 | II-44 |
| T1-15 | I-1 | II-3 | II-50 |
| T1-16 | I-1 | II-3 | II-53 |
| T1-17 | I-1 | II-3 | II-60 |
| T1-18 | I-1 | II-3 | II-62 |
| T1-19 | I-1 | II-3 | II-66 |
| T1-20 | I-1 | II-3 | II-69 |
| T1-21 | I-1 | II-3 | II-70 |
| T1-22 | I-1 | II-3 | II-71 |
| T1-23 | I-1 | II-3 | II-72 |
| T1-24 | I-1 | II-3 | II-74 |
| T1-25 | I-1 | II-3 | II-76 |
| T1-26 | I-1 | II-3 | II-78 |
| T1-27 | I-1 | II-3 | II-84 |
| T1-28 | I-1 | II-3 | II-85 |
| T1-29 | I-1 | II-3 | II-86 |
| T1-30 | I-1 | II-3 | II-92 |
| T1-31 | I-1 | II-5 | II-6 |
| T1-32 | I-1 | II-5 | II-7 |
| T1-33 | I-1 | II-5 | II-8 |
| T1-34 | I-1 | II-5 | II-11 |
| T1-35 | I-1 | II-5 | II-16 |
| T1-36 | I-1 | II-5 | II-21 |
| T1-37 | I-1 | II-5 | II-26 |
| T1-38 | I-1 | II-5 | II-32 |
| T1-39 | I-1 | II-5 | II-33 |
| T1-40 | I-1 | II-5 | II-37 |
| T1-41 | I-1 | II-5 | II-39 |
| T1-42 | I-1 | II-5 | II-42 |
| T1-43 | I-1 | II-5 | II-44 |
| T1-44 | I-1 | II-5 | II-50 |
| T1-45 | I-1 | II-5 | II-53 |
| T1-46 | I-1 | II-5 | II-60 |
| T1-47 | I-1 | II-5 | II-62 |
| T1-48 | I-1 | II-5 | II-66 |
| T1-49 | I-1 | II-5 | II-69 |
| T1-50 | I-1 | II-5 | II-70 |
| T1-51 | I-1 | II-5 | II-71 |
| T1-52 | I-1 | II-5 | II-72 |
| T1-53 | I-1 | II-5 | II-74 |
| T1-54 | I-1 | II-5 | II-76 |
| T1-55 | I-1 | II-5 | II-78 |
| T1-56 | I-1 | II-5 | II-84 |
| T1-57 | I-1 | II-5 | II-85 |
| T1-58 | I-1 | II-5 | II-86 |
| T1-59 | I-1 | II-5 | II-92 |
| T1-60 | I-1 | II-6 | II-7 |
| T1-61 | I-1 | II-6 | II-8 |
| T1-62 | I-1 | II-6 | II-11 |
| T1-63 | I-1 | II-6 | II-16 |
| T1-64 | I-1 | II-6 | II-21 |
| T1-65 | I-1 | II-6 | II-26 |
| T1-66 | I-1 | II-6 | II-32 |
| T1-67 | I-1 | II-6 | II-33 |
| T1-68 | I-1 | II-6 | II-37 |
| T1-69 | I-1 | II-6 | II-39 |
| T1-70 | I-1 | II-6 | II-42 |
| T1-71 | I-1 | II-6 | II-44 |
| T1-72 | I-1 | II-6 | II-50 |
| T1-73 | I-1 | II-6 | II-53 |
| T1-74 | I-1 | II-6 | II-60 |
| T1-75 | I-1 | II-6 | II-62 |
| T1-76 | I-1 | II-6 | II-66 |
| T1-77 | I-1 | II-6 | II-69 |
| T1-78 | I-1 | II-6 | II-70 |
| T1-79 | I-1 | II-6 | II-71 |
| T1-80 | I-1 | II-6 | II-72 |
| T1-81 | I-1 | II-6 | II-74 |

TABLE T1-continued

| composition | I | II | III |
|---|---|---|---|
| T1-82 | I-1 | II-6 | II-76 |
| T1-83 | I-1 | II-6 | II-78 |
| T1-84 | I-1 | II-6 | II-84 |
| T1-85 | I-1 | II-6 | II-85 |
| T1-86 | I-1 | II-6 | II-86 |
| T1-87 | I-1 | II-6 | II-92 |
| T1-88 | I-1 | II-7 | II-8 |
| T1-89 | I-1 | II-7 | II-11 |
| T1-90 | I-1 | II-7 | II-16 |
| T1-91 | I-1 | II-7 | II-21 |
| T1-92 | I-1 | II-7 | II-26 |
| T1-93 | I-1 | II-7 | II-32 |
| T1-94 | I-1 | II-7 | II-33 |
| T1-95 | I-1 | II-7 | II-37 |
| T1-96 | I-1 | II-7 | II-39 |
| T1-97 | I-1 | II-7 | II-42 |
| T1-98 | I-1 | II-7 | II-44 |
| T1-99 | I-1 | II-7 | II-50 |
| T1-100 | I-1 | II-7 | II-53 |
| T1-101 | I-1 | II-7 | II-60 |
| T1-102 | I-1 | II-7 | II-62 |
| T1-103 | I-1 | II-7 | II-66 |
| T1-104 | I-1 | II-7 | II-69 |
| T1-105 | I-1 | II-7 | II-70 |
| T1-106 | I-1 | II-7 | II-71 |
| T1-107 | I-1 | II-7 | II-72 |
| T1-108 | I-1 | II-7 | II-74 |
| T1-109 | I-1 | II-7 | II-76 |
| T1-110 | I-1 | II-7 | II-78 |
| T1-111 | I-1 | II-7 | II-84 |
| T1-112 | I-1 | II-7 | II-85 |
| T1-113 | I-1 | II-7 | II-86 |
| T1-114 | I-1 | II-7 | II-92 |
| T1-115 | I-1 | II-8 | II-11 |
| T1-116 | I-1 | II-8 | II-16 |
| T1-117 | I-1 | II-8 | II-21 |
| T1-118 | I-1 | II-8 | II-26 |
| T1-119 | I-1 | II-8 | II-32 |
| T1-120 | I-1 | II-8 | II-33 |
| T1-121 | I-1 | II-8 | II-37 |
| T1-122 | I-1 | II-8 | II-39 |
| T1-123 | I-1 | II-8 | II-42 |
| T1-124 | I-1 | II-8 | II-44 |
| T1-125 | I-1 | II-8 | II-50 |
| T1-126 | I-1 | II-8 | II-53 |
| T1-127 | I-1 | II-8 | II-60 |
| T1-128 | I-1 | II-8 | II-62 |
| T1-129 | I-1 | II-8 | II-66 |
| T1-130 | I-1 | II-8 | II-69 |
| T1-131 | I-1 | II-8 | II-70 |
| T1-132 | I-1 | II-8 | II-71 |
| T1-133 | I-1 | II-8 | II-72 |
| T1-134 | I-1 | II-8 | II-74 |
| T1-135 | I-1 | II-8 | II-76 |
| T1-136 | I-1 | II-8 | II-78 |
| T1-137 | I-1 | II-8 | II-84 |
| T1-138 | I-1 | II-8 | II-85 |
| T1-139 | I-1 | II-8 | II-86 |
| T1-140 | I-1 | II-8 | II-92 |
| T1-141 | I-1 | II-11 | II-16 |
| T1-142 | I-1 | II-11 | II-21 |
| T1-143 | I-1 | II-11 | II-26 |
| T1-144 | I-1 | II-11 | II-32 |
| T1-145 | I-1 | II-11 | II-33 |
| T1-146 | I-1 | II-11 | II-37 |
| T1-147 | I-1 | II-11 | II-39 |
| T1-148 | I-1 | II-11 | II-42 |
| T1-149 | I-1 | II-11 | II-44 |
| T1-150 | I-1 | II-11 | II-50 |
| T1-151 | I-1 | II-11 | II-53 |
| T1-152 | I-1 | II-11 | II-60 |
| T1-153 | I-1 | II-11 | II-62 |
| T1-154 | I-1 | II-11 | II-66 |
| T1-155 | I-1 | II-11 | II-69 |
| T1-156 | I-1 | II-11 | II-70 |
| T1-157 | I-1 | II-11 | II-71 |
| T1-158 | I-1 | II-11 | II-72 |
| T1-159 | I-1 | II-11 | II-74 |
| T1-160 | I-1 | II-11 | II-76 |
| T1-161 | I-1 | II-11 | II-78 |
| T1-162 | I-1 | II-11 | II-84 |
| T1-163 | I-1 | II-11 | II-85 |
| T1-164 | I-1 | II-11 | II-86 |
| T1-165 | I-1 | II-11 | II-92 |
| T1-166 | I-1 | II-16 | II-21 |
| T1-167 | I-1 | II-16 | II-26 |
| T1-168 | I-1 | II-16 | II-32 |
| T1-169 | I-1 | II-16 | II-33 |
| T1-170 | I-1 | II-16 | II-37 |
| T1-171 | I-1 | II-16 | II-39 |
| T1-172 | I-1 | II-16 | II-42 |
| T1-173 | I-1 | II-16 | II-44 |
| T1-174 | I-1 | II-16 | II-50 |
| T1-175 | I-1 | II-16 | II-53 |
| T1-176 | I-1 | II-16 | II-60 |
| T1-177 | I-1 | II-16 | II-62 |
| T1-178 | I-1 | II-16 | II-66 |
| T1-179 | I-1 | II-16 | II-69 |
| T1-180 | I-1 | II-16 | II-70 |
| T1-181 | I-1 | II-16 | II-71 |
| T1-182 | I-1 | II-16 | II-72 |
| T1-183 | I-1 | II-16 | II-74 |
| T1-184 | I-1 | II-16 | II-76 |
| T1-185 | I-1 | II-16 | II-78 |
| T1-186 | I-1 | II-16 | II-84 |
| T1-187 | I-1 | II-16 | II-85 |
| T1-188 | I-1 | II-16 | II-86 |
| T1-189 | I-1 | II-16 | II-92 |
| T1-190 | I-1 | II-21 | II-26 |
| T1-191 | I-1 | II-21 | II-32 |
| T1-192 | I-1 | II-21 | II-33 |
| T1-193 | I-1 | II-21 | II-37 |
| T1-194 | I-1 | II-21 | II-39 |
| T1-195 | I-1 | II-21 | II-42 |
| T1-196 | I-1 | II-21 | II-44 |
| T1-197 | I-1 | II-21 | II-50 |
| T1-198 | I-1 | II-21 | II-53 |
| T1-199 | I-1 | II-21 | II-60 |
| T1-200 | I-1 | II-21 | II-62 |
| T1-201 | I-1 | II-21 | II-66 |
| T1-202 | I-1 | II-21 | II-69 |
| T1-203 | I-1 | II-21 | II-70 |
| T1-204 | I-1 | II-21 | II-71 |
| T1-205 | I-1 | II-21 | II-72 |
| T1-206 | I-1 | II-21 | II-74 |
| T1-207 | I-1 | II-21 | II-76 |
| T1-208 | I-1 | II-21 | II-78 |
| T1-209 | I-1 | II-21 | II-84 |
| T1-210 | I-1 | II-21 | II-85 |
| T1-211 | I-1 | II-21 | II-86 |
| T1-212 | I-1 | II-21 | II-92 |
| T1-213 | I-1 | II-26 | II-32 |
| T1-214 | I-1 | II-26 | II-33 |
| T1-215 | I-1 | II-26 | II-37 |
| T1-216 | I-1 | II-26 | II-39 |
| T1-217 | I-1 | II-26 | II-42 |
| T1-218 | I-1 | II-26 | II-44 |
| T1-219 | I-1 | II-26 | II-50 |
| T1-220 | I-1 | II-26 | II-53 |
| T1-221 | I-1 | II-26 | II-60 |
| T1-222 | I-1 | II-26 | II-62 |
| T1-223 | I-1 | II-26 | II-66 |
| T1-224 | I-1 | II-26 | II-69 |
| T1-225 | I-1 | II-26 | II-70 |
| T1-226 | I-1 | II-26 | II-71 |
| T1-227 | I-1 | II-26 | II-72 |
| T1-228 | I-1 | II-26 | II-74 |
| T1-229 | I-1 | II-26 | II-76 |
| T1-230 | I-1 | II-26 | II-78 |
| T1-231 | I-1 | II-26 | II-84 |
| T1-232 | I-1 | II-26 | II-85 |
| T1-233 | I-1 | II-26 | II-86 |
| T1-234 | I-1 | II-26 | II-92 |
| T1-235 | I-1 | II-32 | II-33 |
| T1-236 | I-1 | II-32 | II-37 |
| T1-237 | I-1 | II-32 | II-39 |

TABLE T1-continued

| composition | I | II | III |
|---|---|---|---|
| T1-238 | I-1 | II-32 | II-42 |
| T1-239 | I-1 | II-32 | II-44 |
| T1-240 | I-1 | II-32 | II-50 |
| T1-241 | I-1 | II-32 | II-53 |
| T1-242 | I-1 | II-32 | II-60 |
| T1-243 | I-1 | II-32 | II-62 |
| T1-244 | I-1 | II-32 | II-66 |
| T1-245 | I-1 | II-32 | II-69 |
| T1-246 | I-1 | II-32 | II-70 |
| T1-247 | I-1 | II-32 | II-71 |
| T1-248 | I-1 | II-32 | II-72 |
| T1-249 | I-1 | II-32 | II-74 |
| T1-250 | I-1 | II-32 | II-76 |
| T1-251 | I-1 | II-32 | II-78 |
| T1-252 | I-1 | II-32 | II-84 |
| T1-253 | I-1 | II-32 | II-85 |
| T1-254 | I-1 | II-32 | II-86 |
| T1-255 | I-1 | II-32 | II-92 |
| T1-256 | I-1 | II-33 | II-37 |
| T1-257 | I-1 | II-33 | II-39 |
| T1-258 | I-1 | II-33 | II-42 |
| T1-259 | I-1 | II-33 | II-44 |
| T1-260 | I-1 | II-33 | II-50 |
| T1-261 | I-1 | II-33 | II-53 |
| T1-262 | I-1 | II-33 | II-60 |
| T1-263 | I-1 | II-33 | II-62 |
| T1-264 | I-1 | II-33 | II-66 |
| T1-265 | I-1 | II-33 | II-69 |
| T1-266 | I-1 | II-33 | II-70 |
| T1-267 | I-1 | II-33 | II-71 |
| T1-268 | I-1 | II-33 | II-72 |
| T1-269 | I-1 | II-33 | II-74 |
| T1-270 | I-1 | II-33 | II-76 |
| T1-271 | I-1 | II-33 | II-78 |
| T1-272 | I-1 | II-33 | II-84 |
| T1-273 | I-1 | II-33 | II-85 |
| T1-274 | I-1 | II-33 | II-86 |
| T1-275 | I-1 | II-33 | II-92 |
| T1-276 | I-1 | II-37 | II-39 |
| T1-277 | I-1 | II-37 | II-42 |
| T1-278 | I-1 | II-37 | II-44 |
| T1-279 | I-1 | II-37 | II-50 |
| T1-280 | I-1 | II-37 | II-53 |
| T1-281 | I-1 | II-37 | II-60 |
| T1-282 | I-1 | II-37 | II-62 |
| T1-283 | I-1 | II-37 | II-66 |
| T1-284 | I-1 | II-37 | II-69 |
| T1-285 | I-1 | II-37 | II-70 |
| T1-286 | I-1 | II-37 | II-71 |
| T1-287 | I-1 | II-37 | II-72 |
| T1-288 | I-1 | II-37 | II-74 |
| T1-289 | I-1 | II-37 | II-76 |
| T1-290 | I-1 | II-37 | II-78 |
| T1-291 | I-1 | II-37 | II-84 |
| T1-292 | I-1 | II-37 | II-85 |
| T1-293 | I-1 | II-37 | II-86 |
| T1-294 | I-1 | II-37 | II-92 |
| T1-295 | I-1 | II-39 | II-42 |
| T1-296 | I-1 | II-39 | II-44 |
| T1-297 | I-1 | II-39 | II-50 |
| T1-298 | I-1 | II-39 | II-53 |
| T1-299 | I-1 | II-39 | II-60 |
| T1-300 | I-1 | II-39 | II-62 |
| T1-301 | I-1 | II-39 | II-66 |
| T1-302 | I-1 | II-39 | II-69 |
| T1-303 | I-1 | II-39 | II-70 |
| T1-304 | I-1 | II-39 | II-71 |
| T1-305 | I-1 | II-39 | II-72 |
| T1-306 | I-1 | II-39 | II-74 |
| T1-307 | I-1 | II-39 | II-76 |
| T1-308 | I-1 | II-39 | II-78 |
| T1-309 | I-1 | II-39 | II-84 |
| T1-310 | I-1 | II-39 | II-85 |
| T1-311 | I-1 | II-39 | II-86 |
| T1-312 | I-1 | II-39 | II-92 |
| T1-313 | I-1 | II-42 | II-44 |
| T1-314 | I-1 | II-42 | II-50 |
| T1-315 | I-1 | II-42 | II-53 |
| T1-316 | I-1 | II-42 | II-60 |
| T1-317 | I-1 | II-42 | II-62 |
| T1-318 | I-1 | II-42 | II-66 |
| T1-319 | I-1 | II-42 | II-69 |
| T1-320 | I-1 | II-42 | II-70 |
| T1-321 | I-1 | II-42 | II-71 |
| T1-322 | I-1 | II-42 | II-72 |
| T1-323 | I-1 | II-42 | II-74 |
| T1-324 | I-1 | II-42 | II-76 |
| T1-325 | I-1 | II-42 | II-78 |
| T1-326 | I-1 | II-42 | II-84 |
| T1-327 | I-1 | II-42 | II-85 |
| T1-328 | I-1 | II-42 | II-86 |
| T1-329 | I-1 | II-42 | II-92 |
| T1-330 | I-1 | II-44 | II-50 |
| T1-331 | I-1 | II-44 | II-53 |
| T1-332 | I-1 | II-44 | II-60 |
| T1-333 | I-1 | II-44 | II-62 |
| T1-334 | I-1 | II-44 | II-66 |
| T1-335 | I-1 | II-44 | II-69 |
| T1-336 | I-1 | II-44 | II-70 |
| T1-337 | I-1 | II-44 | II-71 |
| T1-338 | I-1 | II-44 | II-72 |
| T1-339 | I-1 | II-44 | II-74 |
| T1-340 | I-1 | II-44 | II-76 |
| T1-341 | I-1 | II-44 | II-78 |
| T1-342 | I-1 | II-44 | II-84 |
| T1-343 | I-1 | II-44 | II-85 |
| T1-344 | I-1 | II-44 | II-86 |
| T1-345 | I-1 | II-44 | II-92 |
| T1-346 | I-1 | II-50 | II-53 |
| T1-347 | I-1 | II-50 | II-60 |
| T1-348 | I-1 | II-50 | II-62 |
| T1-349 | I-1 | II-50 | II-66 |
| T1-350 | I-1 | II-50 | II-69 |
| T1-351 | I-1 | II-50 | II-70 |
| T1-352 | I-1 | II-50 | II-71 |
| T1-353 | I-1 | II-50 | II-72 |
| T1-354 | I-1 | II-50 | II-74 |
| T1-355 | I-1 | II-50 | II-76 |
| T1-356 | I-1 | II-50 | II-78 |
| T1-357 | I-1 | II-50 | II-84 |
| T1-358 | I-1 | II-50 | II-85 |
| T1-359 | I-1 | II-50 | II-86 |
| T1-360 | I-1 | II-50 | II-92 |
| T1-361 | I-1 | II-53 | II-60 |
| T1-362 | I-1 | II-53 | II-62 |
| T1-363 | I-1 | II-53 | II-66 |
| T1-364 | I-1 | II-53 | II-69 |
| T1-365 | I-1 | II-53 | II-70 |
| T1-366 | I-1 | II-53 | II-71 |
| T1-367 | I-1 | II-53 | II-72 |
| T1-368 | I-1 | II-53 | II-74 |
| T1-369 | I-1 | II-53 | II-76 |
| T1-370 | I-1 | II-53 | II-78 |
| T1-371 | I-1 | II-53 | II-84 |
| T1-372 | I-1 | II-53 | II-85 |
| T1-373 | I-1 | II-53 | II-86 |
| T1-374 | I-1 | II-53 | II-92 |
| T1-375 | I-1 | II-60 | II-62 |
| T1-376 | I-1 | II-60 | II-66 |
| T1-377 | I-1 | II-60 | II-69 |
| T1-378 | I-1 | II-60 | II-70 |
| T1-379 | I-1 | II-60 | II-71 |
| T1-380 | I-1 | II-60 | II-72 |
| T1-381 | I-1 | II-60 | II-74 |
| T1-382 | I-1 | II-60 | II-76 |
| T1-383 | I-1 | II-60 | II-78 |
| T1-384 | I-1 | II-60 | II-84 |
| T1-385 | I-1 | II-60 | II-85 |
| T1-386 | I-1 | II-60 | II-86 |
| T1-387 | I-1 | II-60 | II-92 |
| T1-388 | I-1 | II-62 | II-66 |
| T1-389 | I-1 | II-62 | II-69 |
| T1-390 | I-1 | II-62 | II-70 |
| T1-391 | I-1 | II-62 | II-71 |
| T1-392 | I-1 | II-62 | II-72 |
| T1-393 | I-1 | II-62 | II-74 |

TABLE T1-continued

| composition | I | II | III |
|---|---|---|---|
| T1-394 | I-1 | II-62 | II-76 |
| T1-395 | I-1 | II-62 | II-78 |
| T1-396 | I-1 | II-62 | II-84 |
| T1-397 | I-1 | II-62 | II-85 |
| T1-398 | I-1 | II-62 | II-86 |
| T1-399 | I-1 | II-62 | II-92 |
| T1-400 | I-1 | II-66 | II-69 |
| T1-401 | I-1 | II-66 | II-70 |
| T1-402 | I-1 | II-66 | II-71 |
| T1-403 | I-1 | II-66 | II-72 |
| T1-404 | I-1 | II-66 | II-74 |
| T1-405 | I-1 | II-66 | II-76 |
| T1-406 | I-1 | II-66 | II-78 |
| T1-407 | I-1 | II-66 | II-84 |
| T1-408 | I-1 | II-66 | II-85 |
| T1-409 | I-1 | II-66 | II-86 |
| T1-410 | I-1 | II-66 | II-92 |
| T1-411 | I-1 | II-69 | II-70 |
| T1-412 | I-1 | II-69 | II-71 |
| T1-413 | I-1 | II-69 | II-72 |
| T1-414 | I-1 | II-69 | II-74 |
| T1-415 | I-1 | II-69 | II-76 |
| T1-416 | I-1 | II-69 | II-78 |
| T1-417 | I-1 | II-69 | II-84 |
| T1-418 | I-1 | II-69 | II-85 |
| T1-419 | I-1 | II-69 | II-86 |
| T1-420 | I-1 | II-69 | II-92 |
| T1-421 | I-1 | II-70 | II-71 |
| T1-422 | I-1 | II-70 | II-72 |
| T1-423 | I-1 | II-70 | II-74 |
| T1-424 | I-1 | II-70 | II-76 |
| T1-425 | I-1 | II-70 | II-78 |
| T1-426 | I-1 | II-70 | II-84 |
| T1-427 | I-1 | II-70 | II-85 |
| T1-428 | I-1 | II-70 | II-86 |
| T1-429 | I-1 | II-70 | II-92 |
| T1-430 | I-1 | II-71 | II-72 |
| T1-431 | I-1 | II-71 | II-74 |
| T1-432 | I-1 | II-71 | II-76 |
| T1-433 | I-1 | II-71 | II-78 |
| T1-434 | I-1 | II-71 | II-84 |
| T1-435 | I-1 | II-71 | II-85 |
| T1-436 | I-1 | II-71 | II-86 |
| T1-437 | I-1 | II-71 | II-92 |
| T1-438 | I-1 | II-72 | II-74 |
| T1-439 | I-1 | II-74 | II-76 |
| T1-440 | I-1 | II-74 | II-78 |
| T1-441 | I-1 | II-74 | II-84 |
| T1-442 | I-1 | II-74 | II-85 |
| T1-443 | I-1 | II-74 | II-86 |
| T1-444 | I-1 | II-74 | II-92 |
| T1-445 | I-1 | II-76 | II-78 |
| T1-446 | I-1 | II-76 | II-84 |
| T1-447 | I-1 | II-76 | II-85 |
| T1-448 | I-1 | II-76 | II-86 |
| T1-449 | I-1 | II-76 | II-92 |
| T1-450 | I-1 | II-78 | II-84 |
| T1-451 | I-1 | II-78 | II-85 |
| T1-452 | I-1 | II-78 | II-86 |
| T1-453 | I-1 | II-78 | II-92 |
| T1-454 | I-1 | II-84 | II-85 |
| T1-455 | I-1 | II-84 | II-86 |
| T1-456 | I-1 | II-84 | II-92 |
| T1-457 | I-1 | II-85 | II-86 |
| T1-458 | I-1 | II-85 | II-92 |
| T1-459 | I-1 | II-86 | II-92 |
| T1-460 | I-2 | II-3 | II-5 |
| T1-461 | I-2 | II-3 | II-6 |
| T1-462 | I-2 | II-3 | II-7 |
| T1-463 | I-2 | II-3 | II-8 |
| T1-464 | I-2 | II-3 | II-11 |
| T1-465 | I-2 | II-3 | II-16 |
| T1-466 | I-2 | II-3 | II-21 |
| T1-467 | I-2 | II-3 | II-26 |
| T1-468 | I-2 | II-3 | II-32 |
| T1-469 | I-2 | II-3 | II-33 |
| T1-470 | I-2 | II-3 | II-37 |
| T1-471 | I-2 | II-3 | II-39 |
| T1-472 | I-2 | II-3 | II-42 |
| T1-473 | I-2 | II-3 | II-44 |
| T1-474 | I-2 | II-3 | II-50 |
| T1-475 | I-2 | II-3 | II-53 |
| T1-476 | I-2 | II-3 | II-60 |
| T1-477 | I-2 | II-3 | II-62 |
| T1-478 | I-2 | II-3 | II-66 |
| T1-479 | I-2 | II-3 | II-69 |
| T1-480 | I-2 | II-3 | II-70 |
| T1-481 | I-2 | II-3 | II-71 |
| T1-482 | I-2 | II-3 | II-72 |
| T1-483 | I-2 | II-3 | II-74 |
| T1-484 | I-2 | II-3 | II-76 |
| T1-485 | I-2 | II-3 | II-78 |
| T1-486 | I-2 | II-3 | II-84 |
| T1-487 | I-2 | II-3 | II-85 |
| T1-488 | I-2 | II-3 | II-86 |
| T1-489 | I-2 | II-3 | II-92 |
| T1-490 | I-2 | II-5 | II-6 |
| T1-491 | I-2 | II-5 | II-7 |
| T1-492 | I-2 | II-5 | II-8 |
| T1-493 | I-2 | II-5 | II-11 |
| T1-494 | I-2 | II-5 | II-16 |
| T1-495 | I-2 | II-5 | II-21 |
| T1-496 | I-2 | II-5 | II-26 |
| T1-497 | I-2 | II-5 | II-32 |
| T1-498 | I-2 | II-5 | II-33 |
| T1-499 | I-2 | II-5 | II-37 |
| T1-500 | I-2 | II-5 | II-39 |
| T1-501 | I-2 | II-5 | II-42 |
| T1-502 | I-2 | II-5 | II-44 |
| T1-503 | I-2 | II-5 | II-50 |
| T1-504 | I-2 | II-5 | II-53 |
| T1-505 | I-2 | II-5 | II-60 |
| T1-506 | I-2 | II-5 | II-62 |
| T1-507 | I-2 | II-5 | II-66 |
| T1-508 | I-2 | II-5 | II-69 |
| T1-509 | I-2 | II-5 | II-70 |
| T1-510 | I-2 | II-5 | II-71 |
| T1-511 | I-2 | II-5 | II-72 |
| T1-512 | I-2 | II-5 | II-74 |
| T1-513 | I-2 | II-5 | II-76 |
| T1-514 | I-2 | II-5 | II-78 |
| T1-515 | I-2 | II-5 | II-84 |
| T1-516 | I-2 | II-5 | II-85 |
| T1-517 | I-2 | II-5 | II-86 |
| T1-518 | I-2 | II-5 | II-92 |
| T1-519 | I-2 | II-6 | II-7 |
| T1-520 | I-2 | II-6 | II-8 |
| T1-521 | I-2 | II-6 | II-11 |
| T1-522 | I-2 | II-6 | II-16 |
| T1-523 | I-2 | II-6 | II-21 |
| T1-524 | I-2 | II-6 | II-26 |
| T1-525 | I-2 | II-6 | II-32 |
| T1-526 | I-2 | II-6 | II-33 |
| T1-527 | I-2 | II-6 | II-37 |
| T1-528 | I-2 | II-6 | II-39 |
| T1-529 | I-2 | II-6 | II-42 |
| T1-530 | I-2 | II-6 | II-44 |
| T1-531 | I-2 | II-6 | II-50 |
| T1-532 | I-2 | II-6 | II-53 |
| T1-533 | I-2 | II-6 | II-60 |
| T1-534 | I-2 | II-6 | II-62 |
| T1-535 | I-2 | II-6 | II-66 |
| T1-536 | I-2 | II-6 | II-69 |
| T1-537 | I-2 | II-6 | II-70 |
| T1-538 | I-2 | II-6 | II-71 |
| T1-539 | I-2 | II-6 | II-72 |
| T1-540 | I-2 | II-6 | II-74 |
| T1-541 | I-2 | II-6 | II-76 |
| T1-542 | I-2 | II-6 | II-78 |
| T1-543 | I-2 | II-6 | II-84 |
| T1-544 | I-2 | II-6 | II-85 |
| T1-545 | I-2 | II-6 | II-86 |
| T1-546 | I-2 | II-6 | II-92 |
| T1-547 | I-2 | II-7 | II-8 |
| T1-548 | I-2 | II-7 | II-11 |
| T1-549 | I-2 | II-7 | II-16 |

TABLE T1-continued

| composition | I | II | III |
|---|---|---|---|
| T1-550 | I-2 | II-7 | II-21 |
| T1-551 | I-2 | II-7 | II-26 |
| T1-552 | I-2 | II-7 | II-32 |
| T1-553 | I-2 | II-7 | II-33 |
| T1-554 | I-2 | II-7 | II-37 |
| T1-555 | I-2 | II-7 | II-39 |
| T1-556 | I-2 | II-7 | II-42 |
| T1-557 | I-2 | II-7 | II-44 |
| T1-558 | I-2 | II-7 | II-50 |
| T1-559 | I-2 | II-7 | II-53 |
| T1-560 | I-2 | II-7 | II-60 |
| T1-561 | I-2 | II-7 | II-62 |
| T1-562 | I-2 | II-7 | II-66 |
| T1-563 | I-2 | II-7 | II-69 |
| T1-564 | I-2 | II-7 | II-70 |
| T1-565 | I-2 | II-7 | II-71 |
| T1-566 | I-2 | II-7 | II-72 |
| T1-567 | I-2 | II-7 | II-74 |
| T1-568 | I-2 | II-7 | II-76 |
| T1-569 | I-2 | II-7 | II-78 |
| T1-570 | I-2 | II-7 | II-84 |
| T1-571 | I-2 | II-7 | II-85 |
| T1-572 | I-2 | II-7 | II-86 |
| T1-573 | I-2 | II-7 | II-92 |
| T1-574 | I-2 | II-8 | II-11 |
| T1-575 | I-2 | II-8 | II-16 |
| T1-576 | I-2 | II-8 | II-21 |
| T1-577 | I-2 | II-8 | II-26 |
| T1-578 | I-2 | II-8 | II-32 |
| T1-579 | I-2 | II-8 | II-33 |
| T1-580 | I-2 | II-8 | II-37 |
| T1-581 | I-2 | II-8 | II-39 |
| T1-582 | I-2 | II-8 | II-42 |
| T1-583 | I-2 | II-8 | II-44 |
| T1-584 | I-2 | II-8 | II-50 |
| T1-585 | I-2 | II-8 | II-53 |
| T1-586 | I-2 | II-8 | II-60 |
| T1-587 | I-2 | II-8 | II-62 |
| T1-588 | I-2 | II-8 | II-66 |
| T1-589 | I-2 | II-8 | II-69 |
| T1-590 | I-2 | II-8 | II-70 |
| T1-591 | I-2 | II-8 | II-71 |
| T1-592 | I-2 | II-8 | II-72 |
| T1-593 | I-2 | II-8 | II-74 |
| T1-594 | I-2 | II-8 | II-76 |
| T1-595 | I-2 | II-8 | II-78 |
| T1-596 | I-2 | II-8 | II-84 |
| T1-597 | I-2 | II-8 | II-85 |
| T1-598 | I-2 | II-8 | II-86 |
| T1-599 | I-2 | II-8 | II-92 |
| T1-600 | I-2 | II-11 | II-16 |
| T1-601 | I-2 | II-11 | II-21 |
| T1-602 | I-2 | II-11 | II-26 |
| T1-603 | I-2 | II-11 | II-32 |
| T1-604 | I-2 | II-11 | II-33 |
| T1-605 | I-2 | II-11 | II-37 |
| T1-606 | I-2 | II-11 | II-39 |
| T1-607 | I-2 | II-11 | II-42 |
| T1-608 | I-2 | II-11 | II-44 |
| T1-609 | I-2 | II-11 | II-50 |
| T1-610 | I-2 | II-11 | II-53 |
| T1-611 | I-2 | II-11 | II-60 |
| T1-612 | I-2 | II-11 | II-62 |
| T1-613 | I-2 | II-11 | II-66 |
| T1-614 | I-2 | II-11 | II-69 |
| T1-615 | I-2 | II-11 | II-70 |
| T1-616 | I-2 | II-11 | II-71 |
| T1-617 | I-2 | II-11 | II-72 |
| T1-618 | I-2 | II-11 | II-74 |
| T1-619 | I-2 | II-11 | II-76 |
| T1-620 | I-2 | II-11 | II-78 |
| T1-621 | I-2 | II-11 | II-84 |
| T1-622 | I-2 | II-11 | II-85 |
| T1-623 | I-2 | II-11 | II-86 |
| T1-624 | I-2 | II-11 | II-92 |
| T1-625 | I-2 | II-16 | II-21 |
| T1-626 | I-2 | II-16 | II-26 |
| T1-627 | I-2 | II-16 | II-32 |
| T1-628 | I-2 | II-16 | II-33 |
| T1-629 | I-2 | II-16 | II-37 |
| T1-630 | I-2 | II-16 | II-39 |
| T1-631 | I-2 | II-16 | II-42 |
| T1-632 | I-2 | II-16 | II-44 |
| T1-633 | I-2 | II-16 | II-50 |
| T1-634 | I-2 | II-16 | II-53 |
| T1-635 | I-2 | II-16 | II-60 |
| T1-636 | I-2 | II-16 | II-62 |
| T1-637 | I-2 | II-16 | II-66 |
| T1-638 | I-2 | II-16 | II-69 |
| T1-639 | I-2 | II-16 | II-70 |
| T1-640 | I-2 | II-16 | II-71 |
| T1-641 | I-2 | II-16 | II-72 |
| T1-642 | I-2 | II-16 | II-74 |
| T1-643 | I-2 | II-16 | II-76 |
| T1-644 | I-2 | II-16 | II-78 |
| T1-645 | I-2 | II-16 | II-84 |
| T1-646 | I-2 | II-16 | II-85 |
| T1-647 | I-2 | II-16 | II-86 |
| T1-648 | I-2 | II-16 | II-92 |
| T1-649 | I-2 | II-21 | II-26 |
| T1-650 | I-2 | II-21 | II-32 |
| T1-651 | I-2 | II-21 | II-33 |
| T1-652 | I-2 | II-21 | II-37 |
| T1-653 | I-2 | II-21 | II-39 |
| T1-654 | I-2 | II-21 | II-42 |
| T1-655 | I-2 | II-21 | II-44 |
| T1-656 | I-2 | II-21 | II-50 |
| T1-657 | I-2 | II-21 | II-53 |
| T1-658 | I-2 | II-21 | II-60 |
| T1-659 | I-2 | II-21 | II-62 |
| T1-660 | I-2 | II-21 | II-66 |
| T1-661 | I-2 | II-21 | II-69 |
| T1-662 | I-2 | II-21 | II-70 |
| T1-663 | I-2 | II-21 | II-71 |
| T1-664 | I-2 | II-21 | II-72 |
| T1-665 | I-2 | II-21 | II-74 |
| T1-666 | I-2 | II-21 | II-76 |
| T1-667 | I-2 | II-21 | II-78 |
| T1-668 | I-2 | II-21 | II-84 |
| T1-669 | I-2 | II-21 | II-85 |
| T1-670 | I-2 | II-21 | II-86 |
| T1-671 | I-2 | II-21 | II-92 |
| T1-672 | I-2 | II-26 | II-32 |
| T1-673 | I-2 | II-26 | II-33 |
| T1-674 | I-2 | II-26 | II-37 |
| T1-675 | I-2 | II-26 | II-39 |
| T1-676 | I-2 | II-26 | II-42 |
| T1-677 | I-2 | II-26 | II-44 |
| T1-678 | I-2 | II-26 | II-50 |
| T1-679 | I-2 | II-26 | II-53 |
| T1-680 | I-2 | II-26 | II-60 |
| T1-681 | I-2 | II-26 | II-62 |
| T1-682 | I-2 | II-26 | II-66 |
| T1-683 | I-2 | II-26 | II-69 |
| T1-684 | I-2 | II-26 | II-70 |
| T1-685 | I-2 | II-26 | II-71 |
| T1-686 | I-2 | II-26 | II-72 |
| T1-687 | I-2 | II-26 | II-74 |
| T1-688 | I-2 | II-26 | II-76 |
| T1-689 | I-2 | II-26 | II-78 |
| T1-690 | I-2 | II-26 | II-84 |
| T1-691 | I-2 | II-26 | II-85 |
| T1-692 | I-2 | II-26 | II-86 |
| T1-693 | I-2 | II-26 | II-92 |
| T1-694 | I-2 | II-32 | II-33 |
| T1-695 | I-2 | II-32 | II-37 |
| T1-696 | I-2 | II-32 | II-39 |
| T1-697 | I-2 | II-32 | II-42 |
| T1-698 | I-2 | II-32 | II-44 |
| T1-699 | I-2 | II-32 | II-50 |
| T1-700 | I-2 | II-32 | II-53 |
| T1-701 | I-2 | II-32 | II-60 |
| T1-702 | I-2 | II-32 | II-62 |
| T1-703 | I-2 | II-32 | II-66 |
| T1-704 | I-2 | II-32 | II-69 |
| T1-705 | I-2 | II-32 | II-70 |

TABLE T1-continued

| composition | I | II | III |
|---|---|---|---|
| T1-706 | I-2 | II-32 | II-71 |
| T1-707 | I-2 | II-32 | II-72 |
| T1-708 | I-2 | II-32 | II-74 |
| T1-709 | I-2 | II-32 | II-76 |
| T1-710 | I-2 | II-32 | II-78 |
| T1-711 | I-2 | II-32 | II-84 |
| T1-712 | I-2 | II-32 | II-85 |
| T1-713 | I-2 | II-32 | II-86 |
| T1-714 | I-2 | II-32 | II-92 |
| T1-715 | I-2 | II-33 | II-37 |
| T1-716 | I-2 | II-33 | II-39 |
| T1-717 | I-2 | II-33 | II-42 |
| T1-718 | I-2 | II-33 | II-44 |
| T1-719 | I-2 | II-33 | II-50 |
| T1-720 | I-2 | II-33 | II-53 |
| T1-721 | I-2 | II-33 | II-60 |
| T1-722 | I-2 | II-33 | II-62 |
| T1-723 | I-2 | II-33 | II-66 |
| T1-724 | I-2 | II-33 | II-69 |
| T1-725 | I-2 | II-33 | II-70 |
| T1-726 | I-2 | II-33 | II-71 |
| T1-727 | I-2 | II-33 | II-72 |
| T1-728 | I-2 | II-33 | II-74 |
| T1-729 | I-2 | II-33 | II-76 |
| T1-730 | I-2 | II-33 | II-78 |
| T1-731 | I-2 | II-33 | II-84 |
| T1-732 | I-2 | II-33 | II-85 |
| T1-733 | I-2 | II-33 | II-86 |
| T1-734 | I-2 | II-33 | II-92 |
| T1-735 | I-2 | II-37 | II-39 |
| T1-736 | I-2 | II-37 | II-42 |
| T1-737 | I-2 | II-37 | II-44 |
| T1-738 | I-2 | II-37 | II-50 |
| T1-739 | I-2 | II-37 | II-53 |
| T1-740 | I-2 | II-37 | II-60 |
| T1-741 | I-2 | II-37 | II-62 |
| T1-742 | I-2 | II-37 | II-66 |
| T1-743 | I-2 | II-37 | II-69 |
| T1-744 | I-2 | II-37 | II-70 |
| T1-745 | I-2 | II-37 | II-71 |
| T1-746 | I-2 | II-37 | II-72 |
| T1-747 | I-2 | II-37 | II-74 |
| T1-748 | I-2 | II-37 | II-76 |
| T1-749 | I-2 | II-37 | II-78 |
| T1-750 | I-2 | II-37 | II-84 |
| T1-751 | I-2 | II-37 | II-85 |
| T1-752 | I-2 | II-37 | II-86 |
| T1-753 | I-2 | II-37 | II-92 |
| T1-754 | I-2 | II-39 | II-42 |
| T1-755 | I-2 | II-39 | II-44 |
| T1-756 | I-2 | II-39 | II-50 |
| T1-757 | I-2 | II-39 | II-53 |
| T1-758 | I-2 | II-39 | II-60 |
| T1-759 | I-2 | II-39 | II-62 |
| T1-760 | I-2 | II-39 | II-66 |
| T1-761 | I-2 | II-39 | II-69 |
| T1-762 | I-2 | II-39 | II-70 |
| T1-763 | I-2 | II-39 | II-71 |
| T1-764 | I-2 | II-39 | II-72 |
| T1-765 | I-2 | II-39 | II-74 |
| T1-766 | I-2 | II-39 | II-76 |
| T1-767 | I-2 | II-39 | II-78 |
| T1-768 | I-2 | II-39 | II-84 |
| T1-769 | I-2 | II-39 | II-85 |
| T1-770 | I-2 | II-39 | II-86 |
| T1-771 | I-2 | II-39 | II-92 |
| T1-772 | I-2 | II-42 | II-44 |
| T1-773 | I-2 | II-42 | II-50 |
| T1-774 | I-2 | II-42 | II-53 |
| T1-775 | I-2 | II-42 | II-60 |
| T1-776 | I-2 | II-42 | II-62 |
| T1-777 | I-2 | II-42 | II-66 |
| T1-778 | I-2 | II-42 | II-69 |
| T1-779 | I-2 | II-42 | II-70 |
| T1-780 | I-2 | II-42 | II-71 |
| T1-781 | I-2 | II-42 | II-72 |
| T1-782 | I-2 | II-42 | II-74 |
| T1-783 | I-2 | II-42 | II-76 |
| T1-784 | I-2 | II-42 | II-78 |
| T1-785 | I-2 | II-42 | II-84 |
| T1-786 | I-2 | II-42 | II-85 |
| T1-787 | I-2 | II-42 | II-86 |
| T1-788 | I-2 | II-42 | II-92 |
| T1-789 | I-2 | II-44 | II-50 |
| T1-790 | I-2 | II-44 | II-53 |
| T1-791 | I-2 | II-44 | II-60 |
| T1-792 | I-2 | II-44 | II-62 |
| T1-793 | I-2 | II-44 | II-66 |
| T1-794 | I-2 | II-44 | II-69 |
| T1-795 | I-2 | II-44 | II-70 |
| T1-796 | I-2 | II-44 | II-71 |
| T1-797 | I-2 | II-44 | II-72 |
| T1-798 | I-2 | II-44 | II-74 |
| T1-799 | I-2 | II-44 | II-76 |
| T1-800 | I-2 | II-44 | II-78 |
| T1-801 | I-2 | II-44 | II-84 |
| T1-802 | I-2 | II-44 | II-85 |
| T1-803 | I-2 | II-44 | II-86 |
| T1-804 | I-2 | II-44 | II-92 |
| T1-805 | I-2 | II-50 | II-53 |
| T1-806 | I-2 | II-50 | II-60 |
| T1-807 | I-2 | II-50 | II-62 |
| T1-808 | I-2 | II-50 | II-66 |
| T1-809 | I-2 | II-50 | II-69 |
| T1-810 | I-2 | II-50 | II-70 |
| T1-811 | I-2 | II-50 | II-71 |
| T1-812 | I-2 | II-50 | II-72 |
| T1-813 | I-2 | II-50 | II-74 |
| T1-814 | I-2 | II-50 | II-76 |
| T1-815 | I-2 | II-50 | II-78 |
| T1-816 | I-2 | II-50 | II-84 |
| T1-817 | I-2 | II-50 | II-85 |
| T1-818 | I-2 | II-50 | II-86 |
| T1-819 | I-2 | II-50 | II-92 |
| T1-820 | I-2 | II-53 | II-60 |
| T1-821 | I-2 | II-53 | II-62 |
| T1-822 | I-2 | II-53 | II-66 |
| T1-823 | I-2 | II-53 | II-69 |
| T1-824 | I-2 | II-53 | II-70 |
| T1-825 | I-2 | II-53 | II-71 |
| T1-826 | I-2 | II-53 | II-72 |
| T1-827 | I-2 | II-53 | II-74 |
| T1-828 | I-2 | II-53 | II-76 |
| T1-829 | I-2 | II-53 | II-78 |
| T1-830 | I-2 | II-53 | II-84 |
| T1-831 | I-2 | II-53 | II-85 |
| T1-832 | I-2 | II-53 | II-86 |
| T1-833 | I-2 | II-53 | II-92 |
| T1-834 | I-2 | II-60 | II-62 |
| T1-835 | I-2 | II-60 | II-66 |
| T1-836 | I-2 | II-60 | II-69 |
| T1-837 | I-2 | II-60 | II-70 |
| T1-838 | I-2 | II-60 | II-71 |
| T1-839 | I-2 | II-60 | II-72 |
| T1-840 | I-2 | II-60 | II-74 |
| T1-841 | I-2 | II-60 | II-76 |
| T1-842 | I-2 | II-60 | II-78 |
| T1-843 | I-2 | II-60 | II-84 |
| T1-844 | I-2 | II-60 | II-85 |
| T1-845 | I-2 | II-60 | II-86 |
| T1-846 | I-2 | II-60 | II-92 |
| T1-847 | I-2 | II-62 | II-66 |
| T1-848 | I-2 | II-62 | II-69 |
| T1-849 | I-2 | II-62 | II-70 |
| T1-850 | I-2 | II-62 | II-71 |
| T1-851 | I-2 | II-62 | II-72 |
| T1-852 | I-2 | II-62 | II-74 |
| T1-853 | I-2 | II-62 | II-76 |
| T1-854 | I-2 | II-62 | II-78 |
| T1-855 | I-2 | II-62 | II-84 |
| T1-856 | I-2 | II-62 | II-85 |
| T1-857 | I-2 | II-62 | II-86 |
| T1-858 | I-2 | II-62 | II-92 |
| T1-859 | I-2 | II-66 | II-69 |
| T1-860 | I-2 | II-66 | II-70 |
| T1-861 | I-2 | II-66 | II-71 |

TABLE T1-continued

| composition | I | II | III |
|---|---|---|---|
| T1-862 | I-2 | II-66 | II-72 |
| T1-863 | I-2 | II-66 | II-74 |
| T1-864 | I-2 | II-66 | II-76 |
| T1-865 | I-2 | II-66 | II-78 |
| T1-866 | I-2 | II-66 | II-84 |
| T1-867 | I-2 | II-66 | II-85 |
| T1-868 | I-2 | II-66 | II-86 |
| T1-869 | I-2 | II-66 | II-92 |
| T1-870 | I-2 | II-69 | II-70 |
| T1-871 | I-2 | II-69 | II-71 |
| T1-872 | I-2 | II-69 | II-72 |
| T1-873 | I-2 | II-69 | II-74 |
| T1-874 | I-2 | II-69 | II-76 |
| T1-875 | I-2 | II-69 | II-78 |
| T1-876 | I-2 | II-69 | II-84 |
| T1-877 | I-2 | II-69 | II-85 |
| T1-878 | I-2 | II-69 | II-86 |
| T1-879 | I-2 | II-69 | II-92 |
| T1-880 | I-2 | II-70 | II-71 |
| T1-881 | I-2 | II-70 | II-72 |
| T1-882 | I-2 | II-70 | II-74 |
| T1-883 | I-2 | II-70 | II-76 |
| T1-884 | I-2 | II-70 | II-78 |
| T1-885 | I-2 | II-70 | II-84 |
| T1-886 | I-2 | II-70 | II-85 |
| T1-887 | I-2 | II-70 | II-86 |
| T1-888 | I-2 | II-70 | II-92 |
| T1-889 | I-2 | II-71 | II-72 |
| T1-890 | I-2 | II-71 | II-74 |
| T1-891 | I-2 | II-71 | II-76 |
| T1-892 | I-2 | II-71 | II-78 |
| T1-893 | I-2 | II-71 | II-84 |
| T1-894 | I-2 | II-71 | II-85 |
| T1-895 | I-2 | II-71 | II-86 |
| T1-896 | I-2 | II-71 | II-92 |
| T1-897 | I-2 | II-72 | II-74 |
| T1-898 | I-2 | II-74 | II-76 |
| T1-899 | I-2 | II-74 | II-78 |
| T1-900 | I-2 | II-74 | II-84 |
| T1-901 | I-2 | II-74 | II-85 |
| T1-902 | I-2 | II-74 | II-86 |
| T1-903 | I-2 | II-74 | II-92 |
| T1-904 | I-2 | II-76 | II-78 |
| T1-905 | I-2 | II-76 | II-84 |
| T1-906 | I-2 | II-76 | II-85 |
| T1-907 | I-2 | II-76 | II-86 |
| T1-908 | I-2 | II-76 | II-92 |
| T1-909 | I-2 | II-78 | II-84 |
| T1-910 | I-2 | II-78 | II-85 |
| T1-911 | I-2 | II-78 | II-86 |
| T1-912 | I-2 | II-78 | II-92 |
| T1-913 | I-2 | II-84 | II-85 |
| T1-914 | I-2 | II-84 | II-86 |
| T1-915 | I-2 | II-84 | II-92 |
| T1-916 | I-2 | II-85 | II-86 |
| T1-917 | I-2 | II-85 | II-92 |
| T1-918 | I-2 | II-86 | II-92 |
| T1-919 | I-5 | II-3 | II-5 |
| T1-920 | I-5 | II-3 | II-6 |
| T1-921 | I-5 | II-3 | II-7 |
| T1-922 | I-5 | II-3 | II-8 |
| T1-923 | I-5 | II-3 | II-11 |
| T1-924 | I-5 | II-3 | II-16 |
| T1-925 | I-5 | II-3 | II-21 |
| T1-926 | I-5 | II-3 | II-26 |
| T1-927 | I-5 | II-3 | II-32 |
| T1-928 | I-5 | II-3 | II-33 |
| T1-929 | I-5 | II-3 | II-37 |
| T1-930 | I-5 | II-3 | II-39 |
| T1-931 | I-5 | II-3 | II-42 |
| T1-932 | I-5 | II-3 | II-44 |
| T1-933 | I-5 | II-3 | II-50 |
| T1-934 | I-5 | II-3 | II-53 |
| T1-935 | I-5 | II-3 | II-60 |
| T1-936 | I-5 | II-3 | II-62 |
| T1-937 | I-5 | II-3 | II-66 |
| T1-938 | I-5 | II-3 | II-69 |
| T1-939 | I-5 | II-3 | II-70 |
| T1-940 | I-5 | II-3 | II-71 |
| T1-941 | I-5 | II-3 | II-72 |
| T1-942 | I-5 | II-3 | II-74 |
| T1-943 | I-5 | II-3 | II-76 |
| T1-944 | I-5 | II-3 | II-78 |
| T1-945 | I-5 | II-3 | II-84 |
| T1-946 | I-5 | II-3 | II-85 |
| T1-947 | I-5 | II-3 | II-86 |
| T1-948 | I-5 | II-3 | II-92 |
| T1-949 | I-5 | II-5 | II-6 |
| T1-950 | I-5 | II-5 | II-7 |
| T1-951 | I-5 | II-5 | II-8 |
| T1-952 | I-5 | II-5 | II-11 |
| T1-953 | I-5 | II-5 | II-16 |
| T1-954 | I-5 | II-5 | II-21 |
| T1-955 | I-5 | II-5 | II-26 |
| T1-956 | I-5 | II-5 | II-32 |
| T1-957 | I-5 | II-5 | II-33 |
| T1-958 | I-5 | II-5 | II-37 |
| T1-959 | I-5 | II-5 | II-39 |
| T1-960 | I-5 | II-5 | II-42 |
| T1-961 | I-5 | II-5 | II-44 |
| T1-962 | I-5 | II-5 | II-50 |
| T1-963 | I-5 | II-5 | II-53 |
| T1-964 | I-5 | II-5 | II-60 |
| T1-965 | I-5 | II-5 | II-62 |
| T1-966 | I-5 | II-5 | II-66 |
| T1-967 | I-5 | II-5 | II-69 |
| T1-968 | I-5 | II-5 | II-70 |
| T1-969 | I-5 | II-5 | II-71 |
| T1-970 | I-5 | II-5 | II-72 |
| T1-971 | I-5 | II-5 | II-74 |
| T1-972 | I-5 | II-5 | II-76 |
| T1-973 | I-5 | II-5 | II-78 |
| T1-974 | I-5 | II-5 | II-84 |
| T1-975 | I-5 | II-5 | II-85 |
| T1-976 | I-5 | II-5 | II-86 |
| T1-977 | I-5 | II-5 | II-92 |
| T1-978 | I-5 | II-6 | II-7 |
| T1-979 | I-5 | II-6 | II-8 |
| T1-980 | I-5 | II-6 | II-11 |
| T1-981 | I-5 | II-6 | II-16 |
| T1-982 | I-5 | II-6 | II-21 |
| T1-983 | I-5 | II-6 | II-26 |
| T1-984 | I-5 | II-6 | II-32 |
| T1-985 | I-5 | II-6 | II-33 |
| T1-986 | I-5 | II-6 | II-37 |
| T1-987 | I-5 | II-6 | II-39 |
| T1-988 | I-5 | II-6 | II-42 |
| T1-989 | I-5 | II-6 | II-44 |
| T1-990 | I-5 | II-6 | II-50 |
| T1-991 | I-5 | II-6 | II-53 |
| T1-992 | I-5 | II-6 | II-60 |
| T1-993 | I-5 | II-6 | II-62 |
| T1-994 | I-5 | II-6 | II-66 |
| T1-995 | I-5 | II-6 | II-69 |
| T1-996 | I-5 | II-6 | II-70 |
| T1-997 | I-5 | II-6 | II-71 |
| T1-998 | I-5 | II-6 | II-72 |
| T1-999 | I-5 | II-6 | II-74 |
| T1-1000 | I-5 | II-6 | II-76 |
| T1-1001 | I-5 | II-6 | II-78 |
| T1-1002 | I-5 | II-6 | II-84 |
| T1-1003 | I-5 | II-6 | II-85 |
| T1-1004 | I-5 | II-6 | II-86 |
| T1-1005 | I-5 | II-6 | II-92 |
| T1-1006 | I-5 | II-7 | II-8 |
| T1-1007 | I-5 | II-7 | II-11 |
| T1-1008 | I-5 | II-7 | II-16 |
| T1-1009 | I-5 | II-7 | II-21 |
| T1-1010 | I-5 | II-7 | II-26 |
| T1-1011 | I-5 | II-7 | II-32 |
| T1-1012 | I-5 | II-7 | II-33 |
| T1-1013 | I-5 | II-7 | II-37 |
| T1-1014 | I-5 | II-7 | II-39 |
| T1-1015 | I-5 | II-7 | II-42 |
| T1-1016 | I-5 | II-7 | II-44 |
| T1-1017 | I-5 | II-7 | II-50 |

TABLE T1-continued

| composition | I | II | III |
|---|---|---|---|
| T1-1018 | I-5 | II-7 | II-53 |
| T1-1019 | I-5 | II-7 | II-60 |
| T1-1020 | I-5 | II-7 | II-62 |
| T1-1021 | I-5 | II-7 | II-66 |
| T1-1022 | I-5 | II-7 | II-69 |
| T1-1023 | I-5 | II-7 | II-70 |
| T1-1024 | I-5 | II-7 | II-71 |
| T1-1025 | I-5 | II-7 | II-72 |
| T1-1026 | I-5 | II-7 | II-74 |
| T1-1027 | I-5 | II-7 | II-76 |
| T1-1028 | I-5 | II-7 | II-78 |
| T1-1029 | I-5 | II-7 | II-84 |
| T1-1030 | I-5 | II-7 | II-85 |
| T1-1031 | I-5 | II-7 | II-86 |
| T1-1032 | I-5 | II-7 | II-92 |
| T1-1033 | I-5 | II-8 | II-11 |
| T1-1034 | I-5 | II-8 | II-16 |
| T1-1035 | I-5 | II-8 | II-21 |
| T1-1036 | I-5 | II-8 | II-26 |
| T1-1037 | I-5 | II-8 | II-32 |
| T1-1038 | I-5 | II-8 | II-33 |
| T1-1039 | I-5 | II-8 | II-37 |
| T1-1040 | I-5 | II-8 | II-39 |
| T1-1041 | I-5 | II-8 | II-42 |
| T1-1042 | I-5 | II-8 | II-44 |
| T1-1043 | I-5 | II-8 | II-50 |
| T1-1044 | I-5 | II-8 | II-53 |
| T1-1045 | I-5 | II-8 | II-60 |
| T1-1046 | I-5 | II-8 | II-62 |
| T1-1047 | I-5 | II-8 | II-66 |
| T1-1048 | I-5 | II-8 | II-69 |
| T1-1049 | I-5 | II-8 | II-70 |
| T1-1050 | I-5 | II-8 | II-71 |
| T1-1051 | I-5 | II-8 | II-72 |
| T1-1052 | I-5 | II-8 | II-74 |
| T1-1053 | I-5 | II-8 | II-76 |
| T1-1054 | I-5 | II-8 | II-78 |
| T1-1055 | I-5 | II-8 | II-84 |
| T1-1056 | I-5 | II-8 | II-85 |
| T1-1057 | I-5 | II-8 | II-86 |
| T1-1058 | I-5 | II-8 | II-92 |
| T1-1059 | I-5 | II-11 | II-16 |
| T1-1060 | I-5 | II-11 | II-21 |
| T1-1061 | I-5 | II-11 | II-26 |
| T1-1062 | I-5 | II-11 | II-32 |
| T1-1063 | I-5 | II-11 | II-33 |
| T1-1064 | I-5 | II-11 | II-37 |
| T1-1065 | I-5 | II-11 | II-39 |
| T1-1066 | I-5 | II-11 | II-42 |
| T1-1067 | I-5 | II-11 | II-44 |
| T1-1068 | I-5 | II-11 | II-50 |
| T1-1069 | I-5 | II-11 | II-53 |
| T1-1070 | I-5 | II-11 | II-60 |
| T1-1071 | I-5 | II-11 | II-62 |
| T1-1072 | I-5 | II-11 | II-66 |
| T1-1073 | I-5 | II-11 | II-69 |
| T1-1074 | I-5 | II-11 | II-70 |
| T1-1075 | I-5 | II-11 | II-71 |
| T1-1076 | I-5 | II-11 | II-72 |
| T1-1077 | I-5 | II-11 | II-74 |
| T1-1078 | I-5 | II-11 | II-76 |
| T1-1079 | I-5 | II-11 | II-78 |
| T1-1080 | I-5 | II-11 | II-84 |
| T1-1081 | I-5 | II-11 | II-85 |
| T1-1082 | I-5 | II-11 | II-86 |
| T1-1083 | I-5 | II-11 | II-92 |
| T1-1084 | I-5 | II-16 | II-21 |
| T1-1085 | I-5 | II-16 | II-26 |
| T1-1086 | I-5 | II-16 | II-32 |
| T1-1087 | I-5 | II-16 | II-33 |
| T1-1088 | I-5 | II-16 | II-37 |
| T1-1089 | I-5 | II-16 | II-39 |
| T1-1090 | I-5 | II-16 | II-42 |
| T1-1091 | I-5 | II-16 | II-44 |
| T1-1092 | I-5 | II-16 | II-50 |
| T1-1093 | I-5 | II-16 | II-53 |
| T1-1094 | I-5 | II-16 | II-60 |
| T1-1095 | I-5 | II-16 | II-62 |
| T1-1096 | I-5 | II-16 | II-66 |
| T1-1097 | I-5 | II-16 | II-69 |
| T1-1098 | I-5 | II-16 | II-70 |
| T1-1099 | I-5 | II-16 | II-71 |
| T1-1100 | I-5 | II-16 | II-72 |
| T1-1101 | I-5 | II-16 | II-74 |
| T1-1102 | I-5 | II-16 | II-76 |
| T1-1103 | I-5 | II-16 | II-78 |
| T1-1104 | I-5 | II-16 | II-84 |
| T1-1105 | I-5 | II-16 | II-85 |
| T1-1106 | I-5 | II-16 | II-86 |
| T1-1107 | I-5 | II-16 | II-92 |
| T1-1108 | I-5 | II-21 | II-26 |
| T1-1109 | I-5 | II-21 | II-32 |
| T1-1110 | I-5 | II-21 | II-33 |
| T1-1111 | I-5 | II-21 | II-37 |
| T1-1112 | I-5 | II-21 | II-39 |
| T1-1113 | I-5 | II-21 | II-42 |
| T1-1114 | I-5 | II-21 | II-44 |
| T1-1115 | I-5 | II-21 | II-50 |
| T1-1116 | I-5 | II-21 | II-53 |
| T1-1117 | I-5 | II-21 | II-60 |
| T1-1118 | I-5 | II-21 | II-62 |
| T1-1119 | I-5 | II-21 | II-66 |
| T1-1120 | I-5 | II-21 | II-69 |
| T1-1121 | I-5 | II-21 | II-70 |
| T1-1122 | I-5 | II-21 | II-71 |
| T1-1123 | I-5 | II-21 | II-72 |
| T1-1124 | I-5 | II-21 | II-74 |
| T1-1125 | I-5 | II-21 | II-76 |
| T1-1126 | I-5 | II-21 | II-78 |
| T1-1127 | I-5 | II-21 | II-84 |
| T1-1128 | I-5 | II-21 | II-85 |
| T1-1129 | I-5 | II-21 | II-86 |
| T1-1130 | I-5 | II-21 | II-92 |
| T1-1131 | I-5 | II-26 | II-32 |
| T1-1132 | I-5 | II-26 | II-33 |
| T1-1133 | I-5 | II-26 | II-37 |
| T1-1134 | I-5 | II-26 | II-39 |
| T1-1135 | I-5 | II-26 | II-42 |
| T1-1136 | I-5 | II-26 | II-44 |
| T1-1137 | I-5 | II-26 | II-50 |
| T1-1138 | I-5 | II-26 | II-53 |
| T1-1139 | I-5 | II-26 | II-60 |
| T1-1140 | I-5 | II-26 | II-62 |
| T1-1141 | I-5 | II-26 | II-66 |
| T1-1142 | I-5 | II-26 | II-69 |
| T1-1143 | I-5 | II-26 | II-70 |
| T1-1144 | I-5 | II-26 | II-71 |
| T1-1145 | I-5 | II-26 | II-72 |
| T1-1146 | I-5 | II-26 | II-74 |
| T1-1147 | I-5 | II-26 | II-76 |
| T1-1148 | I-5 | II-26 | II-78 |
| T1-1149 | I-5 | II-26 | II-84 |
| T1-1150 | I-5 | II-26 | II-85 |
| T1-1151 | I-5 | II-26 | II-86 |
| T1-1152 | I-5 | II-26 | II-92 |
| T1-1153 | I-5 | II-32 | II-33 |
| T1-1154 | I-5 | II-32 | II-37 |
| T1-1155 | I-5 | II-32 | II-39 |
| T1-1156 | I-5 | II-32 | II-42 |
| T1-1157 | I-5 | II-32 | II-44 |
| T1-1158 | I-5 | II-32 | II-50 |
| T1-1159 | I-5 | II-32 | II-53 |
| T1-1160 | I-5 | II-32 | II-60 |
| T1-1161 | I-5 | II-32 | II-62 |
| T1-1162 | I-5 | II-32 | II-66 |
| T1-1163 | I-5 | II-32 | II-69 |
| T1-1164 | I-5 | II-32 | II-70 |
| T1-1165 | I-5 | II-32 | II-71 |
| T1-1166 | I-5 | II-32 | II-72 |
| T1-1167 | I-5 | II-32 | II-74 |
| T1-1168 | I-5 | II-32 | II-76 |
| T1-1169 | I-5 | II-32 | II-78 |
| T1-1170 | I-5 | II-32 | II-84 |
| T1-1171 | I-5 | II-32 | II-85 |
| T1-1172 | I-5 | II-32 | II-86 |
| T1-1173 | I-5 | II-32 | II-92 |

TABLE T1-continued

| composition | I | II | III |
|---|---|---|---|
| T1-1174 | I-5 | II-33 | II-37 |
| T1-1175 | I-5 | II-33 | II-39 |
| T1-1176 | I-5 | II-33 | II-42 |
| T1-1177 | I-5 | II-33 | II-44 |
| T1-1178 | I-5 | II-33 | II-50 |
| T1-1179 | I-5 | II-33 | II-53 |
| T1-1180 | I-5 | II-33 | II-60 |
| T1-1181 | I-5 | II-33 | II-62 |
| T1-1182 | I-5 | II-33 | II-66 |
| T1-1183 | I-5 | II-33 | II-69 |
| T1-1184 | I-5 | II-33 | II-70 |
| T1-1185 | I-5 | II-33 | II-71 |
| T1-1186 | I-5 | II-33 | II-72 |
| T1-1187 | I-5 | II-33 | II-74 |
| T1-1188 | I-5 | II-33 | II-76 |
| T1-1189 | I-5 | II-33 | II-78 |
| T1-1190 | I-5 | II-33 | II-84 |
| T1-1191 | I-5 | II-33 | II-85 |
| T1-1192 | I-5 | II-33 | II-86 |
| T1-1193 | I-5 | II-33 | II-92 |
| T1-1194 | I-5 | II-37 | II-39 |
| T1-1195 | I-5 | II-37 | II-42 |
| T1-1196 | I-5 | II-37 | II-44 |
| T1-1197 | I-5 | II-37 | II-50 |
| T1-1198 | I-5 | II-37 | II-53 |
| T1-1199 | I-5 | II-37 | II-60 |
| T1-1200 | I-5 | II-37 | II-62 |
| T1-1201 | I-5 | II-37 | II-66 |
| T1-1202 | I-5 | II-37 | II-69 |
| T1-1203 | I-5 | II-37 | II-70 |
| T1-1204 | I-5 | II-37 | II-71 |
| T1-1205 | I-5 | II-37 | II-72 |
| T1-1206 | I-5 | II-37 | II-74 |
| T1-1207 | I-5 | II-37 | II-76 |
| T1-1208 | I-5 | II-37 | II-78 |
| T1-1209 | I-5 | II-37 | II-84 |
| T1-1210 | I-5 | II-37 | II-85 |
| T1-1211 | I-5 | II-37 | II-86 |
| T1-1212 | I-5 | II-37 | II-92 |
| T1-1213 | I-5 | II-39 | II-42 |
| T1-1214 | I-5 | II-39 | II-44 |
| T1-1215 | I-5 | II-39 | II-50 |
| T1-1216 | I-5 | II-39 | II-53 |
| T1-1217 | I-5 | II-39 | II-60 |
| T1-1218 | I-5 | II-39 | II-62 |
| T1-1219 | I-5 | II-39 | II-66 |
| T1-1220 | I-5 | II-39 | II-69 |
| T1-1221 | I-5 | II-39 | II-70 |
| T1-1222 | I-5 | II-39 | II-71 |
| T1-1223 | I-5 | II-39 | II-72 |
| T1-1224 | I-5 | II-39 | II-74 |
| T1-1225 | I-5 | II-39 | II-76 |
| T1-1226 | I-5 | II-39 | II-78 |
| T1-1227 | I-5 | II-39 | II-84 |
| T1-1228 | I-5 | II-39 | II-85 |
| T1-1229 | I-5 | II-39 | II-86 |
| T1-1230 | I-5 | II-39 | II-92 |
| T1-1231 | I-5 | II-42 | II-44 |
| T1-1232 | I-5 | II-42 | II-50 |
| T1-1233 | I-5 | II-42 | II-53 |
| T1-1234 | I-5 | II-42 | II-60 |
| T1-1235 | I-5 | II-42 | II-62 |
| T1-1236 | I-5 | II-42 | II-66 |
| T1-1237 | I-5 | II-42 | II-69 |
| T1-1238 | I-5 | II-42 | II-70 |
| T1-1239 | I-5 | II-42 | II-71 |
| T1-1240 | I-5 | II-42 | II-72 |
| T1-1241 | I-5 | II-42 | II-74 |
| T1-1242 | I-5 | II-42 | II-76 |
| T1-1243 | I-5 | II-42 | II-78 |
| T1-1244 | I-5 | II-42 | II-84 |
| T1-1245 | I-5 | II-42 | II-85 |
| T1-1246 | I-5 | II-42 | II-86 |
| T1-1247 | I-5 | II-42 | II-92 |
| T1-1248 | I-5 | II-44 | II-50 |
| T1-1249 | I-5 | II-44 | II-53 |
| T1-1250 | I-5 | II-44 | II-60 |
| T1-1251 | I-5 | II-44 | II-62 |
| T1-1252 | I-5 | II-44 | II-66 |
| T1-1253 | I-5 | II-44 | II-69 |
| T1-1254 | I-5 | II-44 | II-70 |
| T1-1255 | I-5 | II-44 | II-71 |
| T1-1256 | I-5 | II-44 | II-72 |
| T1-1257 | I-5 | II-44 | II-74 |
| T1-1258 | I-5 | II-44 | II-76 |
| T1-1259 | I-5 | II-44 | II-78 |
| T1-1260 | I-5 | II-44 | II-84 |
| T1-1261 | I-5 | II-44 | II-85 |
| T1-1262 | I-5 | II-44 | II-86 |
| T1-1263 | I-5 | II-44 | II-92 |
| T1-1264 | I-5 | II-50 | II-53 |
| T1-1265 | I-5 | II-50 | II-60 |
| T1-1266 | I-5 | II-50 | II-62 |
| T1-1267 | I-5 | II-50 | II-66 |
| T1-1268 | I-5 | II-50 | II-69 |
| T1-1269 | I-5 | II-50 | II-70 |
| T1-1270 | I-5 | II-50 | II-71 |
| T1-1271 | I-5 | II-50 | II-72 |
| T1-1272 | I-5 | II-50 | II-74 |
| T1-1273 | I-5 | II-50 | II-76 |
| T1-1274 | I-5 | II-50 | II-78 |
| T1-1275 | I-5 | II-50 | II-84 |
| T1-1276 | I-5 | II-50 | II-85 |
| T1-1277 | I-5 | II-50 | II-86 |
| T1-1278 | I-5 | II-50 | II-92 |
| T1-1279 | I-5 | II-53 | II-60 |
| T1-1280 | I-5 | II-53 | II-62 |
| T1-1281 | I-5 | II-53 | II-66 |
| T1-1282 | I-5 | II-53 | II-69 |
| T1-1283 | I-5 | II-53 | II-70 |
| T1-1284 | I-5 | II-53 | II-71 |
| T1-1285 | I-5 | II-53 | II-72 |
| T1-1286 | I-5 | II-53 | II-74 |
| T1-1287 | I-5 | II-53 | II-76 |
| T1-1288 | I-5 | II-53 | II-78 |
| T1-1289 | I-5 | II-53 | II-84 |
| T1-1290 | I-5 | II-53 | II-85 |
| T1-1291 | I-5 | II-53 | II-86 |
| T1-1292 | I-5 | II-53 | II-92 |
| T1-1293 | I-5 | II-60 | II-62 |
| T1-1294 | I-5 | II-60 | II-66 |
| T1-1295 | I-5 | II-60 | II-69 |
| T1-1296 | I-5 | II-60 | II-70 |
| T1-1297 | I-5 | II-60 | II-71 |
| T1-1298 | I-5 | II-60 | II-72 |
| T1-1299 | I-5 | II-60 | II-74 |
| T1-1300 | I-5 | II-60 | II-76 |
| T1-1301 | I-5 | II-60 | II-78 |
| T1-1302 | I-5 | II-60 | II-84 |
| T1-1303 | I-5 | II-60 | II-85 |
| T1-1304 | I-5 | II-60 | II-86 |
| T1-1305 | I-5 | II-60 | II-92 |
| T1-1306 | I-5 | II-62 | II-66 |
| T1-1307 | I-5 | II-62 | II-69 |
| T1-1308 | I-5 | II-62 | II-70 |
| T1-1309 | I-5 | II-62 | II-71 |
| T1-1310 | I-5 | II-62 | II-72 |
| T1-1311 | I-5 | II-62 | II-74 |
| T1-1312 | I-5 | II-62 | II-76 |
| T1-1313 | I-5 | II-62 | II-78 |
| T1-1314 | I-5 | II-62 | II-84 |
| T1-1315 | I-5 | II-62 | II-85 |
| T1-1316 | I-5 | II-62 | II-86 |
| T1-1317 | I-5 | II-62 | II-92 |
| T1-1318 | I-5 | II-66 | II-69 |
| T1-1319 | I-5 | II-66 | II-70 |
| T1-1320 | I-5 | II-66 | II-71 |
| T1-1321 | I-5 | II-66 | II-72 |
| T1-1322 | I-5 | II-66 | II-74 |
| T1-1323 | I-5 | II-66 | II-76 |
| T1-1324 | I-5 | II-66 | II-78 |
| T1-1325 | I-5 | II-66 | II-84 |
| T1-1326 | I-5 | II-66 | II-85 |
| T1-1327 | I-5 | II-66 | II-86 |
| T1-1328 | I-5 | II-66 | II-92 |
| T1-1329 | I-5 | II-69 | II-70 |

TABLE T1-continued

| composition | I | II | III |
|---|---|---|---|
| T1-1330 | I-5 | II-69 | II-71 |
| T1-1331 | I-5 | II-69 | II-72 |
| T1-1332 | I-5 | II-69 | II-74 |
| T1-1333 | I-5 | II-69 | II-76 |
| T1-1334 | I-5 | II-69 | II-78 |
| T1-1335 | I-5 | II-69 | II-84 |
| T1-1336 | I-5 | II-69 | II-85 |
| T1-1337 | I-5 | II-69 | II-86 |
| T1-1338 | I-5 | II-69 | II-92 |
| T1-1339 | I-5 | II-70 | II-71 |
| T1-1340 | I-5 | II-70 | II-72 |
| T1-1341 | I-5 | II-70 | II-74 |
| T1-1342 | I-5 | II-70 | II-76 |
| T1-1343 | I-5 | II-70 | II-78 |
| T1-1344 | I-5 | II-70 | II-84 |
| T1-1345 | I-5 | II-70 | II-85 |
| T1-1346 | I-5 | II-70 | II-86 |
| T1-1347 | I-5 | II-70 | II-92 |
| T1-1348 | I-5 | II-71 | II-72 |
| T1-1349 | I-5 | II-71 | II-74 |
| T1-1350 | I-5 | II-71 | II-76 |
| T1-1351 | I-5 | II-71 | II-78 |
| T1-1352 | I-5 | II-71 | II-84 |
| T1-1353 | I-5 | II-71 | II-85 |
| T1-1354 | I-5 | II-71 | II-86 |
| T1-1355 | I-5 | II-71 | II-92 |
| T1-1356 | I-5 | II-72 | II-74 |
| T1-1357 | I-5 | II-74 | II-76 |
| T1-1358 | I-5 | II-74 | II-78 |
| T1-1359 | I-5 | II-74 | II-84 |
| T1-1360 | I-5 | II-74 | II-85 |
| T1-1361 | I-5 | II-74 | II-86 |
| T1-1362 | I-5 | II-74 | II-92 |
| T1-1363 | I-5 | II-76 | II-78 |
| T1-1364 | I-5 | II-76 | II-84 |
| T1-1365 | I-5 | II-76 | II-85 |
| T1-1366 | I-5 | II-76 | II-86 |
| T1-1367 | I-5 | II-76 | II-92 |
| T1-1368 | I-5 | II-78 | II-84 |
| T1-1369 | I-5 | II-78 | II-85 |
| T1-1370 | I-5 | II-78 | II-86 |
| T1-1371 | I-5 | II-78 | II-92 |
| T1-1372 | I-5 | II-84 | II-85 |
| T1-1373 | I-5 | II-84 | II-86 |
| T1-1374 | I-5 | II-84 | II-92 |
| T1-1375 | I-5 | II-85 | II-86 |
| T1-1376 | I-5 | II-85 | II-92 |
| T1-1377 | I-5 | II-86 | II-92 |
| T1-1378 | I-3 | II-3 | II-5 |
| T1-1379 | I-3 | II-3 | II-6 |
| T1-1380 | I-3 | II-3 | II-7 |
| T1-1381 | I-3 | II-3 | II-8 |
| T1-1382 | I-3 | II-3 | II-11 |
| T1-1383 | I-3 | II-3 | II-16 |
| T1-1384 | I-3 | II-3 | II-21 |
| T1-1385 | I-3 | II-3 | II-26 |
| T1-1386 | I-3 | II-3 | II-32 |
| T1-1387 | I-3 | II-3 | II-33 |
| T1-1388 | I-3 | II-3 | II-37 |
| T1-1389 | I-3 | II-3 | II-39 |
| T1-1390 | I-3 | II-3 | II-42 |
| T1-1391 | I-3 | II-3 | II-44 |
| T1-1392 | I-3 | II-3 | II-50 |
| T1-1393 | I-3 | II-3 | II-53 |
| T1-1394 | I-3 | II-3 | II-60 |
| T1-1395 | I-3 | II-3 | II-62 |
| T1-1396 | I-3 | II-3 | II-66 |
| T1-1397 | I-3 | II-3 | II-69 |
| T1-1398 | I-3 | II-3 | II-70 |
| T1-1399 | I-3 | II-3 | II-71 |
| T1-1400 | I-3 | II-3 | II-72 |
| T1-1401 | I-3 | II-3 | II-74 |
| T1-1402 | I-3 | II-3 | II-76 |
| T1-1403 | I-3 | II-3 | II-78 |
| T1-1404 | I-3 | II-3 | II-84 |
| T1-1405 | I-3 | II-3 | II-85 |
| T1-1406 | I-3 | II-3 | II-86 |
| T1-1407 | I-3 | II-3 | II-92 |
| T1-1408 | I-3 | II-5 | II-6 |
| T1-1409 | I-3 | II-5 | II-7 |
| T1-1410 | I-3 | II-5 | II-8 |
| T1-1411 | I-3 | II-5 | II-11 |
| T1-1412 | I-3 | II-5 | II-16 |
| T1-1413 | I-3 | II-5 | II-21 |
| T1-1414 | I-3 | II-5 | II-26 |
| T1-1415 | I-3 | II-5 | II-32 |
| T1-1416 | I-3 | II-5 | II-33 |
| T1-1417 | I-3 | II-5 | II-37 |
| T1-1418 | I-3 | II-5 | II-39 |
| T1-1419 | I-3 | II-5 | II-42 |
| T1-1420 | I-3 | II-5 | II-44 |
| T1-1421 | I-3 | II-5 | II-50 |
| T1-1422 | I-3 | II-5 | II-53 |
| T1-1423 | I-3 | II-5 | II-60 |
| T1-1424 | I-3 | II-5 | II-62 |
| T1-1425 | I-3 | II-5 | II-66 |
| T1-1426 | I-3 | II-5 | II-69 |
| T1-1427 | I-3 | II-5 | II-70 |
| T1-1428 | I-3 | II-5 | II-71 |
| T1-1429 | I-3 | II-5 | II-72 |
| T1-1430 | I-3 | II-5 | II-74 |
| T1-1431 | I-3 | II-5 | II-76 |
| T1-1432 | I-3 | II-5 | II-78 |
| T1-1433 | I-3 | II-5 | II-84 |
| T1-1434 | I-3 | II-5 | II-85 |
| T1-1435 | I-3 | II-5 | II-86 |
| T1-1436 | I-3 | II-5 | II-92 |
| T1-1437 | I-3 | II-6 | II-7 |
| T1-1438 | I-3 | II-6 | II-8 |
| T1-1439 | I-3 | II-6 | II-11 |
| T1-1440 | I-3 | II-6 | II-16 |
| T1-1441 | I-3 | II-6 | II-21 |
| T1-1442 | I-3 | II-6 | II-26 |
| T1-1443 | I-3 | II-6 | II-32 |
| T1-1444 | I-3 | II-6 | II-33 |
| T1-1445 | I-3 | II-6 | II-37 |
| T1-1446 | I-3 | II-6 | II-39 |
| T1-1447 | I-3 | II-6 | II-42 |
| T1-1448 | I-3 | II-6 | II-44 |
| T1-1449 | I-3 | II-6 | II-50 |
| T1-1450 | I-3 | II-6 | II-53 |
| T1-1451 | I-3 | II-6 | II-60 |
| T1-1452 | I-3 | II-6 | II-62 |
| T1-1453 | I-3 | II-6 | II-66 |
| T1-1454 | I-3 | II-6 | II-69 |
| T1-1455 | I-3 | II-6 | II-70 |
| T1-1456 | I-3 | II-6 | II-71 |
| T1-1457 | I-3 | II-6 | II-72 |
| T1-1458 | I-3 | II-6 | II-74 |
| T1-1459 | I-3 | II-6 | II-76 |
| T1-1460 | I-3 | II-6 | II-78 |
| T1-1461 | I-3 | II-6 | II-84 |
| T1-1462 | I-3 | II-6 | II-85 |
| T1-1463 | I-3 | II-6 | II-86 |
| T1-1464 | I-3 | II-6 | II-92 |
| T1-1465 | I-3 | II-7 | II-8 |
| T1-1466 | I-3 | II-7 | II-11 |
| T1-1467 | I-3 | II-7 | II-16 |
| T1-1468 | I-3 | II-7 | II-21 |
| T1-1469 | I-3 | II-7 | II-26 |
| T1-1470 | I-3 | II-7 | II-32 |
| T1-1471 | I-3 | II-7 | II-33 |
| T1-1472 | I-3 | II-7 | II-37 |
| T1-1473 | I-3 | II-7 | II-39 |
| T1-1474 | I-3 | II-7 | II-42 |
| T1-1475 | I-3 | II-7 | II-44 |
| T1-1476 | I-3 | II-7 | II-50 |
| T1-1477 | I-3 | II-7 | II-53 |
| T1-1478 | I-3 | II-7 | II-60 |
| T1-1479 | I-3 | II-7 | II-62 |
| T1-1480 | I-3 | II-7 | II-66 |
| T1-1481 | I-3 | II-7 | II-69 |
| T1-1482 | I-3 | II-7 | II-70 |
| T1-1483 | I-3 | II-7 | II-71 |
| T1-1484 | I-3 | II-7 | II-72 |
| T1-1485 | I-3 | II-7 | II-74 |

TABLE T1-continued

| composition | I | II | III |
|---|---|---|---|
| T1-1486 | I-3 | II-7 | II-76 |
| T1-1487 | I-3 | II-7 | II-78 |
| T1-1488 | I-3 | II-7 | II-84 |
| T1-1489 | I-3 | II-7 | II-85 |
| T1-1490 | I-3 | II-7 | II-86 |
| T1-1491 | I-3 | II-7 | II-92 |
| T1-1492 | I-3 | II-8 | II-11 |
| T1-1493 | I-3 | II-8 | II-16 |
| T1-1494 | I-3 | II-8 | II-21 |
| T1-1495 | I-3 | II-8 | II-26 |
| T1-1496 | I-3 | II-8 | II-32 |
| T1-1497 | I-3 | II-8 | II-33 |
| T1-1498 | I-3 | II-8 | II-37 |
| T1-1499 | I-3 | II-8 | II-39 |
| T1-1500 | I-3 | II-8 | II-42 |
| T1-1501 | I-3 | II-8 | II-44 |
| T1-1502 | I-3 | II-8 | II-50 |
| T1-1503 | I-3 | II-8 | II-53 |
| T1-1504 | I-3 | II-8 | II-60 |
| T1-1505 | I-3 | II-8 | II-62 |
| T1-1506 | I-3 | II-8 | II-66 |
| T1-1507 | I-3 | II-8 | II-69 |
| T1-1508 | I-3 | II-8 | II-70 |
| T1-1509 | I-3 | II-8 | II-71 |
| T1-1510 | I-3 | II-8 | II-72 |
| T1-1511 | I-3 | II-8 | II-74 |
| T1-1512 | I-3 | II-8 | II-76 |
| T1-1513 | I-3 | II-8 | II-78 |
| T1-1514 | I-3 | II-8 | II-84 |
| T1-1515 | I-3 | II-8 | II-85 |
| T1-1516 | I-3 | II-8 | II-86 |
| T1-1517 | I-3 | II-8 | II-92 |
| T1-1518 | I-3 | II-11 | II-16 |
| T1-1519 | I-3 | II-11 | II-21 |
| T1-1520 | I-3 | II-11 | II-26 |
| T1-1521 | I-3 | II-11 | II-32 |
| T1-1522 | I-3 | II-11 | II-33 |
| T1-1523 | I-3 | II-11 | II-37 |
| T1-1524 | I-3 | II-11 | II-39 |
| T1-1525 | I-3 | II-11 | II-42 |
| T1-1526 | I-3 | II-11 | II-44 |
| T1-1527 | I-3 | II-11 | II-50 |
| T1-1528 | I-3 | II-11 | II-53 |
| T1-1529 | I-3 | II-11 | II-60 |
| T1-1530 | I-3 | II-11 | II-62 |
| T1-1531 | I-3 | II-11 | II-66 |
| T1-1532 | I-3 | II-11 | II-69 |
| T1-1533 | I-3 | II-11 | II-70 |
| T1-1534 | I-3 | II-11 | II-71 |
| T1-1535 | I-3 | II-11 | II-72 |
| T1-1536 | I-3 | II-11 | II-74 |
| T1-1537 | I-3 | II-11 | II-76 |
| T1-1538 | I-3 | II-11 | II-78 |
| T1-1539 | I-3 | II-11 | II-84 |
| T1-1540 | I-3 | II-11 | II-85 |
| T1-1541 | I-3 | II-11 | II-86 |
| T1-1542 | I-3 | II-11 | II-92 |
| T1-1543 | I-3 | II-16 | II-21 |
| T1-1544 | I-3 | II-16 | II-26 |
| T1-1545 | I-3 | II-16 | II-32 |
| T1-1546 | I-3 | II-16 | II-33 |
| T1-1547 | I-3 | II-16 | II-37 |
| T1-1548 | I-3 | II-16 | II-39 |
| T1-1549 | I-3 | II-16 | II-42 |
| T1-1550 | I-3 | II-16 | II-44 |
| T1-1551 | I-3 | II-16 | II-50 |
| T1-1552 | I-3 | II-16 | II-53 |
| T1-1553 | I-3 | II-16 | II-60 |
| T1-1554 | I-3 | II-16 | II-62 |
| T1-1555 | I-3 | II-16 | II-66 |
| T1-1556 | I-3 | II-16 | II-69 |
| T1-1557 | I-3 | II-16 | II-70 |
| T1-1558 | I-3 | II-16 | II-71 |
| T1-1559 | I-3 | II-16 | II-72 |
| T1-1560 | I-3 | II-16 | II-74 |
| T1-1561 | I-3 | II-16 | II-76 |
| T1-1562 | I-3 | II-16 | II-78 |
| T1-1563 | I-3 | II-16 | II-84 |
| T1-1564 | I-3 | II-16 | II-85 |
| T1-1565 | I-3 | II-16 | II-86 |
| T1-1566 | I-3 | II-16 | II-92 |
| T1-1567 | I-3 | II-21 | II-26 |
| T1-1568 | I-3 | II-21 | II-32 |
| T1-1569 | I-3 | II-21 | II-33 |
| T1-1570 | I-3 | II-21 | II-37 |
| T1-1571 | I-3 | II-21 | II-39 |
| T1-1572 | I-3 | II-21 | II-42 |
| T1-1573 | I-3 | II-21 | II-44 |
| T1-1574 | I-3 | II-21 | II-50 |
| T1-1575 | I-3 | II-21 | II-53 |
| T1-1576 | I-3 | II-21 | II-60 |
| T1-1577 | I-3 | II-21 | II-62 |
| T1-1578 | I-3 | II-21 | II-66 |
| T1-1579 | I-3 | II-21 | II-69 |
| T1-1580 | I-3 | II-21 | II-70 |
| T1-1581 | I-3 | II-21 | II-71 |
| T1-1582 | I-3 | II-21 | II-72 |
| T1-1583 | I-3 | II-21 | II-74 |
| T1-1584 | I-3 | II-21 | II-76 |
| T1-1585 | I-3 | II-21 | II-78 |
| T1-1586 | I-3 | II-21 | II-84 |
| T1-1587 | I-3 | II-21 | II-85 |
| T1-1588 | I-3 | II-21 | II-86 |
| T1-1589 | I-3 | II-21 | II-92 |
| T1-1590 | I-3 | II-26 | II-32 |
| T1-1591 | I-3 | II-26 | II-33 |
| T1-1592 | I-3 | II-26 | II-37 |
| T1-1593 | I-3 | II-26 | II-39 |
| T1-1594 | I-3 | II-26 | II-42 |
| T1-1595 | I-3 | II-26 | II-44 |
| T1-1596 | I-3 | II-26 | II-50 |
| T1-1597 | I-3 | II-26 | II-53 |
| T1-1598 | I-3 | II-26 | II-60 |
| T1-1599 | I-3 | II-26 | II-62 |
| T1-1600 | I-3 | II-26 | II-66 |
| T1-1601 | I-3 | II-26 | II-69 |
| T1-1602 | I-3 | II-26 | II-70 |
| T1-1603 | I-3 | II-26 | II-71 |
| T1-1604 | I-3 | II-26 | II-72 |
| T1-1605 | I-3 | II-26 | II-74 |
| T1-1606 | I-3 | II-26 | II-76 |
| T1-1607 | I-3 | II-26 | II-78 |
| T1-1608 | I-3 | II-26 | II-84 |
| T1-1609 | I-3 | II-26 | II-85 |
| T1-1610 | I-3 | II-26 | II-86 |
| T1-1611 | I-3 | II-26 | II-92 |
| T1-1612 | I-3 | II-32 | II-33 |
| T1-1613 | I-3 | II-32 | II-37 |
| T1-1614 | I-3 | II-32 | II-39 |
| T1-1615 | I-3 | II-32 | II-42 |
| T1-1616 | I-3 | II-32 | II-44 |
| T1-1617 | I-3 | II-32 | II-50 |
| T1-1618 | I-3 | II-32 | II-53 |
| T1-1619 | I-3 | II-32 | II-60 |
| T1-1620 | I-3 | II-32 | II-62 |
| T1-1621 | I-3 | II-32 | II-66 |
| T1-1622 | I-3 | II-32 | II-69 |
| T1-1623 | I-3 | II-32 | II-70 |
| T1-1624 | I-3 | II-32 | II-71 |
| T1-1625 | I-3 | II-32 | II-72 |
| T1-1626 | I-3 | II-32 | II-74 |
| T1-1627 | I-3 | II-32 | II-76 |
| T1-1628 | I-3 | II-32 | II-78 |
| T1-1629 | I-3 | II-32 | II-84 |
| T1-1630 | I-3 | II-32 | II-85 |
| T1-1631 | I-3 | II-32 | II-86 |
| T1-1632 | I-3 | II-32 | II-92 |
| T1-1633 | I-3 | II-33 | II-37 |
| T1-1634 | I-3 | II-33 | II-39 |
| T1-1635 | I-3 | II-33 | II-42 |
| T1-1636 | I-3 | II-33 | II-44 |
| T1-1637 | I-3 | II-33 | II-50 |
| T1-1638 | I-3 | II-33 | II-53 |
| T1-1639 | I-3 | II-33 | II-60 |
| T1-1640 | I-3 | II-33 | II-62 |
| T1-1641 | I-3 | II-33 | II-66 |

TABLE T1-continued

| composition | I | II | III |
|---|---|---|---|
| T1-1642 | I-3 | II-33 | II-69 |
| T1-1643 | I-3 | II-33 | II-70 |
| T1-1644 | I-3 | II-33 | II-71 |
| T1-1645 | I-3 | II-33 | II-72 |
| T1-1646 | I-3 | II-33 | II-74 |
| T1-1647 | I-3 | II-33 | II-76 |
| T1-1648 | I-3 | II-33 | II-78 |
| T1-1649 | I-3 | II-33 | II-84 |
| T1-1650 | I-3 | II-33 | II-85 |
| T1-1651 | I-3 | II-33 | II-86 |
| T1-1652 | I-3 | II-33 | II-92 |
| T1-1653 | I-3 | II-37 | II-39 |
| T1-1654 | I-3 | II-37 | II-42 |
| T1-1655 | I-3 | II-37 | II-44 |
| T1-1656 | I-3 | II-37 | II-50 |
| T1-1657 | I-3 | II-37 | II-53 |
| T1-1658 | I-3 | II-37 | II-60 |
| T1-1659 | I-3 | II-37 | II-62 |
| T1-1660 | I-3 | II-37 | II-66 |
| T1-1661 | I-3 | II-37 | II-69 |
| T1-1662 | I-3 | II-37 | II-70 |
| T1-1663 | I-3 | II-37 | II-71 |
| T1-1664 | I-3 | II-37 | II-72 |
| T1-1665 | I-3 | II-37 | II-74 |
| T1-1666 | I-3 | II-37 | II-76 |
| T1-1667 | I-3 | II-37 | II-78 |
| T1-1668 | I-3 | II-37 | II-84 |
| T1-1669 | I-3 | II-37 | II-85 |
| T1-1670 | I-3 | II-37 | II-86 |
| T1-1671 | I-3 | II-37 | II-92 |
| T1-1672 | I-3 | II-39 | II-42 |
| T1-1673 | I-3 | II-39 | II-44 |
| T1-1674 | I-3 | II-39 | II-50 |
| T1-1675 | I-3 | II-39 | II-53 |
| T1-1676 | I-3 | II-39 | II-60 |
| T1-1677 | I-3 | II-39 | II-62 |
| T1-1678 | I-3 | II-39 | II-66 |
| T1-1679 | I-3 | II-39 | II-69 |
| T1-1680 | I-3 | II-39 | II-70 |
| T1-1681 | I-3 | II-39 | II-71 |
| T1-1682 | I-3 | II-39 | II-72 |
| T1-1683 | I-3 | II-39 | II-74 |
| T1-1684 | I-3 | II-39 | II-76 |
| T1-1685 | I-3 | II-39 | II-78 |
| T1-1686 | I-3 | II-39 | II-84 |
| T1-1687 | I-3 | II-39 | II-85 |
| T1-1688 | I-3 | II-39 | II-86 |
| T1-1689 | I-3 | II-39 | II-92 |
| T1-1690 | I-3 | II-42 | II-44 |
| T1-1691 | I-3 | II-42 | II-50 |
| T1-1692 | I-3 | II-42 | II-53 |
| T1-1693 | I-3 | II-42 | II-60 |
| T1-1694 | I-3 | II-42 | II-62 |
| T1-1695 | I-3 | II-42 | II-66 |
| T1-1696 | I-3 | II-42 | II-69 |
| T1-1697 | I-3 | II-42 | II-70 |
| T1-1698 | I-3 | II-42 | II-71 |
| T1-1699 | I-3 | II-42 | II-72 |
| T1-1700 | I-3 | II-42 | II-74 |
| T1-1701 | I-3 | II-42 | II-76 |
| T1-1702 | I-3 | II-42 | II-78 |
| T1-1703 | I-3 | II-42 | II-84 |
| T1-1704 | I-3 | II-42 | II-85 |
| T1-1705 | I-3 | II-42 | II-86 |
| T1-1706 | I-3 | II-42 | II-92 |
| T1-1707 | I-3 | II-44 | II-50 |
| T1-1708 | I-3 | II-44 | II-53 |
| T1-1709 | I-3 | II-44 | II-60 |
| T1-1710 | I-3 | II-44 | II-62 |
| T1-1711 | I-3 | II-44 | II-66 |
| T1-1712 | I-3 | II-44 | II-69 |
| T1-1713 | I-3 | II-44 | II-70 |
| T1-1714 | I-3 | II-44 | II-71 |
| T1-1715 | I-3 | II-44 | II-72 |
| T1-1716 | I-3 | II-44 | II-74 |
| T1-1717 | I-3 | II-44 | II-76 |
| T1-1718 | I-3 | II-44 | II-78 |
| T1-1719 | I-3 | II-44 | II-84 |
| T1-1720 | I-3 | II-44 | II-85 |
| T1-1721 | I-3 | II-44 | II-86 |
| T1-1722 | I-3 | II-44 | II-92 |
| T1-1723 | I-3 | II-50 | II-53 |
| T1-1724 | I-3 | II-50 | II-60 |
| T1-1725 | I-3 | II-50 | II-62 |
| T1-1726 | I-3 | II-50 | II-66 |
| T1-1727 | I-3 | II-50 | II-69 |
| T1-1728 | I-3 | II-50 | II-70 |
| T1-1729 | I-3 | II-50 | II-71 |
| T1-1730 | I-3 | II-50 | II-72 |
| T1-1731 | I-3 | II-50 | II-74 |
| T1-1732 | I-3 | II-50 | II-76 |
| T1-1733 | I-3 | II-50 | II-78 |
| T1-1734 | I-3 | II-50 | II-84 |
| T1-1735 | I-3 | II-50 | II-85 |
| T1-1736 | I-3 | II-50 | II-86 |
| T1-1737 | I-3 | II-50 | II-92 |
| T1-1738 | I-3 | II-53 | II-60 |
| T1-1739 | I-3 | II-53 | II-62 |
| T1-1740 | I-3 | II-53 | II-66 |
| T1-1741 | I-3 | II-53 | II-69 |
| T1-1742 | I-3 | II-53 | II-70 |
| T1-1743 | I-3 | II-53 | II-71 |
| T1-1744 | I-3 | II-53 | II-72 |
| T1-1745 | I-3 | II-53 | II-74 |
| T1-1746 | I-3 | II-53 | II-76 |
| T1-1747 | I-3 | II-53 | II-78 |
| T1-1748 | I-3 | II-53 | II-84 |
| T1-1749 | I-3 | II-53 | II-85 |
| T1-1750 | I-3 | II-53 | II-86 |
| T1-1751 | I-3 | II-53 | II-92 |
| T1-1752 | I-3 | II-60 | II-62 |
| T1-1753 | I-3 | II-60 | II-66 |
| T1-1754 | I-3 | II-60 | II-69 |
| T1-1755 | I-3 | II-60 | II-70 |
| T1-1756 | I-3 | II-60 | II-71 |
| T1-1757 | I-3 | II-60 | II-72 |
| T1-1758 | I-3 | II-60 | II-74 |
| T1-1759 | I-3 | II-60 | II-76 |
| T1-1760 | I-3 | II-60 | II-78 |
| T1-1761 | I-3 | II-60 | II-84 |
| T1-1762 | I-3 | II-60 | II-85 |
| T1-1763 | I-3 | II-60 | II-86 |
| T1-1764 | I-3 | II-60 | II-92 |
| T1-1765 | I-3 | II-62 | II-66 |
| T1-1766 | I-3 | II-62 | II-69 |
| T1-1767 | I-3 | II-62 | II-70 |
| T1-1768 | I-3 | II-62 | II-71 |
| T1-1769 | I-3 | II-62 | II-72 |
| T1-1770 | I-3 | II-62 | II-74 |
| T1-1771 | I-3 | II-62 | II-76 |
| T1-1772 | I-3 | II-62 | II-78 |
| T1-1773 | I-3 | II-62 | II-84 |
| T1-1774 | I-3 | II-62 | II-85 |
| T1-1775 | I-3 | II-62 | II-86 |
| T1-1776 | I-3 | II-62 | II-92 |
| T1-1777 | I-3 | II-66 | II-69 |
| T1-1778 | I-3 | II-66 | II-70 |
| T1-1779 | I-3 | II-66 | II-71 |
| T1-1780 | I-3 | II-66 | II-72 |
| T1-1781 | I-3 | II-66 | II-74 |
| T1-1782 | I-3 | II-66 | II-76 |
| T1-1783 | I-3 | II-66 | II-78 |
| T1-1784 | I-3 | II-66 | II-84 |
| T1-1785 | I-3 | II-66 | II-85 |
| T1-1786 | I-3 | II-66 | II-86 |
| T1-1787 | I-3 | II-66 | II-92 |
| T1-1788 | I-3 | II-69 | II-70 |
| T1-1789 | I-3 | II-69 | II-71 |
| T1-1790 | I-3 | II-69 | II-72 |
| T1-1791 | I-3 | II-69 | II-74 |
| T1-1792 | I-3 | II-69 | II-76 |
| T1-1793 | I-3 | II-69 | II-78 |
| T1-1794 | I-3 | II-69 | II-84 |
| T1-1795 | I-3 | II-69 | II-85 |
| T1-1796 | I-3 | II-69 | II-86 |
| T1-1797 | I-3 | II-69 | II-92 |

TABLE T1-continued

| composition | I | II | III |
|---|---|---|---|
| T1-1798 | I-3 | II-70 | II-71 |
| T1-1799 | I-3 | II-70 | II-72 |
| T1-1800 | I-3 | II-70 | II-74 |
| T1-1801 | I-3 | II-70 | II-76 |
| T1-1802 | I-3 | II-70 | II-78 |
| T1-1803 | I-3 | II-70 | II-84 |
| T1-1804 | I-3 | II-70 | II-85 |
| T1-1805 | I-3 | II-70 | II-86 |
| T1-1806 | I-3 | II-70 | II-92 |
| T1-1807 | I-3 | II-71 | II-72 |
| T1-1808 | I-3 | II-71 | II-74 |
| T1-1809 | I-3 | II-71 | II-76 |
| T1-1810 | I-3 | II-71 | II-78 |
| T1-1811 | I-3 | II-71 | II-84 |
| T1-1812 | I-3 | II-71 | II-85 |
| T1-1813 | I-3 | II-71 | II-86 |
| T1-1814 | I-3 | II-71 | II-92 |
| T1-1815 | I-3 | II-72 | II-74 |
| T1-1816 | I-3 | II-74 | II-76 |
| T1-1817 | I-3 | II-74 | II-78 |
| T1-1818 | I-3 | II-74 | II-84 |
| T1-1819 | I-3 | II-74 | II-85 |
| T1-1820 | I-3 | II-74 | II-86 |
| T1-1821 | I-3 | II-74 | II-92 |
| T1-1822 | I-3 | II-76 | II-78 |
| T1-1823 | I-3 | II-76 | II-84 |
| T1-1824 | I-3 | II-76 | II-85 |
| T1-1825 | I-3 | II-76 | II-86 |
| T1-1826 | I-3 | II-76 | II-92 |
| T1-1827 | I-3 | II-78 | II-84 |
| T1-1828 | I-3 | II-78 | II-85 |
| T1-1829 | I-3 | II-78 | II-86 |
| T1-1830 | I-3 | II-78 | II-92 |
| T1-1831 | I-3 | II-84 | II-85 |
| T1-1832 | I-3 | II-84 | II-86 |
| T1-1833 | I-3 | II-84 | II-92 |
| T1-1834 | I-3 | II-85 | II-86 |
| T1-1835 | I-3 | II-85 | II-92 |
| T1-1836 | I-3 | II-86 | II-92 |
| T1-1837 | I-4 | II-3 | II-5 |
| T1-1838 | I-4 | II-3 | II-6 |
| T1-1839 | I-4 | II-3 | II-7 |
| T1-1840 | I-4 | II-3 | II-8 |
| T1-1841 | I-4 | II-3 | II-11 |
| T1-1842 | I-4 | II-3 | II-16 |
| T1-1843 | I-4 | II-3 | II-21 |
| T1-1844 | I-4 | II-3 | II-26 |
| T1-1845 | I-4 | II-3 | II-32 |
| T1-1846 | I-4 | II-3 | II-33 |
| T1-1847 | I-4 | II-3 | II-37 |
| T1-1848 | I-4 | II-3 | II-39 |
| T1-1849 | I-4 | II-3 | II-42 |
| T1-1850 | I-4 | II-3 | II-44 |
| T1-1851 | I-4 | II-3 | II-50 |
| T1-1852 | I-4 | II-3 | II-53 |
| T1-1853 | I-4 | II-3 | II-60 |
| T1-1854 | I-4 | II-3 | II-62 |
| T1-1855 | I-4 | II-3 | II-66 |
| T1-1856 | I-4 | II-3 | II-69 |
| T1-1857 | I-4 | II-3 | II-70 |
| T1-1858 | I-4 | II-3 | II-71 |
| T1-1859 | I-4 | II-3 | II-72 |
| T1-1860 | I-4 | II-3 | II-74 |
| T1-1861 | I-4 | II-3 | II-76 |
| T1-1862 | I-4 | II-3 | II-78 |
| T1-1863 | I-4 | II-3 | II-84 |
| T1-1864 | I-4 | II-3 | II-85 |
| T1-1865 | I-4 | II-3 | II-86 |
| T1-1866 | I-4 | II-3 | II-92 |
| T1-1867 | I-4 | II-5 | II-6 |
| T1-1868 | I-4 | II-5 | II-7 |
| T1-1869 | I-4 | II-5 | II-8 |
| T1-1870 | I-4 | II-5 | II-11 |
| T1-1871 | I-4 | II-5 | II-16 |
| T1-1872 | I-4 | II-5 | II-21 |
| T1-1873 | I-4 | II-5 | II-26 |
| T1-1874 | I-4 | II-5 | II-32 |
| T1-1875 | I-4 | II-5 | II-33 |
| T1-1876 | I-4 | II-5 | II-37 |
| T1-1877 | I-4 | II-5 | II-39 |
| T1-1878 | I-4 | II-5 | II-42 |
| T1-1879 | I-4 | II-5 | II-44 |
| T1-1880 | I-4 | II-5 | II-50 |
| T1-1881 | I-4 | II-5 | II-53 |
| T1-1882 | I-4 | II-5 | II-60 |
| T1-1883 | I-4 | II-5 | II-62 |
| T1-1884 | I-4 | II-5 | II-66 |
| T1-1885 | I-4 | II-5 | II-69 |
| T1-1886 | I-4 | II-5 | II-70 |
| T1-1887 | I-4 | II-5 | II-71 |
| T1-1888 | I-4 | II-5 | II-72 |
| T1-1889 | I-4 | II-5 | II-74 |
| T1-1890 | I-4 | II-5 | II-76 |
| T1-1891 | I-4 | II-5 | II-78 |
| T1-1892 | I-4 | II-5 | II-84 |
| T1-1893 | I-4 | II-5 | II-85 |
| T1-1894 | I-4 | II-5 | II-86 |
| T1-1895 | I-4 | II-5 | II-92 |
| T1-1896 | I-4 | II-6 | II-7 |
| T1-1897 | I-4 | II-6 | II-8 |
| T1-1898 | I-4 | II-6 | II-11 |
| T1-1899 | I-4 | II-6 | II-16 |
| T1-1900 | I-4 | II-6 | II-21 |
| T1-1901 | I-4 | II-6 | II-26 |
| T1-1902 | I-4 | II-6 | II-32 |
| T1-1903 | I-4 | II-6 | II-33 |
| T1-1904 | I-4 | II-6 | II-37 |
| T1-1905 | I-4 | II-6 | II-39 |
| T1-1906 | I-4 | II-6 | II-42 |
| T1-1907 | I-4 | II-6 | II-44 |
| T1-1908 | I-4 | II-6 | II-50 |
| T1-1909 | I-4 | II-6 | II-53 |
| T1-1910 | I-4 | II-6 | II-60 |
| T1-1911 | I-4 | II-6 | II-62 |
| T1-1912 | I-4 | II-6 | II-66 |
| T1-1913 | I-4 | II-6 | II-69 |
| T1-1914 | I-4 | II-6 | II-70 |
| T1-1915 | I-4 | II-6 | II-71 |
| T1-1916 | I-4 | II-6 | II-72 |
| T1-1917 | I-4 | II-6 | II-74 |
| T1-1918 | I-4 | II-6 | II-76 |
| T1-1919 | I-4 | II-6 | II-78 |
| T1-1920 | I-4 | II-6 | II-84 |
| T1-1921 | I-4 | II-6 | II-85 |
| T1-1922 | I-4 | II-6 | II-86 |
| T1-1923 | I-4 | II-6 | II-92 |
| T1-1924 | I-4 | II-7 | II-8 |
| T1-1925 | I-4 | II-7 | II-11 |
| T1-1926 | I-4 | II-7 | II-16 |
| T1-1927 | I-4 | II-7 | II-21 |
| T1-1928 | I-4 | II-7 | II-26 |
| T1-1929 | I-4 | II-7 | II-32 |
| T1-1930 | I-4 | II-7 | II-33 |
| T1-1931 | I-4 | II-7 | II-37 |
| T1-1932 | I-4 | II-7 | II-39 |
| T1-1933 | I-4 | II-7 | II-42 |
| T1-1934 | I-4 | II-7 | II-44 |
| T1-1935 | I-4 | II-7 | II-50 |
| T1-1936 | I-4 | II-7 | II-53 |
| T1-1937 | I-4 | II-7 | II-60 |
| T1-1938 | I-4 | II-7 | II-62 |
| T1-1939 | I-4 | II-7 | II-66 |
| T1-1940 | I-4 | II-7 | II-69 |
| T1-1941 | I-4 | II-7 | II-70 |
| T1-1942 | I-4 | II-7 | II-71 |
| T1-1943 | I-4 | II-7 | II-72 |
| T1-1944 | I-4 | II-7 | II-74 |
| T1-1945 | I-4 | II-7 | II-76 |
| T1-1946 | I-4 | II-7 | II-78 |
| T1-1947 | I-4 | II-7 | II-84 |
| T1-1948 | I-4 | II-7 | II-85 |
| T1-1949 | I-4 | II-7 | II-86 |
| T1-1950 | I-4 | II-7 | II-92 |
| T1-1951 | I-4 | II-8 | II-11 |
| T1-1952 | I-4 | II-8 | II-16 |
| T1-1953 | I-4 | II-8 | II-21 |

TABLE T1-continued

| composition | I | II | III |
|---|---|---|---|
| T1-1954 | I-4 | II-8 | II-26 |
| T1-1955 | I-4 | II-8 | II-32 |
| T1-1956 | I-4 | II-8 | II-33 |
| T1-1957 | I-4 | II-8 | II-37 |
| T1-1958 | I-4 | II-8 | II-39 |
| T1-1959 | I-4 | II-8 | II-42 |
| T1-1960 | I-4 | II-8 | II-44 |
| T1-1961 | I-4 | II-8 | II-50 |
| T1-1962 | I-4 | II-8 | II-53 |
| T1-1963 | I-4 | II-8 | II-60 |
| T1-1964 | I-4 | II-8 | II-62 |
| T1-1965 | I-4 | II-8 | II-66 |
| T1-1966 | I-4 | II-8 | II-69 |
| T1-1967 | I-4 | II-8 | II-70 |
| T1-1968 | I-4 | II-8 | II-71 |
| T1-1969 | I-4 | II-8 | II-72 |
| T1-1970 | I-4 | II-8 | II-74 |
| T1-1971 | I-4 | II-8 | II-76 |
| T1-1972 | I-4 | II-8 | II-78 |
| T1-1973 | I-4 | II-8 | II-84 |
| T1-1974 | I-4 | II-8 | II-85 |
| T1-1975 | I-4 | II-8 | II-86 |
| T1-1976 | I-4 | II-8 | II-92 |
| T1-1977 | I-4 | II-11 | II-16 |
| T1-1978 | I-4 | II-11 | II-21 |
| T1-1979 | I-4 | II-11 | II-26 |
| T1-1980 | I-4 | II-11 | II-32 |
| T1-1981 | I-4 | II-11 | II-33 |
| T1-1982 | I-4 | II-11 | II-37 |
| T1-1983 | I-4 | II-11 | II-39 |
| T1-1984 | I-4 | II-11 | II-42 |
| T1-1985 | I-4 | II-11 | II-44 |
| T1-1986 | I-4 | II-11 | II-50 |
| T1-1987 | I-4 | II-11 | II-53 |
| T1-1988 | I-4 | II-11 | II-60 |
| T1-1989 | I-4 | II-11 | II-62 |
| T1-1990 | I-4 | II-11 | II-66 |
| T1-1991 | I-4 | II-11 | II-69 |
| T1-1992 | I-4 | II-11 | II-70 |
| T1-1993 | I-4 | II-11 | II-71 |
| T1-1994 | I-4 | II-11 | II-72 |
| T1-1995 | I-4 | II-11 | II-74 |
| T1-1996 | I-4 | II-11 | II-76 |
| T1-1997 | I-4 | II-11 | II-78 |
| T1-1998 | I-4 | II-11 | II-84 |
| T1-1999 | I-4 | II-11 | II-85 |
| T1-2000 | I-4 | II-11 | II-86 |
| T1-2001 | I-4 | II-11 | II-92 |
| T1-2002 | I-4 | II-16 | II-21 |
| T1-2003 | I-4 | II-16 | II-26 |
| T1-2004 | I-4 | II-16 | II-32 |
| T1-2005 | I-4 | II-16 | II-33 |
| T1-2006 | I-4 | II-16 | II-37 |
| T1-2007 | I-4 | II-16 | II-39 |
| T1-2008 | I-4 | II-16 | II-42 |
| T1-2009 | I-4 | II-16 | II-44 |
| T1-2010 | I-4 | II-16 | II-50 |
| T1-2011 | I-4 | II-16 | II-53 |
| T1-2012 | I-4 | II-16 | II-60 |
| T1-2013 | I-4 | II-16 | II-62 |
| T1-2014 | I-4 | II-16 | II-66 |
| T1-2015 | I-4 | II-16 | II-69 |
| T1-2016 | I-4 | II-16 | II-70 |
| T1-2017 | I-4 | II-16 | II-71 |
| T1-2018 | I-4 | II-16 | II-72 |
| T1-2019 | I-4 | II-16 | II-74 |
| T1-2020 | I-4 | II-16 | II-76 |
| T1-2021 | I-4 | II-16 | II-78 |
| T1-2022 | I-4 | II-16 | II-84 |
| T1-2023 | I-4 | II-16 | II-85 |
| T1-2024 | I-4 | II-16 | II-86 |
| T1-2025 | I-4 | II-16 | II-92 |
| T1-2026 | I-4 | II-21 | II-26 |
| T1-2027 | I-4 | II-21 | II-32 |
| T1-2028 | I-4 | II-21 | II-33 |
| T1-2029 | I-4 | II-21 | II-37 |
| T1-2030 | I-4 | II-21 | II-39 |
| T1-2031 | I-4 | II-21 | II-42 |
| T1-2032 | I-4 | II-21 | II-44 |
| T1-2033 | I-4 | II-21 | II-50 |
| T1-2034 | I-4 | II-21 | II-53 |
| T1-2035 | I-4 | II-21 | II-60 |
| T1-2036 | I-4 | II-21 | II-62 |
| T1-2037 | I-4 | II-21 | II-66 |
| T1-2038 | I-4 | II-21 | II-69 |
| T1-2039 | I-4 | II-21 | II-70 |
| T1-2040 | I-4 | II-21 | II-71 |
| T1-2041 | I-4 | II-21 | II-72 |
| T1-2042 | I-4 | II-21 | II-74 |
| T1-2043 | I-4 | II-21 | II-76 |
| T1-2044 | I-4 | II-21 | II-78 |
| T1-2045 | I-4 | II-21 | II-84 |
| T1-2046 | I-4 | II-21 | II-85 |
| T1-2047 | I-4 | II-21 | II-86 |
| T1-2048 | I-4 | II-21 | II-92 |
| T1-2049 | I-4 | II-26 | II-32 |
| T1-2050 | I-4 | II-26 | II-33 |
| T1-2051 | I-4 | II-26 | II-37 |
| T1-2052 | I-4 | II-26 | II-39 |
| T1-2053 | I-4 | II-26 | II-42 |
| T1-2054 | I-4 | II-26 | II-44 |
| T1-2055 | I-4 | II-26 | II-50 |
| T1-2056 | I-4 | II-26 | II-53 |
| T1-2057 | I-4 | II-26 | II-60 |
| T1-2058 | I-4 | II-26 | II-62 |
| T1-2059 | I-4 | II-26 | II-66 |
| T1-2060 | I-4 | II-26 | II-69 |
| T1-2061 | I-4 | II-26 | II-70 |
| T1-2062 | I-4 | II-26 | II-71 |
| T1-2063 | I-4 | II-26 | II-72 |
| T1-2064 | I-4 | II-26 | II-74 |
| T1-2065 | I-4 | II-26 | II-76 |
| T1-2066 | I-4 | II-26 | II-78 |
| T1-2067 | I-4 | II-26 | II-84 |
| T1-2068 | I-4 | II-26 | II-85 |
| T1-2069 | I-4 | II-26 | II-86 |
| T1-2070 | I-4 | II-26 | II-92 |
| T1-2071 | I-4 | II-32 | II-33 |
| T1-2072 | I-4 | II-32 | II-37 |
| T1-2073 | I-4 | II-32 | II-39 |
| T1-2074 | I-4 | II-32 | II-42 |
| T1-2075 | I-4 | II-32 | II-44 |
| T1-2076 | I-4 | II-32 | II-50 |
| T1-2077 | I-4 | II-32 | II-53 |
| T1-2078 | I-4 | II-32 | II-60 |
| T1-2079 | I-4 | II-32 | II-62 |
| T1-2080 | I-4 | II-32 | II-66 |
| T1-2081 | I-4 | II-32 | II-69 |
| T1-2082 | I-4 | II-32 | II-70 |
| T1-2083 | I-4 | II-32 | II-71 |
| T1-2084 | I-4 | II-32 | II-72 |
| T1-2085 | I-4 | II-32 | II-74 |
| T1-2086 | I-4 | II-32 | II-76 |
| T1-2087 | I-4 | II-32 | II-78 |
| T1-2088 | I-4 | II-32 | II-84 |
| T1-2089 | I-4 | II-32 | II-85 |
| T1-2090 | I-4 | II-32 | II-86 |
| T1-2091 | I-4 | II-32 | II-92 |
| T1-2092 | I-4 | II-33 | II-37 |
| T1-2093 | I-4 | II-33 | II-39 |
| T1-2094 | I-4 | II-33 | II-42 |
| T1-2095 | I-4 | II-33 | II-44 |
| T1-2096 | I-4 | II-33 | II-50 |
| T1-2097 | I-4 | II-33 | II-53 |
| T1-2098 | I-4 | II-33 | II-60 |
| T1-2099 | I-4 | II-33 | II-62 |
| T1-2100 | I-4 | II-33 | II-66 |
| T1-2101 | I-4 | II-33 | II-69 |
| T1-2102 | I-4 | II-33 | II-70 |
| T1-2103 | I-4 | II-33 | II-71 |
| T1-2104 | I-4 | II-33 | II-72 |
| T1-2105 | I-4 | II-33 | II-74 |
| T1-2106 | I-4 | II-33 | II-76 |
| T1-2107 | I-4 | II-33 | II-78 |
| T1-2108 | I-4 | II-33 | II-84 |
| T1-2109 | I-4 | II-33 | II-85 |

TABLE T1-continued

| composition | I | II | III |
|---|---|---|---|
| T1-2110 | I-4 | II-33 | II-86 |
| T1-2111 | I-4 | II-33 | II-92 |
| T1-2112 | I-4 | II-37 | II-39 |
| T1-2113 | I-4 | II-37 | II-42 |
| T1-2114 | I-4 | II-37 | II-44 |
| T1-2115 | I-4 | II-37 | II-50 |
| T1-2116 | I-4 | II-37 | II-53 |
| T1-2117 | I-4 | II-37 | II-60 |
| T1-2118 | I-4 | II-37 | II-62 |
| T1-2119 | I-4 | II-37 | II-66 |
| T1-2120 | I-4 | II-37 | II-69 |
| T1-2121 | I-4 | II-37 | II-70 |
| T1-2122 | I-4 | II-37 | II-71 |
| T1-2123 | I-4 | II-37 | II-72 |
| T1-2124 | I-4 | II-37 | II-74 |
| T1-2125 | I-4 | II-37 | II-76 |
| T1-2126 | I-4 | II-37 | II-78 |
| T1-2127 | I-4 | II-37 | II-84 |
| T1-2128 | I-4 | II-37 | II-85 |
| T1-2129 | I-4 | II-37 | II-86 |
| T1-2130 | I-4 | II-37 | II-92 |
| T1-2131 | I-4 | II-39 | II-42 |
| T1-2132 | I-4 | II-39 | II-44 |
| T1-2133 | I-4 | II-39 | II-50 |
| T1-2134 | I-4 | II-39 | II-53 |
| T1-2135 | I-4 | II-39 | II-60 |
| T1-2136 | I-4 | II-39 | II-62 |
| T1-2137 | I-4 | II-39 | II-66 |
| T1-2138 | I-4 | II-39 | II-69 |
| T1-2139 | I-4 | II-39 | II-70 |
| T1-2140 | I-4 | II-39 | II-71 |
| T1-2141 | I-4 | II-39 | II-72 |
| T1-2142 | I-4 | II-39 | II-74 |
| T1-2143 | I-4 | II-39 | II-76 |
| T1-2144 | I-4 | II-39 | II-78 |
| T1-2145 | I-4 | II-39 | II-84 |
| T1-2146 | I-4 | II-39 | II-85 |
| T1-2147 | I-4 | II-39 | II-86 |
| T1-2148 | I-4 | II-39 | II-92 |
| T1-2149 | I-4 | II-42 | II-44 |
| T1-2150 | I-4 | II-42 | II-50 |
| T1-2151 | I-4 | II-42 | II-53 |
| T1-2152 | I-4 | II-42 | II-60 |
| T1-2153 | I-4 | II-42 | II-62 |
| T1-2154 | I-4 | II-42 | II-66 |
| T1-2155 | I-4 | II-42 | II-69 |
| T1-2156 | I-4 | II-42 | II-70 |
| T1-2157 | I-4 | II-42 | II-71 |
| T1-2158 | I-4 | II-42 | II-72 |
| T1-2159 | I-4 | II-42 | II-74 |
| T1-2160 | I-4 | II-42 | II-76 |
| T1-2161 | I-4 | II-42 | II-78 |
| T1-2162 | I-4 | II-42 | II-84 |
| T1-2163 | I-4 | II-42 | II-85 |
| T1-2164 | I-4 | II-42 | II-86 |
| T1-2165 | I-4 | II-42 | II-92 |
| T1-2166 | I-4 | II-44 | II-50 |
| T1-2167 | I-4 | II-44 | II-53 |
| T1-2168 | I-4 | II-44 | II-60 |
| T1-2169 | I-4 | II-44 | II-62 |
| T1-2170 | I-4 | II-44 | II-66 |
| T1-2171 | I-4 | II-44 | II-69 |
| T1-2172 | I-4 | II-44 | II-70 |
| T1-2173 | I-4 | II-44 | II-71 |
| T1-2174 | I-4 | II-44 | II-72 |
| T1-2175 | I-4 | II-44 | II-74 |
| T1-2176 | I-4 | II-44 | II-76 |
| T1-2177 | I-4 | II-44 | II-78 |
| T1-2178 | I-4 | II-44 | II-84 |
| T1-2179 | I-4 | II-44 | II-85 |
| T1-2180 | I-4 | II-44 | II-86 |
| T1-2181 | I-4 | II-44 | II-92 |
| T1-2182 | I-4 | II-50 | II-53 |
| T1-2183 | I-4 | II-50 | II-60 |
| T1-2184 | I-4 | II-50 | II-62 |
| T1-2185 | I-4 | II-50 | II-66 |
| T1-2186 | I-4 | II-50 | II-69 |
| T1-2187 | I-4 | II-50 | II-70 |
| T1-2188 | I-4 | II-50 | II-71 |
| T1-2189 | I-4 | II-50 | II-72 |
| T1-2190 | I-4 | II-50 | II-74 |
| T1-2191 | I-4 | II-50 | II-76 |
| T1-2192 | I-4 | II-50 | II-78 |
| T1-2193 | I-4 | II-50 | II-84 |
| T1-2194 | I-4 | II-50 | II-85 |
| T1-2195 | I-4 | II-50 | II-86 |
| T1-2196 | I-4 | II-50 | II-92 |
| T1-2197 | I-4 | II-53 | II-60 |
| T1-2198 | I-4 | II-53 | II-62 |
| T1-2199 | I-4 | II-53 | II-66 |
| T1-2200 | I-4 | II-53 | II-69 |
| T1-2201 | I-4 | II-53 | II-70 |
| T1-2202 | I-4 | II-53 | II-71 |
| T1-2203 | I-4 | II-53 | II-72 |
| T1-2204 | I-4 | II-53 | II-74 |
| T1-2205 | I-4 | II-53 | II-76 |
| T1-2206 | I-4 | II-53 | II-78 |
| T1-2207 | I-4 | II-53 | II-84 |
| T1-2208 | I-4 | II-53 | II-85 |
| T1-2209 | I-4 | II-53 | II-86 |
| T1-2210 | I-4 | II-53 | II-92 |
| T1-2211 | I-4 | II-60 | II-62 |
| T1-2212 | I-4 | II-60 | II-66 |
| T1-2213 | I-4 | II-60 | II-69 |
| T1-2214 | I-4 | II-60 | II-70 |
| T1-2215 | I-4 | II-60 | II-71 |
| T1-2216 | I-4 | II-60 | II-72 |
| T1-2217 | I-4 | II-60 | II-74 |
| T1-2218 | I-4 | II-60 | II-76 |
| T1-2219 | I-4 | II-60 | II-78 |
| T1-2220 | I-4 | II-60 | II-84 |
| T1-2221 | I-4 | II-60 | II-85 |
| T1-2222 | I-4 | II-60 | II-86 |
| T1-2223 | I-4 | II-60 | II-92 |
| T1-2224 | I-4 | II-62 | II-66 |
| T1-2225 | I-4 | II-62 | II-69 |
| T1-2226 | I-4 | II-62 | II-70 |
| T1-2227 | I-4 | II-62 | II-71 |
| T1-2228 | I-4 | II-62 | II-72 |
| T1-2229 | I-4 | II-62 | II-74 |
| T1-2230 | I-4 | II-62 | II-76 |
| T1-2231 | I-4 | II-62 | II-78 |
| T1-2232 | I-4 | II-62 | II-84 |
| T1-2233 | I-4 | II-62 | II-85 |
| T1-2234 | I-4 | II-62 | II-86 |
| T1-2235 | I-4 | II-62 | II-92 |
| T1-2236 | I-4 | II-66 | II-69 |
| T1-2237 | I-4 | II-66 | II-70 |
| T1-2238 | I-4 | II-66 | II-71 |
| T1-2239 | I-4 | II-66 | II-72 |
| T1-2240 | I-4 | II-66 | II-74 |
| T1-2241 | I-4 | II-66 | II-76 |
| T1-2242 | I-4 | II-66 | II-78 |
| T1-2243 | I-4 | II-66 | II-84 |
| T1-2244 | I-4 | II-66 | II-85 |
| T1-2245 | I-4 | II-66 | II-86 |
| T1-2246 | I-4 | II-66 | II-92 |
| T1-2247 | I-4 | II-69 | II-70 |
| T1-2248 | I-4 | II-69 | II-71 |
| T1-2249 | I-4 | II-69 | II-72 |
| T1-2250 | I-4 | II-69 | II-74 |
| T1-2251 | I-4 | II-69 | II-76 |
| T1-2252 | I-4 | II-69 | II-78 |
| T1-2253 | I-4 | II-69 | II-84 |
| T1-2254 | I-4 | II-69 | II-85 |
| T1-2255 | I-4 | II-69 | II-86 |
| T1-2256 | I-4 | II-69 | II-92 |
| T1-2257 | I-4 | II-70 | II-71 |
| T1-2258 | I-4 | II-70 | II-72 |
| T1-2259 | I-4 | II-70 | II-74 |
| T1-2260 | I-4 | II-70 | II-76 |
| T1-2261 | I-4 | II-70 | II-78 |
| T1-2262 | I-4 | II-70 | II-84 |
| T1-2263 | I-4 | II-70 | II-85 |
| T1-2264 | I-4 | II-70 | II-86 |
| T1-2265 | I-4 | II-70 | II-92 |

TABLE T1-continued

| composition | I | II | III |
|---|---|---|---|
| T1-2266 | I-4 | II-71 | II-72 |
| T1-2267 | I-4 | II-71 | II-74 |
| T1-2268 | I-4 | II-71 | II-76 |
| T1-2269 | I-4 | II-71 | II-78 |
| T1-2270 | I-4 | II-71 | II-84 |
| T1-2271 | I-4 | II-71 | II-85 |
| T1-2272 | I-4 | II-71 | II-86 |
| T1-2273 | I-4 | II-71 | II-92 |
| T1-2274 | I-4 | II-72 | II-74 |
| T1-2275 | I-4 | II-74 | II-76 |
| T1-2276 | I-4 | II-74 | II-78 |
| T1-2277 | I-4 | II-74 | II-84 |
| T1-2278 | I-4 | II-74 | II-85 |
| T1-2279 | I-4 | II-74 | II-86 |
| T1-2280 | I-4 | II-74 | II-92 |
| T1-2281 | I-4 | II-76 | II-78 |
| T1-2282 | I-4 | II-76 | II-84 |
| T1-2283 | I-4 | II-76 | II-85 |
| T1-2284 | I-4 | II-76 | II-86 |
| T1-2285 | I-4 | II-76 | II-92 |
| T1-2286 | I-4 | II-78 | II-84 |
| T1-2287 | I-4 | II-78 | II-85 |
| T1-2288 | I-4 | II-78 | II-86 |
| T1-2289 | I-4 | II-78 | II-92 |
| T1-2290 | I-4 | II-84 | II-85 |
| T1-2291 | I-4 | II-84 | II-86 |
| T1-2292 | I-4 | II-84 | II-92 |
| T1-2293 | I-4 | II-85 | II-86 |
| T1-2294 | I-4 | II-85 | II-92 |
| T1-2295 | I-4 | II-86 | II-92 |

Three-component compositions comprising another compound I as component I, a component II a component III, wherein component II and III are selected from the preferred fungicides detailed above, wherein components II and III are different from each other.

| composition | I | II | III |
|---|---|---|---|
| T1-2296 | I-13 | II-3 | II-5 |
| T1-2297 | I-13 | II-3 | II-6 |
| T1-2298 | I-13 | II-3 | II-7 |
| T1-2299 | I-13 | II-3 | II-8 |
| T1-2300 | I-13 | II-3 | II-11 |
| T1-2301 | I-13 | II-3 | II-16 |
| T1-2302 | I-13 | II-3 | II-21 |
| T1-2303 | I-13 | II-3 | II-26 |
| T1-2304 | I-13 | II-3 | II-32 |
| T1-2305 | I-13 | II-3 | II-33 |
| T1-2306 | I-13 | II-3 | II-37 |
| T1-2307 | I-13 | II-3 | II-39 |
| T1-2308 | I-13 | II-3 | II-42 |
| T1-2309 | I-13 | II-3 | II-44 |
| T1-2310 | I-13 | II-3 | II-50 |
| T1-2311 | I-13 | II-3 | II-53 |
| T1-2312 | I-13 | II-3 | II-60 |
| T1-2313 | I-13 | II-3 | II-62 |
| T1-2314 | I-13 | II-3 | II-66 |
| T1-2315 | I-13 | II-3 | II-69 |
| T1-2316 | I-13 | II-3 | II-70 |
| T1-2317 | I-13 | II-3 | II-71 |
| T1-2318 | I-13 | II-3 | II-72 |
| T1-2319 | I-13 | II-3 | II-74 |
| T1-2320 | I-13 | II-3 | II-76 |
| T1-2321 | I-13 | II-3 | II-78 |
| T1-2322 | I-13 | II-3 | II-84 |
| T1-2323 | I-13 | II-3 | II-85 |
| T1-2324 | I-13 | II-3 | II-86 |
| T1-2325 | I-13 | II-3 | II-92 |
| T1-2326 | I-13 | II-5 | II-6 |
| T1-2327 | I-13 | II-5 | II-7 |
| T1-2328 | I-13 | II-5 | II-8 |
| T1-2329 | I-13 | II-5 | II-11 |
| T1-2330 | I-13 | II-5 | II-16 |
| T1-2331 | I-13 | II-5 | II-21 |
| T1-2332 | I-13 | II-5 | II-26 |
| T1-2333 | I-13 | II-5 | II-32 |
| T1-2334 | I-13 | II-5 | II-33 |
| T1-2335 | I-13 | II-5 | II-37 |
| T1-2336 | I-13 | II-5 | II-39 |
| T1-2337 | I-13 | II-5 | II-42 |
| T1-2338 | I-13 | II-5 | II-44 |
| T1-2339 | I-13 | II-5 | II-50 |
| T1-2340 | I-13 | II-5 | II-53 |
| T1-2341 | I-13 | II-5 | II-60 |
| T1-2342 | I-13 | II-5 | II-62 |
| T1-2343 | I-13 | II-5 | II-66 |
| T1-2344 | I-13 | II-5 | II-69 |
| T1-2345 | I-13 | II-5 | II-70 |
| T1-2346 | I-13 | II-5 | II-71 |
| T1-2347 | I-13 | II-5 | II-72 |
| T1-2348 | I-13 | II-5 | II-74 |
| T1-2349 | I-13 | II-5 | II-76 |
| T1-2350 | I-13 | II-5 | II-78 |
| T1-2351 | I-13 | II-5 | II-84 |
| T1-2352 | I-13 | II-5 | II-85 |
| T1-2353 | I-13 | II-5 | II-86 |
| T1-2354 | I-13 | II-5 | II-92 |
| T1-2355 | I-13 | II-6 | II-7 |
| T1-2356 | I-13 | II-6 | II-8 |
| T1-2357 | I-13 | II-6 | II-11 |
| T1-2358 | I-13 | II-6 | II-16 |
| T1-2359 | I-13 | II-6 | II-21 |
| T1-2360 | I-13 | II-6 | II-26 |
| T1-2361 | I-13 | II-6 | II-32 |
| T1-2362 | I-13 | II-6 | II-33 |
| T1-2363 | I-13 | II-6 | II-37 |
| T1-2364 | I-13 | II-6 | II-39 |
| T1-2365 | I-13 | II-6 | II-42 |
| T1-2366 | I-13 | II-6 | II-44 |
| T1-2367 | I-13 | II-6 | II-50 |
| T1-2368 | I-13 | II-6 | II-53 |
| T1-2369 | I-13 | II-6 | II-60 |
| T1-2370 | I-13 | II-6 | II-62 |
| T1-2371 | I-13 | II-6 | II-66 |
| T1-2372 | I-13 | II-6 | II-69 |
| T1-2373 | I-13 | II-6 | II-70 |
| T1-2374 | I-13 | II-6 | II-71 |
| T1-2375 | I-13 | II-6 | II-72 |
| T1-2376 | I-13 | II-6 | II-74 |
| T1-2377 | I-13 | II-6 | II-76 |
| T1-2378 | I-13 | II-6 | II-78 |
| T1-2379 | I-13 | II-6 | II-84 |
| T1-2380 | I-13 | II-6 | II-85 |
| T1-2381 | I-13 | II-6 | II-86 |
| T1-2382 | I-13 | II-6 | II-92 |
| T1-2383 | I-13 | II-7 | II-8 |
| T1-2384 | I-13 | II-7 | II-11 |
| T1-2385 | I-13 | II-7 | II-16 |
| T1-2386 | I-13 | II-7 | II-21 |
| T1-2387 | I-13 | II-7 | II-26 |
| T1-2388 | I-13 | II-7 | II-32 |
| T1-2389 | I-13 | II-7 | II-33 |
| T1-2390 | I-13 | II-7 | II-37 |
| T1-2391 | I-13 | II-7 | II-39 |
| T1-2392 | I-13 | II-7 | II-42 |
| T1-2393 | I-13 | II-7 | II-44 |
| T1-2394 | I-13 | II-7 | II-50 |
| T1-2395 | I-13 | II-7 | II-53 |
| T1-2396 | I-13 | II-7 | II-60 |
| T1-2397 | I-13 | II-7 | II-62 |
| T1-2398 | I-13 | II-7 | II-66 |
| T1-2399 | I-13 | II-7 | II-69 |
| T1-2400 | I-13 | II-7 | II-70 |
| T1-2401 | I-13 | II-7 | II-71 |
| T1-2402 | I-13 | II-7 | II-72 |
| T1-2403 | I-13 | II-7 | II-74 |
| T1-2404 | I-13 | II-7 | II-76 |
| T1-2405 | I-13 | II-7 | II-78 |
| T1-2406 | I-13 | II-7 | II-84 |
| T1-2407 | I-13 | II-7 | II-85 |
| T1-2408 | I-13 | II-7 | II-86 |
| T1-2409 | I-13 | II-7 | II-92 |
| T1-2410 | I-13 | II-8 | II-11 |
| T1-2411 | I-13 | II-8 | II-16 |
| T1-2412 | I-13 | II-8 | II-21 |
| T1-2413 | I-13 | II-8 | II-26 |
| T1-2414 | I-13 | II-8 | II-32 |
| T1-2415 | I-13 | II-8 | II-33 |
| T1-2416 | I-13 | II-8 | II-37 |

TABLE T1-continued

| composition | I | II | III |
|---|---|---|---|
| T1-2417 | I-13 | II-8 | II-39 |
| T1-2418 | I-13 | II-8 | II-42 |
| T1-2419 | I-13 | II-8 | II-44 |
| T1-2420 | I-13 | II-8 | II-50 |
| T1-2421 | I-13 | II-8 | II-53 |
| T1-2422 | I-13 | II-8 | II-60 |
| T1-2423 | I-13 | II-8 | II-62 |
| T1-2424 | I-13 | II-8 | II-66 |
| T1-2425 | I-13 | II-8 | II-69 |
| T1-2426 | I-13 | II-8 | II-70 |
| T1-2427 | I-13 | II-8 | II-71 |
| T1-2428 | I-13 | II-8 | II-72 |
| T1-2429 | I-13 | II-8 | II-74 |
| T1-2430 | I-13 | II-8 | II-76 |
| T1-2431 | I-13 | II-8 | II-78 |
| T1-2432 | I-13 | II-8 | II-84 |
| T1-2433 | I-13 | II-8 | II-85 |
| T1-2434 | I-13 | II-8 | II-86 |
| T1-2435 | I-13 | II-8 | II-92 |
| T1-2436 | I-13 | II-11 | II-16 |
| T1-2437 | I-13 | II-11 | II-21 |
| T1-2438 | I-13 | II-11 | II-26 |
| T1-2439 | I-13 | II-11 | II-32 |
| T1-2440 | I-13 | II-11 | II-33 |
| T1-2441 | I-13 | II-11 | II-37 |
| T1-2442 | I-13 | II-11 | II-39 |
| T1-2443 | I-13 | II-11 | II-42 |
| T1-2444 | I-13 | II-11 | II-44 |
| T1-2445 | I-13 | II-11 | II-50 |
| T1-2446 | I-13 | II-11 | II-53 |
| T1-2447 | I-13 | II-11 | II-60 |
| T1-2448 | I-13 | II-11 | II-62 |
| T1-2449 | I-13 | II-11 | II-66 |
| T1-2450 | I-13 | II-11 | II-69 |
| T1-2451 | I-13 | II-11 | II-70 |
| T1-2452 | I-13 | II-11 | II-71 |
| T1-2453 | I-13 | II-11 | II-72 |
| T1-2454 | I-13 | II-11 | II-74 |
| T1-2455 | I-13 | II-11 | II-76 |
| T1-2456 | I-13 | II-11 | II-78 |
| T1-2457 | I-13 | II-11 | II-84 |
| T1-2458 | I-13 | II-11 | II-85 |
| T1-2459 | I-13 | II-11 | II-86 |
| T1-2460 | I-13 | II-11 | II-92 |
| T1-2461 | I-13 | II-16 | II-21 |
| T1-2462 | I-13 | II-16 | II-26 |
| T1-2463 | I-13 | II-16 | II-32 |
| T1-2464 | I-13 | II-16 | II-33 |
| T1-2465 | I-13 | II-16 | II-37 |
| T1-2466 | I-13 | II-16 | II-39 |
| T1-2467 | I-13 | II-16 | II-42 |
| T1-2468 | I-13 | II-16 | II-44 |
| T1-2469 | I-13 | II-16 | II-50 |
| T1-2470 | I-13 | II-16 | II-53 |
| T1-2471 | I-13 | II-16 | II-60 |
| T1-2472 | I-13 | II-16 | II-62 |
| T1-2473 | I-13 | II-16 | II-66 |
| T1-2474 | I-13 | II-16 | II-69 |
| T1-2475 | I-13 | II-16 | II-70 |
| T1-2476 | I-13 | II-16 | II-71 |
| T1-2477 | I-13 | II-16 | II-72 |
| T1-2478 | I-13 | II-16 | II-74 |
| T1-2479 | I-13 | II-16 | II-76 |
| T1-2480 | I-13 | II-16 | II-78 |
| T1-2481 | I-13 | II-16 | II-84 |
| T1-2482 | I-13 | II-16 | II-85 |
| T1-2483 | I-13 | II-16 | II-86 |
| T1-2484 | I-13 | II-16 | II-92 |
| T1-2485 | I-13 | II-21 | II-26 |
| T1-2486 | I-13 | II-21 | II-32 |
| T1-2487 | I-13 | II-21 | II-33 |
| T1-2488 | I-13 | II-21 | II-37 |
| T1-2489 | I-13 | II-21 | II-39 |
| T1-2490 | I-13 | II-21 | II-42 |
| T1-2492 | I-13 | II-21 | II-50 |
| T1-2493 | I-13 | II-21 | II-53 |
| T1-2494 | I-13 | II-21 | II-60 |
| T1-2495 | I-13 | II-21 | II-62 |
| T1-2496 | I-13 | II-21 | II-66 |
| T1-2497 | I-13 | II-21 | II-69 |
| T1-2498 | I-13 | II-21 | II-70 |
| T1-2499 | I-13 | II-21 | II-71 |
| T1-2500 | I-13 | II-21 | II-72 |
| T1-2501 | I-13 | II-21 | II-74 |
| T1-2502 | I-13 | II-21 | II-76 |
| T1-2503 | I-13 | II-21 | II-78 |
| T1-2504 | I-13 | II-21 | II-84 |
| T1-2505 | I-13 | II-21 | II-85 |
| T1-2506 | I-13 | II-21 | II-86 |
| T1-2507 | I-13 | II-21 | II-92 |
| T1-2508 | I-13 | II-26 | II-32 |
| T1-2509 | I-13 | II-26 | II-33 |
| T1-2510 | I-13 | II-26 | II-37 |
| T1-2511 | I-13 | II-26 | II-39 |
| T1-2512 | I-13 | II-26 | II-42 |
| T1-2513 | I-13 | II-26 | II-44 |
| T1-2514 | I-13 | II-26 | II-50 |
| T1-2515 | I-13 | II-26 | II-53 |
| T1-2516 | I-13 | II-26 | II-60 |
| T1-2517 | I-13 | II-26 | II-62 |
| T1-2518 | I-13 | II-26 | II-66 |
| T1-2519 | I-13 | II-26 | II-69 |
| T1-2520 | I-13 | II-26 | II-70 |
| T1-2521 | I-13 | II-26 | II-71 |
| T1-2522 | I-13 | II-26 | II-72 |
| T1-2523 | I-13 | II-26 | II-74 |
| T1-2524 | I-13 | II-26 | II-76 |
| T1-2525 | I-13 | II-26 | II-78 |
| T1-2526 | I-13 | II-26 | II-84 |
| T1-2527 | I-13 | II-26 | II-85 |
| T1-2528 | I-13 | II-26 | II-86 |
| T1-2529 | I-13 | II-26 | II-92 |
| T1-2530 | I-13 | II-32 | II-33 |
| T1-2531 | I-13 | II-32 | II-37 |
| T1-2532 | I-13 | II-32 | II-39 |
| T1-2533 | I-13 | II-32 | II-42 |
| T1-2534 | I-13 | II-32 | II-44 |
| T1-2535 | I-13 | II-32 | II-50 |
| T1-2536 | I-13 | II-32 | II-53 |
| T1-2537 | I-13 | II-32 | II-60 |
| T1-2538 | I-13 | II-32 | II-62 |
| T1-2539 | I-13 | II-32 | II-66 |
| T1-2540 | I-13 | II-32 | II-69 |
| T1-2541 | I-13 | II-32 | II-70 |
| T1-2542 | I-13 | II-32 | II-71 |
| T1-2543 | I-13 | II-32 | II-72 |
| T1-2544 | I-13 | II-32 | II-74 |
| T1-2545 | I-13 | II-32 | II-76 |
| T1-2546 | I-13 | II-32 | II-78 |
| T1-2547 | I-13 | II-32 | II-84 |
| T1-2548 | I-13 | II-32 | II-85 |
| T1-2549 | I-13 | II-32 | II-86 |
| T1-2550 | I-13 | II-32 | II-92 |
| T1-2551 | I-13 | II-33 | II-37 |
| T1-2552 | I-13 | II-33 | II-39 |
| T1-2553 | I-13 | II-33 | II-42 |
| T1-2554 | I-13 | II-33 | II-44 |
| T1-2555 | I-13 | II-33 | II-50 |
| T1-2556 | I-13 | II-33 | II-53 |
| T1-2557 | I-13 | II-33 | II-60 |
| T1-2558 | I-13 | II-33 | II-62 |
| T1-2559 | I-13 | II-33 | II-66 |
| T1-2560 | I-13 | II-33 | II-69 |
| T1-2561 | I-13 | II-33 | II-70 |
| T1-2562 | I-13 | II-33 | II-71 |
| T1-2563 | I-13 | II-33 | II-72 |
| T1-2564 | I-13 | II-33 | II-74 |
| T1-2565 | I-13 | II-33 | II-76 |
| T1-2566 | I-13 | II-33 | II-78 |
| T1-2567 | I-13 | II-33 | II-84 |
| T1-2568 | I-13 | II-33 | II-85 |
| T1-2569 | I-13 | II-33 | II-86 |
| T1-2570 | I-13 | II-33 | II-92 |
| T1-2571 | I-13 | II-37 | II-39 |
| T1-2572 | I-13 | II-37 | II-42 |
| T1-2573 | I-13 | II-37 | II-44 |

TABLE T1-continued

| composition | I | II | III |
|---|---|---|---|
| T1-2574 | I-13 | II-37 | II-50 |
| T1-2575 | I-13 | II-37 | II-53 |
| T1-2576 | I-13 | II-37 | II-60 |
| T1-2577 | I-13 | II-37 | II-62 |
| T1-2578 | I-13 | II-37 | II-66 |
| T1-2579 | I-13 | II-37 | II-69 |
| T1-2580 | I-13 | II-37 | II-70 |
| T1-2581 | I-13 | II-37 | II-71 |
| T1-2582 | I-13 | II-37 | II-72 |
| T1-2583 | I-13 | II-37 | II-74 |
| T1-2584 | I-13 | II-37 | II-76 |
| T1-2585 | I-13 | II-37 | II-78 |
| T1-2586 | I-13 | II-37 | II-84 |
| T1-2587 | I-13 | II-37 | II-85 |
| T1-2588 | I-13 | II-37 | II-86 |
| T1-2589 | I-13 | II-37 | II-92 |
| T1-2590 | I-13 | II-39 | II-42 |
| T1-2591 | I-13 | II-39 | II-44 |
| T1-2592 | I-13 | II-39 | II-50 |
| T1-2593 | I-13 | II-39 | II-53 |
| T1-2594 | I-13 | II-39 | II-60 |
| T1-2595 | I-13 | II-39 | II-62 |
| T1-2596 | I-13 | II-39 | II-66 |
| T1-2597 | I-13 | II-39 | II-69 |
| T1-2598 | I-13 | II-39 | II-70 |
| T1-2599 | I-13 | II-39 | II-71 |
| T1-2600 | I-13 | II-39 | II-72 |
| T1-2601 | I-13 | II-39 | II-74 |
| T1-2602 | I-13 | II-39 | II-76 |
| T1-2603 | I-13 | II-39 | II-78 |
| T1-2604 | I-13 | II-39 | II-84 |
| T1-2605 | I-13 | II-39 | II-85 |
| T1-2606 | I-13 | II-39 | II-86 |
| T1-2607 | I-13 | II-39 | II-92 |
| T1-2608 | I-13 | II-42 | II-44 |
| T1-2609 | I-13 | II-42 | II-50 |
| T1-2610 | I-13 | II-42 | II-53 |
| T1-2611 | I-13 | II-42 | II-60 |
| T1-2612 | I-13 | II-42 | II-62 |
| T1-2613 | I-13 | II-42 | II-66 |
| T1-2614 | I-13 | II-42 | II-69 |
| T1-2615 | I-13 | II-42 | II-70 |
| T1-2616 | I-13 | II-42 | II-71 |
| T1-2617 | I-13 | II-42 | II-72 |
| T1-2618 | I-13 | II-42 | II-74 |
| T1-2619 | I-13 | II-42 | II-76 |
| T1-2620 | I-13 | II-42 | II-78 |
| T1-2621 | I-13 | II-42 | II-84 |
| T1-2622 | I-13 | II-42 | II-85 |
| T1-2623 | I-13 | II-42 | II-86 |
| T1-2624 | I-13 | II-42 | II-92 |
| T1-2625 | I-13 | II-44 | II-50 |
| T1-2626 | I-13 | II-44 | II-53 |
| T1-2627 | I-13 | II-44 | II-60 |
| T1-2628 | I-13 | II-44 | II-62 |
| T1-2629 | I-13 | II-44 | II-66 |
| T1-2630 | I-13 | II-44 | II-69 |
| T1-2631 | I-13 | II-44 | II-70 |
| T1-2632 | I-13 | II-44 | II-71 |
| T1-2633 | I-13 | II-44 | II-72 |
| T1-2634 | I-13 | II-44 | II-74 |
| T1-2635 | I-13 | II-44 | II-76 |
| T1-2636 | I-13 | II-44 | II-78 |
| T1-2637 | I-13 | II-44 | II-84 |
| T1-2638 | I-13 | II-44 | II-85 |
| T1-2639 | I-13 | II-44 | II-86 |
| T1-2640 | I-13 | II-44 | II-92 |
| T1-2641 | I-13 | II-50 | II-53 |
| T1-2642 | I-13 | II-50 | II-60 |
| T1-2643 | I-13 | II-50 | II-62 |
| T1-2644 | I-13 | II-50 | II-66 |
| T1-2645 | I-13 | II-50 | II-69 |
| T1-2646 | I-13 | II-50 | II-70 |
| T1-2647 | I-13 | II-50 | II-71 |
| T1-2648 | I-13 | II-50 | II-72 |
| T1-2649 | I-13 | II-50 | II-74 |
| T1-2650 | I-13 | II-50 | II-76 |
| T1-2651 | I-13 | II-50 | II-78 |
| T1-2652 | I-13 | II-50 | II-84 |
| T1-2653 | I-13 | II-50 | II-85 |
| T1-2654 | I-13 | II-50 | II-86 |
| T1-2655 | I-13 | II-50 | II-92 |
| T1-2656 | I-13 | II-53 | II-60 |
| T1-2657 | I-13 | II-53 | II-62 |
| T1-2658 | I-13 | II-53 | II-66 |
| T1-2659 | I-13 | II-53 | II-69 |
| T1-2660 | I-13 | II-53 | II-70 |
| T1-2661 | I-13 | II-53 | II-71 |
| T1-2662 | I-13 | II-53 | II-72 |
| T1-2663 | I-13 | II-53 | II-74 |
| T1-2664 | I-13 | II-53 | II-76 |
| T1-2665 | I-13 | II-53 | II-78 |
| T1-2666 | I-13 | II-53 | II-84 |
| T1-2667 | I-13 | II-53 | II-85 |
| T1-2668 | I-13 | II-53 | II-86 |
| T1-2669 | I-13 | II-53 | II-92 |
| T1-2670 | I-13 | II-60 | II-62 |
| T1-2671 | I-13 | II-60 | II-66 |
| T1-2672 | I-13 | II-60 | II-69 |
| T1-2673 | I-13 | II-60 | II-70 |
| T1-2674 | I-13 | II-60 | II-71 |
| T1-2675 | I-13 | II-60 | II-72 |
| T1-2676 | I-13 | II-60 | II-74 |
| T1-2677 | I-13 | II-60 | II-76 |
| T1-2678 | I-13 | II-60 | II-78 |
| T1-2679 | I-13 | II-60 | II-84 |
| T1-2680 | I-13 | II-60 | II-85 |
| T1-2681 | I-13 | II-60 | II-86 |
| T1-2682 | I-13 | II-60 | II-92 |
| T1-2683 | I-13 | II-62 | II-66 |
| T1-2684 | I-13 | II-62 | II-69 |
| T1-2685 | I-13 | II-62 | II-70 |
| T1-2686 | I-13 | II-62 | II-71 |
| T1-2687 | I-13 | II-62 | II-72 |
| T1-2688 | I-13 | II-62 | II-74 |
| T1-2689 | I-13 | II-62 | II-76 |
| T1-2690 | I-13 | II-62 | II-78 |
| T1-2691 | I-13 | II-62 | II-84 |
| T1-2692 | I-13 | II-62 | II-85 |
| T1-2693 | I-13 | II-62 | II-86 |
| T1-2694 | I-13 | II-62 | II-92 |
| T1-2695 | I-13 | II-66 | II-69 |
| T1-2696 | I-13 | II-66 | II-70 |
| T1-2697 | I-13 | II-66 | II-71 |
| T1-2698 | I-13 | II-66 | II-72 |
| T1-2699 | I-13 | II-66 | II-74 |
| T1-2700 | I-13 | II-66 | II-76 |
| T1-2701 | I-13 | II-66 | II-78 |
| T1-2702 | I-13 | II-66 | II-84 |
| T1-2703 | I-13 | II-66 | II-85 |
| T1-2704 | I-13 | II-66 | II-86 |
| T1-2705 | I-13 | II-66 | II-92 |
| T1-2706 | I-13 | II-69 | II-70 |
| T1-2707 | I-13 | II-69 | II-71 |
| T1-2708 | I-13 | II-69 | II-72 |
| T1-2709 | I-13 | II-69 | II-74 |
| T1-2710 | I-13 | II-69 | II-76 |
| T1-2711 | I-13 | II-69 | II-78 |
| T1-2712 | I-13 | II-69 | II-84 |
| T1-2713 | I-13 | II-69 | II-85 |
| T1-2714 | I-13 | II-69 | II-86 |
| T1-2715 | I-13 | II-69 | II-92 |
| T1-2716 | I-13 | II-70 | II-71 |
| T1-2717 | I-13 | II-70 | II-72 |
| T1-2718 | I-13 | II-70 | II-74 |
| T1-2719 | I-13 | II-70 | II-76 |
| T1-2720 | I-13 | II-70 | II-78 |
| T1-2721 | I-13 | II-70 | II-84 |
| T1-2722 | I-13 | II-70 | II-85 |
| T1-2723 | I-13 | II-70 | II-86 |
| T1-2724 | I-13 | II-70 | II-92 |
| T1-2725 | I-13 | II-71 | II-72 |
| T1-2726 | I-13 | II-71 | II-74 |
| T1-2727 | I-13 | II-71 | II-76 |
| T1-2728 | I-13 | II-71 | II-78 |
| T1-2729 | I-13 | II-71 | II-84 |

TABLE T1-continued

| composition | I | II | III |
| --- | --- | --- | --- |
| T1-2730 | I-13 | II-71 | II-85 |
| T1-2731 | I-13 | II-71 | II-86 |
| T1-2732 | I-13 | II-71 | II-92 |
| T1-2733 | I-13 | II-72 | II-74 |
| T1-2734 | I-13 | II-74 | II-76 |
| T1-2735 | I-13 | II-74 | II-78 |
| T1-2736 | I-13 | II-74 | II-84 |
| T1-2737 | I-13 | II-74 | II-85 |
| T1-2738 | I-13 | II-74 | II-86 |
| T1-2739 | I-13 | II-74 | II-92 |
| T1-2740 | I-13 | II-76 | II-78 |
| T1-2741 | I-13 | II-76 | II-84 |
| T1-2742 | I-13 | II-76 | II-85 |
| T1-2743 | I-13 | II-76 | II-86 |
| T1-2744 | I-13 | II-76 | II-92 |
| T1-2745 | I-13 | II-78 | II-84 |
| T1-2746 | I-13 | II-78 | II-85 |
| T1-2747 | I-13 | II-78 | II-86 |
| T1-2748 | I-13 | II-78 | II-92 |
| T1-2749 | I-13 | II-84 | II-85 |
| T1-2750 | I-13 | II-84 | II-86 |
| T1-2751 | I-13 | II-84 | II-92 |
| T1-2752 | I-13 | II-85 | II-86 |
| T1-2753 | I-13 | II-85 | II-92 |
| T1-2754 | I-13 | II-86 | II-92 |

As detailed above, the components I contain chirality centers and may, therefore, be present as racemic mixtures, as pure enantiomers or in the two enantiomers of one component I may be present in any ratio (S):(R).

According to particular embodiments of the invention, the respective component I is present as (S) enantiomer. Specific three-component compositions comprising the (S) enantiomer of the respective component I are compiled in Table T1s, wherein each row corresponds to one embodiment of the compositions according to the invention, i.e. one specific individualized composition. According to one specific aspect, these are ternary compositions which each only contain these two components as active compounds. Furthermore, also every combination of the compositions individualized in this table represent embodiments of the present invention.

TABLE T1s

Three-component compositions comprising one component I as (S) enantiomer (appreviated as (S)-I, e.g. (S)-I-1 for the (S)-enantiomer of I-1), one component II and one component III, in particular ternary compositions containing the respective component I as (S) enantiomer, II and III as only active ingredients.

| composition | (S)-I | II | III |
| --- | --- | --- | --- |
| T1s-1 | (S)-I-1 | II-3 | II-5 |
| T1s-2 | (S)-I-1 | II-3 | II-6 |
| T1s-3 | (S)-I-1 | II-3 | II-7 |
| T1s-4 | (S)-I-1 | II-3 | II-8 |
| T1s-5 | (S)-I-1 | II-3 | II-11 |
| T1s-6 | (S)-I-1 | II-3 | II-16 |
| T1s-7 | (S)-I-1 | II-3 | II-21 |
| T1s-8 | (S)-I-1 | II-3 | II-26 |
| T1s-9 | (S)-I-1 | II-3 | II-32 |
| T1s-10 | (S)-I-1 | II-3 | II-33 |
| T1s-11 | (S)-I-1 | II-3 | II-37 |
| T1s-12 | (S)-I-1 | II-3 | II-39 |
| T1s-13 | (S)-I-1 | II-3 | II-42 |
| T1s-14 | (S)-I-1 | II-3 | II-44 |
| T1s-15 | (S)-I-1 | II-3 | II-50 |
| T1s-16 | (S)-I-1 | II-3 | II-53 |
| T1s-17 | (S)-I-1 | II-3 | II-60 |
| T1s-18 | (S)-I-1 | II-3 | II-62 |
| T1s-19 | (S)-I-1 | II-3 | II-66 |

TABLE T1s-continued

Three-component compositions comprising one component I as (S) enantiomer (appreviated as (S)-I, e.g. (S)-I-1 for the (S)-enantiomer of I-1), one component II and one component III, in particular ternary compositions containing the respective component I as (S) enantiomer, II and III as only active ingredients.

| composition | (S)-I | II | III |
| --- | --- | --- | --- |
| T1s-20 | (S)-I-1 | II-3 | II-69 |
| T1s-21 | (S)-I-1 | II-3 | II-70 |
| T1s-22 | (S)-I-1 | II-3 | II-71 |
| T1s-23 | (S)-I-1 | II-3 | II-72 |
| T1s-24 | (S)-I-1 | II-3 | II-74 |
| T1s-25 | (S)-I-1 | II-3 | II-76 |
| T1s-26 | (S)-I-1 | II-3 | II-78 |
| T1s-27 | (S)-I-1 | II-3 | II-84 |
| T1s-28 | (S)-I-1 | II-3 | II-85 |
| T1s-29 | (S)-I-1 | II-3 | II-86 |
| T1s-30 | (S)-I-1 | II-3 | II-92 |
| T1s-31 | (S)-I-1 | II-5 | II-6 |
| T1s-32 | (S)-I-1 | II-5 | II-7 |
| T1s-33 | (S)-I-1 | II-5 | II-8 |
| T1s-34 | (S)-I-1 | II-5 | II-11 |
| T1s-35 | (S)-I-1 | II-5 | II-16 |
| T1s-36 | (S)-I-1 | II-5 | II-21 |
| T1s-37 | (S)-I-1 | II-5 | II-26 |
| T1s-38 | (S)-I-1 | II-5 | II-32 |
| T1s-39 | (S)-I-1 | II-5 | II-33 |
| T1s-40 | (S)-I-1 | II-5 | II-37 |
| T1s-41 | (S)-I-1 | II-5 | II-39 |
| T1s-42 | (S)-I-1 | II-5 | II-42 |
| T1s-43 | (S)-I-1 | II-5 | II-44 |
| T1s-44 | (S)-I-1 | II-5 | II-50 |
| T1s-45 | (S)-I-1 | II-5 | II-53 |
| T1s-46 | (S)-I-1 | II-5 | II-60 |
| T1s-47 | (S)-I-1 | II-5 | II-62 |
| T1s-48 | (S)-I-1 | II-5 | II-66 |
| T1s-49 | (S)-I-1 | II-5 | II-69 |
| T1s-50 | (S)-I-1 | II-5 | II-70 |
| T1s-51 | (S)-I-1 | II-5 | II-71 |
| T1s-52 | (S)-I-1 | II-5 | II-72 |
| T1s-53 | (S)-I-1 | II-5 | II-74 |
| T1s-54 | (S)-I-1 | II-5 | II-76 |
| T1s-55 | (S)-I-1 | II-5 | II-78 |
| T1s-56 | (S)-I-1 | II-5 | II-84 |
| T1s-57 | (S)-I-1 | II-5 | II-85 |
| T1s-58 | (S)-I-1 | II-5 | II-86 |
| T1s-59 | (S)-I-1 | II-5 | II-92 |
| T1s-60 | (S)-I-1 | II-6 | II-7 |
| T1s-61 | (S)-I-1 | II-6 | II-8 |
| T1s-62 | (S)-I-1 | II-6 | II-11 |
| T1s-63 | (S)-I-1 | II-6 | II-16 |
| T1s-64 | (S)-I-1 | II-6 | II-21 |
| T1s-65 | (S)-I-1 | II-6 | II-26 |
| T1s-66 | (S)-I-1 | II-6 | II-32 |
| T1s-67 | (S)-I-1 | II-6 | II-33 |
| T1s-68 | (S)-I-1 | II-6 | II-37 |
| T1s-69 | (S)-I-1 | II-6 | II-39 |
| T1s-70 | (S)-I-1 | II-6 | II-42 |
| T1s-71 | (S)-I-1 | II-6 | II-44 |
| T1s-72 | (S)-I-1 | II-6 | II-50 |
| T1s-73 | (S)-I-1 | II-6 | II-53 |
| T1s-74 | (S)-I-1 | II-6 | II-60 |
| T1s-75 | (S)-I-1 | II-6 | II-62 |
| T1s-76 | (S)-I-1 | II-6 | II-66 |
| T1s-77 | (S)-I-1 | II-6 | II-69 |
| T1s-78 | (S)-I-1 | II-6 | II-70 |
| T1s-79 | (S)-I-1 | II-6 | II-71 |
| T1s-80 | (S)-I-1 | II-6 | II-72 |
| T1s-81 | (S)-I-1 | II-6 | II-74 |
| T1s-82 | (S)-I-1 | II-6 | II-76 |
| T1s-83 | (S)-I-1 | II-6 | II-78 |
| T1s-84 | (S)-I-1 | II-6 | II-84 |
| T1s-85 | (S)-I-1 | II-6 | II-85 |
| T1s-86 | (S)-I-1 | II-6 | II-86 |
| T1s-87 | (S)-I-1 | II-6 | II-92 |
| T1s-88 | (S)-I-1 | II-7 | II-8 |
| T1s-89 | (S)-I-1 | II-7 | II-11 |
| T1s-90 | (S)-I-1 | II-7 | II-16 |
| T1s-91 | (S)-I-1 | II-7 | II-21 |

TABLE T1s-continued

Three-component compositions comprising one component I as (S) enantiomer (appreviated as (S)-I, e.g. (S)-I-1 for the (S)-enantiomer of I-1), one component II and one component III, in particular ternary compositions containing the respective component I as (S) enantiomer, II and III as only active ingredients.

| composition | (S)-I | II | III |
|---|---|---|---|
| T1s-92 | (S)-I-1 | II-7 | II-26 |
| T1s-93 | (S)-I-1 | II-7 | II-32 |
| T1s-94 | (S)-I-1 | II-7 | II-33 |
| T1s-95 | (S)-I-1 | II-7 | II-37 |
| T1s-96 | (S)-I-1 | II-7 | II-39 |
| T1s-97 | (S)-I-1 | II-7 | II-42 |
| T1s-98 | (S)-I-1 | II-7 | II-44 |
| T1s-99 | (S)-I-1 | II-7 | II-50 |
| T1s-100 | (S)-I-1 | II-7 | II-53 |
| T1s-101 | (S)-I-1 | II-7 | II-60 |
| T1s-102 | (S)-I-1 | II-7 | II-62 |
| T1s-103 | (S)-I-1 | II-7 | II-66 |
| T1s-104 | (S)-I-1 | II-7 | II-69 |
| T1s-105 | (S)-I-1 | II-7 | II-70 |
| T1s-106 | (S)-I-1 | II-7 | II-71 |
| T1s-107 | (S)-I-1 | II-7 | II-72 |
| T1s-108 | (S)-I-1 | II-7 | II-74 |
| T1s-109 | (S)-I-1 | II-7 | II-76 |
| T1s-110 | (S)-I-1 | II-7 | II-78 |
| T1s-111 | (S)-I-1 | II-7 | II-84 |
| T1s-112 | (S)-I-1 | II-7 | II-85 |
| T1s-113 | (S)-I-1 | II-7 | II-86 |
| T1s-114 | (S)-I-1 | II-7 | II-92 |
| T1s-115 | (S)-I-1 | II-8 | II-11 |
| T1s-116 | (S)-I-1 | II-8 | II-16 |
| T1s-117 | (S)-I-1 | II-8 | II-21 |
| T1s-118 | (S)-I-1 | II-8 | II-26 |
| T1s-119 | (S)-I-1 | II-8 | II-32 |
| T1s-120 | (S)-I-1 | II-8 | II-33 |
| T1s-121 | (S)-I-1 | II-8 | II-37 |
| T1s-122 | (S)-I-1 | II-8 | II-39 |
| T1s-123 | (S)-I-1 | II-8 | II-42 |
| T1s-124 | (S)-I-1 | II-8 | II-44 |
| T1s-125 | (S)-I-1 | II-8 | II-50 |
| T1s-126 | (S)-I-1 | II-8 | II-53 |
| T1s-127 | (S)-I-1 | II-8 | II-60 |
| T1s-128 | (S)-I-1 | II-8 | II-62 |
| T1s-129 | (S)-I-1 | II-8 | II-66 |
| T1s-130 | (S)-I-1 | II-8 | II-69 |
| T1s-131 | (S)-I-1 | II-8 | II-70 |
| T1s-132 | (S)-I-1 | II-8 | II-71 |
| T1s-133 | (S)-I-1 | II-8 | II-72 |
| T1s-134 | (S)-I-1 | II-8 | II-74 |
| T1s-135 | (S)-I-1 | II-8 | II-76 |
| T1s-136 | (S)-I-1 | II-8 | II-78 |
| T1s-137 | (S)-I-1 | II-8 | II-84 |
| T1s-138 | (S)-I-1 | II-8 | II-85 |
| T1s-139 | (S)-I-1 | II-8 | II-86 |
| T1s-140 | (S)-I-1 | II-8 | II-92 |
| T1s-141 | (S)-I-1 | II-11 | II-16 |
| T1s-142 | (S)-I-1 | II-11 | II-21 |
| T1s-143 | (S)-I-1 | II-11 | II-26 |
| T1s-144 | (S)-I-1 | II-11 | II-32 |
| T1s-145 | (S)-I-1 | II-11 | II-33 |
| T1s-146 | (S)-I-1 | II-11 | II-37 |
| T1s-147 | (S)-I-1 | II-11 | II-39 |
| T1s-148 | (S)-I-1 | II-11 | II-42 |
| T1s-149 | (S)-I-1 | II-11 | II-44 |
| T1s-150 | (S)-I-1 | II-11 | II-50 |
| T1s-151 | (S)-I-1 | II-11 | II-53 |
| T1s-152 | (S)-I-1 | II-11 | II-60 |
| T1s-153 | (S)-I-1 | II-11 | II-62 |
| T1s-154 | (S)-I-1 | II-11 | II-66 |
| T1s-155 | (S)-I-1 | II-11 | II-69 |
| T1s-156 | (S)-I-1 | II-11 | II-70 |
| T1s-157 | (S)-I-1 | II-11 | II-71 |
| T1s-158 | (S)-I-1 | II-11 | II-72 |
| T1s-159 | (S)-I-1 | II-11 | II-74 |
| T1s-160 | (S)-I-1 | II-11 | II-76 |
| T1s-161 | (S)-I-1 | II-11 | II-78 |
| T1s-162 | (S)-I-1 | II-11 | II-84 |
| T1s-163 | (S)-I-1 | II-11 | II-85 |
| T1s-164 | (S)-I-1 | II-11 | II-86 |
| T1s-165 | (S)-I-1 | II-11 | II-92 |
| T1s-166 | (S)-I-1 | II-16 | II-21 |
| T1s-167 | (S)-I-1 | II-16 | II-26 |
| T1s-168 | (S)-I-1 | II-16 | II-32 |
| T1s-169 | (S)-I-1 | II-16 | II-33 |
| T1s-170 | (S)-I-1 | II-16 | II-37 |
| T1s-171 | (S)-I-1 | II-16 | II-39 |
| T1s-172 | (S)-I-1 | II-16 | II-42 |
| T1s-173 | (S)-I-1 | II-16 | II-44 |
| T1s-174 | (S)-I-1 | II-16 | II-50 |
| T1s-175 | (S)-I-1 | II-16 | II-53 |
| T1s-176 | (S)-I-1 | II-16 | II-60 |
| T1s-177 | (S)-I-1 | II-16 | II-62 |
| T1s-178 | (S)-I-1 | II-16 | II-66 |
| T1s-179 | (S)-I-1 | II-16 | II-69 |
| T1s-180 | (S)-I-1 | II-16 | II-70 |
| T1s-181 | (S)-I-1 | II-16 | II-71 |
| T1s-182 | (S)-I-1 | II-16 | II-72 |
| T1s-183 | (S)-I-1 | II-16 | II-74 |
| T1s-184 | (S)-I-1 | II-16 | II-76 |
| T1s-185 | (S)-I-1 | II-16 | II-78 |
| T1s-186 | (S)-I-1 | II-16 | II-84 |
| T1s-187 | (S)-I-1 | II-16 | II-85 |
| T1s-188 | (S)-I-1 | II-16 | II-86 |
| T1s-189 | (S)-I-1 | II-16 | II-92 |
| T1s-190 | (S)-I-1 | II-21 | II-26 |
| T1s-191 | (S)-I-1 | II-21 | II-32 |
| T1s-192 | (S)-I-1 | II-21 | II-33 |
| T1s-193 | (S)-I-1 | II-21 | II-37 |
| T1s-194 | (S)-I-1 | II-21 | II-39 |
| T1s-195 | (S)-I-1 | II-21 | II-42 |
| T1s-196 | (S)-I-1 | II-21 | II-44 |
| T1s-197 | (S)-I-1 | II-21 | II-50 |
| T1s-198 | (S)-I-1 | II-21 | II-53 |
| T1s-199 | (S)-I-1 | II-21 | II-60 |
| T1s-200 | (S)-I-1 | II-21 | II-62 |
| T1s-201 | (S)-I-1 | II-21 | II-66 |
| T1s-202 | (S)-I-1 | II-21 | II-69 |
| T1s-203 | (S)-I-1 | II-21 | II-70 |
| T1s-204 | (S)-I-1 | II-21 | II-71 |
| T1s-205 | (S)-I-1 | II-21 | II-72 |
| T1s-206 | (S)-I-1 | II-21 | II-74 |
| T1s-207 | (S)-I-1 | II-21 | II-76 |
| T1s-208 | (S)-I-1 | II-21 | II-78 |
| T1s-209 | (S)-I-1 | II-21 | II-84 |
| T1s-210 | (S)-I-1 | II-21 | II-85 |
| T1s-211 | (S)-I-1 | II-21 | II-86 |
| T1s-212 | (S)-I-1 | II-21 | II-92 |
| T1s-213 | (S)-I-1 | II-26 | II-32 |
| T1s-214 | (S)-I-1 | II-26 | II-33 |
| T1s-215 | (S)-I-1 | II-26 | II-37 |
| T1s-216 | (S)-I-1 | II-26 | II-39 |
| T1s-217 | (S)-I-1 | II-26 | II-42 |
| T1s-218 | (S)-I-1 | II-26 | II-44 |
| T1s-219 | (S)-I-1 | II-26 | II-50 |
| T1s-220 | (S)-I-1 | II-26 | II-53 |
| T1s-221 | (S)-I-1 | II-26 | II-60 |
| T1s-222 | (S)-I-1 | II-26 | II-62 |
| T1s-223 | (S)-I-1 | II-26 | II-66 |
| T1s-224 | (S)-I-1 | II-26 | II-69 |
| T1s-225 | (S)-I-1 | II-26 | II-70 |
| T1s-226 | (S)-I-1 | II-26 | II-71 |
| T1s-227 | (S)-I-1 | II-26 | II-72 |
| T1s-228 | (S)-I-1 | II-26 | II-74 |
| T1s-229 | (S)-I-1 | II-26 | II-76 |
| T1s-230 | (S)-I-1 | II-26 | II-78 |
| T1s-231 | (S)-I-1 | II-26 | II-84 |
| T1s-232 | (S)-I-1 | II-26 | II-85 |
| T1s-233 | (S)-I-1 | II-26 | II-86 |
| T1s-234 | (S)-I-1 | II-26 | II-92 |
| T1s-235 | (S)-I-1 | II-32 | II-33 |

TABLE T1s-continued

Three-component compositions comprising one component I as (S) enantiomer (appreviated as (S)-I, e.g. (S)-I-1 for the (S)-enantiomer of I-1), one component II and one component III, in particular ternary compositions containing the respective component I as (S) enantiomer, II and III as only active ingredients.

| composition | (S)-I | II | III |
|---|---|---|---|
| T1s-236 | (S)-I-1 | II-32 | II-37 |
| T1s-237 | (S)-I-1 | II-32 | II-39 |
| T1s-238 | (S)-I-1 | II-32 | II-42 |
| T1s-239 | (S)-I-1 | II-32 | II-44 |
| T1s-240 | (S)-I-1 | II-32 | II-50 |
| T1s-241 | (S)-I-1 | II-32 | II-53 |
| T1s-242 | (S)-I-1 | II-32 | II-60 |
| T1s-243 | (S)-I-1 | II-32 | II-62 |
| T1s-244 | (S)-I-1 | II-32 | II-66 |
| T1s-245 | (S)-I-1 | II-32 | II-69 |
| T1s-246 | (S)-I-1 | II-32 | II-70 |
| T1s-247 | (S)-I-1 | II-32 | II-71 |
| T1s-248 | (S)-I-1 | II-32 | II-72 |
| T1s-249 | (S)-I-1 | II-32 | II-74 |
| T1s-250 | (S)-I-1 | II-32 | II-76 |
| T1s-251 | (S)-I-1 | II-32 | II-78 |
| T1s-252 | (S)-I-1 | II-32 | II-84 |
| T1s-253 | (S)-I-1 | II-32 | II-85 |
| T1s-254 | (S)-I-1 | II-32 | II-86 |
| T1s-255 | (S)-I-1 | II-32 | II-92 |
| T1s-256 | (S)-I-1 | II-33 | II-37 |
| T1s-257 | (S)-I-1 | II-33 | II-39 |
| T1s-258 | (S)-I-1 | II-33 | II-42 |
| T1s-259 | (S)-I-1 | II-33 | II-44 |
| T1s-260 | (S)-I-1 | II-33 | II-50 |
| T1s-261 | (S)-I-1 | II-33 | II-53 |
| T1s-262 | (S)-I-1 | II-33 | II-60 |
| T1s-263 | (S)-I-1 | II-33 | II-62 |
| T1s-264 | (S)-I-1 | II-33 | II-66 |
| T1s-265 | (S)-I-1 | II-33 | II-69 |
| T1s-266 | (S)-I-1 | II-33 | II-70 |
| T1s-267 | (S)-I-1 | II-33 | II-71 |
| T1s-268 | (S)-I-1 | II-33 | II-72 |
| T1s-269 | (S)-I-1 | II-33 | II-74 |
| T1s-270 | (S)-I-1 | II-33 | II-76 |
| T1s-271 | (S)-I-1 | II-33 | II-78 |
| T1s-272 | (S)-I-1 | II-33 | II-84 |
| T1s-273 | (S)-I-1 | II-33 | II-85 |
| T1s-274 | (S)-I-1 | II-33 | II-86 |
| T1s-275 | (S)-I-1 | II-33 | II-92 |
| T1s-276 | (S)-I-1 | II-37 | II-39 |
| T1s-277 | (S)-I-1 | II-37 | II-42 |
| T1s-278 | (S)-I-1 | II-37 | II-44 |
| T1s-279 | (S)-I-1 | II-37 | II-50 |
| T1s-280 | (S)-I-1 | II-37 | II-53 |
| T1s-281 | (S)-I-1 | II-37 | II-60 |
| T1s-282 | (S)-I-1 | II-37 | II-62 |
| T1s-283 | (S)-I-1 | II-37 | II-66 |
| T1s-284 | (S)-I-1 | II-37 | II-69 |
| T1s-285 | (S)-I-1 | II-37 | II-70 |
| T1s-286 | (S)-I-1 | II-37 | II-71 |
| T1s-287 | (S)-I-1 | II-37 | II-72 |
| T1s-288 | (S)-I-1 | II-37 | II-74 |
| T1s-289 | (S)-I-1 | II-37 | II-76 |
| T1s-290 | (S)-I-1 | II-37 | II-78 |
| T1s-291 | (S)-I-1 | II-37 | II-84 |
| T1s-292 | (S)-I-1 | II-37 | II-85 |
| T1s-293 | (S)-I-1 | II-37 | II-86 |
| T1s-294 | (S)-I-1 | II-37 | II-92 |
| T1s-295 | (S)-I-1 | II-39 | II-42 |
| T1s-296 | (S)-I-1 | II-39 | II-44 |
| T1s-297 | (S)-I-1 | II-39 | II-50 |
| T1s-298 | (S)-I-1 | II-39 | II-53 |
| T1s-299 | (S)-I-1 | II-39 | II-60 |
| T1s-300 | (S)-I-1 | II-39 | II-62 |
| T1s-301 | (S)-I-1 | II-39 | II-66 |
| T1s-302 | (S)-I-1 | II-39 | II-69 |
| T1s-303 | (S)-I-1 | II-39 | II-70 |
| T1s-304 | (S)-I-1 | II-39 | II-71 |
| T1s-305 | (S)-I-1 | II-39 | II-72 |
| T1s-306 | (S)-I-1 | II-39 | II-74 |
| T1s-307 | (S)-I-1 | II-39 | II-76 |
| T1s-308 | (S)-I-1 | II-39 | II-78 |
| T1s-309 | (S)-I-1 | II-39 | II-84 |
| T1s-310 | (S)-I-1 | II-39 | II-85 |
| T1s-311 | (S)-I-1 | II-39 | II-86 |
| T1s-312 | (S)-I-1 | II-39 | II-92 |
| T1s-313 | (S)-I-1 | II-42 | II-44 |
| T1s-314 | (S)-I-1 | II-42 | II-50 |
| T1s-315 | (S)-I-1 | II-42 | II-53 |
| T1s-316 | (S)-I-1 | II-42 | II-60 |
| T1s-317 | (S)-I-1 | II-42 | II-62 |
| T1s-318 | (S)-I-1 | II-42 | II-66 |
| T1s-319 | (S)-I-1 | II-42 | II-69 |
| T1s-320 | (S)-I-1 | II-42 | II-70 |
| T1s-321 | (S)-I-1 | II-42 | II-71 |
| T1s-322 | (S)-I-1 | II-42 | II-72 |
| T1s-323 | (S)-I-1 | II-42 | II-74 |
| T1s-324 | (S)-I-1 | II-42 | II-76 |
| T1s-325 | (S)-I-1 | II-42 | II-78 |
| T1s-326 | (S)-I-1 | II-42 | II-84 |
| T1s-327 | (S)-I-1 | II-42 | II-85 |
| T1s-328 | (S)-I-1 | II-42 | II-86 |
| T1s-329 | (S)-I-1 | II-42 | II-92 |
| T1s-330 | (S)-I-1 | II-44 | II-50 |
| T1s-331 | (S)-I-1 | II-44 | II-53 |
| T1s-332 | (S)-I-1 | II-44 | II-60 |
| T1s-333 | (S)-I-1 | II-44 | II-62 |
| T1s-334 | (S)-I-1 | II-44 | II-66 |
| T1s-335 | (S)-I-1 | II-44 | II-69 |
| T1s-336 | (S)-I-1 | II-44 | II-70 |
| T1s-337 | (S)-I-1 | II-44 | II-71 |
| T1s-338 | (S)-I-1 | II-44 | II-72 |
| T1s-339 | (S)-I-1 | II-44 | II-74 |
| T1s-340 | (S)-I-1 | II-44 | II-76 |
| T1s-341 | (S)-I-1 | II-44 | II-78 |
| T1s-342 | (S)-I-1 | II-44 | II-84 |
| T1s-343 | (S)-I-1 | II-44 | II-85 |
| T1s-344 | (S)-I-1 | II-44 | II-86 |
| T1s-345 | (S)-I-1 | II-44 | II-92 |
| T1s-346 | (S)-I-1 | II-50 | II-53 |
| T1s-347 | (S)-I-1 | II-50 | II-60 |
| T1s-348 | (S)-I-1 | II-50 | II-62 |
| T1s-349 | (S)-I-1 | II-50 | II-66 |
| T1s-350 | (S)-I-1 | II-50 | II-69 |
| T1s-351 | (S)-I-1 | II-50 | II-70 |
| T1s-352 | (S)-I-1 | II-50 | II-71 |
| T1s-353 | (S)-I-1 | II-50 | II-72 |
| T1s-354 | (S)-I-1 | II-50 | II-74 |
| T1s-355 | (S)-I-1 | II-50 | II-76 |
| T1s-356 | (S)-I-1 | II-50 | II-78 |
| T1s-357 | (S)-I-1 | II-50 | II-84 |
| T1s-358 | (S)-I-1 | II-50 | II-85 |
| T1s-359 | (S)-I-1 | II-50 | II-86 |
| T1s-360 | (S)-I-1 | II-50 | II-92 |
| T1s-361 | (S)-I-1 | II-53 | II-60 |
| T1s-362 | (S)-I-1 | II-53 | II-62 |
| T1s-363 | (S)-I-1 | II-53 | II-66 |
| T1s-364 | (S)-I-1 | II-53 | II-69 |
| T1s-365 | (S)-I-1 | II-53 | II-70 |
| T1s-366 | (S)-I-1 | II-53 | II-71 |
| T1s-367 | (S)-I-1 | II-53 | II-72 |
| T1s-368 | (S)-I-1 | II-53 | II-74 |
| T1s-369 | (S)-I-1 | II-53 | II-76 |
| T1s-370 | (S)-I-1 | II-53 | II-78 |
| T1s-371 | (S)-I-1 | II-53 | II-84 |
| T1s-372 | (S)-I-1 | II-53 | II-85 |
| T1s-373 | (S)-I-1 | II-53 | II-86 |
| T1s-374 | (S)-I-1 | II-53 | II-92 |
| T1s-375 | (S)-I-1 | II-60 | II-62 |
| T1s-376 | (S)-I-1 | II-60 | II-66 |
| T1s-377 | (S)-I-1 | II-60 | II-69 |
| T1s-378 | (S)-I-1 | II-60 | II-70 |
| T1s-379 | (S)-I-1 | II-60 | II-71 |

TABLE T1s-continued

Three-component compositions comprising one component I as (S) enantiomer (appreviated as (S)-I, e.g. (S)-I-1 for the (S)-enantiomer of I-1), one component II and one component III, in particular ternary compositions containing the respective component I as (S) enantiomer, II and III as only active ingredients.

| composition | (S)-I | II | III |
|---|---|---|---|
| T1s-380 | (S)-I-1 | II-60 | II-72 |
| T1s-381 | (S)-I-1 | II-60 | II-74 |
| T1s-382 | (S)-I-1 | II-60 | II-76 |
| T1s-383 | (S)-I-1 | II-60 | II-78 |
| T1s-384 | (S)-I-1 | II-60 | II-84 |
| T1s-385 | (S)-I-1 | II-60 | II-85 |
| T1s-386 | (S)-I-1 | II-60 | II-86 |
| T1s-387 | (S)-I-1 | II-60 | II-92 |
| T1s-388 | (S)-I-1 | II-62 | II-66 |
| T1s-389 | (S)-I-1 | II-62 | II-69 |
| T1s-390 | (S)-I-1 | II-62 | II-70 |
| T1s-391 | (S)-I-1 | II-62 | II-71 |
| T1s-392 | (S)-I-1 | II-62 | II-72 |
| T1s-393 | (S)-I-1 | II-62 | II-74 |
| T1s-394 | (S)-I-1 | II-62 | II-76 |
| T1s-395 | (S)-I-1 | II-62 | II-78 |
| T1s-396 | (S)-I-1 | II-62 | II-84 |
| T1s-397 | (S)-I-1 | II-62 | II-85 |
| T1s-398 | (S)-I-1 | II-62 | II-86 |
| T1s-399 | (S)-I-1 | II-62 | II-92 |
| T1s-400 | (S)-I-1 | II-66 | II-69 |
| T1s-401 | (S)-I-1 | II-66 | II-70 |
| T1s-402 | (S)-I-1 | II-66 | II-71 |
| T1s-403 | (S)-I-1 | II-66 | II-72 |
| T1s-404 | (S)-I-1 | II-66 | II-74 |
| T1s-405 | (S)-I-1 | II-66 | II-76 |
| T1s-406 | (S)-I-1 | II-66 | II-78 |
| T1s-407 | (S)-I-1 | II-66 | II-84 |
| T1s-408 | (S)-I-1 | II-66 | II-85 |
| T1s-409 | (S)-I-1 | II-66 | II-86 |
| T1s-410 | (S)-I-1 | II-66 | II-92 |
| T1s-411 | (S)-I-1 | II-69 | II-70 |
| T1s-412 | (S)-I-1 | II-69 | II-71 |
| T1s-413 | (S)-I-1 | II-69 | II-72 |
| T1s-414 | (S)-I-1 | II-69 | II-74 |
| T1s-415 | (S)-I-1 | II-69 | II-76 |
| T1s-416 | (S)-I-1 | II-69 | II-78 |
| T1s-417 | (S)-I-1 | II-69 | II-84 |
| T1s-418 | (S)-I-1 | II-69 | II-85 |
| T1s-419 | (S)-I-1 | II-69 | II-86 |
| T1s-420 | (S)-I-1 | II-69 | II-92 |
| T1s-421 | (S)-I-1 | II-70 | II-71 |
| T1s-422 | (S)-I-1 | II-70 | II-72 |
| T1s-423 | (S)-I-1 | II-70 | II-74 |
| T1s-424 | (S)-I-1 | II-70 | II-76 |
| T1s-425 | (S)-I-1 | II-70 | II-78 |
| T1s-426 | (S)-I-1 | II-70 | II-84 |
| T1s-427 | (S)-I-1 | II-70 | II-85 |
| T1s-428 | (S)-I-1 | II-70 | II-86 |
| T1s-429 | (S)-I-1 | II-70 | II-92 |
| T1s-430 | (S)-I-1 | II-71 | II-72 |
| T1s-431 | (S)-I-1 | II-71 | II-74 |
| T1s-432 | (S)-I-1 | II-71 | II-76 |
| T1s-433 | (S)-I-1 | II-71 | II-78 |
| T1s-434 | (S)-I-1 | II-71 | II-84 |
| T1s-435 | (S)-I-1 | II-71 | II-85 |
| T1s-436 | (S)-I-1 | II-71 | II-86 |
| T1s-437 | (S)-I-1 | II-71 | II-92 |
| T1s-438 | (S)-I-1 | II-72 | II-74 |
| T1s-439 | (S)-I-1 | II-74 | II-76 |
| T1s-440 | (S)-I-1 | II-74 | II-78 |
| T1s-441 | (S)-I-1 | II-74 | II-84 |
| T1s-442 | (S)-I-1 | II-74 | II-85 |
| T1s-443 | (S)-I-1 | II-74 | II-86 |
| T1s-444 | (S)-I-1 | II-74 | II-92 |
| T1s-445 | (S)-I-1 | II-76 | II-78 |
| T1s-446 | (S)-I-1 | II-76 | II-84 |
| T1s-447 | (S)-I-1 | II-76 | II-85 |
| T1s-448 | (S)-I-1 | II-76 | II-86 |
| T1s-449 | (S)-I-1 | II-76 | II-92 |
| T1s-450 | (S)-I-1 | II-78 | II-84 |
| T1s-451 | (S)-I-1 | II-78 | II-85 |
| T1s-452 | (S)-I-1 | II-78 | II-86 |
| T1s-453 | (S)-I-1 | II-78 | II-92 |
| T1s-454 | (S)-I-1 | II-84 | II-85 |
| T1s-455 | (S)-I-1 | II-84 | II-86 |
| T1s-456 | (S)-I-1 | II-84 | II-92 |
| T1s-457 | (S)-I-1 | II-85 | II-86 |
| T1s-458 | (S)-I-1 | II-85 | II-92 |
| T1s-459 | (S)-I-1 | II-86 | II-92 |
| T1s-460 | (S)-I-5 | II-3 | II-5 |
| T1s-461 | (S)-I-5 | II-3 | II-6 |
| T1s-462 | (S)-I-5 | II-3 | II-7 |
| T1s-463 | (S)-I-5 | II-3 | II-8 |
| T1s-464 | (S)-I-5 | II-3 | II-11 |
| T1s-465 | (S)-I-5 | II-3 | II-16 |
| T1s-466 | (S)-I-5 | II-3 | II-21 |
| T1s-467 | (S)-I-5 | II-3 | II-26 |
| T1s-468 | (S)-I-5 | II-3 | II-32 |
| T1s-469 | (S)-I-5 | II-3 | II-33 |
| T1s-470 | (S)-I-5 | II-3 | II-37 |
| T1s-471 | (S)-I-5 | II-3 | II-39 |
| T1s-472 | (S)-I-5 | II-3 | II-42 |
| T1s-473 | (S)-I-5 | II-3 | II-44 |
| T1s-474 | (S)-I-5 | II-3 | II-50 |
| T1s-475 | (S)-I-5 | II-3 | II-53 |
| T1s-476 | (S)-I-5 | II-3 | II-60 |
| T1s-477 | (S)-I-5 | II-3 | II-62 |
| T1s-478 | (S)-I-5 | II-3 | II-66 |
| T1s-479 | (S)-I-5 | II-3 | II-69 |
| T1s-480 | (S)-I-5 | II-3 | II-70 |
| T1s-481 | (S)-I-5 | II-3 | II-71 |
| T1s-482 | (S)-I-5 | II-3 | II-72 |
| T1s-483 | (S)-I-5 | II-3 | II-74 |
| T1s-484 | (S)-I-5 | II-3 | II-76 |
| T1s-485 | (S)-I-5 | II-3 | II-78 |
| T1s-486 | (S)-I-5 | II-3 | II-84 |
| T1s-487 | (S)-I-5 | II-3 | II-85 |
| T1s-488 | (S)-I-5 | II-3 | II-86 |
| T1s-489 | (S)-I-5 | II-3 | II-92 |
| T1s-490 | (S)-I-5 | II-5 | II-6 |
| T1s-491 | (S)-I-5 | II-5 | II-7 |
| T1s-492 | (S)-I-5 | II-5 | II-8 |
| T1s-493 | (S)-I-5 | II-5 | II-11 |
| T1s-494 | (S)-I-5 | II-5 | II-16 |
| T1s-495 | (S)-I-5 | II-5 | II-21 |
| T1s-496 | (S)-I-5 | II-5 | II-26 |
| T1s-497 | (S)-I-5 | II-5 | II-32 |
| T1s-498 | (S)-I-5 | II-5 | II-33 |
| T1s-499 | (S)-I-5 | II-5 | II-37 |
| T1s-500 | (S)-I-5 | II-5 | II-39 |
| T1s-501 | (S)-I-5 | II-5 | II-42 |
| T1s-502 | (S)-I-5 | II-5 | II-44 |
| T1s-503 | (S)-I-5 | II-5 | II-50 |
| T1s-504 | (S)-I-5 | II-5 | II-53 |
| T1s-505 | (S)-I-5 | II-5 | II-60 |
| T1s-506 | (S)-I-5 | II-5 | II-62 |
| T1s-507 | (S)-I-5 | II-5 | II-66 |
| T1s-508 | (S)-I-5 | II-5 | II-69 |
| T1s-509 | (S)-I-5 | II-5 | II-70 |
| T1s-510 | (S)-I-5 | II-5 | II-71 |
| T1s-511 | (S)-I-5 | II-5 | II-72 |
| T1s-512 | (S)-I-5 | II-5 | II-74 |
| T1s-513 | (S)-I-5 | II-5 | II-76 |
| T1s-514 | (S)-I-5 | II-5 | II-78 |
| T1s-515 | (S)-I-5 | II-5 | II-84 |
| T1s-516 | (S)-I-5 | II-5 | II-85 |
| T1s-517 | (S)-I-5 | II-5 | II-86 |
| T1s-518 | (S)-I-5 | II-5 | II-92 |
| T1s-519 | (S)-I-5 | II-6 | II-7 |
| T1s-520 | (S)-I-5 | II-6 | II-8 |
| T1s-521 | (S)-I-5 | II-6 | II-11 |
| T1s-522 | (S)-I-5 | II-6 | II-16 |
| T1s-523 | (S)-I-5 | II-6 | II-21 |

TABLE T1s-continued

Three-component compositions comprising one component I as (S) enantiomer (appreviated as (S)-I, e.g. (S)-I-1 for the (S)-enantiomer of I-1), one component II and one component III, in particular ternary compositions containing the respective component I as (S) enantiomer, II and III as only active ingredients.

| composition | (S)-I | II | III |
|---|---|---|---|
| T1s-524 | (S)-I-5 | II-6 | II-26 |
| T1s-525 | (S)-I-5 | II-6 | II-32 |
| T1s-526 | (S)-I-5 | II-6 | II-33 |
| T1s-527 | (S)-I-5 | II-6 | II-37 |
| T1s-528 | (S)-I-5 | II-6 | II-39 |
| T1s-529 | (S)-I-5 | II-6 | II-42 |
| T1s-530 | (S)-I-5 | II-6 | II-44 |
| T1s-531 | (S)-I-5 | II-6 | II-50 |
| T1s-532 | (S)-I-5 | II-6 | II-53 |
| T1s-533 | (S)-I-5 | II-6 | II-60 |
| T1s-534 | (S)-I-5 | II-6 | II-62 |
| T1s-535 | (S)-I-5 | II-6 | II-66 |
| T1s-536 | (S)-I-5 | II-6 | II-69 |
| T1s-537 | (S)-I-5 | II-6 | II-70 |
| T1s-538 | (S)-I-5 | II-6 | II-71 |
| T1s-539 | (S)-I-5 | II-6 | II-72 |
| T1s-540 | (S)-I-5 | II-6 | II-74 |
| T1s-541 | (S)-I-5 | II-6 | II-76 |
| T1s-542 | (S)-I-5 | II-6 | II-78 |
| T1s-543 | (S)-I-5 | II-6 | II-84 |
| T1s-544 | (S)-I-5 | II-6 | II-85 |
| T1s-545 | (S)-I-5 | II-6 | II-86 |
| T1s-546 | (S)-I-5 | II-6 | II-92 |
| T1s-547 | (S)-I-5 | II-7 | II-8 |
| T1s-548 | (S)-I-5 | II-7 | II-11 |
| T1s-549 | (S)-I-5 | II-7 | II-16 |
| T1s-550 | (S)-I-5 | II-7 | II-21 |
| T1s-551 | (S)-I-5 | II-7 | II-26 |
| T1s-552 | (S)-I-5 | II-7 | II-32 |
| T1s-553 | (S)-I-5 | II-7 | II-33 |
| T1s-554 | (S)-I-5 | II-7 | II-37 |
| T1s-555 | (S)-I-5 | II-7 | II-39 |
| T1s-556 | (S)-I-5 | II-7 | II-42 |
| T1s-557 | (S)-I-5 | II-7 | II-44 |
| T1s-558 | (S)-I-5 | II-7 | II-50 |
| T1s-559 | (S)-I-5 | II-7 | II-53 |
| T1s-560 | (S)-I-5 | II-7 | II-60 |
| T1s-561 | (S)-I-5 | II-7 | II-62 |
| T1s-562 | (S)-I-5 | II-7 | II-66 |
| T1s-563 | (S)-I-5 | II-7 | II-69 |
| T1s-564 | (S)-I-5 | II-7 | II-70 |
| T1s-565 | (S)-I-5 | II-7 | II-71 |
| T1s-566 | (S)-I-5 | II-7 | II-72 |
| T1s-567 | (S)-I-5 | II-7 | II-74 |
| T1s-568 | (S)-I-5 | II-7 | II-76 |
| T1s-569 | (S)-I-5 | II-7 | II-78 |
| T1s-570 | (S)-I-5 | II-7 | II-84 |
| T1s-571 | (S)-I-5 | II-7 | II-85 |
| T1s-572 | (S)-I-5 | II-7 | II-86 |
| T1s-573 | (S)-I-5 | II-7 | II-92 |
| T1s-574 | (S)-I-5 | II-8 | II-11 |
| T1s-575 | (S)-I-5 | II-8 | II-16 |
| T1s-576 | (S)-I-5 | II-8 | II-21 |
| T1s-577 | (S)-I-5 | II-8 | II-26 |
| T1s-578 | (S)-I-5 | II-8 | II-32 |
| T1s-579 | (S)-I-5 | II-8 | II-33 |
| T1s-580 | (S)-I-5 | II-8 | II-37 |
| T1s-581 | (S)-I-5 | II-8 | II-39 |
| T1s-582 | (S)-I-5 | II-8 | II-42 |
| T1s-583 | (S)-I-5 | II-8 | II-44 |
| T1s-584 | (S)-I-5 | II-8 | II-50 |
| T1s-585 | (S)-I-5 | II-8 | II-53 |
| T1s-586 | (S)-I-5 | II-8 | II-60 |
| T1s-587 | (S)-I-5 | II-8 | II-62 |
| T1s-588 | (S)-I-5 | II-8 | II-66 |
| T1s-589 | (S)-I-5 | II-8 | II-69 |
| T1s-590 | (S)-I-5 | II-8 | II-70 |
| T1s-591 | (S)-I-5 | II-8 | II-71 |
| T1s-592 | (S)-I-5 | II-8 | II-72 |
| T1s-593 | (S)-I-5 | II-8 | II-74 |
| T1s-594 | (S)-I-5 | II-8 | II-76 |
| T1s-595 | (S)-I-5 | II-8 | II-78 |
| T1s-596 | (S)-I-5 | II-8 | II-84 |
| T1s-597 | (S)-I-5 | II-8 | II-85 |
| T1s-598 | (S)-I-5 | II-8 | II-86 |
| T1s-599 | (S)-I-5 | II-8 | II-92 |
| T1s-600 | (S)-I-5 | II-11 | II-16 |
| T1s-601 | (S)-I-5 | II-11 | II-21 |
| T1s-602 | (S)-I-5 | II-11 | II-26 |
| T1s-603 | (S)-I-5 | II-11 | II-32 |
| T1s-604 | (S)-I-5 | II-11 | II-33 |
| T1s-605 | (S)-I-5 | II-11 | II-37 |
| T1s-606 | (S)-I-5 | II-11 | II-39 |
| T1s-607 | (S)-I-5 | II-11 | II-42 |
| T1s-608 | (S)-I-5 | II-11 | II-44 |
| T1s-609 | (S)-I-5 | II-11 | II-50 |
| T1s-610 | (S)-I-5 | II-11 | II-53 |
| T1s-611 | (S)-I-5 | II-11 | II-60 |
| T1s-612 | (S)-I-5 | II-11 | II-62 |
| T1s-613 | (S)-I-5 | II-11 | II-66 |
| T1s-614 | (S)-I-5 | II-11 | II-69 |
| T1s-615 | (S)-I-5 | II-11 | II-70 |
| T1s-616 | (S)-I-5 | II-11 | II-71 |
| T1s-617 | (S)-I-5 | II-11 | II-72 |
| T1s-618 | (S)-I-5 | II-11 | II-74 |
| T1s-619 | (S)-I-5 | II-11 | II-76 |
| T1s-620 | (S)-I-5 | II-11 | II-78 |
| T1s-621 | (S)-I-5 | II-11 | II-84 |
| T1s-622 | (S)-I-5 | II-11 | II-85 |
| T1s-623 | (S)-I-5 | II-11 | II-86 |
| T1s-624 | (S)-I-5 | II-11 | II-92 |
| T1s-625 | (S)-I-5 | II-16 | II-21 |
| T1s-626 | (S)-I-5 | II-16 | II-26 |
| T1s-627 | (S)-I-5 | II-16 | II-32 |
| T1s-628 | (S)-I-5 | II-16 | II-33 |
| T1s-629 | (S)-I-5 | II-16 | II-37 |
| T1s-630 | (S)-I-5 | II-16 | II-39 |
| T1s-631 | (S)-I-5 | II-16 | II-42 |
| T1s-632 | (S)-I-5 | II-16 | II-44 |
| T1s-633 | (S)-I-5 | II-16 | II-50 |
| T1s-634 | (S)-I-5 | II-16 | II-53 |
| T1s-635 | (S)-I-5 | II-16 | II-60 |
| T1s-636 | (S)-I-5 | II-16 | II-62 |
| T1s-637 | (S)-I-5 | II-16 | II-66 |
| T1s-638 | (S)-I-5 | II-16 | II-69 |
| T1s-639 | (S)-I-5 | II-16 | II-70 |
| T1s-640 | (S)-I-5 | II-16 | II-71 |
| T1s-641 | (S)-I-5 | II-16 | II-72 |
| T1s-642 | (S)-I-5 | II-16 | II-74 |
| T1s-643 | (S)-I-5 | II-16 | II-76 |
| T1s-644 | (S)-I-5 | II-16 | II-78 |
| T1s-645 | (S)-I-5 | II-16 | II-84 |
| T1s-646 | (S)-I-5 | II-16 | II-85 |
| T1s-647 | (S)-I-5 | II-16 | II-86 |
| T1s-648 | (S)-I-5 | II-16 | II-92 |
| T1s-649 | (S)-I-5 | II-21 | II-26 |
| T1s-650 | (S)-I-5 | II-21 | II-32 |
| T1s-651 | (S)-I-5 | II-21 | II-33 |
| T1s-652 | (S)-I-5 | II-21 | II-37 |
| T1s-653 | (S)-I-5 | II-21 | II-39 |
| T1s-654 | (S)-I-5 | II-21 | II-42 |
| T1s-655 | (S)-I-5 | II-21 | II-44 |
| T1s-656 | (S)-I-5 | II-21 | II-50 |
| T1s-657 | (S)-I-5 | II-21 | II-53 |
| T1s-658 | (S)-I-5 | II-21 | II-60 |
| T1s-659 | (S)-I-5 | II-21 | II-62 |
| T1s-660 | (S)-I-5 | II-21 | II-66 |
| T1s-661 | (S)-I-5 | II-21 | II-69 |
| T1s-662 | (S)-I-5 | II-21 | II-70 |
| T1s-663 | (S)-I-5 | II-21 | II-71 |
| T1s-664 | (S)-I-5 | II-21 | II-72 |
| T1s-665 | (S)-I-5 | II-21 | II-74 |
| T1s-666 | (S)-I-5 | II-21 | II-76 |
| T1s-667 | (S)-I-5 | II-21 | II-78 |

TABLE T1s-continued

Three-component compositions comprising one component I as (S) enantiomer (appreviated as (S)-I, e.g. (S)-I-1 for the (S)-enantiomer of I-1), one component II and one component III, in particular ternary compositions containing the respective component I as (S) enantiomer, II and III as only active ingredients.

| composition | (S)-I | II | III |
|---|---|---|---|
| T1s-668 | (S)-I-5 | II-21 | II-84 |
| T1s-669 | (S)-I-5 | II-21 | II-85 |
| T1s-670 | (S)-I-5 | II-21 | II-86 |
| T1s-671 | (S)-I-5 | II-21 | II-92 |
| T1s-672 | (S)-I-5 | II-26 | II-32 |
| T1s-673 | (S)-I-5 | II-26 | II-33 |
| T1s-674 | (S)-I-5 | II-26 | II-37 |
| T1s-675 | (S)-I-5 | II-26 | II-39 |
| T1s-676 | (S)-I-5 | II-26 | II-42 |
| T1s-677 | (S)-I-5 | II-26 | II-44 |
| T1s-678 | (S)-I-5 | II-26 | II-50 |
| T1s-679 | (S)-I-5 | II-26 | II-53 |
| T1s-680 | (S)-I-5 | II-26 | II-60 |
| T1s-681 | (S)-I-5 | II-26 | II-62 |
| T1s-682 | (S)-I-5 | II-26 | II-66 |
| T1s-683 | (S)-I-5 | II-26 | II-69 |
| T1s-684 | (S)-I-5 | II-26 | II-70 |
| T1s-685 | (S)-I-5 | II-26 | II-71 |
| T1s-686 | (S)-I-5 | II-26 | II-72 |
| T1s-687 | (S)-I-5 | II-26 | II-74 |
| T1s-688 | (S)-I-5 | II-26 | II-76 |
| T1s-689 | (S)-I-5 | II-26 | II-78 |
| T1s-690 | (S)-I-5 | II-26 | II-84 |
| T1s-691 | (S)-I-5 | II-26 | II-85 |
| T1s-692 | (S)-I-5 | II-26 | II-86 |
| T1s-693 | (S)-I-5 | II-26 | II-92 |
| T1s-694 | (S)-I-5 | II-32 | II-33 |
| T1s-695 | (S)-I-5 | II-32 | II-37 |
| T1s-696 | (S)-I-5 | II-32 | II-39 |
| T1s-697 | (S)-I-5 | II-32 | II-42 |
| T1s-698 | (S)-I-5 | II-32 | II-44 |
| T1s-699 | (S)-I-5 | II-32 | II-50 |
| T1s-700 | (S)-I-5 | II-32 | II-53 |
| T1s-701 | (S)-I-5 | II-32 | II-60 |
| T1s-702 | (S)-I-5 | II-32 | II-62 |
| T1s-703 | (S)-I-5 | II-32 | II-66 |
| T1s-704 | (S)-I-5 | II-32 | II-69 |
| T1s-705 | (S)-I-5 | II-32 | II-70 |
| T1s-706 | (S)-I-5 | II-32 | II-71 |
| T1s-707 | (S)-I-5 | II-32 | II-72 |
| T1s-708 | (S)-I-5 | II-32 | II-74 |
| T1s-709 | (S)-I-5 | II-32 | II-76 |
| T1s-710 | (S)-I-5 | II-32 | II-78 |
| T1s-711 | (S)-I-5 | II-32 | II-84 |
| T1s-712 | (S)-I-5 | II-32 | II-85 |
| T1s-713 | (S)-I-5 | II-32 | II-86 |
| T1s-714 | (S)-I-5 | II-32 | II-92 |
| T1s-715 | (S)-I-5 | II-33 | II-37 |
| T1s-716 | (S)-I-5 | II-33 | II-39 |
| T1s-717 | (S)-I-5 | II-33 | II-42 |
| T1s-718 | (S)-I-5 | II-33 | II-44 |
| T1s-719 | (S)-I-5 | II-33 | II-50 |
| T1s-720 | (S)-I-5 | II-33 | II-53 |
| T1s-721 | (S)-I-5 | II-33 | II-60 |
| T1s-722 | (S)-I-5 | II-33 | II-62 |
| T1s-723 | (S)-I-5 | II-33 | II-66 |
| T1s-724 | (S)-I-5 | II-33 | II-69 |
| T1s-725 | (S)-I-5 | II-33 | II-70 |
| T1s-726 | (S)-I-5 | II-33 | II-71 |
| T1s-727 | (S)-I-5 | II-33 | II-72 |
| T1s-728 | (S)-I-5 | II-33 | II-74 |
| T1s-729 | (S)-I-5 | II-33 | II-76 |
| T1s-730 | (S)-I-5 | II-33 | II-78 |
| T1s-731 | (S)-I-5 | II-33 | II-84 |
| T1s-732 | (S)-I-5 | II-33 | II-85 |
| T1s-733 | (S)-I-5 | II-33 | II-86 |
| T1s-734 | (S)-I-5 | II-33 | II-92 |
| T1s-735 | (S)-I-5 | II-37 | II-39 |
| T1s-736 | (S)-I-5 | II-37 | II-42 |
| T1s-737 | (S)-I-5 | II-37 | II-44 |
| T1s-738 | (S)-I-5 | II-37 | II-50 |
| T1s-739 | (S)-I-5 | II-37 | II-53 |
| T1s-740 | (S)-I-5 | II-37 | II-60 |
| T1s-741 | (S)-I-5 | II-37 | II-62 |
| T1s-742 | (S)-I-5 | II-37 | II-66 |
| T1s-743 | (S)-I-5 | II-37 | II-69 |
| T1s-744 | (S)-I-5 | II-37 | II-70 |
| T1s-745 | (S)-I-5 | II-37 | II-71 |
| T1s-746 | (S)-I-5 | II-37 | II-72 |
| T1s-747 | (S)-I-5 | II-37 | II-74 |
| T1s-748 | (S)-I-5 | II-37 | II-76 |
| T1s-749 | (S)-I-5 | II-37 | II-78 |
| T1s-750 | (S)-I-5 | II-37 | II-84 |
| T1s-751 | (S)-I-5 | II-37 | II-85 |
| T1s-752 | (S)-I-5 | II-37 | II-86 |
| T1s-753 | (S)-I-5 | II-37 | II-92 |
| T1s-754 | (S)-I-5 | II-39 | II-42 |
| T1s-755 | (S)-I-5 | II-39 | II-44 |
| T1s-756 | (S)-I-5 | II-39 | II-50 |
| T1s-757 | (S)-I-5 | II-39 | II-53 |
| T1s-758 | (S)-I-5 | II-39 | II-60 |
| T1s-759 | (S)-I-5 | II-39 | II-62 |
| T1s-760 | (S)-I-5 | II-39 | II-66 |
| T1s-761 | (S)-I-5 | II-39 | II-69 |
| T1s-762 | (S)-I-5 | II-39 | II-70 |
| T1s-763 | (S)-I-5 | II-39 | II-71 |
| T1s-764 | (S)-I-5 | II-39 | II-72 |
| T1s-765 | (S)-I-5 | II-39 | II-74 |
| T1s-766 | (S)-I-5 | II-39 | II-76 |
| T1s-767 | (S)-I-5 | II-39 | II-78 |
| T1s-768 | (S)-I-5 | II-39 | II-84 |
| T1s-769 | (S)-I-5 | II-39 | II-85 |
| T1s-770 | (S)-I-5 | II-39 | II-86 |
| T1s-771 | (S)-I-5 | II-39 | II-92 |
| T1s-772 | (S)-I-5 | II-42 | II-44 |
| T1s-773 | (S)-I-5 | II-42 | II-50 |
| T1s-774 | (S)-I-5 | II-42 | II-53 |
| T1s-775 | (S)-I-5 | II-42 | II-60 |
| T1s-776 | (S)-I-5 | II-42 | II-62 |
| T1s-777 | (S)-I-5 | II-42 | II-66 |
| T1s-778 | (S)-I-5 | II-42 | II-69 |
| T1s-779 | (S)-I-5 | II-42 | II-70 |
| T1s-780 | (S)-I-5 | II-42 | II-71 |
| T1s-781 | (S)-I-5 | II-42 | II-72 |
| T1s-782 | (S)-I-5 | II-42 | II-74 |
| T1s-783 | (S)-I-5 | II-42 | II-76 |
| T1s-784 | (S)-I-5 | II-42 | II-78 |
| T1s-785 | (S)-I-5 | II-42 | II-84 |
| T1s-786 | (S)-I-5 | II-42 | II-85 |
| T1s-787 | (S)-I-5 | II-42 | II-86 |
| T1s-788 | (S)-I-5 | II-42 | II-92 |
| T1s-789 | (S)-I-5 | II-44 | II-50 |
| T1s-790 | (S)-I-5 | II-44 | II-53 |
| T1s-791 | (S)-I-5 | II-44 | II-60 |
| T1s-792 | (S)-I-5 | II-44 | II-62 |
| T1s-793 | (S)-I-5 | II-44 | II-66 |
| T1s-794 | (S)-I-5 | II-44 | II-69 |
| T1s-795 | (S)-I-5 | II-44 | II-70 |
| T1s-796 | (S)-I-5 | II-44 | II-71 |
| T1s-797 | (S)-I-5 | II-44 | II-72 |
| T1s-798 | (S)-I-5 | II-44 | II-74 |
| T1s-799 | (S)-I-5 | II-44 | II-76 |
| T1s-800 | (S)-I-5 | II-44 | II-78 |
| T1s-801 | (S)-I-5 | II-44 | II-84 |
| T1s-802 | (S)-I-5 | II-44 | II-85 |
| T1s-803 | (S)-I-5 | II-44 | II-86 |
| T1s-804 | (S)-I-5 | II-44 | II-92 |
| T1s-805 | (S)-I-5 | II-50 | II-53 |
| T1s-806 | (S)-I-5 | II-50 | II-60 |
| T1s-807 | (S)-I-5 | II-50 | II-62 |
| T1s-808 | (S)-I-5 | II-50 | II-66 |
| T1s-809 | (S)-I-5 | II-50 | II-69 |
| T1s-810 | (S)-I-5 | II-50 | II-70 |
| T1s-811 | (S)-I-5 | II-50 | II-71 |

TABLE T1s-continued

Three-component compositions comprising one component I as (S) enantiomer (appreviated as (S)-I, e.g. (S)-I-1 for the (S)-enantiomer of I-1), one component II and one component III, in particular ternary compositions containing the respective component I as (S) enantiomer, II and III as only active ingredients.

| composition | (S)-I | II | III |
|---|---|---|---|
| T1s-812 | (S)-I-5 | II-50 | II-72 |
| T1s-813 | (S)-I-5 | II-50 | II-74 |
| T1s-814 | (S)-I-5 | II-50 | II-76 |
| T1s-815 | (S)-I-5 | II-50 | II-78 |
| T1s-816 | (S)-I-5 | II-50 | II-84 |
| T1s-817 | (S)-I-5 | II-50 | II-85 |
| T1s-818 | (S)-I-5 | II-50 | II-86 |
| T1s-819 | (S)-I-5 | II-50 | II-92 |
| T1s-820 | (S)-I-5 | II-53 | II-60 |
| T1s-821 | (S)-I-5 | II-53 | II-62 |
| T1s-822 | (S)-I-5 | II-53 | II-66 |
| T1s-823 | (S)-I-5 | II-53 | II-69 |
| T1s-824 | (S)-I-5 | II-53 | II-70 |
| T1s-825 | (S)-I-5 | II-53 | II-71 |
| T1s-826 | (S)-I-5 | II-53 | II-72 |
| T1s-827 | (S)-I-5 | II-53 | II-74 |
| T1s-828 | (S)-I-5 | II-53 | II-76 |
| T1s-829 | (S)-I-5 | II-53 | II-78 |
| T1s-830 | (S)-I-5 | II-53 | II-84 |
| T1s-831 | (S)-I-5 | II-53 | II-85 |
| T1s-832 | (S)-I-5 | II-53 | II-86 |
| T1s-833 | (S)-I-5 | II-53 | II-92 |
| T1s-834 | (S)-I-5 | II-60 | II-62 |
| T1s-835 | (S)-I-5 | II-60 | II-66 |
| T1s-836 | (S)-I-5 | II-60 | II-69 |
| T1s-837 | (S)-I-5 | II-60 | II-70 |
| T1s-838 | (S)-I-5 | II-60 | II-71 |
| T1s-839 | (S)-I-5 | II-60 | II-72 |
| T1s-840 | (S)-I-5 | II-60 | II-74 |
| T1s-841 | (S)-I-5 | II-60 | II-76 |
| T1s-842 | (S)-I-5 | II-60 | II-78 |
| T1s-843 | (S)-I-5 | II-60 | II-84 |
| T1s-844 | (S)-I-5 | II-60 | II-85 |
| T1s-845 | (S)-I-5 | II-60 | II-86 |
| T1s-846 | (S)-I-5 | II-60 | II-92 |
| T1s-847 | (S)-I-5 | II-62 | II-66 |
| T1s-848 | (S)-I-5 | II-62 | II-69 |
| T1s-849 | (S)-I-5 | II-62 | II-70 |
| T1s-850 | (S)-I-5 | II-62 | II-71 |
| T1s-851 | (S)-I-5 | II-62 | II-72 |
| T1s-852 | (S)-I-5 | II-62 | II-74 |
| T1s-853 | (S)-I-5 | II-62 | II-76 |
| T1s-854 | (S)-I-5 | II-62 | II-78 |
| T1s-855 | (S)-I-5 | II-62 | II-84 |
| T1s-856 | (S)-I-5 | II-62 | II-85 |
| T1s-857 | (S)-I-5 | II-62 | II-86 |
| T1s-858 | (S)-I-5 | II-62 | II-92 |
| T1s-859 | (S)-I-5 | II-66 | II-69 |
| T1s-860 | (S)-I-5 | II-66 | II-70 |
| T1s-861 | (S)-I-5 | II-66 | II-71 |
| T1s-862 | (S)-I-5 | II-66 | II-72 |
| T1s-863 | (S)-I-5 | II-66 | II-74 |
| T1s-864 | (S)-I-5 | II-66 | II-76 |
| T1s-865 | (S)-I-5 | II-66 | II-78 |
| T1s-866 | (S)-I-5 | II-66 | II-84 |
| T1s-867 | (S)-I-5 | II-66 | II-85 |
| T1s-868 | (S)-I-5 | II-66 | II-86 |
| T1s-869 | (S)-I-5 | II-66 | II-92 |
| T1s-870 | (S)-I-5 | II-69 | II-70 |
| T1s-871 | (S)-I-5 | II-69 | II-71 |
| T1s-872 | (S)-I-5 | II-69 | II-72 |
| T1s-873 | (S)-I-5 | II-69 | II-74 |
| T1s-874 | (S)-I-5 | II-69 | II-76 |
| T1s-875 | (S)-I-5 | II-69 | II-78 |
| T1s-876 | (S)-I-5 | II-69 | II-84 |
| T1s-877 | (S)-I-5 | II-69 | II-85 |
| T1s-878 | (S)-I-5 | II-69 | II-86 |
| T1s-879 | (S)-I-5 | II-69 | II-92 |
| T1s-880 | (S)-I-5 | II-70 | II-71 |
| T1s-881 | (S)-I-5 | II-70 | II-72 |
| T1s-882 | (S)-I-5 | II-70 | II-74 |
| T1s-883 | (S)-I-5 | II-70 | II-76 |
| T1s-884 | (S)-I-5 | II-70 | II-78 |
| T1s-885 | (S)-I-5 | II-70 | II-84 |
| T1s-886 | (S)-I-5 | II-70 | II-85 |
| T1s-887 | (S)-I-5 | II-70 | II-86 |
| T1s-888 | (S)-I-5 | II-70 | II-92 |
| T1s-889 | (S)-I-5 | II-71 | II-72 |
| T1s-890 | (S)-I-5 | II-71 | II-74 |
| T1s-891 | (S)-I-5 | II-71 | II-76 |
| T1s-892 | (S)-I-5 | II-71 | II-78 |
| T1s-893 | (S)-I-5 | II-71 | II-84 |
| T1s-894 | (S)-I-5 | II-71 | II-85 |
| T1s-895 | (S)-I-5 | II-71 | II-86 |
| T1s-896 | (S)-I-5 | II-71 | II-92 |
| T1s-897 | (S)-I-5 | II-72 | II-74 |
| T1s-898 | (S)-I-5 | II-74 | II-76 |
| T1s-899 | (S)-I-5 | II-74 | II-78 |
| T1s-900 | (S)-I-5 | II-74 | II-84 |
| T1s-901 | (S)-I-5 | II-74 | II-85 |
| T1s-902 | (S)-I-5 | II-74 | II-86 |
| T1s-903 | (S)-I-5 | II-74 | II-92 |
| T1s-904 | (S)-I-5 | II-76 | II-78 |
| T1s-905 | (S)-I-5 | II-76 | II-84 |
| T1s-906 | (S)-I-5 | II-76 | II-85 |
| T1s-907 | (S)-I-5 | II-76 | II-86 |
| T1s-908 | (S)-I-5 | II-76 | II-92 |
| T1s-909 | (S)-I-5 | II-78 | II-84 |
| T1s-910 | (S)-I-5 | II-78 | II-85 |
| T1s-911 | (S)-I-5 | II-78 | II-86 |
| T1s-912 | (S)-I-5 | II-78 | II-92 |
| T1s-913 | (S)-I-5 | II-84 | II-85 |
| T1s-914 | (S)-I-5 | II-84 | II-86 |
| T1s-915 | (S)-I-5 | II-84 | II-92 |
| T1s-916 | (S)-I-5 | II-85 | II-86 |
| T1s-917 | (S)-I-5 | II-85 | II-92 |
| T1s-918 | (S)-I-5 | II-86 | II-92 |
| T1s-919 | (S)-I-3 | II-3 | II-5 |
| T1s-920 | (S)-I-3 | II-3 | II-6 |
| T1s-921 | (S)-I-3 | II-3 | II-7 |
| T1s-922 | (S)-I-3 | II-3 | II-8 |
| T1s-923 | (S)-I-3 | II-3 | II-11 |
| T1s-924 | (S)-I-3 | II-3 | II-16 |
| T1s-925 | (S)-I-3 | II-3 | II-21 |
| T1s-926 | (S)-I-3 | II-3 | II-26 |
| T1s-927 | (S)-I-3 | II-3 | II-32 |
| T1s-928 | (S)-I-3 | II-3 | II-33 |
| T1s-929 | (S)-I-3 | II-3 | II-37 |
| T1s-930 | (S)-I-3 | II-3 | II-39 |
| T1s-931 | (S)-I-3 | II-3 | II-42 |
| T1s-932 | (S)-I-3 | II-3 | II-44 |
| T1s-933 | (S)-I-3 | II-3 | II-50 |
| T1s-934 | (S)-I-3 | II-3 | II-53 |
| T1s-935 | (S)-I-3 | II-3 | II-60 |
| T1s-936 | (S)-I-3 | II-3 | II-62 |
| T1s-937 | (S)-I-3 | II-3 | II-66 |
| T1s-938 | (S)-I-3 | II-3 | II-69 |
| T1s-939 | (S)-I-3 | II-3 | II-70 |
| T1s-940 | (S)-I-3 | II-3 | II-71 |
| T1s-941 | (S)-I-3 | II-3 | II-72 |
| T1s-942 | (S)-I-3 | II-3 | II-74 |
| T1s-943 | (S)-I-3 | II-3 | II-76 |
| T1s-944 | (S)-I-3 | II-3 | II-78 |
| T1s-945 | (S)-I-3 | II-3 | II-84 |
| T1s-946 | (S)-I-3 | II-3 | II-85 |
| T1s-947 | (S)-I-3 | II-3 | II-86 |
| T1s-948 | (S)-I-3 | II-3 | II-92 |
| T1s-949 | (S)-I-3 | II-5 | II-6 |
| T1s-950 | (S)-I-3 | II-5 | II-7 |
| T1s-951 | (S)-I-3 | II-5 | II-8 |
| T1s-952 | (S)-I-3 | II-5 | II-11 |
| T1s-953 | (S)-I-3 | II-5 | II-16 |
| T1s-954 | (S)-I-3 | II-5 | II-21 |
| T1s-955 | (S)-I-3 | II-5 | II-26 |

TABLE T1s-continued

Three-component compositions comprising one component I as (S) enantiomer (appreviated as (S)-I, e.g. (S)-I-1 for the (S)-enantiomer of I-1), one component II and one component III, in particular ternary compositions containing the respective component I as (S) enantiomer, II and III as only active ingredients.

| composition | (S)-I | II | III |
|---|---|---|---|
| T1s-956 | (S)-I-3 | II-5 | II-32 |
| T1s-957 | (S)-I-3 | II-5 | II-33 |
| T1s-958 | (S)-I-3 | II-5 | II-37 |
| T1s-959 | (S)-I-3 | II-5 | II-39 |
| T1s-960 | (S)-I-3 | II-5 | II-42 |
| T1s-961 | (S)-I-3 | II-5 | II-44 |
| T1s-962 | (S)-I-3 | II-5 | II-50 |
| T1s-963 | (S)-I-3 | II-5 | II-53 |
| T1s-964 | (S)-I-3 | II-5 | II-60 |
| T1s-965 | (S)-I-3 | II-5 | II-62 |
| T1s-966 | (S)-I-3 | II-5 | II-66 |
| T1s-967 | (S)-I-3 | II-5 | II-69 |
| T1s-968 | (S)-I-3 | II-5 | II-70 |
| T1s-969 | (S)-I-3 | II-5 | II-71 |
| T1s-970 | (S)-I-3 | II-5 | II-72 |
| T1s-971 | (S)-I-3 | II-5 | II-74 |
| T1s-972 | (S)-I-3 | II-5 | II-76 |
| T1s-973 | (S)-I-3 | II-5 | II-78 |
| T1s-974 | (S)-I-3 | II-5 | II-84 |
| T1s-975 | (S)-I-3 | II-5 | II-85 |
| T1s-976 | (S)-I-3 | II-5 | II-86 |
| T1s-977 | (S)-I-3 | II-5 | II-92 |
| T1s-978 | (S)-I-3 | II-6 | II-7 |
| T1s-979 | (S)-I-3 | II-6 | II-8 |
| T1s-980 | (S)-I-3 | II-6 | II-11 |
| T1s-981 | (S)-I-3 | II-6 | II-16 |
| T1s-982 | (S)-I-3 | II-6 | II-21 |
| T1s-983 | (S)-I-3 | II-6 | II-26 |
| T1s-984 | (S)-I-3 | II-6 | II-32 |
| T1s-985 | (S)-I-3 | II-6 | II-33 |
| T1s-986 | (S)-I-3 | II-6 | II-37 |
| T1s-987 | (S)-I-3 | II-6 | II-39 |
| T1s-988 | (S)-I-3 | II-6 | II-42 |
| T1s-989 | (S)-I-3 | II-6 | II-44 |
| T1s-990 | (S)-I-3 | II-6 | II-50 |
| T1s-991 | (S)-I-3 | II-6 | II-53 |
| T1s-992 | (S)-I-3 | II-6 | II-60 |
| T1s-993 | (S)-I-3 | II-6 | II-62 |
| T1s-994 | (S)-I-3 | II-6 | II-66 |
| T1s-995 | (S)-I-3 | II-6 | II-69 |
| T1s-996 | (S)-I-3 | II-6 | II-70 |
| T1s-997 | (S)-I-3 | II-6 | II-71 |
| T1s-998 | (S)-I-3 | II-6 | II-72 |
| T1s-999 | (S)-I-3 | II-6 | II-74 |
| T1s-1000 | (S)-I-3 | II-6 | II-76 |
| T1s-1001 | (S)-I-3 | II-6 | II-78 |
| T1s-1002 | (S)-I-3 | II-6 | II-84 |
| T1s-1003 | (S)-I-3 | II-6 | II-85 |
| T1s-1004 | (S)-I-3 | II-6 | II-86 |
| T1s-1005 | (S)-I-3 | II-6 | II-92 |
| T1s-1006 | (S)-I-3 | II-7 | II-8 |
| T1s-1007 | (S)-I-3 | II-7 | II-11 |
| T1s-1008 | (S)-I-3 | II-7 | II-16 |
| T1s-1009 | (S)-I-3 | II-7 | II-21 |
| T1s-1010 | (S)-I-3 | II-7 | II-26 |
| T1s-1011 | (S)-I-3 | II-7 | II-32 |
| T1s-1012 | (S)-I-3 | II-7 | II-33 |
| T1s-1013 | (S)-I-3 | II-7 | II-37 |
| T1s-1014 | (S)-I-3 | II-7 | II-39 |
| T1s-1015 | (S)-I-3 | II-7 | II-42 |
| T1s-1016 | (S)-I-3 | II-7 | II-44 |
| T1s-1017 | (S)-I-3 | II-7 | II-50 |
| T1s-1018 | (S)-I-3 | II-7 | II-53 |
| T1s-1019 | (S)-I-3 | II-7 | II-60 |
| T1s-1020 | (S)-I-3 | II-7 | II-62 |
| T1s-1021 | (S)-I-3 | II-7 | II-66 |
| T1s-1022 | (S)-I-3 | II-7 | II-69 |
| T1s-1023 | (S)-I-3 | II-7 | II-70 |
| T1s-1024 | (S)-I-3 | II-7 | II-71 |
| T1s-1025 | (S)-I-3 | II-7 | II-72 |
| T1s-1026 | (S)-I-3 | II-7 | II-74 |
| T1s-1027 | (S)-I-3 | II-7 | II-76 |
| T1s-1028 | (S)-I-3 | II-7 | II-78 |
| T1s-1029 | (S)-I-3 | II-7 | II-84 |
| T1s-1030 | (S)-I-3 | II-7 | II-85 |
| T1s-1031 | (S)-I-3 | II-7 | II-86 |
| T1s-1032 | (S)-I-3 | II-7 | II-92 |
| T1s-1033 | (S)-I-3 | II-8 | II-11 |
| T1s-1034 | (S)-I-3 | II-8 | II-16 |
| T1s-1035 | (S)-I-3 | II-8 | II-21 |
| T1s-1036 | (S)-I-3 | II-8 | II-26 |
| T1s-1037 | (S)-I-3 | II-8 | II-32 |
| T1s-1038 | (S)-I-3 | II-8 | II-33 |
| T1s-1039 | (S)-I-3 | II-8 | II-37 |
| T1s-1040 | (S)-I-3 | II-8 | II-39 |
| T1s-1041 | (S)-I-3 | II-8 | II-42 |
| T1s-1042 | (S)-I-3 | II-8 | II-44 |
| T1s-1043 | (S)-I-3 | II-8 | II-50 |
| T1s-1044 | (S)-I-3 | II-8 | II-53 |
| T1s-1045 | (S)-I-3 | II-8 | II-60 |
| T1s-1046 | (S)-I-3 | II-8 | II-62 |
| T1s-1047 | (S)-I-3 | II-8 | II-66 |
| T1s-1048 | (S)-I-3 | II-8 | II-69 |
| T1s-1049 | (S)-I-3 | II-8 | II-70 |
| T1s-1050 | (S)-I-3 | II-8 | II-71 |
| T1s-1051 | (S)-I-3 | II-8 | II-72 |
| T1s-1052 | (S)-I-3 | II-8 | II-74 |
| T1s-1053 | (S)-I-3 | II-8 | II-76 |
| T1s-1054 | (S)-I-3 | II-8 | II-78 |
| T1s-1055 | (S)-I-3 | II-8 | II-84 |
| T1s-1056 | (S)-I-3 | II-8 | II-85 |
| T1s-1057 | (S)-I-3 | II-8 | II-86 |
| T1s-1058 | (S)-I-3 | II-8 | II-92 |
| T1s-1059 | (S)-I-3 | II-11 | II-16 |
| T1s-1060 | (S)-I-3 | II-11 | II-21 |
| T1s-1061 | (S)-I-3 | II-11 | II-26 |
| T1s-1062 | (S)-I-3 | II-11 | II-32 |
| T1s-1063 | (S)-I-3 | II-11 | II-33 |
| T1s-1064 | (S)-I-3 | II-11 | II-37 |
| T1s-1065 | (S)-I-3 | II-11 | II-39 |
| T1s-1066 | (S)-I-3 | II-11 | II-42 |
| T1s-1067 | (S)-I-3 | II-11 | II-44 |
| T1s-1068 | (S)-I-3 | II-11 | II-50 |
| T1s-1069 | (S)-I-3 | II-11 | II-53 |
| T1s-1070 | (S)-I-3 | II-11 | II-60 |
| T1s-1071 | (S)-I-3 | II-11 | II-62 |
| T1s-1072 | (S)-I-3 | II-11 | II-66 |
| T1s-1073 | (S)-I-3 | II-11 | II-69 |
| T1s-1074 | (S)-I-3 | II-11 | II-70 |
| T1s-1075 | (S)-I-3 | II-11 | II-71 |
| T1s-1076 | (S)-I-3 | II-11 | II-72 |
| T1s-1077 | (S)-I-3 | II-11 | II-74 |
| T1s-1078 | (S)-I-3 | II-11 | II-76 |
| T1s-1079 | (S)-I-3 | II-11 | II-78 |
| T1s-1080 | (S)-I-3 | II-11 | II-84 |
| T1s-1081 | (S)-I-3 | II-11 | II-85 |
| T1s-1082 | (S)-I-3 | II-11 | II-86 |
| T1s-1083 | (S)-I-3 | II-11 | II-92 |
| T1s-1084 | (S)-I-3 | II-16 | II-21 |
| T1s-1085 | (S)-I-3 | II-16 | II-26 |
| T1s-1086 | (S)-I-3 | II-16 | II-32 |
| T1s-1087 | (S)-I-3 | II-16 | II-33 |
| T1s-1088 | (S)-I-3 | II-16 | II-37 |
| T1s-1089 | (S)-I-3 | II-16 | II-39 |
| T1s-1090 | (S)-I-3 | II-16 | II-42 |
| T1s-1091 | (S)-I-3 | II-16 | II-44 |
| T1s-1092 | (S)-I-3 | II-16 | II-50 |
| T1s-1093 | (S)-I-3 | II-16 | II-53 |
| T1s-1094 | (S)-I-3 | II-16 | II-60 |
| T1s-1095 | (S)-I-3 | II-16 | II-62 |
| T1s-1096 | (S)-I-3 | II-16 | II-66 |
| T1s-1097 | (S)-I-3 | II-16 | II-69 |
| T1s-1098 | (S)-I-3 | II-16 | II-70 |
| T1s-1099 | (S)-I-3 | II-16 | II-71 |

TABLE T1s-continued

Three-component compositions comprising one component I as (S) enantiomer (appreviated as (S)-I, e.g. (S)-I-1 for the (S)-enantiomer of I-1), one component II and one component III, in particular ternary compositions containing the respective component I as (S) enantiomer, II and III as only active ingredients.

| composition | (S)-I | II | III |
| --- | --- | --- | --- |
| T1s-1100 | (S)-I-3 | II-16 | II-72 |
| T1s-1101 | (S)-I-3 | II-16 | II-74 |
| T1s-1102 | (S)-I-3 | II-16 | II-76 |
| T1s-1103 | (S)-I-3 | II-16 | II-78 |
| T1s-1104 | (S)-I-3 | II-16 | II-84 |
| T1s-1105 | (S)-I-3 | II-16 | II-85 |
| T1s-1106 | (S)-I-3 | II-16 | II-86 |
| T1s-1107 | (S)-I-3 | II-16 | II-92 |
| T1s-1108 | (S)-I-3 | II-21 | II-26 |
| T1s-1109 | (S)-I-3 | II-21 | II-32 |
| T1s-1110 | (S)-I-3 | II-21 | II-33 |
| T1s-1111 | (S)-I-3 | II-21 | II-37 |
| T1s-1112 | (S)-I-3 | II-21 | II-39 |
| T1s-1113 | (S)-I-3 | II-21 | II-42 |
| T1s-1114 | (S)-I-3 | II-21 | II-44 |
| T1s-1115 | (S)-I-3 | II-21 | II-50 |
| T1s-1116 | (S)-I-3 | II-21 | II-53 |
| T1s-1117 | (S)-I-3 | II-21 | II-60 |
| T1s-1118 | (S)-I-3 | II-21 | II-62 |
| T1s-1119 | (S)-I-3 | II-21 | II-66 |
| T1s-1120 | (S)-I-3 | II-21 | II-69 |
| T1s-1121 | (S)-I-3 | II-21 | II-70 |
| T1s-1122 | (S)-I-3 | II-21 | II-71 |
| T1s-1123 | (S)-I-3 | II-21 | II-72 |
| T1s-1124 | (S)-I-3 | II-21 | II-74 |
| T1s-1125 | (S)-I-3 | II-21 | II-76 |
| T1s-1126 | (S)-I-3 | II-21 | II-78 |
| T1s-1127 | (S)-I-3 | II-21 | II-84 |
| T1s-1128 | (S)-I-3 | II-21 | II-85 |
| T1s-1129 | (S)-I-3 | II-21 | II-86 |
| T1s-1130 | (S)-I-3 | II-21 | II-92 |
| T1s-1131 | (S)-I-3 | II-26 | II-32 |
| T1s-1132 | (S)-I-3 | II-26 | II-33 |
| T1s-1133 | (S)-I-3 | II-26 | II-37 |
| T1s-1134 | (S)-I-3 | II-26 | II-39 |
| T1s-1135 | (S)-I-3 | II-26 | II-42 |
| T1s-1136 | (S)-I-3 | II-26 | II-44 |
| T1s-1137 | (S)-I-3 | II-26 | II-50 |
| T1s-1138 | (S)-I-3 | II-26 | II-53 |
| T1s-1139 | (S)-I-3 | II-26 | II-60 |
| T1s-1140 | (S)-I-3 | II-26 | II-62 |
| T1s-1141 | (S)-I-3 | II-26 | II-66 |
| T1s-1142 | (S)-I-3 | II-26 | II-69 |
| T1s-1143 | (S)-I-3 | II-26 | II-70 |
| T1s-1144 | (S)-I-3 | II-26 | II-71 |
| T1s-1145 | (S)-I-3 | II-26 | II-72 |
| T1s-1146 | (S)-I-3 | II-26 | II-74 |
| T1s-1147 | (S)-I-3 | II-26 | II-76 |
| T1s-1148 | (S)-I-3 | II-26 | II-78 |
| T1s-1149 | (S)-I-3 | II-26 | II-84 |
| T1s-1150 | (S)-I-3 | II-26 | II-85 |
| T1s-1151 | (S)-I-3 | II-26 | II-86 |
| T1s-1152 | (S)-I-3 | II-26 | II-92 |
| T1s-1153 | (S)-I-3 | II-32 | II-33 |
| T1s-1154 | (S)-I-3 | II-32 | II-37 |
| T1s-1155 | (S)-I-3 | II-32 | II-39 |
| T1s-1156 | (S)-I-3 | II-32 | II-42 |
| T1s-1157 | (S)-I-3 | II-32 | II-44 |
| T1s-1158 | (S)-I-3 | II-32 | II-50 |
| T1s-1159 | (S)-I-3 | II-32 | II-53 |
| T1s-1160 | (S)-I-3 | II-32 | II-60 |
| T1s-1161 | (S)-I-3 | II-32 | II-62 |
| T1s-1162 | (S)-I-3 | II-32 | II-66 |
| T1s-1163 | (S)-I-3 | II-32 | II-69 |
| T1s-1164 | (S)-I-3 | II-32 | II-70 |
| T1s-1165 | (S)-I-3 | II-32 | II-71 |
| T1s-1166 | (S)-I-3 | II-32 | II-72 |
| T1s-1167 | (S)-I-3 | II-32 | II-74 |
| T1s-1168 | (S)-I-3 | II-32 | II-76 |
| T1s-1169 | (S)-I-3 | II-32 | II-78 |
| T1s-1170 | (S)-I-3 | II-32 | II-84 |
| T1s-1171 | (S)-I-3 | II-32 | II-85 |
| T1s-1172 | (S)-I-3 | II-32 | II-86 |
| T1s-1173 | (S)-I-3 | II-32 | II-92 |
| T1s-1174 | (S)-I-3 | II-33 | II-37 |
| T1s-1175 | (S)-I-3 | II-33 | II-39 |
| T1s-1176 | (S)-I-3 | II-33 | II-42 |
| T1s-1177 | (S)-I-3 | II-33 | II-44 |
| T1s-1178 | (S)-I-3 | II-33 | II-50 |
| T1s-1179 | (S)-I-3 | II-33 | II-53 |
| T1s-1180 | (S)-I-3 | II-33 | II-60 |
| T1s-1181 | (S)-I-3 | II-33 | II-62 |
| T1s-1182 | (S)-I-3 | II-33 | II-66 |
| T1s-1183 | (S)-I-3 | II-33 | II-69 |
| T1s-1184 | (S)-I-3 | II-33 | II-70 |
| T1s-1185 | (S)-I-3 | II-33 | II-71 |
| T1s-1186 | (S)-I-3 | II-33 | II-72 |
| T1s-1187 | (S)-I-3 | II-33 | II-74 |
| T1s-1188 | (S)-I-3 | II-33 | II-76 |
| T1s-1189 | (S)-I-3 | II-33 | II-78 |
| T1s-1190 | (S)-I-3 | II-33 | II-84 |
| T1s-1191 | (S)-I-3 | II-33 | II-85 |
| T1s-1192 | (S)-I-3 | II-33 | II-86 |
| T1s-1193 | (S)-I-3 | II-33 | II-92 |
| T1s-1194 | (S)-I-3 | II-37 | II-39 |
| T1s-1195 | (S)-I-3 | II-37 | II-42 |
| T1s-1196 | (S)-I-3 | II-37 | II-44 |
| T1s-1197 | (S)-I-3 | II-37 | II-50 |
| T1s-1198 | (S)-I-3 | II-37 | II-53 |
| T1s-1199 | (S)-I-3 | II-37 | II-60 |
| T1s-1200 | (S)-I-3 | II-37 | II-62 |
| T1s-1201 | (S)-I-3 | II-37 | II-66 |
| T1s-1202 | (S)-I-3 | II-37 | II-69 |
| T1s-1203 | (S)-I-3 | II-37 | II-70 |
| T1s-1204 | (S)-I-3 | II-37 | II-71 |
| T1s-1205 | (S)-I-3 | II-37 | II-72 |
| T1s-1206 | (S)-I-3 | II-37 | II-74 |
| T1s-1207 | (S)-I-3 | II-37 | II-76 |
| T1s-1208 | (S)-I-3 | II-37 | II-78 |
| T1s-1209 | (S)-I-3 | II-37 | II-84 |
| T1s-1210 | (S)-I-3 | II-37 | II-85 |
| T1s-1211 | (S)-I-3 | II-37 | II-86 |
| T1s-1212 | (S)-I-3 | II-37 | II-92 |
| T1s-1213 | (S)-I-3 | II-39 | II-42 |
| T1s-1214 | (S)-I-3 | II-39 | II-44 |
| T1s-1215 | (S)-I-3 | II-39 | II-50 |
| T1s-1216 | (S)-I-3 | II-39 | II-53 |
| T1s-1217 | (S)-I-3 | II-39 | II-60 |
| T1s-1218 | (S)-I-3 | II-39 | II-62 |
| T1s-1219 | (S)-I-3 | II-39 | II-66 |
| T1s-1220 | (S)-I-3 | II-39 | II-69 |
| T1s-1221 | (S)-I-3 | II-39 | II-70 |
| T1s-1222 | (S)-I-3 | II-39 | II-71 |
| T1s-1223 | (S)-I-3 | II-39 | II-72 |
| T1s-1224 | (S)-I-3 | II-39 | II-74 |
| T1s-1225 | (S)-I-3 | II-39 | II-76 |
| T1s-1226 | (S)-I-3 | II-39 | II-78 |
| T1s-1227 | (S)-I-3 | II-39 | II-84 |
| T1s-1228 | (S)-I-3 | II-39 | II-85 |
| T1s-1229 | (S)-I-3 | II-39 | II-86 |
| T1s-1230 | (S)-I-3 | II-39 | II-92 |
| T1s-1231 | (S)-I-3 | II-42 | II-44 |
| T1s-1232 | (S)-I-3 | II-42 | II-50 |
| T1s-1233 | (S)-I-3 | II-42 | II-53 |
| T1s-1234 | (S)-I-3 | II-42 | II-60 |
| T1s-1235 | (S)-I-3 | II-42 | II-62 |
| T1s-1236 | (S)-I-3 | II-42 | II-66 |
| T1s-1237 | (S)-I-3 | II-42 | II-69 |
| T1s-1238 | (S)-I-3 | II-42 | II-70 |
| T1s-1239 | (S)-I-3 | II-42 | II-71 |
| T1s-1240 | (S)-I-3 | II-42 | II-72 |
| T1s-1241 | (S)-I-3 | II-42 | II-74 |
| T1s-1242 | (S)-I-3 | II-42 | II-76 |
| T1s-1243 | (S)-I-3 | II-42 | II-78 |

TABLE T1s-continued

Three-component compositions comprising one component I as (S) enantiomer (appreviated as (S)-I, e.g. (S)-I-1 for the (S)-enantiomer of I-1), one component II and one component III, in particular ternary compositions containing the respective component I as (S) enantiomer, II and III as only active ingredients.

| composition | (S)-I | II | III |
|---|---|---|---|
| T1s-1244 | (S)-I-3 | II-42 | II-84 |
| T1s-1245 | (S)-I-3 | II-42 | II-85 |
| T1s-1246 | (S)-I-3 | II-42 | II-86 |
| T1s-1247 | (S)-I-3 | II-42 | II-92 |
| T1s-1248 | (S)-I-3 | II-44 | II-50 |
| T1s-1249 | (S)-I-3 | II-44 | II-53 |
| T1s-1250 | (S)-I-3 | II-44 | II-60 |
| T1s-1251 | (S)-I-3 | II-44 | II-62 |
| T1s-1252 | (S)-I-3 | II-44 | II-66 |
| T1s-1253 | (S)-I-3 | II-44 | II-69 |
| T1s-1254 | (S)-I-3 | II-44 | II-70 |
| T1s-1255 | (S)-I-3 | II-44 | II-71 |
| T1s-1256 | (S)-I-3 | II-44 | II-72 |
| T1s-1257 | (S)-I-3 | II-44 | II-74 |
| T1s-1258 | (S)-I-3 | II-44 | II-76 |
| T1s-1259 | (S)-I-3 | II-44 | II-78 |
| T1s-1260 | (S)-I-3 | II-44 | II-84 |
| T1s-1261 | (S)-I-3 | II-44 | II-85 |
| T1s-1262 | (S)-I-3 | II-44 | II-86 |
| T1s-1263 | (S)-I-3 | II-44 | II-92 |
| T1s-1264 | (S)-I-3 | II-50 | II-53 |
| T1s-1265 | (S)-I-3 | II-50 | II-60 |
| T1s-1266 | (S)-I-3 | II-50 | II-62 |
| T1s-1267 | (S)-I-3 | II-50 | II-66 |
| T1s-1268 | (S)-I-3 | II-50 | II-69 |
| T1s-1269 | (S)-I-3 | II-50 | II-70 |
| T1s-1270 | (S)-I-3 | II-50 | II-71 |
| T1s-1271 | (S)-I-3 | II-50 | II-72 |
| T1s-1272 | (S)-I-3 | II-50 | II-74 |
| T1s-1273 | (S)-I-3 | II-50 | II-76 |
| T1s-1274 | (S)-I-3 | II-50 | II-78 |
| T1s-1275 | (S)-I-3 | II-50 | II-84 |
| T1s-1276 | (S)-I-3 | II-50 | II-85 |
| T1s-1277 | (S)-I-3 | II-50 | II-86 |
| T1s-1278 | (S)-I-3 | II-50 | II-92 |
| T1s-1279 | (S)-I-3 | II-53 | II-60 |
| T1s-1280 | (S)-I-3 | II-53 | II-62 |
| T1s-1281 | (S)-I-3 | II-53 | II-66 |
| T1s-1282 | (S)-I-3 | II-53 | II-69 |
| T1s-1283 | (S)-I-3 | II-53 | II-70 |
| T1s-1284 | (S)-I-3 | II-53 | II-71 |
| T1s-1285 | (S)-I-3 | II-53 | II-72 |
| T1s-1286 | (S)-I-3 | II-53 | II-74 |
| T1s-1287 | (S)-I-3 | II-53 | II-76 |
| T1s-1288 | (S)-I-3 | II-53 | II-78 |
| T1s-1289 | (S)-I-3 | II-53 | II-84 |
| T1s-1290 | (S)-I-3 | II-53 | II-85 |
| T1s-1291 | (S)-I-3 | II-53 | II-86 |
| T1s-1292 | (S)-I-3 | II-53 | II-92 |
| T1s-1293 | (S)-I-3 | II-60 | II-62 |
| T1s-1294 | (S)-I-3 | II-60 | II-66 |
| T1s-1295 | (S)-I-3 | II-60 | II-69 |
| T1s-1296 | (S)-I-3 | II-60 | II-70 |
| T1s-1297 | (S)-I-3 | II-60 | II-71 |
| T1s-1298 | (S)-I-3 | II-60 | II-72 |
| T1s-1299 | (S)-I-3 | II-60 | II-74 |
| T1s-1300 | (S)-I-3 | II-60 | II-76 |
| T1s-1301 | (S)-I-3 | II-60 | II-78 |
| T1s-1302 | (S)-I-3 | II-60 | II-84 |
| T1s-1303 | (S)-I-3 | II-60 | II-85 |
| T1s-1304 | (S)-I-3 | II-60 | II-86 |
| T1s-1305 | (S)-I-3 | II-60 | II-92 |
| T1s-1306 | (S)-I-3 | II-62 | II-66 |
| T1s-1307 | (S)-I-3 | II-62 | II-69 |
| T1s-1308 | (S)-I-3 | II-62 | II-70 |
| T1s-1309 | (S)-I-3 | II-62 | II-71 |
| T1s-1310 | (S)-I-3 | II-62 | II-72 |
| T1s-1311 | (S)-I-3 | II-62 | II-74 |
| T1s-1312 | (S)-I-3 | II-62 | II-76 |
| T1s-1313 | (S)-I-3 | II-62 | II-78 |
| T1s-1314 | (S)-I-3 | II-62 | II-84 |
| T1s-1315 | (S)-I-3 | II-62 | II-85 |
| T1s-1316 | (S)-I-3 | II-62 | II-86 |
| T1s-1317 | (S)-I-3 | II-62 | II-92 |
| T1s-1318 | (S)-I-3 | II-66 | II-69 |
| T1s-1319 | (S)-I-3 | II-66 | II-70 |
| T1s-1320 | (S)-I-3 | II-66 | II-71 |
| T1s-1321 | (S)-I-3 | II-66 | II-72 |
| T1s-1322 | (S)-I-3 | II-66 | II-74 |
| T1s-1323 | (S)-I-3 | II-66 | II-76 |
| T1s-1324 | (S)-I-3 | II-66 | II-78 |
| T1s-1325 | (S)-I-3 | II-66 | II-84 |
| T1s-1326 | (S)-I-3 | II-66 | II-85 |
| T1s-1327 | (S)-I-3 | II-66 | II-86 |
| T1s-1328 | (S)-I-3 | II-66 | II-92 |
| T1s-1329 | (S)-I-3 | II-69 | II-70 |
| T1s-1330 | (S)-I-3 | II-69 | II-71 |
| T1s-1331 | (S)-I-3 | II-69 | II-72 |
| T1s-1332 | (S)-I-3 | II-69 | II-74 |
| T1s-1333 | (S)-I-3 | II-69 | II-76 |
| T1s-1334 | (S)-I-3 | II-69 | II-78 |
| T1s-1335 | (S)-I-3 | II-69 | II-84 |
| T1s-1336 | (S)-I-3 | II-69 | II-85 |
| T1s-1337 | (S)-I-3 | II-69 | II-86 |
| T1s-1338 | (S)-I-3 | II-69 | II-92 |
| T1s-1339 | (S)-I-3 | II-70 | II-71 |
| T1s-1340 | (S)-I-3 | II-70 | II-72 |
| T1s-1341 | (S)-I-3 | II-70 | II-74 |
| T1s-1342 | (S)-I-3 | II-70 | II-76 |
| T1s-1343 | (S)-I-3 | II-70 | II-78 |
| T1s-1344 | (S)-I-3 | II-70 | II-84 |
| T1s-1345 | (S)-I-3 | II-70 | II-85 |
| T1s-1346 | (S)-I-3 | II-70 | II-86 |
| T1s-1347 | (S)-I-3 | II-70 | II-92 |
| T1s-1348 | (S)-I-3 | II-71 | II-72 |
| T1s-1349 | (S)-I-3 | II-71 | II-74 |
| T1s-1350 | (S)-I-3 | II-71 | II-76 |
| T1s-1351 | (S)-I-3 | II-71 | II-78 |
| T1s-1352 | (S)-I-3 | II-71 | II-84 |
| T1s-1353 | (S)-I-3 | II-71 | II-85 |
| T1s-1354 | (S)-I-3 | II-71 | II-86 |
| T1s-1355 | (S)-I-3 | II-71 | II-92 |
| T1s-1356 | (S)-I-3 | II-72 | II-74 |
| T1s-1357 | (S)-I-3 | II-74 | II-76 |
| T1s-1358 | (S)-I-3 | II-74 | II-78 |
| T1s-1359 | (S)-I-3 | II-74 | II-84 |
| T1s-1360 | (S)-I-3 | II-74 | II-85 |
| T1s-1361 | (S)-I-3 | II-74 | II-86 |
| T1s-1362 | (S)-I-3 | II-74 | II-92 |
| T1s-1363 | (S)-I-3 | II-76 | II-78 |
| T1s-1364 | (S)-I-3 | II-76 | II-84 |
| T1s-1365 | (S)-I-3 | II-76 | II-85 |
| T1s-1366 | (S)-I-3 | II-76 | II-86 |
| T1s-1367 | (S)-I-3 | II-76 | II-92 |
| T1s-1368 | (S)-I-3 | II-78 | II-84 |
| T1s-1369 | (S)-I-3 | II-78 | II-85 |
| T1s-1370 | (S)-I-3 | II-78 | II-86 |
| T1s-1371 | (S)-I-3 | II-78 | II-92 |
| T1s-1372 | (S)-I-3 | II-84 | II-85 |
| T1s-1373 | (S)-I-3 | II-84 | II-86 |
| T1s-1374 | (S)-I-3 | II-84 | II-92 |
| T1s-1375 | (S)-I-3 | II-85 | II-86 |
| T1s-1376 | (S)-I-3 | II-85 | II-92 |
| T1s-1377 | (S)-I-3 | II-86 | II-92 |
| T1s-1378 | (S)-I-4 | II-3 | II-5 |
| T1s-1379 | (S)-I-4 | II-3 | II-6 |
| T1s-1380 | (S)-I-4 | II-3 | II-7 |
| T1s-1381 | (S)-I-4 | II-3 | II-8 |
| T1s-1382 | (S)-I-4 | II-3 | II-11 |
| T1s-1383 | (S)-I-4 | II-3 | II-16 |
| T1s-1384 | (S)-I-4 | II-3 | II-21 |
| T1s-1385 | (S)-I-4 | II-3 | II-26 |
| T1s-1386 | (S)-I-4 | II-3 | II-32 |
| T1s-1387 | (S)-I-4 | II-3 | II-33 |

TABLE T1s-continued

Three-component compositions comprising one component I as (S) enantiomer (appreviated as (S)-I, e.g. (S)-I-1 for the (S)-enantiomer of I-1), one component II and one component III, in particular ternary compositions containing the respective component I as (S) enantiomer, II and III as only active ingredients.

| composition | (S)-I | II | III |
|---|---|---|---|
| T1s-1388 | (S)-I-4 | II-3 | II-37 |
| T1s-1389 | (S)-I-4 | II-3 | II-39 |
| T1s-1390 | (S)-I-4 | II-3 | II-42 |
| T1s-1391 | (S)-I-4 | II-3 | II-44 |
| T1s-1392 | (S)-I-4 | II-3 | II-50 |
| T1s-1393 | (S)-I-4 | II-3 | II-53 |
| T1s-1394 | (S)-I-4 | II-3 | II-60 |
| T1s-1395 | (S)-I-4 | II-3 | II-62 |
| T1s-1396 | (S)-I-4 | II-3 | II-66 |
| T1s-1397 | (S)-I-4 | II-3 | II-69 |
| T1s-1398 | (S)-I-4 | II-3 | II-70 |
| T1s-1399 | (S)-I-4 | II-3 | II-71 |
| T1s-1400 | (S)-I-4 | II-3 | II-72 |
| T1s-1401 | (S)-I-4 | II-3 | II-74 |
| T1s-1402 | (S)-I-4 | II-3 | II-76 |
| T1s-1403 | (S)-I-4 | II-3 | II-78 |
| T1s-1404 | (S)-I-4 | II-3 | II-84 |
| T1s-1405 | (S)-I-4 | II-3 | II-85 |
| T1s-1406 | (S)-I-4 | II-3 | II-86 |
| T1s-1407 | (S)-I-4 | II-3 | II-92 |
| T1s-1408 | (S)-I-4 | II-5 | II-6 |
| T1s-1409 | (S)-I-4 | II-5 | II-7 |
| T1s-1410 | (S)-I-4 | II-5 | II-8 |
| T1s-1411 | (S)-I-4 | II-5 | II-11 |
| T1s-1412 | (S)-I-4 | II-5 | II-16 |
| T1s-1413 | (S)-I-4 | II-5 | II-21 |
| T1s-1414 | (S)-I-4 | II-5 | II-26 |
| T1s-1415 | (S)-I-4 | II-5 | II-32 |
| T1s-1416 | (S)-I-4 | II-5 | II-33 |
| T1s-1417 | (S)-I-4 | II-5 | II-37 |
| T1s-1418 | (S)-I-4 | II-5 | II-39 |
| T1s-1419 | (S)-I-4 | II-5 | II-42 |
| T1s-1420 | (S)-I-4 | II-5 | II-44 |
| T1s-1421 | (S)-I-4 | II-5 | II-50 |
| T1s-1422 | (S)-I-4 | II-5 | II-53 |
| T1s-1423 | (S)-I-4 | II-5 | II-60 |
| T1s-1424 | (S)-I-4 | II-5 | II-62 |
| T1s-1425 | (S)-I-4 | II-5 | II-66 |
| T1s-1426 | (S)-I-4 | II-5 | II-69 |
| T1s-1427 | (S)-I-4 | II-5 | II-70 |
| T1s-1428 | (S)-I-4 | II-5 | II-71 |
| T1s-1429 | (S)-I-4 | II-5 | II-72 |
| T1s-1430 | (S)-I-4 | II-5 | II-74 |
| T1s-1431 | (S)-I-4 | II-5 | II-76 |
| T1s-1432 | (S)-I-4 | II-5 | II-78 |
| T1s-1433 | (S)-I-4 | II-5 | II-84 |
| T1s-1434 | (S)-I-4 | II-5 | II-85 |
| T1s-1435 | (S)-I-4 | II-5 | II-86 |
| T1s-1436 | (S)-I-4 | II-5 | II-92 |
| T1s-1437 | (S)-I-4 | II-6 | II-7 |
| T1s-1438 | (S)-I-4 | II-6 | II-8 |
| T1s-1439 | (S)-I-4 | II-6 | II-11 |
| T1s-1440 | (S)-I-4 | II-6 | II-16 |
| T1s-1441 | (S)-I-4 | II-6 | II-21 |
| T1s-1442 | (S)-I-4 | II-6 | II-26 |
| T1s-1443 | (S)-I-4 | II-6 | II-32 |
| T1s-1444 | (S)-I-4 | II-6 | II-33 |
| T1s-1445 | (S)-I-4 | II-6 | II-37 |
| T1s-1446 | (S)-I-4 | II-6 | II-39 |
| T1s-1447 | (S)-I-4 | II-6 | II-42 |
| T1s-1448 | (S)-I-4 | II-6 | II-44 |
| T1s-1449 | (S)-I-4 | II-6 | II-50 |
| T1s-1450 | (S)-I-4 | II-6 | II-53 |
| T1s-1451 | (S)-I-4 | II-6 | II-60 |
| T1s-1452 | (S)-I-4 | II-6 | II-62 |
| T1s-1453 | (S)-I-4 | II-6 | II-66 |
| T1s-1454 | (S)-I-4 | II-6 | II-69 |
| T1s-1455 | (S)-I-4 | II-6 | II-70 |
| T1s-1456 | (S)-I-4 | II-6 | II-71 |
| T1s-1457 | (S)-I-4 | II-6 | II-72 |
| T1s-1458 | (S)-I-4 | II-6 | II-74 |
| T1s-1459 | (S)-I-4 | II-6 | II-76 |
| T1s-1460 | (S)-I-4 | II-6 | II-78 |
| T1s-1461 | (S)-I-4 | II-6 | II-84 |
| T1s-1462 | (S)-I-4 | II-6 | II-85 |
| T1s-1463 | (S)-I-4 | II-6 | II-86 |
| T1s-1464 | (S)-I-4 | II-6 | II-92 |
| T1s-1465 | (S)-I-4 | II-7 | II-8 |
| T1s-1466 | (S)-I-4 | II-7 | II-11 |
| T1s-1467 | (S)-I-4 | II-7 | II-16 |
| T1s-1468 | (S)-I-4 | II-7 | II-21 |
| T1s-1469 | (S)-I-4 | II-7 | II-26 |
| T1s-1470 | (S)-I-4 | II-7 | II-32 |
| T1s-1471 | (S)-I-4 | II-7 | II-33 |
| T1s-1472 | (S)-I-4 | II-7 | II-37 |
| T1s-1473 | (S)-I-4 | II-7 | II-39 |
| T1s-1474 | (S)-I-4 | II-7 | II-42 |
| T1s-1475 | (S)-I-4 | II-7 | II-44 |
| T1s-1476 | (S)-I-4 | II-7 | II-50 |
| T1s-1477 | (S)-I-4 | II-7 | II-53 |
| T1s-1478 | (S)-I-4 | II-7 | II-60 |
| T1s-1479 | (S)-I-4 | II-7 | II-62 |
| T1s-1480 | (S)-I-4 | II-7 | II-66 |
| T1s-1481 | (S)-I-4 | II-7 | II-69 |
| T1s-1482 | (S)-I-4 | II-7 | II-70 |
| T1s-1483 | (S)-I-4 | II-7 | II-71 |
| T1s-1484 | (S)-I-4 | II-7 | II-72 |
| T1s-1485 | (S)-I-4 | II-7 | II-74 |
| T1s-1486 | (S)-I-4 | II-7 | II-76 |
| T1s-1487 | (S)-I-4 | II-7 | II-78 |
| T1s-1488 | (S)-I-4 | II-7 | II-84 |
| T1s-1489 | (S)-I-4 | II-7 | II-85 |
| T1s-1490 | (S)-I-4 | II-7 | II-86 |
| T1s-1491 | (S)-I-4 | II-7 | II-92 |
| T1s-1492 | (S)-I-4 | II-8 | II-11 |
| T1s-1493 | (S)-I-4 | II-8 | II-16 |
| T1s-1494 | (S)-I-4 | II-8 | II-21 |
| T1s-1495 | (S)-I-4 | II-8 | II-26 |
| T1s-1496 | (S)-I-4 | II-8 | II-32 |
| T1s-1497 | (S)-I-4 | II-8 | II-33 |
| T1s-1498 | (S)-I-4 | II-8 | II-37 |
| T1s-1499 | (S)-I-4 | II-8 | II-39 |
| T1s-1500 | (S)-I-4 | II-8 | II-42 |
| T1s-1501 | (S)-I-4 | II-8 | II-44 |
| T1s-1502 | (S)-I-4 | II-8 | II-50 |
| T1s-1503 | (S)-I-4 | II-8 | II-53 |
| T1s-1504 | (S)-I-4 | II-8 | II-60 |
| T1s-1505 | (S)-I-4 | II-8 | II-62 |
| T1s-1506 | (S)-I-4 | II-8 | II-66 |
| T1s-1507 | (S)-I-4 | II-8 | II-69 |
| T1s-1508 | (S)-I-4 | II-8 | II-70 |
| T1s-1509 | (S)-I-4 | II-8 | II-71 |
| T1s-1510 | (S)-I-4 | II-8 | II-72 |
| T1s-1511 | (S)-I-4 | II-8 | II-74 |
| T1s-1512 | (S)-I-4 | II-8 | II-76 |
| T1s-1513 | (S)-I-4 | II-8 | II-78 |
| T1s-1514 | (S)-I-4 | II-8 | II-84 |
| T1s-1515 | (S)-I-4 | II-8 | II-85 |
| T1s-1516 | (S)-I-4 | II-8 | II-86 |
| T1s-1517 | (S)-I-4 | II-8 | II-92 |
| T1s-1518 | (S)-I-4 | II-11 | II-16 |
| T1s-1519 | (S)-I-4 | II-11 | II-21 |
| T1s-1520 | (S)-I-4 | II-11 | II-26 |
| T1s-1521 | (S)-I-4 | II-11 | II-32 |
| T1s-1522 | (S)-I-4 | II-11 | II-33 |
| T1s-1523 | (S)-I-4 | II-11 | II-37 |
| T1s-1524 | (S)-I-4 | II-11 | II-39 |
| T1s-1525 | (S)-I-4 | II-11 | II-42 |
| T1s-1526 | (S)-I-4 | II-11 | II-44 |
| T1s-1527 | (S)-I-4 | II-11 | II-50 |
| T1s-1528 | (S)-I-4 | II-11 | II-53 |
| T1s-1529 | (S)-I-4 | II-11 | II-60 |
| T1s-1530 | (S)-I-4 | II-11 | II-62 |
| T1s-1531 | (S)-I-4 | II-11 | II-66 |

TABLE T1s-continued

Three-component compositions comprising one component I as (S) enantiomer (appreviated as (S)-I, e.g. (S)-I-1 for the (S)-enantiomer of I-1), one component II and one component III, in particular ternary compositions containing the respective component I as (S) enantiomer, II and III as only active ingredients.

| composition | (S)-I | II | III |
|---|---|---|---|
| T1s-1532 | (S)-I-4 | II-11 | II-69 |
| T1s-1533 | (S)-I-4 | II-11 | II-70 |
| T1s-1534 | (S)-I-4 | II-11 | II-71 |
| T1s-1535 | (S)-I-4 | II-11 | II-72 |
| T1s-1536 | (S)-I-4 | II-11 | II-74 |
| T1s-1537 | (S)-I-4 | II-11 | II-76 |
| T1s-1538 | (S)-I-4 | II-11 | II-78 |
| T1s-1539 | (S)-I-4 | II-11 | II-84 |
| T1s-1540 | (S)-I-4 | II-11 | II-85 |
| T1s-1541 | (S)-I-4 | II-11 | II-86 |
| T1s-1542 | (S)-I-4 | II-11 | II-92 |
| T1s-1543 | (S)-I-4 | II-16 | II-21 |
| T1s-1544 | (S)-I-4 | II-16 | II-26 |
| T1s-1545 | (S)-I-4 | II-16 | II-32 |
| T1s-1546 | (S)-I-4 | II-16 | II-33 |
| T1s-1547 | (S)-I-4 | II-16 | II-37 |
| T1s-1548 | (S)-I-4 | II-16 | II-39 |
| T1s-1549 | (S)-I-4 | II-16 | II-42 |
| T1s-1550 | (S)-I-4 | II-16 | II-44 |
| T1s-1551 | (S)-I-4 | II-16 | II-50 |
| T1s-1552 | (S)-I-4 | II-16 | II-53 |
| T1s-1553 | (S)-I-4 | II-16 | II-60 |
| T1s-1554 | (S)-I-4 | II-16 | II-62 |
| T1s-1555 | (S)-I-4 | II-16 | II-66 |
| T1s-1556 | (S)-I-4 | II-16 | II-69 |
| T1s-1557 | (S)-I-4 | II-16 | II-70 |
| T1s-1558 | (S)-I-4 | II-16 | II-71 |
| T1s-1559 | (S)-I-4 | II-16 | II-72 |
| T1s-1560 | (S)-I-4 | II-16 | II-74 |
| T1s-1561 | (S)-I-4 | II-16 | II-76 |
| T1s-1562 | (S)-I-4 | II-16 | II-78 |
| T1s-1563 | (S)-I-4 | II-16 | II-84 |
| T1s-1564 | (S)-I-4 | II-16 | II-85 |
| T1s-1565 | (S)-I-4 | II-16 | II-86 |
| T1s-1566 | (S)-I-4 | II-16 | II-92 |
| T1s-1567 | (S)-I-4 | II-21 | II-26 |
| T1s-1568 | (S)-I-4 | II-21 | II-32 |
| T1s-1569 | (S)-I-4 | II-21 | II-33 |
| T1s-1570 | (S)-I-4 | II-21 | II-37 |
| T1s-1571 | (S)-I-4 | II-21 | II-39 |
| T1s-1572 | (S)-I-4 | II-21 | II-42 |
| T1s-1573 | (S)-I-4 | II-21 | II-44 |
| T1s-1574 | (S)-I-4 | II-21 | II-50 |
| T1s-1575 | (S)-I-4 | II-21 | II-53 |
| T1s-1576 | (S)-I-4 | II-21 | II-60 |
| T1s-1577 | (S)-I-4 | II-21 | II-62 |
| T1s-1578 | (S)-I-4 | II-21 | II-66 |
| T1s-1579 | (S)-I-4 | II-21 | II-69 |
| T1s-1580 | (S)-I-4 | II-21 | II-70 |
| T1s-1581 | (S)-I-4 | II-21 | II-71 |
| T1s-1582 | (S)-I-4 | II-21 | II-72 |
| T1s-1583 | (S)-I-4 | II-21 | II-74 |
| T1s-1584 | (S)-I-4 | II-21 | II-76 |
| T1s-1585 | (S)-I-4 | II-21 | II-78 |
| T1s-1586 | (S)-I-4 | II-21 | II-84 |
| T1s-1587 | (S)-I-4 | II-21 | II-85 |
| T1s-1588 | (S)-I-4 | II-21 | II-86 |
| T1s-1589 | (S)-I-4 | II-21 | II-92 |
| T1s-1590 | (S)-I-4 | II-26 | N-32 |
| T1s-1591 | (S)-I-4 | II-26 | II-33 |
| T1s-1592 | (S)-I-4 | II-26 | II-37 |
| T1s-1593 | (S)-I-4 | II-26 | II-39 |
| T1s-1594 | (S)-I-4 | II-26 | II-42 |
| T1s-1595 | (S)-I-4 | II-26 | II-44 |
| T1s-1596 | (S)-I-4 | II-26 | II-50 |
| T1s-1597 | (S)-I-4 | II-26 | II-53 |
| T1s-1598 | (S)-I-4 | II-26 | II-60 |
| T1s-1599 | (S)-I-4 | II-26 | II-62 |
| T1s-1600 | (S)-I-4 | II-26 | II-66 |
| T1s-1601 | (S)-I-4 | II-26 | II-69 |
| T1s-1602 | (S)-I-4 | II-26 | II-70 |
| T1s-1603 | (S)-I-4 | II-26 | II-71 |
| T1s-1604 | (S)-I-4 | II-26 | II-72 |
| T1s-1605 | (S)-I-4 | II-26 | II-74 |
| T1s-1606 | (S)-I-4 | II-26 | II-76 |
| T1s-1607 | (S)-I-4 | II-26 | II-78 |
| T1s-1608 | (S)-I-4 | II-26 | II-84 |
| T1s-1609 | (S)-I-4 | II-26 | II-85 |
| T1s-1610 | (S)-I-4 | II-26 | II-86 |
| T1s-1611 | (S)-I-4 | II-26 | II-92 |
| T1s-1612 | (S)-I-4 | II-32 | II-33 |
| T1s-1613 | (S)-I-4 | II-32 | II-37 |
| T1s-1614 | (S)-I-4 | II-32 | II-39 |
| T1s-1615 | (S)-I-4 | II-32 | II-42 |
| T1s-1616 | (S)-I-4 | II-32 | II-44 |
| T1s-1617 | (S)-I-4 | II-32 | II-50 |
| T1s-1618 | (S)-I-4 | II-32 | II-53 |
| T1s-1619 | (S)-I-4 | II-32 | II-60 |
| T1s-1620 | (S)-I-4 | II-32 | II-62 |
| T1s-1621 | (S)-I-4 | II-32 | II-66 |
| T1s-1622 | (S)-I-4 | II-32 | II-69 |
| T1s-1623 | (S)-I-4 | II-32 | II-70 |
| T1s-1624 | (S)-I-4 | II-32 | II-71 |
| T1s-1625 | (S)-I-4 | II-32 | II-72 |
| T1s-1626 | (S)-I-4 | II-32 | II-74 |
| T1s-1627 | (S)-I-4 | II-32 | II-76 |
| T1s-1628 | (S)-I-4 | II-32 | II-78 |
| T1s-1629 | (S)-I-4 | II-32 | II-84 |
| T1s-1630 | (S)-I-4 | II-32 | II-85 |
| T1s-1631 | (S)-I-4 | II-32 | II-86 |
| T1s-1632 | (S)-I-4 | II-32 | II-92 |
| T1s-1633 | (S)-I-4 | II-33 | II-37 |
| T1s-1634 | (S)-I-4 | II-33 | II-39 |
| T1s-1635 | (S)-I-4 | II-33 | II-42 |
| T1s-1636 | (S)-I-4 | II-33 | II-44 |
| T1s-1637 | (S)-I-4 | II-33 | II-50 |
| T1s-1638 | (S)-I-4 | II-33 | II-53 |
| T1s-1639 | (S)-I-4 | II-33 | II-60 |
| T1s-1640 | (S)-I-4 | II-33 | II-62 |
| T1s-1641 | (S)-I-4 | II-33 | II-66 |
| T1s-1642 | (S)-I-4 | II-33 | II-69 |
| T1s-1643 | (S)-I-4 | II-33 | II-70 |
| T1s-1644 | (S)-I-4 | II-33 | II-71 |
| T1s-1645 | (S)-I-4 | II-33 | II-72 |
| T1s-1646 | (S)-I-4 | II-33 | II-74 |
| T1s-1647 | (S)-I-4 | II-33 | II-76 |
| T1s-1648 | (S)-I-4 | II-33 | II-78 |
| T1s-1649 | (S)-I-4 | II-33 | II-84 |
| T1s-1650 | (S)-I-4 | II-33 | II-85 |
| T1s-1651 | (S)-I-4 | II-33 | II-86 |
| T1s-1652 | (S)-I-4 | II-33 | II-92 |
| T1s-1653 | (S)-I-4 | II-37 | II-39 |
| T1s-1654 | (S)-I-4 | II-37 | II-42 |
| T1s-1655 | (S)-I-4 | II-37 | II-44 |
| T1s-1656 | (S)-I-4 | II-37 | II-50 |
| T1s-1657 | (S)-I-4 | II-37 | II-53 |
| T1s-1658 | (S)-I-4 | II-37 | II-60 |
| T1s-1659 | (S)-I-4 | II-37 | II-62 |
| T1s-1660 | (S)-I-4 | II-37 | II-66 |
| T1s-1661 | (S)-I-4 | II-37 | II-69 |
| T1s-1662 | (S)-I-4 | II-37 | II-70 |
| T1s-1663 | (S)-I-4 | II-37 | II-71 |
| T1s-1664 | (S)-I-4 | II-37 | II-72 |
| T1s-1665 | (S)-I-4 | II-37 | II-74 |
| T1s-1666 | (S)-I-4 | II-37 | II-76 |
| T1s-1667 | (S)-I-4 | II-37 | II-78 |
| T1s-1668 | (S)-I-4 | II-37 | II-84 |
| T1s-1669 | (S)-I-4 | II-37 | II-85 |
| T1s-1670 | (S)-I-4 | II-37 | II-86 |
| T1s-1671 | (S)-I-4 | II-37 | II-92 |
| T1s-1672 | (S)-I-4 | II-39 | II-42 |
| T1s-1673 | (S)-I-4 | II-39 | II-44 |
| T1s-1674 | (S)-I-4 | II-39 | II-50 |
| T1s-1675 | (S)-I-4 | II-39 | II-53 |

TABLE T1s-continued

Three-component compositions comprising one component I as (S) enantiomer (appreviated as (S)-I, e.g. (S)-I-1 for the (S)-enantiomer of I-1), one component II and one component III, in particular ternary compositions containing the respective component I as (S) enantiomer, II and III as only active ingredients.

| composition | (S)-I | II | III |
| --- | --- | --- | --- |
| T1s-1676 | (S)-I-4 | II-39 | II-60 |
| T1s-1677 | (S)-I-4 | II-39 | II-62 |
| T1s-1678 | (S)-I-4 | II-39 | II-66 |
| T1s-1679 | (S)-I-4 | II-39 | II-69 |
| T1s-1680 | (S)-I-4 | II-39 | II-70 |
| T1s-1681 | (S)-I-4 | II-39 | II-71 |
| T1s-1682 | (S)-I-4 | II-39 | II-72 |
| T1s-1683 | (S)-I-4 | II-39 | II-74 |
| T1s-1684 | (S)-I-4 | II-39 | II-76 |
| T1s-1685 | (S)-I-4 | II-39 | II-78 |
| T1s-1686 | (S)-I-4 | II-39 | II-84 |
| T1s-1687 | (S)-I-4 | II-39 | II-85 |
| T1s-1688 | (S)-I-4 | II-39 | II-86 |
| T1s-1689 | (S)-I-4 | II-39 | II-92 |
| T1s-1690 | (S)-I-4 | II-42 | II-44 |
| T1s-1691 | (S)-I-4 | II-42 | II-50 |
| T1s-1692 | (S)-I-4 | II-42 | II-53 |
| T1s-1693 | (S)-I-4 | II-42 | II-60 |
| T1s-1694 | (S)-I-4 | II-42 | II-62 |
| T1s-1695 | (S)-I-4 | II-42 | II-66 |
| T1s-1696 | (S)-I-4 | II-42 | II-69 |
| T1s-1697 | (S)-I-4 | II-42 | II-70 |
| T1s-1698 | (S)-I-4 | II-42 | II-71 |
| T1s-1699 | (S)-I-4 | II-42 | II-72 |
| T1s-1700 | (S)-I-4 | II-42 | II-74 |
| T1s-1701 | (S)-I-4 | II-42 | II-76 |
| T1s-1702 | (S)-I-4 | II-42 | II-78 |
| T1s-1703 | (S)-I-4 | II-42 | II-84 |
| T1s-1704 | (S)-I-4 | II-42 | II-85 |
| T1s-1705 | (S)-I-4 | II-42 | II-86 |
| T1s-1706 | (S)-I-4 | II-42 | II-92 |
| T1s-1707 | (S)-I-4 | II-44 | II-50 |
| T1s-1708 | (S)-I-4 | II-44 | II-53 |
| T1s-1709 | (S)-I-4 | II-44 | II-60 |
| T1s-1710 | (S)-I-4 | II-44 | II-62 |
| T1s-1711 | (S)-I-4 | II-44 | II-66 |
| T1s-1712 | (S)-I-4 | II-44 | II-69 |
| T1s-1713 | (S)-I-4 | II-44 | II-70 |
| T1s-1714 | (S)-I-4 | II-44 | II-71 |
| T1s-1715 | (S)-I-4 | II-44 | II-72 |
| T1s-1716 | (S)-I-4 | II-44 | II-74 |
| T1s-1717 | (S)-I-4 | II-44 | II-76 |
| T1s-1718 | (S)-I-4 | II-44 | II-78 |
| T1s-1719 | (S)-I-4 | II-44 | II-84 |
| T1s-1720 | (S)-I-4 | II-44 | II-85 |
| T1s-1721 | (S)-I-4 | II-44 | II-86 |
| T1s-1722 | (S)-I-4 | II-44 | II-92 |
| T1s-1723 | (S)-I-4 | II-50 | II-53 |
| T1s-1724 | (S)-I-4 | II-50 | II-60 |
| T1s-1725 | (S)-I-4 | II-50 | II-62 |
| T1s-1726 | (S)-I-4 | II-50 | II-66 |
| T1s-1727 | (S)-I-4 | II-50 | II-69 |
| T1s-1728 | (S)-I-4 | II-50 | II-70 |
| T1s-1729 | (S)-I-4 | II-50 | II-71 |
| T1s-1730 | (S)-I-4 | II-50 | II-72 |
| T1s-1731 | (S)-I-4 | II-50 | II-74 |
| T1s-1732 | (S)-I-4 | II-50 | II-76 |
| T1s-1733 | (S)-I-4 | II-50 | II-78 |
| T1s-1734 | (S)-I-4 | II-50 | II-84 |
| T1s-1735 | (S)-I-4 | II-50 | II-85 |
| T1s-1736 | (S)-I-4 | II-50 | II-86 |
| T1s-1737 | (S)-I-4 | II-50 | II-92 |
| T1s-1738 | (S)-I-4 | II-53 | II-60 |
| T1s-1739 | (S)-I-4 | II-53 | II-62 |
| T1s-1740 | (S)-I-4 | II-53 | II-66 |
| T1s-1741 | (S)-I-4 | II-53 | II-69 |
| T1s-1742 | (S)-I-4 | II-53 | II-70 |
| T1s-1743 | (S)-I-4 | II-53 | II-71 |
| T1s-1744 | (S)-I-4 | II-53 | II-72 |
| T1s-1745 | (S)-I-4 | II-53 | II-74 |
| T1s-1746 | (S)-I-4 | II-53 | II-76 |
| T1s-1747 | (S)-I-4 | II-53 | II-78 |
| T1s-1748 | (S)-I-4 | II-53 | II-84 |
| T1s-1749 | (S)-I-4 | II-53 | II-85 |
| T1s-1750 | (S)-I-4 | II-53 | II-86 |
| T1s-1751 | (S)-I-4 | II-53 | II-92 |
| T1s-1752 | (S)-I-4 | II-60 | II-62 |
| T1s-1753 | (S)-I-4 | II-60 | II-66 |
| T1s-1754 | (S)-I-4 | II-60 | II-69 |
| T1s-1755 | (S)-I-4 | II-60 | II-70 |
| T1s-1756 | (S)-I-4 | II-60 | II-71 |
| T1s-1757 | (S)-I-4 | II-60 | II-72 |
| T1s-1758 | (S)-I-4 | II-60 | II-74 |
| T1s-1759 | (S)-I-4 | II-60 | II-76 |
| T1s-1760 | (S)-I-4 | II-60 | II-78 |
| T1s-1761 | (S)-I-4 | II-60 | II-84 |
| T1s-1762 | (S)-I-4 | II-60 | II-85 |
| T1s-1763 | (S)-I-4 | II-60 | II-86 |
| T1s-1764 | (S)-I-4 | II-60 | II-92 |
| T1s-1765 | (S)-I-4 | II-62 | II-66 |
| T1s-1766 | (S)-I-4 | II-62 | II-69 |
| T1s-1767 | (S)-I-4 | II-62 | II-70 |
| T1s-1768 | (S)-I-4 | II-62 | II-71 |
| T1s-1769 | (S)-I-4 | II-62 | II-72 |
| T1s-1770 | (S)-I-4 | II-62 | II-74 |
| T1s-1771 | (S)-I-4 | II-62 | II-76 |
| T1s-1772 | (S)-I-4 | II-62 | II-78 |
| T1s-1773 | (S)-I-4 | II-62 | II-84 |
| T1s-1774 | (S)-I-4 | II-62 | II-85 |
| T1s-1775 | (S)-I-4 | II-62 | II-86 |
| T1s-1776 | (S)-I-4 | II-62 | II-92 |
| T1s-1777 | (S)-I-4 | II-66 | N-69 |
| T1s-1778 | (S)-I-4 | II-66 | II-70 |
| T1s-1779 | (S)-I-4 | II-66 | II-71 |
| T1s-1780 | (S)-I-4 | II-66 | II-72 |
| T1s-1781 | (S)-I-4 | II-66 | II-74 |
| T1s-1782 | (S)-I-4 | II-66 | II-76 |
| T1s-1783 | (S)-I-4 | II-66 | II-78 |
| T1s-1784 | (S)-I-4 | II-66 | II-84 |
| T1s-1785 | (S)-I-4 | II-66 | II-85 |
| T1s-1786 | (S)-I-4 | II-66 | II-86 |
| T1s-1787 | (S)-I-4 | II-66 | II-92 |
| T1s-1788 | (S)-I-4 | II-69 | II-70 |
| T1s-1789 | (S)-I-4 | II-69 | II-71 |
| T1s-1790 | (S)-I-4 | II-69 | II-72 |
| T1s-1791 | (S)-I-4 | II-69 | II-74 |
| T1s-1792 | (S)-I-4 | II-69 | II-76 |
| T1s-1793 | (S)-I-4 | II-69 | II-78 |
| T1s-1794 | (S)-I-4 | II-69 | II-84 |
| T1s-1795 | (S)-I-4 | II-69 | II-85 |
| T1s-1796 | (S)-I-4 | II-69 | II-86 |
| T1s-1797 | (S)-I-4 | II-69 | II-92 |
| T1s-1798 | (S)-I-4 | II-70 | II-71 |
| T1s-1799 | (S)-I-4 | II-70 | II-72 |
| T1s-1800 | (S)-I-4 | II-70 | II-74 |
| T1s-1801 | (S)-I-4 | II-70 | II-76 |
| T1s-1802 | (S)-I-4 | II-70 | II-78 |
| T1s-1803 | (S)-I-4 | II-70 | II-84 |
| T1s-1804 | (S)-I-4 | II-70 | II-85 |
| T1s-1805 | (S)-I-4 | II-70 | II-86 |
| T1s-1806 | (S)-I-4 | II-70 | II-92 |
| T1s-1807 | (S)-I-4 | II-71 | II-72 |
| T1s-1808 | (S)-I-4 | II-71 | II-74 |
| T1s-1809 | (S)-I-4 | II-71 | II-76 |
| T1s-1810 | (S)-I-4 | II-71 | II-78 |
| T1s-1811 | (S)-I-4 | II-71 | II-84 |
| T1s-1812 | (S)-I-4 | II-71 | II-85 |
| T1s-1813 | (S)-I-4 | II-71 | II-86 |
| T1s-1814 | (S)-I-4 | II-71 | II-92 |
| T1s-1815 | (S)-I-4 | II-72 | II-74 |
| T1s-1816 | (S)-I-4 | II-74 | II-76 |
| T1s-1817 | (S)-I-4 | II-74 | II-78 |
| T1s-1818 | (S)-I-4 | II-74 | II-84 |
| T1s-1819 | (S)-I-4 | II-74 | II-85 |

TABLE T1s-continued

Three-component compositions comprising one component I as (S) enantiomer (appreviated as (S)-I, e.g. (S)-I-1 for the (S)-enantiomer of I-1), one component II and one component III, in particular ternary compositions containing the respective component I as (S) enantiomer, II and III as only active ingredients.

| composition | (S)-I | II | III |
|---|---|---|---|
| T1s-1820 | (S)-I-4 | II-74 | II-86 |
| T1s-1821 | (S)-I-4 | II-74 | II-92 |
| T1s-1822 | (S)-I-4 | II-76 | II-78 |
| T1s-1823 | (S)-I-4 | II-76 | II-84 |
| T1s-1824 | (S)-I-4 | II-76 | II-85 |
| T1s-1825 | (S)-I-4 | II-76 | II-86 |
| T1s-1826 | (S)-I-4 | II-76 | II-92 |
| T1s-1827 | (S)-I-4 | II-78 | II-84 |
| T1s-1828 | (S)-I-4 | II-78 | II-85 |
| T1s-1829 | (S)-I-4 | II-78 | II-86 |
| T1s-1830 | (S)-I-4 | II-78 | II-92 |
| T1s-1831 | (S)-I-4 | II-84 | II-85 |
| T1s-1832 | (S)-I-4 | II-84 | II-86 |
| T1s-1833 | (S)-I-4 | II-84 | II-92 |
| T1s-1834 | (S)-I-4 | II-85 | II-86 |
| T1s-1835 | (S)-I-4 | II-85 | II-92 |
| T1s-1836 | (S)-I-4 | II-86 | II-92 |
| T1s-1837 | (S)-I-13 | II-3 | II-5 |
| T1s-1838 | (S)-I-13 | II-3 | II-6 |
| T1s-1839 | (S)-I-13 | II-3 | II-7 |
| T1s-1840 | (S)-I-13 | II-3 | II-8 |
| T1s-1841 | (S)-I-13 | II-3 | II-11 |
| T1s-1842 | (S)-I-13 | II-3 | II-16 |
| T1s-1843 | (S)-I-13 | II-3 | II-21 |
| T1s-1844 | (S)-I-13 | II-3 | II-26 |
| T1s-1845 | (S)-I-13 | II-3 | II-32 |
| T1s-1846 | (S)-I-13 | II-3 | II-33 |
| T1s-1847 | (S)-I-13 | II-3 | II-37 |
| T1s-1848 | (S)-I-13 | II-3 | II-39 |
| T1s-1849 | (S)-I-13 | II-3 | II-42 |
| T1s-1850 | (S)-I-13 | II-3 | II-44 |
| T1s-1851 | (S)-I-13 | II-3 | II-50 |
| T1s-1852 | (S)-I-13 | II-3 | II-53 |
| T1s-1853 | (S)-I-13 | II-3 | II-60 |
| T1s-1854 | (S)-I-13 | II-3 | II-62 |
| T1s-1855 | (S)-I-13 | II-3 | II-66 |
| T1s-1856 | (S)-I-13 | II-3 | II-69 |
| T1s-1857 | (S)-I-13 | II-3 | II-70 |
| T1s-1858 | (S)-I-13 | II-3 | II-71 |
| T1s-1859 | (S)-I-13 | II-3 | II-72 |
| T1s-1860 | (S)-I-13 | II-3 | II-74 |
| T1s-1861 | (S)-I-13 | II-3 | II-76 |
| T1s-1862 | (S)-I-13 | II-3 | II-78 |
| T1s-1863 | (S)-I-13 | II-3 | II-84 |
| T1s-1864 | (S)-I-13 | II-3 | II-85 |
| T1s-1865 | (S)-I-13 | II-3 | II-86 |
| T1s-1866 | (S)-I-13 | II-3 | II-92 |
| T1s-1867 | (S)-I-13 | II-5 | II-6 |
| T1s-1868 | (S)-I-13 | II-5 | II-7 |
| T1s-1869 | (S)-I-13 | II-5 | II-8 |
| T1s-1870 | (S)-I-13 | II-5 | II-11 |
| T1s-1871 | (S)-I-13 | II-5 | II-16 |
| T1s-1872 | (S)-I-13 | II-5 | II-21 |
| T1s-1873 | (S)-I-13 | II-5 | II-26 |
| T1s-1874 | (S)-I-13 | II-5 | II-32 |
| T1s-1875 | (S)-I-13 | II-5 | II-33 |
| T1s-1876 | (S)-I-13 | II-5 | II-37 |
| T1s-1877 | (S)-I-13 | II-5 | II-39 |
| T1s-1878 | (S)-I-13 | II-5 | II-42 |
| T1s-1879 | (S)-I-13 | II-5 | II-44 |
| T1s-1880 | (S)-I-13 | II-5 | II-50 |
| T1s-1881 | (S)-I-13 | II-5 | II-53 |
| T1s-1882 | (S)-I-13 | II-5 | II-60 |
| T1s-1883 | (S)-I-13 | II-5 | II-62 |
| T1s-1884 | (S)-I-13 | II-5 | II-66 |
| T1s-1885 | (S)-I-13 | II-5 | II-69 |
| T1s-1886 | (S)-I-13 | II-5 | II-70 |
| T1s-1887 | (S)-I-13 | II-5 | II-71 |
| T1s-1888 | (S)-I-13 | II-5 | II-72 |
| T1s-1889 | (S)-I-13 | II-5 | II-74 |
| T1s-1890 | (S)-I-13 | II-5 | II-76 |
| T1s-1891 | (S)-I-13 | II-5 | II-78 |
| T1s-1892 | (S)-I-13 | II-5 | II-84 |
| T1s-1893 | (S)-I-13 | II-5 | II-85 |
| T1s-1894 | (S)-I-13 | II-5 | II-86 |
| T1s-1895 | (S)-I-13 | II-5 | II-92 |
| T1s-1896 | (S)-I-13 | II-6 | II-7 |
| T1s-1897 | (S)-I-13 | II-6 | II-8 |
| T1s-1898 | (S)-I-13 | II-6 | II-11 |
| T1s-1899 | (S)-I-13 | II-6 | II-16 |
| T1s-1900 | (S)-I-13 | II-6 | II-21 |
| T1s-1901 | (S)-I-13 | II-6 | II-26 |
| T1s-1902 | (S)-I-13 | II-6 | II-32 |
| T1s-1903 | (S)-I-13 | II-6 | II-33 |
| T1s-1904 | (S)-I-13 | II-6 | II-37 |
| T1s-1905 | (S)-I-13 | II-6 | II-39 |
| T1s-1906 | (S)-I-13 | II-6 | II-42 |
| T1s-1907 | (S)-I-13 | II-6 | II-44 |
| T1s-1908 | (S)-I-13 | II-6 | II-50 |
| T1s-1909 | (S)-I-13 | II-6 | II-53 |
| T1s-1910 | (S)-I-13 | II-6 | II-60 |
| T1s-1911 | (S)-I-13 | II-6 | II-62 |
| T1s-1912 | (S)-I-13 | II-6 | II-66 |
| T1s-1913 | (S)-I-13 | II-6 | II-69 |
| T1s-1914 | (S)-I-13 | II-6 | II-70 |
| T1s-1915 | (S)-I-13 | II-6 | II-71 |
| T1s-1916 | (S)-I-13 | II-6 | II-72 |
| T1s-1917 | (S)-I-13 | II-6 | II-74 |
| T1s-1918 | (S)-I-13 | II-6 | II-76 |
| T1s-1919 | (S)-I-13 | II-6 | II-78 |
| T1s-1920 | (S)-I-13 | II-6 | II-84 |
| T1s-1921 | (S)-I-13 | II-6 | II-85 |
| T1s-1922 | (S)-I-13 | II-6 | II-86 |
| T1s-1923 | (S)-I-13 | II-6 | II-92 |
| T1s-1924 | (S)-I-13 | II-7 | II-8 |
| T1s-1925 | (S)-I-13 | II-7 | II-11 |
| T1s-1926 | (S)-I-13 | II-7 | II-16 |
| T1s-1927 | (S)-I-13 | II-7 | II-21 |
| T1s-1928 | (S)-I-13 | II-7 | II-26 |
| T1s-1929 | (S)-I-13 | II-7 | II-32 |
| T1s-1930 | (S)-I-13 | II-7 | II-33 |
| T1s-1931 | (S)-I-13 | II-7 | II-37 |
| T1s-1932 | (S)-I-13 | II-7 | II-39 |
| T1s-1933 | (S)-I-13 | II-7 | II-42 |
| T1s-1934 | (S)-I-13 | II-7 | II-44 |
| T1s-1935 | (S)-I-13 | II-7 | II-50 |
| T1s-1936 | (S)-I-13 | II-7 | II-53 |
| T1s-1937 | (S)-I-13 | II-7 | II-60 |
| T1s-1938 | (S)-I-13 | II-7 | II-62 |
| T1s-1939 | (S)-I-13 | II-7 | II-66 |
| T1s-1940 | (S)-I-13 | II-7 | II-69 |
| T1s-1941 | (S)-I-13 | II-7 | II-70 |
| T1s-1942 | (S)-I-13 | II-7 | II-71 |
| T1s-1943 | (S)-I-13 | II-7 | II-72 |
| T1s-1944 | (S)-I-13 | II-7 | II-74 |
| T1s-1945 | (S)-I-13 | II-7 | II-76 |
| T1s-1946 | (S)-I-13 | II-7 | II-78 |
| T1s-1947 | (S)-I-13 | II-7 | II-84 |
| T1s-1948 | (S)-I-13 | II-7 | II-85 |
| T1s-1949 | (S)-I-13 | II-7 | II-86 |
| T1s-1950 | (S)-I-13 | II-7 | II-92 |
| T1s-1951 | (S)-I-13 | II-8 | II-11 |
| T1s-1952 | (S)-I-13 | II-8 | II-16 |
| T1s-1953 | (S)-I-13 | II-8 | II-21 |
| T1s-1954 | (S)-I-13 | II-8 | II-26 |
| T1s-1955 | (S)-I-13 | II-8 | II-32 |
| T1s-1956 | (S)-I-13 | II-8 | II-33 |
| T1s-1957 | (S)-I-13 | II-8 | II-37 |
| T1s-1958 | (S)-I-13 | II-8 | II-39 |
| T1s-1959 | (S)-I-13 | II-8 | II-42 |
| T1s-1960 | (S)-I-13 | II-8 | II-44 |
| T1s-1961 | (S)-I-13 | II-8 | II-50 |
| T1s-1962 | (S)-I-13 | II-8 | II-53 |
| T1s-1963 | (S)-I-13 | II-8 | II-60 |

TABLE T1s-continued

Three-component compositions comprising one component I as (S) enantiomer (appreviated as (S)-I, e.g. (S)-I-1 for the (S)-enantiomer of I-1), one component II and one component III, in particular ternary compositions containing the respective component I as (S) enantiomer, II and III as only active ingredients.

| composition | (S)-I | II | III |
|---|---|---|---|
| T1s-1964 | (S)-I-13 | II-8 | II-62 |
| T1s-1965 | (S)-I-13 | II-8 | II-66 |
| T1s-1966 | (S)-I-13 | II-8 | II-69 |
| T1s-1967 | (S)-I-13 | II-8 | II-70 |
| T1s-1968 | (S)-I-13 | II-8 | II-71 |
| T1s-1969 | (S)-I-13 | II-8 | II-72 |
| T1s-1970 | (S)-I-13 | II-8 | II-74 |
| T1s-1971 | (S)-I-13 | II-8 | II-76 |
| T1s-1972 | (S)-I-13 | II-8 | II-78 |
| T1s-1973 | (S)-I-13 | II-8 | II-84 |
| T1s-1974 | (S)-I-13 | II-8 | II-85 |
| T1s-1975 | (S)-I-13 | II-8 | II-86 |
| T1s-1976 | (S)-I-13 | II-8 | II-92 |
| T1s-1977 | (S)-I-13 | II-11 | II-16 |
| T1s-1978 | (S)-I-13 | II-11 | II-21 |
| T1s-1979 | (S)-I-13 | II-11 | II-26 |
| T1s-1980 | (S)-I-13 | II-11 | II-32 |
| T1s-1981 | (S)-I-13 | II-11 | II-33 |
| T1s-1982 | (S)-I-13 | II-11 | II-37 |
| T1s-1983 | (S)-I-13 | II-11 | II-39 |
| T1s-1984 | (S)-I-13 | II-11 | II-42 |
| T1s-1985 | (S)-I-13 | II-11 | II-44 |
| T1s-1986 | (S)-I-13 | II-11 | II-50 |
| T1s-1987 | (S)-I-13 | II-11 | II-53 |
| T1s-1988 | (S)-I-13 | II-11 | II-60 |
| T1s-1989 | (S)-I-13 | II-11 | II-62 |
| T1s-1990 | (S)-I-13 | II-11 | II-66 |
| T1s-1991 | (S)-I-13 | II-11 | II-69 |
| T1s-1992 | (S)-I-13 | II-11 | II-70 |
| T1s-1993 | (S)-I-13 | II-11 | II-71 |
| T1s-1994 | (S)-I-13 | II-11 | II-72 |
| T1s-1995 | (S)-I-13 | II-11 | II-74 |
| T1s-1996 | (S)-I-13 | II-11 | II-76 |
| T1s-1997 | (S)-I-13 | II-11 | II-78 |
| T1s-1998 | (S)-I-13 | II-11 | II-84 |
| T1s-1999 | (S)-I-13 | II-11 | II-85 |
| T1s-2000 | (S)-I-13 | II-11 | II-86 |
| T1s-2001 | (S)-I-13 | II-11 | II-92 |
| T1s-2002 | (S)-I-13 | II-16 | II-21 |
| T1s-2003 | (S)-I-13 | II-16 | II-26 |
| T1s-2004 | (S)-I-13 | II-16 | II-32 |
| T1s-2005 | (S)-I-13 | II-16 | II-33 |
| T1s-2006 | (S)-I-13 | II-16 | II-37 |
| T1s-2007 | (S)-I-13 | II-16 | II-39 |
| T1s-2008 | (S)-I-13 | II-16 | II-42 |
| T1s-2009 | (S)-I-13 | II-16 | II-44 |
| T1s-2010 | (S)-I-13 | II-16 | II-50 |
| T1s-2011 | (S)-I-13 | II-16 | II-53 |
| T1s-2012 | (S)-I-13 | II-16 | II-60 |
| T1s-2013 | (S)-I-13 | II-16 | II-62 |
| T1s-2014 | (S)-I-13 | II-16 | II-66 |
| T1s-2015 | (S)-I-13 | II-16 | II-69 |
| T1s-2016 | (S)-I-13 | II-16 | II-70 |
| T1s-2017 | (S)-I-13 | II-16 | II-71 |
| T1s-2018 | (S)-I-13 | II-16 | II-72 |
| T1s-2019 | (S)-I-13 | II-16 | II-74 |
| T1s-2020 | (S)-I-13 | II-16 | II-76 |
| T1s-2021 | (S)-I-13 | II-16 | II-78 |
| T1s-2022 | (S)-I-13 | II-16 | II-84 |
| T1s-2023 | (S)-I-13 | II-16 | II-85 |
| T1s-2024 | (S)-I-13 | II-16 | II-86 |
| T1s-2025 | (S)-I-13 | II-16 | II-92 |
| T1s-2026 | (S)-I-13 | II-21 | II-26 |
| T1s-2027 | (S)-I-13 | II-21 | II-32 |
| T1s-2028 | (S)-I-13 | II-21 | II-33 |
| T1s-2029 | (S)-I-13 | II-21 | II-37 |
| T1s-2030 | (S)-I-13 | II-21 | II-39 |
| T1s-2031 | (S)-I-13 | II-21 | II-42 |
| T1s-2032 | (S)-I-13 | II-21 | II-44 |
| T1s-2033 | (S)-I-13 | II-21 | II-50 |
| T1s-2034 | (S)-I-13 | II-21 | II-53 |
| T1s-2035 | (S)-I-13 | II-21 | II-60 |
| T1s-2036 | (S)-I-13 | II-21 | II-62 |
| T1s-2037 | (S)-I-13 | II-21 | II-66 |
| T1s-2038 | (S)-I-13 | II-21 | II-69 |
| T1s-2039 | (S)-I-13 | II-21 | II-70 |
| T1s-2040 | (S)-I-13 | II-21 | II-71 |
| T1s-2041 | (S)-I-13 | II-21 | II-72 |
| T1s-2042 | (S)-I-13 | II-21 | II-74 |
| T1s-2043 | (S)-I-13 | II-21 | II-76 |
| T1s-2044 | (S)-I-13 | II-21 | II-78 |
| T1s-2045 | (S)-I-13 | II-21 | II-84 |
| T1s-2046 | (S)-I-13 | II-21 | II-85 |
| T1s-2047 | (S)-I-13 | II-21 | II-86 |
| T1s-2048 | (S)-I-13 | II-21 | II-92 |
| T1s-2049 | (S)-I-13 | II-26 | II-32 |
| T1s-2050 | (S)-I-13 | II-26 | II-33 |
| T1s-2051 | (S)-I-13 | II-26 | II-37 |
| T1s-2052 | (S)-I-13 | II-26 | II-39 |
| T1s-2053 | (S)-I-13 | II-26 | II-42 |
| T1s-2054 | (S)-I-13 | II-26 | II-44 |
| T1s-2055 | (S)-I-13 | II-26 | II-50 |
| T1s-2056 | (S)-I-13 | II-26 | II-53 |
| T1s-2057 | (S)-I-13 | II-26 | II-60 |
| T1s-2058 | (S)-I-13 | II-26 | II-62 |
| T1s-2059 | (S)-I-13 | II-26 | II-66 |
| T1s-2060 | (S)-I-13 | II-26 | II-69 |
| T1s-2061 | (S)-I-13 | II-26 | II-70 |
| T1s-2062 | (S)-I-13 | II-26 | II-71 |
| T1s-2063 | (S)-I-13 | II-26 | II-72 |
| T1s-2064 | (S)-I-13 | II-26 | II-74 |
| T1s-2065 | (S)-I-13 | II-26 | II-76 |
| T1s-2066 | (S)-I-13 | II-26 | II-78 |
| T1s-2067 | (S)-I-13 | II-26 | II-84 |
| T1s-2068 | (S)-I-13 | II-26 | II-85 |
| T1s-2069 | (S)-I-13 | II-26 | II-86 |
| T1s-2070 | (S)-I-13 | II-26 | II-92 |
| T1s-2071 | (S)-I-13 | II-32 | II-33 |
| T1s-2072 | (S)-I-13 | II-32 | II-37 |
| T1s-2073 | (S)-I-13 | II-32 | II-39 |
| T1s-2074 | (S)-I-13 | II-32 | II-42 |
| T1s-2075 | (S)-I-13 | II-32 | II-44 |
| T1s-2076 | (S)-I-13 | II-32 | II-50 |
| T1s-2077 | (S)-I-13 | II-32 | II-53 |
| T1s-2078 | (S)-I-13 | II-32 | II-60 |
| T1s-2079 | (S)-I-13 | II-32 | II-62 |
| T1s-2080 | (S)-I-13 | II-32 | II-66 |
| T1s-2081 | (S)-I-13 | II-32 | II-69 |
| T1s-2082 | (S)-I-13 | II-32 | II-70 |
| T1s-2083 | (S)-I-13 | II-32 | II-71 |
| T1s-2084 | (S)-I-13 | II-32 | II-72 |
| T1s-2085 | (S)-I-13 | II-32 | II-74 |
| T1s-2086 | (S)-I-13 | II-32 | II-76 |
| T1s-2087 | (S)-I-13 | II-32 | II-78 |
| T1s-2088 | (S)-I-13 | II-32 | II-84 |
| T1s-2089 | (S)-I-13 | II-32 | II-85 |
| T1s-2090 | (S)-I-13 | II-32 | II-86 |
| T1s-2091 | (S)-I-13 | II-32 | II-92 |
| T1s-2092 | (S)-I-13 | II-33 | II-37 |
| T1s-2093 | (S)-I-13 | II-33 | II-39 |
| T1s-2094 | (S)-I-13 | II-33 | II-42 |
| T1s-2095 | (S)-I-13 | II-33 | II-44 |
| T1s-2096 | (S)-I-13 | II-33 | II-50 |
| T1s-2097 | (S)-I-13 | II-33 | II-53 |
| T1s-2098 | (S)-I-13 | II-33 | II-60 |
| T1s-2099 | (S)-I-13 | II-33 | II-62 |
| T1s-2100 | (S)-I-13 | II-33 | II-66 |
| T1s-2101 | (S)-I-13 | II-33 | II-69 |
| T1s-2102 | (S)-I-13 | II-33 | II-70 |
| T1s-2103 | (S)-I-13 | II-33 | II-71 |
| T1s-2104 | (S)-I-13 | II-33 | II-72 |
| T1s-2105 | (S)-I-13 | II-33 | II-74 |
| T1s-2106 | (S)-I-13 | II-33 | II-76 |
| T1s-2107 | (S)-I-13 | II-33 | II-78 |

TABLE T1s-continued

Three-component compositions comprising one component I as (S) enantiomer (appreviated as (S)-I, e.g. (S)-I-1 for the (S)-enantiomer of I-1), one component II and one component III, in particular ternary compositions containing the respective component I as (S) enantiomer, II and III as only active ingredients.

| composition | (S)-I | II | III |
|---|---|---|---|
| T1s-2108 | (S)-I-13 | II-33 | II-84 |
| T1s-2109 | (S)-I-13 | II-33 | II-85 |
| T1s-2110 | (S)-I-13 | II-33 | II-86 |
| T1s-2111 | (S)-I-13 | II-33 | II-92 |
| T1s-2112 | (S)-I-13 | II-37 | II-39 |
| T1s-2113 | (S)-I-13 | II-37 | II-42 |
| T1s-2114 | (S)-I-13 | II-37 | II-44 |
| T1s-2115 | (S)-I-13 | II-37 | II-50 |
| T1s-2116 | (S)-I-13 | II-37 | II-53 |
| T1s-2117 | (S)-I-13 | II-37 | II-60 |
| T1s-2118 | (S)-I-13 | II-37 | II-62 |
| T1s-2119 | (S)-I-13 | II-37 | II-66 |
| T1s-2120 | (S)-I-13 | II-37 | II-69 |
| T1s-2121 | (S)-I-13 | II-37 | II-70 |
| T1s-2122 | (S)-I-13 | II-37 | II-71 |
| T1s-2123 | (S)-I-13 | II-37 | II-72 |
| T1s-2124 | (S)-I-13 | II-37 | II-74 |
| T1s-2125 | (S)-I-13 | II-37 | II-76 |
| T1s-2126 | (S)-I-13 | II-37 | II-78 |
| T1s-2127 | (S)-I-13 | II-37 | II-84 |
| T1s-2128 | (S)-I-13 | II-37 | II-85 |
| T1s-2129 | (S)-I-13 | II-37 | II-86 |
| T1s-2130 | (S)-I-13 | II-37 | II-92 |
| T1s-2131 | (S)-I-13 | II-39 | II-42 |
| T1s-2132 | (S)-I-13 | II-39 | II-44 |
| T1s-2133 | (S)-I-13 | II-39 | II-50 |
| T1s-2134 | (S)-I-13 | II-39 | II-53 |
| T1s-2135 | (S)-I-13 | II-39 | II-60 |
| T1s-2136 | (S)-I-13 | II-39 | II-62 |
| T1s-2137 | (S)-I-13 | II-39 | II-66 |
| T1s-2138 | (S)-I-13 | II-39 | II-69 |
| T1s-2139 | (S)-I-13 | II-39 | II-70 |
| T1s-2140 | (S)-I-13 | II-39 | II-71 |
| T1s-2141 | (S)-I-13 | II-39 | II-72 |
| T1s-2142 | (S)-I-13 | II-39 | II-74 |
| T1s-2143 | (S)-I-13 | II-39 | II-76 |
| T1s-2144 | (S)-I-13 | II-39 | II-78 |
| T1s-2145 | (S)-I-13 | II-39 | II-84 |
| T1s-2146 | (S)-I-13 | II-39 | II-85 |
| T1s-2147 | (S)-I-13 | II-39 | II-86 |
| T1s-2148 | (S)-I-13 | II-39 | II-92 |
| T1s-2149 | (S)-I-13 | II-42 | II-44 |
| T1s-2150 | (S)-I-13 | II-42 | II-50 |
| T1s-2151 | (S)-I-13 | II-42 | II-53 |
| T1s-2152 | (S)-I-13 | II-42 | II-60 |
| T1s-2153 | (S)-I-13 | II-42 | II-62 |
| T1s-2154 | (S)-I-13 | II-42 | II-66 |
| T1s-2155 | (S)-I-13 | II-42 | II-69 |
| T1s-2156 | (S)-I-13 | II-42 | II-70 |
| T1s-2157 | (S)-I-13 | II-42 | II-71 |
| T1s-2158 | (S)-I-13 | II-42 | II-72 |
| T1s-2159 | (S)-I-13 | II-42 | II-74 |
| T1s-2160 | (S)-I-13 | II-42 | II-76 |
| T1s-2161 | (S)-I-13 | II-42 | II-78 |
| T1s-2162 | (S)-I-13 | II-42 | II-84 |
| T1s-2163 | (S)-I-13 | II-42 | II-85 |
| T1s-2164 | (S)-I-13 | II-42 | II-86 |
| T1s-2165 | (S)-I-13 | II-42 | II-92 |
| T1s-2166 | (S)-I-13 | II-44 | II-50 |
| T1s-2167 | (S)-I-13 | II-44 | II-53 |
| T1s-2168 | (S)-I-13 | II-44 | II-60 |
| T1s-2169 | (S)-I-13 | II-44 | II-62 |
| T1s-2170 | (S)-I-13 | II-44 | II-66 |
| T1s-2171 | (S)-I-13 | II-44 | II-69 |
| T1s-2172 | (S)-I-13 | II-44 | II-70 |
| T1s-2173 | (S)-I-13 | II-44 | II-71 |
| T1s-2174 | (S)-I-13 | II-44 | II-72 |
| T1s-2175 | (S)-I-13 | II-44 | II-74 |
| T1s-2176 | (S)-I-13 | II-44 | II-76 |
| T1s-2177 | (S)-I-13 | II-44 | II-78 |
| T1s-2178 | (S)-I-13 | II-44 | II-84 |
| T1s-2179 | (S)-I-13 | II-44 | II-85 |
| T1s-2180 | (S)-I-13 | II-44 | II-86 |
| T1s-2181 | (S)-I-13 | II-44 | II-92 |
| T1s-2182 | (S)-I-13 | II-50 | II-53 |
| T1s-2183 | (S)-I-13 | II-50 | II-60 |
| T1s-2184 | (S)-I-13 | II-50 | II-62 |
| T1s-2185 | (S)-I-13 | II-50 | II-66 |
| T1s-2186 | (S)-I-13 | II-50 | II-69 |
| T1s-2187 | (S)-I-13 | II-50 | II-70 |
| T1s-2188 | (S)-I-13 | II-50 | II-71 |
| T1s-2189 | (S)-I-13 | II-50 | II-72 |
| T1s-2190 | (S)-I-13 | II-50 | II-74 |
| T1s-2191 | (S)-I-13 | II-50 | II-76 |
| T1s-2192 | (S)-I-13 | II-50 | II-78 |
| T1s-2193 | (S)-I-13 | II-50 | II-84 |
| T1s-2194 | (S)-I-13 | II-50 | II-85 |
| T1s-2195 | (S)-I-13 | II-50 | II-86 |
| T1s-2196 | (S)-I-13 | II-50 | II-92 |
| T1s-2197 | (S)-I-13 | II-53 | II-60 |
| T1s-2198 | (S)-I-13 | II-53 | II-62 |
| T1s-2199 | (S)-I-13 | II-53 | II-66 |
| T1s-2200 | (S)-I-13 | II-53 | II-69 |
| T1s-2201 | (S)-I-13 | II-53 | II-70 |
| T1s-2202 | (S)-I-13 | II-53 | II-71 |
| T1s-2203 | (S)-I-13 | II-53 | II-72 |
| T1s-2204 | (S)-I-13 | II-53 | II-74 |
| T1s-2205 | (S)-I-13 | II-53 | II-76 |
| T1s-2206 | (S)-I-13 | II-53 | II-78 |
| T1s-2207 | (S)-I-13 | II-53 | II-84 |
| T1s-2208 | (S)-I-13 | II-53 | II-85 |
| T1s-2209 | (S)-I-13 | II-53 | II-86 |
| T1s-2210 | (S)-I-13 | II-53 | II-92 |
| T1s-2211 | (S)-I-13 | II-60 | II-62 |
| T1s-2212 | (S)-I-13 | II-60 | II-66 |
| T1s-2213 | (S)-I-13 | II-60 | II-69 |
| T1s-2214 | (S)-I-13 | II-60 | II-70 |
| T1s-2215 | (S)-I-13 | II-60 | II-71 |
| T1s-2216 | (S)-I-13 | II-60 | II-72 |
| T1s-2217 | (S)-I-13 | II-60 | II-74 |
| T1s-2218 | (S)-I-13 | II-60 | II-76 |
| T1s-2219 | (S)-I-13 | II-60 | II-78 |
| T1s-2220 | (S)-I-13 | II-60 | II-84 |
| T1s-2221 | (S)-I-13 | II-60 | II-85 |
| T1s-2222 | (S)-I-13 | II-60 | II-86 |
| T1s-2223 | (S)-I-13 | II-60 | II-92 |
| T1s-2224 | (S)-I-13 | II-62 | II-66 |
| T1s-2225 | (S)-I-13 | II-62 | II-69 |
| T1s-2226 | (S)-I-13 | II-62 | II-70 |
| T1s-2227 | (S)-I-13 | II-62 | II-71 |
| T1s-2228 | (S)-I-13 | II-62 | II-72 |
| T1s-2229 | (S)-I-13 | II-62 | II-74 |
| T1s-2230 | (S)-I-13 | II-62 | II-76 |
| T1s-2231 | (S)-I-13 | II-62 | II-78 |
| T1s-2232 | (S)-I-13 | II-62 | II-84 |
| T1s-2233 | (S)-I-13 | II-62 | II-85 |
| T1s-2234 | (S)-I-13 | II-62 | II-86 |
| T1s-2235 | (S)-I-13 | II-62 | II-92 |
| T1s-2236 | (S)-I-13 | II-66 | II-69 |
| T1s-2237 | (S)-I-13 | II-66 | II-70 |
| T1s-2238 | (S)-I-13 | II-66 | II-71 |
| T1s-2239 | (S)-I-13 | II-66 | II-72 |
| T1s-2240 | (S)-I-13 | II-66 | II-74 |
| T1s-2241 | (S)-I-13 | II-66 | II-76 |
| T1s-2242 | (S)-I-13 | II-66 | II-78 |
| T1s-2243 | (S)-I-13 | II-66 | II-84 |
| T1s-2244 | (S)-I-13 | II-66 | II-85 |
| T1s-2245 | (S)-I-13 | II-66 | II-86 |
| T1s-2246 | (S)-I-13 | II-66 | II-92 |
| T1s-2247 | (S)-I-13 | II-69 | II-70 |
| T1s-2248 | (S)-I-13 | II-69 | II-71 |
| T1s-2249 | (S)-I-13 | II-69 | II-72 |
| T1s-2250 | (S)-I-13 | II-69 | II-74 |
| T1s-2251 | (S)-I-13 | II-69 | II-76 |

TABLE T1s-continued

Three-component compositions comprising one component I as (S) enantiomer (appreviated as (S)-I, e.g. (S)-I-1 for the (S)-enantiomer of I-1), one component II and one component III, in particular ternary compositions containing the respective component I as (S) enantiomer, II and III as only active ingredients.

| composition | (S)-I | II | III |
| --- | --- | --- | --- |
| T1s-2252 | (S)-I-13 | II-69 | II-78 |
| T1s-2253 | (S)-I-13 | II-69 | II-84 |
| T1s-2254 | (S)-I-13 | II-69 | II-85 |
| T1s-2255 | (S)-I-13 | II-69 | II-86 |
| T1s-2256 | (S)-I-13 | II-69 | II-92 |
| T1s-2257 | (S)-I-13 | II-70 | II-71 |
| T1s-2258 | (S)-I-13 | II-70 | II-72 |
| T1s-2259 | (S)-I-13 | II-70 | II-74 |
| T1s-2260 | (S)-I-13 | II-70 | II-76 |
| T1s-2261 | (S)-I-13 | II-70 | II-78 |
| T1s-2262 | (S)-I-13 | II-70 | II-84 |
| T1s-2263 | (S)-I-13 | II-70 | II-85 |
| T1s-2264 | (S)-I-13 | II-70 | II-86 |
| T1s-2265 | (S)-I-13 | II-70 | II-92 |
| T1s-2266 | (S)-I-13 | II-71 | II-72 |
| T1s-2267 | (S)-I-13 | II-71 | II-74 |
| T1s-2268 | (S)-I-13 | II-71 | II-76 |
| T1s-2269 | (S)-I-13 | II-71 | II-78 |
| T1s-2270 | (S)-I-13 | II-71 | II-84 |
| T1s-2271 | (S)-I-13 | II-71 | II-85 |
| T1s-2272 | (S)-I-13 | II-71 | II-86 |
| T1s-2273 | (S)-I-13 | II-71 | II-92 |
| T1s-2274 | (S)-I-13 | II-72 | II-74 |
| T1s-2275 | (S)-I-13 | II-74 | II-76 |
| T1s-2276 | (S)-I-13 | II-74 | II-78 |
| T1s-2277 | (S)-I-13 | II-74 | II-84 |
| T1s-2278 | (S)-I-13 | II-74 | II-85 |
| T1s-2279 | (S)-I-13 | II-74 | II-86 |
| T1s-2280 | (S)-I-13 | II-74 | II-92 |
| T1s-2281 | (S)-I-13 | II-76 | II-78 |
| T1s-2282 | (S)-I-13 | II-76 | II-84 |
| T1s-2283 | (S)-I-13 | II-76 | II-85 |
| T1s-2284 | (S)-I-13 | II-76 | II-86 |
| T1s-2285 | (S)-I-13 | II-76 | II-92 |
| T1s-2286 | (S)-I-13 | II-78 | II-84 |
| T1s-2287 | (S)-I-13 | II-78 | II-85 |
| T1s-2288 | (S)-I-13 | II-78 | II-86 |
| T1s-2289 | (S)-I-13 | II-78 | II-92 |
| T1s-2290 | (S)-I-13 | II-84 | II-85 |
| T1s-2291 | (S)-I-13 | II-84 | II-86 |
| T1s-2292 | (S)-I-13 | II-84 | II-92 |
| T1s-2293 | (S)-I-13 | II-85 | II-86 |
| T1s-2294 | (S)-I-13 | II-85 | II-92 |
| T1s-2295 | (S)-I-13 | II-86 | II-92 |

According to particular embodiments of the invention, the respective component I is present as (R) enantiomer. Specific three-component compositions comprising the (R) enantiomer of the respective component I are compiled in Table T1r, wherein each row corresponds to one embodiment of the compositions according to the invention, i.e. one specific individualized composition. According to one specific aspect, these are ternary compositions which each only contain these two components as active compounds. Furthermore, also every combination of the compositions individualized in this table represent embodiments of the present invention.

TABLE T1s

Three-component compositions comprising one component I as (R) enantiomer (appreviated as (R)-I, e.g. (R)-I-1 for the (R)-enantiomer of I-1), one component II and one component III, in particular ternary compositions containing the respective component I as (R) enantiomer, II and III as only active ingredients.

| composition | (R)-I | II | III |
| --- | --- | --- | --- |
| T1r-1 | (R)-I-1 | II-3 | II-5 |
| T1r-2 | (R)-I-1 | II-3 | II-6 |
| T1r-3 | (R)-I-1 | II-3 | II-7 |
| T1r-4 | (R)-I-1 | II-3 | II-8 |
| T1r-5 | (R)-I-1 | II-3 | II-11 |
| T1r-6 | (R)-I-1 | II-3 | II-16 |
| T1r-7 | (R)-I-1 | II-3 | II-21 |
| T1r-8 | (R)-I-1 | II-3 | II-26 |
| T1r-9 | (R)-I-1 | II-3 | II-32 |
| T1r-10 | (R)-I-1 | II-3 | II-33 |
| T1r-11 | (R)-I-1 | II-3 | II-37 |
| T1r-12 | (R)-I-1 | II-3 | II-39 |
| T1r-13 | (R)-I-1 | II-3 | II-42 |
| T1r-14 | (R)-I-1 | II-3 | II-44 |
| T1r-15 | (R)-I-1 | II-3 | II-50 |
| T1r-16 | (R)-I-1 | II-3 | II-53 |
| T1r-17 | (R)-I-1 | II-3 | II-60 |
| T1r-18 | (R)-I-1 | II-3 | II-62 |
| T1r-19 | (R)-I-1 | II-3 | II-66 |
| T1r-20 | (R)-I-1 | II-3 | II-69 |
| T1r-21 | (R)-I-1 | II-3 | II-70 |
| T1r-22 | (R)-I-1 | II-3 | II-71 |
| T1r-23 | (R)-I-1 | II-3 | II-72 |
| T1r-24 | (R)-I-1 | II-3 | II-74 |
| T1r-25 | (R)-I-1 | II-3 | II-76 |
| T1r-26 | (R)-I-1 | II-3 | II-78 |
| T1r-27 | (R)-I-1 | II-3 | II-84 |
| T1r-28 | (R)-I-1 | II-3 | II-85 |
| T1r-29 | (R)-I-1 | II-3 | II-86 |
| T1r-30 | (R)-I-1 | II-3 | II-92 |
| T1r-31 | (R)-I-1 | II-5 | II-6 |
| T1r-32 | (R)-I-1 | II-5 | II-7 |
| T1r-33 | (R)-I-1 | II-5 | II-8 |
| T1r-34 | (R)-I-1 | II-5 | II-11 |
| T1r-35 | (R)-I-1 | II-5 | II-16 |
| T1r-36 | (R)-I-1 | II-5 | II-21 |
| T1r-37 | (R)-I-1 | II-5 | II-26 |
| T1r-38 | (R)-I-1 | II-5 | II-32 |
| T1r-39 | (R)-I-1 | II-5 | II-33 |
| T1r-40 | (R)-I-1 | II-5 | II-37 |
| T1r-41 | (R)-I-1 | II-5 | II-39 |
| T1r-42 | (R)-I-1 | II-5 | II-42 |
| T1r-43 | (R)-I-1 | II-5 | II-44 |
| T1r-44 | (R)-I-1 | II-5 | II-50 |
| T1r-45 | (R)-I-1 | II-5 | II-53 |
| T1r-46 | (R)-I-1 | II-5 | II-60 |
| T1r-47 | (R)-I-1 | II-5 | II-62 |
| T1r-48 | (R)-I-1 | II-5 | II-66 |
| T1r-49 | (R)-I-1 | II-5 | II-69 |
| T1r-50 | (R)-I-1 | II-5 | II-70 |
| T1r-51 | (R)-I-1 | II-5 | II-71 |
| T1r-52 | (R)-I-1 | II-5 | II-72 |
| T1r-53 | (R)-I-1 | II-5 | II-74 |
| T1r-54 | (R)-I-1 | II-5 | II-76 |
| T1r-55 | (R)-I-1 | II-5 | II-78 |
| T1r-56 | (R)-I-1 | II-5 | II-84 |
| T1r-57 | (R)-I-1 | II-5 | II-85 |
| T1r-58 | (R)-I-1 | II-5 | II-86 |
| T1r-59 | (R)-I-1 | II-5 | II-92 |
| T1r-60 | (R)-I-1 | II-6 | II-7 |
| T1r-61 | (R)-I-1 | II-6 | II-8 |
| T1r-62 | (R)-I-1 | II-6 | II-11 |
| T1r-63 | (R)-I-1 | II-6 | II-16 |
| T1r-64 | (R)-I-1 | II-6 | II-21 |
| T1r-65 | (R)-I-1 | II-6 | II-26 |
| T1r-66 | (R)-I-1 | II-6 | II-32 |
| T1r-67 | (R)-I-1 | II-6 | II-33 |
| T1r-68 | (R)-I-1 | II-6 | II-37 |
| T1r-69 | (R)-I-1 | II-6 | II-39 |
| T1r-70 | (R)-I-1 | II-6 | II-42 |
| T1r-71 | (R)-I-1 | II-6 | II-44 |
| T1r-72 | (R)-I-1 | II-6 | II-50 |

TABLE T1s-continued

Three-component compositions comprising one component I as (R) enantiomer (appreviated as (R)-I, e.g. (R)-I-1 for the (R)-enantiomer of I-1), one component II and one component III, in particular ternary compositions containing the respective component I as (R) enantiomer, II and III as only active ingredients.

| composition | (R)-I | II | III |
| --- | --- | --- | --- |
| T1r-73 | (R)-I-1 | II-6 | II-53 |
| T1r-74 | (R)-I-1 | II-6 | II-60 |
| T1r-75 | (R)-I-1 | II-6 | II-62 |
| T1r-76 | (R)-I-1 | II-6 | II-66 |
| T1r-77 | (R)-I-1 | II-6 | II-69 |
| T1r-78 | (R)-I-1 | II-6 | II-70 |
| T1r-79 | (R)-I-1 | II-6 | II-71 |
| T1r-80 | (R)-I-1 | II-6 | II-72 |
| T1r-81 | (R)-I-1 | II-6 | II-74 |
| T1r-82 | (R)-I-1 | II-6 | II-76 |
| T1r-83 | (R)-I-1 | II-6 | II-78 |
| T1r-84 | (R)-I-1 | II-6 | II-84 |
| T1r-85 | (R)-I-1 | II-6 | II-85 |
| T1r-86 | (R)-I-1 | II-6 | II-86 |
| T1r-87 | (R)-I-1 | II-6 | II-92 |
| T1r-88 | (R)-I-1 | II-7 | II-8 |
| T1r-89 | (R)-I-1 | II-7 | II-11 |
| T1r-90 | (R)-I-1 | II-7 | II-16 |
| T1r-91 | (R)-I-1 | II-7 | II-21 |
| T1r-92 | (R)-I-1 | II-7 | II-26 |
| T1r-93 | (R)-I-1 | II-7 | II-32 |
| T1r-94 | (R)-I-1 | II-7 | II-33 |
| T1r-95 | (R)-I-1 | II-7 | II-37 |
| T1r-96 | (R)-I-1 | II-7 | II-39 |
| T1r-97 | (R)-I-1 | II-7 | II-42 |
| T1r-98 | (R)-I-1 | II-7 | II-44 |
| T1r-99 | (R)-I-1 | II-7 | II-50 |
| T1r-100 | (R)-I-1 | II-7 | II-53 |
| T1r-101 | (R)-I-1 | II-7 | II-60 |
| T1r-102 | (R)-I-1 | II-7 | II-62 |
| T1r-103 | (R)-I-1 | II-7 | II-66 |
| T1r-104 | (R)-I-1 | II-7 | II-69 |
| T1r-105 | (R)-I-1 | II-7 | II-70 |
| T1r-106 | (R)-I-1 | II-7 | II-71 |
| T1r-107 | (R)-I-1 | II-7 | II-72 |
| T1r-108 | (R)-I-1 | II-7 | II-74 |
| T1r-109 | (R)-I-1 | II-7 | II-76 |
| T1r-110 | (R)-I-1 | II-7 | II-78 |
| T1r-111 | (R)-I-1 | II-7 | II-84 |
| T1r-112 | (R)-I-1 | II-7 | II-85 |
| T1r-113 | (R)-I-1 | II-7 | II-86 |
| T1r-114 | (R)-I-1 | II-7 | II-92 |
| T1r-115 | (R)-I-1 | II-8 | II-11 |
| T1r-116 | (R)-I-1 | II-8 | II-16 |
| T1r-117 | (R)-I-1 | II-8 | II-21 |
| T1r-118 | (R)-I-1 | II-8 | II-26 |
| T1r-119 | (R)-I-1 | II-8 | II-32 |
| T1r-120 | (R)-I-1 | II-8 | II-33 |
| T1r-121 | (R)-I-1 | II-8 | II-37 |
| T1r-122 | (R)-I-1 | II-8 | II-39 |
| T1r-123 | (R)-I-1 | II-8 | II-42 |
| T1r-124 | (R)-I-1 | II-8 | II-44 |
| T1r-125 | (R)-I-1 | II-8 | II-50 |
| T1r-126 | (R)-I-1 | II-8 | II-53 |
| T1r-127 | (R)-I-1 | II-8 | II-60 |
| T1r-128 | (R)-I-1 | II-8 | II-62 |
| T1r-129 | (R)-I-1 | II-8 | II-66 |
| T1r-130 | (R)-I-1 | II-8 | II-69 |
| T1r-131 | (R)-I-1 | II-8 | II-70 |
| T1r-132 | (R)-I-1 | II-8 | II-71 |
| T1r-133 | (R)-I-1 | II-8 | II-72 |
| T1r-134 | (R)-I-1 | II-8 | II-74 |
| T1r-135 | (R)-I-1 | II-8 | II-76 |
| T1r-136 | (R)-I-1 | II-8 | II-78 |
| T1r-137 | (R)-I-1 | II-8 | II-84 |
| T1r-138 | (R)-I-1 | II-8 | II-85 |
| T1r-139 | (R)-I-1 | II-8 | II-86 |
| T1r-140 | (R)-I-1 | II-8 | II-92 |
| T1r-141 | (R)-I-1 | II-11 | II-16 |
| T1r-142 | (R)-I-1 | II-11 | II-21 |
| T1r-143 | (R)-I-1 | II-11 | II-26 |
| T1r-144 | (R)-I-1 | II-11 | II-32 |
| T1r-145 | (R)-I-1 | II-11 | II-33 |
| T1r-146 | (R)-I-1 | II-11 | II-37 |
| T1r-147 | (R)-I-1 | II-11 | II-39 |
| T1r-148 | (R)-I-1 | II-11 | II-42 |
| T1r-149 | (R)-I-1 | II-11 | II-44 |
| T1r-150 | (R)-I-1 | II-11 | II-50 |
| T1r-151 | (R)-I-1 | II-11 | II-53 |
| T1r-152 | (R)-I-1 | II-11 | II-60 |
| T1r-153 | (R)-I-1 | II-11 | II-62 |
| T1r-154 | (R)-I-1 | II-11 | II-66 |
| T1r-155 | (R)-I-1 | II-11 | II-69 |
| T1r-156 | (R)-I-1 | II-11 | II-70 |
| T1r-157 | (R)-I-1 | II-11 | II-71 |
| T1r-158 | (R)-I-1 | II-11 | II-72 |
| T1r-159 | (R)-I-1 | II-11 | II-74 |
| T1r-160 | (R)-I-1 | II-11 | II-76 |
| T1r-161 | (R)-I-1 | II-11 | II-78 |
| T1r-162 | (R)-I-1 | II-11 | II-84 |
| T1r-163 | (R)-I-1 | II-11 | II-85 |
| T1r-164 | (R)-I-1 | II-11 | II-86 |
| T1r-165 | (R)-I-1 | II-11 | II-92 |
| T1r-166 | (R)-I-1 | II-16 | II-21 |
| T1r-167 | (R)-I-1 | II-16 | II-26 |
| T1r-168 | (R)-I-1 | II-16 | II-32 |
| T1r-169 | (R)-I-1 | II-16 | II-33 |
| T1r-170 | (R)-I-1 | II-16 | II-37 |
| T1r-171 | (R)-I-1 | II-16 | II-39 |
| T1r-172 | (R)-I-1 | II-16 | II-42 |
| T1r-173 | (R)-I-1 | II-16 | II-44 |
| T1r-174 | (R)-I-1 | II-16 | II-50 |
| T1r-175 | (R)-I-1 | II-16 | II-53 |
| T1r-176 | (R)-I-1 | II-16 | II-60 |
| T1r-177 | (R)-I-1 | II-16 | II-62 |
| T1r-178 | (R)-I-1 | II-16 | II-66 |
| T1r-179 | (R)-I-1 | II-16 | II-69 |
| T1r-180 | (R)-I-1 | II-16 | II-70 |
| T1r-181 | (R)-I-1 | II-16 | II-71 |
| T1r-182 | (R)-I-1 | II-16 | II-72 |
| T1r-183 | (R)-I-1 | II-16 | II-74 |
| T1r-184 | (R)-I-1 | II-16 | II-76 |
| T1r-185 | (R)-I-1 | II-16 | II-78 |
| T1r-186 | (R)-I-1 | II-16 | II-84 |
| T1r-187 | (R)-I-1 | II-16 | II-85 |
| T1r-188 | (R)-I-1 | II-16 | II-86 |
| T1r-189 | (R)-I-1 | II-16 | II-92 |
| T1r-190 | (R)-I-1 | II-21 | II-26 |
| T1r-191 | (R)-I-1 | II-21 | II-32 |
| T1r-192 | (R)-I-1 | II-21 | II-33 |
| T1r-193 | (R)-I-1 | II-21 | II-37 |
| T1r-194 | (R)-I-1 | II-21 | II-39 |
| T1r-195 | (R)-I-1 | II-21 | II-42 |
| T1r-196 | (R)-I-1 | II-21 | II-44 |
| T1r-197 | (R)-I-1 | II-21 | II-50 |
| T1r-198 | (R)-I-1 | II-21 | II-53 |
| T1r-199 | (R)-I-1 | II-21 | II-60 |
| T1r-200 | (R)-I-1 | II-21 | II-62 |
| T1r-201 | (R)-I-1 | II-21 | II-66 |
| T1r-202 | (R)-I-1 | II-21 | II-69 |
| T1r-203 | (R)-I-1 | II-21 | II-70 |
| T1r-204 | (R)-I-1 | II-21 | II-71 |
| T1r-205 | (R)-I-1 | II-21 | II-72 |
| T1r-206 | (R)-I-1 | II-21 | II-74 |
| T1r-207 | (R)-I-1 | II-21 | II-76 |
| T1r-208 | (R)-I-1 | II-21 | II-78 |
| T1r-209 | (R)-I-1 | II-21 | II-84 |
| T1r-210 | (R)-I-1 | II-21 | II-85 |
| T1r-211 | (R)-I-1 | II-21 | II-86 |
| T1r-212 | (R)-I-1 | II-21 | II-92 |
| T1r-213 | (R)-I-1 | II-26 | II-32 |
| T1r-214 | (R)-I-1 | II-26 | II-33 |
| T1r-215 | (R)-I-1 | II-26 | II-37 |
| T1r-216 | (R)-I-1 | II-26 | II-39 |

TABLE T1s-continued

Three-component compositions comprising one component I as (R) enantiomer (appreviated as (R)-I, e.g. (R)-I-1 for the (R)-enantiomer of I-1), one component II and one component III, in particular ternary compositions containing the respective component I as (R) enantiomer, II and III as only active ingredients.

| composition | (R)-I | II | III |
|---|---|---|---|
| T1r-217 | (R)-I-1 | II-26 | II-42 |
| T1r-218 | (R)-I-1 | II-26 | II-44 |
| T1r-219 | (R)-I-1 | II-26 | II-50 |
| T1r-220 | (R)-I-1 | II-26 | II-53 |
| T1r-221 | (R)-I-1 | II-26 | II-60 |
| T1r-222 | (R)-I-1 | II-26 | II-62 |
| T1r-223 | (R)-I-1 | II-26 | II-66 |
| T1r-224 | (R)-I-1 | II-26 | II-69 |
| T1r-225 | (R)-I-1 | II-26 | II-70 |
| T1r-226 | (R)-I-1 | II-26 | II-71 |
| T1r-227 | (R)-I-1 | II-26 | II-72 |
| T1r-228 | (R)-I-1 | II-26 | II-74 |
| T1r-229 | (R)-I-1 | II-26 | II-76 |
| T1r-230 | (R)-I-1 | II-26 | II-78 |
| T1r-231 | (R)-I-1 | II-26 | II-84 |
| T1r-232 | (R)-I-1 | II-26 | II-85 |
| T1r-233 | (R)-I-1 | II-26 | II-86 |
| T1r-234 | (R)-I-1 | II-26 | II-92 |
| T1r-235 | (R)-I-1 | II-32 | II-33 |
| T1r-236 | (R)-I-1 | II-32 | II-37 |
| T1r-237 | (R)-I-1 | II-32 | II-39 |
| T1r-238 | (R)-I-1 | II-32 | II-42 |
| T1r-239 | (R)-I-1 | II-32 | II-44 |
| T1r-240 | (R)-I-1 | II-32 | II-50 |
| T1r-241 | (R)-I-1 | II-32 | II-53 |
| T1r-242 | (R)-I-1 | II-32 | II-60 |
| T1r-243 | (R)-I-1 | II-32 | II-62 |
| T1r-244 | (R)-I-1 | II-32 | II-66 |
| T1r-245 | (R)-I-1 | II-32 | II-69 |
| T1r-246 | (R)-I-1 | II-32 | II-70 |
| T1r-247 | (R)-I-1 | II-32 | II-71 |
| T1r-248 | (R)-I-1 | II-32 | II-72 |
| T1r-249 | (R)-I-1 | II-32 | II-74 |
| T1r-250 | (R)-I-1 | II-32 | II-76 |
| T1r-251 | (R)-I-1 | II-32 | II-78 |
| T1r-252 | (R)-I-1 | II-32 | II-84 |
| T1r-253 | (R)-I-1 | II-32 | II-85 |
| T1r-254 | (R)-I-1 | II-32 | II-86 |
| T1r-255 | (R)-I-1 | II-32 | II-92 |
| T1r-256 | (R)-I-1 | II-33 | II-37 |
| T1r-257 | (R)-I-1 | II-33 | II-39 |
| T1r-258 | (R)-I-1 | II-33 | II-42 |
| T1r-259 | (R)-I-1 | II-33 | II-44 |
| T1r-260 | (R)-I-1 | II-33 | II-50 |
| T1r-261 | (R)-I-1 | II-33 | II-53 |
| T1r-262 | (R)-I-1 | II-33 | II-60 |
| T1r-263 | (R)-I-1 | II-33 | II-62 |
| T1r-264 | (R)-I-1 | II-33 | II-66 |
| T1r-265 | (R)-I-1 | II-33 | II-69 |
| T1r-266 | (R)-I-1 | II-33 | II-70 |
| T1r-267 | (R)-I-1 | II-33 | II-71 |
| T1r-268 | (R)-I-1 | II-33 | II-72 |
| T1r-269 | (R)-I-1 | II-33 | II-74 |
| T1r-270 | (R)-I-1 | II-33 | II-76 |
| T1r-271 | (R)-I-1 | II-33 | II-78 |
| T1r-272 | (R)-I-1 | II-33 | II-84 |
| T1r-273 | (R)-I-1 | II-33 | II-85 |
| T1r-274 | (R)-I-1 | II-33 | II-86 |
| T1r-275 | (R)-I-1 | II-33 | II-92 |
| T1r-276 | (R)-I-1 | II-37 | II-39 |
| T1r-277 | (R)-I-1 | II-37 | II-42 |
| T1r-278 | (R)-I-1 | II-37 | II-44 |
| T1r-279 | (R)-I-1 | II-37 | II-50 |
| T1r-280 | (R)-I-1 | II-37 | II-53 |
| T1r-281 | (R)-I-1 | II-37 | II-60 |
| T1r-282 | (R)-I-1 | II-37 | II-62 |
| T1r-283 | (R)-I-1 | II-37 | II-66 |
| T1r-284 | (R)-I-1 | II-37 | II-69 |
| T1r-285 | (R)-I-1 | II-37 | II-70 |
| T1r-286 | (R)-I-1 | II-37 | II-71 |
| T1r-287 | (R)-I-1 | II-37 | II-72 |
| T1r-288 | (R)-I-1 | II-37 | II-74 |
| T1r-289 | (R)-I-1 | II-37 | II-76 |
| T1r-290 | (R)-I-1 | II-37 | II-78 |
| T1r-291 | (R)-I-1 | II-37 | II-84 |
| T1r-292 | (R)-I-1 | II-37 | II-85 |
| T1r-293 | (R)-I-1 | II-37 | II-86 |
| T1r-294 | (R)-I-1 | II-37 | II-92 |
| T1r-295 | (R)-I-1 | II-39 | II-42 |
| T1r-296 | (R)-I-1 | II-39 | II-44 |
| T1r-297 | (R)-I-1 | II-39 | II-50 |
| T1r-298 | (R)-I-1 | II-39 | II-53 |
| T1r-299 | (R)-I-1 | II-39 | II-60 |
| T1r-300 | (R)-I-1 | II-39 | II-62 |
| T1r-301 | (R)-I-1 | II-39 | II-66 |
| T1r-302 | (R)-I-1 | II-39 | II-69 |
| T1r-303 | (R)-I-1 | II-39 | II-70 |
| T1r-304 | (R)-I-1 | II-39 | II-71 |
| T1r-305 | (R)-I-1 | II-39 | II-72 |
| T1r-306 | (R)-I-1 | II-39 | II-74 |
| T1r-307 | (R)-I-1 | II-39 | II-76 |
| T1r-308 | (R)-I-1 | II-39 | II-78 |
| T1r-309 | (R)-I-1 | II-39 | II-84 |
| T1r-310 | (R)-I-1 | II-39 | II-85 |
| T1r-311 | (R)-I-1 | II-39 | II-86 |
| T1r-312 | (R)-I-1 | II-39 | II-92 |
| T1r-313 | (R)-I-1 | II-42 | II-44 |
| T1r-314 | (R)-I-1 | II-42 | II-50 |
| T1r-315 | (R)-I-1 | II-42 | II-53 |
| T1r-316 | (R)-I-1 | II-42 | II-60 |
| T1r-317 | (R)-I-1 | II-42 | II-62 |
| T1r-318 | (R)-I-1 | II-42 | II-66 |
| T1r-319 | (R)-I-1 | II-42 | II-69 |
| T1r-320 | (R)-I-1 | II-42 | II-70 |
| T1r-321 | (R)-I-1 | II-42 | II-71 |
| T1r-322 | (R)-I-1 | II-42 | II-72 |
| T1r-323 | (R)-I-1 | II-42 | II-74 |
| T1r-324 | (R)-I-1 | II-42 | II-76 |
| T1r-325 | (R)-I-1 | II-42 | II-78 |
| T1r-326 | (R)-I-1 | II-42 | II-84 |
| T1r-327 | (R)-I-1 | II-42 | II-85 |
| T1r-328 | (R)-I-1 | II-42 | II-86 |
| T1r-329 | (R)-I-1 | II-42 | II-92 |
| T1r-330 | (R)-I-1 | II-44 | II-50 |
| T1r-331 | (R)-I-1 | II-44 | II-53 |
| T1r-332 | (R)-I-1 | II-44 | II-60 |
| T1r-333 | (R)-I-1 | II-44 | II-62 |
| T1r-334 | (R)-I-1 | II-44 | II-66 |
| T1r-335 | (R)-I-1 | II-44 | II-69 |
| T1r-336 | (R)-I-1 | II-44 | II-70 |
| T1r-337 | (R)-I-1 | II-44 | II-71 |
| T1r-338 | (R)-I-1 | II-44 | II-72 |
| T1r-339 | (R)-I-1 | II-44 | II-74 |
| T1r-340 | (R)-I-1 | II-44 | II-76 |
| T1r-341 | (R)-I-1 | II-44 | II-78 |
| T1r-342 | (R)-I-1 | II-44 | II-84 |
| T1r-343 | (R)-I-1 | II-44 | II-85 |
| T1r-344 | (R)-I-1 | II-44 | II-86 |
| T1r-345 | (R)-I-1 | II-44 | II-92 |
| T1r-346 | (R)-I-1 | II-50 | II-53 |
| T1r-347 | (R)-I-1 | II-50 | II-60 |
| T1r-348 | (R)-I-1 | II-50 | II-62 |
| T1r-349 | (R)-I-1 | II-50 | II-66 |
| T1r-350 | (R)-I-1 | II-50 | II-69 |
| T1r-351 | (R)-I-1 | II-50 | II-70 |
| T1r-352 | (R)-I-1 | II-50 | II-71 |
| T1r-353 | (R)-I-1 | II-50 | II-72 |
| T1r-354 | (R)-I-1 | II-50 | II-74 |
| T1r-355 | (R)-I-1 | II-50 | II-76 |
| T1r-356 | (R)-I-1 | II-50 | II-78 |
| T1r-357 | (R)-I-1 | II-50 | II-84 |
| T1r-358 | (R)-I-1 | II-50 | II-85 |
| T1r-359 | (R)-I-1 | II-50 | II-86 |
| T1r-360 | (R)-I-1 | II-50 | II-92 |

TABLE T1s-continued

Three-component compositions comprising one component I as (R) enantiomer (appreviated as (R)-I, e.g. (R)-I-1 for the (R)-enantiomer of I-1), one component II and one component III, in particular ternary compositions containing the respective component I as (R) enantiomer, II and III as only active ingredients.

| composition | (R)-I | II | III |
|---|---|---|---|
| T1r-361 | (R)-I-1 | II-53 | II-60 |
| T1r-362 | (R)-I-1 | II-53 | II-62 |
| T1r-363 | (R)-I-1 | II-53 | II-66 |
| T1r-364 | (R)-I-1 | II-53 | II-69 |
| T1r-365 | (R)-I-1 | II-53 | II-70 |
| T1r-366 | (R)-I-1 | II-53 | II-71 |
| T1r-367 | (R)-I-1 | II-53 | II-72 |
| T1r-368 | (R)-I-1 | II-53 | II-74 |
| T1r-369 | (R)-I-1 | II-53 | II-76 |
| T1r-370 | (R)-I-1 | II-53 | II-78 |
| T1r-371 | (R)-I-1 | II-53 | II-84 |
| T1r-372 | (R)-I-1 | II-53 | II-85 |
| T1r-373 | (R)-I-1 | II-53 | II-86 |
| T1r-374 | (R)-I-1 | II-53 | II-92 |
| T1r-375 | (R)-I-1 | II-60 | II-62 |
| T1r-376 | (R)-I-1 | II-60 | II-66 |
| T1r-377 | (R)-I-1 | II-60 | II-69 |
| T1r-378 | (R)-I-1 | II-60 | II-70 |
| T1r-379 | (R)-I-1 | II-60 | II-71 |
| T1r-380 | (R)-I-1 | II-60 | II-72 |
| T1r-381 | (R)-I-1 | II-60 | II-74 |
| T1r-382 | (R)-I-1 | II-60 | II-76 |
| T1r-383 | (R)-I-1 | II-60 | II-78 |
| T1r-384 | (R)-I-1 | II-60 | II-84 |
| T1r-385 | (R)-I-1 | II-60 | II-85 |
| T1r-386 | (R)-I-1 | II-60 | II-86 |
| T1r-387 | (R)-I-1 | II-60 | II-92 |
| T1r-388 | (R)-I-1 | II-62 | II-66 |
| T1r-389 | (R)-I-1 | II-62 | II-69 |
| T1r-390 | (R)-I-1 | II-62 | II-70 |
| T1r-391 | (R)-I-1 | II-62 | II-71 |
| T1r-392 | (R)-I-1 | II-62 | II-72 |
| T1r-393 | (R)-I-1 | II-62 | II-74 |
| T1r-394 | (R)-I-1 | II-62 | II-76 |
| T1r-395 | (R)-I-1 | II-62 | II-78 |
| T1r-396 | (R)-I-1 | II-62 | II-84 |
| T1r-397 | (R)-I-1 | II-62 | II-85 |
| T1r-398 | (R)-I-1 | II-62 | II-86 |
| T1r-399 | (R)-I-1 | II-62 | II-92 |
| T1r-400 | (R)-I-1 | II-66 | II-69 |
| T1r-401 | (R)-I-1 | II-66 | II-70 |
| T1r-402 | (R)-I-1 | II-66 | II-71 |
| T1r-403 | (R)-I-1 | II-66 | II-72 |
| T1r-404 | (R)-I-1 | II-66 | II-74 |
| T1r-405 | (R)-I-1 | II-66 | II-76 |
| T1r-406 | (R)-I-1 | II-66 | II-78 |
| T1r-407 | (R)-I-1 | II-66 | II-84 |
| T1r-408 | (R)-I-1 | II-66 | II-85 |
| T1r-409 | (R)-I-1 | II-66 | II-86 |
| T1r-410 | (R)-I-1 | II-66 | II-92 |
| T1r-411 | (R)-I-1 | II-69 | II-70 |
| T1r-412 | (R)-I-1 | II-69 | II-71 |
| T1r-413 | (R)-I-1 | II-69 | II-72 |
| T1r-414 | (R)-I-1 | II-69 | II-74 |
| T1r-415 | (R)-I-1 | II-69 | II-76 |
| T1r-416 | (R)-I-1 | II-69 | II-78 |
| T1r-417 | (R)-I-1 | II-69 | II-84 |
| T1r-418 | (R)-I-1 | II-69 | II-85 |
| T1r-419 | (R)-I-1 | II-69 | II-86 |
| T1r-420 | (R)-I-1 | II-69 | II-92 |
| T1r-421 | (R)-I-1 | II-70 | II-71 |
| T1r-422 | (R)-I-1 | II-70 | II-72 |
| T1r-423 | (R)-I-1 | II-70 | II-74 |
| T1r-424 | (R)-I-1 | II-70 | II-76 |
| T1r-425 | (R)-I-1 | II-70 | II-78 |
| T1r-426 | (R)-I-1 | II-70 | II-84 |
| T1r-427 | (R)-I-1 | II-70 | II-85 |
| T1r-428 | (R)-I-1 | II-70 | II-86 |
| T1r-429 | (R)-I-1 | II-70 | II-92 |
| T1r-430 | (R)-I-1 | II-71 | II-72 |
| T1r-431 | (R)-I-1 | II-71 | II-74 |
| T1r-432 | (R)-I-1 | II-71 | II-76 |
| T1r-433 | (R)-I-1 | II-71 | II-78 |
| T1r-434 | (R)-I-1 | II-71 | II-84 |
| T1r-435 | (R)-I-1 | II-71 | II-85 |
| T1r-436 | (R)-I-1 | II-71 | II-86 |
| T1r-437 | (R)-I-1 | II-71 | II-92 |
| T1r-438 | (R)-I-1 | II-72 | II-74 |
| T1r-439 | (R)-I-1 | II-74 | II-76 |
| T1r-440 | (R)-I-1 | II-74 | II-78 |
| T1r-441 | (R)-I-1 | II-74 | II-84 |
| T1r-442 | (R)-I-1 | II-74 | II-85 |
| T1r-443 | (R)-I-1 | II-74 | II-86 |
| T1r-444 | (R)-I-1 | II-74 | II-92 |
| T1r-445 | (R)-I-1 | II-76 | II-78 |
| T1r-446 | (R)-I-1 | II-76 | II-84 |
| T1r-447 | (R)-I-1 | II-76 | II-85 |
| T1r-448 | (R)-I-1 | II-76 | II-86 |
| T1r-449 | (R)-I-1 | II-76 | II-92 |
| T1r-450 | (R)-I-1 | II-78 | II-84 |
| T1r-451 | (R)-I-1 | II-78 | II-85 |
| T1r-452 | (R)-I-1 | II-78 | II-86 |
| T1r-453 | (R)-I-1 | II-78 | II-92 |
| T1r-454 | (R)-I-1 | II-84 | II-85 |
| T1r-455 | (R)-I-1 | II-84 | II-86 |
| T1r-456 | (R)-I-1 | II-84 | II-92 |
| T1r-457 | (R)-I-1 | II-85 | II-86 |
| T1r-458 | (R)-I-1 | II-85 | II-92 |
| T1r-459 | (R)-I-1 | II-86 | II-92 |
| T1r-460 | (R)-I-5 | II-3 | II-5 |
| T1r-461 | (R)-I-5 | II-3 | II-6 |
| T1r-462 | (R)-I-5 | II-3 | II-7 |
| T1r-463 | (R)-I-5 | II-3 | II-8 |
| T1r-464 | (R)-I-5 | II-3 | II-11 |
| T1r-465 | (R)-I-5 | II-3 | II-16 |
| T1r-466 | (R)-I-5 | II-3 | II-21 |
| T1r-467 | (R)-I-5 | II-3 | II-26 |
| T1r-468 | (R)-I-5 | II-3 | II-32 |
| T1r-469 | (R)-I-5 | II-3 | II-33 |
| T1r-470 | (R)-I-5 | II-3 | II-37 |
| T1r-471 | (R)-I-5 | II-3 | II-39 |
| T1r-472 | (R)-I-5 | II-3 | II-42 |
| T1r-473 | (R)-I-5 | II-3 | II-44 |
| T1r-474 | (R)-I-5 | II-3 | II-50 |
| T1r-475 | (R)-I-5 | II-3 | II-53 |
| T1r-476 | (R)-I-5 | II-3 | II-60 |
| T1r-477 | (R)-I-5 | II-3 | II-62 |
| T1r-478 | (R)-I-5 | II-3 | II-66 |
| T1r-479 | (R)-I-5 | II-3 | II-69 |
| T1r-480 | (R)-I-5 | II-3 | II-70 |
| T1r-481 | (R)-I-5 | II-3 | II-71 |
| T1r-482 | (R)-I-5 | II-3 | II-72 |
| T1r-483 | (R)-I-5 | II-3 | II-74 |
| T1r-484 | (R)-I-5 | II-3 | II-76 |
| T1r-485 | (R)-I-5 | II-3 | II-78 |
| T1r-486 | (R)-I-5 | II-3 | II-84 |
| T1r-487 | (R)-I-5 | II-3 | II-85 |
| T1r-488 | (R)-I-5 | II-3 | II-86 |
| T1r-489 | (R)-I-5 | II-3 | II-92 |
| T1r-490 | (R)-I-5 | II-5 | II-6 |
| T1r-491 | (R)-I-5 | II-5 | II-7 |
| T1r-492 | (R)-I-5 | II-5 | II-8 |
| T1r-493 | (R)-I-5 | II-5 | II-11 |
| T1r-494 | (R)-I-5 | II-5 | II-16 |
| T1r-495 | (R)-I-5 | II-5 | II-21 |
| T1r-496 | (R)-I-5 | II-5 | II-26 |
| T1r-497 | (R)-I-5 | II-5 | II-32 |
| T1r-498 | (R)-I-5 | II-5 | II-33 |
| T1r-499 | (R)-I-5 | II-5 | II-37 |
| T1r-500 | (R)-I-5 | II-5 | II-39 |
| T1r-501 | (R)-I-5 | II-5 | II-42 |
| T1r-502 | (R)-I-5 | II-5 | II-44 |
| T1r-503 | (R)-I-5 | II-5 | II-50 |
| T1r-504 | (R)-I-5 | II-5 | II-53 |

TABLE T1s-continued

Three-component compositions comprising one component I as (R) enantiomer (appreviated as (R)-I, e.g. (R)-I-1 for the (R)-enantiomer of I-1), one component II and one component III, in particular ternary compositions containing the respective component I as (R) enantiomer, II and III as only active ingredients.

| composition | (R)-I | II | III |
|---|---|---|---|
| T1r-505 | (R)-I-5 | II-5 | II-60 |
| T1r-506 | (R)-I-5 | II-5 | II-62 |
| T1r-507 | (R)-I-5 | II-5 | II-66 |
| T1r-508 | (R)-I-5 | II-5 | II-69 |
| T1r-509 | (R)-I-5 | II-5 | II-70 |
| T1r-510 | (R)-I-5 | II-5 | II-71 |
| T1r-511 | (R)-I-5 | II-5 | II-72 |
| T1r-512 | (R)-I-5 | II-5 | II-74 |
| T1r-513 | (R)-I-5 | II-5 | II-76 |
| T1r-514 | (R)-I-5 | II-5 | II-78 |
| T1r-515 | (R)-I-5 | II-5 | II-84 |
| T1r-516 | (R)-I-5 | II-5 | II-85 |
| T1r-517 | (R)-I-5 | II-5 | II-86 |
| T1r-518 | (R)-I-5 | II-5 | II-92 |
| T1r-519 | (R)-I-5 | II-6 | II-7 |
| T1r-520 | (R)-I-5 | II-6 | II-8 |
| T1r-521 | (R)-I-5 | II-6 | II-11 |
| T1r-522 | (R)-I-5 | II-6 | II-16 |
| T1r-523 | (R)-I-5 | II-6 | II-21 |
| T1r-524 | (R)-I-5 | II-6 | II-26 |
| T1r-525 | (R)-I-5 | II-6 | II-32 |
| T1r-526 | (R)-I-5 | II-6 | II-33 |
| T1r-527 | (R)-I-5 | II-6 | II-37 |
| T1r-528 | (R)-I-5 | II-6 | II-39 |
| T1r-529 | (R)-I-5 | II-6 | II-42 |
| T1r-530 | (R)-I-5 | II-6 | II-44 |
| T1r-531 | (R)-I-5 | II-6 | II-50 |
| T1r-532 | (R)-I-5 | II-6 | II-53 |
| T1r-533 | (R)-I-5 | II-6 | II-60 |
| T1r-534 | (R)-I-5 | II-6 | II-62 |
| T1r-535 | (R)-I-5 | II-6 | II-66 |
| T1r-536 | (R)-I-5 | II-6 | II-69 |
| T1r-537 | (R)-I-5 | II-6 | II-70 |
| T1r-538 | (R)-I-5 | II-6 | II-71 |
| T1r-539 | (R)-I-5 | II-6 | II-72 |
| T1r-540 | (R)-I-5 | II-6 | II-74 |
| T1r-541 | (R)-I-5 | II-6 | II-76 |
| T1r-542 | (R)-I-5 | II-6 | II-78 |
| T1r-543 | (R)-I-5 | II-6 | II-84 |
| T1r-544 | (R)-I-5 | II-6 | II-85 |
| T1r-545 | (R)-I-5 | II-6 | II-86 |
| T1r-546 | (R)-I-5 | II-6 | II-92 |
| T1r-547 | (R)-I-5 | II-7 | II-8 |
| T1r-548 | (R)-I-5 | II-7 | II-11 |
| T1r-549 | (R)-I-5 | II-7 | II-16 |
| T1r-550 | (R)-I-5 | II-7 | II-21 |
| T1r-551 | (R)-I-5 | II-7 | II-26 |
| T1r-552 | (R)-I-5 | II-7 | II-32 |
| T1r-553 | (R)-I-5 | II-7 | II-33 |
| T1r-554 | (R)-I-5 | II-7 | II-37 |
| T1r-555 | (R)-I-5 | II-7 | II-39 |
| T1r-556 | (R)-I-5 | II-7 | II-42 |
| T1r-557 | (R)-I-5 | II-7 | II-44 |
| T1r-558 | (R)-I-5 | II-7 | II-50 |
| T1r-559 | (R)-I-5 | II-7 | II-53 |
| T1r-560 | (R)-I-5 | II-7 | II-60 |
| T1r-561 | (R)-I-5 | II-7 | II-62 |
| T1r-562 | (R)-I-5 | II-7 | II-66 |
| T1r-563 | (R)-I-5 | II-7 | II-69 |
| T1r-564 | (R)-I-5 | II-7 | II-70 |
| T1r-565 | (R)-I-5 | II-7 | II-71 |
| T1r-566 | (R)-I-5 | II-7 | II-72 |
| T1r-567 | (R)-I-5 | II-7 | II-74 |
| T1r-568 | (R)-I-5 | II-7 | II-76 |
| T1r-569 | (R)-I-5 | II-7 | II-78 |
| T1r-570 | (R)-I-5 | II-7 | II-84 |
| T1r-571 | (R)-I-5 | II-7 | II-85 |
| T1r-572 | (R)-I-5 | II-7 | II-86 |
| T1r-573 | (R)-I-5 | II-7 | II-92 |
| T1r-574 | (R)-I-5 | II-8 | II-11 |
| T1r-575 | (R)-I-5 | II-8 | II-16 |
| T1r-576 | (R)-I-5 | II-8 | II-21 |
| T1r-577 | (R)-I-5 | II-8 | II-26 |
| T1r-578 | (R)-I-5 | II-8 | II-32 |
| T1r-579 | (R)-I-5 | II-8 | II-33 |
| T1r-580 | (R)-I-5 | II-8 | II-37 |
| T1r-581 | (R)-I-5 | II-8 | II-39 |
| T1r-582 | (R)-I-5 | II-8 | II-42 |
| T1r-583 | (R)-I-5 | II-8 | II-44 |
| T1r-584 | (R)-I-5 | II-8 | II-50 |
| T1r-585 | (R)-I-5 | II-8 | II-53 |
| T1r-586 | (R)-I-5 | II-8 | II-60 |
| T1r-587 | (R)-I-5 | II-8 | II-62 |
| T1r-588 | (R)-I-5 | II-8 | II-66 |
| T1r-589 | (R)-I-5 | II-8 | II-69 |
| T1r-590 | (R)-I-5 | II-8 | II-70 |
| T1r-591 | (R)-I-5 | II-8 | II-71 |
| T1r-592 | (R)-I-5 | II-8 | II-72 |
| T1r-593 | (R)-I-5 | II-8 | II-74 |
| T1r-594 | (R)-I-5 | II-8 | II-76 |
| T1r-595 | (R)-I-5 | II-8 | II-78 |
| T1r-596 | (R)-I-5 | II-8 | II-84 |
| T1r-597 | (R)-I-5 | II-8 | II-85 |
| T1r-598 | (R)-I-5 | II-8 | II-86 |
| T1r-599 | (R)-I-5 | II-8 | II-92 |
| T1r-600 | (R)-I-5 | II-11 | II-16 |
| T1r-601 | (R)-I-5 | II-11 | II-21 |
| T1r-602 | (R)-I-5 | II-11 | II-26 |
| T1r-603 | (R)-I-5 | II-11 | II-32 |
| T1r-604 | (R)-I-5 | II-11 | II-33 |
| T1r-605 | (R)-I-5 | II-11 | II-37 |
| T1r-606 | (R)-I-5 | II-11 | II-39 |
| T1r-607 | (R)-I-5 | II-11 | II-42 |
| T1r-608 | (R)-I-5 | II-11 | II-44 |
| T1r-609 | (R)-I-5 | II-11 | II-50 |
| T1r-610 | (R)-I-5 | II-11 | II-53 |
| T1r-611 | (R)-I-5 | II-11 | II-60 |
| T1r-612 | (R)-I-5 | II-11 | II-62 |
| T1r-613 | (R)-I-5 | II-11 | II-66 |
| T1r-614 | (R)-I-5 | II-11 | II-69 |
| T1r-615 | (R)-I-5 | II-11 | II-70 |
| T1r-616 | (R)-I-5 | II-11 | II-71 |
| T1r-617 | (R)-I-5 | II-11 | II-72 |
| T1r-618 | (R)-I-5 | II-11 | II-74 |
| T1r-619 | (R)-I-5 | II-11 | II-76 |
| T1r-620 | (R)-I-5 | II-11 | II-78 |
| T1r-621 | (R)-I-5 | II-11 | II-84 |
| T1r-622 | (R)-I-5 | II-11 | II-85 |
| T1r-623 | (R)-I-5 | II-11 | II-86 |
| T1r-624 | (R)-I-5 | II-11 | II-92 |
| T1r-625 | (R)-I-5 | II-16 | II-21 |
| T1r-626 | (R)-I-5 | II-16 | II-26 |
| T1r-627 | (R)-I-5 | II-16 | II-32 |
| T1r-628 | (R)-I-5 | II-16 | II-33 |
| T1r-629 | (R)-I-5 | II-16 | II-37 |
| T1r-630 | (R)-I-5 | II-16 | II-39 |
| T1r-631 | (R)-I-5 | II-16 | II-42 |
| T1r-632 | (R)-I-5 | II-16 | II-44 |
| T1r-633 | (R)-I-5 | II-16 | II-50 |
| T1r-634 | (R)-I-5 | II-16 | II-53 |
| T1r-635 | (R)-I-5 | II-16 | II-60 |
| T1r-636 | (R)-I-5 | II-16 | II-62 |
| T1r-637 | (R)-I-5 | II-16 | II-66 |
| T1r-638 | (R)-I-5 | II-16 | II-69 |
| T1r-639 | (R)-I-5 | II-16 | II-70 |
| T1r-640 | (R)-I-5 | II-16 | II-71 |
| T1r-641 | (R)-I-5 | II-16 | II-72 |
| T1r-642 | (R)-I-5 | II-16 | II-74 |
| T1r-643 | (R)-I-5 | II-16 | II-76 |
| T1r-644 | (R)-I-5 | II-16 | II-78 |
| T1r-645 | (R)-I-5 | II-16 | II-84 |
| T1r-646 | (R)-I-5 | II-16 | II-85 |
| T1r-647 | (R)-I-5 | II-16 | II-86 |
| T1r-648 | (R)-I-5 | II-16 | II-92 |

TABLE T1s-continued

Three-component compositions comprising one component I as (R) enantiomer (appreviated as (R)-I, e.g. (R)-I-1 for the (R)-enantiomer of I-1), one component II and one component III, in particular ternary compositions containing the respective component I as (R) enantiomer, II and III as only active ingredients.

| composition | (R)-I | II | III |
|---|---|---|---|
| T1r-649 | (R)-I-5 | II-21 | II-26 |
| T1r-650 | (R)-I-5 | II-21 | II-32 |
| T1r-651 | (R)-I-5 | II-21 | II-33 |
| T1r-652 | (R)-I-5 | II-21 | II-37 |
| T1r-653 | (R)-I-5 | II-21 | II-39 |
| T1r-654 | (R)-I-5 | II-21 | II-42 |
| T1r-655 | (R)-I-5 | II-21 | II-44 |
| T1r-656 | (R)-I-5 | II-21 | II-50 |
| T1r-657 | (R)-I-5 | II-21 | II-53 |
| T1r-658 | (R)-I-5 | II-21 | II-60 |
| T1r-659 | (R)-I-5 | II-21 | II-62 |
| T1r-660 | (R)-I-5 | II-21 | II-66 |
| T1r-661 | (R)-I-5 | II-21 | II-69 |
| T1r-662 | (R)-I-5 | II-21 | II-70 |
| T1r-663 | (R)-I-5 | II-21 | II-71 |
| T1r-664 | (R)-I-5 | II-21 | II-72 |
| T1r-665 | (R)-I-5 | II-21 | II-74 |
| T1r-666 | (R)-I-5 | II-21 | II-76 |
| T1r-667 | (R)-I-5 | II-21 | II-78 |
| T1r-668 | (R)-I-5 | II-21 | II-84 |
| T1r-669 | (R)-I-5 | II-21 | II-85 |
| T1r-670 | (R)-I-5 | II-21 | II-86 |
| T1r-671 | (R)-I-5 | II-21 | II-92 |
| T1r-672 | (R)-I-5 | II-26 | II-32 |
| T1r-673 | (R)-I-5 | II-26 | II-33 |
| T1r-674 | (R)-I-5 | II-26 | II-37 |
| T1r-675 | (R)-I-5 | II-26 | II-39 |
| T1r-676 | (R)-I-5 | II-26 | II-42 |
| T1r-677 | (R)-I-5 | II-26 | II-44 |
| T1r-678 | (R)-I-5 | II-26 | II-50 |
| T1r-679 | (R)-I-5 | II-26 | II-53 |
| T1r-680 | (R)-I-5 | II-26 | II-60 |
| T1r-681 | (R)-I-5 | II-26 | II-62 |
| T1r-682 | (R)-I-5 | II-26 | II-66 |
| T1r-683 | (R)-I-5 | II-26 | II-69 |
| T1r-684 | (R)-I-5 | II-26 | II-70 |
| T1r-685 | (R)-I-5 | II-26 | II-71 |
| T1r-686 | (R)-I-5 | II-26 | II-72 |
| T1r-687 | (R)-I-5 | II-26 | II-74 |
| T1r-688 | (R)-I-5 | II-26 | II-76 |
| T1r-689 | (R)-I-5 | II-26 | II-78 |
| T1r-690 | (R)-I-5 | II-26 | II-84 |
| T1r-691 | (R)-I-5 | II-26 | II-85 |
| T1r-692 | (R)-I-5 | II-26 | II-86 |
| T1r-693 | (R)-I-5 | II-26 | II-92 |
| T1r-694 | (R)-I-5 | II-32 | II-33 |
| T1r-695 | (R)-I-5 | II-32 | II-37 |
| T1r-696 | (R)-I-5 | II-32 | II-39 |
| T1r-697 | (R)-I-5 | II-32 | II-42 |
| T1r-698 | (R)-I-5 | II-32 | II-44 |
| T1r-699 | (R)-I-5 | II-32 | II-50 |
| T1r-700 | (R)-I-5 | II-32 | II-53 |
| T1r-701 | (R)-I-5 | II-32 | II-60 |
| T1r-702 | (R)-I-5 | II-32 | II-62 |
| T1r-703 | (R)-I-5 | II-32 | II-66 |
| T1r-704 | (R)-I-5 | II-32 | II-69 |
| T1r-705 | (R)-I-5 | II-32 | II-70 |
| T1r-706 | (R)-I-5 | II-32 | II-71 |
| T1r-707 | (R)-I-5 | II-32 | II-72 |
| T1r-708 | (R)-I-5 | II-32 | II-74 |
| T1r-709 | (R)-I-5 | II-32 | II-76 |
| T1r-710 | (R)-I-5 | II-32 | II-78 |
| T1r-711 | (R)-I-5 | II-32 | II-84 |
| T1r-712 | (R)-I-5 | II-32 | II-85 |
| T1r-713 | (R)-I-5 | II-32 | II-86 |
| T1r-714 | (R)-I-5 | II-32 | II-92 |
| T1r-715 | (R)-I-5 | II-33 | II-37 |
| T1r-716 | (R)-I-5 | II-33 | II-39 |
| T1r-717 | (R)-I-5 | II-33 | II-42 |
| T1r-718 | (R)-I-5 | II-33 | II-44 |
| T1r-719 | (R)-I-5 | II-33 | II-50 |
| T1r-720 | (R)-I-5 | II-33 | II-53 |
| T1r-721 | (R)-I-5 | II-33 | II-60 |
| T1r-722 | (R)-I-5 | II-33 | II-62 |
| T1r-723 | (R)-I-5 | II-33 | II-66 |
| T1r-724 | (R)-I-5 | II-33 | II-69 |
| T1r-725 | (R)-I-5 | II-33 | II-70 |
| T1r-726 | (R)-I-5 | II-33 | II-71 |
| T1r-727 | (R)-I-5 | II-33 | II-72 |
| T1r-728 | (R)-I-5 | II-33 | II-74 |
| T1r-729 | (R)-I-5 | II-33 | II-76 |
| T1r-730 | (R)-I-5 | II-33 | II-78 |
| T1r-731 | (R)-I-5 | II-33 | II-84 |
| T1r-732 | (R)-I-5 | II-33 | II-85 |
| T1r-733 | (R)-I-5 | II-33 | II-86 |
| T1r-734 | (R)-I-5 | II-33 | II-92 |
| T1r-735 | (R)-I-5 | II-37 | II-39 |
| T1r-736 | (R)-I-5 | II-37 | II-42 |
| T1r-737 | (R)-I-5 | II-37 | II-44 |
| T1r-738 | (R)-I-5 | II-37 | II-50 |
| T1r-739 | (R)-I-5 | II-37 | II-53 |
| T1r-740 | (R)-I-5 | II-37 | II-60 |
| T1r-741 | (R)-I-5 | II-37 | II-62 |
| T1r-742 | (R)-I-5 | II-37 | II-66 |
| T1r-743 | (R)-I-5 | II-37 | II-69 |
| T1r-744 | (R)-I-5 | II-37 | II-70 |
| T1r-745 | (R)-I-5 | II-37 | II-71 |
| T1r-746 | (R)-I-5 | II-37 | II-72 |
| T1r-747 | (R)-I-5 | II-37 | II-74 |
| T1r-748 | (R)-I-5 | II-37 | II-76 |
| T1r-749 | (R)-I-5 | II-37 | II-78 |
| T1r-750 | (R)-I-5 | II-37 | II-84 |
| T1r-751 | (R)-I-5 | II-37 | II-85 |
| T1r-752 | (R)-I-5 | II-37 | II-86 |
| T1r-753 | (R)-I-5 | II-37 | II-92 |
| T1r-754 | (R)-I-5 | II-39 | II-42 |
| T1r-755 | (R)-I-5 | II-39 | II-44 |
| T1r-756 | (R)-I-5 | II-39 | II-50 |
| T1r-757 | (R)-I-5 | II-39 | II-53 |
| T1r-758 | (R)-I-5 | II-39 | II-60 |
| T1r-759 | (R)-I-5 | II-39 | II-62 |
| T1r-760 | (R)-I-5 | II-39 | II-66 |
| T1r-761 | (R)-I-5 | II-39 | II-69 |
| T1r-762 | (R)-I-5 | II-39 | II-70 |
| T1r-763 | (R)-I-5 | II-39 | II-71 |
| T1r-764 | (R)-I-5 | II-39 | II-72 |
| T1r-765 | (R)-I-5 | II-39 | II-74 |
| T1r-766 | (R)-I-5 | II-39 | II-76 |
| T1r-767 | (R)-I-5 | II-39 | II-78 |
| T1r-768 | (R)-I-5 | II-39 | II-84 |
| T1r-769 | (R)-I-5 | II-39 | II-85 |
| T1r-770 | (R)-I-5 | II-39 | II-86 |
| T1r-771 | (R)-I-5 | II-39 | II-92 |
| T1r-772 | (R)-I-5 | II-42 | II-44 |
| T1r-773 | (R)-I-5 | II-42 | II-50 |
| T1r-774 | (R)-I-5 | II-42 | II-53 |
| T1r-775 | (R)-I-5 | II-42 | II-60 |
| T1r-776 | (R)-I-5 | II-42 | II-62 |
| T1r-777 | (R)-I-5 | II-42 | II-66 |
| T1r-778 | (R)-I-5 | II-42 | II-69 |
| T1r-779 | (R)-I-5 | II-42 | II-70 |
| T1r-780 | (R)-I-5 | II-42 | II-71 |
| T1r-781 | (R)-I-5 | II-42 | II-72 |
| T1r-782 | (R)-I-5 | II-42 | II-74 |
| T1r-783 | (R)-I-5 | II-42 | II-76 |
| T1r-784 | (R)-I-5 | II-42 | II-78 |
| T1r-785 | (R)-I-5 | II-42 | II-84 |
| T1r-786 | (R)-I-5 | II-42 | II-85 |
| T1r-787 | (R)-I-5 | II-42 | II-86 |
| T1r-788 | (R)-I-5 | II-42 | II-92 |
| T1r-789 | (R)-I-5 | II-44 | II-50 |
| T1r-790 | (R)-I-5 | II-44 | II-53 |
| T1r-791 | (R)-I-5 | II-44 | II-60 |
| T1r-792 | (R)-I-5 | II-44 | II-62 |

TABLE T1s-continued

Three-component compositions comprising one component I as (R) enantiomer (appreviated as (R)-I, e.g. (R)-I-1 for the (R)-enantiomer of I-1), one component II and one component III, in particular ternary compositions containing the respective component I as (R) enantiomer, II and III as only active ingredients.

| composition | (R)-I | II | III |
|---|---|---|---|
| T1r-793 | (R)-I-5 | II-44 | II-66 |
| T1r-794 | (R)-I-5 | II-44 | II-69 |
| T1r-795 | (R)-I-5 | II-44 | II-70 |
| T1r-796 | (R)-I-5 | II-44 | II-71 |
| T1r-797 | (R)-I-5 | II-44 | II-72 |
| T1r-798 | (R)-I-5 | II-44 | II-74 |
| T1r-799 | (R)-I-5 | II-44 | II-76 |
| T1r-800 | (R)-I-5 | II-44 | II-78 |
| T1r-801 | (R)-I-5 | II-44 | II-84 |
| T1r-802 | (R)-I-5 | II-44 | II-85 |
| T1r-803 | (R)-I-5 | II-44 | II-86 |
| T1r-804 | (R)-I-5 | II-44 | II-92 |
| T1r-805 | (R)-I-5 | II-50 | II-53 |
| T1r-806 | (R)-I-5 | II-50 | II-60 |
| T1r-807 | (R)-I-5 | II-50 | II-62 |
| T1r-808 | (R)-I-5 | II-50 | II-66 |
| T1r-809 | (R)-I-5 | II-50 | II-69 |
| T1r-810 | (R)-I-5 | II-50 | II-70 |
| T1r-811 | (R)-I-5 | II-50 | II-71 |
| T1r-812 | (R)-I-5 | II-50 | II-72 |
| T1r-813 | (R)-I-5 | II-50 | II-74 |
| T1r-814 | (R)-I-5 | II-50 | II-76 |
| T1r-815 | (R)-I-5 | II-50 | II-78 |
| T1r-816 | (R)-I-5 | II-50 | II-84 |
| T1r-817 | (R)-I-5 | II-50 | II-85 |
| T1r-818 | (R)-I-5 | II-50 | II-86 |
| T1r-819 | (R)-I-5 | II-50 | II-92 |
| T1r-820 | (R)-I-5 | II-53 | II-60 |
| T1r-821 | (R)-I-5 | II-53 | II-62 |
| T1r-822 | (R)-I-5 | II-53 | II-66 |
| T1r-823 | (R)-I-5 | II-53 | II-69 |
| T1r-824 | (R)-I-5 | II-53 | II-70 |
| T1r-825 | (R)-I-5 | II-53 | II-71 |
| T1r-826 | (R)-I-5 | II-53 | II-72 |
| T1r-827 | (R)-I-5 | II-53 | II-74 |
| T1r-828 | (R)-I-5 | II-53 | II-76 |
| T1r-829 | (R)-I-5 | II-53 | II-78 |
| T1r-830 | (R)-I-5 | II-53 | II-84 |
| T1r-831 | (R)-I-5 | II-53 | II-85 |
| T1r-832 | (R)-I-5 | II-53 | II-86 |
| T1r-833 | (R)-I-5 | II-53 | II-92 |
| T1r-834 | (R)-I-5 | II-60 | II-62 |
| T1r-835 | (R)-I-5 | II-60 | II-66 |
| T1r-836 | (R)-I-5 | II-60 | II-69 |
| T1r-837 | (R)-I-5 | II-60 | II-70 |
| T1r-838 | (R)-I-5 | II-60 | II-71 |
| T1r-839 | (R)-I-5 | II-60 | II-72 |
| T1r-840 | (R)-I-5 | II-60 | II-74 |
| T1r-841 | (R)-I-5 | II-60 | II-76 |
| T1r-842 | (R)-I-5 | II-60 | II-78 |
| T1r-843 | (R)-I-5 | II-60 | II-84 |
| T1r-844 | (R)-I-5 | II-60 | II-85 |
| T1r-845 | (R)-I-5 | II-60 | II-86 |
| T1r-846 | (R)-I-5 | II-60 | II-92 |
| T1r-847 | (R)-I-5 | II-62 | II-66 |
| T1r-848 | (R)-I-5 | II-62 | II-69 |
| T1r-849 | (R)-I-5 | II-62 | II-70 |
| T1r-850 | (R)-I-5 | II-62 | II-71 |
| T1r-851 | (R)-I-5 | II-62 | II-72 |
| T1r-852 | (R)-I-5 | II-62 | II-74 |
| T1r-853 | (R)-I-5 | II-62 | II-76 |
| T1r-854 | (R)-I-5 | II-62 | II-78 |
| T1r-855 | (R)-I-5 | II-62 | II-84 |
| T1r-856 | (R)-I-5 | II-62 | II-85 |
| T1r-857 | (R)-I-5 | II-62 | II-86 |
| T1r-858 | (R)-I-5 | II-62 | II-92 |
| T1r-859 | (R)-I-5 | II-66 | II-69 |
| T1r-860 | (R)-I-5 | II-66 | II-70 |
| T1r-861 | (R)-I-5 | II-66 | II-71 |
| T1r-862 | (R)-I-5 | II-66 | II-72 |
| T1r-863 | (R)-I-5 | II-66 | II-74 |
| T1r-864 | (R)-I-5 | II-66 | II-76 |
| T1r-865 | (R)-I-5 | II-66 | II-78 |
| T1r-866 | (R)-I-5 | II-66 | II-84 |
| T1r-867 | (R)-I-5 | II-66 | II-85 |
| T1r-868 | (R)-I-5 | II-66 | II-86 |
| T1r-869 | (R)-I-5 | II-66 | II-92 |
| T1r-870 | (R)-I-5 | II-69 | II-70 |
| T1r-871 | (R)-I-5 | II-69 | II-71 |
| T1r-872 | (R)-I-5 | II-69 | II-72 |
| T1r-873 | (R)-I-5 | II-69 | II-74 |
| T1r-874 | (R)-I-5 | II-69 | II-76 |
| T1r-875 | (R)-I-5 | II-69 | II-78 |
| T1r-876 | (R)-I-5 | II-69 | II-84 |
| T1r-877 | (R)-I-5 | II-69 | II-85 |
| T1r-878 | (R)-I-5 | II-69 | II-86 |
| T1r-879 | (R)-I-5 | II-69 | II-92 |
| T1r-880 | (R)-I-5 | II-70 | II-71 |
| T1r-881 | (R)-I-5 | II-70 | II-72 |
| T1r-882 | (R)-I-5 | II-70 | II-74 |
| T1r-883 | (R)-I-5 | II-70 | II-76 |
| T1r-884 | (R)-I-5 | II-70 | II-78 |
| T1r-885 | (R)-I-5 | II-70 | II-84 |
| T1r-886 | (R)-I-5 | II-70 | II-85 |
| T1r-887 | (R)-I-5 | II-70 | II-86 |
| T1r-888 | (R)-I-5 | II-70 | II-92 |
| T1r-889 | (R)-I-5 | II-71 | II-72 |
| T1r-890 | (R)-I-5 | II-71 | II-74 |
| T1r-891 | (R)-I-5 | II-71 | II-76 |
| T1r-892 | (R)-I-5 | II-71 | II-78 |
| T1r-893 | (R)-I-5 | II-71 | II-84 |
| T1r-894 | (R)-I-5 | II-71 | II-85 |
| T1r-895 | (R)-I-5 | II-71 | II-86 |
| T1r-896 | (R)-I-5 | II-71 | II-92 |
| T1r-897 | (R)-I-5 | II-72 | II-74 |
| T1r-898 | (R)-I-5 | II-74 | II-76 |
| T1r-899 | (R)-I-5 | II-74 | II-78 |
| T1r-900 | (R)-I-5 | II-74 | II-84 |
| T1r-901 | (R)-I-5 | II-74 | II-85 |
| T1r-902 | (R)-I-5 | II-74 | II-86 |
| T1r-903 | (R)-I-5 | II-74 | II-92 |
| T1r-904 | (R)-I-5 | II-76 | II-78 |
| T1r-905 | (R)-I-5 | II-76 | II-84 |
| T1r-906 | (R)-I-5 | II-76 | II-85 |
| T1r-907 | (R)-I-5 | II-76 | II-86 |
| T1r-908 | (R)-I-5 | II-76 | II-92 |
| T1r-909 | (R)-I-5 | II-78 | II-84 |
| T1r-910 | (R)-I-5 | II-78 | II-85 |
| T1r-911 | (R)-I-5 | II-78 | II-86 |
| T1r-912 | (R)-I-5 | II-78 | II-92 |
| T1r-913 | (R)-I-5 | II-84 | II-85 |
| T1r-914 | (R)-I-5 | II-84 | II-86 |
| T1r-915 | (R)-I-5 | II-84 | II-92 |
| T1r-916 | (R)-I-5 | II-85 | II-86 |
| T1r-917 | (R)-I-5 | II-85 | II-92 |
| T1r-918 | (R)-I-5 | II-86 | II-92 |
| T1r-919 | (R)-I-3 | II-3 | II-5 |
| T1r-920 | (R)-I-3 | II-3 | II-6 |
| T1r-921 | (R)-I-3 | II-3 | II-7 |
| T1r-922 | (R)-I-3 | II-3 | II-8 |
| T1r-923 | (R)-I-3 | II-3 | II-11 |
| T1r-924 | (R)-I-3 | II-3 | II-16 |
| T1r-925 | (R)-I-3 | II-3 | II-21 |
| T1r-926 | (R)-I-3 | II-3 | II-26 |
| T1r-927 | (R)-I-3 | II-3 | II-32 |
| T1r-928 | (R)-I-3 | II-3 | II-33 |
| T1r-929 | (R)-I-3 | II-3 | II-37 |
| T1r-930 | (R)-I-3 | II-3 | II-39 |
| T1r-931 | (R)-I-3 | II-3 | II-42 |
| T1r-932 | (R)-I-3 | II-3 | II-44 |
| T1r-933 | (R)-I-3 | II-3 | II-50 |
| T1r-934 | (R)-I-3 | II-3 | II-53 |
| T1r-935 | (R)-I-3 | II-3 | II-60 |
| T1r-936 | (R)-I-3 | II-3 | II-62 |

TABLE T1s-continued

Three-component compositions comprising one component I as (R) enantiomer (appreviated as (R)-I, e.g. (R)-I-1 for the (R)-enantiomer of I-1), one component II and one component III, in particular ternary compositions containing the respective component I as (R) enantiomer, II and III as only active ingredients.

| composition | (R)-I | II | III |
|---|---|---|---|
| T1r-937 | (R)-I-3 | II-3 | II-66 |
| T1r-938 | (R)-I-3 | II-3 | II-69 |
| T1r-939 | (R)-I-3 | II-3 | II-70 |
| T1r-940 | (R)-I-3 | II-3 | II-71 |
| T1r-941 | (R)-I-3 | II-3 | II-72 |
| T1r-942 | (R)-I-3 | II-3 | II-74 |
| T1r-943 | (R)-I-3 | II-3 | II-76 |
| T1r-944 | (R)-I-3 | II-3 | II-78 |
| T1r-945 | (R)-I-3 | II-3 | II-84 |
| T1r-946 | (R)-I-3 | II-3 | II-85 |
| T1r-947 | (R)-I-3 | II-3 | II-86 |
| T1r-948 | (R)-I-3 | II-3 | II-92 |
| T1r-949 | (R)-I-3 | II-5 | II-6 |
| T1r-950 | (R)-I-3 | II-5 | II-7 |
| T1r-951 | (R)-I-3 | II-5 | II-8 |
| T1r-952 | (R)-I-3 | II-5 | II-11 |
| T1r-953 | (R)-I-3 | II-5 | II-16 |
| T1r-954 | (R)-I-3 | II-5 | II-21 |
| T1r-955 | (R)-I-3 | II-5 | II-26 |
| T1r-956 | (R)-I-3 | II-5 | II-32 |
| T1r-957 | (R)-I-3 | II-5 | II-33 |
| T1r-958 | (R)-I-3 | II-5 | II-37 |
| T1r-959 | (R)-I-3 | II-5 | II-39 |
| T1r-960 | (R)-I-3 | II-5 | II-42 |
| T1r-961 | (R)-I-3 | II-5 | II-44 |
| T1r-962 | (R)-I-3 | II-5 | II-50 |
| T1r-963 | (R)-I-3 | II-5 | II-53 |
| T1r-964 | (R)-I-3 | II-5 | II-60 |
| T1r-965 | (R)-I-3 | II-5 | II-62 |
| T1r-966 | (R)-I-3 | II-5 | II-66 |
| T1r-967 | (R)-I-3 | II-5 | II-69 |
| T1r-968 | (R)-I-3 | II-5 | II-70 |
| T1r-969 | (R)-I-3 | II-5 | II-71 |
| T1r-970 | (R)-I-3 | II-5 | II-72 |
| T1r-971 | (R)-I-3 | II-5 | II-74 |
| T1r-972 | (R)-I-3 | II-5 | II-76 |
| T1r-973 | (R)-I-3 | II-5 | II-78 |
| T1r-974 | (R)-I-3 | II-5 | II-84 |
| T1r-975 | (R)-I-3 | II-5 | II-85 |
| T1r-976 | (R)-I-3 | II-5 | II-86 |
| T1r-977 | (R)-I-3 | II-5 | II-92 |
| T1r-978 | (R)-I-3 | II-6 | II-7 |
| T1r-979 | (R)-I-3 | II-6 | II-8 |
| T1r-980 | (R)-I-3 | II-6 | II-11 |
| T1r-981 | (R)-I-3 | II-6 | II-16 |
| T1r-982 | (R)-I-3 | II-6 | II-21 |
| T1r-983 | (R)-I-3 | II-6 | II-26 |
| T1r-984 | (R)-I-3 | II-6 | II-32 |
| T1r-985 | (R)-I-3 | II-6 | II-33 |
| T1r-986 | (R)-I-3 | II-6 | II-37 |
| T1r-987 | (R)-I-3 | II-6 | II-39 |
| T1r-988 | (R)-I-3 | II-6 | II-42 |
| T1r-989 | (R)-I-3 | II-6 | II-44 |
| T1r-990 | (R)-I-3 | II-6 | II-50 |
| T1r-991 | (R)-I-3 | II-6 | II-53 |
| T1r-992 | (R)-I-3 | II-6 | II-60 |
| T1r-993 | (R)-I-3 | II-6 | II-62 |
| T1r-994 | (R)-I-3 | II-6 | II-66 |
| T1r-995 | (R)-I-3 | II-6 | II-69 |
| T1r-996 | (R)-I-3 | II-6 | II-70 |
| T1r-997 | (R)-I-3 | II-6 | II-71 |
| T1r-998 | (R)-I-3 | II-6 | II-72 |
| T1r-999 | (R)-I-3 | II-6 | II-74 |
| T1r-1000 | (R)-I-3 | II-6 | II-76 |
| T1r-1001 | (R)-I-3 | II-6 | II-78 |
| T1r-1002 | (R)-I-3 | II-6 | II-84 |
| T1r-1003 | (R)-I-3 | II-6 | II-85 |
| T1r-1004 | (R)-I-3 | II-6 | II-86 |
| T1r-1005 | (R)-I-3 | II-6 | II-92 |
| T1r-1006 | (R)-I-3 | II-7 | II-8 |
| T1r-1007 | (R)-I-3 | II-7 | II-11 |
| T1r-1008 | (R)-I-3 | II-7 | II-16 |
| T1r-1009 | (R)-I-3 | II-7 | II-21 |
| T1r-1010 | (R)-I-3 | II-7 | II-26 |
| T1r-1011 | (R)-I-3 | II-7 | II-32 |
| T1r-1012 | (R)-I-3 | II-7 | II-33 |
| T1r-1013 | (R)-I-3 | II-7 | II-37 |
| T1r-1014 | (R)-I-3 | II-7 | II-39 |
| T1r-1015 | (R)-I-3 | II-7 | II-42 |
| T1r-1016 | (R)-I-3 | II-7 | II-44 |
| T1r-1017 | (R)-I-3 | II-7 | II-50 |
| T1r-1018 | (R)-I-3 | II-7 | II-53 |
| T1r-1019 | (R)-I-3 | II-7 | II-60 |
| T1r-1020 | (R)-I-3 | II-7 | II-62 |
| T1r-1021 | (R)-I-3 | II-7 | II-66 |
| T1r-1022 | (R)-I-3 | II-7 | II-69 |
| T1r-1023 | (R)-I-3 | II-7 | II-70 |
| T1r-1024 | (R)-I-3 | II-7 | II-71 |
| T1r-1025 | (R)-I-3 | II-7 | II-72 |
| T1r-1026 | (R)-I-3 | II-7 | II-74 |
| T1r-1027 | (R)-I-3 | II-7 | II-76 |
| T1r-1028 | (R)-I-3 | II-7 | II-78 |
| T1r-1029 | (R)-I-3 | II-7 | II-84 |
| T1r-1030 | (R)-I-3 | II-7 | II-85 |
| T1r-1031 | (R)-I-3 | II-7 | II-86 |
| T1r-1032 | (R)-I-3 | II-7 | II-92 |
| T1r-1033 | (R)-I-3 | II-8 | II-11 |
| T1r-1034 | (R)-I-3 | II-8 | II-16 |
| T1r-1035 | (R)-I-3 | II-8 | II-21 |
| T1r-1036 | (R)-I-3 | II-8 | II-26 |
| T1r-1037 | (R)-I-3 | II-8 | II-32 |
| T1r-1038 | (R)-I-3 | II-8 | II-33 |
| T1r-1039 | (R)-I-3 | II-8 | II-37 |
| T1r-1040 | (R)-I-3 | II-8 | II-39 |
| T1r-1041 | (R)-I-3 | II-8 | II-42 |
| T1r-1042 | (R)-I-3 | II-8 | II-44 |
| T1r-1043 | (R)-I-3 | II-8 | II-50 |
| T1r-1044 | (R)-I-3 | II-8 | II-53 |
| T1r-1045 | (R)-I-3 | II-8 | II-60 |
| T1r-1046 | (R)-I-3 | II-8 | II-62 |
| T1r-1047 | (R)-I-3 | II-8 | II-66 |
| T1r-1048 | (R)-I-3 | II-8 | II-69 |
| T1r-1049 | (R)-I-3 | II-8 | II-70 |
| T1r-1050 | (R)-I-3 | II-8 | II-71 |
| T1r-1051 | (R)-I-3 | II-8 | II-72 |
| T1r-1052 | (R)-I-3 | II-8 | II-74 |
| T1r-1053 | (R)-I-3 | II-8 | II-76 |
| T1r-1054 | (R)-I-3 | II-8 | II-78 |
| T1r-1055 | (R)-I-3 | II-8 | II-84 |
| T1r-1056 | (R)-I-3 | II-8 | II-85 |
| T1r-1057 | (R)-I-3 | II-8 | II-86 |
| T1r-1058 | (R)-I-3 | II-8 | II-92 |
| T1r-1059 | (R)-I-3 | II-11 | II-16 |
| T1r-1060 | (R)-I-3 | II-11 | II-21 |
| T1r-1061 | (R)-I-3 | II-11 | II-26 |
| T1r-1062 | (R)-I-3 | II-11 | II-32 |
| T1r-1063 | (R)-I-3 | II-11 | II-33 |
| T1r-1064 | (R)-I-3 | II-11 | II-37 |
| T1r-1065 | (R)-I-3 | II-11 | II-39 |
| T1r-1066 | (R)-I-3 | II-11 | II-42 |
| T1r-1067 | (R)-I-3 | II-11 | II-44 |
| T1r-1068 | (R)-I-3 | II-11 | II-50 |
| T1r-1069 | (R)-I-3 | II-11 | II-53 |
| T1r-1070 | (R)-I-3 | II-11 | II-60 |
| T1r-1071 | (R)-I-3 | II-11 | II-62 |
| T1r-1072 | (R)-I-3 | II-11 | II-66 |
| T1r-1073 | (R)-I-3 | II-11 | II-69 |
| T1r-1074 | (R)-I-3 | II-11 | II-70 |
| T1r-1075 | (R)-I-3 | II-11 | II-71 |
| T1r-1076 | (R)-I-3 | II-11 | II-72 |
| T1r-1077 | (R)-I-3 | II-11 | II-74 |
| T1r-1078 | (R)-I-3 | II-11 | II-76 |
| T1r-1079 | (R)-I-3 | II-11 | II-78 |
| T1r-1080 | (R)-I-3 | II-11 | II-84 |

TABLE T1s-continued

Three-component compositions comprising one component I as (R) enantiomer (appreviated as (R)-I, e.g. (R)-I-1 for the (R)-enantiomer of I-1), one component II and one component III, in particular ternary compositions containing the respective component I as (R) enantiomer, II and III as only active ingredients.

| composition | (R)-I | II | III |
|---|---|---|---|
| T1r-1081 | (R)-I-3 | II-11 | II-85 |
| T1r-1082 | (R)-I-3 | II-11 | II-86 |
| T1r-1083 | (R)-I-3 | II-11 | II-92 |
| T1r-1084 | (R)-I-3 | II-16 | II-21 |
| T1r-1085 | (R)-I-3 | II-16 | II-26 |
| T1r-1086 | (R)-I-3 | II-16 | II-32 |
| T1r-1087 | (R)-I-3 | II-16 | II-33 |
| T1r-1088 | (R)-I-3 | II-16 | II-37 |
| T1r-1089 | (R)-I-3 | II-16 | II-39 |
| T1r-1090 | (R)-I-3 | II-16 | II-42 |
| T1r-1091 | (R)-I-3 | II-16 | II-44 |
| T1r-1092 | (R)-I-3 | II-16 | II-50 |
| T1r-1093 | (R)-I-3 | II-16 | II-53 |
| T1r-1094 | (R)-I-3 | II-16 | II-60 |
| T1r-1095 | (R)-I-3 | II-16 | II-62 |
| T1r-1096 | (R)-I-3 | II-16 | II-66 |
| T1r-1097 | (R)-I-3 | II-16 | II-69 |
| T1r-1098 | (R)-I-3 | II-16 | II-70 |
| T1r-1099 | (R)-I-3 | II-16 | II-71 |
| T1r-1100 | (R)-I-3 | II-16 | II-72 |
| T1r-1101 | (R)-I-3 | II-16 | II-74 |
| T1r-1102 | (R)-I-3 | II-16 | II-76 |
| T1r-1103 | (R)-I-3 | II-16 | II-78 |
| T1r-1104 | (R)-I-3 | II-16 | II-84 |
| T1r-1105 | (R)-I-3 | II-16 | II-85 |
| T1r-1106 | (R)-I-3 | II-16 | II-86 |
| T1r-1107 | (R)-I-3 | II-16 | II-92 |
| T1r-1108 | (R)-I-3 | II-21 | II-26 |
| T1r-1109 | (R)-I-3 | II-21 | II-32 |
| T1r-1110 | (R)-I-3 | II-21 | II-33 |
| T1r-1111 | (R)-I-3 | II-21 | II-37 |
| T1r-1112 | (R)-I-3 | II-21 | II-39 |
| T1r-1113 | (R)-I-3 | II-21 | II-42 |
| T1r-1114 | (R)-I-3 | II-21 | II-44 |
| T1r-1115 | (R)-I-3 | II-21 | II-50 |
| T1r-1116 | (R)-I-3 | II-21 | II-53 |
| T1r-1117 | (R)-I-3 | II-21 | II-60 |
| T1r-1118 | (R)-I-3 | II-21 | II-62 |
| T1r-1119 | (R)-I-3 | II-21 | II-66 |
| T1r-1120 | (R)-I-3 | II-21 | II-69 |
| T1r-1121 | (R)-I-3 | II-21 | II-70 |
| T1r-1122 | (R)-I-3 | II-21 | II-71 |
| T1r-1123 | (R)-I-3 | II-21 | II-72 |
| T1r-1124 | (R)-I-3 | II-21 | II-74 |
| T1r-1125 | (R)-I-3 | II-21 | II-76 |
| T1r-1126 | (R)-I-3 | II-21 | II-78 |
| T1r-1127 | (R)-I-3 | II-21 | II-84 |
| T1r-1128 | (R)-I-3 | II-21 | II-85 |
| T1r-1129 | (R)-I-3 | II-21 | II-86 |
| T1r-1130 | (R)-I-3 | II-21 | II-92 |
| T1r-1131 | (R)-I-3 | II-26 | II-32 |
| T1r-1132 | (R)-I-3 | II-26 | II-33 |
| T1r-1133 | (R)-I-3 | II-26 | II-37 |
| T1r-1134 | (R)-I-3 | II-26 | II-39 |
| T1r-1135 | (R)-I-3 | II-26 | II-42 |
| T1r-1136 | (R)-I-3 | II-26 | II-44 |
| T1r-1137 | (R)-I-3 | II-26 | II-50 |
| T1r-1138 | (R)-I-3 | II-26 | II-53 |
| T1r-1139 | (R)-I-3 | II-26 | II-60 |
| T1r-1140 | (R)-I-3 | II-26 | II-62 |
| T1r-1141 | (R)-I-3 | II-26 | II-66 |
| T1r-1142 | (R)-I-3 | II-26 | II-69 |
| T1r-1143 | (R)-I-3 | II-26 | II-70 |
| T1r-1144 | (R)-I-3 | II-26 | II-71 |
| T1r-1145 | (R)-I-3 | II-26 | II-72 |
| T1r-1146 | (R)-I-3 | II-26 | II-74 |
| T1r-1147 | (R)-I-3 | II-26 | II-76 |
| T1r-1148 | (R)-I-3 | II-26 | II-78 |
| T1r-1149 | (R)-I-3 | II-26 | II-84 |
| T1r-1150 | (R)-I-3 | II-26 | II-85 |
| T1r-1151 | (R)-I-3 | II-26 | II-86 |
| T1r-1152 | (R)-I-3 | II-26 | II-92 |
| T1r-1153 | (R)-I-3 | II-32 | II-33 |
| T1r-1154 | (R)-I-3 | II-32 | II-37 |
| T1r-1155 | (R)-I-3 | II-32 | II-39 |
| T1r-1156 | (R)-I-3 | II-32 | II-42 |
| T1r-1157 | (R)-I-3 | II-32 | II-44 |
| T1r-1158 | (R)-I-3 | II-32 | II-50 |
| T1r-1159 | (R)-I-3 | II-32 | II-53 |
| T1r-1160 | (R)-I-3 | II-32 | II-60 |
| T1r-1161 | (R)-I-3 | II-32 | II-62 |
| T1r-1162 | (R)-I-3 | II-32 | II-66 |
| T1r-1163 | (R)-I-3 | II-32 | II-69 |
| T1r-1164 | (R)-I-3 | II-32 | II-70 |
| T1r-1165 | (R)-I-3 | II-32 | II-71 |
| T1r-1166 | (R)-I-3 | II-32 | II-72 |
| T1r-1167 | (R)-I-3 | II-32 | II-74 |
| T1r-1168 | (R)-I-3 | II-32 | II-76 |
| T1r-1169 | (R)-I-3 | II-32 | II-78 |
| T1r-1170 | (R)-I-3 | II-32 | II-84 |
| T1r-1171 | (R)-I-3 | II-32 | II-85 |
| T1r-1172 | (R)-I-3 | II-32 | II-86 |
| T1r-1173 | (R)-I-3 | II-32 | II-92 |
| T1r-1174 | (R)-I-3 | II-33 | II-37 |
| T1r-1175 | (R)-I-3 | II-33 | II-39 |
| T1r-1176 | (R)-I-3 | II-33 | II-42 |
| T1r-1177 | (R)-I-3 | II-33 | II-44 |
| T1r-1178 | (R)-I-3 | II-33 | II-50 |
| T1r-1179 | (R)-I-3 | II-33 | II-53 |
| T1r-1180 | (R)-I-3 | II-33 | II-60 |
| T1r-1181 | (R)-I-3 | II-33 | II-62 |
| T1r-1182 | (R)-I-3 | II-33 | II-66 |
| T1r-1183 | (R)-I-3 | II-33 | II-69 |
| T1r-1184 | (R)-I-3 | II-33 | II-70 |
| T1r-1185 | (R)-I-3 | II-33 | II-71 |
| T1r-1186 | (R)-I-3 | II-33 | II-72 |
| T1r-1187 | (R)-I-3 | II-33 | II-74 |
| T1r-1188 | (R)-I-3 | II-33 | II-76 |
| T1r-1189 | (R)-I-3 | II-33 | II-78 |
| T1r-1190 | (R)-I-3 | II-33 | II-84 |
| T1r-1191 | (R)-I-3 | II-33 | II-85 |
| T1r-1192 | (R)-I-3 | II-33 | II-86 |
| T1r-1193 | (R)-I-3 | II-33 | II-92 |
| T1r-1194 | (R)-I-3 | II-37 | II-39 |
| T1r-1195 | (R)-I-3 | II-37 | II-42 |
| T1r-1196 | (R)-I-3 | II-37 | II-44 |
| T1r-1197 | (R)-I-3 | II-37 | II-50 |
| T1r-1198 | (R)-I-3 | II-37 | II-53 |
| T1r-1199 | (R)-I-3 | II-37 | II-60 |
| T1r-1200 | (R)-I-3 | II-37 | II-62 |
| T1r-1201 | (R)-I-3 | II-37 | II-66 |
| T1r-1202 | (R)-I-3 | II-37 | II-69 |
| T1r-1203 | (R)-I-3 | II-37 | II-70 |
| T1r-1204 | (R)-I-3 | II-37 | II-71 |
| T1r-1205 | (R)-I-3 | II-37 | II-72 |
| T1r-1206 | (R)-I-3 | II-37 | II-74 |
| T1r-1207 | (R)-I-3 | II-37 | II-76 |
| T1r-1208 | (R)-I-3 | II-37 | II-78 |
| T1r-1209 | (R)-I-3 | II-37 | II-84 |
| T1r-1210 | (R)-I-3 | II-37 | II-85 |
| T1r-1211 | (R)-I-3 | II-37 | II-86 |
| T1r-1212 | (R)-I-3 | II-37 | II-92 |
| T1r-1213 | (R)-I-3 | II-39 | II-42 |
| T1r-1214 | (R)-I-3 | II-39 | II-44 |
| T1r-1215 | (R)-I-3 | II-39 | II-50 |
| T1r-1216 | (R)-I-3 | II-39 | II-53 |
| T1r-1217 | (R)-I-3 | II-39 | II-60 |
| T1r-1218 | (R)-I-3 | II-39 | II-62 |
| T1r-1219 | (R)-I-3 | II-39 | II-66 |
| T1r-1220 | (R)-I-3 | II-39 | II-69 |
| T1r-1221 | (R)-I-3 | II-39 | II-70 |
| T1r-1222 | (R)-I-3 | II-39 | II-71 |
| T1r-1223 | (R)-I-3 | II-39 | II-72 |
| T1r-1224 | (R)-I-3 | II-39 | II-74 |

TABLE T1s-continued

Three-component compositions comprising one component I as (R) enantiomer (appreviated as (R)-I, e.g. (R)-I-1 for the (R)-enantiomer of I-1), one component II and one component III, in particular ternary compositions containing the respective component I as (R) enantiomer, II and III as only active ingredients.

| composition | (R)-I | II | III |
|---|---|---|---|
| T1r-1225 | (R)-I-3 | II-39 | II-76 |
| T1r-1226 | (R)-I-3 | II-39 | II-78 |
| T1r-1227 | (R)-I-3 | II-39 | II-84 |
| T1r-1228 | (R)-I-3 | II-39 | II-85 |
| T1r-1229 | (R)-I-3 | II-39 | II-86 |
| T1r-1230 | (R)-I-3 | II-39 | II-92 |
| T1r-1231 | (R)-I-3 | II-42 | II-44 |
| T1r-1232 | (R)-I-3 | II-42 | II-50 |
| T1r-1233 | (R)-I-3 | II-42 | II-53 |
| T1r-1234 | (R)-I-3 | II-42 | II-60 |
| T1r-1235 | (R)-I-3 | II-42 | II-62 |
| T1r-1236 | (R)-I-3 | II-42 | II-66 |
| T1r-1237 | (R)-I-3 | II-42 | II-69 |
| T1r-1238 | (R)-I-3 | II-42 | II-70 |
| T1r-1239 | (R)-I-3 | II-42 | II-71 |
| T1r-1240 | (R)-I-3 | II-42 | II-72 |
| T1r-1241 | (R)-I-3 | II-42 | II-74 |
| T1r-1242 | (R)-I-3 | II-42 | II-76 |
| T1r-1243 | (R)-I-3 | II-42 | II-78 |
| T1r-1244 | (R)-I-3 | II-42 | II-84 |
| T1r-1245 | (R)-I-3 | II-42 | II-85 |
| T1r-1246 | (R)-I-3 | II-42 | II-86 |
| T1r-1247 | (R)-I-3 | II-42 | II-92 |
| T1r-1248 | (R)-I-3 | II-44 | II-50 |
| T1r-1249 | (R)-I-3 | II-44 | II-53 |
| T1r-1250 | (R)-I-3 | II-44 | II-60 |
| T1r-1251 | (R)-I-3 | II-44 | II-62 |
| T1r-1252 | (R)-I-3 | II-44 | II-66 |
| T1r-1253 | (R)-I-3 | II-44 | II-69 |
| T1r-1254 | (R)-I-3 | II-44 | II-70 |
| T1r-1255 | (R)-I-3 | II-44 | II-71 |
| T1r-1256 | (R)-I-3 | II-44 | II-72 |
| T1r-1257 | (R)-I-3 | II-44 | II-74 |
| T1r-1258 | (R)-I-3 | II-44 | II-76 |
| T1r-1259 | (R)-I-3 | II-44 | II-78 |
| T1r-1260 | (R)-I-3 | II-44 | II-84 |
| T1r-1261 | (R)-I-3 | II-44 | II-85 |
| T1r-1262 | (R)-I-3 | II-44 | II-86 |
| T1r-1263 | (R)-I-3 | II-44 | II-92 |
| T1r-1264 | (R)-I-3 | II-50 | II-53 |
| T1r-1265 | (R)-I-3 | II-50 | II-60 |
| T1r-1266 | (R)-I-3 | II-50 | II-62 |
| T1r-1267 | (R)-I-3 | II-50 | II-66 |
| T1r-1268 | (R)-I-3 | II-50 | II-69 |
| T1r-1269 | (R)-I-3 | II-50 | II-70 |
| T1r-1270 | (R)-I-3 | II-50 | II-71 |
| T1r-1271 | (R)-I-3 | II-50 | II-72 |
| T1r-1272 | (R)-I-3 | II-50 | II-74 |
| T1r-1273 | (R)-I-3 | II-50 | II-76 |
| T1r-1274 | (R)-I-3 | II-50 | II-78 |
| T1r-1275 | (R)-I-3 | II-50 | II-84 |
| T1r-1276 | (R)-I-3 | II-50 | II-85 |
| T1r-1277 | (R)-I-3 | II-50 | II-86 |
| T1r-1278 | (R)-I-3 | II-50 | II-92 |
| T1r-1279 | (R)-I-3 | II-53 | II-60 |
| T1r-1280 | (R)-I-3 | II-53 | II-62 |
| T1r-1281 | (R)-I-3 | II-53 | II-66 |
| T1r-1282 | (R)-I-3 | II-53 | II-69 |
| T1r-1283 | (R)-I-3 | II-53 | II-70 |
| T1r-1284 | (R)-I-3 | II-53 | II-71 |
| T1r-1285 | (R)-I-3 | II-53 | II-72 |
| T1r-1286 | (R)-I-3 | II-53 | II-74 |
| T1r-1287 | (R)-I-3 | II-53 | II-76 |
| T1r-1288 | (R)-I-3 | II-53 | II-78 |
| T1r-1289 | (R)-I-3 | II-53 | II-84 |
| T1r-1290 | (R)-I-3 | II-53 | II-85 |
| T1r-1291 | (R)-I-3 | II-53 | II-86 |
| T1r-1292 | (R)-I-3 | II-53 | II-92 |
| T1r-1293 | (R)-I-3 | II-60 | II-62 |
| T1r-1294 | (R)-I-3 | II-60 | II-66 |
| T1r-1295 | (R)-I-3 | II-60 | II-69 |
| T1r-1296 | (R)-I-3 | II-60 | II-70 |
| T1r-1297 | (R)-I-3 | II-60 | II-71 |
| T1r-1298 | (R)-I-3 | II-60 | II-72 |
| T1r-1299 | (R)-I-3 | II-60 | II-74 |
| T1r-1300 | (R)-I-3 | II-60 | II-76 |
| T1r-1301 | (R)-I-3 | II-60 | II-78 |
| T1r-1302 | (R)-I-3 | II-60 | II-84 |
| T1r-1303 | (R)-I-3 | II-60 | II-85 |
| T1r-1304 | (R)-I-3 | II-60 | II-86 |
| T1r-1305 | (R)-I-3 | II-60 | II-92 |
| T1r-1306 | (R)-I-3 | II-62 | II-66 |
| T1r-1307 | (R)-I-3 | II-62 | II-69 |
| T1r-1308 | (R)-I-3 | II-62 | II-70 |
| T1r-1309 | (R)-I-3 | II-62 | II-71 |
| T1r-1310 | (R)-I-3 | II-62 | II-72 |
| T1r-1311 | (R)-I-3 | II-62 | II-74 |
| T1r-1312 | (R)-I-3 | II-62 | II-76 |
| T1r-1313 | (R)-I-3 | II-62 | II-78 |
| T1r-1314 | (R)-I-3 | II-62 | II-84 |
| T1r-1315 | (R)-I-3 | II-62 | II-85 |
| T1r-1316 | (R)-I-3 | II-62 | II-86 |
| T1r-1317 | (R)-I-3 | II-62 | II-92 |
| T1r-1318 | (R)-I-3 | II-66 | II-69 |
| T1r-1319 | (R)-I-3 | II-66 | II-70 |
| T1r-1320 | (R)-I-3 | II-66 | II-71 |
| T1r-1321 | (R)-I-3 | II-66 | II-72 |
| T1r-1322 | (R)-I-3 | II-66 | II-74 |
| T1r-1323 | (R)-I-3 | II-66 | II-76 |
| T1r-1324 | (R)-I-3 | II-66 | II-78 |
| T1r-1325 | (R)-I-3 | II-66 | II-84 |
| T1r-1326 | (R)-I-3 | II-66 | II-85 |
| T1r-1327 | (R)-I-3 | II-66 | II-86 |
| T1r-1328 | (R)-I-3 | II-66 | II-92 |
| T1r-1329 | (R)-I-3 | II-69 | II-70 |
| T1r-1330 | (R)-I-3 | II-69 | II-71 |
| T1r-1331 | (R)-I-3 | II-69 | II-72 |
| T1r-1332 | (R)-I-3 | II-69 | II-74 |
| T1r-1333 | (R)-I-3 | II-69 | II-76 |
| T1r-1334 | (R)-I-3 | II-69 | II-78 |
| T1r-1335 | (R)-I-3 | II-69 | II-84 |
| T1r-1336 | (R)-I-3 | II-69 | II-85 |
| T1r-1337 | (R)-I-3 | II-69 | II-86 |
| T1r-1338 | (R)-I-3 | II-69 | II-92 |
| T1r-1339 | (R)-I-3 | II-70 | II-71 |
| T1r-1340 | (R)-I-3 | II-70 | II-72 |
| T1r-1341 | (R)-I-3 | II-70 | II-74 |
| T1r-1342 | (R)-I-3 | II-70 | II-76 |
| T1r-1343 | (R)-I-3 | II-70 | II-78 |
| T1r-1344 | (R)-I-3 | II-70 | II-84 |
| T1r-1345 | (R)-I-3 | II-70 | II-85 |
| T1r-1346 | (R)-I-3 | II-70 | II-86 |
| T1r-1347 | (R)-I-3 | II-70 | II-92 |
| T1r-1348 | (R)-I-3 | II-71 | II-72 |
| T1r-1349 | (R)-I-3 | II-71 | II-74 |
| T1r-1350 | (R)-I-3 | II-71 | II-76 |
| T1r-1351 | (R)-I-3 | II-71 | II-78 |
| T1r-1352 | (R)-I-3 | II-71 | II-84 |
| T1r-1353 | (R)-I-3 | II-71 | II-85 |
| T1r-1354 | (R)-I-3 | II-71 | II-86 |
| T1r-1355 | (R)-I-3 | II-71 | II-92 |
| T1r-1356 | (R)-I-3 | II-72 | II-74 |
| T1r-1357 | (R)-I-3 | II-74 | II-76 |
| T1r-1358 | (R)-I-3 | II-74 | II-78 |
| T1r-1359 | (R)-I-3 | II-74 | II-84 |
| T1r-1360 | (R)-I-3 | II-74 | II-85 |
| T1r-1361 | (R)-I-3 | II-74 | II-86 |
| T1r-1362 | (R)-I-3 | II-74 | II-92 |
| T1r-1363 | (R)-I-3 | II-76 | II-78 |
| T1r-1364 | (R)-I-3 | II-76 | II-84 |
| T1r-1365 | (R)-I-3 | II-76 | II-85 |
| T1r-1366 | (R)-I-3 | II-76 | II-86 |
| T1r-1367 | (R)-I-3 | II-76 | II-92 |
| T1r-1368 | (R)-I-3 | II-78 | II-84 |

TABLE T1s-continued

Three-component compositions comprising one component I as (R) enantiomer (appreviated as (R)-I, e.g. (R)-I-1 for the (R)-enantiomer of I-1), one component II and one component III, in particular ternary compositions containing the respective component I as (R) enantiomer, II and III as only active ingredients.

| composition | (R)-I | II | III |
|---|---|---|---|
| T1r-1369 | (R)-I-3 | II-78 | II-85 |
| T1r-1370 | (R)-I-3 | II-78 | II-86 |
| T1r-1371 | (R)-I-3 | II-78 | II-92 |
| T1r-1372 | (R)-I-3 | II-84 | II-85 |
| T1r-1373 | (R)-I-3 | II-84 | II-86 |
| T1r-1374 | (R)-I-3 | II-84 | II-92 |
| T1r-1375 | (R)-I-3 | II-85 | II-86 |
| T1r-1376 | (R)-I-3 | II-85 | II-92 |
| T1r-1377 | (R)-I-3 | II-86 | II-92 |
| T1r-1378 | (R)-I-4 | II-3 | II-5 |
| T1r-1379 | (R)-I-4 | II-3 | II-6 |
| T1r-1380 | (R)-I-4 | II-3 | II-7 |
| T1r-1381 | (R)-I-4 | II-3 | II-8 |
| T1r-1382 | (R)-I-4 | II-3 | II-11 |
| T1r-1383 | (R)-I-4 | II-3 | II-16 |
| T1r-1384 | (R)-I-4 | II-3 | II-21 |
| T1r-1385 | (R)-I-4 | II-3 | II-26 |
| T1r-1386 | (R)-I-4 | II-3 | II-32 |
| T1r-1387 | (R)-I-4 | II-3 | II-33 |
| T1r-1388 | (R)-I-4 | II-3 | II-37 |
| T1r-1389 | (R)-I-4 | II-3 | II-39 |
| T1r-1390 | (R)-I-4 | II-3 | II-42 |
| T1r-1391 | (R)-I-4 | II-3 | II-44 |
| T1r-1392 | (R)-I-4 | II-3 | II-50 |
| T1r-1393 | (R)-I-4 | II-3 | II-53 |
| T1r-1394 | (R)-I-4 | II-3 | II-60 |
| T1r-1395 | (R)-I-4 | II-3 | II-62 |
| T1r-1396 | (R)-I-4 | II-3 | II-66 |
| T1r-1397 | (R)-I-4 | II-3 | II-69 |
| T1r-1398 | (R)-I-4 | II-3 | II-70 |
| T1r-1399 | (R)-I-4 | II-3 | II-71 |
| T1r-1400 | (R)-I-4 | II-3 | II-72 |
| T1r-1401 | (R)-I-4 | II-3 | II-74 |
| T1r-1402 | (R)-I-4 | II-3 | II-76 |
| T1r-1403 | (R)-I-4 | II-3 | II-78 |
| T1r-1404 | (R)-I-4 | II-3 | II-84 |
| T1r-1405 | (R)-I-4 | II-3 | II-85 |
| T1r-1406 | (R)-I-4 | II-3 | II-86 |
| T1r-1407 | (R)-I-4 | II-3 | II-92 |
| T1r-1408 | (R)-I-4 | II-5 | II-6 |
| T1r-1409 | (R)-I-4 | II-5 | II-7 |
| T1r-1410 | (R)-I-4 | II-5 | II-8 |
| T1r-1411 | (R)-I-4 | II-5 | II-11 |
| T1r-1412 | (R)-I-4 | II-5 | II-16 |
| T1r-1413 | (R)-I-4 | II-5 | II-21 |
| T1r-1414 | (R)-I-4 | II-5 | II-26 |
| T1r-1415 | (R)-I-4 | II-5 | II-32 |
| T1r-1416 | (R)-I-4 | II-5 | II-33 |
| T1r-1417 | (R)-I-4 | II-5 | II-37 |
| T1r-1418 | (R)-I-4 | II-5 | II-39 |
| T1r-1419 | (R)-I-4 | II-5 | II-42 |
| T1r-1420 | (R)-I-4 | II-5 | II-44 |
| T1r-1421 | (R)-I-4 | II-5 | II-50 |
| T1r-1422 | (R)-I-4 | II-5 | II-53 |
| T1r-1423 | (R)-I-4 | II-5 | II-60 |
| T1r-1424 | (R)-I-4 | II-5 | II-62 |
| T1r-1425 | (R)-I-4 | II-5 | II-66 |
| T1r-1426 | (R)-I-4 | II-5 | II-69 |
| T1r-1427 | (R)-I-4 | II-5 | II-70 |
| T1r-1428 | (R)-I-4 | II-5 | II-71 |
| T1r-1429 | (R)-I-4 | II-5 | II-72 |
| T1r-1430 | (R)-I-4 | II-5 | II-74 |
| T1r-1431 | (R)-I-4 | II-5 | II-76 |
| T1r-1432 | (R)-I-4 | II-5 | II-78 |
| T1r-1433 | (R)-I-4 | II-5 | II-84 |
| T1r-1434 | (R)-I-4 | II-5 | II-85 |
| T1r-1435 | (R)-I-4 | II-5 | II-86 |
| T1r-1436 | (R)-I-4 | II-5 | II-92 |
| T1r-1437 | (R)-I-4 | II-6 | II-7 |
| T1r-1438 | (R)-I-4 | II-6 | II-8 |
| T1r-1439 | (R)-I-4 | II-6 | II-11 |
| T1r-1440 | (R)-I-4 | II-6 | II-16 |
| T1r-1441 | (R)-I-4 | II-6 | II-21 |
| T1r-1442 | (R)-I-4 | II-6 | II-26 |
| T1r-1443 | (R)-I-4 | II-6 | II-32 |
| T1r-1444 | (R)-I-4 | II-6 | II-33 |
| T1r-1445 | (R)-I-4 | II-6 | II-37 |
| T1r-1446 | (R)-I-4 | II-6 | II-39 |
| T1r-1447 | (R)-I-4 | II-6 | II-42 |
| T1r-1448 | (R)-I-4 | II-6 | II-44 |
| T1r-1449 | (R)-I-4 | II-6 | II-50 |
| T1r-1450 | (R)-I-4 | II-6 | II-53 |
| T1r-1451 | (R)-I-4 | II-6 | II-60 |
| T1r-1452 | (R)-I-4 | II-6 | II-62 |
| T1r-1453 | (R)-I-4 | II-6 | II-66 |
| T1r-1454 | (R)-I-4 | II-6 | II-69 |
| T1r-1455 | (R)-I-4 | II-6 | II-70 |
| T1r-1456 | (R)-I-4 | II-6 | II-71 |
| T1r-1457 | (R)-I-4 | II-6 | II-72 |
| T1r-1458 | (R)-I-4 | II-6 | II-74 |
| T1r-1459 | (R)-I-4 | II-6 | II-76 |
| T1r-1460 | (R)-I-4 | II-6 | II-78 |
| T1r-1461 | (R)-I-4 | II-6 | II-84 |
| T1r-1462 | (R)-I-4 | II-6 | II-85 |
| T1r-1463 | (R)-I-4 | II-6 | II-86 |
| T1r-1464 | (R)-I-4 | II-6 | II-92 |
| T1r-1465 | (R)-I-4 | II-7 | II-8 |
| T1r-1466 | (R)-I-4 | II-7 | II-11 |
| T1r-1467 | (R)-I-4 | II-7 | II-16 |
| T1r-1468 | (R)-I-4 | II-7 | II-21 |
| T1r-1469 | (R)-I-4 | II-7 | II-26 |
| T1r-1470 | (R)-I-4 | II-7 | II-32 |
| T1r-1471 | (R)-I-4 | II-7 | II-33 |
| T1r-1472 | (R)-I-4 | II-7 | II-37 |
| T1r-1473 | (R)-I-4 | II-7 | II-39 |
| T1r-1474 | (R)-I-4 | II-7 | II-42 |
| T1r-1475 | (R)-I-4 | II-7 | II-44 |
| T1r-1476 | (R)-I-4 | II-7 | II-50 |
| T1r-1477 | (R)-I-4 | II-7 | II-53 |
| T1r-1478 | (R)-I-4 | II-7 | II-60 |
| T1r-1479 | (R)-I-4 | II-7 | II-62 |
| T1r-1480 | (R)-I-4 | II-7 | II-66 |
| T1r-1481 | (R)-I-4 | II-7 | II-69 |
| T1r-1482 | (R)-I-4 | II-7 | II-70 |
| T1r-1483 | (R)-I-4 | II-7 | II-71 |
| T1r-1484 | (R)-I-4 | II-7 | II-72 |
| T1r-1485 | (R)-I-4 | II-7 | II-74 |
| T1r-1486 | (R)-I-4 | II-7 | II-76 |
| T1r-1487 | (R)-I-4 | II-7 | II-78 |
| T1r-1488 | (R)-I-4 | II-7 | II-84 |
| T1r-1489 | (R)-I-4 | II-7 | II-85 |
| T1r-1490 | (R)-I-4 | II-7 | II-86 |
| T1r-1491 | (R)-I-4 | II-7 | II-92 |
| T1r-1492 | (R)-I-4 | II-8 | II-11 |
| T1r-1493 | (R)-I-4 | II-8 | II-16 |
| T1r-1494 | (R)-I-4 | II-8 | II-21 |
| T1r-1495 | (R)-I-4 | II-8 | II-26 |
| T1r-1496 | (R)-I-4 | II-8 | II-32 |
| T1r-1497 | (R)-I-4 | II-8 | II-33 |
| T1r-1498 | (R)-I-4 | II-8 | II-37 |
| T1r-1499 | (R)-I-4 | II-8 | II-39 |
| T1r-1500 | (R)-I-4 | II-8 | II-42 |
| T1r-1501 | (R)-I-4 | II-8 | II-44 |
| T1r-1502 | (R)-I-4 | II-8 | II-50 |
| T1r-1503 | (R)-I-4 | II-8 | II-53 |
| T1r-1504 | (R)-I-4 | II-8 | II-60 |
| T1r-1505 | (R)-I-4 | II-8 | II-62 |
| T1r-1506 | (R)-I-4 | II-8 | II-66 |
| T1r-1507 | (R)-I-4 | II-8 | II-69 |
| T1r-1508 | (R)-I-4 | II-8 | II-70 |
| T1r-1509 | (R)-I-4 | II-8 | II-71 |
| T1r-1510 | (R)-I-4 | II-8 | II-72 |
| T1r-1511 | (R)-I-4 | II-8 | II-74 |
| T1r-1512 | (R)-I-4 | II-8 | II-76 |

TABLE T1s-continued

Three-component compositions comprising one component I as (R) enantiomer (appreviated as (R)-I, e.g. (R)-I-1 for the (R)-enantiomer of I-1), one component II and one component III, in particular ternary compositions containing the respective component I as (R) enantiomer, II and III as only active ingredients.

| composition | (R)-I | II | III |
|---|---|---|---|
| T1r-1513 | (R)-I-4 | II-8 | II-78 |
| T1r-1514 | (R)-I-4 | II-8 | II-84 |
| T1r-1515 | (R)-I-4 | II-8 | II-85 |
| T1r-1516 | (R)-I-4 | II-8 | II-86 |
| T1r-1517 | (R)-I-4 | II-8 | II-92 |
| T1r-1518 | (R)-I-4 | II-11 | II-16 |
| T1r-1519 | (R)-I-4 | II-11 | II-21 |
| T1r-1520 | (R)-I-4 | II-11 | II-26 |
| T1r-1521 | (R)-I-4 | II-11 | II-32 |
| T1r-1522 | (R)-I-4 | II-11 | II-33 |
| T1r-1523 | (R)-I-4 | II-11 | II-37 |
| T1r-1524 | (R)-I-4 | II-11 | II-39 |
| T1r-1525 | (R)-I-4 | II-11 | II-42 |
| T1r-1526 | (R)-I-4 | II-11 | II-44 |
| T1r-1527 | (R)-I-4 | II-11 | II-50 |
| T1r-1528 | (R)-I-4 | II-11 | II-53 |
| T1r-1529 | (R)-I-4 | II-11 | II-60 |
| T1r-1530 | (R)-I-4 | II-11 | II-62 |
| T1r-1531 | (R)-I-4 | II-11 | II-66 |
| T1r-1532 | (R)-I-4 | II-11 | II-69 |
| T1r-1533 | (R)-I-4 | II-11 | II-70 |
| T1r-1534 | (R)-I-4 | II-11 | II-71 |
| T1r-1535 | (R)-I-4 | II-11 | II-72 |
| T1r-1536 | (R)-I-4 | II-11 | II-74 |
| T1r-1537 | (R)-I-4 | II-11 | II-76 |
| T1r-1538 | (R)-I-4 | II-11 | II-78 |
| T1r-1539 | (R)-I-4 | II-11 | II-84 |
| T1r-1540 | (R)-I-4 | II-11 | II-85 |
| T1r-1541 | (R)-I-4 | II-11 | II-86 |
| T1r-1542 | (R)-I-4 | II-11 | II-92 |
| T1r-1543 | (R)-I-4 | II-16 | II-21 |
| T1r-1544 | (R)-I-4 | II-16 | II-26 |
| T1r-1545 | (R)-I-4 | II-16 | II-32 |
| T1r-1546 | (R)-I-4 | II-16 | II-33 |
| T1r-1547 | (R)-I-4 | II-16 | II-37 |
| T1r-1548 | (R)-I-4 | II-16 | II-39 |
| T1r-1549 | (R)-I-4 | II-16 | II-42 |
| T1r-1550 | (R)-I-4 | II-16 | II-44 |
| T1r-1551 | (R)-I-4 | II-16 | II-50 |
| T1r-1552 | (R)-I-4 | II-16 | II-53 |
| T1r-1553 | (R)-I-4 | II-16 | II-60 |
| T1r-1554 | (R)-I-4 | II-16 | II-62 |
| T1r-1555 | (R)-I-4 | II-16 | II-66 |
| T1r-1556 | (R)-I-4 | II-16 | II-69 |
| T1r-1557 | (R)-I-4 | II-16 | II-70 |
| T1r-1558 | (R)-I-4 | II-16 | II-71 |
| T1r-1559 | (R)-I-4 | II-16 | II-72 |
| T1r-1560 | (R)-I-4 | II-16 | II-74 |
| T1r-1561 | (R)-I-4 | II-16 | II-76 |
| T1r-1562 | (R)-I-4 | II-16 | II-78 |
| T1r-1563 | (R)-I-4 | II-16 | II-84 |
| T1r-1564 | (R)-I-4 | II-16 | II-85 |
| T1r-1565 | (R)-I-4 | II-16 | II-86 |
| T1r-1566 | (R)-I-4 | II-16 | II-92 |
| T1r-1567 | (R)-I-4 | II-21 | II-26 |
| T1r-1568 | (R)-I-4 | II-21 | II-32 |
| T1r-1569 | (R)-I-4 | II-21 | II-33 |
| T1r-1570 | (R)-I-4 | II-21 | II-37 |
| T1r-1571 | (R)-I-4 | II-21 | II-39 |
| T1r-1572 | (R)-I-4 | II-21 | II-42 |
| T1r-1573 | (R)-I-4 | II-21 | II-44 |
| T1r-1574 | (R)-I-4 | II-21 | II-50 |
| T1r-1575 | (R)-I-4 | II-21 | II-53 |
| T1r-1576 | (R)-I-4 | II-21 | II-60 |
| T1r-1577 | (R)-I-4 | II-21 | II-62 |
| T1r-1578 | (R)-I-4 | II-21 | II-66 |
| T1r-1579 | (R)-I-4 | II-21 | II-69 |
| T1r-1580 | (R)-I-4 | II-21 | II-70 |
| T1r-1581 | (R)-I-4 | II-21 | II-71 |
| T1r-1582 | (R)-I-4 | II-21 | II-72 |
| T1r-1583 | (R)-I-4 | II-21 | II-74 |
| T1r-1584 | (R)-I-4 | II-21 | II-76 |
| T1r-1585 | (R)-I-4 | II-21 | II-78 |
| T1r-1586 | (R)-I-4 | II-21 | II-84 |
| T1r-1587 | (R)-I-4 | II-21 | II-85 |
| T1r-1588 | (R)-I-4 | II-21 | II-86 |
| T1r-1589 | (R)-I-4 | II-21 | II-92 |
| T1r-1590 | (R)-I-4 | II-26 | II-32 |
| T1r-1591 | (R)-I-4 | II-26 | II-33 |
| T1r-1592 | (R)-I-4 | II-26 | II-37 |
| T1r-1593 | (R)-I-4 | II-26 | II-39 |
| T1r-1594 | (R)-I-4 | II-26 | II-42 |
| T1r-1595 | (R)-I-4 | II-26 | II-44 |
| T1r-1596 | (R)-I-4 | II-26 | II-50 |
| T1r-1597 | (R)-I-4 | II-26 | II-53 |
| T1r-1598 | (R)-I-4 | II-26 | II-60 |
| T1r-1599 | (R)-I-4 | II-26 | II-62 |
| T1r-1600 | (R)-I-4 | II-26 | II-66 |
| T1r-1601 | (R)-I-4 | II-26 | II-69 |
| T1r-1602 | (R)-I-4 | II-26 | II-70 |
| T1r-1603 | (R)-I-4 | II-26 | II-71 |
| T1r-1604 | (R)-I-4 | II-26 | II-72 |
| T1r-1605 | (R)-I-4 | II-26 | II-74 |
| T1r-1606 | (R)-I-4 | II-26 | II-76 |
| T1r-1607 | (R)-I-4 | II-26 | II-78 |
| T1r-1608 | (R)-I-4 | II-26 | II-84 |
| T1r-1609 | (R)-I-4 | II-26 | II-85 |
| T1r-1610 | (R)-I-4 | II-26 | II-86 |
| T1r-1611 | (R)-I-4 | II-26 | II-92 |
| T1r-1612 | (R)-I-4 | II-32 | II-33 |
| T1r-1613 | (R)-I-4 | II-32 | II-37 |
| T1r-1614 | (R)-I-4 | II-32 | II-39 |
| T1r-1615 | (R)-I-4 | II-32 | II-42 |
| T1r-1616 | (R)-I-4 | II-32 | II-44 |
| T1r-1617 | (R)-I-4 | II-32 | II-50 |
| T1r-1618 | (R)-I-4 | II-32 | II-53 |
| T1r-1619 | (R)-I-4 | II-32 | II-60 |
| T1r-1620 | (R)-I-4 | II-32 | II-62 |
| T1r-1621 | (R)-I-4 | II-32 | II-66 |
| T1r-1622 | (R)-I-4 | II-32 | II-69 |
| T1r-1623 | (R)-I-4 | II-32 | II-70 |
| T1r-1624 | (R)-I-4 | II-32 | II-71 |
| T1r-1625 | (R)-I-4 | II-32 | II-72 |
| T1r-1626 | (R)-I-4 | II-32 | II-74 |
| T1r-1627 | (R)-I-4 | II-32 | II-76 |
| T1r-1628 | (R)-I-4 | II-32 | II-78 |
| T1r-1629 | (R)-I-4 | II-32 | II-84 |
| T1r-1630 | (R)-I-4 | II-32 | II-85 |
| T1r-1631 | (R)-I-4 | II-32 | II-86 |
| T1r-1632 | (R)-I-4 | II-32 | II-92 |
| T1r-1633 | (R)-I-4 | II-33 | II-37 |
| T1r-1634 | (R)-I-4 | II-33 | II-39 |
| T1r-1635 | (R)-I-4 | II-33 | II-42 |
| T1r-1636 | (R)-I-4 | II-33 | II-44 |
| T1r-1637 | (R)-I-4 | II-33 | II-50 |
| T1r-1638 | (R)-I-4 | II-33 | II-53 |
| T1r-1639 | (R)-I-4 | II-33 | II-60 |
| T1r-1640 | (R)-I-4 | II-33 | II-62 |
| T1r-1641 | (R)-I-4 | II-33 | II-66 |
| T1r-1642 | (R)-I-4 | II-33 | II-69 |
| T1r-1643 | (R)-I-4 | II-33 | II-70 |
| T1r-1644 | (R)-I-4 | II-33 | II-71 |
| T1r-1645 | (R)-I-4 | II-33 | II-72 |
| T1r-1646 | (R)-I-4 | II-33 | II-74 |
| T1r-1647 | (R)-I-4 | II-33 | II-76 |
| T1r-1648 | (R)-I-4 | II-33 | II-78 |
| T1r-1649 | (R)-I-4 | II-33 | II-84 |
| T1r-1650 | (R)-I-4 | II-33 | II-85 |
| T1r-1651 | (R)-I-4 | II-33 | II-86 |
| T1r-1652 | (R)-I-4 | II-33 | II-92 |
| T1r-1653 | (R)-I-4 | II-37 | II-39 |
| T1r-1654 | (R)-I-4 | II-37 | II-42 |
| T1r-1655 | (R)-I-4 | II-37 | II-44 |
| T1r-1656 | (R)-I-4 | II-37 | II-50 |

TABLE T1s-continued

Three-component compositions comprising one component I as (R) enantiomer (appreviated as (R)-I, e.g. (R)-I-1 for the (R)-enantiomer of I-1), one component II and one component III, in particular ternary compositions containing the respective component I as (R) enantiomer, II and III as only active ingredients.

| composition | (R)-I | II | III |
|---|---|---|---|
| T1r-1657 | (R)-I-4 | II-37 | II-53 |
| T1r-1658 | (R)-I-4 | II-37 | II-60 |
| T1r-1659 | (R)-I-4 | II-37 | II-62 |
| T1r-1660 | (R)-I-4 | II-37 | II-66 |
| T1r-1661 | (R)-I-4 | II-37 | II-69 |
| T1r-1662 | (R)-I-4 | II-37 | II-70 |
| T1r-1663 | (R)-I-4 | II-37 | II-71 |
| T1r-1664 | (R)-I-4 | II-37 | II-72 |
| T1r-1665 | (R)-I-4 | II-37 | II-74 |
| T1r-1666 | (R)-I-4 | II-37 | II-76 |
| T1r-1667 | (R)-I-4 | II-37 | II-78 |
| T1r-1668 | (R)-I-4 | II-37 | II-84 |
| T1r-1669 | (R)-I-4 | II-37 | II-85 |
| T1r-1670 | (R)-I-4 | II-37 | II-86 |
| T1r-1671 | (R)-I-4 | II-37 | II-92 |
| T1r-1672 | (R)-I-4 | II-39 | II-42 |
| T1r-1673 | (R)-I-4 | II-39 | II-44 |
| T1r-1674 | (R)-I-4 | II-39 | II-50 |
| T1r-1675 | (R)-I-4 | II-39 | II-53 |
| T1r-1676 | (R)-I-4 | II-39 | II-60 |
| T1r-1677 | (R)-I-4 | II-39 | II-62 |
| T1r-1678 | (R)-I-4 | II-39 | II-66 |
| T1r-1679 | (R)-I-4 | II-39 | II-69 |
| T1r-1680 | (R)-I-4 | II-39 | II-70 |
| T1r-1681 | (R)-I-4 | II-39 | II-71 |
| T1r-1682 | (R)-I-4 | II-39 | II-72 |
| T1r-1683 | (R)-I-4 | II-39 | II-74 |
| T1r-1684 | (R)-I-4 | II-39 | II-76 |
| T1r-1685 | (R)-I-4 | II-39 | II-78 |
| T1r-1686 | (R)-I-4 | II-39 | II-84 |
| T1r-1687 | (R)-I-4 | II-39 | II-85 |
| T1r-1688 | (R)-I-4 | II-39 | II-86 |
| T1r-1689 | (R)-I-4 | II-39 | II-92 |
| T1r-1690 | (R)-I-4 | II-42 | II-44 |
| T1r-1691 | (R)-I-4 | II-42 | II-50 |
| T1r-1692 | (R)-I-4 | II-42 | II-53 |
| T1r-1693 | (R)-I-4 | II-42 | II-60 |
| T1r-1694 | (R)-I-4 | II-42 | II-62 |
| T1r-1695 | (R)-I-4 | II-42 | II-66 |
| T1r-1696 | (R)-I-4 | II-42 | II-69 |
| T1r-1697 | (R)-I-4 | II-42 | II-70 |
| T1r-1698 | (R)-I-4 | II-42 | II-71 |
| T1r-1699 | (R)-I-4 | II-42 | II-72 |
| T1r-1700 | (R)-I-4 | II-42 | II-74 |
| T1r-1701 | (R)-I-4 | II-42 | II-76 |
| T1r-1702 | (R)-I-4 | II-42 | II-78 |
| T1r-1703 | (R)-I-4 | II-42 | II-84 |
| T1r-1704 | (R)-I-4 | II-42 | II-85 |
| T1r-1705 | (R)-I-4 | II-42 | II-86 |
| T1r-1706 | (R)-I-4 | II-42 | II-92 |
| T1r-1707 | (R)-I-4 | II-44 | II-50 |
| T1r-1708 | (R)-I-4 | II-44 | II-53 |
| T1r-1709 | (R)-I-4 | II-44 | II-60 |
| T1r-1710 | (R)-I-4 | II-44 | II-62 |
| T1r-1711 | (R)-I-4 | II-44 | II-66 |
| T1r-1712 | (R)-I-4 | II-44 | II-69 |
| T1r-1713 | (R)-I-4 | II-44 | II-70 |
| T1r-1714 | (R)-I-4 | II-44 | II-71 |
| T1r-1715 | (R)-I-4 | II-44 | II-72 |
| T1r-1716 | (R)-I-4 | II-44 | II-74 |
| T1r-1717 | (R)-I-4 | II-44 | II-76 |
| T1r-1718 | (R)-I-4 | II-44 | II-78 |
| T1r-1719 | (R)-I-4 | II-44 | II-84 |
| T1r-1720 | (R)-I-4 | II-44 | II-85 |
| T1r-1721 | (R)-I-4 | II-44 | II-86 |
| T1r-1722 | (R)-I-4 | II-44 | II-92 |
| T1r-1723 | (R)-I-4 | II-50 | II-53 |
| T1r-1724 | (R)-I-4 | II-50 | II-60 |
| T1r-1725 | (R)-I-4 | II-50 | II-62 |
| T1r-1726 | (R)-I-4 | II-50 | II-66 |
| T1r-1727 | (R)-I-4 | II-50 | II-69 |
| T1r-1728 | (R)-I-4 | II-50 | II-70 |
| T1r-1729 | (R)-I-4 | II-50 | II-71 |
| T1r-1730 | (R)-I-4 | II-50 | II-72 |
| T1r-1731 | (R)-I-4 | II-50 | II-74 |
| T1r-1732 | (R)-I-4 | II-50 | II-76 |
| T1r-1733 | (R)-I-4 | II-50 | II-78 |
| T1r-1734 | (R)-I-4 | II-50 | II-84 |
| T1r-1735 | (R)-I-4 | II-50 | II-85 |
| T1r-1736 | (R)-I-4 | II-50 | II-86 |
| T1r-1737 | (R)-I-4 | II-50 | II-92 |
| T1r-1738 | (R)-I-4 | II-53 | II-60 |
| T1r-1739 | (R)-I-4 | II-53 | II-62 |
| T1r-1740 | (R)-I-4 | II-53 | II-66 |
| T1r-1741 | (R)-I-4 | II-53 | II-69 |
| T1r-1742 | (R)-I-4 | II-53 | II-70 |
| T1r-1743 | (R)-I-4 | II-53 | II-71 |
| T1r-1744 | (R)-I-4 | II-53 | II-72 |
| T1r-1745 | (R)-I-4 | II-53 | II-74 |
| T1r-1746 | (R)-I-4 | II-53 | II-76 |
| T1r-1747 | (R)-I-4 | II-53 | II-78 |
| T1r-1748 | (R)-I-4 | II-53 | II-84 |
| T1r-1749 | (R)-I-4 | II-53 | II-85 |
| T1r-1750 | (R)-I-4 | II-53 | II-86 |
| T1r-1751 | (R)-I-4 | II-53 | II-92 |
| T1r-1752 | (R)-I-4 | II-60 | II-62 |
| T1r-1753 | (R)-I-4 | II-60 | II-66 |
| T1r-1754 | (R)-I-4 | II-60 | II-69 |
| T1r-1755 | (R)-I-4 | II-60 | II-70 |
| T1r-1756 | (R)-I-4 | II-60 | II-71 |
| T1r-1757 | (R)-I-4 | II-60 | II-72 |
| T1r-1758 | (R)-I-4 | II-60 | II-74 |
| T1r-1759 | (R)-I-4 | II-60 | II-76 |
| T1r-1760 | (R)-I-4 | II-60 | II-78 |
| T1r-1761 | (R)-I-4 | II-60 | II-84 |
| T1r-1762 | (R)-I-4 | II-60 | II-85 |
| T1r-1763 | (R)-I-4 | II-60 | II-86 |
| T1r-1764 | (R)-I-4 | II-60 | II-92 |
| T1r-1765 | (R)-I-4 | II-62 | II-66 |
| T1r-1766 | (R)-I-4 | II-62 | II-69 |
| T1r-1767 | (R)-I-4 | II-62 | II-70 |
| T1r-1768 | (R)-I-4 | II-62 | II-71 |
| T1r-1769 | (R)-I-4 | II-62 | II-72 |
| T1r-1770 | (R)-I-4 | II-62 | II-74 |
| T1r-1771 | (R)-I-4 | II-62 | II-76 |
| T1r-1772 | (R)-I-4 | II-62 | II-78 |
| T1r-1773 | (R)-I-4 | II-62 | II-84 |
| T1r-1774 | (R)-I-4 | II-62 | II-85 |
| T1r-1775 | (R)-I-4 | II-62 | II-86 |
| T1r-1776 | (R)-I-4 | II-62 | II-92 |
| T1r-1777 | (R)-I-4 | II-66 | II-69 |
| T1r-1778 | (R)-I-4 | II-66 | II-70 |
| T1r-1779 | (R)-I-4 | II-66 | II-71 |
| T1r-1780 | (R)-I-4 | II-66 | II-72 |
| T1r-1781 | (R)-I-4 | II-66 | II-74 |
| T1r-1782 | (R)-I-4 | II-66 | II-76 |
| T1r-1783 | (R)-I-4 | II-66 | II-78 |
| T1r-1784 | (R)-I-4 | II-66 | II-84 |
| T1r-1785 | (R)-I-4 | II-66 | II-85 |
| T1r-1786 | (R)-I-4 | II-66 | II-86 |
| T1r-1787 | (R)-I-4 | II-66 | II-92 |
| T1r-1788 | (R)-I-4 | II-69 | II-70 |
| T1r-1789 | (R)-I-4 | II-69 | II-71 |
| T1r-1790 | (R)-I-4 | II-69 | II-72 |
| T1r-1791 | (R)-I-4 | II-69 | II-74 |
| T1r-1792 | (R)-I-4 | II-69 | II-76 |
| T1r-1793 | (R)-I-4 | II-69 | II-78 |
| T1r-1794 | (R)-I-4 | II-69 | II-84 |
| T1r-1795 | (R)-I-4 | II-69 | II-85 |
| T1r-1796 | (R)-I-4 | II-69 | II-86 |
| T1r-1797 | (R)-I-4 | II-69 | II-92 |
| T1r-1798 | (R)-I-4 | II-70 | II-71 |
| T1r-1799 | (R)-I-4 | II-70 | II-72 |
| T1r-1800 | (R)-I-4 | II-70 | II-74 |

TABLE T1s-continued

Three-component compositions comprising one component I as (R) enantiomer (appreviated as (R)-I, e.g. (R)-I-1 for the (R)-enantiomer of I-1), one component II and one component III, in particular ternary compositions containing the respective component I as (R) enantiomer, II and III as only active ingredients.

| composition | (R)-I | II | III |
|---|---|---|---|
| T1r-1801 | (R)-I-4 | II-70 | II-76 |
| T1r-1802 | (R)-I-4 | II-70 | II-78 |
| T1r-1803 | (R)-I-4 | II-70 | II-84 |
| T1r-1804 | (R)-I-4 | II-70 | II-85 |
| T1r-1805 | (R)-I-4 | II-70 | II-86 |
| T1r-1806 | (R)-I-4 | II-70 | II-92 |
| T1r-1807 | (R)-I-4 | II-71 | II-72 |
| T1r-1808 | (R)-I-4 | II-71 | II-74 |
| T1r-1809 | (R)-I-4 | II-71 | II-76 |
| T1r-1810 | (R)-I-4 | II-71 | II-78 |
| T1r-1811 | (R)-I-4 | II-71 | II-84 |
| T1r-1812 | (R)-I-4 | II-71 | II-85 |
| T1r-1813 | (R)-I-4 | II-71 | II-86 |
| T1r-1814 | (R)-I-4 | II-71 | II-92 |
| T1r-1815 | (R)-I-4 | II-72 | II-74 |
| T1r-1816 | (R)-I-4 | II-74 | II-76 |
| T1r-1817 | (R)-I-4 | II-74 | II-78 |
| T1r-1818 | (R)-I-4 | II-74 | II-84 |
| T1r-1819 | (R)-I-4 | II-74 | II-85 |
| T1r-1820 | (R)-I-4 | II-74 | II-86 |
| T1r-1821 | (R)-I-4 | II-74 | II-92 |
| T1r-1822 | (R)-I-4 | II-76 | II-78 |
| T1r-1823 | (R)-I-4 | II-76 | II-84 |
| T1r-1824 | (R)-I-4 | II-76 | II-85 |
| T1r-1825 | (R)-I-4 | II-76 | II-86 |
| T1r-1826 | (R)-I-4 | II-76 | II-92 |
| T1r-1827 | (R)-I-4 | II-78 | II-84 |
| T1r-1828 | (R)-I-4 | II-78 | II-85 |
| T1r-1829 | (R)-I-4 | II-78 | II-86 |
| T1r-1830 | (R)-I-4 | II-78 | II-92 |
| T1r-1831 | (R)-I-4 | II-84 | II-85 |
| T1r-1832 | (R)-I-4 | II-84 | II-86 |
| T1r-1833 | (R)-I-4 | II-84 | II-92 |
| T1r-1834 | (R)-I-4 | II-85 | II-86 |
| T1r-1835 | (R)-I-4 | II-85 | II-92 |
| T1r-1836 | (R)-I-4 | II-86 | II-92 |
| T1r-1837 | (R)-I-13 | II-3 | II-5 |
| T1r-1838 | (R)-I-13 | II-3 | II-6 |
| T1r-1839 | (R)-I-13 | II-3 | II-7 |
| T1r-1840 | (R)-I-13 | II-3 | II-8 |
| T1r-1841 | (R)-I-13 | II-3 | II-11 |
| T1r-1842 | (R)-I-13 | II-3 | II-16 |
| T1r-1843 | (R)-I-13 | II-3 | II-21 |
| T1r-1844 | (R)-I-13 | II-3 | II-26 |
| T1r-1845 | (R)-I-13 | II-3 | II-32 |
| T1r-1846 | (R)-I-13 | II-3 | II-33 |
| T1r-1847 | (R)-I-13 | II-3 | II-37 |
| T1r-1848 | (R)-I-13 | II-3 | II-39 |
| T1r-1849 | (R)-I-13 | II-3 | II-42 |
| T1r-1850 | (R)-I-13 | II-3 | II-44 |
| T1r-1851 | (R)-I-13 | II-3 | II-50 |
| T1r-1852 | (R)-I-13 | II-3 | II-53 |
| T1r-1853 | (R)-I-13 | II-3 | II-60 |
| T1r-1854 | (R)-I-13 | II-3 | II-62 |
| T1r-1855 | (R)-I-13 | II-3 | II-66 |
| T1r-1856 | (R)-I-13 | II-3 | II-69 |
| T1r-1857 | (R)-I-13 | II-3 | II-70 |
| T1r-1858 | (R)-I-13 | II-3 | II-71 |
| T1r-1859 | (R)-I-13 | II-3 | II-72 |
| T1r-1860 | (R)-I-13 | II-3 | II-74 |
| T1r-1861 | (R)-I-13 | II-3 | II-76 |
| T1r-1862 | (R)-I-13 | II-3 | II-78 |
| T1r-1863 | (R)-I-13 | II-3 | II-84 |
| T1r-1864 | (R)-I-13 | II-3 | II-85 |
| T1r-1865 | (R)-I-13 | II-3 | II-86 |
| T1r-1866 | (R)-I-13 | II-3 | II-92 |
| T1r-1867 | (R)-I-13 | II-5 | II-6 |
| T1r-1868 | (R)-I-13 | II-5 | II-7 |
| T1r-1869 | (R)-I-13 | II-5 | II-8 |
| T1r-1870 | (R)-I-13 | II-5 | II-11 |
| T1r-1871 | (R)-I-13 | II-5 | II-16 |
| T1r-1872 | (R)-I-13 | II-5 | II-21 |
| T1r-1873 | (R)-I-13 | II-5 | II-26 |
| T1r-1874 | (R)-I-13 | II-5 | II-32 |
| T1r-1875 | (R)-I-13 | II-5 | II-33 |
| T1r-1876 | (R)-I-13 | II-5 | II-37 |
| T1r-1877 | (R)-I-13 | II-5 | II-39 |
| T1r-1878 | (R)-I-13 | II-5 | II-42 |
| T1r-1879 | (R)-I-13 | II-5 | II-44 |
| T1r-1880 | (R)-I-13 | II-5 | II-50 |
| T1r-1881 | (R)-I-13 | II-5 | II-53 |
| T1r-1882 | (R)-I-13 | II-5 | II-60 |
| T1r-1883 | (R)-I-13 | II-5 | II-62 |
| T1r-1884 | (R)-I-13 | II-5 | II-66 |
| T1r-1885 | (R)-I-13 | II-5 | II-69 |
| T1r-1886 | (R)-I-13 | II-5 | II-70 |
| T1r-1887 | (R)-I-13 | II-5 | II-71 |
| T1r-1888 | (R)-I-13 | II-5 | II-72 |
| T1r-1889 | (R)-I-13 | II-5 | II-74 |
| T1r-1890 | (R)-I-13 | II-5 | II-76 |
| T1r-1891 | (R)-I-13 | II-5 | II-78 |
| T1r-1892 | (R)-I-13 | II-5 | II-84 |
| T1r-1893 | (R)-I-13 | II-5 | II-85 |
| T1r-1894 | (R)-I-13 | II-5 | II-86 |
| T1r-1895 | (R)-I-13 | II-5 | II-92 |
| T1r-1896 | (R)-I-13 | II-6 | II-7 |
| T1r-1897 | (R)-I-13 | II-6 | II-8 |
| T1r-1898 | (R)-I-13 | II-6 | II-11 |
| T1r-1899 | (R)-I-13 | II-6 | II-16 |
| T1r-1900 | (R)-I-13 | II-6 | II-21 |
| T1r-1901 | (R)-I-13 | II-6 | II-26 |
| T1r-1902 | (R)-I-13 | II-6 | II-32 |
| T1r-1903 | (R)-I-13 | II-6 | II-33 |
| T1r-1904 | (R)-I-13 | II-6 | II-37 |
| T1r-1905 | (R)-I-13 | II-6 | II-39 |
| T1r-1906 | (R)-I-13 | II-6 | II-42 |
| T1r-1907 | (R)-I-13 | II-6 | II-44 |
| T1r-1908 | (R)-I-13 | II-6 | II-50 |
| T1r-1909 | (R)-I-13 | II-6 | II-53 |
| T1r-1910 | (R)-I-13 | II-6 | II-60 |
| T1r-1911 | (R)-I-13 | II-6 | II-62 |
| T1r-1912 | (R)-I-13 | II-6 | II-66 |
| T1r-1913 | (R)-I-13 | II-6 | II-69 |
| T1r-1914 | (R)-I-13 | II-6 | II-70 |
| T1r-1915 | (R)-I-13 | II-6 | II-71 |
| T1r-1916 | (R)-I-13 | II-6 | II-72 |
| T1r-1917 | (R)-I-13 | II-6 | II-74 |
| T1r-1918 | (R)-I-13 | II-6 | II-76 |
| T1r-1919 | (R)-I-13 | II-6 | II-78 |
| T1r-1920 | (R)-I-13 | II-6 | II-84 |
| T1r-1921 | (R)-I-13 | II-6 | II-85 |
| T1r-1922 | (R)-I-13 | II-6 | II-86 |
| T1r-1923 | (R)-I-13 | II-6 | II-92 |
| T1r-1924 | (R)-I-13 | II-7 | II-8 |
| T1r-1925 | (R)-I-13 | II-7 | II-11 |
| T1r-1926 | (R)-I-13 | II-7 | II-16 |
| T1r-1927 | (R)-I-13 | II-7 | II-21 |
| T1r-1928 | (R)-I-13 | II-7 | II-26 |
| T1r-1929 | (R)-I-13 | II-7 | II-32 |
| T1r-1930 | (R)-I-13 | II-7 | II-33 |
| T1r-1931 | (R)-I-13 | II-7 | II-37 |
| T1r-1932 | (R)-I-13 | II-7 | II-39 |
| T1r-1933 | (R)-I-13 | II-7 | II-42 |
| T1r-1934 | (R)-I-13 | II-7 | II-44 |
| T1r-1935 | (R)-I-13 | II-7 | II-50 |
| T1r-1936 | (R)-I-13 | II-7 | II-53 |
| T1r-1937 | (R)-I-13 | II-7 | II-60 |
| T1r-1938 | (R)-I-13 | II-7 | II-62 |
| T1r-1939 | (R)-I-13 | II-7 | II-66 |
| T1r-1940 | (R)-I-13 | II-7 | II-69 |
| T1r-1941 | (R)-I-13 | II-7 | II-70 |
| T1r-1942 | (R)-I-13 | II-7 | II-71 |
| T1r-1943 | (R)-I-13 | II-7 | II-72 |
| T1r-1944 | (R)-I-13 | II-7 | II-74 |

TABLE T1s-continued

Three-component compositions comprising one component I as (R) enantiomer (appreviated as (R)-I, e.g. (R)-I-1 for the (R)-enantiomer of I-1), one component II and one component III, in particular ternary compositions containing the respective component I as (R) enantiomer, II and III as only active ingredients.

| composition | (R)-I | II | III |
| --- | --- | --- | --- |
| T1r-1945 | (R)-I-13 | II-7 | II-76 |
| T1r-1946 | (R)-I-13 | II-7 | II-78 |
| T1r-1947 | (R)-I-13 | II-7 | II-84 |
| T1r-1948 | (R)-I-13 | II-7 | II-85 |
| T1r-1949 | (R)-I-13 | II-7 | II-86 |
| T1r-1950 | (R)-I-13 | II-7 | II-92 |
| T1r-1951 | (R)-I-13 | II-8 | II-11 |
| T1r-1952 | (R)-I-13 | II-8 | II-16 |
| T1r-1953 | (R)-I-13 | II-8 | II-21 |
| T1r-1954 | (R)-I-13 | II-8 | II-26 |
| T1r-1955 | (R)-I-13 | II-8 | II-32 |
| T1r-1956 | (R)-I-13 | II-8 | II-33 |
| T1r-1957 | (R)-I-13 | II-8 | II-37 |
| T1r-1958 | (R)-I-13 | II-8 | II-39 |
| T1r-1959 | (R)-I-13 | II-8 | II-42 |
| T1r-1960 | (R)-I-13 | II-8 | II-44 |
| T1r-1961 | (R)-I-13 | II-8 | II-50 |
| T1r-1962 | (R)-I-13 | II-8 | II-53 |
| T1r-1963 | (R)-I-13 | II-8 | II-60 |
| T1r-1964 | (R)-I-13 | II-8 | II-62 |
| T1r-1965 | (R)-I-13 | II-8 | II-66 |
| T1r-1966 | (R)-I-13 | II-8 | II-69 |
| T1r-1967 | (R)-I-13 | II-8 | II-70 |
| T1r-1968 | (R)-I-13 | II-8 | II-71 |
| T1r-1969 | (R)-I-13 | II-8 | II-72 |
| T1r-1970 | (R)-I-13 | II-8 | II-74 |
| T1r-1971 | (R)-I-13 | II-8 | II-76 |
| T1r-1972 | (R)-I-13 | II-8 | II-78 |
| T1r-1973 | (R)-I-13 | II-8 | II-84 |
| T1r-1974 | (R)-I-13 | II-8 | II-85 |
| T1r-1975 | (R)-I-13 | II-8 | II-86 |
| T1r-1976 | (R)-I-13 | II-8 | II-92 |
| T1r-1977 | (R)-I-13 | II-11 | II-16 |
| T1r-1978 | (R)-I-13 | II-11 | II-21 |
| T1r-1979 | (R)-I-13 | II-11 | II-26 |
| T1r-1980 | (R)-I-13 | II-11 | II-32 |
| T1r-1981 | (R)-I-13 | II-11 | II-33 |
| T1r-1982 | (R)-I-13 | II-11 | II-37 |
| T1r-1983 | (R)-I-13 | II-11 | II-39 |
| T1r-1984 | (R)-I-13 | II-11 | II-42 |
| T1r-1985 | (R)-I-13 | II-11 | II-44 |
| T1r-1986 | (R)-I-13 | II-11 | II-50 |
| T1r-1987 | (R)-I-13 | II-11 | II-53 |
| T1r-1988 | (R)-I-13 | II-11 | II-60 |
| T1r-1989 | (R)-I-13 | II-11 | II-62 |
| T1r-1990 | (R)-I-13 | II-11 | II-66 |
| T1r-1991 | (R)-I-13 | II-11 | II-69 |
| T1r-1992 | (R)-I-13 | II-11 | II-70 |
| T1r-1993 | (R)-I-13 | II-11 | II-71 |
| T1r-1994 | (R)-I-13 | II-11 | II-72 |
| T1r-1995 | (R)-I-13 | II-11 | II-74 |
| T1r-1996 | (R)-I-13 | II-11 | II-76 |
| T1r-1997 | (R)-I-13 | II-11 | II-78 |
| T1r-1998 | (R)-I-13 | II-11 | II-84 |
| T1r-1999 | (R)-I-13 | II-11 | II-85 |
| T1r-2000 | (R)-I-13 | II-11 | II-86 |
| T1r-2001 | (R)-I-13 | II-11 | II-92 |
| T1r-2002 | (R)-I-13 | II-16 | II-21 |
| T1r-2003 | (R)-I-13 | II-16 | II-26 |
| T1r-2004 | (R)-I-13 | II-16 | II-32 |
| T1r-2005 | (R)-I-13 | II-16 | II-33 |
| T1r-2006 | (R)-I-13 | II-16 | II-37 |
| T1r-2007 | (R)-I-13 | II-16 | II-39 |
| T1r-2008 | (R)-I-13 | II-16 | II-42 |
| T1r-2009 | (R)-I-13 | II-16 | II-44 |
| T1r-2010 | (R)-I-13 | II-16 | II-50 |
| T1r-2011 | (R)-I-13 | II-16 | II-53 |
| T1r-2012 | (R)-I-13 | II-16 | II-60 |
| T1r-2013 | (R)-I-13 | II-16 | II-62 |
| T1r-2014 | (R)-I-13 | II-16 | II-66 |
| T1r-2015 | (R)-I-13 | II-16 | II-69 |
| T1r-2016 | (R)-I-13 | II-16 | II-70 |
| T1r-2017 | (R)-I-13 | II-16 | II-71 |
| T1r-2018 | (R)-I-13 | II-16 | II-72 |
| T1r-2019 | (R)-I-13 | II-16 | II-74 |
| T1r-2020 | (R)-I-13 | II-16 | II-76 |
| T1r-2021 | (R)-I-13 | II-16 | II-78 |
| T1r-2022 | (R)-I-13 | II-16 | II-84 |
| T1r-2023 | (R)-I-13 | II-16 | II-85 |
| T1r-2024 | (R)-I-13 | II-16 | II-86 |
| T1r-2025 | (R)-I-13 | II-16 | II-92 |
| T1r-2026 | (R)-I-13 | II-21 | II-26 |
| T1r-2027 | (R)-I-13 | II-21 | II-32 |
| T1r-2028 | (R)-I-13 | II-21 | II-33 |
| T1r-2029 | (R)-I-13 | II-21 | II-37 |
| T1r-2030 | (R)-I-13 | II-21 | II-39 |
| T1r-2031 | (R)-I-13 | II-21 | II-42 |
| T1r-2032 | (R)-I-13 | II-21 | II-44 |
| T1r-2033 | (R)-I-13 | II-21 | II-50 |
| T1r-2034 | (R)-I-13 | II-21 | II-53 |
| T1r-2035 | (R)-I-13 | II-21 | II-60 |
| T1r-2036 | (R)-I-13 | II-21 | II-62 |
| T1r-2037 | (R)-I-13 | II-21 | II-66 |
| T1r-2038 | (R)-I-13 | II-21 | II-69 |
| T1r-2039 | (R)-I-13 | II-21 | II-70 |
| T1r-2040 | (R)-I-13 | II-21 | II-71 |
| T1r-2041 | (R)-I-13 | II-21 | II-72 |
| T1r-2042 | (R)-I-13 | II-21 | II-74 |
| T1r-2043 | (R)-I-13 | II-21 | II-76 |
| T1r-2044 | (R)-I-13 | II-21 | II-78 |
| T1r-2045 | (R)-I-13 | II-21 | II-84 |
| T1r-2046 | (R)-I-13 | II-21 | II-85 |
| T1r-2047 | (R)-I-13 | II-21 | II-86 |
| T1r-2048 | (R)-I-13 | II-21 | II-92 |
| T1r-2049 | (R)-I-13 | II-26 | II-32 |
| T1r-2050 | (R)-I-13 | II-26 | II-33 |
| T1r-2051 | (R)-I-13 | II-26 | II-37 |
| T1r-2052 | (R)-I-13 | II-26 | II-39 |
| T1r-2053 | (R)-I-13 | II-26 | II-42 |
| T1r-2054 | (R)-I-13 | II-26 | II-44 |
| T1r-2055 | (R)-I-13 | II-26 | II-50 |
| T1r-2056 | (R)-I-13 | II-26 | II-53 |
| T1r-2057 | (R)-I-13 | II-26 | II-60 |
| T1r-2058 | (R)-I-13 | II-26 | II-62 |
| T1r-2059 | (R)-I-13 | II-26 | II-66 |
| T1r-2060 | (R)-I-13 | II-26 | II-69 |
| T1r-2061 | (R)-I-13 | II-26 | II-70 |
| T1r-2062 | (R)-I-13 | II-26 | II-71 |
| T1r-2063 | (R)-I-13 | II-26 | II-72 |
| T1r-2064 | (R)-I-13 | II-26 | II-74 |
| T1r-2065 | (R)-I-13 | II-26 | II-76 |
| T1r-2066 | (R)-I-13 | II-26 | II-78 |
| T1r-2067 | (R)-I-13 | II-26 | II-84 |
| T1r-2068 | (R)-I-13 | II-26 | II-85 |
| T1r-2069 | (R)-I-13 | II-26 | II-86 |
| T1r-2070 | (R)-I-13 | II-26 | II-92 |
| T1r-2071 | (R)-I-13 | II-32 | II-33 |
| T1r-2072 | (R)-I-13 | II-32 | II-37 |
| T1r-2073 | (R)-I-13 | II-32 | II-39 |
| T1r-2074 | (R)-I-13 | II-32 | II-42 |
| T1r-2075 | (R)-I-13 | II-32 | II-44 |
| T1r-2076 | (R)-I-13 | II-32 | II-50 |
| T1r-2077 | (R)-I-13 | II-32 | II-53 |
| T1r-2078 | (R)-I-13 | II-32 | II-60 |
| T1r-2079 | (R)-I-13 | II-32 | II-62 |
| T1r-2080 | (R)-I-13 | II-32 | II-66 |
| T1r-2081 | (R)-I-13 | II-32 | II-69 |
| T1r-2082 | (R)-I-13 | II-32 | II-70 |
| T1r-2083 | (R)-I-13 | II-32 | II-71 |
| T1r-2084 | (R)-I-13 | II-32 | II-72 |
| T1r-2085 | (R)-I-13 | II-32 | II-74 |
| T1r-2086 | (R)-I-13 | II-32 | II-76 |
| T1r-2087 | (R)-I-13 | II-32 | II-78 |
| T1r-2088 | (R)-I-13 | II-32 | II-84 |

TABLE T1s-continued

Three-component compositions comprising one component I as (R) enantiomer (appreviated as (R)-I, e.g. (R)-I-1 for the (R)-enantiomer of I-1), one component II and one component III, in particular ternary compositions containing the respective component I as (R) enantiomer, II and III as only active ingredients.

| composition | (R)-I | II | III |
|---|---|---|---|
| T1r-2089 | (R)-I-13 | II-32 | II-85 |
| T1r-2090 | (R)-I-13 | II-32 | II-86 |
| T1r-2091 | (R)-I-13 | II-32 | II-92 |
| T1r-2092 | (R)-I-13 | II-33 | II-37 |
| T1r-2093 | (R)-I-13 | II-33 | II-39 |
| T1r-2094 | (R)-I-13 | II-33 | II-42 |
| T1r-2095 | (R)-I-13 | II-33 | II-44 |
| T1r-2096 | (R)-I-13 | II-33 | II-50 |
| T1r-2097 | (R)-I-13 | II-33 | II-53 |
| T1r-2098 | (R)-I-13 | II-33 | II-60 |
| T1r-2099 | (R)-I-13 | II-33 | II-62 |
| T1r-2100 | (R)-I-13 | II-33 | II-66 |
| T1r-2101 | (R)-I-13 | II-33 | II-69 |
| T1r-2102 | (R)-I-13 | II-33 | II-70 |
| T1r-2103 | (R)-I-13 | II-33 | II-71 |
| T1r-2104 | (R)-I-13 | II-33 | II-72 |
| T1r-2105 | (R)-I-13 | II-33 | II-74 |
| T1r-2106 | (R)-I-13 | II-33 | II-76 |
| T1r-2107 | (R)-I-13 | II-33 | II-78 |
| T1r-2108 | (R)-I-13 | II-33 | II-84 |
| T1r-2109 | (R)-I-13 | II-33 | II-85 |
| T1r-2110 | (R)-I-13 | II-33 | II-86 |
| T1r-2111 | (R)-I-13 | II-33 | II-92 |
| T1r-2112 | (R)-I-13 | II-37 | II-39 |
| T1r-2113 | (R)-I-13 | II-37 | II-42 |
| T1r-2114 | (R)-I-13 | II-37 | II-44 |
| T1r-2115 | (R)-I-13 | II-37 | II-50 |
| T1r-2116 | (R)-I-13 | II-37 | II-53 |
| T1r-2117 | (R)-I-13 | II-37 | II-60 |
| T1r-2118 | (R)-I-13 | II-37 | II-62 |
| T1r-2119 | (R)-I-13 | II-37 | II-66 |
| T1r-2120 | (R)-I-13 | II-37 | II-69 |
| T1r-2121 | (R)-I-13 | II-37 | II-70 |
| T1r-2122 | (R)-I-13 | II-37 | II-71 |
| T1r-2123 | (R)-I-13 | II-37 | II-72 |
| T1r-2124 | (R)-I-13 | II-37 | II-74 |
| T1r-2125 | (R)-I-13 | II-37 | II-76 |
| T1r-2126 | (R)-I-13 | II-37 | II-78 |
| T1r-2127 | (R)-I-13 | II-37 | II-84 |
| T1r-2128 | (R)-I-13 | II-37 | II-85 |
| T1r-2129 | (R)-I-13 | II-37 | II-86 |
| T1r-2130 | (R)-I-13 | II-37 | II-92 |
| T1r-2131 | (R)-I-13 | II-39 | II-42 |
| T1r-2132 | (R)-I-13 | II-39 | II-44 |
| T1r-2133 | (R)-I-13 | II-39 | II-50 |
| T1r-2134 | (R)-I-13 | II-39 | II-53 |
| T1r-2135 | (R)-I-13 | II-39 | II-60 |
| T1r-2136 | (R)-I-13 | II-39 | II-62 |
| T1r-2137 | (R)-I-13 | II-39 | II-66 |
| T1r-2138 | (R)-I-13 | II-39 | II-69 |
| T1r-2139 | (R)-I-13 | II-39 | II-70 |
| T1r-2140 | (R)-I-13 | II-39 | II-71 |
| T1r-2141 | (R)-I-13 | II-39 | II-72 |
| T1r-2142 | (R)-I-13 | II-39 | II-74 |
| T1r-2143 | (R)-I-13 | II-39 | II-76 |
| T1r-2144 | (R)-I-13 | II-39 | II-78 |
| T1r-2145 | (R)-I-13 | II-39 | II-84 |
| T1r-2146 | (R)-I-13 | II-39 | II-85 |
| T1r-2147 | (R)-I-13 | II-39 | II-86 |
| T1r-2148 | (R)-I-13 | II-39 | II-92 |
| T1r-2149 | (R)-I-13 | II-42 | II-44 |
| T1r-2150 | (R)-I-13 | II-42 | II-50 |
| T1r-2151 | (R)-I-13 | II-42 | II-53 |
| T1r-2152 | (R)-I-13 | II-42 | II-60 |
| T1r-2153 | (R)-I-13 | II-42 | II-62 |
| T1r-2154 | (R)-I-13 | II-42 | II-66 |
| T1r-2155 | (R)-I-13 | II-42 | II-69 |
| T1r-2156 | (R)-I-13 | II-42 | II-70 |
| T1r-2157 | (R)-I-13 | II-42 | II-71 |
| T1r-2158 | (R)-I-13 | II-42 | II-72 |
| T1r-2159 | (R)-I-13 | II-42 | II-74 |
| T1r-2160 | (R)-I-13 | II-42 | II-76 |
| T1r-2161 | (R)-I-13 | II-42 | II-78 |
| T1r-2162 | (R)-I-13 | II-42 | II-84 |
| T1r-2163 | (R)-I-13 | II-42 | II-85 |
| T1r-2164 | (R)-I-13 | II-42 | II-86 |
| T1r-2165 | (R)-I-13 | II-42 | II-92 |
| T1r-2166 | (R)-I-13 | II-44 | II-50 |
| T1r-2167 | (R)-I-13 | II-44 | II-53 |
| T1r-2168 | (R)-I-13 | II-44 | II-60 |
| T1r-2169 | (R)-I-13 | II-44 | II-62 |
| T1r-2170 | (R)-I-13 | II-44 | II-66 |
| T1r-2171 | (R)-I-13 | II-44 | II-69 |
| T1r-2172 | (R)-I-13 | II-44 | II-70 |
| T1r-2173 | (R)-I-13 | II-44 | II-71 |
| T1r-2174 | (R)-I-13 | II-44 | II-72 |
| T1r-2175 | (R)-I-13 | II-44 | II-74 |
| T1r-2176 | (R)-I-13 | II-44 | II-76 |
| T1r-2177 | (R)-I-13 | II-44 | II-78 |
| T1r-2178 | (R)-I-13 | II-44 | II-84 |
| T1r-2179 | (R)-I-13 | II-44 | II-85 |
| T1r-2180 | (R)-I-13 | II-44 | II-86 |
| T1r-2181 | (R)-I-13 | II-44 | II-92 |
| T1r-2182 | (R)-I-13 | II-50 | II-53 |
| T1r-2183 | (R)-I-13 | II-50 | II-60 |
| T1r-2184 | (R)-I-13 | II-50 | II-62 |
| T1r-2185 | (R)-I-13 | II-50 | II-66 |
| T1r-2186 | (R)-I-13 | II-50 | II-69 |
| T1r-2187 | (R)-I-13 | II-50 | II-70 |
| T1r-2188 | (R)-I-13 | II-50 | II-71 |
| T1r-2189 | (R)-I-13 | II-50 | II-72 |
| T1r-2190 | (R)-I-13 | II-50 | II-74 |
| T1r-2191 | (R)-I-13 | II-50 | II-76 |
| T1r-2192 | (R)-I-13 | II-50 | II-78 |
| T1r-2193 | (R)-I-13 | II-50 | II-84 |
| T1r-2194 | (R)-I-13 | II-50 | II-85 |
| T1r-2195 | (R)-I-13 | II-50 | II-86 |
| T1r-2196 | (R)-I-13 | II-50 | II-92 |
| T1r-2197 | (R)-I-13 | II-53 | II-60 |
| T1r-2198 | (R)-I-13 | II-53 | II-62 |
| T1r-2199 | (R)-I-13 | II-53 | II-66 |
| T1r-2200 | (R)-I-13 | II-53 | II-69 |
| T1r-2201 | (R)-I-13 | II-53 | II-70 |
| T1r-2202 | (R)-I-13 | II-53 | II-71 |
| T1r-2203 | (R)-I-13 | II-53 | II-72 |
| T1r-2204 | (R)-I-13 | II-53 | II-74 |
| T1r-2205 | (R)-I-13 | II-53 | II-76 |
| T1r-2206 | (R)-I-13 | II-53 | II-78 |
| T1r-2207 | (R)-I-13 | II-53 | II-84 |
| T1r-2208 | (R)-I-13 | II-53 | II-85 |
| T1r-2209 | (R)-I-13 | II-53 | II-86 |
| T1r-2210 | (R)-I-13 | II-53 | II-92 |
| T1r-2211 | (R)-I-13 | II-60 | II-62 |
| T1r-2212 | (R)-I-13 | II-60 | II-66 |
| T1r-2213 | (R)-I-13 | II-60 | II-69 |
| T1r-2214 | (R)-I-13 | II-60 | II-70 |
| T1r-2215 | (R)-I-13 | II-60 | II-71 |
| T1r-2216 | (R)-I-13 | II-60 | II-72 |
| T1r-2217 | (R)-I-13 | II-60 | II-74 |
| T1r-2218 | (R)-I-13 | II-60 | II-76 |
| T1r-2219 | (R)-I-13 | II-60 | II-78 |
| T1r-2220 | (R)-I-13 | II-60 | II-84 |
| T1r-2221 | (R)-I-13 | II-60 | II-85 |
| T1r-2222 | (R)-I-13 | II-60 | II-86 |
| T1r-2223 | (R)-I-13 | II-60 | II-92 |
| T1r-2224 | (R)-I-13 | II-62 | II-66 |
| T1r-2225 | (R)-I-13 | II-62 | II-69 |
| T1r-2226 | (R)-I-13 | II-62 | II-70 |
| T1r-2227 | (R)-I-13 | II-62 | II-71 |
| T1r-2228 | (R)-I-13 | II-62 | II-72 |
| T1r-2229 | (R)-I-13 | II-62 | II-74 |
| T1r-2230 | (R)-I-13 | II-62 | II-76 |
| T1r-2231 | (R)-I-13 | II-62 | II-78 |
| T1r-2232 | (R)-I-13 | II-62 | II-84 |

TABLE T1s-continued

Three-component compositions comprising one component I as (R) enantiomer (appreviated as (R)-I, e.g. (R)-I-1 for the (R)-enantiomer of I-1), one component II and one component III, in particular ternary compositions containing the respective component I as (R) enantiomer, II and III as only active ingredients.

| composition | (R)-I | II | III |
|---|---|---|---|
| T1r-2233 | (R)-I-13 | II-62 | II-85 |
| T1r-2234 | (R)-I-13 | II-62 | II-86 |
| T1r-2235 | (R)-I-13 | II-62 | II-92 |
| T1r-2236 | (R)-I-13 | II-66 | II-69 |
| T1r-2237 | (R)-I-13 | II-66 | II-70 |
| T1r-2238 | (R)-I-13 | II-66 | II-71 |
| T1r-2239 | (R)-I-13 | II-66 | II-72 |
| T1r-2240 | (R)-I-13 | II-66 | II-74 |
| T1r-2241 | (R)-I-13 | II-66 | II-76 |
| T1r-2242 | (R)-I-13 | II-66 | II-78 |
| T1r-2243 | (R)-I-13 | II-66 | II-84 |
| T1r-2244 | (R)-I-13 | II-66 | II-85 |
| T1r-2245 | (R)-I-13 | II-66 | II-86 |
| T1r-2246 | (R)-I-13 | II-66 | II-92 |
| T1r-2247 | (R)-I-13 | II-69 | II-70 |
| T1r-2248 | (R)-I-13 | II-69 | II-71 |
| T1r-2249 | (R)-I-13 | II-69 | II-72 |
| T1r-2250 | (R)-I-13 | II-69 | II-74 |
| T1r-2251 | (R)-I-13 | II-69 | II-76 |
| T1r-2252 | (R)-I-13 | II-69 | II-78 |
| T1r-2253 | (R)-I-13 | II-69 | II-84 |
| T1r-2254 | (R)-I-13 | II-69 | II-85 |
| T1r-2255 | (R)-I-13 | II-69 | II-86 |
| T1r-2256 | (R)-I-13 | II-69 | II-92 |
| T1r-2257 | (R)-I-13 | II-70 | II-71 |
| T1r-2258 | (R)-I-13 | II-70 | II-72 |
| T1r-2259 | (R)-I-13 | II-70 | II-74 |
| T1r-2260 | (R)-I-13 | II-70 | II-76 |
| T1r-2261 | (R)-I-13 | II-70 | II-78 |
| T1r-2262 | (R)-I-13 | II-70 | II-84 |
| T1r-2263 | (R)-I-13 | II-70 | II-85 |
| T1r-2264 | (R)-I-13 | II-70 | II-86 |
| T1r-2265 | (R)-I-13 | II-70 | II-92 |
| T1r-2266 | (R)-I-13 | II-71 | II-72 |
| T1r-2267 | (R)-I-13 | II-71 | II-74 |
| T1r-2268 | (R)-I-13 | II-71 | II-76 |
| T1r-2269 | (R)-I-13 | II-71 | II-78 |
| T1r-2270 | (R)-I-13 | II-71 | II-84 |
| T1r-2271 | (R)-I-13 | II-71 | II-85 |
| T1r-2272 | (R)-I-13 | II-71 | II-86 |
| T1r-2273 | (R)-I-13 | II-71 | II-92 |
| T1r-2274 | (R)-I-13 | II-72 | II-74 |
| T1r-2275 | (R)-I-13 | II-74 | II-76 |
| T1r-2276 | (R)-I-13 | II-74 | II-78 |
| T1r-2277 | (R)-I-13 | II-74 | II-84 |
| T1r-2278 | (R)-I-13 | II-74 | II-85 |
| T1r-2279 | (R)-I-13 | II-74 | II-86 |
| T1r-2280 | (R)-I-13 | II-74 | II-92 |
| T1r-2281 | (R)-I-13 | II-76 | II-78 |
| T1r-2282 | (R)-I-13 | II-76 | II-84 |
| T1r-2283 | (R)-I-13 | II-76 | II-85 |
| T1r-2284 | (R)-I-13 | II-76 | II-86 |
| T1r-2285 | (R)-I-13 | II-76 | II-92 |
| T1r-2286 | (R)-I-13 | II-78 | II-84 |
| T1r-2287 | (R)-I-13 | II-78 | II-85 |
| T1r-2288 | (R)-I-13 | II-78 | II-86 |
| T1r-2289 | (R)-I-13 | II-78 | II-92 |
| T1r-2290 | (R)-I-13 | II-84 | II-85 |
| T1r-2291 | (R)-I-13 | II-84 | II-86 |
| T1r-2292 | (R)-I-13 | II-84 | II-92 |
| T1r-2293 | (R)-I-13 | II-85 | II-86 |
| T1r-2294 | (R)-I-13 | II-85 | II-92 |
| T1r-2295 | (R)-I-13 | II-86 | II-92 |

Further particularly preferred compositions are the three-component compositions, wherein component I is as defined above, i.e a compound I, in particular a compound selected from compounds I-1, I-2, I-3, I-4, I-5, I-6, I-7, I-8, I-9, I-11, I-13, I-14, I-15 and I-16 or any group of compounds I detailed above, components II are selected from II-15 cyproconazole
II-38 fluquinconazole
II-60 metconazole
II-76 propiconazole
II-78 prothioconazole
and component III is selected from
II-66 pyraclostrobin
II-9 captan
II-11 chlorothalonil
II-17 copper
II-18 copper hydroxide
II-20 dodine
II-25 dithianon
II-43 folpet
II-54 mancozeb
II-61 metiram
II-98 2,6-dimethyl-1H,5H-[1,4]dithiino[2,3-c:5,6-c']dipyrrole-1,3,5,7(2H,6H)-tetraone
II-99 maneb
II-100 Bordeaux mixture
II-101 copper oxychloride
II-102 basic copper sulfate Such inventive composition are compiled in Table T1a, where each row corresponds to one embodiment of the compositions according to the invention, i.e. one specific individualized three-component composition. According to one specific aspect, these are ternary compositions which each only contain these three components as the active compound. Furthermore, also every combination of the compositions individualized in this table represent embodiments of the present invention.

TABLE T1a

Further preferred three-component compositions comprising a component I, a component II and a component III, wherein component II and III are selected from the preferred fungicides detailed above, wherein components II and III are different from each other.

| composition | I | II | III |
|---|---|---|---|
| T1a-1 | I-1 | II-15 | II-66 |
| T1a-2 | I-2 | II-15 | II-66 |
| T1a-3 | I-3 | II-15 | II-66 |
| T1a-4 | I-4 | II-15 | II-66 |
| T1a-5 | I-5 | II-15 | II-66 |
| T1a-6 | I-13 | II-15 | II-66 |
| T1a-7 | I-1 | II-38 | II-66 |
| T1a-8 | I-2 | II-38 | II-66 |
| T1a-9 | I-3 | II-38 | II-66 |
| T1a-10 | I-4 | II-38 | II-66 |
| T1a-11 | I-5 | II-38 | II-66 |
| T1a-12 | I-13 | II-38 | II-66 |
| T1a-13 | I-1 | II-60 | II-66 |
| T1a-14 | I-2 | II-60 | II-66 |
| T1a-15 | I-3 | II-60 | II-66 |
| T1a-16 | I-4 | II-60 | II-66 |
| T1a-17 | I-5 | II-60 | II-66 |
| T1a-18 | I-13 | II-60 | II-66 |
| T1a-19 | I-1 | II-76 | II-66 |
| T1a-20 | I-2 | II-76 | II-66 |
| T1a-21 | I-3 | II-76 | II-66 |
| T1a-22 | I-4 | II-76 | II-66 |
| T1a-23 | I-5 | II-76 | II-66 |
| T1a-24 | I-13 | II-76 | II-66 |
| T1a-25 | I-1 | II-78 | II-66 |
| T1a-26 | I-2 | II-78 | II-66 |
| T1a-27 | I-3 | II-78 | II-66 |
| T1a-28 | I-4 | II-78 | II-66 |
| T1a-29 | I-5 | II-78 | II-66 |
| T1a-30 | I-13 | II-78 | II-66 |
| T1a-31 | I-1 | II-15 | II-9 |
| T1a-32 | I-2 | II-15 | II-9 |
| T1a-33 | I-3 | II-15 | II-9 |

TABLE T1a-continued

Further preferred three-component compositions comprising a component I, a component II and a component III, wherein component II and III are selected from the preferred fungicides detailed above, wherein components II and III are different from each other.

| composition | I | II | III |
|---|---|---|---|
| T1a-34 | I-4 | II-15 | II-9 |
| T1a-35 | I-5 | II-15 | II-9 |
| T1a-36 | I-13 | II-15 | II-9 |
| T1a-37 | I-1 | II-38 | II-9 |
| T1a-38 | I-2 | II-38 | II-9 |
| T1a-39 | I-3 | II-38 | II-9 |
| T1a-40 | I-4 | II-38 | II-9 |
| T1a-41 | I-5 | II-38 | II-9 |
| T1a-42 | I-13 | II-38 | II-9 |
| T1a-43 | I-1 | II-60 | II-9 |
| T1a-44 | I-2 | II-60 | II-9 |
| T1a-45 | I-3 | II-60 | II-9 |
| T1a-46 | I-4 | II-60 | II-9 |
| T1a-47 | I-5 | II-60 | II-9 |
| T1a-48 | I-13 | II-60 | II-9 |
| T1a-49 | I-1 | II-76 | II-9 |
| T1a-50 | I-2 | II-76 | II-9 |
| T1a-51 | I-3 | II-76 | II-9 |
| T1a-52 | I-4 | II-76 | II-9 |
| T1a-53 | I-5 | II-76 | II-9 |
| T1a-54 | I-13 | II-76 | II-9 |
| T1a-55 | I-1 | II-78 | II-9 |
| T1a-56 | I-2 | II-78 | II-9 |
| T1a-57 | I-3 | II-78 | II-9 |
| T1a-58 | I-4 | II-78 | II-9 |
| T1a-59 | I-5 | II-78 | II-9 |
| T1a-60 | I-13 | II-78 | II-9 |
| T1a-61 | I-1 | II-15 | II-11 |
| T1a-62 | I-2 | II-15 | II-11 |
| T1a-63 | I-3 | II-15 | II-11 |
| T1a-64 | I-4 | II-15 | II-11 |
| T1a-65 | I-5 | II-15 | II-11 |
| T1a-66 | I-13 | II-15 | II-11 |
| T1a-67 | I-1 | II-38 | II-11 |
| T1a-68 | I-2 | II-38 | II-11 |
| T1a-69 | I-3 | II-38 | II-11 |
| T1a-70 | I-4 | II-38 | II-11 |
| T1a-71 | I-5 | II-38 | II-11 |
| T1a-72 | I-13 | II-38 | II-11 |
| T1a-73 | I-1 | II-60 | II-11 |
| T1a-74 | I-2 | II-60 | II-11 |
| T1a-75 | I-3 | II-60 | II-11 |
| T1a-76 | I-4 | II-60 | II-11 |
| T1a-77 | I-5 | II-60 | II-11 |
| T1a-78 | I-13 | II-60 | II-11 |
| T1a-79 | I-1 | II-76 | II-11 |
| T1a-80 | I-2 | II-76 | II-11 |
| T1a-81 | I-3 | II-76 | II-11 |
| T1a-82 | I-4 | II-76 | II-11 |
| T1a-83 | I-5 | II-76 | II-11 |
| T1a-84 | I-13 | II-76 | II-11 |
| T1a-85 | I-1 | II-78 | II-11 |
| T1a-86 | I-2 | II-78 | II-11 |
| T1a-87 | I-3 | II-78 | II-11 |
| T1a-88 | I-4 | II-78 | II-11 |
| T1a-89 | I-5 | II-78 | II-11 |
| T1a-90 | I-13 | II-78 | II-11 |
| T1a-91 | I-1 | II-15 | II-17 |
| T1a-92 | I-2 | II-15 | II-17 |
| T1a-93 | I-3 | II-15 | II-17 |
| T1a-94 | I-4 | II-15 | II-17 |
| T1a-95 | I-5 | II-15 | II-17 |
| T1a-96 | I-13 | II-15 | II-17 |
| T1a-97 | I-1 | II-38 | II-17 |
| T1a-98 | I-2 | II-38 | II-17 |
| T1a-99 | I-3 | II-38 | II-17 |
| T1a-100 | I-4 | II-38 | II-17 |
| T1a-101 | I-5 | II-38 | II-17 |
| T1a-102 | I-13 | II-38 | II-17 |
| T1a-103 | I-1 | II-60 | II-17 |
| T1a-104 | I-2 | II-60 | II-17 |
| T1a-105 | I-3 | II-60 | II-17 |
| T1a-106 | I-4 | II-60 | II-17 |
| T1a-107 | I-5 | II-60 | II-17 |
| T1a-108 | I-13 | II-60 | II-17 |
| T1a-109 | I-1 | II-76 | II-17 |
| T1a-110 | I-2 | II-76 | II-17 |
| T1a-111 | I-3 | II-76 | II-17 |
| T1a-112 | I-4 | II-76 | II-17 |
| T1a-113 | I-5 | II-76 | II-17 |
| T1a-114 | I-13 | II-76 | II-17 |
| T1a-115 | I-1 | II-78 | II-17 |
| T1a-116 | I-2 | II-78 | II-17 |
| T1a-117 | I-3 | II-78 | II-17 |
| T1a-118 | I-4 | II-78 | II-17 |
| T1a-119 | I-5 | II-78 | II-17 |
| T1a-120 | I-13 | II-78 | II-17 |
| T1a-121 | I-1 | II-15 | II-18 |
| T1a-122 | I-2 | II-15 | II-18 |
| T1a-123 | I-3 | II-15 | II-18 |
| T1a-124 | I-4 | II-15 | II-18 |
| T1a-125 | I-5 | II-15 | II-18 |
| T1a-126 | I-13 | II-15 | II-18 |
| T1a-127 | I-1 | II-38 | II-18 |
| T1a-128 | I-2 | II-38 | II-18 |
| T1a-129 | I-3 | II-38 | II-18 |
| T1a-130 | I-4 | II-38 | II-18 |
| T1a-131 | I-5 | II-38 | II-18 |
| T1a-132 | I-13 | II-38 | II-18 |
| T1a-133 | I-1 | II-60 | II-18 |
| T1a-134 | I-2 | II-60 | II-18 |
| T1a-135 | I-3 | II-60 | II-18 |
| T1a-136 | I-4 | II-60 | II-18 |
| T1a-137 | I-5 | II-60 | II-18 |
| T1a-138 | I-13 | II-60 | II-18 |
| T1a-139 | I-1 | II-76 | II-18 |
| T1a-140 | I-2 | II-76 | II-18 |
| T1a-141 | I-3 | II-76 | II-18 |
| T1a-142 | I-4 | II-76 | II-18 |
| T1a-143 | I-5 | II-76 | II-18 |
| T1a-144 | I-13 | II-76 | II-18 |
| T1a-145 | I-1 | II-78 | II-18 |
| T1a-146 | I-2 | II-78 | II-18 |
| T1a-147 | I-3 | II-78 | II-18 |
| T1a-148 | I-4 | II-78 | II-18 |
| T1a-149 | I-5 | II-78 | II-18 |
| T1a-150 | I-13 | II-78 | II-18 |
| T1a-151 | I-1 | II-15 | II-20 |
| T1a-152 | I-2 | II-15 | II-20 |
| T1a-153 | I-3 | II-15 | II-20 |
| T1a-154 | I-4 | II-15 | II-20 |
| T1a-155 | I-5 | II-15 | II-20 |
| T1a-156 | I-13 | II-15 | II-20 |
| T1a-157 | I-1 | II-38 | II-20 |
| T1a-158 | I-2 | II-38 | II-20 |
| T1a-159 | I-3 | II-38 | II-20 |
| T1a-160 | I-4 | II-38 | II-20 |
| T1a-161 | I-5 | II-38 | II-20 |
| T1a-162 | I-13 | II-38 | II-20 |
| T1a-163 | I-1 | II-60 | II-20 |
| T1a-164 | I-2 | II-60 | II-20 |
| T1a-165 | I-3 | II-60 | II-20 |
| T1a-166 | I-4 | II-60 | II-20 |
| T1a-167 | I-5 | II-60 | II-20 |
| T1a-168 | I-13 | II-60 | II-20 |
| T1a-169 | I-1 | II-76 | II-20 |
| T1a-170 | I-2 | II-76 | II-20 |
| T1a-171 | I-3 | II-76 | II-20 |
| T1a-172 | I-4 | II-76 | II-20 |
| T1a-173 | I-5 | II-76 | II-20 |
| T1a-174 | I-13 | II-76 | II-20 |
| T1a-175 | I-1 | II-78 | II-20 |
| T1a-176 | I-2 | II-78 | II-20 |
| T1a-177 | I-3 | II-78 | II-20 |

TABLE T1a-continued

Further preferred three-component compositions comprising a component I, a component II and a component III, wherein component II and III are selected from the preferred fungicides detailed above, wherein components II and III are different from each other.

| composition | I | II | III |
|---|---|---|---|
| T1a-178 | I-4 | II-78 | II-20 |
| T1a-179 | I-5 | II-78 | II-20 |
| T1a-180 | I-13 | II-78 | II-20 |
| T1a-181 | I-1 | II-15 | II-25 |
| T1a-182 | I-2 | II-15 | II-25 |
| T1a-183 | I-3 | II-15 | II-25 |
| T1a-184 | I-4 | II-15 | II-25 |
| T1a-185 | I-5 | II-15 | II-25 |
| T1a-186 | I-13 | II-15 | II-25 |
| T1a-187 | I-1 | II-38 | II-25 |
| T1a-188 | I-2 | II-38 | II-25 |
| T1a-189 | I-3 | II-38 | II-25 |
| T1a-190 | I-4 | II-38 | II-25 |
| T1a-191 | I-5 | II-38 | II-25 |
| T1a-192 | I-13 | II-38 | II-25 |
| T1a-193 | I-1 | II-60 | II-25 |
| T1a-194 | I-2 | II-60 | II-25 |
| T1a-195 | I-3 | II-60 | II-25 |
| T1a-196 | I-4 | II-60 | II-25 |
| T1a-197 | I-5 | II-60 | II-25 |
| T1a-198 | I-13 | II-60 | II-25 |
| T1a-199 | I-1 | II-76 | II-25 |
| T1a-200 | I-2 | II-76 | II-25 |
| T1a-201 | I-3 | II-76 | II-25 |
| T1a-202 | I-4 | II-76 | II-25 |
| T1a-203 | I-5 | II-76 | II-25 |
| T1a-204 | I-13 | II-76 | II-25 |
| T1a-205 | I-1 | II-78 | II-25 |
| T1a-206 | I-2 | II-78 | II-25 |
| T1a-207 | I-3 | II-78 | II-25 |
| T1a-208 | I-4 | II-78 | II-25 |
| T1a-209 | I-5 | II-78 | II-25 |
| T1a-210 | I-13 | II-78 | II-25 |
| T1a-211 | I-1 | II-15 | II-43 |
| T1a-212 | I-2 | II-15 | II-43 |
| T1a-213 | I-3 | II-15 | II-43 |
| T1a-214 | I-4 | II-15 | II-43 |
| T1a-215 | I-5 | II-15 | II-43 |
| T1a-216 | I-13 | II-15 | II-43 |
| T1a-217 | I-1 | II-38 | II-43 |
| T1a-218 | I-2 | II-38 | II-43 |
| T1a-219 | I-3 | II-38 | II-43 |
| T1a-220 | I-4 | II-38 | II-43 |
| T1a-221 | I-5 | II-38 | II-43 |
| T1a-222 | I-13 | II-38 | II-43 |
| T1a-223 | I-1 | II-60 | II-43 |
| T1a-224 | I-2 | II-60 | II-43 |
| T1a-225 | I-3 | II-60 | II-43 |
| T1a-226 | I-4 | II-60 | II-43 |
| T1a-227 | I-5 | II-60 | II-43 |
| T1a-228 | I-13 | II-60 | II-43 |
| T1a-229 | I-1 | II-76 | II-43 |
| T1a-230 | I-2 | II-76 | II-43 |
| T1a-231 | I-3 | II-76 | II-43 |
| T1a-232 | I-4 | II-76 | II-43 |
| T1a-233 | I-5 | II-76 | II-43 |
| T1a-234 | I-13 | II-76 | II-43 |
| T1a-235 | I-1 | II-78 | II-43 |
| T1a-236 | I-2 | II-78 | II-43 |
| T1a-237 | I-3 | II-78 | II-43 |
| T1a-238 | I-4 | II-78 | II-43 |
| T1a-239 | I-5 | II-78 | II-43 |
| T1a-240 | I-13 | II-78 | II-43 |
| T1a-241 | I-1 | II-15 | II-54 |
| T1a-242 | I-2 | II-15 | II-54 |
| T1a-243 | I-3 | II-15 | II-54 |
| T1a-244 | I-4 | II-15 | II-54 |
| T1a-245 | I-5 | II-15 | II-54 |
| T1a-246 | I-13 | II-15 | II-54 |
| T1a-247 | I-1 | II-38 | II-54 |
| T1a-248 | I-2 | II-38 | II-54 |
| T1a-249 | I-3 | II-38 | II-54 |
| T1a-250 | I-4 | II-38 | II-54 |
| T1a-251 | I-5 | II-38 | II-54 |
| T1a-252 | I-13 | II-38 | II-54 |
| T1a-253 | I-1 | II-60 | II-54 |
| T1a-254 | I-2 | II-60 | II-54 |
| T1a-255 | I-3 | II-60 | II-54 |
| T1a-256 | I-4 | II-60 | II-54 |
| T1a-257 | I-5 | II-60 | II-54 |
| T1a-258 | I-13 | II-60 | II-54 |
| T1a-259 | I-1 | II-76 | II-54 |
| T1a-260 | I-2 | II-76 | II-54 |
| T1a-261 | I-3 | II-76 | II-54 |
| T1a-262 | I-4 | II-76 | II-54 |
| T1a-263 | I-5 | II-76 | II-54 |
| T1a-264 | I-13 | II-76 | II-54 |
| T1a-265 | I-1 | II-78 | II-54 |
| T1a-266 | I-2 | II-78 | II-54 |
| T1a-267 | I-3 | II-78 | II-54 |
| T1a-268 | I-4 | II-78 | II-54 |
| T1a-269 | I-5 | II-78 | II-54 |
| T1a-270 | I-13 | II-78 | II-54 |
| T1a-271 | I-1 | II-15 | II-61 |
| T1a-272 | I-2 | II-15 | II-61 |
| T1a-273 | I-3 | II-15 | II-61 |
| T1a-274 | I-4 | II-15 | II-61 |
| T1a-275 | I-5 | II-15 | II-61 |
| T1a-276 | I-13 | II-15 | II-61 |
| T1a-277 | I-1 | II-38 | II-61 |
| T1a-278 | I-2 | II-38 | II-61 |
| T1a-279 | I-3 | II-38 | II-61 |
| T1a-280 | I-4 | II-38 | II-61 |
| T1a-281 | I-5 | II-38 | II-61 |
| T1a-282 | I-13 | II-38 | II-61 |
| T1a-283 | I-1 | II-60 | II-61 |
| T1a-284 | I-2 | II-60 | II-61 |
| T1a-285 | I-3 | II-60 | II-61 |
| T1a-286 | I-4 | II-60 | II-61 |
| T1a-287 | I-5 | II-60 | II-61 |
| T1a-288 | I-13 | II-60 | II-61 |
| T1a-289 | I-1 | II-76 | II-61 |
| T1a-290 | I-2 | II-76 | II-61 |
| T1a-291 | I-3 | II-76 | II-61 |
| T1a-292 | I-4 | II-76 | II-61 |
| T1a-293 | I-5 | II-76 | II-61 |
| T1a-294 | I-13 | II-76 | II-61 |
| T1a-295 | I-1 | II-78 | II-61 |
| T1a-296 | I-2 | II-78 | II-61 |
| T1a-297 | I-3 | II-78 | II-61 |
| T1a-298 | I-4 | II-78 | II-61 |
| T1a-299 | I-5 | II-78 | II-61 |
| T1a-300 | I-13 | II-78 | II-61 |
| T1a-301 | I-1 | II-15 | II-98 |
| T1a-302 | I-2 | II-15 | II-98 |
| T1a-303 | I-3 | II-15 | II-98 |
| T1a-304 | I-4 | II-15 | II-98 |
| T1a-305 | I-5 | II-15 | II-98 |
| T1a-306 | I-13 | II-15 | II-98 |
| T1a-307 | I-1 | II-38 | II-98 |
| T1a-308 | I-2 | II-38 | II-98 |
| T1a-309 | I-3 | II-38 | II-98 |
| T1a-310 | I-4 | II-38 | II-98 |
| T1a-311 | I-5 | II-38 | II-98 |
| T1a-312 | I-13 | II-38 | II-98 |
| T1a-313 | I-1 | II-60 | II-98 |
| T1a-314 | I-2 | II-60 | II-98 |
| T1a-315 | I-3 | II-60 | II-98 |
| T1a-316 | I-4 | II-60 | II-98 |
| T1a-317 | I-5 | II-60 | II-98 |
| T1a-318 | I-13 | II-60 | II-98 |
| T1a-319 | I-1 | II-76 | II-98 |
| T1a-320 | I-2 | II-76 | II-98 |
| T1a-321 | I-3 | II-76 | II-98 |

TABLE T1a-continued

Further preferred three-component compositions comprising a component I, a component II and a component III, wherein component II and III are selected from the preferred fungicides detailed above, wherein components II and III are different from each other.

| composition | I | II | III |
|---|---|---|---|
| T1a-322 | I-4 | II-76 | II-98 |
| T1a-323 | I-5 | II-76 | II-98 |
| T1a-324 | I-13 | II-76 | II-98 |
| T1a-325 | I-1 | II-78 | II-98 |
| T1a-326 | I-2 | II-78 | II-98 |
| T1a-327 | I-3 | II-78 | II-98 |
| T1a-328 | I-4 | II-78 | II-98 |
| T1a-329 | I-5 | II-78 | II-98 |
| T1a-330 | I-13 | II-78 | II-98 |
| T1a-331 | I-1 | II-15 | II-99 |
| T1a-332 | I-2 | II-15 | II-99 |
| T1a-333 | I-3 | II-15 | II-99 |
| T1a-334 | I-4 | II-15 | II-99 |
| T1a-335 | I-5 | II-15 | II-99 |
| T1a-336 | I-13 | II-15 | II-99 |
| T1a-337 | I-1 | II-38 | II-99 |
| T1a-338 | I-2 | II-38 | II-99 |
| T1a-339 | I-3 | II-38 | II-99 |
| T1a-340 | I-4 | II-38 | II-99 |
| T1a-341 | I-5 | II-38 | II-99 |
| T1a-342 | I-13 | II-38 | II-99 |
| T1a-343 | I-1 | II-60 | II-99 |
| T1a-344 | I-2 | II-60 | II-99 |
| T1a-345 | I-3 | II-60 | II-99 |
| T1a-346 | I-4 | II-60 | II-99 |
| T1a-347 | I-5 | II-60 | II-99 |
| T1a-348 | I-13 | II-60 | II-99 |
| T1a-349 | I-1 | II-76 | II-99 |
| T1a-350 | I-2 | II-76 | II-99 |
| T1a-351 | I-3 | II-76 | II-99 |
| T1a-352 | I-4 | II-76 | II-99 |
| T1a-353 | I-5 | II-76 | II-99 |
| T1a-354 | I-13 | II-76 | II-99 |
| T1a-355 | I-1 | II-78 | II-99 |
| T1a-356 | I-2 | II-78 | II-99 |
| T1a-357 | I-3 | II-78 | II-99 |
| T1a-358 | I-4 | II-78 | II-99 |
| T1a-359 | I-5 | II-78 | II-99 |
| T1a-360 | I-13 | II-78 | II-99 |
| T1a-361 | I-1 | II-15 | II-100 |
| T1a-362 | I-2 | II-15 | II-100 |
| T1a-363 | I-3 | II-15 | II-100 |
| T1a-364 | I-4 | II-15 | II-100 |
| T1a-365 | I-5 | II-15 | II-100 |
| T1a-366 | I-13 | II-15 | II-100 |
| T1a-367 | I-1 | II-38 | II-100 |
| T1a-368 | I-2 | II-38 | II-100 |
| T1a-369 | I-3 | II-38 | II-100 |
| T1a-370 | I-4 | II-38 | II-100 |
| T1a-371 | I-5 | II-38 | II-100 |
| T1a-372 | I-13 | II-38 | II-100 |
| T1a-373 | I-1 | II-60 | II-100 |
| T1a-374 | I-2 | II-60 | II-100 |
| T1a-375 | I-3 | II-60 | II-100 |
| T1a-376 | I-4 | II-60 | II-100 |
| T1a-377 | I-5 | II-60 | II-100 |
| T1a-378 | I-13 | II-60 | II-100 |
| T1a-379 | I-1 | II-76 | II-100 |
| T1a-380 | I-2 | II-76 | II-100 |
| T1a-381 | I-3 | II-76 | II-100 |
| T1a-382 | I-4 | II-76 | II-100 |
| T1a-383 | I-5 | II-76 | II-100 |
| T1a-384 | I-13 | II-76 | II-100 |
| T1a-385 | I-1 | II-78 | II-100 |
| T1a-386 | I-2 | II-78 | II-100 |
| T1a-387 | I-3 | II-78 | II-100 |
| T1a-388 | I-4 | II-78 | II-100 |
| T1a-389 | I-5 | II-78 | II-100 |
| T1a-390 | I-13 | II-78 | II-100 |
| T1a-391 | I-1 | II-15 | II-101 |
| T1a-392 | I-2 | II-15 | II-101 |
| T1a-393 | I-3 | II-15 | II-101 |
| T1a-394 | I-4 | II-15 | II-101 |
| T1a-395 | I-5 | II-15 | II-101 |
| T1a-396 | I-13 | II-15 | II-101 |
| T1a-397 | I-1 | II-38 | II-101 |
| T1a-398 | I-2 | II-38 | II-101 |
| T1a-399 | I-3 | II-38 | II-101 |
| T1a-400 | I-4 | II-38 | II-101 |
| T1a-401 | I-5 | II-38 | II-101 |
| T1a-402 | I-13 | II-38 | II-101 |
| T1a-403 | I-1 | II-60 | II-101 |
| T1a-404 | I-2 | II-60 | II-101 |
| T1a-405 | I-3 | II-60 | II-101 |
| T1a-406 | I-4 | II-60 | II-101 |
| T1a-407 | I-5 | II-60 | II-101 |
| T1a-408 | I-13 | II-60 | II-101 |
| T1a-409 | I-1 | II-76 | II-101 |
| T1a-410 | I-2 | II-76 | II-101 |
| T1a-411 | I-3 | II-76 | II-101 |
| T1a-412 | I-4 | II-76 | II-101 |
| T1a-413 | I-5 | II-76 | II-101 |
| T1a-414 | I-13 | II-76 | II-101 |
| T1a-415 | I-1 | II-78 | II-101 |
| T1a-416 | I-2 | II-78 | II-101 |
| T1a-417 | I-3 | II-78 | II-101 |
| T1a-418 | I-4 | II-78 | II-101 |
| T1a-419 | I-5 | II-78 | II-101 |
| T1a-420 | I-13 | II-78 | II-101 |
| T1a-421 | I-1 | II-15 | II-102 |
| T1a-422 | I-2 | II-15 | II-102 |
| T1a-423 | I-3 | II-15 | II-102 |
| T1a-424 | I-4 | II-15 | II-102 |
| T1a-425 | I-5 | II-15 | II-102 |
| T1a-426 | I-13 | II-15 | II-102 |
| T1a-427 | I-1 | II-38 | II-102 |
| T1a-428 | I-2 | II-38 | II-102 |
| T1a-429 | I-3 | II-38 | II-102 |
| T1a-430 | I-4 | II-38 | II-102 |
| T1a-431 | I-5 | II-38 | II-102 |
| T1a-432 | I-13 | II-38 | II-102 |
| T1a-433 | I-1 | II-60 | II-102 |
| T1a-434 | I-2 | II-60 | II-102 |
| T1a-435 | I-3 | II-60 | II-102 |
| T1a-436 | I-4 | II-60 | II-102 |
| T1a-437 | I-5 | II-60 | II-102 |
| T1a-438 | I-13 | II-60 | II-102 |
| T1a-439 | I-1 | II-76 | II-102 |
| T1a-440 | I-2 | II-76 | II-102 |
| T1a-441 | I-3 | II-76 | II-102 |
| T1a-442 | I-4 | II-76 | II-102 |
| T1a-443 | I-5 | II-76 | II-102 |
| T1a-444 | I-13 | II-76 | II-102 |
| T1a-445 | I-1 | II-78 | II-102 |
| T1a-446 | I-2 | II-78 | II-102 |
| T1a-447 | I-3 | II-78 | II-102 |
| T1a-448 | I-4 | II-78 | II-102 |
| T1a-449 | I-5 | II-78 | II-102 |
| T1a-450 | I-13 | II-78 | II-102 |
| T1a-451 | I-1 | II-15 | II-102 |
| T1a-452 | I-2 | II-15 | II-102 |
| T1a-453 | I-3 | II-15 | II-102 |
| T1a-454 | I-4 | II-15 | II-102 |
| T1a-455 | I-5 | II-15 | II-102 |
| T1a-456 | I-13 | II-15 | II-102 |
| T1a-457 | I-1 | II-38 | II-102 |
| T1a-458 | I-2 | II-38 | II-102 |
| T1a-459 | I-3 | II-38 | II-102 |
| T1a-460 | I-4 | II-38 | II-102 |
| T1a-461 | I-5 | II-38 | II-102 |
| T1a-462 | I-13 | II-38 | II-102 |
| T1a-463 | I-1 | II-60 | II-102 |
| T1a-464 | I-2 | II-60 | II-102 |
| T1a-465 | I-3 | II-60 | II-102 |

TABLE T1a-continued

Further preferred three-component compositions comprising a component I, a component II and a component III, wherein component II and III are selected from the preferred fungicides detailed above, wherein components II and III are different from each other.

| composition | I | II | III |
|---|---|---|---|
| T1a-466 | I-4 | II-60 | II-102 |
| T1a-467 | I-5 | II-60 | II-102 |
| T1a-468 | I-13 | II-60 | II-102 |
| T1a-469 | I-1 | II-76 | II-102 |
| T1a-470 | I-2 | II-76 | II-102 |
| T1a-471 | I-3 | II-76 | II-102 |
| T1a-472 | I-4 | II-76 | II-102 |
| T1a-473 | I-5 | II-76 | II-102 |
| T1a-474 | I-13 | II-76 | II-102 |
| T1a-475 | I-1 | II-78 | II-102 |
| T1a-476 | I-2 | II-78 | II-102 |
| T1a-477 | I-3 | II-78 | II-102 |
| T1a-478 | I-4 | II-78 | II-102 |
| T1a-479 | I-5 | II-78 | II-102 |
| T1a-480 | I-13 | II-78 | II-102 |

In table T1a, according to particular embodiments of the invention, the respective component I is present as (S) enantiomer, wherein each row corresponds to one embodiment of the compositions according to the invention, i.e. one specific individualized composition. According to one specific aspect, these are ternary compositions which each only contain these two components as active compounds. Furthermore, also every combination of the compositions individualized in this table represent embodiments of the present invention (S) enantiomer.

In table T1a, according to a further particular embodiments of the invention, the respective component I is present as (R) enantiomer, wherein each row corresponds to one embodiment of the compositions according to the invention, i.e. one specific individualized composition. According to one specific aspect, these are ternary compositions which each only contain these two components as active compounds. Furthermore, also every combination of the compositions individualized in this table represent embodiments of the present invention (R) enantiomer.

One further aspect of the present invention are the novel two-component compositions comprising the component II and the component III as listed the above Table T1, i.e. the compositions given in the following Table BT1 as far as they are novel:

TABLE BT1

Two-component compositions comprising a component II and a component III, wherein component II and III are selected from the preferred fungicides detailed above, wherein components II and III are different from each other. Each line of line BT1-1 to BT1-459 corresponds to one particular individidualized composition. Furthermore, also every combination of the compositions individualized in this table represent embodiments of the present invention.

| composition | II | III |
|---|---|---|
| BT1-1 | II-3 | II-5 |
| BT1-2 | II-3 | II-6 |
| BT1-3 | II-3 | II-7 |
| BT1-4 | II-3 | II-8 |
| BT1-5 | II-3 | II-11 |
| BT1-6 | II-3 | II-16 |
| BT1-7 | II-3 | II-21 |
| BT1-8 | II-3 | II-26 |
| BT1-9 | II-3 | II-32 |
| BT1-10 | II-3 | II-33 |
| BT1-11 | II-3 | II-37 |
| BT1-12 | II-3 | II-39 |
| BT1-13 | II-3 | II-42 |
| BT1-14 | II-3 | II-44 |
| BT1-15 | II-3 | II-50 |
| BT1-16 | II-3 | II-53 |
| BT1-17 | II-3 | II-60 |
| BT1-18 | II-3 | II-62 |
| BT1-19 | II-3 | II-66 |
| BT1-20 | II-3 | II-69 |
| BT1-21 | II-3 | II-70 |
| BT1-22 | II-3 | II-71 |
| BT1-23 | II-3 | II-72 |
| BT1-24 | II-3 | II-74 |
| BT1-25 | II-3 | II-76 |
| BT1-26 | II-3 | II-78 |
| BT1-27 | II-3 | II-84 |
| BT1-28 | II-3 | II-85 |
| BT1-29 | II-3 | II-86 |
| BT1-30 | II-3 | II-92 |
| BT1-31 | II-5 | II-6 |
| BT1-32 | II-5 | II-7 |
| BT1-33 | II-5 | II-8 |
| BT1-34 | II-5 | II-11 |
| BT1-35 | II-5 | II-16 |
| BT1-36 | II-5 | II-21 |
| BT1-37 | II-5 | II-26 |
| BT1-38 | II-5 | II-32 |
| BT1-39 | II-5 | II-33 |
| BT1-40 | II-5 | II-37 |
| BT1-41 | II-5 | II-39 |
| BT1-42 | II-5 | II-42 |
| BT1-43 | II-5 | II-44 |
| BT1-44 | II-5 | II-50 |
| BT1-45 | II-5 | II-53 |
| BT1-46 | II-5 | II-60 |
| BT1-47 | II-5 | II-62 |
| BT1-48 | II-5 | II-66 |
| BT1-49 | II-5 | II-69 |
| BT1-50 | II-5 | II-70 |
| BT1-51 | II-5 | II-71 |
| BT1-52 | II-5 | II-72 |
| BT1-53 | II-5 | II-74 |
| BT1-54 | II-5 | II-76 |
| BT1-55 | II-5 | II-78 |
| BT1-56 | II-5 | II-84 |
| BT1-57 | II-5 | II-85 |
| BT1-58 | II-5 | II-86 |
| BT1-59 | II-5 | II-92 |
| BT1-60 | II-6 | II-7 |
| BT1-61 | II-6 | II-8 |
| BT1-62 | II-6 | II-11 |
| BT1-63 | II-6 | II-16 |
| BT1-64 | II-6 | II-21 |
| BT1-65 | II-6 | II-26 |
| BT1-66 | II-6 | II-32 |
| BT1-67 | II-6 | II-33 |
| BT1-68 | II-6 | II-37 |
| BT1-69 | II-6 | II-39 |
| BT1-70 | II-6 | II-42 |
| BT1-71 | II-6 | II-44 |
| BT1-72 | II-6 | II-50 |
| BT1-73 | II-6 | II-53 |
| BT1-74 | II-6 | II-60 |
| BT1-75 | II-6 | II-62 |
| BT1-76 | II-6 | II-66 |
| BT1-77 | II-6 | II-69 |
| BT1-78 | II-6 | II-70 |

TABLE BT1-continued

Two-component compositions comprising a component II and a component III, wherein component II and III are selected from the preferred fungicides detailed above, wherein components II and III are different from each other. Each line of line BT1-1 to BT1-459 corresponds to one particular individidualized composition. Furthermore, also every combination of the compositions individualized in this table represent embodiments of the present invention.

| composition | II | III |
|---|---|---|
| BT1-79 | II-6 | II-71 |
| BT1-80 | II-6 | II-72 |
| BT1-81 | II-6 | II-74 |
| BT1-82 | II-6 | II-76 |
| BT1-83 | II-6 | II-78 |
| BT1-84 | II-6 | II-84 |
| BT1-85 | II-6 | II-85 |
| BT1-86 | II-6 | II-86 |
| BT1-87 | II-6 | II-92 |
| BT1-88 | II-7 | II-8 |
| BT1-89 | II-7 | II-11 |
| BT1-90 | II-7 | II-16 |
| BT1-91 | II-7 | II-21 |
| BT1-92 | II-7 | II-26 |
| BT1-93 | II-7 | II-32 |
| BT1-94 | II-7 | II-33 |
| BT1-95 | II-7 | II-37 |
| BT1-96 | II-7 | II-39 |
| BT1-97 | II-7 | II-42 |
| BT1-98 | II-7 | II-44 |
| BT1-99 | II-7 | II-50 |
| BT1-100 | II-7 | II-53 |
| BT1-101 | II-7 | II-60 |
| BT1-102 | II-7 | II-62 |
| BT1-103 | II-7 | II-66 |
| BT1-104 | II-7 | II-69 |
| BT1-105 | II-7 | II-70 |
| BT1-106 | II-7 | II-71 |
| BT1-107 | II-7 | II-72 |
| BT1-108 | II-7 | II-74 |
| BT1-109 | II-7 | II-76 |
| BT1-110 | II-7 | II-78 |
| BT1-111 | II-7 | II-84 |
| BT1-112 | II-7 | II-85 |
| BT1-113 | II-7 | II-86 |
| BT1-114 | II-7 | II-92 |
| BT1-115 | II-8 | II-11 |
| BT1-116 | II-8 | II-16 |
| BT1-117 | II-8 | II-21 |
| BT1-118 | II-8 | II-26 |
| BT1-119 | II-8 | II-32 |
| BT1-120 | II-8 | II-33 |
| BT1-121 | II-8 | II-37 |
| BT1-122 | II-8 | II-39 |
| BT1-123 | II-8 | II-42 |
| BT1-124 | II-8 | II-44 |
| BT1-125 | II-8 | II-50 |
| BT1-126 | II-8 | II-53 |
| BT1-127 | II-8 | II-60 |
| BT1-128 | II-8 | II-62 |
| BT1-129 | II-8 | II-66 |
| BT1-130 | II-8 | II-69 |
| BT1-131 | II-8 | II-70 |
| BT1-132 | II-8 | II-71 |
| BT1-133 | II-8 | II-72 |
| BT1-134 | II-8 | II-74 |
| BT1-135 | II-8 | II-76 |
| BT1-136 | II-8 | II-78 |
| BT1-137 | II-8 | II-84 |
| BT1-138 | II-8 | II-85 |
| BT1-139 | II-8 | II-86 |
| BT1-140 | II-8 | II-92 |
| BT1-141 | II-11 | II-16 |
| BT1-142 | II-11 | II-21 |
| BT1-143 | II-11 | II-26 |
| BT1-144 | II-11 | II-32 |
| BT1-145 | II-11 | II-33 |
| BT1-146 | II-11 | II-37 |
| BT1-147 | II-11 | II-39 |
| BT1-148 | II-11 | II-42 |
| BT1-149 | II-11 | II-44 |
| BT1-150 | II-11 | II-50 |
| BT1-151 | II-11 | II-53 |
| BT1-152 | II-11 | II-60 |
| BT1-153 | II-11 | II-62 |
| BT1-154 | II-11 | II-66 |
| BT1-155 | II-11 | II-69 |
| BT1-156 | II-11 | II-70 |
| BT1-157 | II-11 | II-71 |
| BT1-158 | II-11 | II-72 |
| BT1-159 | II-11 | II-74 |
| BT1-160 | II-11 | II-76 |
| BT1-161 | II-11 | II-78 |
| BT1-162 | II-11 | II-84 |
| BT1-163 | II-11 | II-85 |
| BT1-164 | II-11 | II-86 |
| BT1-165 | II-11 | II-92 |
| BT1-166 | II-16 | II-21 |
| BT1-167 | II-16 | II-26 |
| BT1-168 | II-16 | II-32 |
| BT1-169 | II-16 | II-33 |
| BT1-170 | II-16 | II-37 |
| BT1-171 | II-16 | II-39 |
| BT1-172 | II-16 | II-42 |
| BT1-173 | II-16 | II-44 |
| BT1-174 | II-16 | II-50 |
| BT1-175 | II-16 | II-53 |
| BT1-176 | II-16 | II-60 |
| BT1-177 | II-16 | II-62 |
| BT1-178 | II-16 | II-66 |
| BT1-179 | II-16 | II-69 |
| BT1-180 | II-16 | II-70 |
| BT1-181 | II-16 | II-71 |
| BT1-182 | II-16 | II-72 |
| BT1-183 | II-16 | II-74 |
| BT1-184 | II-16 | II-76 |
| BT1-185 | II-16 | II-78 |
| BT1-186 | II-16 | II-84 |
| BT1-187 | II-16 | II-85 |
| BT1-188 | II-16 | II-86 |
| BT1-189 | II-16 | II-92 |
| BT1-190 | II-21 | II-26 |
| BT1-191 | II-21 | II-32 |
| BT1-192 | II-21 | II-33 |
| BT1-193 | II-21 | II-37 |
| BT1-194 | II-21 | II-39 |
| BT1-195 | II-21 | II-42 |
| BT1-196 | II-21 | II-44 |
| BT1-197 | II-21 | II-50 |
| BT1-198 | II-21 | II-53 |
| BT1-199 | II-21 | II-60 |
| BT1-200 | II-21 | II-62 |
| BT1-201 | II-21 | II-66 |
| BT1-202 | II-21 | II-69 |
| BT1-203 | II-21 | II-70 |
| BT1-204 | II-21 | II-71 |
| BT1-205 | II-21 | II-72 |
| BT1-206 | II-21 | II-74 |
| BT1-207 | II-21 | II-76 |
| BT1-208 | II-21 | II-78 |
| BT1-209 | II-21 | II-84 |
| BT1-210 | II-21 | II-85 |
| BT1-211 | II-21 | II-86 |
| BT1-212 | II-21 | II-92 |
| BT1-213 | II-26 | II-32 |
| BT1-214 | II-26 | II-33 |
| BT1-215 | II-26 | II-37 |
| BT1-216 | II-26 | II-39 |

TABLE BT1-continued

Two-component compositions comprising a component II and a component III, wherein component II and III are selected from the preferred fungicides detailed above, wherein components II and III are different from each other. Each line of line BT1-1 to BT1-459 corresponds to one particular individidualized composition. Furthermore, also every combination of the compositions individualized in this table represent embodiments of the present invention.

| composition | II | III |
|---|---|---|
| BT1-217 | II-26 | II-42 |
| BT1-218 | II-26 | II-44 |
| BT1-219 | II-26 | II-50 |
| BT1-220 | II-26 | II-53 |
| BT1-221 | II-26 | II-60 |
| BT1-222 | II-26 | II-62 |
| BT1-223 | II-26 | II-66 |
| BT1-224 | II-26 | II-69 |
| BT1-225 | II-26 | II-70 |
| BT1-226 | II-26 | II-71 |
| BT1-227 | II-26 | II-72 |
| BT1-228 | II-26 | II-74 |
| BT1-229 | II-26 | II-76 |
| BT1-230 | II-26 | II-78 |
| BT1-231 | II-26 | II-84 |
| BT1-232 | II-26 | II-85 |
| BT1-233 | II-26 | II-86 |
| BT1-234 | II-26 | II-92 |
| BT1-235 | II-32 | II-33 |
| BT1-236 | II-32 | II-37 |
| BT1-237 | II-32 | II-39 |
| BT1-238 | II-32 | II-42 |
| BT1-239 | II-32 | II-44 |
| BT1-240 | II-32 | II-50 |
| BT1-241 | II-32 | II-53 |
| BT1-242 | II-32 | II-60 |
| BT1-243 | II-32 | II-62 |
| BT1-244 | II-32 | II-66 |
| BT1-245 | II-32 | II-69 |
| BT1-246 | II-32 | II-70 |
| BT1-247 | II-32 | II-71 |
| BT1-248 | II-32 | II-72 |
| BT1-249 | II-32 | II-74 |
| BT1-250 | II-32 | II-76 |
| BT1-251 | II-32 | II-78 |
| BT1-252 | II-32 | II-84 |
| BT1-253 | II-32 | II-85 |
| BT1-254 | II-32 | II-86 |
| BT1-255 | II-32 | II-92 |
| BT1-256 | II-33 | II-37 |
| BT1-257 | II-33 | II-39 |
| BT1-258 | II-33 | II-42 |
| BT1-259 | II-33 | II-44 |
| BT1-260 | II-33 | II-50 |
| BT1-261 | II-33 | II-53 |
| BT1-262 | II-33 | II-60 |
| BT1-263 | II-33 | II-62 |
| BT1-264 | II-33 | II-66 |
| BT1-265 | II-33 | II-69 |
| BT1-266 | II-33 | II-70 |
| BT1-267 | II-33 | II-71 |
| BT1-268 | II-33 | II-72 |
| BT1-269 | II-33 | II-74 |
| BT1-270 | II-33 | II-76 |
| BT1-271 | II-33 | II-78 |
| BT1-272 | II-33 | II-84 |
| BT1-273 | II-33 | II-85 |
| BT1-274 | II-33 | II-86 |
| BT1-275 | II-33 | II-92 |
| BT1-276 | II-37 | II-39 |
| BT1-277 | II-37 | II-42 |
| BT1-278 | II-37 | II-44 |
| BT1-279 | II-37 | II-50 |
| BT1-280 | II-37 | II-53 |
| BT1-281 | II-37 | II-60 |
| BT1-282 | II-37 | II-62 |
| BT1-283 | II-37 | II-66 |
| BT1-284 | II-37 | II-69 |
| BT1-285 | II-37 | II-70 |
| BT1-286 | II-37 | II-71 |
| BT1-287 | II-37 | II-72 |
| BT1-288 | II-37 | II-74 |
| BT1-289 | II-37 | II-76 |
| BT1-290 | II-37 | II-78 |
| BT1-291 | II-37 | II-84 |
| BT1-292 | II-37 | II-85 |
| BT1-293 | II-37 | II-86 |
| BT1-294 | II-37 | II-92 |
| BT1-295 | II-39 | II-42 |
| BT1-296 | II-39 | II-44 |
| BT1-297 | II-39 | II-50 |
| BT1-298 | II-39 | II-53 |
| BT1-299 | II-39 | II-60 |
| BT1-300 | II-39 | II-62 |
| BT1-301 | II-39 | II-66 |
| BT1-302 | II-39 | II-69 |
| BT1-303 | II-39 | II-70 |
| BT1-304 | II-39 | II-71 |
| BT1-305 | II-39 | II-72 |
| BT1-306 | II-39 | II-74 |
| BT1-307 | II-39 | II-76 |
| BT1-308 | II-39 | II-78 |
| BT1-309 | II-39 | II-84 |
| BT1-310 | II-39 | II-85 |
| BT1-311 | II-39 | II-86 |
| BT1-312 | II-39 | II-92 |
| BT1-313 | II-42 | II-44 |
| BT1-314 | II-42 | II-50 |
| BT1-315 | II-42 | II-53 |
| BT1-316 | II-42 | II-60 |
| BT1-317 | II-42 | II-62 |
| BT1-318 | II-42 | II-66 |
| BT1-319 | II-42 | II-69 |
| BT1-320 | II-42 | II-70 |
| BT1-321 | II-42 | II-71 |
| BT1-322 | II-42 | II-72 |
| BT1-323 | II-42 | II-74 |
| BT1-324 | II-42 | II-76 |
| BT1-325 | II-42 | II-78 |
| BT1-326 | II-42 | II-84 |
| BT1-327 | II-42 | II-85 |
| BT1-328 | II-42 | II-86 |
| BT1-329 | II-42 | II-92 |
| BT1-330 | II-44 | II-50 |
| BT1-331 | II-44 | II-53 |
| BT1-332 | II-44 | II-60 |
| BT1-333 | II-44 | II-62 |
| BT1-334 | II-44 | II-66 |
| BT1-335 | II-44 | II-69 |
| BT1-336 | II-44 | II-70 |
| BT1-337 | II-44 | II-71 |
| BT1-338 | II-44 | II-72 |
| BT1-339 | II-44 | II-74 |
| BT1-340 | II-44 | II-76 |
| BT1-341 | II-44 | II-78 |
| BT1-342 | II-44 | II-84 |
| BT1-343 | II-44 | II-85 |
| BT1-344 | II-44 | II-86 |
| BT1-345 | II-44 | II-92 |
| BT1-346 | II-50 | II-53 |
| BT1-347 | II-50 | II-60 |
| BT1-348 | II-50 | II-62 |
| BT1-349 | II-50 | II-66 |
| BT1-350 | II-50 | II-69 |
| BT1-351 | II-50 | II-70 |
| BT1-352 | II-50 | II-71 |
| BT1-353 | II-50 | II-72 |
| BT1-354 | II-50 | II-74 |

TABLE BT1-continued

Two-component compositions comprising a component II and a component III, wherein component II and III are selected from the preferred fungicides detailed above, wherein components II and III are different from each other. Each line of line BT1-1 to BT1-459 corresponds to one particular individidualized composition. Furthermore, also every combination of the compositions individualized in this table represent embodiments of the present invention.

| composition | II | III |
|---|---|---|
| BT1-355 | II-50 | II-76 |
| BT1-356 | II-50 | II-78 |
| BT1-357 | II-50 | II-84 |
| BT1-358 | II-50 | II-85 |
| BT1-359 | II-50 | II-86 |
| BT1-360 | II-50 | II-92 |
| BT1-361 | II-53 | II-60 |
| BT1-362 | II-53 | II-62 |
| BT1-363 | II-53 | II-66 |
| BT1-364 | II-53 | II-69 |
| BT1-365 | II-53 | II-70 |
| BT1-366 | II-53 | II-71 |
| BT1-367 | II-53 | II-72 |
| BT1-368 | II-53 | II-74 |
| BT1-369 | II-53 | II-76 |
| BT1-370 | II-53 | II-78 |
| BT1-371 | II-53 | II-84 |
| BT1-372 | II-53 | II-85 |
| BT1-373 | II-53 | II-86 |
| BT1-374 | II-53 | II-92 |
| BT1-375 | II-60 | II-62 |
| BT1-376 | II-60 | II-66 |
| BT1-377 | II-60 | II-69 |
| BT1-378 | II-60 | II-70 |
| BT1-379 | II-60 | II-71 |
| BT1-380 | II-60 | II-72 |
| BT1-381 | II-60 | II-74 |
| BT1-382 | II-60 | II-76 |
| BT1-383 | II-60 | II-78 |
| BT1-384 | II-60 | II-84 |
| BT1-385 | II-60 | II-85 |
| BT1-386 | II-60 | II-86 |
| BT1-387 | II-60 | II-92 |
| BT1-388 | II-62 | II-66 |
| BT1-389 | II-62 | II-69 |
| BT1-390 | II-62 | II-70 |
| BT1-391 | II-62 | II-71 |
| BT1-392 | II-62 | II-72 |
| BT1-393 | II-62 | II-74 |
| BT1-394 | II-62 | II-76 |
| BT1-395 | II-62 | II-78 |
| BT1-396 | II-62 | II-84 |
| BT1-397 | II-62 | II-85 |
| BT1-398 | II-62 | II-86 |
| BT1-399 | II-62 | II-92 |
| BT1-400 | II-66 | II-69 |
| BT1-401 | II-66 | II-70 |
| BT1-402 | II-66 | II-71 |
| BT1-403 | II-66 | II-72 |
| BT1-404 | II-66 | II-74 |
| BT1-405 | II-66 | II-76 |
| BT1-406 | II-66 | II-78 |
| BT1-407 | II-66 | II-84 |
| BT1-408 | II-66 | II-85 |
| BT1-409 | II-66 | II-86 |
| BT1-410 | II-66 | II-92 |
| BT1-411 | II-69 | II-70 |
| BT1-412 | II-69 | II-71 |
| BT1-413 | II-69 | II-72 |
| BT1-414 | II-69 | II-74 |
| BT1-415 | II-69 | II-76 |
| BT1-416 | II-69 | II-78 |
| BT1-417 | II-69 | II-84 |
| BT1-418 | II-69 | II-85 |
| BT1-419 | II-69 | II-86 |
| BT1-420 | II-69 | II-92 |
| BT1-421 | II-70 | II-71 |
| BT1-422 | II-70 | II-72 |
| BT1-423 | II-70 | II-74 |
| BT1-424 | II-70 | II-76 |
| BT1-425 | II-70 | II-78 |
| BT1-426 | II-70 | II-84 |
| BT1-427 | II-70 | II-85 |
| BT1-428 | II-70 | II-86 |
| BT1-429 | II-70 | II-92 |
| BT1-430 | II-71 | II-72 |
| BT1-431 | II-71 | II-74 |
| BT1-432 | II-71 | II-76 |
| BT1-433 | II-71 | II-78 |
| BT1-434 | II-71 | II-84 |
| BT1-435 | II-71 | II-85 |
| BT1-436 | II-71 | II-86 |
| BT1-437 | II-71 | II-92 |
| BT1-438 | II-72 | II-74 |
| BT1-439 | II-74 | II-76 |
| BT1-440 | II-74 | II-78 |
| BT1-441 | II-74 | II-84 |
| BT1-442 | II-74 | II-85 |
| BT1-443 | II-74 | II-86 |
| BT1-444 | II-74 | II-92 |
| BT1-445 | II-76 | II-78 |
| BT1-446 | II-76 | II-84 |
| BT1-447 | II-76 | II-85 |
| BT1-448 | II-76 | II-86 |
| BT1-449 | II-76 | II-92 |
| BT1-450 | II-78 | II-84 |
| BT1-451 | II-78 | II-85 |
| BT1-452 | II-78 | II-86 |
| BT1-453 | II-78 | II-92 |
| BT1-454 | II-84 | II-85 |
| BT1-455 | II-84 | II-86 |
| BT1-456 | II-84 | II-92 |
| BT1-457 | II-85 | II-86 |
| BT1-458 | II-85 | II-92 |
| BT1-459 | II-86 | II-92 |
| BT1-460 | II-15 | II-66 |
| BT1-461 | II-15 | II-9 |
| BT1-462 | II-15 | II-11 |
| BT1-463 | II-15 | II-17 |
| BT1-464 | II-15 | II-18 |
| BT1-465 | II-15 | II-20 |
| BT1-466 | II-15 | II-25 |
| BT1-467 | II-15 | II-43 |
| BT1-468 | II-15 | II-54 |
| BT1-469 | II-15 | II-61 |
| BT1-470 | II-15 | II-98 |
| BT1-471 | II-15 | II-99 |
| BT1-472 | II-15 | II-100 |
| BT1-473 | II-15 | II-101 |
| BT1-474 | II-15 | II-102 |
| BT1-475 | II-38 | II-66 |
| BT1-476 | II-38 | II-9 |
| BT1-477 | II-38 | II-11 |
| BT1-478 | II-38 | II-17 |
| BT1-479 | II-38 | II-18 |
| BT1-480 | II-38 | II-20 |
| BT1-481 | II-38 | II-25 |
| BT1-482 | II-38 | II-43 |
| BT1-483 | II-38 | II-54 |
| BT1-484 | II-38 | II-61 |
| BT1-485 | II-38 | II-98 |
| BT1-486 | II-38 | II-99 |
| BT1-487 | II-38 | II-100 |
| BT1-488 | II-38 | II-101 |
| BT1-489 | II-38 | II-102 |
| BT1-490 | II-60 | II-66 |
| BT1-491 | II-60 | II-9 |
| BT1-492 | II-60 | II-11 |

TABLE BT1-continued

Two-component compositions comprising a component II and a component III, wherein component II and III are selected from the preferred fungicides detailled above, wherein components II and III aredifferent from each other. Each line of line BT1-1 to BT1-459 corresponds to one particular individidualized composition. Furthermore, also every combination of the compositions individualized in this table represent embodiments of the present invention.

| composition | II | III |
|---|---|---|
| BT1-493 | II-60 | II-17 |
| BT1-494 | II-60 | II-18 |
| BT1-495 | II-60 | II-20 |
| BT1-496 | II-60 | II-25 |
| BT1-497 | II-60 | II-43 |
| BT1-498 | II-60 | II-54 |
| BT1-499 | II-60 | II-61 |
| BT1-500 | II-60 | II-98 |
| BT1-501 | II-60 | II-99 |
| BT1-502 | II-60 | II-100 |
| BT1-503 | II-60 | II-101 |
| BT1-504 | II-60 | II-102 |
| BT1-505 | II-76 | II-66 |
| BT1-506 | II-76 | II-9 |
| BT1-507 | II-76 | II-11 |
| BT1-508 | II-76 | II-17 |
| BT1-509 | II-76 | II-18 |
| BT1-510 | II-76 | II-20 |
| BT1-511 | II-76 | II-25 |
| BT1-512 | II-76 | II-43 |
| BT1-513 | II-76 | II-54 |
| BT1-514 | II-76 | II-61 |
| BT1-515 | II-76 | II-98 |
| BT1-516 | II-76 | II-99 |
| BT1-517 | II-76 | II-100 |
| BT1-518 | II-76 | II-101 |
| BT1-519 | II-76 | II-102 |
| BT1-520 | II-78 | II-66 |
| BT1-521 | II-78 | II-9 |
| BT1-522 | II-78 | II-11 |
| BT1-523 | II-78 | II-17 |
| BT1-524 | II-78 | II-18 |
| BT1-525 | II-78 | II-20 |
| BT1-526 | II-78 | II-25 |
| BT1-527 | II-78 | II-43 |
| BT1-528 | II-78 | II-54 |
| BT1-529 | II-78 | II-61 |
| BT1-530 | II-78 | II-98 |
| BT1-531 | II-78 | II-99 |
| BT1-532 | II-78 | II-100 |
| BT1-533 | II-78 | II-101 |
| BT1-534 | II-78 | II-102 |

Also particularly preferred compositions are the three-component compositions, wherein component I is as defined above, i.e a compound I, in particular a compound selected from compounds I-1, I-2, I-3, I-4, I-5, I-6, I-7, I-8, I-9, I-11, I-13, I-14, I-15 and I-16 or any group of compounds I detailed above, component II is selected from

| II-3 | azoxystrobin |
|---|---|
| II-5 | benzovindiflupyr |
| II-6 | bixafen |
| II-7 | boscalid |
| II-8 | carbendazim |
| II-11 | chlorothalonil |
| II-16 | cyprodinil |
| II-21 | difenoconazole |
| II-26 | epoxiconazole |
| II-32 | fenpropimorph |
| II-33 | fluazinam |
| II-37 | fluoxastrobin |
| II-39 | flusilazole |
| II-42 | fluxapyroxad |
| II-44 | fosetyl-Al |
| II-50 | isopyrazam |
| II-53 | kresoxim-methyl |
| II-60 | metconazole |
| II-62 | metrafenone |
| II-66 | pyraclostrobin |
| II-69 | phosporous acid |
| II-70 | potassium salt of phosphorous acid |
| II-71 | sodium salt of phosphorous acid |
| II-72 | penthiopyrad |
| II-74 | prochloraz |
| II-76 | propiconazole |
| II-78 | prothioconazole |
| II-84 | spiroxamine |
| II-85 | sulfur |
| II-86 | tebuconazole |
| II-92 | trifloxystrobin | and component III is a growth regulator, selected from:

| II-1a | mepiquat chloride |
|---|---|
| II-2a | chlormequat chloride |
| II-3a | trinexapac-ethyl |
| II-4a | prohexadione-calcium |
| II-5a | ethophon |

Particularly preferred compositions of these compositions are compiled in Table T2, where each row corresponds to one embodiment of the compositions according to the invention, i.e. one specific individualized three-component composition. According to one specific aspect, these are ternary compositions which each only contain these three components as the active compound. Furthermore, also every combination of the compositions individualized in this table represent embodiments of the present invention.

TABLE T2

| composition | I | II | III |
|---|---|---|---|
| Three-component compositions comprising a component I, a fungicidal component II and a growth regulator as component III, | | | |
| T2-1 | I-1 | II-3 | II-1a |
| T2-2 | I-1 | II-5 | II-1a |
| T2-3 | I-1 | II-6 | II-1a |
| T2-4 | I-1 | II-7 | II-1a |
| T2-5 | I-1 | II-8 | II-1a |
| T2-6 | I-1 | II-11 | II-1a |
| T2-7 | I-1 | II-16 | II-1a |
| T2-8 | I-1 | II-21 | II-1a |
| T2-9 | I-1 | II-26 | II-1a |
| T2-10 | I-1 | II-32 | II-1a |
| T2-11 | I-1 | II-33 | II-1a |
| T2-12 | I-1 | II-37 | II-1a |
| T2-13 | I-1 | II-39 | II-1a |
| T2-14 | I-1 | II-42 | II-1a |
| T2-15 | I-1 | II-44 | II-1a |
| T2-16 | I-1 | II-50 | II-1a |
| T2-17 | I-1 | II-53 | II-1a |
| T2-18 | I-1 | II-60 | II-1a |
| T2-19 | I-1 | II-62 | II-1a |
| T2-20 | I-1 | II-66 | II-1a |
| T2-21 | I-1 | II-69 | II-1a |
| T2-22 | I-1 | II-70 | II-1a |
| T2-23 | I-1 | II-71 | II-1a |
| T2-24 | I-1 | II-72 | II-1a |
| T2-25 | I-1 | II-74 | II-1a |
| T2-26 | I-1 | II-76 | II-1a |
| T2-27 | I-1 | II-78 | II-1a |
| T2-28 | I-1 | II-84 | II-1a |
| T2-29 | I-1 | II-85 | II-1a |
| T2-30 | I-1 | II-86 | II-1a |
| T2-31 | I-1 | II-92 | II-1a |

TABLE T2-continued

| composition | I | II | III |
|---|---|---|---|
| T2-32 | I-1 | II-3 | II-2a |
| T2-33 | I-1 | II-5 | II-2a |
| T2-34 | I-1 | II-6 | II-2a |
| T2-35 | I-1 | II-7 | II-2a |
| T2-36 | I-1 | II-8 | II-2a |
| T2-37 | I-1 | II-11 | II-2a |
| T2-38 | I-1 | II-16 | II-2a |
| T2-39 | I-1 | II-21 | II-2a |
| T2-40 | I-1 | II-26 | II-2a |
| T2-41 | I-1 | II-32 | II-2a |
| T2-42 | I-1 | II-33 | II-2a |
| T2-43 | I-1 | II-37 | II-2a |
| T2-44 | I-1 | II-39 | II-2a |
| T2-45 | I-1 | II-42 | II-2a |
| T2-46 | I-1 | II-44 | II-2a |
| T2-47 | I-1 | II-50 | II-2a |
| T2-48 | I-1 | II-53 | II-2a |
| T2-49 | I-1 | II-60 | II-2a |
| T2-50 | I-1 | II-62 | II-2a |
| T2-51 | I-1 | II-66 | II-2a |
| T2-52 | I-1 | II-69 | II-2a |
| T2-53 | I-1 | II-70 | II-2a |
| T2-54 | I-1 | II-71 | II-2a |
| T2-55 | I-1 | II-72 | II-2a |
| T2-56 | I-1 | II-74 | II-2a |
| T2-57 | I-1 | II-76 | II-2a |
| T2-58 | I-1 | II-78 | II-2a |
| T2-59 | I-1 | II-84 | II-2a |
| T2-60 | I-1 | II-85 | II-2a |
| T2-61 | I-1 | II-86 | II-2a |
| T2-62 | I-1 | II-92 | II-2a |
| T2-63 | I-1 | II-3 | II-3a |
| T2-64 | I-1 | II-5 | II-3a |
| T2-65 | I-1 | II-6 | II-3a |
| T2-66 | I-1 | II-7 | II-3a |
| T2-67 | I-1 | II-8 | II-3a |
| T2-68 | I-1 | II-11 | II-3a |
| T2-69 | I-1 | II-16 | II-3a |
| T2-70 | I-1 | II-21 | II-3a |
| T2-71 | I-1 | II-26 | II-3a |
| T2-72 | I-1 | II-32 | II-3a |
| T2-73 | I-1 | II-33 | II-3a |
| T2-74 | I-1 | II-37 | II-3a |
| T2-75 | I-1 | II-39 | II-3a |
| T2-76 | I-1 | II-42 | II-3a |
| T2-77 | I-1 | II-44 | II-3a |
| T2-78 | I-1 | II-50 | II-3a |
| T2-79 | I-1 | II-53 | II-3a |
| T2-80 | I-1 | II-60 | II-3a |
| T2-81 | I-1 | II-62 | II-3a |
| T2-82 | I-1 | II-66 | II-3a |
| T2-83 | I-1 | II-69 | II-3a |
| T2-84 | I-1 | II-70 | II-3a |
| T2-85 | I-1 | II-71 | II-3a |
| T2-86 | I-1 | II-72 | II-3a |
| T2-87 | I-1 | II-74 | II-3a |
| T2-88 | I-1 | II-76 | II-3a |
| T2-89 | I-1 | II-78 | II-3a |
| T2-90 | I-1 | II-84 | II-3a |
| T2-91 | I-1 | II-85 | II-3a |
| T2-92 | I-1 | II-86 | II-3a |
| T2-93 | I-1 | II-92 | II-3a |
| T2-94 | I-1 | II-3 | II-4a |
| T2-95 | I-1 | II-5 | II-4a |
| T2-96 | I-1 | II-6 | II-4a |
| T2-97 | I-1 | II-7 | II-4a |
| T2-98 | I-1 | II-8 | II-4a |
| T2-99 | I-1 | II-11 | II-4a |
| T2-100 | I-1 | II-16 | II-4a |
| T2-101 | I-1 | II-21 | II-4a |
| T2-102 | I-1 | II-26 | II-4a |
| T2-103 | I-1 | II-32 | II-4a |
| T2-104 | I-1 | II-33 | II-4a |
| T2-105 | I-1 | II-37 | II-4a |
| T2-106 | I-1 | II-39 | II-4a |
| T2-107 | I-1 | II-42 | II-4a |
| T2-108 | I-1 | II-44 | II-4a |
| T2-109 | I-1 | II-50 | II-4a |
| T2-110 | I-1 | II-53 | II-4a |
| T2-111 | I-1 | II-60 | II-4a |
| T2-112 | I-1 | II-62 | II-4a |
| T2-113 | I-1 | II-66 | II-4a |
| T2-114 | I-1 | II-69 | II-4a |
| T2-115 | I-1 | II-70 | II-4a |
| T2-116 | I-1 | II-71 | II-4a |
| T2-117 | I-1 | II-72 | II-4a |
| T2-118 | I-1 | II-74 | II-4a |
| T2-119 | I-1 | II-76 | II-4a |
| T2-120 | I-1 | II-78 | II-4a |
| T2-121 | I-1 | II-84 | II-4a |
| T2-122 | I-1 | II-85 | II-4a |
| T2-123 | I-1 | II-86 | II-4a |
| T2-124 | I-1 | II-92 | II-4a |
| T2-125 | I-1 | II-3 | II-5a |
| T2-126 | I-1 | II-5 | II-5a |
| T2-127 | I-1 | II-6 | II-5a |
| T2-128 | I-1 | II-7 | II-5a |
| T2-129 | I-1 | II-8 | II-5a |
| T2-130 | I-1 | II-11 | II-5a |
| T2-131 | I-1 | II-16 | II-5a |
| T2-132 | I-1 | II-21 | II-5a |
| T2-133 | I-1 | II-26 | II-5a |
| T2-134 | I-1 | II-32 | II-5a |
| T2-135 | I-1 | II-33 | II-5a |
| T2-136 | I-1 | II-37 | II-5a |
| T2-137 | I-1 | II-39 | II-5a |
| T2-138 | I-1 | II-42 | II-5a |
| T2-139 | I-1 | II-44 | II-5a |
| T2-140 | I-1 | II-50 | II-5a |
| T2-141 | I-1 | II-53 | II-5a |
| T2-142 | I-1 | II-60 | II-5a |
| T2-143 | I-1 | II-62 | II-5a |
| T2-144 | I-1 | II-66 | II-5a |
| T2-145 | I-1 | II-69 | II-5a |
| T2-146 | I-1 | II-70 | II-5a |
| T2-147 | I-1 | II-71 | II-5a |
| T2-148 | I-1 | II-72 | II-5a |
| T2-149 | I-1 | II-74 | II-5a |
| T2-150 | I-1 | II-76 | II-5a |
| T2-151 | I-1 | II-78 | II-5a |
| T2-152 | I-1 | II-84 | II-5a |
| T2-153 | I-1 | II-85 | II-5a |
| T2-154 | I-1 | II-86 | II-5a |
| T2-155 | I-1 | II-92 | II-5a |
| T2-156 | I-2 | II-3 | II-1a |
| T2-157 | I-2 | II-5 | II-1a |
| T2-158 | I-2 | II-6 | II-1a |
| T2-159 | I-2 | II-7 | II-1a |
| T2-160 | I-2 | II-8 | II-1a |
| T2-161 | I-2 | II-11 | II-1a |
| T2-162 | I-2 | II-16 | II-1a |
| T2-163 | I-2 | II-21 | II-1a |
| T2-164 | I-2 | II-26 | II-1a |
| T2-165 | I-2 | II-32 | II-1a |
| T2-166 | I-2 | II-33 | II-1a |
| T2-167 | I-2 | II-37 | II-1a |
| T2-168 | I-2 | II-39 | II-1a |
| T2-169 | I-2 | II-42 | II-1a |
| T2-170 | I-2 | II-44 | II-1a |
| T2-171 | I-2 | II-50 | II-1a |
| T2-172 | I-2 | II-53 | II-1a |
| T2-173 | I-2 | II-60 | II-1a |
| T2-174 | I-2 | II-62 | II-1a |
| T2-175 | I-2 | II-66 | II-1a |
| T2-176 | I-2 | II-69 | II-1a |
| T2-177 | I-2 | II-70 | II-1a |
| T2-178 | I-2 | II-71 | II-1a |
| T2-179 | I-2 | II-72 | II-1a |
| T2-180 | I-2 | II-74 | II-1a |
| T2-181 | I-2 | II-76 | II-1a |
| T2-182 | I-2 | II-78 | II-1a |
| T2-183 | I-2 | II-84 | II-1a |
| T2-184 | I-2 | II-85 | II-1a |
| T2-185 | I-2 | II-86 | II-1a |
| T2-186 | I-2 | II-92 | II-1a |
| T2-187 | I-2 | II-3 | II-2a |

TABLE T2-continued

| composition | I | II | III |
|---|---|---|---|
| T2-188 | I-2 | II-5 | II-2a |
| T2-189 | I-2 | II-6 | II-2a |
| T2-190 | I-2 | II-7 | II-2a |
| T2-191 | I-2 | II-8 | II-2a |
| T2-192 | I-2 | II-11 | II-2a |
| T2-193 | I-2 | II-16 | II-2a |
| T2-194 | I-2 | II-21 | II-2a |
| T2-195 | I-2 | II-26 | II-2a |
| T2-196 | I-2 | II-32 | II-2a |
| T2-197 | I-2 | II-33 | II-2a |
| T2-198 | I-2 | II-37 | II-2a |
| T2-199 | I-2 | II-39 | II-2a |
| T2-200 | I-2 | II-42 | II-2a |
| T2-201 | I-2 | II-44 | II-2a |
| T2-202 | I-2 | II-50 | II-2a |
| T2-203 | I-2 | II-53 | II-2a |
| T2-204 | I-2 | II-60 | II-2a |
| T2-205 | I-2 | II-62 | II-2a |
| T2-206 | I-2 | II-66 | II-2a |
| T2-207 | I-2 | II-69 | II-2a |
| T2-208 | I-2 | II-70 | II-2a |
| T2-209 | I-2 | II-71 | II-2a |
| T2-210 | I-2 | II-72 | II-2a |
| T2-211 | I-2 | II-74 | II-2a |
| T2-212 | I-2 | II-76 | II-2a |
| T2-213 | I-2 | II-78 | II-2a |
| T2-214 | I-2 | II-84 | II-2a |
| T2-215 | I-2 | II-85 | II-2a |
| T2-216 | I-2 | II-86 | II-2a |
| T2-217 | I-2 | II-92 | II-2a |
| T2-218 | I-2 | II-3 | II-3a |
| T2-219 | I-2 | II-5 | II-3a |
| T2-220 | I-2 | II-6 | II-3a |
| T2-221 | I-2 | II-7 | II-3a |
| T2-222 | I-2 | II-8 | II-3a |
| T2-223 | I-2 | II-11 | II-3a |
| T2-224 | I-2 | II-16 | II-3a |
| T2-225 | I-2 | II-21 | II-3a |
| T2-226 | I-2 | II-26 | II-3a |
| T2-227 | I-2 | II-32 | II-3a |
| T2-228 | I-2 | II-33 | II-3a |
| T2-229 | I-2 | II-37 | II-3a |
| T2-230 | I-2 | II-39 | II-3a |
| T2-231 | I-2 | II-42 | II-3a |
| T2-232 | I-2 | II-44 | II-3a |
| T2-233 | I-2 | II-50 | II-3a |
| T2-234 | I-2 | II-53 | II-3a |
| T2-235 | I-2 | II-60 | II-3a |
| T2-236 | I-2 | II-62 | II-3a |
| T2-237 | I-2 | II-66 | II-3a |
| T2-238 | I-2 | II-69 | II-3a |
| T2-239 | I-2 | II-70 | II-3a |
| T2-240 | I-2 | II-71 | II-3a |
| T2-241 | I-2 | II-72 | II-3a |
| T2-242 | I-2 | II-74 | II-3a |
| T2-243 | I-2 | II-76 | II-3a |
| T2-244 | I-2 | II-78 | II-3a |
| T2-245 | I-2 | II-84 | II-3a |
| T2-246 | I-2 | II-85 | II-3a |
| T2-247 | I-2 | II-86 | II-3a |
| T2-248 | I-2 | II-92 | II-3a |
| T2-249 | I-2 | II-3 | II-4a |
| T2-250 | I-2 | II-5 | II-4a |
| T2-251 | I-2 | II-6 | II-4a |
| T2-252 | I-2 | II-7 | II-4a |
| T2-253 | I-2 | II-8 | II-4a |
| T2-254 | I-2 | II-11 | II-4a |
| T2-255 | I-2 | II-16 | II-4a |
| T2-256 | I-2 | II-21 | II-4a |
| T2-257 | I-2 | II-26 | II-4a |
| T2-258 | I-2 | II-32 | II-4a |
| T2-259 | I-2 | II-33 | II-4a |
| T2-260 | I-2 | II-37 | II-4a |
| T2-261 | I-2 | II-39 | II-4a |
| T2-262 | I-2 | II-42 | II-4a |
| T2-263 | I-2 | II-44 | II-4a |
| T2-264 | I-2 | II-50 | II-4a |
| T2-265 | I-2 | II-53 | II-4a |
| T2-266 | I-2 | II-60 | II-4a |
| T2-267 | I-2 | II-62 | II-4a |
| T2-268 | I-2 | II-66 | II-4a |
| T2-269 | I-2 | II-69 | II-4a |
| T2-270 | I-2 | II-70 | II-4a |
| T2-271 | I-2 | II-71 | II-4a |
| T2-272 | I-2 | II-72 | II-4a |
| T2-273 | I-2 | II-74 | II-4a |
| T2-274 | I-2 | II-76 | II-4a |
| T2-275 | I-2 | II-78 | II-4a |
| T2-276 | I-2 | II-84 | II-4a |
| T2-277 | I-2 | II-85 | II-4a |
| T2-278 | I-2 | II-86 | II-4a |
| T2-279 | I-2 | II-92 | II-4a |
| T2-280 | I-2 | II-3 | II-5a |
| T2-281 | I-2 | II-5 | II-5a |
| T2-282 | I-2 | II-6 | II-5a |
| T2-283 | I-2 | II-7 | II-5a |
| T2-284 | I-2 | II-8 | II-5a |
| T2-285 | I-2 | II-11 | II-5a |
| T2-286 | I-2 | II-16 | II-5a |
| T2-287 | I-2 | II-21 | II-5a |
| T2-288 | I-2 | II-26 | II-5a |
| T2-289 | I-2 | II-32 | II-5a |
| T2-290 | I-2 | II-33 | II-5a |
| T2-291 | I-2 | II-37 | II-5a |
| T2-292 | I-2 | II-39 | II-5a |
| T2-293 | I-2 | II-42 | II-5a |
| T2-294 | I-2 | II-44 | II-5a |
| T2-295 | I-2 | II-50 | II-5a |
| T2-296 | I-2 | II-53 | II-5a |
| T2-297 | I-2 | II-60 | II-5a |
| T2-298 | I-2 | II-62 | II-5a |
| T2-299 | I-2 | II-66 | II-5a |
| T2-300 | I-2 | II-69 | II-5a |
| T2-301 | I-2 | II-70 | II-5a |
| T2-302 | I-2 | II-71 | II-5a |
| T2-303 | I-2 | II-72 | II-5a |
| T2-304 | I-2 | II-74 | II-5a |
| T2-305 | I-2 | II-76 | II-5a |
| T2-306 | I-2 | II-78 | II-5a |
| T2-307 | I-2 | II-84 | II-5a |
| T2-308 | I-2 | II-85 | II-5a |
| T2-309 | I-2 | II-86 | II-5a |
| T2-310 | I-2 | II-92 | II-5a |
| T2-311 | I-5 | II-3 | II-1a |
| T2-312 | I-5 | II-5 | II-1a |
| T2-313 | I-5 | II-6 | II-1a |
| T2-314 | I-5 | II-7 | II-1a |
| T2-315 | I-5 | II-8 | II-1a |
| T2-316 | I-5 | II-11 | II-1a |
| T2-317 | I-5 | II-16 | II-1a |
| T2-318 | I-5 | II-21 | II-1a |
| T2-319 | I-5 | II-26 | II-1a |
| T2-320 | I-5 | II-32 | II-1a |
| T2-321 | I-5 | II-33 | II-1a |
| T2-322 | I-5 | II-37 | II-1a |
| T2-323 | I-5 | II-39 | II-1a |
| T2-324 | I-5 | II-42 | II-1a |
| T2-325 | I-5 | II-44 | II-1a |
| T2-326 | I-5 | II-50 | II-1a |
| T2-327 | I-5 | II-53 | II-1a |
| T2-328 | I-5 | II-60 | II-1a |
| T2-329 | I-5 | II-62 | II-1a |
| T2-330 | I-5 | II-66 | II-1a |
| T2-331 | I-5 | II-69 | II-1a |
| T2-332 | I-5 | II-70 | II-1a |
| T2-333 | I-5 | II-71 | II-1a |
| T2-334 | I-5 | II-72 | II-1a |
| T2-335 | I-5 | II-74 | II-1a |
| T2-336 | I-5 | II-76 | II-1a |
| T2-337 | I-5 | II-78 | II-1a |
| T2-338 | I-5 | II-84 | II-1a |
| T2-339 | I-5 | II-85 | II-1a |
| T2-340 | I-5 | II-86 | II-1a |
| T2-341 | I-5 | II-92 | II-1a |
| T2-342 | I-5 | II-3 | II-2a |
| T2-343 | I-5 | II-5 | II-2a |

TABLE T2-continued

| composition | I | II | III |
|---|---|---|---|
| T2-344 | I-5 | II-6 | II-2a |
| T2-345 | I-5 | II-7 | II-2a |
| T2-346 | I-5 | II-8 | II-2a |
| T2-347 | I-5 | II-11 | II-2a |
| T2-348 | I-5 | II-16 | II-2a |
| T2-349 | I-5 | II-21 | II-2a |
| T2-350 | I-5 | II-26 | II-2a |
| T2-351 | I-5 | II-32 | II-2a |
| T2-352 | I-5 | II-33 | II-2a |
| T2-353 | I-5 | II-37 | II-2a |
| T2-354 | I-5 | II-39 | II-2a |
| T2-355 | I-5 | II-42 | II-2a |
| T2-356 | I-5 | II-44 | II-2a |
| T2-357 | I-5 | II-50 | II-2a |
| T2-358 | I-5 | II-53 | II-2a |
| T2-359 | I-5 | II-60 | II-2a |
| T2-360 | I-5 | II-62 | II-2a |
| T2-361 | I-5 | II-66 | II-2a |
| T2-362 | I-5 | II-69 | II-2a |
| T2-363 | I-5 | II-70 | II-2a |
| T2-364 | I-5 | II-71 | II-2a |
| T2-365 | I-5 | II-72 | II-2a |
| T2-366 | I-5 | II-74 | II-2a |
| T2-367 | I-5 | II-76 | II-2a |
| T2-368 | I-5 | II-78 | II-2a |
| T2-369 | I-5 | II-84 | II-2a |
| T2-370 | I-5 | II-85 | II-2a |
| T2-371 | I-5 | II-86 | II-2a |
| T2-372 | I-5 | II-92 | II-2a |
| T2-373 | I-5 | II-3 | II-3a |
| T2-374 | I-5 | II-5 | II-3a |
| T2-375 | I-5 | II-6 | II-3a |
| T2-376 | I-5 | II-7 | II-3a |
| T2-377 | I-5 | II-8 | II-3a |
| T2-378 | I-5 | II-11 | II-3a |
| T2-379 | I-5 | II-16 | II-3a |
| T2-380 | I-5 | II-21 | II-3a |
| T2-381 | I-5 | II-26 | II-3a |
| T2-382 | I-5 | II-32 | II-3a |
| T2-383 | I-5 | II-33 | II-3a |
| T2-384 | I-5 | II-37 | II-3a |
| T2-385 | I-5 | II-39 | II-3a |
| T2-386 | I-5 | II-42 | II-3a |
| T2-387 | I-5 | II-44 | II-3a |
| T2-388 | I-5 | II-50 | II-3a |
| T2-389 | I-5 | II-53 | II-3a |
| T2-390 | I-5 | II-60 | II-3a |
| T2-391 | I-5 | II-62 | II-3a |
| T2-392 | I-5 | II-66 | II-3a |
| T2-393 | I-5 | II-69 | II-3a |
| T2-394 | I-5 | II-70 | II-3a |
| T2-395 | I-5 | II-71 | II-3a |
| T2-396 | I-5 | II-72 | II-3a |
| T2-397 | I-5 | II-74 | II-3a |
| T2-398 | I-5 | II-76 | II-3a |
| T2-399 | I-5 | II-78 | II-3a |
| T2-400 | I-5 | II-84 | II-3a |
| T2-401 | I-5 | II-85 | II-3a |
| T2-402 | I-5 | II-86 | II-3a |
| T2-403 | I-5 | II-92 | II-3a |
| T2-404 | I-5 | II-3 | II-4a |
| T2-405 | I-5 | II-5 | II-4a |
| T2-406 | I-5 | II-6 | II-4a |
| T2-407 | I-5 | II-7 | II-4a |
| T2-408 | I-5 | II-8 | II-4a |
| T2-409 | I-5 | II-11 | II-4a |
| T2-410 | I-5 | II-16 | II-4a |
| T2-411 | I-5 | II-21 | II-4a |
| T2-412 | I-5 | II-26 | II-4a |
| T2-413 | I-5 | II-32 | II-4a |
| T2-414 | I-5 | II-33 | II-4a |
| T2-415 | I-5 | II-37 | II-4a |
| T2-416 | I-5 | II-39 | II-4a |
| T2-417 | I-5 | II-42 | II-4a |
| T2-418 | I-5 | II-44 | II-4a |
| T2-419 | I-5 | II-50 | II-4a |
| T2-420 | I-5 | II-53 | II-4a |
| T2-421 | I-5 | II-60 | II-4a |
| T2-422 | I-5 | II-62 | II-4a |
| T2-423 | I-5 | II-66 | II-4a |
| T2-424 | I-5 | II-69 | II-4a |
| T2-425 | I-5 | II-70 | II-4a |
| T2-426 | I-5 | II-71 | II-4a |
| T2-427 | I-5 | II-72 | II-4a |
| T2-428 | I-5 | II-74 | II-4a |
| T2-429 | I-5 | II-76 | II-4a |
| T2-430 | I-5 | II-78 | II-4a |
| T2-431 | I-5 | II-84 | II-4a |
| T2-432 | I-5 | II-85 | II-4a |
| T2-433 | I-5 | II-86 | II-4a |
| T2-434 | I-5 | II-92 | II-4a |
| T2-435 | I-5 | II-3 | II-5a |
| T2-436 | I-5 | II-5 | II-5a |
| T2-437 | I-5 | II-6 | II-5a |
| T2-438 | I-5 | II-7 | II-5a |
| T2-439 | I-5 | II-8 | II-5a |
| T2-440 | I-5 | II-11 | II-5a |
| T2-441 | I-5 | II-16 | II-5a |
| T2-442 | I-5 | II-21 | II-5a |
| T2-443 | I-5 | II-26 | II-5a |
| T2-444 | I-5 | II-32 | II-5a |
| T2-445 | I-5 | II-33 | II-5a |
| T2-446 | I-5 | II-37 | II-5a |
| T2-447 | I-5 | II-39 | II-5a |
| T2-448 | I-5 | II-42 | II-5a |
| T2-449 | I-5 | II-44 | II-5a |
| T2-450 | I-5 | II-50 | II-5a |
| T2-451 | I-5 | II-53 | II-5a |
| T2-452 | I-5 | II-60 | II-5a |
| T2-453 | I-5 | II-62 | II-5a |
| T2-454 | I-5 | II-66 | II-5a |
| T2-455 | I-5 | II-69 | II-5a |
| T2-456 | I-5 | II-70 | II-5a |
| T2-457 | I-5 | II-71 | II-5a |
| T2-458 | I-5 | II-72 | II-5a |
| T2-459 | I-5 | II-74 | II-5a |
| T2-460 | I-5 | II-76 | II-5a |
| T2-461 | I-5 | II-78 | II-5a |
| T2-462 | I-5 | II-84 | II-5a |
| T2-463 | I-5 | II-85 | II-5a |
| T2-464 | I-5 | II-86 | II-5a |
| T2-465 | I-5 | II-92 | II-5a |
| T2-466 | I-3 | II-3 | II-1a |
| T2-467 | I-3 | II-5 | II-1a |
| T2-468 | I-3 | II-6 | II-1a |
| T2-469 | I-3 | II-7 | II-1a |
| T2-470 | I-3 | II-8 | II-1a |
| T2-471 | I-3 | II-11 | II-1a |
| T2-472 | I-3 | II-16 | II-1a |
| T2-473 | I-3 | II-21 | II-1a |
| T2-474 | I-3 | II-26 | II-1a |
| T2-475 | I-3 | II-32 | II-1a |
| T2-476 | I-3 | II-33 | II-1a |
| T2-477 | I-3 | II-37 | II-1a |
| T2-478 | I-3 | II-39 | II-1a |
| T2-479 | I-3 | II-42 | II-1a |
| T2-480 | I-3 | II-44 | II-1a |
| T2-481 | I-3 | II-50 | II-1a |
| T2-482 | I-3 | II-53 | II-1a |
| T2-483 | I-3 | II-60 | II-1a |
| T2-484 | I-3 | II-62 | II-1a |
| T2-485 | I-3 | II-66 | II-1a |
| T2-486 | I-3 | II-69 | II-1a |
| T2-487 | I-3 | II-70 | II-1a |
| T2-488 | I-3 | II-71 | II-1a |
| T2-489 | I-3 | II-72 | II-1a |
| T2-490 | I-3 | II-74 | II-1a |
| T2-491 | I-3 | II-76 | II-1a |
| T2-492 | I-3 | II-78 | II-1a |
| T2-493 | I-3 | II-84 | II-1a |
| T2-494 | I-3 | II-85 | II-1a |
| T2-495 | I-3 | II-86 | II-1a |
| T2-496 | I-3 | II-92 | II-1a |
| T2-497 | I-3 | II-3 | II-2a |
| T2-498 | I-3 | II-5 | II-2a |
| T2-499 | I-3 | II-6 | II-2a |

TABLE T2-continued

| composition | I | II | III |
|---|---|---|---|
| T2-500 | I-3 | II-7 | II-2a |
| T2-501 | I-3 | II-8 | II-2a |
| T2-502 | I-3 | II-11 | II-2a |
| T2-503 | I-3 | II-16 | II-2a |
| T2-504 | I-3 | II-21 | II-2a |
| T2-505 | I-3 | II-26 | II-2a |
| T2-506 | I-3 | II-32 | II-2a |
| T2-507 | I-3 | II-33 | II-2a |
| T2-508 | I-3 | II-37 | II-2a |
| T2-509 | I-3 | II-39 | II-2a |
| T2-510 | I-3 | II-42 | II-2a |
| T2-511 | I-3 | II-44 | II-2a |
| T2-512 | I-3 | II-50 | II-2a |
| T2-513 | I-3 | II-53 | II-2a |
| T2-514 | I-3 | II-60 | II-2a |
| T2-515 | I-3 | II-62 | II-2a |
| T2-516 | I-3 | II-66 | II-2a |
| T2-517 | I-3 | II-69 | II-2a |
| T2-518 | I-3 | II-70 | II-2a |
| T2-519 | I-3 | II-71 | II-2a |
| T2-520 | I-3 | II-72 | II-2a |
| T2-521 | I-3 | II-74 | II-2a |
| T2-522 | I-3 | II-76 | II-2a |
| T2-523 | I-3 | II-78 | II-2a |
| T2-524 | I-3 | II-84 | II-2a |
| T2-525 | I-3 | II-85 | II-2a |
| T2-526 | I-3 | II-86 | II-2a |
| T2-527 | I-3 | II-92 | II-2a |
| T2-528 | I-3 | II-3 | II-3a |
| T2-529 | I-3 | II-5 | II-3a |
| T2-530 | I-3 | II-6 | II-3a |
| T2-531 | I-3 | II-7 | II-3a |
| T2-532 | I-3 | II-8 | II-3a |
| T2-533 | I-3 | II-11 | II-3a |
| T2-534 | I-3 | II-16 | II-3a |
| T2-535 | I-3 | II-21 | II-3a |
| T2-536 | I-3 | II-26 | II-3a |
| T2-537 | I-3 | II-32 | II-3a |
| T2-538 | I-3 | II-33 | II-3a |
| T2-539 | I-3 | II-37 | II-3a |
| T2-540 | I-3 | II-39 | II-3a |
| T2-541 | I-3 | II-42 | II-3a |
| T2-542 | I-3 | II-44 | II-3a |
| T2-543 | I-3 | II-50 | II-3a |
| T2-544 | I-3 | II-53 | II-3a |
| T2-545 | I-3 | II-60 | II-3a |
| T2-546 | I-3 | II-62 | II-3a |
| T2-547 | I-3 | II-66 | II-3a |
| T2-548 | I-3 | II-69 | II-3a |
| T2-549 | I-3 | II-70 | II-3a |
| T2-550 | I-3 | II-71 | II-3a |
| T2-551 | I-3 | II-72 | II-3a |
| T2-552 | I-3 | II-74 | II-3a |
| T2-553 | I-3 | II-76 | II-3a |
| T2-554 | I-3 | II-78 | II-3a |
| T2-555 | I-3 | II-84 | II-3a |
| T2-556 | I-3 | II-85 | II-3a |
| T2-557 | I-3 | II-86 | II-3a |
| T2-558 | I-3 | II-92 | II-3a |
| T2-559 | I-3 | II-3 | II-4a |
| T2-560 | I-3 | II-5 | II-4a |
| T2-561 | I-3 | II-6 | II-4a |
| T2-562 | I-3 | II-7 | II-4a |
| T2-563 | I-3 | II-8 | II-4a |
| T2-564 | I-3 | II-11 | II-4a |
| T2-565 | I-3 | II-16 | II-4a |
| T2-566 | I-3 | II-21 | II-4a |
| T2-567 | I-3 | II-26 | II-4a |
| T2-568 | I-3 | II-32 | II-4a |
| T2-569 | I-3 | II-33 | II-4a |
| T2-570 | I-3 | II-37 | II-4a |
| T2-571 | I-3 | II-39 | II-4a |
| T2-572 | I-3 | II-42 | II-4a |
| T2-573 | I-3 | II-44 | II-4a |
| T2-574 | I-3 | II-50 | II-4a |
| T2-575 | I-3 | II-53 | II-4a |
| T2-576 | I-3 | II-60 | II-4a |
| T2-577 | I-3 | II-62 | II-4a |
| T2-578 | I-3 | II-66 | II-4a |
| T2-579 | I-3 | II-69 | II-4a |
| T2-580 | I-3 | II-70 | II-4a |
| T2-581 | I-3 | II-71 | II-4a |
| T2-582 | I-3 | II-72 | II-4a |
| T2-583 | I-3 | II-74 | II-4a |
| T2-584 | I-3 | II-76 | II-4a |
| T2-585 | I-3 | II-78 | II-4a |
| T2-586 | I-3 | II-84 | II-4a |
| T2-587 | I-3 | II-85 | II-4a |
| T2-588 | I-3 | II-86 | II-4a |
| T2-589 | I-3 | II-92 | II-4a |
| T2-590 | I-3 | II-3 | II-5a |
| T2-591 | I-3 | II-5 | II-5a |
| T2-592 | I-3 | II-6 | II-5a |
| T2-593 | I-3 | II-7 | II-5a |
| T2-594 | I-3 | II-8 | II-5a |
| T2-595 | I-3 | II-11 | II-5a |
| T2-596 | I-3 | II-16 | II-5a |
| T2-597 | I-3 | II-21 | II-5a |
| T2-598 | I-3 | II-26 | II-5a |
| T2-599 | I-3 | II-32 | II-5a |
| T2-600 | I-3 | II-33 | II-5a |
| T2-601 | I-3 | II-37 | II-5a |
| T2-602 | I-3 | II-39 | II-5a |
| T2-603 | I-3 | II-42 | II-5a |
| T2-604 | I-3 | II-44 | II-5a |
| T2-605 | I-3 | II-50 | II-5a |
| T2-606 | I-3 | II-53 | II-5a |
| T2-607 | I-3 | II-60 | II-5a |
| T2-608 | I-3 | II-62 | II-5a |
| T2-609 | I-3 | II-66 | II-5a |
| T2-610 | I-3 | II-69 | II-5a |
| T2-611 | I-3 | II-70 | II-5a |
| T2-612 | I-3 | II-71 | II-5a |
| T2-613 | I-3 | II-72 | II-5a |
| T2-614 | I-3 | II-74 | II-5a |
| T2-615 | I-3 | II-76 | II-5a |
| T2-616 | I-3 | II-78 | II-5a |
| T2-617 | I-3 | II-84 | II-5a |
| T2-618 | I-3 | II-85 | II-5a |
| T2-619 | I-3 | II-86 | II-5a |
| T2-620 | I-3 | II-92 | II-5a |
| T2-621 | I-4 | II-3 | II-1a |
| T2-622 | I-4 | II-5 | II-1a |
| T2-623 | I-4 | II-6 | II-1a |
| T2-624 | I-4 | II-7 | II-1a |
| T2-625 | I-4 | II-8 | II-1a |
| T2-626 | I-4 | II-11 | II-1a |
| T2-627 | I-4 | II-16 | II-1a |
| T2-628 | I-4 | II-21 | II-1a |
| T2-629 | I-4 | II-26 | II-1a |
| T2-630 | I-4 | II-32 | II-1a |
| T2-631 | I-4 | II-33 | II-1a |
| T2-632 | I-4 | II-37 | II-1a |
| T2-633 | I-4 | II-39 | II-1a |
| T2-634 | I-4 | II-42 | II-1a |
| T2-635 | I-4 | II-44 | II-1a |
| T2-636 | I-4 | II-50 | II-1a |
| T2-637 | I-4 | II-53 | II-1a |
| T2-638 | I-4 | II-60 | II-1a |
| T2-639 | I-4 | II-62 | II-1a |
| T2-640 | I-4 | II-66 | II-1a |
| T2-641 | I-4 | II-69 | II-1a |
| T2-642 | I-4 | II-70 | II-1a |
| T2-643 | I-4 | II-71 | II-1a |
| T2-644 | I-4 | II-72 | II-1a |
| T2-645 | I-4 | II-74 | II-1a |
| T2-646 | I-4 | II-76 | II-1a |
| T2-647 | I-4 | II-78 | II-1a |
| T2-648 | I-4 | II-84 | II-1a |
| T2-649 | I-4 | II-85 | II-1a |
| T2-650 | I-4 | II-86 | II-1a |
| T2-651 | I-4 | II-92 | II-1a |
| T2-652 | I-4 | II-3 | II-2a |
| T2-653 | I-4 | II-5 | II-2a |
| T2-654 | I-4 | II-6 | II-2a |
| T2-655 | I-4 | II-7 | II-2a |

TABLE T2-continued

| composition | I | II | III |
|---|---|---|---|
| T2-656 | I-4 | II-8 | II-2a |
| T2-657 | I-4 | II-11 | II-2a |
| T2-658 | I-4 | II-16 | II-2a |
| T2-659 | I-4 | II-21 | II-2a |
| T2-660 | I-4 | II-26 | II-2a |
| T2-661 | I-4 | II-32 | II-2a |
| T2-662 | I-4 | II-33 | II-2a |
| T2-663 | I-4 | II-37 | II-2a |
| T2-664 | I-4 | II-39 | II-2a |
| T2-665 | I-4 | II-42 | II-2a |
| T2-666 | I-4 | II-44 | II-2a |
| T2-667 | I-4 | II-50 | II-2a |
| T2-668 | I-4 | II-53 | II-2a |
| T2-669 | I-4 | II-60 | II-2a |
| T2-670 | I-4 | II-62 | II-2a |
| T2-671 | I-4 | II-66 | II-2a |
| T2-672 | I-4 | II-69 | II-2a |
| T2-673 | I-4 | II-70 | II-2a |
| T2-674 | I-4 | II-71 | II-2a |
| T2-675 | I-4 | II-72 | II-2a |
| T2-676 | I-4 | II-74 | II-2a |
| T2-677 | I-4 | II-76 | II-2a |
| T2-678 | I-4 | II-78 | II-2a |
| T2-679 | I-4 | II-84 | II-2a |
| T2-680 | I-4 | II-85 | II-2a |
| T2-681 | I-4 | II-86 | II-2a |
| T2-682 | I-4 | II-92 | II-2a |
| T2-683 | I-4 | II-3 | II-3a |
| T2-684 | I-4 | II-5 | II-3a |
| T2-685 | I-4 | II-6 | II-3a |
| T2-686 | I-4 | II-7 | II-3a |
| T2-687 | I-4 | II-8 | II-3a |
| T2-688 | I-4 | II-11 | II-3a |
| T2-689 | I-4 | II-16 | II-3a |
| T2-690 | I-4 | II-21 | II-3a |
| T2-691 | I-4 | II-26 | II-3a |
| T2-692 | I-4 | II-32 | II-3a |
| T2-693 | I-4 | II-33 | II-3a |
| T2-694 | I-4 | II-37 | II-3a |
| T2-695 | I-4 | II-39 | II-3a |
| T2-696 | I-4 | II-42 | II-3a |
| T2-697 | I-4 | II-44 | II-3a |
| T2-698 | I-4 | II-50 | II-3a |
| T2-699 | I-4 | II-53 | II-3a |
| T2-700 | I-4 | II-60 | II-3a |
| T2-701 | I-4 | II-62 | II-3a |
| T2-702 | I-4 | II-66 | II-3a |
| T2-703 | I-4 | II-69 | II-3a |
| T2-704 | I-4 | II-70 | II-3a |
| T2-705 | I-4 | II-71 | II-3a |
| T2-706 | I-4 | II-72 | II-3a |
| T2-707 | I-4 | II-74 | II-3a |
| T2-708 | I-4 | II-76 | II-3a |
| T2-709 | I-4 | II-78 | II-3a |
| T2-710 | I-4 | II-84 | II-3a |
| T2-711 | I-4 | II-85 | II-3a |
| T2-712 | I-4 | II-86 | II-3a |
| T2-713 | I-4 | II-92 | II-3a |
| T2-714 | I-4 | II-3 | II-4a |
| T2-715 | I-4 | II-5 | II-4a |
| T2-716 | I-4 | II-6 | II-4a |
| T2-717 | I-4 | II-7 | II-4a |
| T2-718 | I-4 | II-8 | II-4a |
| T2-719 | I-4 | II-11 | II-4a |
| T2-720 | I-4 | II-16 | II-4a |
| T2-721 | I-4 | II-21 | II-4a |
| T2-722 | I-4 | II-26 | II-4a |
| T2-723 | I-4 | II-32 | II-4a |
| T2-724 | I-4 | II-33 | II-4a |
| T2-725 | I-4 | II-37 | II-4a |
| T2-726 | I-4 | II-39 | II-4a |
| T2-727 | I-4 | II-42 | II-4a |
| T2-728 | I-4 | II-44 | II-4a |
| T2-729 | I-4 | II-50 | II-4a |
| T2-730 | I-4 | II-53 | II-4a |
| T2-731 | I-4 | II-60 | II-4a |
| T2-732 | I-4 | II-62 | II-4a |
| T2-733 | I-4 | II-66 | II-4a |
| T2-734 | I-4 | II-69 | II-4a |
| T2-735 | I-4 | II-70 | II-4a |
| T2-736 | I-4 | II-71 | II-4a |
| T2-737 | I-4 | II-72 | II-4a |
| T2-738 | I-4 | II-74 | II-4a |
| T2-739 | I-4 | II-76 | II-4a |
| T2-740 | I-4 | II-78 | II-4a |
| T2-741 | I-4 | II-84 | II-4a |
| T2-742 | I-4 | II-85 | II-4a |
| T2-743 | I-4 | II-86 | II-4a |
| T2-744 | I-4 | II-92 | II-4a |
| T2-745 | I-4 | II-3 | II-5a |
| T2-746 | I-4 | II-5 | II-5a |
| T2-747 | I-4 | II-6 | II-5a |
| T2-748 | I-4 | II-7 | II-5a |
| T2-749 | I-4 | II-8 | II-5a |
| T2-750 | I-4 | II-11 | II-5a |
| T2-751 | I-4 | II-16 | II-5a |
| T2-752 | I-4 | II-21 | II-5a |
| T2-753 | I-4 | II-26 | II-5a |
| T2-754 | I-4 | II-32 | II-5a |
| T2-755 | I-4 | II-33 | II-5a |
| T2-756 | I-4 | II-37 | II-5a |
| T2-757 | I-4 | II-39 | II-5a |
| T2-758 | I-4 | II-42 | II-5a |
| T2-759 | I-4 | II-44 | II-5a |
| T2-760 | I-4 | II-50 | II-5a |
| T2-761 | I-4 | II-53 | II-5a |
| T2-762 | I-4 | II-60 | II-5a |
| T2-763 | I-4 | II-62 | II-5a |
| T2-764 | I-4 | II-66 | II-5a |
| T2-765 | I-4 | II-69 | II-5a |
| T2-766 | I-4 | II-70 | II-5a |
| T2-767 | I-4 | II-71 | II-5a |
| T2-768 | I-4 | II-72 | II-5a |
| T2-769 | I-4 | II-74 | II-5a |
| T2-770 | I-4 | II-76 | II-5a |
| T2-771 | I-4 | II-78 | II-5a |
| T2-772 | I-4 | II-84 | II-5a |
| T2-773 | I-4 | II-85 | II-5a |
| T2-774 | I-4 | II-86 | II-5a |
| T2-775 | I-4 | II-92 | II-5a |

Three-component compositions comprising another compound I as component I, a fungicidal component II and a growth regulator as component III,

| composition | I | II | III |
|---|---|---|---|
| T2-776 | I-13 | II-3 | II-1a |
| T2-777 | I-13 | II-5 | II-1a |
| T2-778 | I-13 | II-6 | II-1a |
| T2-779 | I-13 | II-7 | II-1a |
| T2-780 | I-13 | II-8 | II-1a |
| T2-781 | I-13 | II-11 | II-1a |
| T2-782 | I-13 | II-16 | II-1a |
| T2-783 | I-13 | II-21 | II-1a |
| T2-784 | I-13 | II-26 | II-1a |
| T2-785 | I-13 | II-32 | II-1a |
| T2-786 | I-13 | II-33 | II-1a |
| T2-787 | I-13 | II-37 | II-1a |
| T2-788 | I-13 | II-39 | II-1a |
| T2-789 | I-13 | II-42 | II-1a |
| T2-790 | I-13 | II-44 | II-1a |
| T2-791 | I-13 | II-50 | II-1a |
| T2-792 | I-13 | II-53 | II-1a |
| T2-793 | I-13 | II-60 | II-1a |
| T2-794 | I-13 | II-62 | II-1a |
| T2-795 | I-13 | II-66 | II-1a |
| T2-796 | I-13 | II-69 | II-1a |
| T2-797 | I-13 | II-70 | II-1a |
| T2-798 | I-13 | II-71 | II-1a |
| T2-799 | I-13 | II-72 | II-1a |
| T2-800 | I-13 | II-74 | II-1a |
| T2-801 | I-13 | II-76 | II-1a |
| T2-802 | I-13 | II-78 | II-1a |
| T2-803 | I-13 | II-84 | II-1a |
| T2-804 | I-13 | II-85 | II-1a |
| T2-805 | I-13 | II-86 | II-1a |
| T2-806 | I-13 | II-92 | II-1a |
| T2-807 | I-13 | II-3 | II-2a |

TABLE T2-continued

| composition | I | II | III |
| --- | --- | --- | --- |
| T2-808 | I-13 | II-5 | II-2a |
| T2-809 | I-13 | II-6 | II-2a |
| T2-810 | I-13 | II-7 | II-2a |
| T2-811 | I-13 | II-8 | II-2a |
| T2-812 | I-13 | II-11 | II-2a |
| T2-813 | I-13 | II-16 | II-2a |
| T2-814 | I-13 | II-21 | II-2a |
| T2-815 | I-13 | II-26 | II-2a |
| T2-816 | I-13 | II-32 | II-2a |
| T2-817 | I-13 | II-33 | II-2a |
| T2-818 | I-13 | II-37 | II-2a |
| T2-819 | I-13 | II-39 | II-2a |
| T2-820 | I-13 | II-42 | II-2a |
| T2-821 | I-13 | II-44 | II-2a |
| T2-822 | I-13 | II-50 | II-2a |
| T2-823 | I-13 | II-53 | II-2a |
| T2-824 | I-13 | II-60 | II-2a |
| T2-825 | I-13 | II-62 | II-2a |
| T2-826 | I-13 | II-66 | II-2a |
| T2-827 | I-13 | II-69 | II-2a |
| T2-828 | I-13 | II-70 | II-2a |
| T2-829 | I-13 | II-71 | II-2a |
| T2-830 | I-13 | II-72 | II-2a |
| T2-831 | I-13 | II-74 | II-2a |
| T2-832 | I-13 | II-76 | II-2a |
| T2-833 | I-13 | II-78 | II-2a |
| T2-834 | I-13 | II-84 | II-2a |
| T2-835 | I-13 | II-85 | II-2a |
| T2-836 | I-13 | II-86 | II-2a |
| T2-837 | I-13 | II-92 | II-2a |
| T2-838 | I-13 | II-3 | II-3a |
| T2-839 | I-13 | II-5 | II-3a |
| T2-840 | I-13 | II-6 | II-3a |
| T2-841 | I-13 | II-7 | II-3a |
| T2-842 | I-13 | II-8 | II-3a |
| T2-843 | I-13 | II-11 | II-3a |
| T2-844 | I-13 | II-16 | II-3a |
| T2-845 | I-13 | II-21 | II-3a |
| T2-846 | I-13 | II-26 | II-3a |
| T2-847 | I-13 | II-32 | II-3a |
| T2-848 | I-13 | II-33 | II-3a |
| T2-849 | I-13 | II-37 | II-3a |
| T2-850 | I-13 | II-39 | II-3a |
| T2-851 | I-13 | II-42 | II-3a |
| T2-852 | I-13 | II-44 | II-3a |
| T2-853 | I-13 | II-50 | II-3a |
| T2-854 | I-13 | II-53 | II-3a |
| T2-855 | I-13 | II-60 | II-3a |
| T2-856 | I-13 | II-62 | II-3a |
| T2-857 | I-13 | II-66 | II-3a |
| T2-858 | I-13 | II-69 | II-3a |
| T2-859 | I-13 | II-70 | II-3a |
| T2-860 | I-13 | II-71 | II-3a |
| T2-861 | I-13 | II-72 | II-3a |
| T2-862 | I-13 | II-74 | II-3a |
| T2-863 | I-13 | II-76 | II-3a |
| T2-864 | I-13 | II-78 | II-3a |
| T2-865 | I-13 | II-84 | II-3a |
| T2-866 | I-13 | II-85 | II-3a |
| T2-867 | I-13 | II-86 | II-3a |
| T2-868 | I-13 | II-92 | II-3a |
| T2-869 | I-13 | II-3 | II-4a |
| T2-870 | I-13 | II-5 | II-4a |
| T2-871 | I-13 | II-6 | II-4a |
| T2-872 | I-13 | II-7 | II-4a |
| T2-873 | I-13 | II-8 | II-4a |
| T2-874 | I-13 | II-11 | II-4a |
| T2-875 | I-13 | II-16 | II-4a |
| T2-876 | I-13 | II-21 | II-4a |
| T2-877 | I-13 | II-26 | II-4a |
| T2-878 | I-13 | II-32 | II-4a |
| T2-879 | I-13 | II-33 | II-4a |
| T2-880 | I-13 | II-37 | II-4a |
| T2-881 | I-13 | II-39 | II-4a |
| T2-882 | I-13 | II-42 | II-4a |
| T2-883 | I-13 | II-44 | II-4a |
| T2-884 | I-13 | II-50 | II-4a |
| T2-885 | I-13 | II-53 | II-4a |
| T2-886 | I-13 | II-60 | II-4a |
| T2-887 | I-13 | II-62 | II-4a |
| T2-888 | I-13 | II-66 | II-4a |
| T2-889 | I-13 | II-69 | II-4a |
| T2-890 | I-13 | II-70 | II-4a |
| T2-891 | I-13 | II-71 | II-4a |
| T2-892 | I-13 | II-72 | II-4a |
| T2-893 | I-13 | II-74 | II-4a |
| T2-894 | I-13 | II-76 | II-4a |
| T2-895 | I-13 | II-78 | II-4a |
| T2-896 | I-13 | II-84 | II-4a |
| T2-897 | I-13 | II-85 | II-4a |
| T2-898 | I-13 | II-86 | II-4a |
| T2-899 | I-13 | II-92 | II-4a |
| T2-900 | I-13 | II-3 | II-5a |
| T2-901 | I-13 | II-5 | II-5a |
| T2-902 | I-13 | II-6 | II-5a |
| T2-903 | I-13 | II-7 | II-5a |
| T2-904 | I-13 | II-8 | II-5a |
| T2-905 | I-13 | II-11 | II-5a |
| T2-906 | I-13 | II-16 | II-5a |
| T2-907 | I-13 | II-21 | II-5a |
| T2-908 | I-13 | II-26 | II-5a |
| T2-909 | I-13 | II-32 | II-5a |
| T2-910 | I-13 | II-33 | II-5a |
| T2-911 | I-13 | II-37 | II-5a |
| T2-912 | I-13 | II-39 | II-5a |
| T2-913 | I-13 | II-42 | II-5a |
| T2-914 | I-13 | II-44 | II-5a |
| T2-915 | I-13 | II-50 | II-5a |
| T2-916 | I-13 | II-53 | II-5a |
| T2-917 | I-13 | II-60 | II-5a |
| T2-918 | I-13 | II-62 | II-5a |
| T2-919 | I-13 | II-66 | II-5a |
| T2-920 | I-13 | II-69 | II-5a |
| T2-921 | I-13 | II-70 | II-5a |
| T2-922 | I-13 | II-71 | II-5a |
| T2-923 | I-13 | II-72 | II-5a |
| T2-924 | I-13 | II-74 | II-5a |
| T2-925 | I-13 | II-76 | II-5a |
| T2-926 | I-13 | II-78 | II-5a |
| T2-927 | I-13 | II-84 | II-5a |
| T2-928 | I-13 | II-85 | II-5a |
| T2-929 | I-13 | II-86 | II-5a |
| T2-930 | I-13 | II-92 | II-5a |

In table T2, according to particular embodiments of the invention, the respective component I is present as (S) enantiomer, wherein each row corresponds to one embodiment of the compositions according to the invention, i.e. one specific individualized composition. According to one specific aspect, these are ternary compositions which each only contain these two components as active compounds. Furthermore, also every combination of the compositions individualized in this table represent embodiments of the present invention (S) enantiomer.

In table T2, according to a further particular embodiments of the invention, the respective component I is present as (R) enantiomer, wherein each row corresponds to one embodiment of the compositions according to the invention, i.e. one specific individualized composition. According to one specific aspect, these are ternary compositions which each only contain these two components as active compounds. Furthermore, also every combination of the compositions individualized in this table represent embodiments of the present invention (R) enantiomer.

One further aspect of the present invention are novel two-component compositions comprising the component II and the component III as listed the above Table T2, i.e. the compositions given in the following Table BT2, as far as they are novel:

TABLE BT2

Two-component compositions comprising a fungicidal component II and a growth regulator as component III. Each line of line BT2-1 to BT1-155 corresponds to one particular individualized composition. Furthermore, also every combination of the compositions individualized in this table represent embodiments of the present invention.

| composition | II | III |
|---|---|---|
| BT2-1 | II-3 | II-1a |
| BT2-2 | II-5 | II-1a |
| BT2-3 | II-6 | II-1a |
| BT2-4 | II-7 | II-1a |
| BT2-5 | II-8 | II-1a |
| BT2-6 | II-11 | II-1a |
| BT2-7 | II-16 | II-1a |
| BT2-8 | II-21 | II-1a |
| BT2-9 | II-26 | II-1a |
| BT2-10 | II-32 | II-1a |
| BT2-11 | II-33 | II-1a |
| BT2-12 | II-37 | II-1a |
| BT2-13 | II-39 | II-1a |
| BT2-14 | II-42 | II-1a |
| BT2-15 | II-44 | II-1a |
| BT2-16 | II-50 | II-1a |
| BT2-17 | II-53 | II-1a |
| BT2-18 | II-60 | II-1a |
| BT2-19 | II-62 | II-1a |
| BT2-20 | II-66 | II-1a |
| BT2-21 | II-69 | II-1a |
| BT2-22 | II-70 | II-1a |
| BT2-23 | II-71 | II-1a |
| BT2-24 | II-72 | II-1a |
| BT2-25 | II-74 | II-1a |
| BT2-26 | II-76 | II-1a |
| BT2-27 | II-78 | II-1a |
| BT2-28 | II-84 | II-1a |
| BT2-29 | II-85 | II-1a |
| BT2-30 | II-86 | II-1a |
| BT2-31 | II-92 | II-1a |
| BT2-32 | II-3 | II-2a |
| BT2-33 | II-5 | II-2a |
| BT2-34 | II-6 | II-2a |
| BT2-35 | II-7 | II-2a |
| BT2-36 | II-8 | II-2a |
| BT2-37 | II-11 | II-2a |
| BT2-38 | II-16 | II-2a |
| BT2-39 | II-21 | II-2a |
| BT2-40 | II-26 | II-2a |
| BT2-41 | II-32 | II-2a |
| BT2-42 | II-33 | II-2a |
| BT2-43 | II-37 | II-2a |
| BT2-44 | II-39 | II-2a |
| BT2-45 | II-42 | II-2a |
| BT2-46 | II-44 | II-2a |
| BT2-47 | II-50 | II-2a |
| BT2-48 | II-53 | II-2a |
| BT2-49 | II-60 | II-2a |
| BT2-50 | II-62 | II-2a |
| BT2-51 | II-66 | II-2a |
| BT2-52 | II-69 | II-2a |
| BT2-53 | II-70 | II-2a |
| BT2-54 | II-71 | II-2a |
| BT2-55 | II-72 | II-2a |
| BT2-56 | II-74 | II-2a |
| BT2-57 | II-76 | II-2a |
| BT2-58 | II-78 | II-2a |
| BT2-59 | II-84 | II-2a |
| BT2-60 | II-85 | II-2a |
| BT2-61 | II-86 | II-2a |
| BT2-62 | II-92 | II-2a |
| BT2-63 | II-3 | II-3a |
| BT2-64 | II-5 | II-3a |
| BT2-65 | II-6 | II-3a |
| BT2-66 | II-7 | II-3a |
| BT2-67 | II-8 | II-3a |
| BT2-68 | II-11 | II-3a |
| BT2-69 | II-16 | II-3a |
| BT2-70 | II-21 | II-3a |
| BT2-71 | II-26 | II-3a |
| BT2-72 | II-32 | II-3a |
| BT2-73 | II-33 | II-3a |
| BT2-74 | II-37 | II-3a |
| BT2-75 | II-39 | II-3a |
| BT2-76 | II-42 | II-3a |
| BT2-77 | II-44 | II-3a |
| BT2-78 | II-50 | II-3a |
| BT2-79 | II-53 | II-3a |
| BT2-80 | II-60 | II-3a |
| BT2-81 | II-62 | II-3a |
| BT2-82 | II-66 | II-3a |
| BT2-83 | II-69 | II-3a |
| BT2-84 | II-70 | II-3a |
| BT2-85 | II-71 | II-3a |
| BT2-86 | II-72 | II-3a |
| BT2-87 | II-74 | II-3a |
| BT2-88 | II-76 | II-3a |
| BT2-89 | II-78 | II-3a |
| BT2-90 | II-84 | II-3a |
| BT2-91 | II-85 | II-3a |
| BT2-92 | II-86 | II-3a |
| BT2-93 | II-92 | II-3a |
| BT2-94 | II-3 | II-4a |
| BT2-95 | II-5 | II-4a |
| BT2-96 | II-6 | II-4a |
| BT2-97 | II-7 | II-4a |
| BT2-98 | II-8 | II-4a |
| BT2-99 | II-11 | II-4a |
| BT2-10 | II-16 | II-4a |
| BT2-10 | II-21 | II-4a |
| BT2-10 | II-26 | II-4a |
| BT2-10 | II-32 | II-4a |
| BT2-10 | II-33 | II-4a |
| BT2-10 | II-37 | II-4a |
| BT2-10 | II-39 | II-4a |
| BT2-10 | II-42 | II-4a |
| BT2-10 | II-44 | II-4a |
| BT2-10 | II-50 | II-4a |
| BT2-11 | II-53 | II-4a |
| BT2-11 | II-60 | II-4a |
| BT2-11 | II-62 | II-4a |
| BT2-11 | II-66 | II-4a |
| BT2-11 | II-69 | II-4a |
| BT2-11 | II-70 | II-4a |
| BT2-11 | II-71 | II-4a |
| BT2-11 | II-72 | II-4a |
| BT2-11 | II-74 | II-4a |
| BT2-11 | II-76 | II-4a |
| BT2-12 | II-78 | II-4a |
| BT2-12 | II-84 | II-4a |
| BT2-12 | II-85 | II-4a |
| BT2-12 | II-86 | II-4a |
| BT2-12 | II-92 | II-4a |
| BT2-12 | II-3 | II-5a |
| BT2-12 | II-5 | II-5a |
| BT2-12 | II-6 | II-5a |
| BT2-12 | II-7 | II-5a |
| BT2-12 | II-8 | II-5a |
| BT2-13 | II-11 | II-5a |
| BT2-13 | II-16 | II-5a |
| BT2-13 | II-21 | II-5a |
| BT2-13 | II-26 | II-5a |
| BT2-13 | II-32 | II-5a |
| BT2-13 | II-33 | II-5a |
| BT2-13 | II-37 | II-5a |
| BT2-13 | II-39 | II-5a |
| BT2-13 | II-42 | II-5a |
| BT2-13 | II-44 | II-5a |
| BT2-14 | II-50 | II-5a |
| BT2-14 | II-53 | II-5a |
| BT2-14 | II-60 | II-5a |

TABLE BT2-continued

Two-component compositions comprising a fungicidal component II and a growth regulator as component III. Each line of line BT2-1 to BT1-155 corresponds to one particular individidualized composition. Furthermore, also every combination of the compositions individualized in this table represent embodiments of the present invention.

| composition | II | III |
|---|---|---|
| BT2-14 | II-62 | II-5a |
| BT2-14 | II-66 | II-5a |
| BT2-14 | II-69 | II-5a |
| BT2-14 | II-70 | II-5a |
| BT2-14 | II-71 | II-5a |
| BT2-14 | II-72 | II-5a |
| BT2-14 | II-74 | II-5a |
| BT2-15 | II-76 | II-5a |
| BT2-15 | II-78 | II-5a |
| BT2-15 | II-84 | II-5a |
| BT2-15 | II-85 | II-5a |
| BT2-15 | II-86 | II-5a |
| BT2-15 | II-92 | II-5a |

Particularly preferred compositions are the three-component compositions, wherein component I is as defined above, i.e a compound I, in particular a compound selected from compounds I-1, I-2, I-3, I-4, I-5, I-6, I-7, I-8, I-9, I-11, I-13, I-14, I-15 and I-16 or any group of compounds I detailed above, and components 11 and III are growth regulators, selected from:

| | |
|---|---|
| II-1a | mepiquat chloride |
| II-2a | chlormequat chloride |
| II-3a | trinexapac-ethyl |
| II-4a | prohexadione-calcium |
| II-5a | ethophon | wherein components II and III are different from each other.

Particularly preferred compositions of these compositions are compiled in Table T3, where each row corresponds to one embodiment of the compositions according to the invention, i.e. one specific individualized three-component composition. According to one specific aspect, these are ternary compositions which each only contain these three components as the active compound. Furthermore, also every combination of the compositions individualized in this table represent embodiments of the present invention.

TABLE T3

| composition | I | II | III |
|---|---|---|---|

Three-component compositions comprising a component I and two plant growth regulators as component II and component III, wherein componentsII and III are different from each other.

| T3-1 | I-1 | II-1a | II-2a |
| T3-2 | I-1 | II-1a | II-3a |
| T3-3 | I-1 | II-1a | II-4a |
| T3-4 | I-1 | II-1a | II-5a |
| T3-5 | I-1 | II-2a | II-3a |
| T3-6 | I-1 | II-2a | II-4a |
| T3-7 | I-1 | II-2a | II-5a |
| T3-8 | I-1 | II-3a | II-4a |
| T3-9 | I-1 | II-3a | II-5a |
| T3-10 | I-1 | II-4a | II-5a |
| T3-11 | I-2 | II-1a | II-2a |
| T3-12 | I-2 | II-1a | II-3a |
| T3-13 | I-2 | II-1a | II-4a |
| T3-14 | I-2 | II-1a | II-5a |
| T3-15 | I-2 | II-2a | II-3a |
| T3-16 | I-2 | II-2a | II-4a |
| T3-17 | I-2 | II-2a | II-5a |
| T3-18 | I-2 | II-3a | II-4a |
| T3-19 | I-2 | II-3a | II-5a |
| T3-20 | I-2 | II-4a | II-5a |
| T3-21 | I-5 | II-1a | II-2a |
| T3-22 | I-5 | II-1a | II-3a |
| T3-23 | I-5 | II-1a | II-4a |
| T3-24 | I-5 | II-1a | II-5a |
| T3-25 | I-5 | II-2a | II-3a |
| T3-26 | I-5 | II-2a | II-4a |
| T3-27 | I-5 | II-2a | II-5a |
| T3-28 | I-5 | II-3a | II-4a |
| T3-29 | I-5 | II-3a | II-5a |
| T3-30 | I-5 | II-4a | II-5a |
| T3-31 | I-3 | II-1a | II-2a |
| T3-32 | I-3 | II-1a | II-3a |
| T3-33 | I-3 | II-1a | II-4a |
| T3-34 | I-3 | II-1a | II-5a |
| T3-35 | I-3 | II-2a | II-3a |
| T3-36 | I-3 | II-2a | II-4a |
| T3-37 | I-3 | II-2a | II-5a |
| T3-38 | I-3 | II-3a | II-4a |
| T3-39 | I-3 | II-3a | II-5a |
| T3-40 | I-3 | II-4a | II-5a |
| T3-41 | I-4 | II-1a | II-2a |
| T3-42 | I-4 | II-1a | II-3a |
| T3-43 | I-4 | II-1a | II-4a |
| T3-44 | I-4 | II-1a | II-5a |
| T3-45 | I-4 | II-2a | II-3a |
| T3-46 | I-4 | II-2a | II-4a |
| T3-47 | I-4 | II-2a | II-5a |
| T3-48 | I-4 | II-3a | II-4a |
| T3-49 | I-4 | II-3a | II-5a |
| T3-50 | I-4 | II-4a | II-5a |

Three-component compositions comprising another compound I as component I and two plant growth regulators as component II and component III, wherein componentsII and III are different from each other.

| T3-51 | I-13 | II-1a | II-2a |
| T3-52 | I-13 | II-1a | II-3a |
| T3-53 | I-13 | II-1a | II-4a |
| T3-54 | I-13 | II-1a | II-5a |
| T3-55 | I-13 | II-2a | II-3a |
| T3-56 | I-13 | II-2a | II-4a |
| T3-57 | I-13 | II-2a | II-5a |
| T3-58 | I-13 | II-3a | II-4a |
| T3-59 | I-13 | II-3a | II-5a |
| T3-60 | I-13 | II-4a | II-5a |

In table T3, according to particular embodiments of the invention, the respective component I is present as (S) enantiomer, wherein each row corresponds to one embodiment of the compositions according to the invention, i.e. one specific individualized composition. According to one specific aspect, these are ternary compositions which each only contain these two components as active compounds. Furthermore, also every combination of the compositions individualized in this table represent embodiments of the present invention (S) enantiomer.

In table T3, according to a further particular embodiments of the invention, the respective component I is present as (R) enantiomer, wherein each row corresponds to one embodiment of the compositions according to the invention, i.e. one specific individualized composition. According to one specific aspect, these are ternary compositions which each only contain these two components as active compounds. Furthermore, also every combination of the compositions individualized in this table represent embodiments of the present invention (R) enantiomer.

Particularly preferred compositions are the three-component compositions, wherein component I is as defined above, i.e a compound I, in particular a compound selected from compounds I-1, I-2, I-3, I-4, I-5, I-6, I-7, I-8, I-9, I-11, I-13, I-14, I-15 and I-16 or any group of compounds I detailed above, component II is selected from the following fungicidal compounds

| | |
|---|---|
| II-3 | azoxystrobin |
| II-5 | benzovindiflupyr |
| II-6 | bixafen |
| II-7 | boscalid |
| II-8 | carbendazim |
| II-11 | chlorothalonil |
| II-16 | cyprodinil |
| II-21 | difenoconazole |
| II-26 | epoxiconazole |
| II-32 | fenpropimorph |
| II-33 | fluazinam |
| II-37 | fluoxastrobin |
| II-39 | flusilazole |
| II-42 | fluxapyroxad |
| II-44 | fosetyl-Al |
| II-50 | isopyrazam |
| II-53 | kresoxim-methyl |
| II-60 | metconazole |
| II-62 | metrafenone |
| II-66 | pyraclostrobin |
| II-69 | phosporous acid |
| II-70 | potassium salt of phosphorous acid |
| II-71 | sodium salt of phosphorous acid |
| II-72 | penthiopyrad |
| II-74 | prochloraz |
| II-76 | propiconazole |
| II-78 | prothioconazole |
| II-84 | spiroxamine |
| II-85 | sulfur |
| II-86 | tebuconazole |
| II-92 | trifloxystrobin | and component III is an insecticide selected from

| | |
|---|---|
| II-11c | clothianidin |
| II-20c | fipronil |
| II-24c | imidacloprid; and |
| II-42c | thiamethoxam |

Particularly preferred compositions of these compositions are compiled in Table T4, where each row corresponds to one embodiment of the compositions according to the invention, i.e. one specific individualized three-component composition. According to one specific aspect, these are ternary compositions which each only contain these three components as the active compound. Furthermore, also every combination of the compositions individualized in this table represent embodiments of the present invention.

TABLE T4

| composition | I | II | III |
|---|---|---|---|
| Three-component compositions comprising a component I, a further specific fungicide compound as component II and an insecticide as component III. | | | |
| T4-1 | I-1 | II-3 | II-11c |
| T4-2 | I-1 | II-5 | II-11c |
| T4-3 | I-1 | II-6 | II-11c |
| T4-4 | I-1 | II-7 | II-11c |
| T4-5 | I-1 | II-8 | II-11c |
| T4-6 | I-1 | II-11 | II-11c |
| T4-7 | I-1 | II-16 | II-11c |
| T4-8 | I-1 | II-21 | II-11c |
| T4-9 | I-1 | II-26 | II-11c |
| T4-10 | I-1 | II-32 | II-11c |
| T4-11 | I-1 | II-33 | II-11c |
| T4-12 | I-1 | II-37 | II-11c |
| T4-13 | I-1 | II-39 | II-11c |
| T4-14 | I-1 | II-42 | II-11c |
| T4-15 | I-1 | II-44 | II-11c |
| T4-16 | I-1 | II-50 | II-11c |
| T4-17 | I-1 | II-53 | II-11c |
| T4-18 | I-1 | II-60 | II-11c |
| T4-19 | I-1 | II-62 | II-11c |
| T4-20 | I-1 | II-66 | II-11c |
| T4-21 | I-1 | II-69 | II-11c |
| T4-22 | I-1 | II-70 | II-11c |
| T4-23 | I-1 | II-71 | II-11c |
| T4-24 | I-1 | II-72 | II-11c |
| T4-25 | I-1 | II-74 | II-11c |
| T4-26 | I-1 | II-76 | II-11c |
| T4-27 | I-1 | II-78 | II-11c |
| T4-28 | I-1 | II-84 | II-11c |
| T4-29 | I-1 | II-85 | II-11c |
| T4-30 | I-1 | II-86 | II-11c |
| T4-31 | I-1 | II-92 | II-11c |
| T4-32 | I-1 | II-3 | II-20c |
| T4-33 | I-1 | II-5 | II-20c |
| T4-34 | I-1 | II-6 | II-20c |
| T4-35 | I-1 | II-7 | II-20c |
| T4-36 | I-1 | II-8 | II-20c |
| T4-37 | I-1 | II-11 | II-20c |
| T4-38 | I-1 | II-16 | II-20c |
| T4-39 | I-1 | II-21 | II-20c |
| T4-40 | I-1 | II-26 | II-20c |
| T4-41 | I-1 | II-32 | II-20c |
| T4-42 | I-1 | II-33 | II-20c |
| T4-43 | I-1 | II-37 | II-20c |
| T4-44 | I-1 | II-39 | II-20c |
| T4-45 | I-1 | II-42 | II-20c |
| T4-46 | I-1 | II-44 | II-20c |
| T4-47 | I-1 | II-50 | II-20c |
| T4-48 | I-1 | II-53 | II-20c |
| T4-49 | I-1 | II-60 | II-20c |
| T4-50 | I-1 | II-62 | II-20c |
| T4-51 | I-1 | II-66 | II-20c |
| T4-52 | I-1 | II-69 | II-20c |
| T4-53 | I-1 | II-70 | II-20c |
| T4-54 | I-1 | II-71 | II-20c |
| T4-55 | I-1 | II-72 | II-20c |
| T4-56 | I-1 | II-74 | II-20c |
| T4-57 | I-1 | II-76 | II-20c |
| T4-58 | I-1 | II-78 | II-20c |
| T4-59 | I-1 | II-84 | II-20c |
| T4-60 | I-1 | II-85 | II-20c |
| T4-61 | I-1 | II-86 | II-20c |
| T4-62 | I-1 | II-92 | II-20c |
| T4-63 | I-1 | II-3 | II-24c |
| T4-64 | I-1 | II-5 | II-24c |
| T4-65 | I-1 | II-6 | II-24c |
| T4-66 | I-1 | II-7 | II-24c |
| T4-67 | I-1 | II-8 | II-24c |
| T4-68 | I-1 | II-11 | II-24c |
| T4-69 | I-1 | II-16 | II-24c |
| T4-70 | I-1 | II-21 | II-24c |
| T4-71 | I-1 | II-26 | II-24c |
| T4-72 | I-1 | II-32 | II-24c |
| T4-73 | I-1 | II-33 | II-24c |
| T4-74 | I-1 | II-37 | II-24c |
| T4-75 | I-1 | II-39 | II-24c |
| T4-76 | I-1 | II-42 | II-24c |
| T4-77 | I-1 | II-44 | II-24c |
| T4-78 | I-1 | II-50 | II-24c |
| T4-79 | I-1 | II-53 | II-24c |
| T4-80 | I-1 | II-60 | II-24c |
| T4-81 | I-1 | II-62 | II-24c |
| T4-82 | I-1 | II-66 | II-24c |
| T4-83 | I-1 | II-69 | II-24c |
| T4-84 | I-1 | II-70 | II-24c |
| T4-85 | I-1 | II-71 | II-24c |
| T4-86 | I-1 | II-72 | II-24c |
| T4-87 | I-1 | II-74 | II-24c |
| T4-88 | I-1 | II-76 | II-24c |

TABLE T4-continued

| composition | I | II | III |
|---|---|---|---|
| T4-89 | I-1 | II-78 | II-24c |
| T4-90 | I-1 | II-84 | II-24c |
| T4-91 | I-1 | II-85 | II-24c |
| T4-92 | I-1 | II-86 | II-24c |
| T4-93 | I-1 | II-92 | II-24c |
| T4-94 | I-1 | II-3 | II-42c |
| T4-95 | I-1 | II-5 | II-42c |
| T4-96 | I-1 | II-6 | II-42c |
| T4-97 | I-1 | II-7 | II-42c |
| T4-98 | I-1 | II-8 | II-42c |
| T4-99 | I-1 | II-11 | II-42c |
| T4-100 | I-1 | II-16 | II-42c |
| T4-101 | I-1 | II-21 | II-42c |
| T4-102 | I-1 | II-26 | II-42c |
| T4-103 | I-1 | II-32 | II-42c |
| T4-104 | I-1 | II-33 | II-42c |
| T4-105 | I-1 | II-37 | II-42c |
| T4-106 | I-1 | II-39 | II-42c |
| T4-107 | I-1 | II-42 | II-42c |
| T4-108 | I-1 | II-44 | II-42c |
| T4-109 | I-1 | II-50 | II-42c |
| T4-110 | I-1 | II-53 | II-42c |
| T4-111 | I-1 | II-60 | II-42c |
| T4-112 | I-1 | II-62 | II-42c |
| T4-113 | I-1 | II-66 | II-42c |
| T4-114 | I-1 | II-69 | II-42c |
| T4-115 | I-1 | II-70 | II-42c |
| T4-116 | I-1 | II-71 | II-42c |
| T4-117 | I-1 | II-72 | II-42c |
| T4-118 | I-1 | II-74 | II-42c |
| T4-119 | I-1 | II-76 | II-42c |
| T4-120 | I-1 | II-78 | II-42c |
| T4-121 | I-1 | II-84 | II-42c |
| T4-122 | I-1 | II-85 | II-42c |
| T4-123 | I-1 | II-86 | II-42c |
| T4-124 | I-1 | II-92 | II-42c |
| T4-125 | I-2 | II-3 | II-11c |
| T4-126 | I-2 | II-5 | II-11c |
| T4-127 | I-2 | II-6 | II-11c |
| T4-128 | I-2 | II-7 | II-11c |
| T4-129 | I-2 | II-8 | II-11c |
| T4-130 | I-2 | II-11 | II-11c |
| T4-131 | I-2 | II-16 | II-11c |
| T4-132 | I-2 | II-21 | II-11c |
| T4-133 | I-2 | II-26 | II-11c |
| T4-134 | I-2 | II-32 | II-11c |
| T4-135 | I-2 | II-33 | II-11c |
| T4-136 | I-2 | II-37 | II-11c |
| T4-137 | I-2 | II-39 | II-11c |
| T4-138 | I-2 | II-42 | II-11c |
| T4-139 | I-2 | II-44 | II-11c |
| T4-140 | I-2 | II-50 | II-11c |
| T4-141 | I-2 | II-53 | II-11c |
| T4-142 | I-2 | II-60 | II-11c |
| T4-143 | I-2 | II-62 | II-11c |
| T4-144 | I-2 | II-66 | II-11c |
| T4-145 | I-2 | II-69 | II-11c |
| T4-146 | I-2 | II-70 | II-11c |
| T4-147 | I-2 | II-71 | II-11c |
| T4-148 | I-2 | II-72 | II-11c |
| T4-149 | I-2 | II-74 | II-11c |
| T4-150 | I-2 | II-76 | II-11c |
| T4-151 | I-2 | II-78 | II-11c |
| T4-152 | I-2 | II-84 | II-11c |
| T4-153 | I-2 | II-85 | II-11c |
| T4-154 | I-2 | II-86 | II-11c |
| T4-155 | I-2 | II-92 | II-11c |
| T4-156 | I-2 | II-3 | II-20c |
| T4-157 | I-2 | II-5 | II-20c |
| T4-158 | I-2 | II-6 | II-20c |
| T4-159 | I-2 | II-7 | II-20c |
| T4-160 | I-2 | II-8 | II-20c |
| T4-161 | I-2 | II-11 | II-20c |
| T4-162 | I-2 | II-16 | II-20c |
| T4-163 | I-2 | II-21 | II-20c |
| T4-164 | I-2 | II-26 | II-20c |
| T4-165 | I-2 | II-32 | II-20c |
| T4-166 | I-2 | II-33 | II-20c |
| T4-167 | I-2 | II-37 | II-20c |
| T4-168 | I-2 | II-39 | II-20c |
| T4-169 | I-2 | II-42 | II-20c |
| T4-170 | I-2 | II-44 | II-20c |
| T4-171 | I-2 | II-50 | II-20c |
| T4-172 | I-2 | II-53 | II-20c |
| T4-173 | I-2 | II-60 | II-20c |
| T4-174 | I-2 | II-62 | II-20c |
| T4-175 | I-2 | II-66 | II-20c |
| T4-176 | I-2 | II-69 | II-20c |
| T4-177 | I-2 | II-70 | II-20c |
| T4-178 | I-2 | II-71 | II-20c |
| T4-179 | I-2 | II-72 | II-20c |
| T4-180 | I-2 | II-74 | II-20c |
| T4-181 | I-2 | II-76 | II-20c |
| T4-182 | I-2 | II-78 | II-20c |
| T4-183 | I-2 | II-84 | II-20c |
| T4-184 | I-2 | II-85 | II-20c |
| T4-185 | I-2 | II-86 | II-20c |
| T4-186 | I-2 | II-92 | II-20c |
| T4-187 | I-2 | II-3 | II-24c |
| T4-188 | I-2 | II-5 | II-24c |
| T4-189 | I-2 | II-6 | II-24c |
| T4-190 | I-2 | II-7 | II-24c |
| T4-191 | I-2 | II-8 | II-24c |
| T4-192 | I-2 | II-11 | II-24c |
| T4-193 | I-2 | II-16 | II-24c |
| T4-194 | I-2 | II-21 | II-24c |
| T4-195 | I-2 | II-26 | II-24c |
| T4-196 | I-2 | II-32 | II-24c |
| T4-197 | I-2 | II-33 | II-24c |
| T4-198 | I-2 | II-37 | II-24c |
| T4-199 | I-2 | II-39 | II-24c |
| T4-200 | I-2 | II-42 | II-24c |
| T4-201 | I-2 | II-44 | II-24c |
| T4-202 | I-2 | II-50 | II-24c |
| T4-203 | I-2 | II-53 | II-24c |
| T4-204 | I-2 | II-60 | II-24c |
| T4-205 | I-2 | II-62 | II-24c |
| T4-206 | I-2 | II-66 | II-24c |
| T4-207 | I-2 | II-69 | II-24c |
| T4-208 | I-2 | II-70 | II-24c |
| T4-209 | I-2 | II-71 | II-24c |
| T4-210 | I-2 | II-72 | II-24c |
| T4-211 | I-2 | II-74 | II-24c |
| T4-212 | I-2 | II-76 | II-24c |
| T4-213 | I-2 | II-78 | II-24c |
| T4-214 | I-2 | II-84 | II-24c |
| T4-215 | I-2 | II-85 | II-24c |
| T4-216 | I-2 | II-86 | II-24c |
| T4-217 | I-2 | II-92 | II-24c |
| T4-218 | I-2 | II-3 | II-42c |
| T4-219 | I-2 | II-5 | II-42c |
| T4-220 | I-2 | II-6 | II-42c |
| T4-221 | I-2 | II-7 | II-42c |
| T4-222 | I-2 | II-8 | II-42c |
| T4-223 | I-2 | II-11 | II-42c |
| T4-224 | I-2 | II-16 | II-42c |
| T4-225 | I-2 | II-21 | II-42c |
| T4-226 | I-2 | II-26 | II-42c |
| T4-227 | I-2 | II-32 | II-42c |
| T4-228 | I-2 | II-33 | II-42c |
| T4-229 | I-2 | II-37 | II-42c |
| T4-230 | I-2 | II-39 | II-42c |
| T4-231 | I-2 | II-42 | II-42c |
| T4-232 | I-2 | II-44 | II-42c |
| T4-233 | I-2 | II-50 | II-42c |
| T4-234 | I-2 | II-53 | II-42c |
| T4-235 | I-2 | II-60 | II-42c |
| T4-236 | I-2 | II-62 | II-42c |
| T4-237 | I-2 | II-66 | II-42c |
| T4-238 | I-2 | II-69 | II-42c |
| T4-239 | I-2 | II-70 | II-42c |
| T4-240 | I-2 | II-71 | II-42c |
| T4-241 | I-2 | II-72 | II-42c |
| T4-242 | I-2 | II-74 | II-42c |
| T4-243 | I-2 | II-76 | II-42c |
| T4-244 | I-2 | II-78 | II-42c |

TABLE T4-continued

| composition | I | II | III |
|---|---|---|---|
| T4-245 | I-2 | II-84 | II-42c |
| T4-246 | I-2 | II-85 | II-42c |
| T4-247 | I-2 | II-86 | II-42c |
| T4-248 | I-2 | II-92 | II-42c |
| T4-249 | I-5 | II-3 | II-11c |
| T4-250 | I-5 | II-5 | II-11c |
| T4-251 | I-5 | II-6 | II-11c |
| T4-252 | I-5 | II-7 | II-11c |
| T4-253 | I-5 | II-8 | II-11c |
| T4-254 | I-5 | II-11 | II-11c |
| T4-255 | I-5 | II-16 | II-11c |
| T4-256 | I-5 | II-21 | II-11c |
| T4-257 | I-5 | II-26 | II-11c |
| T4-258 | I-5 | II-32 | II-11c |
| T4-259 | I-5 | II-33 | II-11c |
| T4-260 | I-5 | II-37 | II-11c |
| T4-261 | I-5 | II-39 | II-11c |
| T4-262 | I-5 | II-42 | II-11c |
| T4-263 | I-5 | II-44 | II-11c |
| T4-264 | I-5 | II-50 | II-11c |
| T4-265 | I-5 | II-53 | II-11c |
| T4-266 | I-5 | II-60 | II-11c |
| T4-267 | I-5 | II-62 | II-11c |
| T4-268 | I-5 | II-66 | II-11c |
| T4-269 | I-5 | II-69 | II-11c |
| T4-270 | I-5 | II-70 | II-11c |
| T4-271 | I-5 | II-71 | II-11c |
| T4-272 | I-5 | II-72 | II-11c |
| T4-273 | I-5 | II-74 | II-11c |
| T4-274 | I-5 | II-76 | II-11c |
| T4-275 | I-5 | II-78 | II-11c |
| T4-276 | I-5 | II-84 | II-11c |
| T4-277 | I-5 | II-85 | II-11c |
| T4-278 | I-5 | II-86 | II-11c |
| T4-279 | I-5 | II-92 | II-11c |
| T4-280 | I-5 | II-3 | II-20c |
| T4-281 | I-5 | II-5 | II-20c |
| T4-282 | I-5 | II-6 | II-20c |
| T4-283 | I-5 | II-7 | II-20c |
| T4-284 | I-5 | II-8 | II-20c |
| T4-285 | I-5 | II-11 | II-20c |
| T4-286 | I-5 | II-16 | II-20c |
| T4-287 | I-5 | II-21 | II-20c |
| T4-288 | I-5 | II-26 | II-20c |
| T4-289 | I-5 | II-32 | II-20c |
| T4-290 | I-5 | II-33 | II-20c |
| T4-291 | I-5 | II-37 | II-20c |
| T4-292 | I-5 | II-39 | II-20c |
| T4-293 | I-5 | II-42 | II-20c |
| T4-294 | I-5 | II-44 | II-20c |
| T4-295 | I-5 | II-50 | II-20c |
| T4-296 | I-5 | II-53 | II-20c |
| T4-297 | I-5 | II-60 | II-20c |
| T4-298 | I-5 | II-62 | II-20c |
| T4-299 | I-5 | II-66 | II-20c |
| T4-300 | I-5 | II-69 | II-20c |
| T4-301 | I-5 | II-70 | II-20c |
| T4-302 | I-5 | II-71 | II-20c |
| T4-303 | I-5 | II-72 | II-20c |
| T4-304 | I-5 | II-74 | II-20c |
| T4-305 | I-5 | II-76 | II-20c |
| T4-306 | I-5 | II-78 | II-20c |
| T4-307 | I-5 | II-84 | II-20c |
| T4-308 | I-5 | II-85 | II-20c |
| T4-309 | I-5 | II-86 | II-20c |
| T4-310 | I-5 | II-92 | II-20c |
| T4-311 | I-5 | II-3 | II-24c |
| T4-312 | I-5 | II-5 | II-24c |
| T4-313 | I-5 | II-6 | II-24c |
| T4-314 | I-5 | II-7 | II-24c |
| T4-315 | I-5 | II-8 | II-24c |
| T4-316 | I-5 | II-11 | II-24c |
| T4-317 | I-5 | II-16 | II-24c |
| T4-318 | I-5 | II-21 | II-24c |
| T4-319 | I-5 | II-26 | II-24c |
| T4-320 | I-5 | II-32 | II-24c |
| T4-321 | I-5 | II-33 | II-24c |
| T4-322 | I-5 | II-37 | II-24c |
| T4-323 | I-5 | II-39 | II-24c |
| T4-324 | I-5 | II-42 | II-24c |
| T4-325 | I-5 | II-44 | II-24c |
| T4-326 | I-5 | II-50 | II-24c |
| T4-327 | I-5 | II-53 | II-24c |
| T4-328 | I-5 | II-60 | II-24c |
| T4-329 | I-5 | II-62 | II-24c |
| T4-330 | I-5 | II-66 | II-24c |
| T4-331 | I-5 | II-69 | II-24c |
| T4-332 | I-5 | II-70 | II-24c |
| T4-333 | I-5 | II-71 | II-24c |
| T4-334 | I-5 | II-72 | II-24c |
| T4-335 | I-5 | II-74 | II-24c |
| T4-336 | I-5 | II-76 | II-24c |
| T4-337 | I-5 | II-78 | II-24c |
| T4-338 | I-5 | II-84 | II-24c |
| T4-339 | I-5 | II-85 | II-24c |
| T4-340 | I-5 | II-86 | II-24c |
| T4-341 | I-5 | II-92 | II-24c |
| T4-342 | I-5 | II-3 | II-42c |
| T4-343 | I-5 | II-5 | II-42c |
| T4-344 | I-5 | II-6 | II-42c |
| T4-345 | I-5 | II-7 | II-42c |
| T4-346 | I-5 | II-8 | II-42c |
| T4-347 | I-5 | II-11 | II-42c |
| T4-348 | I-5 | II-16 | II-42c |
| T4-349 | I-5 | II-21 | II-42c |
| T4-350 | I-5 | II-26 | II-42c |
| T4-351 | I-5 | II-32 | II-42c |
| T4-352 | I-5 | II-33 | II-42c |
| T4-353 | I-5 | II-37 | II-42c |
| T4-354 | I-5 | II-39 | II-42c |
| T4-355 | I-5 | II-42 | II-42c |
| T4-356 | I-5 | II-44 | II-42c |
| T4-357 | I-5 | II-50 | II-42c |
| T4-358 | I-5 | II-53 | II-42c |
| T4-359 | I-5 | II-60 | II-42c |
| T4-360 | I-5 | II-62 | II-42c |
| T4-361 | I-5 | II-66 | II-42c |
| T4-362 | I-5 | II-69 | II-42c |
| T4-363 | I-5 | II-70 | II-42c |
| T4-364 | I-5 | II-71 | II-42c |
| T4-365 | I-5 | II-72 | II-42c |
| T4-366 | I-5 | II-74 | II-42c |
| T4-367 | I-5 | II-76 | II-42c |
| T4-368 | I-5 | II-78 | II-42c |
| T4-369 | I-5 | II-84 | II-42c |
| T4-370 | I-5 | II-85 | II-42c |
| T4-371 | I-5 | II-86 | II-42c |
| T4-372 | I-5 | II-92 | II-42c |
| T4-373 | I-3 | II-3 | II-11c |
| T4-374 | I-3 | II-5 | II-11c |
| T4-375 | I-3 | II-6 | II-11c |
| T4-376 | I-3 | II-7 | II-11c |
| T4-377 | I-3 | II-8 | II-11c |
| T4-378 | I-3 | II-11 | II-11c |
| T4-379 | I-3 | II-16 | II-11c |
| T4-380 | I-3 | II-21 | II-11c |
| T4-381 | I-3 | II-26 | II-11c |
| T4-382 | I-3 | II-32 | II-11c |
| T4-383 | I-3 | II-33 | II-11c |
| T4-384 | I-3 | II-37 | II-11c |
| T4-385 | I-3 | II-39 | II-11c |
| T4-386 | I-3 | II-42 | II-11c |
| T4-387 | I-3 | II-44 | II-11c |
| T4-388 | I-3 | II-50 | II-11c |
| T4-389 | I-3 | II-53 | II-11c |
| T4-390 | I-3 | II-60 | II-11c |
| T4-391 | I-3 | II-62 | II-11c |
| T4-392 | I-3 | II-66 | II-11c |
| T4-393 | I-3 | II-69 | II-11c |
| T4-394 | I-3 | II-70 | II-11c |
| T4-395 | I-3 | II-71 | II-11c |
| T4-396 | I-3 | II-72 | II-11c |
| T4-397 | I-3 | II-74 | II-11c |
| T4-398 | I-3 | II-76 | II-11c |
| T4-399 | I-3 | II-78 | II-11c |
| T4-400 | I-3 | II-84 | II-11c |

TABLE T4-continued

| composition | I | II | III |
|---|---|---|---|
| T4-401 | I-3 | II-85 | II-11c |
| T4-402 | I-3 | II-86 | II-11c |
| T4-403 | I-3 | II-92 | II-11c |
| T4-404 | I-3 | II-3 | II-20c |
| T4-405 | I-3 | II-5 | II-20c |
| T4-406 | I-3 | II-6 | II-20c |
| T4-407 | I-3 | II-7 | II-20c |
| T4-408 | I-3 | II-8 | II-20c |
| T4-409 | I-3 | II-11 | II-20c |
| T4-410 | I-3 | II-16 | II-20c |
| T4-411 | I-3 | II-21 | II-20c |
| T4-412 | I-3 | II-26 | II-20c |
| T4-413 | I-3 | II-32 | II-20c |
| T4-414 | I-3 | II-33 | II-20c |
| T4-415 | I-3 | II-37 | II-20c |
| T4-416 | I-3 | II-39 | II-20c |
| T4-417 | I-3 | II-42 | II-20c |
| T4-418 | I-3 | II-44 | II-20c |
| T4-419 | I-3 | II-50 | II-20c |
| T4-420 | I-3 | II-53 | II-20c |
| T4-421 | I-3 | II-60 | II-20c |
| T4-422 | I-3 | II-62 | II-20c |
| T4-423 | I-3 | II-66 | II-20c |
| T4-424 | I-3 | II-69 | II-20c |
| T4-425 | I-3 | II-70 | II-20c |
| T4-426 | I-3 | II-71 | II-20c |
| T4-427 | I-3 | II-72 | II-20c |
| T4-428 | I-3 | II-74 | II-20c |
| T4-429 | I-3 | II-76 | II-20c |
| T4-430 | I-3 | II-78 | II-20c |
| T4-431 | I-3 | II-84 | II-20c |
| T4-432 | I-3 | II-85 | II-20c |
| T4-433 | I-3 | II-86 | II-20c |
| T4-434 | I-3 | II-92 | II-20c |
| T4-435 | I-3 | II-3 | II-24c |
| T4-436 | I-3 | II-5 | II-24c |
| T4-437 | I-3 | II-6 | II-24c |
| T4-438 | I-3 | II-7 | II-24c |
| T4-439 | I-3 | II-8 | II-24c |
| T4-440 | I-3 | II-11 | II-24c |
| T4-441 | I-3 | II-16 | II-24c |
| T4-442 | I-3 | II-21 | II-24c |
| T4-443 | I-3 | II-26 | II-24c |
| T4-444 | I-3 | II-32 | II-24c |
| T4-445 | I-3 | II-33 | II-24c |
| T4-446 | I-3 | II-37 | II-24c |
| T4-447 | I-3 | II-39 | II-24c |
| T4-448 | I-3 | II-42 | II-24c |
| T4-449 | I-3 | II-44 | II-24c |
| T4-450 | I-3 | II-50 | II-24c |
| T4-451 | I-3 | II-53 | II-24c |
| T4-452 | I-3 | II-60 | II-24c |
| T4-453 | I-3 | II-62 | II-24c |
| T4-454 | I-3 | II-66 | II-24c |
| T4-455 | I-3 | II-69 | II-24c |
| T4-456 | I-3 | II-70 | II-24c |
| T4-457 | I-3 | II-71 | II-24c |
| T4-458 | I-3 | II-72 | II-24c |
| T4-459 | I-3 | II-74 | II-24c |
| T4-460 | I-3 | II-76 | II-24c |
| T4-461 | I-3 | II-78 | II-24c |
| T4-462 | I-3 | II-84 | II-24c |
| T4-463 | I-3 | II-85 | II-24c |
| T4-464 | I-3 | II-86 | II-24c |
| T4-465 | I-3 | II-92 | II-24c |
| T4-466 | I-3 | II-3 | II-42c |
| T4-467 | I-3 | II-5 | II-42c |
| T4-468 | I-3 | II-6 | II-42c |
| T4-469 | I-3 | II-7 | II-42c |
| T4-470 | I-3 | II-8 | II-42c |
| T4-471 | I-3 | II-11 | II-42c |
| T4-472 | I-3 | II-16 | II-42c |
| T4-473 | I-3 | II-21 | II-42c |
| T4-474 | I-3 | II-26 | II-42c |
| T4-475 | I-3 | II-32 | II-42c |
| T4-476 | I-3 | II-33 | II-42c |
| T4-477 | I-3 | II-37 | II-42c |
| T4-478 | I-3 | II-39 | II-42c |
| T4-479 | I-3 | II-42 | II-42c |
| T4-480 | I-3 | II-44 | II-42c |
| T4-481 | I-3 | II-50 | II-42c |
| T4-482 | I-3 | II-53 | II-42c |
| T4-483 | I-3 | II-60 | II-42c |
| T4-484 | I-3 | II-62 | II-42c |
| T4-485 | I-3 | II-66 | II-42c |
| T4-486 | I-3 | II-69 | II-42c |
| T4-487 | I-3 | II-70 | II-42c |
| T4-488 | I-3 | II-71 | II-42c |
| T4-489 | I-3 | II-72 | II-42c |
| T4-490 | I-3 | II-74 | II-42c |
| T4-491 | I-3 | II-76 | II-42c |
| T4-492 | I-3 | II-78 | II-42c |
| T4-493 | I-3 | II-84 | II-42c |
| T4-494 | I-3 | II-85 | II-42c |
| T4-495 | I-3 | II-86 | II-42c |
| T4-496 | I-3 | II-92 | II-42c |
| T4-497 | I-4 | II-3 | II-11c |
| T4-498 | I-4 | II-5 | II-11c |
| T4-499 | I-4 | II-6 | II-11c |
| T4-500 | I-4 | II-7 | II-11c |
| T4-501 | I-4 | II-8 | II-11c |
| T4-502 | I-4 | II-11 | II-11c |
| T4-503 | I-4 | II-16 | II-11c |
| T4-504 | I-4 | II-21 | II-11c |
| T4-505 | I-4 | II-26 | II-11c |
| T4-506 | I-4 | II-32 | II-11c |
| T4-507 | I-4 | II-33 | II-11c |
| T4-508 | I-4 | II-37 | II-11c |
| T4-509 | I-4 | II-39 | II-11c |
| T4-510 | I-4 | II-42 | II-11c |
| T4-511 | I-4 | II-44 | II-11c |
| T4-512 | I-4 | II-50 | II-11c |
| T4-513 | I-4 | II-53 | II-11c |
| T4-514 | I-4 | II-60 | II-11c |
| T4-515 | I-4 | II-62 | II-11c |
| T4-516 | I-4 | II-66 | II-11c |
| T4-517 | I-4 | II-69 | II-11c |
| T4-518 | I-4 | II-70 | II-11c |
| T4-519 | I-4 | II-71 | II-11c |
| T4-520 | I-4 | II-72 | II-11c |
| T4-521 | I-4 | II-74 | II-11c |
| T4-522 | I-4 | II-76 | II-11c |
| T4-523 | I-4 | II-78 | II-11c |
| T4-524 | I-4 | II-84 | II-11c |
| T4-525 | I-4 | II-85 | II-11c |
| T4-526 | I-4 | II-86 | II-11c |
| T4-527 | I-4 | II-92 | II-11c |
| T4-528 | I-4 | II-3 | II-20c |
| T4-529 | I-4 | II-5 | II-20c |
| T4-530 | I-4 | II-6 | II-20c |
| T4-531 | I-4 | II-7 | II-20c |
| T4-532 | I-4 | II-8 | II-20c |
| T4-533 | I-4 | II-11 | II-20c |
| T4-534 | I-4 | II-16 | II-20c |
| T4-535 | I-4 | II-21 | II-20c |
| T4-536 | I-4 | II-26 | II-20c |
| T4-537 | I-4 | II-32 | II-20c |
| T4-538 | I-4 | II-33 | II-20c |
| T4-539 | I-4 | II-37 | II-20c |
| T4-540 | I-4 | II-39 | II-20c |
| T4-541 | I-4 | II-42 | II-20c |
| T4-542 | I-4 | II-44 | II-20c |
| T4-543 | I-4 | II-50 | II-20c |
| T4-544 | I-4 | II-53 | II-20c |
| T4-545 | I-4 | II-60 | II-20c |
| T4-546 | I-4 | II-62 | II-20c |
| T4-547 | I-4 | II-66 | II-20c |
| T4-548 | I-4 | II-69 | II-20c |
| T4-549 | I-4 | II-70 | II-20c |
| T4-550 | I-4 | II-71 | II-20c |
| T4-551 | I-4 | II-72 | II-20c |
| T4-552 | I-4 | II-74 | II-20c |
| T4-553 | I-4 | II-76 | II-20c |
| T4-554 | I-4 | II-78 | II-20c |
| T4-555 | I-4 | II-84 | II-20c |
| T4-556 | I-4 | II-85 | II-20c |

TABLE T4-continued

| composition | I | II | III |
|---|---|---|---|
| T4-557 | I-4 | II-86 | II-20c |
| T4-558 | I-4 | II-92 | II-20c |
| T4-559 | I-4 | II-3 | II-24c |
| T4-560 | I-4 | II-5 | II-24c |
| T4-561 | I-4 | II-6 | II-24c |
| T4-562 | I-4 | II-7 | II-24c |
| T4-563 | I-4 | II-8 | II-24c |
| T4-564 | I-4 | II-11 | II-24c |
| T4-565 | I-4 | II-16 | II-24c |
| T4-566 | I-4 | II-21 | II-24c |
| T4-567 | I-4 | II-26 | II-24c |
| T4-568 | I-4 | II-32 | II-24c |
| T4-569 | I-4 | II-33 | II-24c |
| T4-570 | I-4 | II-37 | II-24c |
| T4-571 | I-4 | II-39 | II-24c |
| T4-572 | I-4 | II-42 | II-24c |
| T4-573 | I-4 | II-44 | II-24c |
| T4-574 | I-4 | II-50 | II-24c |
| T4-575 | I-4 | II-53 | II-24c |
| T4-576 | I-4 | II-60 | II-24c |
| T4-577 | I-4 | II-62 | II-24c |
| T4-578 | I-4 | II-66 | II-24c |
| T4-579 | I-4 | II-69 | II-24c |
| T4-580 | I-4 | II-70 | II-24c |
| T4-581 | I-4 | II-71 | II-24c |
| T4-582 | I-4 | II-72 | II-24c |
| T4-583 | I-4 | II-74 | II-24c |
| T4-584 | I-4 | II-76 | II-24c |
| T4-585 | I-4 | II-78 | II-24c |
| T4-586 | I-4 | II-84 | II-24c |
| T4-587 | I-4 | II-85 | II-24c |
| T4-588 | I-4 | II-86 | II-24c |
| T4-589 | I-4 | II-92 | II-24c |
| T4-590 | I-4 | II-3 | II-42c |
| T4-591 | I-4 | II-5 | II-42c |
| T4-592 | I-4 | II-6 | II-42c |
| T4-593 | I-4 | II-7 | II-42c |
| T4-594 | I-4 | II-8 | II-42c |
| T4-595 | I-4 | II-11 | II-42c |
| T4-596 | I-4 | II-16 | II-42c |
| T4-597 | I-4 | II-21 | II-42c |
| T4-598 | I-4 | II-26 | II-42c |
| T4-599 | I-4 | II-32 | II-42c |
| T4-600 | I-4 | II-33 | II-42c |
| T4-601 | I-4 | II-37 | II-42c |
| T4-602 | I-4 | II-39 | II-42c |
| T4-603 | I-4 | II-42 | II-42c |
| T4-604 | I-4 | II-44 | II-42c |
| T4-605 | I-4 | II-50 | II-42c |
| T4-606 | I-4 | II-53 | II-42c |
| T4-607 | I-4 | II-60 | II-42c |
| T4-608 | I-4 | II-62 | II-42c |
| T4-609 | I-4 | II-66 | II-42c |
| T4-610 | I-4 | II-69 | II-42c |
| T4-611 | I-4 | II-70 | II-42c |
| T4-612 | I-4 | II-71 | II-42c |
| T4-613 | I-4 | II-72 | II-42c |
| T4-614 | I-4 | II-74 | II-42c |
| T4-615 | I-4 | II-76 | II-42c |
| T4-616 | I-4 | II-78 | II-42c |
| T4-617 | I-4 | II-84 | II-42c |
| T4-618 | I-4 | II-85 | II-42c |
| T4-619 | I-4 | II-86 | II-42c |
| T4-620 | I-4 | II-92 | II-42c |

Three-component compositions comprising another compound I as component I, a further specific fungicide compound as component II and an insecticide as component III.

| composition | I | II | III |
|---|---|---|---|
| T4-621 | I-13 | II-3 | II-11c |
| T4-622 | I-13 | II-5 | II-11c |
| T4-623 | I-13 | II-6 | II-11c |
| T4-624 | I-13 | II-7 | II-11c |
| T4-625 | I-13 | II-8 | II-11c |
| T4-626 | I-13 | II-11 | II-11c |
| T4-627 | I-13 | II-16 | II-11c |
| T4-628 | I-13 | II-21 | II-11c |
| T4-629 | I-13 | II-26 | II-11c |
| T4-630 | I-13 | II-32 | II-11c |
| T4-631 | I-13 | II-33 | II-11c |
| T4-632 | I-13 | II-37 | II-11c |
| T4-633 | I-13 | II-39 | II-11c |
| T4-634 | I-13 | II-42 | II-11c |
| T4-635 | I-13 | II-44 | II-11c |
| T4-636 | I-13 | II-50 | II-11c |
| T4-637 | I-13 | II-53 | II-11c |
| T4-638 | I-13 | II-60 | II-11c |
| T4-639 | I-13 | II-62 | II-11c |
| T4-640 | I-13 | II-66 | II-11c |
| T4-641 | I-13 | II-69 | II-11c |
| T4-642 | I-13 | II-70 | II-11c |
| T4-643 | I-13 | II-71 | II-11c |
| T4-644 | I-13 | II-72 | II-11c |
| T4-645 | I-13 | II-74 | II-11c |
| T4-646 | I-13 | II-76 | II-11c |
| T4-647 | I-13 | II-78 | II-11c |
| T4-648 | I-13 | II-84 | II-11c |
| T4-649 | I-13 | II-85 | II-11c |
| T4-650 | I-13 | II-86 | II-11c |
| T4-651 | I-13 | II-92 | II-11c |
| T4-652 | I-13 | II-3 | II-20c |
| T4-653 | I-13 | II-5 | II-20c |
| T4-654 | I-13 | II-6 | II-20c |
| T4-655 | I-13 | II-7 | II-20c |
| T4-656 | I-13 | II-8 | II-20c |
| T4-657 | I-13 | II-11 | II-20c |
| T4-658 | I-13 | II-16 | II-20c |
| T4-659 | I-13 | II-21 | II-20c |
| T4-660 | I-13 | II-26 | II-20c |
| T4-661 | I-13 | II-32 | II-20c |
| T4-662 | I-13 | II-33 | II-20c |
| T4-663 | I-13 | II-37 | II-20c |
| T4-664 | I-13 | II-39 | II-20c |
| T4-665 | I-13 | II-42 | II-20c |
| T4-666 | I-13 | II-44 | II-20c |
| T4-667 | I-13 | II-50 | II-20c |
| T4-668 | I-13 | II-53 | II-20c |
| T4-669 | I-13 | II-60 | II-20c |
| T4-670 | I-13 | II-62 | II-20c |
| T4-671 | I-13 | II-66 | II-20c |
| T4-672 | I-13 | II-69 | II-20c |
| T4-673 | I-13 | II-70 | II-20c |
| T4-674 | I-13 | II-71 | II-20c |
| T4-675 | I-13 | II-72 | II-20c |
| T4-676 | I-13 | II-74 | II-20c |
| T4-677 | I-13 | II-76 | II-20c |
| T4-678 | I-13 | II-78 | II-20c |
| T4-679 | I-13 | II-84 | II-20c |
| T4-680 | I-13 | II-85 | II-20c |
| T4-681 | I-13 | II-86 | II-20c |
| T4-682 | I-13 | II-92 | II-20c |
| T4-683 | I-13 | II-3 | II-24c |
| T4-684 | I-13 | II-5 | II-24c |
| T4-685 | I-13 | II-6 | II-24c |
| T4-686 | I-13 | II-7 | II-24c |
| T4-687 | I-13 | II-8 | II-24c |
| T4-688 | I-13 | II-11 | II-24c |
| T4-689 | I-13 | II-16 | II-24c |
| T4-690 | I-13 | II-21 | II-24c |
| T4-691 | I-13 | II-26 | II-24c |
| T4-692 | I-13 | II-32 | II-24c |
| T4-693 | I-13 | II-33 | II-24c |
| T4-694 | I-13 | II-37 | II-24c |
| T4-695 | I-13 | II-39 | II-24c |
| T4-696 | I-13 | II-42 | II-24c |
| T4-697 | I-13 | II-44 | II-24c |
| T4-698 | I-13 | II-50 | II-24c |
| T4-699 | I-13 | II-53 | II-24c |
| T4-700 | I-13 | II-60 | II-24c |
| T4-701 | I-13 | II-62 | II-24c |
| T4-702 | I-13 | II-66 | II-24c |
| T4-703 | I-13 | II-69 | II-24c |
| T4-704 | I-13 | II-70 | II-24c |
| T4-705 | I-13 | II-71 | II-24c |
| T4-706 | I-13 | II-72 | II-24c |
| T4-707 | I-13 | II-74 | II-24c |
| T4-708 | I-13 | II-76 | II-24c |

TABLE T4-continued

| composition | I | II | III |
|---|---|---|---|
| T4-709 | I-13 | II-78 | II-24c |
| T4-710 | I-13 | II-84 | II-24c |
| T4-711 | I-13 | II-85 | II-24c |
| T4-712 | I-13 | II-86 | II-24c |
| T4-713 | I-13 | II-92 | II-24c |
| T4-714 | I-13 | II-3 | II-42c |
| T4-715 | I-13 | II-5 | II-42c |
| T4-716 | I-13 | II-6 | II-42c |
| T4-717 | I-13 | II-7 | II-42c |
| T4-718 | I-13 | II-8 | II-42c |
| T4-719 | I-13 | II-11 | II-42c |
| T4-720 | I-13 | II-16 | II-42c |
| T4-721 | I-13 | II-21 | II-42c |
| T4-722 | I-13 | II-26 | II-42c |
| T4-723 | I-13 | II-32 | II-42c |
| T4-724 | I-13 | II-33 | II-42c |
| T4-725 | I-13 | II-37 | II-42c |
| T4-726 | I-13 | II-39 | II-42c |
| T4-727 | I-13 | II-42 | II-42c |
| T4-728 | I-13 | II-44 | II-42c |
| T4-729 | I-13 | II-50 | II-42c |
| T4-730 | I-13 | II-53 | II-42c |
| T4-731 | I-13 | II-60 | II-42c |
| T4-732 | I-13 | II-62 | II-42c |
| T4-733 | I-13 | II-66 | II-42c |
| T4-734 | I-13 | II-69 | II-42c |
| T4-735 | I-13 | II-70 | II-42c |
| T4-736 | I-13 | II-71 | II-42c |
| T4-737 | I-13 | II-72 | II-42c |
| T4-738 | I-13 | II-74 | II-42c |
| T4-739 | I-13 | II-76 | II-42c |
| T4-740 | I-13 | II-78 | II-42c |
| T4-741 | I-13 | II-84 | II-42c |
| T4-742 | I-13 | II-85 | II-42c |
| T4-743 | I-13 | II-86 | II-42c |
| T4-744 | I-13 | II-92 | II-42c |

In table T4, according to particular embodiments of the invention, the respective component I is present as (S) enantiomer, wherein each row corresponds to one embodiment of the compositions according to the invention, i.e. one specific individualized composition. According to one specific aspect, these are ternary compositions which each only contain these two components as active compounds. Furthermore, also every combination of the compositions individualized in this table represent embodiments of the present invention (S) enantiomer.

In table T4, according to a further particular embodiments of the invention, the respective component I is present as (R) enantiomer, wherein each row corresponds to one embodiment of the compositions according to the invention, i.e. one specific individualized composition. According to one specific aspect, these are ternary compositions which each only contain these two components as active compounds. Furthermore, also every combination of the compositions individualized in this table represent embodiments of the present invention (R) enantiomer.

One further aspect of the present invention are novel two-component compositions comprising the component II and the component III as listed the above Table T4, i.e. the compositions given in the following Table BT4, as far as they are novel.

TABLE BT4

Two-component compositions comprising a fungicidal component II and an insecticide as component III. Each line of line BT4-1 to BT1-124 corresponds to one particular individidualized composition. Furthermore, also every combination of the compositions individualized in this table represent embodiments of the present invention.

| composition | II | III |
|---|---|---|
| BT4-1 | II-3 | II-11c |
| BT4-2 | II-5 | II-11c |
| BT4-3 | II-6 | II-11c |
| BT4-4 | II-7 | II-11c |
| BT4-5 | II-8 | II-11c |
| BT4-6 | II-11 | II-11c |
| BT4-7 | II-16 | II-11c |
| BT4-8 | II-21 | II-11c |
| BT4-9 | II-26 | II-11c |
| BT4-10 | II-32 | II-11c |
| BT4-11 | II-33 | II-11c |
| BT4-12 | II-37 | II-11c |
| BT4-13 | II-39 | II-11c |
| BT4-14 | II-42 | II-11c |
| BT4-15 | II-44 | II-11c |
| BT4-16 | II-50 | II-11c |
| BT4-17 | II-53 | II-11c |
| BT4-18 | II-60 | II-11c |
| BT4-19 | II-62 | II-11c |
| BT4-20 | II-66 | II-11c |
| BT4-21 | II-69 | II-11c |
| BT4-22 | II-70 | II-11c |
| BT4-23 | II-71 | II-11c |
| BT4-24 | II-72 | II-11c |
| BT4-25 | II-74 | II-11c |
| BT4-26 | II-76 | II-11c |
| BT4-27 | II-78 | II-11c |
| BT4-28 | II-84 | II-11c |
| BT4-29 | II-85 | II-11c |
| BT4-30 | II-86 | II-11c |
| BT4-31 | II-92 | II-11c |
| BT4-32 | II-3 | II-20c |
| BT4-33 | II-5 | II-20c |
| BT4-34 | II-6 | II-20c |
| BT4-35 | II-7 | II-20c |
| BT4-36 | II-8 | II-20c |
| BT4-37 | II-11 | II-20c |
| BT4-38 | II-16 | II-20c |
| BT4-39 | II-21 | II-20c |
| BT4-40 | II-26 | II-20c |
| BT4-41 | II-32 | II-20c |
| BT4-42 | II-33 | II-20c |
| BT4-43 | II-37 | II-20c |
| BT4-44 | II-39 | II-20c |
| BT4-45 | II-42 | II-20c |
| BT4-46 | II-44 | II-20c |
| BT4-47 | II-50 | II-20c |
| BT4-48 | II-53 | II-20c |
| BT4-49 | II-60 | II-20c |
| BT4-50 | II-62 | II-20c |
| BT4-51 | II-66 | II-20c |
| BT4-52 | II-69 | II-20c |
| BT4-53 | II-70 | II-20c |
| BT4-54 | II-71 | II-20c |
| BT4-55 | II-72 | II-20c |
| BT4-56 | II-74 | II-20c |
| BT4-57 | II-76 | II-20c |
| BT4-58 | II-78 | II-20c |
| BT4-59 | II-84 | II-20c |
| BT4-60 | II-85 | II-20c |
| BT4-61 | II-86 | II-20c |
| BT4-62 | II-92 | II-20c |
| BT4-63 | II-3 | II-24c |
| BT4-64 | II-5 | II-24c |
| BT4-65 | II-6 | II-24c |
| BT4-66 | II-7 | II-24c |
| BT4-67 | II-8 | II-24c |
| BT4-68 | II-11 | II-24c |
| BT4-69 | II-16 | II-24c |
| BT4-70 | II-21 | II-24c |
| BT4-71 | II-26 | II-24c |
| BT4-72 | II-32 | II-24c |

TABLE BT4-continued

Two-component compositions comprising a fungicidal component II and an insecticide as component III. Each line of line BT4-1 to BT1-124 corresponds to one particular individidualized composition. Furthermore, also every combination of the compositions individualized in this table represent embodiments of the present invention.

| composition | II | III |
| --- | --- | --- |
| BT4-73 | II-33 | II-24c |
| BT4-74 | II-37 | II-24c |
| BT4-75 | II-39 | II-24c |
| BT4-76 | II-42 | II-24c |
| BT4-77 | II-44 | II-24c |
| BT4-78 | II-50 | II-24c |
| BT4-79 | II-53 | II-24c |
| BT4-80 | II-60 | II-24c |
| BT4-81 | II-62 | II-24c |
| BT4-82 | II-66 | II-24c |
| BT4-83 | II-69 | II-24c |
| BT4-84 | II-70 | II-24c |
| BT4-85 | II-71 | II-24c |
| BT4-86 | II-72 | II-24c |
| BT4-87 | II-74 | II-24c |
| BT4-88 | II-76 | II-24c |
| BT4-89 | II-78 | II-24c |
| BT4-90 | II-84 | II-24c |
| BT4-91 | II-85 | II-24c |
| BT4-92 | II-86 | II-24c |
| BT4-93 | II-92 | II-24c |
| BT4-94 | II-3 | II-42c |
| BT4-95 | II-5 | II-42c |
| BT4-96 | II-6 | II-42c |
| BT4-97 | II-7 | II-42c |
| BT4-98 | II-8 | II-42c |
| BT4-99 | II-11 | II-42c |
| BT4-100 | II-16 | II-42c |
| BT4-101 | II-21 | II-42c |
| BT4-102 | II-26 | II-42c |
| BT4-103 | II-32 | II-42c |
| BT4-104 | II-33 | II-42c |
| BT4-105 | II-37 | II-42c |
| BT4-106 | II-39 | II-42c |
| BT4-107 | II-42 | II-42c |
| BT4-108 | II-44 | II-42c |
| BT4-109 | II-50 | II-42c |
| BT4-110 | II-53 | II-42c |
| BT4-111 | II-60 | II-42c |
| BT4-112 | II-62 | II-42c |
| BT4-113 | II-66 | II-42c |
| BT4-114 | II-69 | II-42c |
| BT4-115 | II-70 | II-42c |
| BT4-116 | II-71 | II-42c |
| BT4-117 | II-72 | II-42c |
| BT4-118 | II-74 | II-42c |
| BT4-119 | II-76 | II-42c |
| BT4-120 | II-78 | II-42c |
| BT4-121 | II-84 | II-42c |
| BT4-122 | II-85 | II-42c |
| BT4-123 | II-86 | II-42c |
| BT4-124 | II-92 | II-42c |

Particularly preferred compositions are the three-component compositions, wherein component I is as defined above, i.e a compound I, in particular a compound selected from compounds I-1, I-2, I-3, I-4, I-5, I-6, I-7, I-8, I-9, I-11, I-13, I-14, I-15 and I-16 or any group of compounds I detailed above, and component II is selected from the following insecticides

| | |
| --- | --- |
| II-11c | clothianidin |
| II-24c | imidacloprid |
| II-42c | thiamethoxam, | and component III is fipronil (compound II-20c).

Particularly preferred compositions of these compositions are compiled in Table T5, where each row corresponds to one embodiment of the compositions according to the invention, i.e. one specific individualized three-component composition. According to one specific aspect, these are ternary compositions which each only contain these three components as the active compound.

TABLE T5

| composition | I | II | III |
| --- | --- | --- | --- |

Three-component compositions comprising a component I, an insecticide compound as component II and fipronil as component III.

| | | | |
| --- | --- | --- | --- |
| T5-1 | I-1 | II-11c | II-20c |
| T5-2 | I-1 | II-24c | II-20c |
| T5-3 | I-1 | II-42c | II-20c |
| T5-4 | I-2 | II-11c | II-20c |
| T5-5 | I-2 | II-24c | II-20c |
| T5-6 | I-2 | II-42c | II-20c |
| T5-7 | I-3 | II-11c | II-20c |
| T5-8 | I-3 | II-24c | II-20c |
| T5-9 | I-3 | II-42c | II-20c |
| T5-10 | I-4 | II-11c | II-20c |
| T5-11 | I-4 | II-24c | II-20c |
| T5-12 | I-4 | II-42c | II-20c |
| T5-13 | I-5 | II-11c | II-20c |
| T5-14 | I-5 | II-24c | II-20c |
| T5-15 | I-5 | II-42c | II-20c |

Three-component compositions comprising another compound I as component I, an insecticide compound as component II and fipronil as component III.

| | | | |
| --- | --- | --- | --- |
| T5-16 | I-13 | II-11c | II-20c |
| T5-17 | I-13 | II-24c | II-20c |
| T5-18 | I-13 | II-42c | II-20c |

In table T5, according to particular embodiments of the invention, the respective component I is present as (S) enantiomer, wherein each row corresponds to one embodiment of the compositions according to the invention, i.e. one specific individualized composition. According to one specific aspect, these are ternary compositions which each only contain these two components as active compounds. Furthermore, also every combination of the compositions individualized in this table represent embodiments of the present invention (S) enantiomer.

In table T5, according to a further particular embodiments of the invention, the respective component I is present as (R) enantiomer, wherein each row corresponds to one embodiment of the compositions according to the invention, i.e. one specific individualized composition. According to one specific aspect, these are ternary compositions which each only contain these two components as active compounds. Furthermore, also every combination of the compositions individualized in this table represent embodiments of the present invention (R) enantiomer.

According to a further aspect, the present invention relates to four-component compositions, i.e. compositions comprising component I, i.e a compound I, in particular a compound selected from compounds I-1, I-2, I-3, I-4, I-5, I-6, I-7, I-8, I-9, I-11, I-13, I-14, I-15 and I-16 or any group of compounds I detailed above, a component II selected from groups A) to O), a component III selected from groups A) to O) and a component IV, also selected from groups A) to O), wherein components II, III and IV are different active ingredients. According to a specific embodiment thereof, exactly four active compounds as defined are present in these compositions (herein also called "quarternary compositions"). The composition may, of course, contain any kind of additive or the like as detailed below in order to provide a formulation suitable for use in agriculture.

In the four-component compositions of the invention, the weight ratio of component I to the $1^{st}$ further active compound (component II) depends on the properties of the active compounds in question and may particularly be 1000:1 to 1:1000, specifically 500:1 to 1:500. Preferably, it is in the range of from 1:100 to 100:1, preferably in the range of from 1:50 to 50:1 and in particular in the range of from 1:20 to 20:1. It may be preferable for the weight ratio to be in the region of from 1:10 to 10:1, preferably from 1:3 to 3:1, in particular from 1:2 to 2:1. The weight ratio of compound I to the $2^{nd}$ further active compound (component III) may particularly be 1000:1 to 1:1000, specifically 500:1 to 1:500. It is preferably in the range of from 1:100 to 100:1, preferably in the range of from 1:50 to 50:1 and in particular in the range of from 1:20 to 20:1. It may be preferable for the weight ratio to be in the region of from 1:10 to 10:1, preferably from 1:3 to 3:1, in particular from 1:2 to 2:1. The weight ratio of compound I to the 3rd further active compound (component IV) is preferably in the range of from 1:100 to 100:1, preferably in the range of from 1:50 to 50:1 and in particular in the range of from 1:20 to 20:1. It may be preferable for the weight ratio to be in the region of from 1:10 to 10:1, preferably from 1:3 to 3:1, in particular from 1:2 to 2:1. The weight ratio of $1^{st}$ further active compound (component II) to $2^{nd}$ further active compound (component III) may particularly be 1000:1 to 1:1000, specifically 500:1 to 1:500. It is preferably in the range of from 1:100 to 100:1, preferably in the range of from 1:50 to 50:1 and in particular in the range of from 2:10 to 20:1. It may be preferable for the weight ratio to be in the region of from 1:10 to 10:1, preferably from 1:3 to 3:1, in particular from 1:2 to 2:1. The weight ratio of $1^{st}$ further active compound (component II) to 3rd further active compound (component IV) is preferably in the range of from 1:100 to 100:1, preferably in the range of from 1:50 to 50:1 and in particular in the range of from 1:20 to 20:1. It may be preferable for the weight ratio to be in the region of from 1:10 to 10:1, preferably from 1:3 to 3:1, in particular from 1:2 to 2:1. The weight ratio of $2^{nd}$ further active compound (component III) to 3rd further active compound (component IV) may particularly be 1000:1 to 1:1000, specifically 500:1 to 1:500. It is preferably in the range of from 1:100 to 100:1, preferably in the range of from 1:50 to 50:1, and in particular in the range of from 1:20 to 20:1. It may be preferable for the weight ratio to be in the region of from 1:10 to 10:1, preferably from 1:3 to 3:1, in particular from 1:2 to 2:1.

According to one embodiment, the present invention relates to four-component compositions, comprising a component I, i.e a compound I, in particular a compound selected from compounds I-1, I-2, I-3, I-4, I-5, I-6, I-7, I-8, I-9, I-11, I-13, I-14, I-15 and I-16 or any group of compounds I detailed above, a component II selected from groups groups A) to K), a component III selected from groups A) to K) and a component IV selected from groups A) to K), wherein components II, III and IV are different active compounds.

One specific embodiment relates to four-component compositions, wherein component I is as defined above and component II is selected from group A) of the respiration inhibitors of complex III at $Q_o$ site, component III is selected from the group of B) of the sterol biosynthesis inhibitors (SBI fungicides) and component IV is selected from the respiration inhibitors of complex II. According to one specific embodiment thereof, component II is selected from the group of strobilurins. Specifically, component II is selected from the group consisting of azoxystrobin, dimoxystrobin, fluoxastrobin, kresoxim-methyl, orysastrobin, picoxystrobin, pyraclostrobin and trifloxystrobin. According to a further specific embodiment thereof, component III is selected from the group of the C14 demethylase inhibitors (DMI fungicides), in particular selected from cyproconazole, difenoconazole, epoxiconazole, fluquinconazole, flusilazole, flutriafol, metconazole, myclobutanil, penconazole, propiconazole, prothioconazole, triadimefon, triadimenol, tebuconazole, tetraconazole, triticonazole and prochloraz. According to a further specific embodiment thereof, component IV is selected from the group of the carboxamides, in particular selected from benodanil, benzovindiflupyr, bixafen, boscalid, carboxin, fenfuram, fluopyram, flutolanil, fluxapyroxad, furametpyr, isopyrazam, mepronil, oxycarboxin, penflufen, penthiopyrad, sedaxane, tecloftalam, thifluzamide, N-(4'-trifluoromethylthiobiphenyl-2-yl)-3-difluoromethyl-1-methyl-1H-pyrazole-4-carboxamide, N-(2-(1,3,3-trimethyl-butyl)-phenyl)-1,3-dimethyl-5-fluoro-1H-pyrazole-4-carboxamide, 3-(difluoromethyl)-1-methyl-N-(1,1,3-trimethylindan-4-yl)pyrazole-4-carboxamide, 3-(trifluoromethyl)-1-methyl-N-(1,1,3-trimethylindan-4-yl)pyrazole-4-carboxamide, 1,3-dimethyl-N-(1,1,3-trimethylindan-4-yl)pyrazole-4-carboxamide, 3-(trifluoromethyl)-1,5-dimethyl-N-(1,1,3-trimethylindan-4-yl)pyrazole-4-carboxamide, 3-(difluoromethyl)-1,5-dimethyl-N-(1,1,3-trimethylindan-4-yl)pyrazole-4-carboxamide and 1,3,5-trimethyl-N-(1,1,3-trimethylindan-4-yl)pyrazole-4-carboxamide, in particular selected from benzovindiflupyr, bixafen, boscalid, fluopyram, fluxapyroxad, isopyrazam, penflufen, penthiopyrad and sedaxane. According to a further specific embodiment, these are quarternary compositions which, as active compounds, comprise in each case only the mentioned four active components I, II, III and IV.

One further specific embodiment relates to four-component compositions, wherein component I is as defined above and component II is selected from group A) of the respiration inhibitors of complex III at $Q_o$ site, component III is selected from the group of B) of the sterol biosynthesis inhibitors (SBI fungicides) and component IV is selected from the Inhibitors with Multi Site Action. According to one specific embodiment thereof, component II is selected from the group of strobilurins. Specifically, component II is selected from the group consisting of azoxystrobin, dimoxystrobin, fluoxastrobin, kresoxim-methyl, orysastrobin, picoxystrobin, pyraclostrobin and trifloxystrobin. According to a further specific embodiment thereof, component III is selected from the group of the C14 demethylase inhibitors (DMI fungicides), in particular selected from cyproconazole, difenoconazole, epoxiconazole, fluquinconazole, flusilazole, flutriafol, metconazole, myclobutanil, penconazole, propiconazole, prothioconazole, triadimefon, triadimenol, tebuconazole, tetraconazole, triticonazole and prochloraz. According to a further specific embodiment thereof, component IV is selected from copper acetate, copper hydroxide, copper oxychloride, copper sulfate, sulfur, (tri)basic copper sulfate, mancozeb, maneb, metiram, propineb, thiram, captafol, folpet, chlorothalonil, dichlofluanid, dithianon and 2,6-dimethyl-1H,5H-[1,4]dithiino[2,3-c:5,6-c']dipyrrole-1,3,5,7(2H,6H)-tetraone, in particular chlorothalonil. According to a further specific embodiment, these are quarternary compositions which, as active compounds, comprise in each case only the mentioned four active components I, II, III and IV.

One further specific embodiment relates to four-component compositions, wherein component I is as defined above and component II is selected from group A) of the respiration inhibitors of complex III at $Q_o$ site, component III is selected from the group of B) of the respiration inhibitors of complex II and component IV is selected IV is selected from the Inhibitors with Multi Site Action. According to one specific embodiment thereof, component II is selected from the group of strobilurins. Specifically, component II is selected from the group consisting of azoxystrobin, dimoxystrobin, fluoxastrobin, kresoxim-methyl, orysastrobin, picoxystrobin, pyraclostrobin and trifloxystrobin. According to a further specific embodiment thereof, component III is selected from the group of the carboxamides, in particular selected from benodanil, benzovindiflupyr, bixafen, boscalid, carboxin, fenfuram, fluopyram, flutolanil, fluxapyroxad, furametpyr, isopyrazam, mepronil, oxycarboxin, penflufen, penthiopyrad, sedaxane, tecloftalam, thifluzamide, N-(4'-trifluoromethylthiobiphenyl-2-yl)-3-difluoromethyl-1-methyl-1H-pyrazole-4-carboxamide, N-(2-(1,3,3-trimethyl-butyl)-phenyl)-1,3-dimethyl-5-fluoro-1H-pyrazole-4-carboxamide, 3-(difluoromethyl)-1-methyl-N-(1,1,3-trimethylindan-4-yl)pyrazole-4-carboxamide, 3-(trifluoromethyl)-1-methyl-N-(1,1,3-trimethyl-indan-4-yl)pyrazole-4-carboxamide, 1,3-dimethyl-N-(1,1,3-trimethylindan-4-yl)pyrazole-4-carboxamide, 3-(trifluoromethyl)-1,5-dimethyl-N-(1,1,3-trimethylindan-4-yl)pyrazole-4-carboxamide, 3-(difluoromethyl)-1,5-dimethyl-N-(1,1,3-trimethylindan-4-yl)pyrazole-4-carboxamide and 1,3,5-trimethyl-N-(1,1,3-trimethylindan-4-yl)pyrazole-4-carboxamide, in particular selected from benzovindiflupyr, bixafen, boscalid, fluopyram, fluxapyroxad, isopyrazam, penflufen, penthiopyrad and sedaxane. According to a further specific embodiment thereof, component IV is chlorothalonil According to a further specific embodiment, these are quarternary compositions which, as active compounds, comprise in each case only the mentioned four active components I, II, III and IV.

One further specific embodiment relates to four-component compositions, wherein component I is as defined above, component II is selected from group A) of the respiration inhibitors of complex III at $Q_o$ site, component III is selected from the group of B) of the respiration inhibitors of complex II and component IV is selected from the Sterol biosynthesis inhibitors (SBI fungicides), in particular Delta14-reductase inhibitors. According to one specific embodiment thereof, component II is selected from the group of strobilurins. Specifically, component II is selected from the group consisting of azoxystrobin, dimoxystrobin, fluoxastrobin, kresoxim-methyl, orysastrobin, picoxystrobin, pyraclostrobin and trifloxystrobin. According to a further specific embodiment thereof, component III is selected from the group of the carboxamides, in particular selected from benodanil, benzovindiflupyr, bixafen, boscalid, carboxin, fenfuram, fluopyram, flutolanil, fluxapyroxad, furametpyr, isopyrazam, mepronil, oxycarboxin, penflufen, penthiopyrad, sedaxane, tecloftalam, thifluzamide, N-(4'-trifluoromethylthiobiphenyl-2-yl)-3-difluoromethyl-1-methyl-1H-pyrazole-4-carboxamide, N-(2-(1,3,3-trimethyl-butyl)-phenyl)-1,3-dimethyl-5-fluoro-1H-pyrazole-4-carboxamide, 3-(difluoromethyl)-1-methyl-N-(1,1,3-trimethylindan-4-yl)pyrazole-4-carboxamide, 3-(trifluoromethyl)-1-methyl-N-(1,1,3-trimethylindan-4-yl)pyrazole-4-carboxamide, 1,3-dimethyl-N-(1,1,3-trimethylindan-4-yl)pyrazole-4-carboxamide, 3-(trifluoromethyl)-1,5-dimethyl-N-(1,1,3-trimethylindan-4-yl)pyrazole-4-carboxamide, 3-(difluoromethyl)-1,5-dimethyl-N-(1,1,3-trimethylindan-4-yl)pyrazole-4-carboxamide and 1,3,5-trimethyl-N-(1,1,3-trimethylindan-4-yl)pyrazole-4-carboxamide, in particular selected from benzovindiflupyr, bixafen, boscalid, fluopyram, fluxapyroxad, isopyrazam, penflufen, penthiopyrad and sedaxane. According to a further specific embodiment thereof, component IV is fenpropimorph According to a further specific embodiment, these are quarternary compositions which, as active compounds, comprise in each case only the mentioned four active components I, II, III and IV.

One further specific embodiment relates to four-component compositions, wherein component I is as defined above, component II is selected from group A) of the respiration inhibitors of complex III at $Q_o$ site, component III is selected from the group of B) of the respiration inhibitors of complex II and component IV is selected from the from the Inhibitors of cell division and cytoskeleton. According to one specific embodiment thereof, component II is selected from the group of strobilurins. Specifically, component II is selected from the group consisting of azoxystrobin, dimoxystrobin, fluoxastrobin, kresoxim-methyl, orysastrobin, picoxystrobin, pyraclostrobin and trifloxystrobin. According to a further specific embodiment thereof, component III is selected from the group of the carboxamides, in particular selected from benodanil, benzovindiflupyr, bixafen, boscalid, carboxin, fenfuram, fluopyram, flutolanil, fluxapyroxad, furametpyr, isopyrazam, mepronil, oxycarboxin, penflufen, penthiopyrad, sedaxane, tecloftalam, thifluzamide, N-(4'-trifluoromethylthiobiphenyl-2-yl)-3-difluoromethyl-1-methyl-1H-pyrazole-4-carboxamide, N-(2-(1,3,3-trimethyl-butyl)-phenyl)-1,3-dimethyl-5-fluoro-1H-pyrazole-4-carboxamide, 3-(difluoromethyl)-1-methyl-N-(1,1,3-trimethylindan-4-yl)pyrazole-4-carboxamide, 3-(trifluoromethyl)-1-methyl-N-(1,1,3-trimethyl-indan-4-yl)pyrazole-4-carboxamide, 1,3-dimethyl-N-(1,1,3-trimethylindan-4-yl)pyrazole-4-carboxamide, 3-(trifluoromethyl)-1,5-dimethyl-N-(1,1,3-trimethylindan-4-yl)pyrazole-4-carboxamide, 3-(difluoromethyl)-1,5-dimethyl-N-(1,1,3-trimethylindan-4-yl)pyrazole-4-carboxamide and 1,3,5-trimethyl-N-(1,1,3-trimethylindan-4-yl)pyrazole-4-carboxamide, in particular selected from benzovindiflupyr, bixafen, boscalid, fluopyram, fluxapyroxad, isopyrazam, penflufen, penthiopyrad and sedaxane. According to a further specific embodiment thereof, component IV is selected from cell division inhibitors such as tubulin inhibitors such as metrafenone. According to a further specific embodiment, these are quarternary compositions which, as active compounds, comprise in each case only the mentioned four active components I, II, III and IV.

Still a further specific embodiment relates to four-component compositions, wherein component I is as defined above, component II is selected from the sterol biosynthesis inhibitors (SBI fungicides), in particular from the C14 demethylase inhibitors (DMI fungicides), component III is selected from the Signal transduction inhibitors and component IV is selected from the group of the carboxamides, in particular selected from benodanil, benzovindiflupyr, bixafen, boscalid, carboxin, fenfuram, fluopyram, flutolanil, fluxapyroxad, furametpyr, isopyrazam, mepronil, oxycarboxin, penflufen, penthiopyrad, sedaxane, tecloftalam, thifluzamide, N-(4'-trifluoromethylthiobiphenyl-2-yl)-3-difluoromethyl-1-methyl-1H-pyrazole-4-carboxamide, N-(2-(1,3,3-trimethyl-butyl)-phenyl)-1,3-dimethyl-5-fluoro-1H-pyrazole-4-carboxamide, 3-(difluoromethyl)-1-methyl-N-(1,1,3-trimethylindan-4-yl)pyrazole-4-carboxamide, 3-(trifluoromethyl)-1-methyl-N-(1,1,3-trimethylindan-4-yl)pyrazole-4-carboxamide, 1,3-dimethyl-N-(1,1,3-trimethyl-indan-4-yl)pyrazole-4-carboxamide, 3-(trifluoromethyl)-1,5-dimethyl-N-(1,1,3-trimethylindan-4-yl)pyrazole-4-carboxamide, 3-(difluoromethyl)-1,5-dimethyl-N-(1,1,3-trimethylindan-4-yl)pyrazole-4-carboxamide and 1,3,5-trimethyl-N-(1,1,3-trimethylindan-4-yl)pyrazole-4- carboxamide, in particular selected from benzovindiflupyr, bixafen, boscalid, fluopyram, fluxapyroxad, isopyrazam, penflufen, penthiopyrad and sedaxane. In a specific embodiment, component II is triticonazole, component III is fludioxonil and component IV is fluxapyroxad.

According to a further embodiment of the four-component compositions, component I is as defined above and components II, III and IV are selected from Group M), the growth regulators, in particular selected from chlormequat (chlormequat chloride), mepiquat (mepiquat chloride), paclobutrazole, prohexadione (prohexadione-calcium), trinexapac-ethyl and uniconazole, wherein components II, III and IV are different active ingredients.

Particularly preferred compositions are the four-component compositions, wherein component I is as defined above, i.e. a compound I, in particular a compound selected from compounds I-1, I-2, I-3, I-4, I-5, I-6, I-7, I-8, I-9, I-11, I-13, I-14, I-15 and I-16 or any group of compounds I detailed above, and component II and III are selected from the following fungicides and growth regulators

| | |
|---|---|
| II-3 | azoxystrobin |
| II-6 | bixafen |
| II-8 | carbendazim |
| II-11 | chlorothalonil |
| II-16 | cyprodinil |
| II-21 | difenoconazole |
| II-26 | epoxiconazole |
| II-32 | fenpropimorph |
| II-34 | fludioxonil |
| II-37 | fluoxastrobin |
| II-39 | flusilazole |
| II-42 | fluxapyroxad |
| II-50 | isopyrazam |
| II-62 | metrafenone |
| II-66 | pyraclostrobin |
| II-76 | propiconazole |
| II-78 | prothioconazole |
| II-84 | spiroxamine |
| II-86 | tebuconazole |
| II-93 | triticonazole |
| II-92 | trifloxystrobin |
| II-1a | mepiquat chloride |
| II-2a | chlormequat chloride |
| II-3a | trinexapac-ethyl |
| II-4a | prohexadione-calcium |
| II-5a | ethophon | and component IV is

| | |
|---|---|
| II-42 | fluxapyroxad or |
| II-66 | pyraclostrobin | wherein components II, III and IV are different active compounds.

These compositions are compiled in Table Q1 and Q1a, where each row corresponds to one embodiment of the compositions according to the invention, i.e. one specific individualized four-component composition. According to one specific aspect, these are quarternary compositions which each only contain these four components as the active compound. Furthermore, also every combination of the compositions individualized in this table represent embodiments of the present invention.

TABLE Q1

Four-component compositions comprising a component I, a fungicide or growth regulator as component II and III and a fungicidal component IV.

| composition | I | II | III | IV |
|---|---|---|---|---|
| Q1-1 | I-1 | II-3 | II-6 | II-42 |
| Q1-2 | I-1 | II-3 | II-8 | II-42 |
| Q1-3 | I-1 | II-3 | II-11 | II-42 |
| Q1-4 | I-1 | II-3 | II-16 | II-42 |
| Q1-5 | I-1 | II-3 | II-21 | II-42 |
| Q1-6 | I-1 | II-3 | II-26 | II-42 |
| Q1-7 | I-1 | II-3 | II-32 | II-42 |
| Q1-8 | I-1 | II-3 | II-37 | II-42 |
| Q1-9 | I-1 | II-3 | II-39 | II-42 |
| Q1-10 | I-1 | II-3 | II-50 | II-42 |
| Q1-11 | I-1 | II-3 | II-62 | II-42 |
| Q1-12 | I-1 | II-3 | II-76 | II-42 |
| Q1-13 | I-1 | II-3 | II-78 | II-42 |
| Q1-14 | I-1 | II-3 | II-84 | II-42 |
| Q1-15 | I-1 | II-3 | II-86 | II-42 |
| Q1-16 | I-1 | II-3 | II-92 | II-42 |
| Q1-17 | I-1 | II-3 | II-1a | II-42 |
| Q1-18 | I-1 | II-3 | II-2a | II-42 |
| Q1-19 | I-1 | II-3 | II-3a | II-42 |
| Q1-20 | I-1 | II-3 | II-4a | II-42 |
| Q1-21 | I-1 | II-3 | II-5a | II-42 |
| Q1-22 | I-1 | II-6 | II-8 | II-42 |
| Q1-23 | I-1 | II-6 | II-11 | II-42 |
| Q1-24 | I-1 | II-6 | II-16 | II-42 |
| Q1-25 | I-1 | II-6 | II-21 | II-42 |
| Q1-26 | I-1 | II-6 | II-26 | II-42 |
| Q1-27 | I-1 | II-6 | II-32 | II-42 |
| Q1-28 | I-1 | II-6 | II-37 | II-42 |
| Q1-29 | I-1 | II-6 | II-39 | II-42 |
| Q1-30 | I-1 | II-6 | II-50 | II-42 |
| Q1-31 | I-1 | II-6 | II-62 | II-42 |
| Q1-32 | I-1 | II-6 | II-76 | II-42 |
| Q1-33 | I-1 | II-6 | II-78 | II-42 |
| Q1-34 | I-1 | II-6 | II-84 | II-42 |
| Q1-35 | I-1 | II-6 | II-86 | II-42 |
| Q1-36 | I-1 | II-6 | II-92 | II-42 |
| Q1-37 | I-1 | II-6 | II-1a | II-42 |
| Q1-38 | I-1 | II-6 | II-2a | II-42 |
| Q1-39 | I-1 | II-6 | II-3a | II-42 |
| Q1-40 | I-1 | II-6 | II-4a | II-42 |
| Q1-41 | I-1 | II-6 | II-5a | II-42 |
| Q1-42 | I-1 | II-8 | II-11 | II-42 |
| Q1-43 | I-1 | II-8 | II-16 | II-42 |
| Q1-44 | I-1 | II-8 | II-21 | II-42 |
| Q1-45 | I-1 | II-8 | II-26 | II-42 |
| Q1-46 | I-1 | II-8 | II-32 | II-42 |
| Q1-47 | I-1 | II-8 | II-37 | II-42 |
| Q1-48 | I-1 | II-8 | II-39 | II-42 |
| Q1-49 | I-1 | II-8 | II-50 | II-42 |
| Q1-50 | I-1 | II-8 | II-62 | II-42 |
| Q1-51 | I-1 | II-8 | II-76 | II-42 |
| Q1-52 | I-1 | II-8 | II-78 | II-42 |
| Q1-53 | I-1 | II-8 | II-84 | II-42 |
| Q1-54 | I-1 | II-8 | II-86 | II-42 |
| Q1-55 | I-1 | II-8 | II-92 | II-42 |
| Q1-56 | I-1 | II-8 | II-1a | II-42 |
| Q1-57 | I-1 | II-8 | II-2a | II-42 |
| Q1-58 | I-1 | II-8 | II-3a | II-42 |
| Q1-59 | I-1 | II-8 | II-4a | II-42 |
| Q1-60 | I-1 | II-8 | II-5a | II-42 |
| Q1-61 | I-1 | II-11 | II-16 | II-42 |
| Q1-62 | I-1 | II-11 | II-21 | II-42 |
| Q1-63 | I-1 | II-11 | II-26 | II-42 |
| Q1-64 | I-1 | II-11 | II-32 | II-42 |
| Q1-65 | I-1 | II-11 | II-37 | II-42 |
| Q1-66 | I-1 | II-11 | II-39 | II-42 |
| Q1-67 | I-1 | II-11 | II-50 | II-42 |
| Q1-68 | I-1 | II-11 | II-62 | II-42 |
| Q1-69 | I-1 | II-11 | II-76 | II-42 |
| Q1-70 | I-1 | II-11 | II-78 | II-42 |
| Q1-71 | I-1 | II-11 | II-84 | II-42 |
| Q1-72 | I-1 | II-11 | II-86 | II-42 |
| Q1-73 | I-1 | II-11 | II-92 | II-42 |
| Q1-74 | I-1 | II-11 | II-1a | II-42 |

TABLE Q1-continued

Four-component compositions comprising a component I, a fungicide or growth regulator as component II and III and a fungicidal component IV.

| composition | I | II | III | IV |
|---|---|---|---|---|
| Q1-75 | I-1 | II-11 | II-2a | II-42 |
| Q1-76 | I-1 | II-11 | II-3a | II-42 |
| Q1-77 | I-1 | II-11 | II-4a | II-42 |
| Q1-78 | I-1 | II-11 | II-5a | II-42 |
| Q1-79 | I-1 | II-16 | II-21 | II-42 |
| Q1-80 | I-1 | II-16 | II-26 | II-42 |
| Q1-81 | I-1 | II-16 | II-32 | II-42 |
| Q1-82 | I-1 | II-16 | II-37 | II-42 |
| Q1-83 | I-1 | II-16 | II-39 | II-42 |
| Q1-84 | I-1 | II-16 | II-50 | II-42 |
| Q1-85 | I-1 | II-16 | II-62 | II-42 |
| Q1-86 | I-1 | II-16 | II-76 | II-42 |
| Q1-87 | I-1 | II-16 | II-78 | II-42 |
| Q1-88 | I-1 | II-16 | II-84 | II-42 |
| Q1-89 | I-1 | II-16 | II-86 | II-42 |
| Q1-90 | I-1 | II-16 | II-92 | II-42 |
| Q1-91 | I-1 | II-16 | II-1a | II-42 |
| Q1-92 | I-1 | II-16 | II-2a | II-42 |
| Q1-93 | I-1 | II-16 | II-3a | II-42 |
| Q1-94 | I-1 | II-16 | II-4a | II-42 |
| Q1-95 | I-1 | II-16 | II-5a | II-42 |
| Q1-96 | I-1 | II-21 | II-26 | II-42 |
| Q1-97 | I-1 | II-21 | II-32 | II-42 |
| Q1-98 | I-1 | II-21 | II-37 | II-42 |
| Q1-99 | I-1 | II-21 | II-39 | II-42 |
| Q1-100 | I-1 | II-21 | II-50 | II-42 |
| Q1-101 | I-1 | II-21 | II-62 | II-42 |
| Q1-102 | I-1 | II-21 | II-76 | II-42 |
| Q1-103 | I-1 | II-21 | II-78 | II-42 |
| Q1-104 | I-1 | II-21 | II-84 | II-42 |
| Q1-105 | I-1 | II-21 | II-86 | II-42 |
| Q1-106 | I-1 | II-21 | II-92 | II-42 |
| Q1-107 | I-1 | II-21 | II-1a | II-42 |
| Q1-108 | I-1 | II-21 | II-2a | II-42 |
| Q1-109 | I-1 | II-21 | II-3a | II-42 |
| Q1-110 | I-1 | II-21 | II-4a | II-42 |
| Q1-111 | I-1 | II-21 | II-5a | II-42 |
| Q1-112 | I-1 | II-26 | II-32 | II-42 |
| Q1-113 | I-1 | II-26 | II-37 | II-42 |
| Q1-114 | I-1 | II-26 | II-39 | II-42 |
| Q1-115 | I-1 | II-26 | II-50 | II-42 |
| Q1-116 | I-1 | II-26 | II-62 | II-42 |
| Q1-117 | I-1 | II-26 | II-76 | II-42 |
| Q1-118 | I-1 | II-26 | II-78 | II-42 |
| Q1-119 | I-1 | II-26 | II-84 | II-42 |
| Q1-120 | I-1 | II-26 | II-86 | II-42 |
| Q1-121 | I-1 | II-26 | II-92 | II-42 |
| Q1-122 | I-1 | II-26 | II-1a | II-42 |
| Q1-123 | I-1 | II-26 | II-2a | II-42 |
| Q1-124 | I-1 | II-26 | II-3a | II-42 |
| Q1-125 | I-1 | II-26 | II-4a | II-42 |
| Q1-126 | I-1 | II-26 | II-5a | II-42 |
| Q1-127 | I-1 | II-32 | II-37 | II-42 |
| Q1-128 | I-1 | II-32 | II-39 | II-42 |
| Q1-129 | I-1 | II-32 | II-50 | II-42 |
| Q1-130 | I-1 | II-32 | II-62 | II-42 |
| Q1-131 | I-1 | II-32 | II-76 | II-42 |
| Q1-132 | I-1 | II-32 | II-78 | II-42 |
| Q1-133 | I-1 | II-32 | II-84 | II-42 |
| Q1-134 | I-1 | II-32 | II-86 | II-42 |
| Q1-135 | I-1 | II-32 | II-92 | II-42 |
| Q1-136 | I-1 | II-32 | II-1a | II-42 |
| Q1-137 | I-1 | II-32 | II-2a | II-42 |
| Q1-138 | I-1 | II-32 | II-3a | II-42 |
| Q1-139 | I-1 | II-32 | II-4a | II-42 |
| Q1-140 | I-1 | II-32 | II-5a | II-42 |
| Q1-141 | I-1 | II-37 | II-39 | II-42 |
| Q1-142 | I-1 | II-37 | II-50 | II-42 |
| Q1-143 | I-1 | II-37 | II-62 | II-42 |
| Q1-144 | I-1 | II-37 | II-76 | II-42 |
| Q1-145 | I-1 | II-37 | II-78 | II-42 |
| Q1-146 | I-1 | II-37 | II-84 | II-42 |
| Q1-147 | I-1 | II-37 | II-86 | II-42 |
| Q1-148 | I-1 | II-37 | II-92 | II-42 |
| Q1-149 | I-1 | II-37 | II-1a | II-42 |
| Q1-150 | I-1 | II-37 | II-2a | II-42 |
| Q1-151 | I-1 | II-37 | II-3a | II-42 |
| Q1-152 | I-1 | II-37 | II-4a | II-42 |
| Q1-153 | I-1 | II-37 | II-5a | II-42 |
| Q1-154 | I-1 | II-39 | II-50 | II-42 |
| Q1-155 | I-1 | II-39 | II-62 | II-42 |
| Q1-156 | I-1 | II-39 | II-76 | II-42 |
| Q1-157 | I-1 | II-39 | II-78 | II-42 |
| Q1-158 | I-1 | II-39 | II-84 | II-42 |
| Q1-159 | I-1 | II-39 | II-86 | II-42 |
| Q1-160 | I-1 | II-39 | II-92 | II-42 |
| Q1-161 | I-1 | II-39 | II-1a | II-42 |
| Q1-162 | I-1 | II-39 | II-2a | II-42 |
| Q1-163 | I-1 | II-39 | II-3a | II-42 |
| Q1-164 | I-1 | II-39 | II-4a | II-42 |
| Q1-165 | I-1 | II-39 | II-5a | II-42 |
| Q1-166 | I-1 | II-50 | II-62 | II-42 |
| Q1-167 | I-1 | II-50 | II-76 | II-42 |
| Q1-168 | I-1 | II-50 | II-78 | II-42 |
| Q1-169 | I-1 | II-50 | II-84 | II-42 |
| Q1-170 | I-1 | II-50 | II-86 | II-42 |
| Q1-171 | I-1 | II-50 | II-92 | II-42 |
| Q1-172 | I-1 | II-50 | II-1a | II-42 |
| Q1-173 | I-1 | II-50 | II-2a | II-42 |
| Q1-174 | I-1 | II-50 | II-3a | II-42 |
| Q1-175 | I-1 | II-50 | II-4a | II-42 |
| Q1-176 | I-1 | II-50 | II-5a | II-42 |
| Q1-177 | I-1 | II-62 | II-76 | II-42 |
| Q1-178 | I-1 | II-62 | II-78 | II-42 |
| Q1-179 | I-1 | II-62 | II-84 | II-42 |
| Q1-180 | I-1 | II-62 | II-86 | II-42 |
| Q1-181 | I-1 | II-62 | II-92 | II-42 |
| Q1-182 | I-1 | II-62 | II-1a | II-42 |
| Q1-183 | I-1 | II-62 | II-2a | II-42 |
| Q1-184 | I-1 | II-62 | II-3a | II-42 |
| Q1-185 | I-1 | II-62 | II-4a | II-42 |
| Q1-186 | I-1 | II-62 | II-5a | II-42 |
| Q1-187 | I-1 | II-76 | II-78 | II-42 |
| Q1-188 | I-1 | II-76 | II-84 | II-42 |
| Q1-189 | I-1 | II-76 | II-86 | II-42 |
| Q1-190 | I-1 | II-76 | II-92 | II-42 |
| Q1-191 | I-1 | II-76 | II-1a | II-42 |
| Q1-192 | I-1 | II-76 | II-2a | II-42 |
| Q1-193 | I-1 | II-76 | II-3a | II-42 |
| Q1-194 | I-1 | II-76 | II-4a | II-42 |
| Q1-195 | I-1 | II-76 | II-5a | II-42 |
| Q1-196 | I-1 | II-78 | II-84 | II-42 |
| Q1-197 | I-1 | II-78 | II-86 | II-42 |
| Q1-198 | I-1 | II-78 | II-92 | II-42 |
| Q1-199 | I-1 | II-78 | II-1a | II-42 |
| Q1-200 | I-1 | II-78 | II-2a | II-42 |
| Q1-201 | I-1 | II-78 | II-3a | II-42 |
| Q1-202 | I-1 | II-78 | II-4a | II-42 |
| Q1-203 | I-1 | II-78 | II-5a | II-42 |
| Q1-204 | I-1 | II-84 | II-86 | II-42 |
| Q1-205 | I-1 | II-84 | II-92 | II-42 |
| Q1-206 | I-1 | II-84 | II-1a | II-42 |
| Q1-207 | I-1 | II-84 | II-2a | II-42 |
| Q1-208 | I-1 | II-84 | II-3a | II-42 |
| Q1-209 | I-1 | II-84 | II-4a | II-42 |
| Q1-210 | I-1 | II-84 | II-5a | II-42 |
| Q1-211 | I-1 | II-86 | II-92 | II-42 |
| Q1-212 | I-1 | II-86 | II-1a | II-42 |
| Q1-213 | I-1 | II-86 | II-2a | II-42 |
| Q1-214 | I-1 | II-86 | II-3a | II-42 |
| Q1-215 | I-1 | II-86 | II-4a | II-42 |
| Q1-216 | I-1 | II-86 | II-5a | II-42 |
| Q1-217 | I-1 | II-92 | II-1a | II-42 |
| Q1-218 | I-1 | II-92 | II-2a | II-42 |
| Q1-219 | I-1 | II-92 | II-3a | II-42 |
| Q1-220 | I-1 | II-92 | II-4a | II-42 |
| Q1-221 | I-1 | II-92 | II-5a | II-42 |
| Q1-222 | I-1 | II-1a | II-2a | II-42 |

TABLE Q1-continued

Four-component compositions comprising a component I, a fungicide or growth regulator as component II and III and a fungicidal component IV.

| composition | I | II | III | IV |
|---|---|---|---|---|
| Q1-223 | I-1 | II-1a | II-3a | II-42 |
| Q1-224 | I-1 | II-1a | II-4a | II-42 |
| Q1-225 | I-1 | II-1a | II-5a | II-42 |
| Q1-226 | I-1 | II-2a | II-3a | II-42 |
| Q1-227 | I-1 | II-2a | II-4a | II-42 |
| Q1-228 | I-1 | II-2a | II-5a | II-42 |
| Q1-229 | I-1 | II-3a | II-4a | II-42 |
| Q1-230 | I-1 | II-3a | II-5a | II-42 |
| Q1-231 | I-1 | II-4a | II-5a | II-42 |
| Q1-232 | I-1 | II-3 | II-6 | II-66 |
| Q1-233 | I-1 | II-3 | II-8 | II-66 |
| Q1-234 | I-1 | II-3 | II-11 | II-66 |
| Q1-235 | I-1 | II-3 | II-16 | II-66 |
| Q1-236 | I-1 | II-3 | II-21 | II-66 |
| Q1-237 | I-1 | II-3 | II-26 | II-66 |
| Q1-238 | I-1 | II-3 | II-32 | II-66 |
| Q1-239 | I-1 | II-3 | II-37 | II-66 |
| Q1-240 | I-1 | II-3 | II-39 | II-66 |
| Q1-241 | I-1 | II-3 | II-42 | II-66 |
| Q1-242 | I-1 | II-3 | II-50 | II-66 |
| Q1-243 | I-1 | II-3 | II-62 | II-66 |
| Q1-244 | I-1 | II-3 | II-76 | II-66 |
| Q1-245 | I-1 | II-3 | II-78 | II-66 |
| Q1-246 | I-1 | II-3 | II-84 | II-66 |
| Q1-247 | I-1 | II-3 | II-86 | II-66 |
| Q1-248 | I-1 | II-3 | II-92 | II-66 |
| Q1-249 | I-1 | II-3 | II-1a | II-66 |
| Q1-250 | I-1 | II-3 | II-2a | II-66 |
| Q1-251 | I-1 | II-3 | II-3a | II-66 |
| Q1-252 | I-1 | II-3 | II-4a | II-66 |
| Q1-253 | I-1 | II-3 | II-5a | II-66 |
| Q1-254 | I-1 | II-6 | II-8 | II-66 |
| Q1-255 | I-1 | II-6 | II-11 | II-66 |
| Q1-256 | I-1 | II-6 | II-16 | II-66 |
| Q1-257 | I-1 | II-6 | II-21 | II-66 |
| Q1-258 | I-1 | II-6 | II-26 | II-66 |
| Q1-259 | I-1 | II-6 | II-32 | II-66 |
| Q1-260 | I-1 | II-6 | II-37 | II-66 |
| Q1-261 | I-1 | II-6 | II-39 | II-66 |
| Q1-262 | I-1 | II-6 | II-42 | II-66 |
| Q1-263 | I-1 | II-6 | II-50 | II-66 |
| Q1-264 | I-1 | II-6 | II-62 | II-66 |
| Q1-265 | I-1 | II-6 | II-76 | II-66 |
| Q1-266 | I-1 | II-6 | II-78 | II-66 |
| Q1-267 | I-1 | II-6 | II-84 | II-66 |
| Q1-268 | I-1 | II-6 | II-86 | II-66 |
| Q1-269 | I-1 | II-6 | II-92 | II-66 |
| Q1-270 | I-1 | II-6 | II-1a | II-66 |
| Q1-271 | I-1 | II-6 | II-2a | II-66 |
| Q1-272 | I-1 | II-6 | II-3a | II-66 |
| Q1-273 | I-1 | II-6 | II-4a | II-66 |
| Q1-274 | I-1 | II-6 | II-5a | II-66 |
| Q1-275 | I-1 | II-8 | II-11 | II-66 |
| Q1-276 | I-1 | II-8 | II-16 | II-66 |
| Q1-277 | I-1 | II-8 | II-21 | II-66 |
| Q1-278 | I-1 | II-8 | II-26 | II-66 |
| Q1-279 | I-1 | II-8 | II-32 | II-66 |
| Q1-280 | I-1 | II-8 | II-37 | II-66 |
| Q1-281 | I-1 | II-8 | II-39 | II-66 |
| Q1-282 | I-1 | II-8 | II-42 | II-66 |
| Q1-283 | I-1 | II-8 | II-50 | II-66 |
| Q1-284 | I-1 | II-8 | II-62 | II-66 |
| Q1-285 | I-1 | II-8 | II-76 | II-66 |
| Q1-286 | I-1 | II-8 | II-78 | II-66 |
| Q1-287 | I-1 | II-8 | II-84 | II-66 |
| Q1-288 | I-1 | II-8 | II-86 | II-66 |
| Q1-289 | I-1 | II-8 | II-92 | II-66 |
| Q1-290 | I-1 | II-8 | II-1a | II-66 |
| Q1-291 | I-1 | II-8 | II-2a | II-66 |
| Q1-292 | I-1 | II-8 | II-3a | II-66 |
| Q1-293 | I-1 | II-8 | II-4a | II-66 |
| Q1-294 | I-1 | II-8 | II-5a | II-66 |
| Q1-295 | I-1 | II-11 | II-16 | II-66 |
| Q1-296 | I-1 | II-11 | II-21 | II-66 |
| Q1-297 | I-1 | II-11 | II-26 | II-66 |
| Q1-298 | I-1 | II-11 | II-32 | II-66 |
| Q1-299 | I-1 | II-11 | II-37 | II-66 |
| Q1-300 | I-1 | II-11 | II-39 | II-66 |
| Q1-301 | I-1 | II-11 | II-42 | II-66 |
| Q1-302 | I-1 | II-11 | II-50 | II-66 |
| Q1-303 | I-1 | II-11 | II-62 | II-66 |
| Q1-304 | I-1 | II-11 | II-76 | II-66 |
| Q1-305 | I-1 | II-11 | II-78 | II-66 |
| Q1-306 | I-1 | II-11 | II-84 | II-66 |
| Q1-307 | I-1 | II-11 | II-86 | II-66 |
| Q1-308 | I-1 | II-11 | II-92 | II-66 |
| Q1-309 | I-1 | II-11 | II-1a | II-66 |
| Q1-310 | I-1 | II-11 | II-2a | II-66 |
| Q1-311 | I-1 | II-11 | II-3a | II-66 |
| Q1-312 | I-1 | II-11 | II-4a | II-66 |
| Q1-313 | I-1 | II-11 | II-5a | II-66 |
| Q1-314 | I-1 | II-16 | II-21 | II-66 |
| Q1-315 | I-1 | II-16 | II-26 | II-66 |
| Q1-316 | I-1 | II-16 | II-32 | II-66 |
| Q1-317 | I-1 | II-16 | II-37 | II-66 |
| Q1-318 | I-1 | II-16 | II-39 | II-66 |
| Q1-319 | I-1 | II-16 | II-42 | II-66 |
| Q1-320 | I-1 | II-16 | II-50 | II-66 |
| Q1-321 | I-1 | II-16 | II-62 | II-66 |
| Q1-322 | I-1 | II-16 | II-76 | II-66 |
| Q1-323 | I-1 | II-16 | II-78 | II-66 |
| Q1-324 | I-1 | II-16 | II-84 | II-66 |
| Q1-325 | I-1 | II-16 | II-86 | II-66 |
| Q1-326 | I-1 | II-16 | II-92 | II-66 |
| Q1-327 | I-1 | II-16 | II-1a | II-66 |
| Q1-328 | I-1 | II-16 | II-2a | II-66 |
| Q1-329 | I-1 | II-16 | II-3a | II-66 |
| Q1-330 | I-1 | II-16 | II-4a | II-66 |
| Q1-331 | I-1 | II-16 | II-5a | II-66 |
| Q1-332 | I-1 | II-21 | II-26 | II-66 |
| Q1-333 | I-1 | II-21 | II-32 | II-66 |
| Q1-334 | I-1 | II-21 | II-37 | II-66 |
| Q1-335 | I-1 | II-21 | II-39 | II-66 |
| Q1-336 | I-1 | II-21 | II-42 | II-66 |
| Q1-337 | I-1 | II-21 | II-50 | II-66 |
| Q1-338 | I-1 | II-21 | II-62 | II-66 |
| Q1-339 | I-1 | II-21 | II-76 | II-66 |
| Q1-340 | I-1 | II-21 | II-78 | II-66 |
| Q1-341 | I-1 | II-21 | II-84 | II-66 |
| Q1-342 | I-1 | II-21 | II-86 | II-66 |
| Q1-343 | I-1 | II-21 | II-92 | II-66 |
| Q1-344 | I-1 | II-21 | II-1a | II-66 |
| Q1-345 | I-1 | II-21 | II-2a | II-66 |
| Q1-346 | I-1 | II-21 | II-3a | II-66 |
| Q1-347 | I-1 | II-21 | II-4a | II-66 |
| Q1-348 | I-1 | II-21 | II-5a | II-66 |
| Q1-349 | I-1 | II-26 | II-32 | II-66 |
| Q1-350 | I-1 | II-26 | II-37 | II-66 |
| Q1-351 | I-1 | II-26 | II-39 | II-66 |
| Q1-352 | I-1 | II-26 | II-42 | II-66 |
| Q1-353 | I-1 | II-26 | II-50 | II-66 |
| Q1-354 | I-1 | II-26 | II-62 | II-66 |
| Q1-355 | I-1 | II-26 | II-76 | II-66 |
| Q1-356 | I-1 | II-26 | II-78 | II-66 |
| Q1-357 | I-1 | II-26 | II-84 | II-66 |
| Q1-358 | I-1 | II-26 | II-86 | II-66 |
| Q1-359 | I-1 | II-26 | II-92 | II-66 |
| Q1-360 | I-1 | II-26 | II-1a | II-66 |
| Q1-361 | I-1 | II-26 | II-2a | II-66 |
| Q1-362 | I-1 | II-26 | II-3a | II-66 |
| Q1-363 | I-1 | II-26 | II-4a | II-66 |
| Q1-364 | I-1 | II-26 | II-5a | II-66 |
| Q1-365 | I-1 | II-32 | II-37 | II-66 |
| Q1-366 | I-1 | II-32 | II-39 | II-66 |
| Q1-367 | I-1 | II-32 | II-42 | II-66 |
| Q1-368 | I-1 | II-32 | II-50 | II-66 |
| Q1-369 | I-1 | II-32 | II-62 | II-66 |
| Q1-370 | I-1 | II-32 | II-76 | II-66 |

TABLE Q1-continued

Four-component compositions comprising a component I, a fungicide or growth regulator as component II and III and a fungicidal component IV.

| composition | I | II | III | IV |
|---|---|---|---|---|
| Q1-371 | I-1 | II-32 | II-78 | II-66 |
| Q1-372 | I-1 | II-32 | II-84 | II-66 |
| Q1-373 | I-1 | II-32 | II-86 | II-66 |
| Q1-374 | I-1 | II-32 | II-92 | II-66 |
| Q1-375 | I-1 | II-32 | II-1a | II-66 |
| Q1-376 | I-1 | II-32 | II-2a | II-66 |
| Q1-377 | I-1 | II-32 | II-3a | II-66 |
| Q1-378 | I-1 | II-32 | II-4a | II-66 |
| Q1-379 | I-1 | II-32 | II-5a | II-66 |
| Q1-380 | I-1 | II-37 | II-39 | II-66 |
| Q1-381 | I-1 | II-37 | II-42 | II-66 |
| Q1-382 | I-1 | II-37 | II-50 | II-66 |
| Q1-383 | I-1 | II-37 | II-62 | II-66 |
| Q1-384 | I-1 | II-37 | II-76 | II-66 |
| Q1-385 | I-1 | II-37 | II-78 | II-66 |
| Q1-386 | I-1 | II-37 | II-84 | II-66 |
| Q1-387 | I-1 | II-37 | II-86 | II-66 |
| Q1-388 | I-1 | II-37 | II-92 | II-66 |
| Q1-389 | I-1 | II-37 | II-1a | II-66 |
| Q1-390 | I-1 | II-37 | II-2a | II-66 |
| Q1-391 | I-1 | II-37 | II-3a | II-66 |
| Q1-392 | I-1 | II-37 | II-4a | II-66 |
| Q1-393 | I-1 | II-37 | II-5a | II-66 |
| Q1-394 | I-1 | II-39 | II-42 | II-66 |
| Q1-395 | I-1 | II-39 | II-50 | II-66 |
| Q1-396 | I-1 | II-39 | II-62 | II-66 |
| Q1-397 | I-1 | II-39 | II-76 | II-66 |
| Q1-398 | I-1 | II-39 | II-78 | II-66 |
| Q1-399 | I-1 | II-39 | II-84 | II-66 |
| Q1-400 | I-1 | II-39 | II-86 | II-66 |
| Q1-401 | I-1 | II-39 | II-92 | II-66 |
| Q1-402 | I-1 | II-39 | II-1a | II-66 |
| Q1-403 | I-1 | II-39 | II-2a | II-66 |
| Q1-404 | I-1 | II-39 | II-3a | II-66 |
| Q1-405 | I-1 | II-39 | II-4a | II-66 |
| Q1-406 | I-1 | II-39 | II-5a | II-66 |
| Q1-407 | I-1 | II-42 | II-50 | II-66 |
| Q1-408 | I-1 | II-42 | II-62 | II-66 |
| Q1-409 | I-1 | II-42 | II-76 | II-66 |
| Q1-410 | I-1 | II-42 | II-78 | II-66 |
| Q1-411 | I-1 | II-42 | II-84 | II-66 |
| Q1-412 | I-1 | II-42 | II-86 | II-66 |
| Q1-413 | I-1 | II-42 | II-92 | II-66 |
| Q1-414 | I-1 | II-42 | II-1a | II-66 |
| Q1-415 | I-1 | II-42 | II-2a | II-66 |
| Q1-416 | I-1 | II-42 | II-3a | II-66 |
| Q1-417 | I-1 | II-42 | II-4a | II-66 |
| Q1-418 | I-1 | II-42 | II-5a | II-66 |
| Q1-419 | I-1 | II-50 | II-62 | II-66 |
| Q1-420 | I-1 | II-50 | II-76 | II-66 |
| Q1-421 | I-1 | II-50 | II-78 | II-66 |
| Q1-422 | I-1 | II-50 | II-84 | II-66 |
| Q1-423 | I-1 | II-50 | II-86 | II-66 |
| Q1-424 | I-1 | II-50 | II-92 | II-66 |
| Q1-425 | I-1 | II-50 | II-1a | II-66 |
| Q1-426 | I-1 | II-50 | II-2a | II-66 |
| Q1-427 | I-1 | II-50 | II-3a | II-66 |
| Q1-428 | I-1 | II-50 | II-4a | II-66 |
| Q1-429 | I-1 | II-50 | II-5a | II-66 |
| Q1-430 | I-1 | II-62 | II-76 | II-66 |
| Q1-431 | I-1 | II-62 | II-78 | II-66 |
| Q1-432 | I-1 | II-62 | II-84 | II-66 |
| Q1-433 | I-1 | II-62 | II-86 | II-66 |
| Q1-434 | I-1 | II-62 | II-92 | II-66 |
| Q1-435 | I-1 | II-62 | II-1a | II-66 |
| Q1-436 | I-1 | II-62 | II-2a | II-66 |
| Q1-437 | I-1 | II-62 | II-3a | II-66 |
| Q1-438 | I-1 | II-62 | II-4a | II-66 |
| Q1-439 | I-1 | II-62 | II-5a | II-66 |
| Q1-440 | I-1 | II-76 | II-78 | II-66 |
| Q1-441 | I-1 | II-76 | II-84 | II-66 |
| Q1-442 | I-1 | II-76 | II-86 | II-66 |
| Q1-443 | I-1 | II-76 | II-92 | II-66 |
| Q1-444 | I-1 | II-76 | II-1a | II-66 |
| Q1-445 | I-1 | II-76 | II-2a | II-66 |
| Q1-446 | I-1 | II-76 | II-3a | II-66 |
| Q1-447 | I-1 | II-76 | II-4a | II-66 |
| Q1-448 | I-1 | II-76 | II-5a | II-66 |
| Q1-449 | I-1 | II-78 | II-84 | II-66 |
| Q1-450 | I-1 | II-78 | II-86 | II-66 |
| Q1-451 | I-1 | II-78 | II-92 | II-66 |
| Q1-452 | I-1 | II-78 | II-1a | II-66 |
| Q1-453 | I-1 | II-78 | II-2a | II-66 |
| Q1-454 | I-1 | II-78 | II-3a | II-66 |
| Q1-455 | I-1 | II-78 | II-4a | II-66 |
| Q1-456 | I-1 | II-78 | II-5a | II-66 |
| Q1-457 | I-1 | II-84 | II-86 | II-66 |
| Q1-458 | I-1 | II-84 | II-92 | II-66 |
| Q1-459 | I-1 | II-84 | II-1a | II-66 |
| Q1-460 | I-1 | II-84 | II-2a | II-66 |
| Q1-461 | I-1 | II-84 | II-3a | II-66 |
| Q1-462 | I-1 | II-84 | II-4a | II-66 |
| Q1-463 | I-1 | II-84 | II-5a | II-66 |
| Q1-464 | I-1 | II-86 | II-92 | II-66 |
| Q1-465 | I-1 | II-86 | II-1a | II-66 |
| Q1-466 | I-1 | II-86 | II-2a | II-66 |
| Q1-467 | I-1 | II-86 | II-3a | II-66 |
| Q1-468 | I-1 | II-86 | II-4a | II-66 |
| Q1-469 | I-1 | II-86 | II-5a | II-66 |
| Q1-470 | I-1 | II-92 | II-1a | II-66 |
| Q1-471 | I-1 | II-92 | II-2a | II-66 |
| Q1-472 | I-1 | II-92 | II-3a | II-66 |
| Q1-473 | I-1 | II-92 | II-4a | II-66 |
| Q1-474 | I-1 | II-92 | II-5a | II-66 |
| Q1-475 | I-1 | II-1a | II-2a | II-66 |
| Q1-476 | I-1 | II-1a | II-3a | II-66 |
| Q1-477 | I-1 | II-1a | II-4a | II-66 |
| Q1-478 | I-1 | II-1a | II-5a | II-66 |
| Q1-479 | I-1 | II-2a | II-3a | II-66 |
| Q1-480 | I-1 | II-2a | II-4a | II-66 |
| Q1-481 | I-1 | II-2a | II-5a | II-66 |
| Q1-482 | I-1 | II-3a | II-4a | II-66 |
| Q1-483 | I-1 | II-3a | II-5a | II-66 |
| Q1-484 | I-1 | II-4a | II-5a | II-66 |
| Q1-485 | I-2 | II-3 | II-6 | II-42 |
| Q1-486 | I-2 | II-3 | II-8 | II-42 |
| Q1-487 | I-2 | II-3 | II-11 | II-42 |
| Q1-488 | I-2 | II-3 | II-16 | II-42 |
| Q1-489 | I-2 | II-3 | II-21 | II-42 |
| Q1-490 | I-2 | II-3 | II-26 | II-42 |
| Q1-491 | I-2 | II-3 | II-32 | II-42 |
| Q1-492 | I-2 | II-3 | II-37 | II-42 |
| Q1-493 | I-2 | II-3 | II-39 | II-42 |
| Q1-494 | I-2 | II-3 | II-50 | II-42 |
| Q1-495 | I-2 | II-3 | II-62 | II-42 |
| Q1-496 | I-2 | II-3 | II-76 | II-42 |
| Q1-497 | I-2 | II-3 | II-78 | II-42 |
| Q1-498 | I-2 | II-3 | II-84 | II-42 |
| Q1-499 | I-2 | II-3 | II-86 | II-42 |
| Q1-500 | I-2 | II-3 | II-92 | II-42 |
| Q1-501 | I-2 | II-3 | II-1a | II-42 |
| Q1-502 | I-2 | II-3 | II-2a | II-42 |
| Q1-503 | I-2 | II-3 | II-3a | II-42 |
| Q1-504 | I-2 | II-3 | II-4a | II-42 |
| Q1-505 | I-2 | II-3 | II-5a | II-42 |
| Q1-506 | I-2 | II-6 | II-8 | II-42 |
| Q1-507 | I-2 | II-6 | II-11 | II-42 |
| Q1-508 | I-2 | II-6 | II-16 | II-42 |
| Q1-509 | I-2 | II-6 | II-21 | II-42 |
| Q1-510 | I-2 | II-6 | II-26 | II-42 |
| Q1-511 | I-2 | II-6 | II-32 | II-42 |
| Q1-512 | I-2 | II-6 | II-37 | II-42 |
| Q1-513 | I-2 | II-6 | II-39 | II-42 |
| Q1-514 | I-2 | II-6 | II-50 | II-42 |
| Q1-515 | I-2 | II-6 | II-62 | II-42 |
| Q1-516 | I-2 | II-6 | II-76 | II-42 |
| Q1-517 | I-2 | II-6 | II-78 | II-42 |
| Q1-518 | I-2 | II-6 | II-84 | II-42 |

TABLE Q1-continued

Four-component compositions comprising a component I, a fungicide or growth regulator as component II and III and a fungicidal component IV.

| composition | I | II | III | IV |
|---|---|---|---|---|
| Q1-519 | I-2 | II-6 | II-86 | II-42 |
| Q1-520 | I-2 | II-6 | II-92 | II-42 |
| Q1-521 | I-2 | II-6 | II-1a | II-42 |
| Q1-522 | I-2 | II-6 | II-2a | II-42 |
| Q1-523 | I-2 | II-6 | II-3a | II-42 |
| Q1-524 | I-2 | II-6 | II-4a | II-42 |
| Q1-525 | I-2 | II-6 | II-5a | II-42 |
| Q1-526 | I-2 | II-8 | II-11 | II-42 |
| Q1-527 | I-2 | II-8 | II-16 | II-42 |
| Q1-528 | I-2 | II-8 | II-21 | II-42 |
| Q1-529 | I-2 | II-8 | II-26 | II-42 |
| Q1-530 | I-2 | II-8 | II-32 | II-42 |
| Q1-531 | I-2 | II-8 | II-37 | II-42 |
| Q1-532 | I-2 | II-8 | II-39 | II-42 |
| Q1-533 | I-2 | II-8 | II-50 | II-42 |
| Q1-534 | I-2 | II-8 | II-62 | II-42 |
| Q1-535 | I-2 | II-8 | II-76 | II-42 |
| Q1-536 | I-2 | II-8 | II-78 | II-42 |
| Q1-537 | I-2 | II-8 | II-84 | II-42 |
| Q1-538 | I-2 | II-8 | II-86 | II-42 |
| Q1-539 | I-2 | II-8 | II-92 | II-42 |
| Q1-540 | I-2 | II-8 | II-1a | II-42 |
| Q1-541 | I-2 | II-8 | II-2a | II-42 |
| Q1-542 | I-2 | II-8 | II-3a | II-42 |
| Q1-543 | I-2 | II-8 | II-4a | II-42 |
| Q1-544 | I-2 | II-8 | II-5a | II-42 |
| Q1-545 | I-2 | II-11 | II-16 | II-42 |
| Q1-546 | I-2 | II-11 | II-21 | II-42 |
| Q1-547 | I-2 | II-11 | II-26 | II-42 |
| Q1-548 | I-2 | II-11 | II-32 | II-42 |
| Q1-549 | I-2 | II-11 | II-37 | II-42 |
| Q1-550 | I-2 | II-11 | II-39 | II-42 |
| Q1-551 | I-2 | II-11 | II-50 | II-42 |
| Q1-552 | I-2 | II-11 | II-62 | II-42 |
| Q1-553 | I-2 | II-11 | II-76 | II-42 |
| Q1-554 | I-2 | II-11 | II-78 | II-42 |
| Q1-555 | I-2 | II-11 | II-84 | II-42 |
| Q1-556 | I-2 | II-11 | II-86 | II-42 |
| Q1-557 | I-2 | II-11 | II-92 | II-42 |
| Q1-558 | I-2 | II-11 | II-1a | II-42 |
| Q1-559 | I-2 | II-11 | II-2a | II-42 |
| Q1-560 | I-2 | II-11 | II-3a | II-42 |
| Q1-561 | I-2 | II-11 | II-4a | II-42 |
| Q1-562 | I-2 | II-11 | II-5a | II-42 |
| Q1-563 | I-2 | II-16 | II-21 | II-42 |
| Q1-564 | I-2 | II-16 | II-26 | II-42 |
| Q1-565 | I-2 | II-16 | II-32 | II-42 |
| Q1-566 | I-2 | II-16 | II-37 | II-42 |
| Q1-567 | I-2 | II-16 | II-39 | II-42 |
| Q1-568 | I-2 | II-16 | II-50 | II-42 |
| Q1-569 | I-2 | II-16 | II-62 | II-42 |
| Q1-570 | I-2 | II-16 | II-76 | II-42 |
| Q1-571 | I-2 | II-16 | II-78 | II-42 |
| Q1-572 | I-2 | II-16 | II-84 | II-42 |
| Q1-573 | I-2 | II-16 | II-86 | II-42 |
| Q1-574 | I-2 | II-16 | II-92 | II-42 |
| Q1-575 | I-2 | II-16 | II-1a | II-42 |
| Q1-576 | I-2 | II-16 | II-2a | II-42 |
| Q1-577 | I-2 | II-16 | II-3a | II-42 |
| Q1-578 | I-2 | II-16 | II-4a | II-42 |
| Q1-579 | I-2 | II-16 | II-5a | II-42 |
| Q1-580 | I-2 | II-21 | II-26 | II-42 |
| Q1-581 | I-2 | II-21 | II-32 | II-42 |
| Q1-582 | I-2 | II-21 | II-37 | II-42 |
| Q1-583 | I-2 | II-21 | II-39 | II-42 |
| Q1-584 | I-2 | II-21 | II-50 | II-42 |
| Q1-585 | I-2 | II-21 | II-62 | II-42 |
| Q1-586 | I-2 | II-21 | II-76 | II-42 |
| Q1-587 | I-2 | II-21 | II-78 | II-42 |
| Q1-588 | I-2 | II-21 | II-84 | II-42 |
| Q1-589 | I-2 | II-21 | II-86 | II-42 |
| Q1-590 | I-2 | II-21 | II-92 | II-42 |
| Q1-591 | I-2 | II-21 | II-1a | II-42 |
| Q1-592 | I-2 | II-21 | II-2a | II-42 |
| Q1-593 | I-2 | II-21 | II-3a | II-42 |
| Q1-594 | I-2 | II-21 | II-4a | II-42 |
| Q1-595 | I-2 | II-21 | II-5a | II-42 |
| Q1-596 | I-2 | II-26 | II-32 | II-42 |
| Q1-597 | I-2 | II-26 | II-37 | II-42 |
| Q1-598 | I-2 | II-26 | II-39 | II-42 |
| Q1-599 | I-2 | II-26 | II-50 | II-42 |
| Q1-600 | I-2 | II-26 | II-62 | II-42 |
| Q1-601 | I-2 | II-26 | II-76 | II-42 |
| Q1-602 | I-2 | II-26 | II-78 | II-42 |
| Q1-603 | I-2 | II-26 | II-84 | II-42 |
| Q1-604 | I-2 | II-26 | II-86 | II-42 |
| Q1-605 | I-2 | II-26 | II-92 | II-42 |
| Q1-606 | I-2 | II-26 | II-1a | II-42 |
| Q1-607 | I-2 | II-26 | II-2a | II-42 |
| Q1-608 | I-2 | II-26 | II-3a | II-42 |
| Q1-609 | I-2 | II-26 | II-4a | II-42 |
| Q1-610 | I-2 | II-26 | II-5a | II-42 |
| Q1-611 | I-2 | II-32 | II-37 | II-42 |
| Q1-612 | I-2 | II-32 | II-39 | II-42 |
| Q1-613 | I-2 | II-32 | II-50 | II-42 |
| Q1-614 | I-2 | II-32 | II-62 | II-42 |
| Q1-615 | I-2 | II-32 | II-76 | II-42 |
| Q1-616 | I-2 | II-32 | II-78 | II-42 |
| Q1-617 | I-2 | II-32 | II-84 | II-42 |
| Q1-618 | I-2 | II-32 | II-86 | II-42 |
| Q1-619 | I-2 | II-32 | II-92 | II-42 |
| Q1-620 | I-2 | II-32 | II-1a | II-42 |
| Q1-621 | I-2 | II-32 | II-2a | II-42 |
| Q1-622 | I-2 | II-32 | II-3a | II-42 |
| Q1-623 | I-2 | II-32 | II-4a | II-42 |
| Q1-624 | I-2 | II-32 | II-5a | II-42 |
| Q1-625 | I-2 | II-37 | II-39 | II-42 |
| Q1-626 | I-2 | II-37 | II-50 | II-42 |
| Q1-627 | I-2 | II-37 | II-62 | II-42 |
| Q1-628 | I-2 | II-37 | II-76 | II-42 |
| Q1-629 | I-2 | II-37 | II-78 | II-42 |
| Q1-630 | I-2 | II-37 | II-84 | II-42 |
| Q1-631 | I-2 | II-37 | II-86 | II-42 |
| Q1-632 | I-2 | II-37 | II-92 | II-42 |
| Q1-633 | I-2 | II-37 | II-1a | II-42 |
| Q1-634 | I-2 | II-37 | II-2a | II-42 |
| Q1-635 | I-2 | II-37 | II-3a | II-42 |
| Q1-636 | I-2 | II-37 | II-4a | II-42 |
| Q1-637 | I-2 | II-37 | II-5a | II-42 |
| Q1-638 | I-2 | II-39 | II-50 | II-42 |
| Q1-639 | I-2 | II-39 | II-62 | II-42 |
| Q1-640 | I-2 | II-39 | II-76 | II-42 |
| Q1-641 | I-2 | II-39 | II-78 | II-42 |
| Q1-642 | I-2 | II-39 | II-84 | II-42 |
| Q1-643 | I-2 | II-39 | II-86 | II-42 |
| Q1-644 | I-2 | II-39 | II-92 | II-42 |
| Q1-645 | I-2 | II-39 | II-1a | II-42 |
| Q1-646 | I-2 | II-39 | II-2a | II-42 |
| Q1-647 | I-2 | II-39 | II-3a | II-42 |
| Q1-648 | I-2 | II-39 | II-4a | II-42 |
| Q1-649 | I-2 | II-39 | II-5a | II-42 |
| Q1-650 | I-2 | II-50 | II-62 | II-42 |
| Q1-651 | I-2 | II-50 | II-76 | II-42 |
| Q1-652 | I-2 | II-50 | II-78 | II-42 |
| Q1-653 | I-2 | II-50 | II-84 | II-42 |
| Q1-654 | I-2 | II-50 | II-86 | II-42 |
| Q1-655 | I-2 | II-50 | II-92 | II-42 |
| Q1-656 | I-2 | II-50 | II-1a | II-42 |
| Q1-657 | I-2 | II-50 | II-2a | II-42 |
| Q1-658 | I-2 | II-50 | II-3a | II-42 |
| Q1-659 | I-2 | II-50 | II-4a | II-42 |
| Q1-660 | I-2 | II-50 | II-5a | II-42 |
| Q1-661 | I-2 | II-62 | II-76 | II-42 |
| Q1-662 | I-2 | II-62 | II-78 | II-42 |
| Q1-663 | I-2 | II-62 | II-84 | II-42 |
| Q1-664 | I-2 | II-62 | II-86 | II-42 |
| Q1-665 | I-2 | II-62 | II-92 | II-42 |
| Q1-666 | I-2 | II-62 | II-1a | II-42 |

TABLE Q1-continued

Four-component compositions comprising a component I, a fungicide or growth regulator as component II and III and a fungicidal component IV.

| composition | I | II | III | IV |
|---|---|---|---|---|
| Q1-667 | I-2 | II-62 | II-2a | II-42 |
| Q1-668 | I-2 | II-62 | II-3a | II-42 |
| Q1-669 | I-2 | II-62 | II-4a | II-42 |
| Q1-670 | I-2 | II-62 | II-5a | II-42 |
| Q1-671 | I-2 | II-76 | II-78 | II-42 |
| Q1-672 | I-2 | II-76 | II-84 | II-42 |
| Q1-673 | I-2 | II-76 | II-86 | II-42 |
| Q1-674 | I-2 | II-76 | II-92 | II-42 |
| Q1-675 | I-2 | II-76 | II-1a | II-42 |
| Q1-676 | I-2 | II-76 | II-2a | II-42 |
| Q1-677 | I-2 | II-76 | II-3a | II-42 |
| Q1-678 | I-2 | II-76 | II-4a | II-42 |
| Q1-679 | I-2 | II-76 | II-5a | II-42 |
| Q1-680 | I-2 | II-78 | II-84 | II-42 |
| Q1-681 | I-2 | II-78 | II-86 | II-42 |
| Q1-682 | I-2 | II-78 | II-92 | II-42 |
| Q1-683 | I-2 | II-78 | II-1a | II-42 |
| Q1-684 | I-2 | II-78 | II-2a | II-42 |
| Q1-685 | I-2 | II-78 | II-3a | II-42 |
| Q1-686 | I-2 | II-78 | II-4a | II-42 |
| Q1-687 | I-2 | II-78 | II-5a | II-42 |
| Q1-688 | I-2 | II-84 | II-86 | II-42 |
| Q1-689 | I-2 | II-84 | II-92 | II-42 |
| Q1-690 | I-2 | II-84 | II-1a | II-42 |
| Q1-691 | I-2 | II-84 | II-2a | II-42 |
| Q1-692 | I-2 | II-84 | II-3a | II-42 |
| Q1-693 | I-2 | II-84 | II-4a | II-42 |
| Q1-694 | I-2 | II-84 | II-5a | II-42 |
| Q1-695 | I-2 | II-86 | II-92 | II-42 |
| Q1-696 | I-2 | II-86 | II-1a | II-42 |
| Q1-697 | I-2 | II-86 | II-2a | II-42 |
| Q1-698 | I-2 | II-86 | II-3a | II-42 |
| Q1-699 | I-2 | II-86 | II-4a | II-42 |
| Q1-700 | I-2 | II-86 | II-5a | II-42 |
| Q1-701 | I-2 | II-92 | II-1a | II-42 |
| Q1-702 | I-2 | II-92 | II-2a | II-42 |
| Q1-703 | I-2 | II-92 | II-3a | II-42 |
| Q1-704 | I-2 | II-92 | II-4a | II-42 |
| Q1-705 | I-2 | II-92 | II-5a | II-42 |
| Q1-706 | I-2 | II-1a | II-2a | II-42 |
| Q1-707 | I-2 | II-1a | II-3a | II-42 |
| Q1-708 | I-2 | II-1a | II-4a | II-42 |
| Q1-709 | I-2 | II-1a | II-5a | II-42 |
| Q1-710 | I-2 | II-2a | II-3a | II-42 |
| Q1-711 | I-2 | II-2a | II-4a | II-42 |
| Q1-712 | I-2 | II-2a | II-5a | II-42 |
| Q1-713 | I-2 | II-3a | II-4a | II-42 |
| Q1-714 | I-2 | II-3a | II-5a | II-42 |
| Q1-715 | I-2 | II-4a | II-5a | II-42 |
| Q1-716 | I-2 | II-3 | II-6 | II-66 |
| Q1-717 | I-2 | II-3 | II-8 | II-66 |
| Q1-718 | I-2 | II-3 | II-11 | II-66 |
| Q1-719 | I-2 | II-3 | II-16 | II-66 |
| Q1-720 | I-2 | II-3 | II-21 | II-66 |
| Q1-721 | I-2 | II-3 | II-26 | II-66 |
| Q1-722 | I-2 | II-3 | II-32 | II-66 |
| Q1-723 | I-2 | II-3 | II-37 | II-66 |
| Q1-724 | I-2 | II-3 | II-39 | II-66 |
| Q1-725 | I-2 | II-3 | II-42 | II-66 |
| Q1-726 | I-2 | II-3 | II-50 | II-66 |
| Q1-727 | I-2 | II-3 | II-62 | II-66 |
| Q1-728 | I-2 | II-3 | II-76 | II-66 |
| Q1-729 | I-2 | II-3 | II-78 | II-66 |
| Q1-730 | I-2 | II-3 | II-84 | II-66 |
| Q1-731 | I-2 | II-3 | II-86 | II-66 |
| Q1-732 | I-2 | II-3 | II-92 | II-66 |
| Q1-733 | I-2 | II-3 | II-1a | II-66 |
| Q1-734 | I-2 | II-3 | II-2a | II-66 |
| Q1-735 | I-2 | II-3 | II-3a | II-66 |
| Q1-736 | I-2 | II-3 | II-4a | II-66 |
| Q1-737 | I-2 | II-3 | II-5a | II-66 |
| Q1-738 | I-2 | II-6 | II-8 | II-66 |
| Q1-739 | I-2 | II-6 | II-11 | II-66 |
| Q1-740 | I-2 | II-6 | II-16 | II-66 |
| Q1-741 | I-2 | II-6 | II-21 | II-66 |
| Q1-742 | I-2 | II-6 | II-26 | II-66 |
| Q1-743 | I-2 | II-6 | II-32 | II-66 |
| Q1-744 | I-2 | II-6 | II-37 | II-66 |
| Q1-745 | I-2 | II-6 | II-39 | II-66 |
| Q1-746 | I-2 | II-6 | II-42 | II-66 |
| Q1-747 | I-2 | II-6 | II-50 | II-66 |
| Q1-748 | I-2 | II-6 | II-62 | II-66 |
| Q1-749 | I-2 | II-6 | II-76 | II-66 |
| Q1-750 | I-2 | II-6 | II-78 | II-66 |
| Q1-751 | I-2 | II-6 | II-84 | II-66 |
| Q1-752 | I-2 | II-6 | II-86 | II-66 |
| Q1-753 | I-2 | II-6 | II-92 | II-66 |
| Q1-754 | I-2 | II-6 | II-1a | II-66 |
| Q1-755 | I-2 | II-6 | II-2a | II-66 |
| Q1-756 | I-2 | II-6 | II-3a | II-66 |
| Q1-757 | I-2 | II-6 | II-4a | II-66 |
| Q1-758 | I-2 | II-6 | II-5a | II-66 |
| Q1-759 | I-2 | II-8 | II-11 | II-66 |
| Q1-760 | I-2 | II-8 | II-16 | II-66 |
| Q1-761 | I-2 | II-8 | II-21 | II-66 |
| Q1-762 | I-2 | II-8 | II-26 | II-66 |
| Q1-763 | I-2 | II-8 | II-32 | II-66 |
| Q1-764 | I-2 | II-8 | II-37 | II-66 |
| Q1-765 | I-2 | II-8 | II-39 | II-66 |
| Q1-766 | I-2 | II-8 | II-42 | II-66 |
| Q1-767 | I-2 | II-8 | II-50 | II-66 |
| Q1-768 | I-2 | II-8 | II-62 | II-66 |
| Q1-769 | I-2 | II-8 | II-76 | II-66 |
| Q1-770 | I-2 | II-8 | II-78 | II-66 |
| Q1-771 | I-2 | II-8 | II-84 | II-66 |
| Q1-772 | I-2 | II-8 | II-86 | II-66 |
| Q1-773 | I-2 | II-8 | II-92 | II-66 |
| Q1-774 | I-2 | II-8 | II-1a | II-66 |
| Q1-775 | I-2 | II-8 | II-2a | II-66 |
| Q1-776 | I-2 | II-8 | II-3a | II-66 |
| Q1-777 | I-2 | II-8 | II-4a | II-66 |
| Q1-778 | I-2 | II-8 | II-5a | II-66 |
| Q1-779 | I-2 | II-11 | II-16 | II-66 |
| Q1-780 | I-2 | II-11 | II-21 | II-66 |
| Q1-781 | I-2 | II-11 | II-26 | II-66 |
| Q1-782 | I-2 | II-11 | II-32 | II-66 |
| Q1-783 | I-2 | II-11 | II-37 | II-66 |
| Q1-784 | I-2 | II-11 | II-39 | II-66 |
| Q1-785 | I-2 | II-11 | II-42 | II-66 |
| Q1-786 | I-2 | II-11 | II-50 | II-66 |
| Q1-787 | I-2 | II-11 | II-62 | II-66 |
| Q1-788 | I-2 | II-11 | II-76 | II-66 |
| Q1-789 | I-2 | II-11 | II-78 | II-66 |
| Q1-790 | I-2 | II-11 | II-84 | II-66 |
| Q1-791 | I-2 | II-11 | II-86 | II-66 |
| Q1-792 | I-2 | II-11 | II-92 | II-66 |
| Q1-793 | I-2 | II-11 | II-1a | II-66 |
| Q1-794 | I-2 | II-11 | II-2a | II-66 |
| Q1-795 | I-2 | II-11 | II-3a | II-66 |
| Q1-796 | I-2 | II-11 | II-4a | II-66 |
| Q1-797 | I-2 | II-11 | II-5a | II-66 |
| Q1-798 | I-2 | II-16 | II-21 | II-66 |
| Q1-799 | I-2 | II-16 | II-26 | II-66 |
| Q1-800 | I-2 | II-16 | II-32 | II-66 |
| Q1-801 | I-2 | II-16 | II-37 | II-66 |
| Q1-802 | I-2 | II-16 | II-39 | II-66 |
| Q1-803 | I-2 | II-16 | II-42 | II-66 |
| Q1-804 | I-2 | II-16 | II-50 | II-66 |
| Q1-805 | I-2 | II-16 | II-62 | II-66 |
| Q1-806 | I-2 | II-16 | II-76 | II-66 |
| Q1-807 | I-2 | II-16 | II-78 | II-66 |
| Q1-808 | I-2 | II-16 | II-84 | II-66 |
| Q1-809 | I-2 | II-16 | II-86 | II-66 |
| Q1-810 | I-2 | II-16 | II-92 | II-66 |
| Q1-811 | I-2 | II-16 | II-1a | II-66 |
| Q1-812 | I-2 | II-16 | II-2a | II-66 |
| Q1-813 | I-2 | II-16 | II-3a | II-66 |
| Q1-814 | I-2 | II-16 | II-4a | II-66 |

TABLE Q1-continued

Four-component compositions comprising a component I, a fungicide or growth regulator as component II and III and a fungicidal component IV.

| composition | I | II | III | IV |
|---|---|---|---|---|
| Q1-815 | I-2 | II-16 | II-5a | II-66 |
| Q1-816 | I-2 | II-21 | II-26 | II-66 |
| Q1-817 | I-2 | II-21 | II-32 | II-66 |
| Q1-818 | I-2 | II-21 | II-37 | II-66 |
| Q1-819 | I-2 | II-21 | II-39 | II-66 |
| Q1-820 | I-2 | II-21 | II-42 | II-66 |
| Q1-821 | I-2 | II-21 | II-50 | II-66 |
| Q1-822 | I-2 | II-21 | II-62 | II-66 |
| Q1-823 | I-2 | II-21 | II-76 | II-66 |
| Q1-824 | I-2 | II-21 | II-78 | II-66 |
| Q1-825 | I-2 | II-21 | II-84 | II-66 |
| Q1-826 | I-2 | II-21 | II-86 | II-66 |
| Q1-827 | I-2 | II-21 | II-92 | II-66 |
| Q1-828 | I-2 | II-21 | II-1a | II-66 |
| Q1-829 | I-2 | II-21 | II-2a | II-66 |
| Q1-830 | I-2 | II-21 | II-3a | II-66 |
| Q1-831 | I-2 | II-21 | II-4a | II-66 |
| Q1-832 | I-2 | II-21 | II-5a | II-66 |
| Q1-833 | I-2 | II-26 | II-32 | II-66 |
| Q1-834 | I-2 | II-26 | II-37 | II-66 |
| Q1-835 | I-2 | II-26 | II-39 | II-66 |
| Q1-836 | I-2 | II-26 | II-42 | II-66 |
| Q1-837 | I-2 | II-26 | II-50 | II-66 |
| Q1-838 | I-2 | II-26 | II-62 | II-66 |
| Q1-839 | I-2 | II-26 | II-76 | II-66 |
| Q1-840 | I-2 | II-26 | II-78 | II-66 |
| Q1-841 | I-2 | II-26 | II-84 | II-66 |
| Q1-842 | I-2 | II-26 | II-86 | II-66 |
| Q1-843 | I-2 | II-26 | II-92 | II-66 |
| Q1-844 | I-2 | II-26 | II-1a | II-66 |
| Q1-845 | I-2 | II-26 | II-2a | II-66 |
| Q1-846 | I-2 | II-26 | II-3a | II-66 |
| Q1-847 | I-2 | II-26 | II-4a | II-66 |
| Q1-848 | I-2 | II-26 | II-5a | II-66 |
| Q1-849 | I-2 | II-32 | II-37 | II-66 |
| Q1-850 | I-2 | II-32 | II-39 | II-66 |
| Q1-851 | I-2 | II-32 | II-42 | II-66 |
| Q1-852 | I-2 | II-32 | II-50 | II-66 |
| Q1-853 | I-2 | II-32 | II-62 | II-66 |
| Q1-854 | I-2 | II-32 | II-76 | II-66 |
| Q1-855 | I-2 | II-32 | II-78 | II-66 |
| Q1-856 | I-2 | II-32 | II-84 | II-66 |
| Q1-857 | I-2 | II-32 | II-86 | II-66 |
| Q1-858 | I-2 | II-32 | II-92 | II-66 |
| Q1-859 | I-2 | II-32 | II-1a | II-66 |
| Q1-860 | I-2 | II-32 | II-2a | II-66 |
| Q1-861 | I-2 | II-32 | II-3a | II-66 |
| Q1-862 | I-2 | II-32 | II-4a | II-66 |
| Q1-863 | I-2 | II-32 | II-5a | II-66 |
| Q1-864 | I-2 | II-37 | II-39 | II-66 |
| Q1-865 | I-2 | II-37 | II-42 | II-66 |
| Q1-866 | I-2 | II-37 | II-50 | II-66 |
| Q1-867 | I-2 | II-37 | II-62 | II-66 |
| Q1-868 | I-2 | II-37 | II-76 | II-66 |
| Q1-869 | I-2 | II-37 | II-78 | II-66 |
| Q1-870 | I-2 | II-37 | II-84 | II-66 |
| Q1-871 | I-2 | II-37 | II-86 | II-66 |
| Q1-872 | I-2 | II-37 | II-92 | II-66 |
| Q1-873 | I-2 | II-37 | II-1a | II-66 |
| Q1-874 | I-2 | II-37 | II-2a | II-66 |
| Q1-875 | I-2 | II-37 | II-3a | II-66 |
| Q1-876 | I-2 | II-37 | II-4a | II-66 |
| Q1-877 | I-2 | II-37 | II-5a | II-66 |
| Q1-878 | I-2 | II-39 | II-42 | II-66 |
| Q1-879 | I-2 | II-39 | II-50 | II-66 |
| Q1-880 | I-2 | II-39 | II-62 | II-66 |
| Q1-881 | I-2 | II-39 | II-76 | II-66 |
| Q1-882 | I-2 | II-39 | II-78 | II-66 |
| Q1-883 | I-2 | II-39 | II-84 | II-66 |
| Q1-884 | I-2 | II-39 | II-86 | II-66 |
| Q1-885 | I-2 | II-39 | II-92 | II-66 |
| Q1-886 | I-2 | II-39 | II-1a | II-66 |
| Q1-887 | I-2 | II-39 | II-2a | II-66 |
| Q1-888 | I-2 | II-39 | II-3a | II-66 |
| Q1-889 | I-2 | II-39 | II-4a | II-66 |
| Q1-890 | I-2 | II-39 | II-5a | II-66 |
| Q1-891 | I-2 | II-42 | II-50 | II-66 |
| Q1-892 | I-2 | II-42 | II-62 | II-66 |
| Q1-893 | I-2 | II-42 | II-76 | II-66 |
| Q1-894 | I-2 | II-42 | II-78 | II-66 |
| Q1-895 | I-2 | II-42 | II-84 | II-66 |
| Q1-896 | I-2 | II-42 | II-86 | II-66 |
| Q1-897 | I-2 | II-42 | II-92 | II-66 |
| Q1-898 | I-2 | II-42 | II-1a | II-66 |
| Q1-899 | I-2 | II-42 | II-2a | II-66 |
| Q1-900 | I-2 | II-42 | II-3a | II-66 |
| Q1-901 | I-2 | II-42 | II-4a | II-66 |
| Q1-902 | I-2 | II-42 | II-5a | II-66 |
| Q1-903 | I-2 | II-50 | II-62 | II-66 |
| Q1-904 | I-2 | II-50 | II-76 | II-66 |
| Q1-905 | I-2 | II-50 | II-78 | II-66 |
| Q1-906 | I-2 | II-50 | II-84 | II-66 |
| Q1-907 | I-2 | II-50 | II-86 | II-66 |
| Q1-908 | I-2 | II-50 | II-92 | II-66 |
| Q1-909 | I-2 | II-50 | II-1a | II-66 |
| Q1-910 | I-2 | II-50 | II-2a | II-66 |
| Q1-911 | I-2 | II-50 | II-3a | II-66 |
| Q1-912 | I-2 | II-50 | II-4a | II-66 |
| Q1-913 | I-2 | II-50 | II-5a | II-66 |
| Q1-914 | I-2 | II-62 | II-76 | II-66 |
| Q1-915 | I-2 | II-62 | II-78 | II-66 |
| Q1-916 | I-2 | II-62 | II-84 | II-66 |
| Q1-917 | I-2 | II-62 | II-86 | II-66 |
| Q1-918 | I-2 | II-62 | II-92 | II-66 |
| Q1-919 | I-2 | II-62 | II-1a | II-66 |
| Q1-920 | I-2 | II-62 | II-2a | II-66 |
| Q1-921 | I-2 | II-62 | II-3a | II-66 |
| Q1-922 | I-2 | II-62 | II-4a | II-66 |
| Q1-923 | I-2 | II-62 | II-5a | II-66 |
| Q1-924 | I-2 | II-76 | II-78 | II-66 |
| Q1-925 | I-2 | II-76 | II-84 | II-66 |
| Q1-926 | I-2 | II-76 | II-86 | II-66 |
| Q1-927 | I-2 | II-76 | II-92 | II-66 |
| Q1-928 | I-2 | II-76 | II-1a | II-66 |
| Q1-929 | I-2 | II-76 | II-2a | II-66 |
| Q1-930 | I-2 | II-76 | II-3a | II-66 |
| Q1-931 | I-2 | II-76 | II-4a | II-66 |
| Q1-932 | I-2 | II-76 | II-5a | II-66 |
| Q1-933 | I-2 | II-78 | II-84 | II-66 |
| Q1-934 | I-2 | II-78 | II-86 | II-66 |
| Q1-935 | I-2 | II-78 | II-92 | II-66 |
| Q1-936 | I-2 | II-78 | II-1a | II-66 |
| Q1-937 | I-2 | II-78 | II-2a | II-66 |
| Q1-938 | I-2 | II-78 | II-3a | II-66 |
| Q1-939 | I-2 | II-78 | II-4a | II-66 |
| Q1-940 | I-2 | II-78 | II-5a | II-66 |
| Q1-941 | I-2 | II-84 | II-86 | II-66 |
| Q1-942 | I-2 | II-84 | II-92 | II-66 |
| Q1-943 | I-2 | II-84 | II-1a | II-66 |
| Q1-944 | I-2 | II-84 | II-2a | II-66 |
| Q1-945 | I-2 | II-84 | II-3a | II-66 |
| Q1-946 | I-2 | II-84 | II-4a | II-66 |
| Q1-947 | I-2 | II-84 | II-5a | II-66 |
| Q1-948 | I-2 | II-86 | II-92 | II-66 |
| Q1-949 | I-2 | II-86 | II-1a | II-66 |
| Q1-950 | I-2 | II-86 | II-2a | II-66 |
| Q1-951 | I-2 | II-86 | II-3a | II-66 |
| Q1-952 | I-2 | II-86 | II-4a | II-66 |
| Q1-953 | I-2 | II-86 | II-5a | II-66 |
| Q1-954 | I-2 | II-92 | II-1a | II-66 |
| Q1-955 | I-2 | II-92 | II-2a | II-66 |
| Q1-956 | I-2 | II-92 | II-3a | II-66 |
| Q1-957 | I-2 | II-92 | II-4a | II-66 |
| Q1-958 | I-2 | II-92 | II-5a | II-66 |
| Q1-959 | I-2 | II-1a | II-2a | II-66 |
| Q1-960 | I-2 | II-1a | II-3a | II-66 |
| Q1-961 | I-2 | II-1a | II-4a | II-66 |
| Q1-962 | I-2 | II-1a | II-5a | II-66 |

TABLE Q1-continued

Four-component compositions comprising a component I, a fungicide or growth regulator as component II and III and a fungicidal component IV.

| composition | I | II | III | IV |
|---|---|---|---|---|
| Q1-963 | I-2 | II-2a | II-3a | II-66 |
| Q1-964 | I-2 | II-2a | II-4a | II-66 |
| Q1-965 | I-2 | II-2a | II-5a | II-66 |
| Q1-966 | I-2 | II-3a | II-4a | II-66 |
| Q1-967 | I-2 | II-3a | II-5a | II-66 |
| Q1-968 | I-2 | II-4a | II-5a | II-66 |
| Q1-969 | I-3 | II-3 | II-6 | II-42 |
| Q1-970 | I-3 | II-3 | II-8 | II-42 |
| Q1-971 | I-3 | II-3 | II-11 | II-42 |
| Q1-972 | I-3 | II-3 | II-16 | II-42 |
| Q1-973 | I-3 | II-3 | II-21 | II-42 |
| Q1-974 | I-3 | II-3 | II-26 | II-42 |
| Q1-975 | I-3 | II-3 | II-32 | II-42 |
| Q1-976 | I-3 | II-3 | II-37 | II-42 |
| Q1-977 | I-3 | II-3 | II-39 | II-42 |
| Q1-978 | I-3 | II-3 | II-50 | II-42 |
| Q1-979 | I-3 | II-3 | II-62 | II-42 |
| Q1-980 | I-3 | II-3 | II-76 | II-42 |
| Q1-981 | I-3 | II-3 | II-78 | II-42 |
| Q1-982 | I-3 | II-3 | II-84 | II-42 |
| Q1-983 | I-3 | II-3 | II-86 | II-42 |
| Q1-984 | I-3 | II-3 | II-92 | II-42 |
| Q1-985 | I-3 | II-3 | II-1a | II-42 |
| Q1-986 | I-3 | II-3 | II-2a | II-42 |
| Q1-987 | I-3 | II-3 | II-3a | II-42 |
| Q1-988 | I-3 | II-3 | II-4a | II-42 |
| Q1-989 | I-3 | II-3 | II-5a | II-42 |
| Q1-990 | I-3 | II-6 | II-8 | II-42 |
| Q1-991 | I-3 | II-6 | II-11 | II-42 |
| Q1-992 | I-3 | II-6 | II-16 | II-42 |
| Q1-993 | I-3 | II-6 | II-21 | II-42 |
| Q1-994 | I-3 | II-6 | II-26 | II-42 |
| Q1-995 | I-3 | II-6 | II-32 | II-42 |
| Q1-996 | I-3 | II-6 | II-37 | II-42 |
| Q1-997 | I-3 | II-6 | II-39 | II-42 |
| Q1-998 | I-3 | II-6 | II-50 | II-42 |
| Q1-999 | I-3 | II-6 | II-62 | II-42 |
| Q1-1000 | I-3 | II-6 | II-76 | II-42 |
| Q1-1001 | I-3 | II-6 | II-78 | II-42 |
| Q1-1002 | I-3 | II-6 | II-84 | II-42 |
| Q1-1003 | I-3 | II-6 | II-86 | II-42 |
| Q1-1004 | I-3 | II-6 | II-92 | II-42 |
| Q1-1005 | I-3 | II-6 | II-1a | II-42 |
| Q1-1006 | I-3 | II-6 | II-2a | II-42 |
| Q1-1007 | I-3 | II-6 | II-3a | II-42 |
| Q1-1008 | I-3 | II-6 | II-4a | II-42 |
| Q1-1009 | I-3 | II-6 | II-5a | II-42 |
| Q1-1010 | I-3 | II-8 | II-11 | II-42 |
| Q1-1011 | I-3 | II-8 | II-16 | II-42 |
| Q1-1012 | I-3 | II-8 | II-21 | II-42 |
| Q1-1013 | I-3 | II-8 | II-26 | II-42 |
| Q1-1014 | I-3 | II-8 | II-32 | II-42 |
| Q1-1015 | I-3 | II-8 | II-37 | II-42 |
| Q1-1016 | I-3 | II-8 | II-39 | II-42 |
| Q1-1017 | I-3 | II-8 | II-50 | II-42 |
| Q1-1018 | I-3 | II-8 | II-62 | II-42 |
| Q1-1019 | I-3 | II-8 | II-76 | II-42 |
| Q1-1020 | I-3 | II-8 | II-78 | II-42 |
| Q1-1021 | I-3 | II-8 | II-84 | II-42 |
| Q1-1022 | I-3 | II-8 | II-86 | II-42 |
| Q1-1023 | I-3 | II-8 | II-92 | II-42 |
| Q1-1024 | I-3 | II-8 | II-1a | II-42 |
| Q1-1025 | I-3 | II-8 | II-2a | II-42 |
| Q1-1026 | I-3 | II-8 | II-3a | II-42 |
| Q1-1027 | I-3 | II-8 | II-4a | II-42 |
| Q1-1028 | I-3 | II-8 | II-5a | II-42 |
| Q1-1029 | I-3 | II-11 | II-16 | II-42 |
| Q1-1030 | I-3 | II-11 | II-21 | II-42 |
| Q1-1031 | I-3 | II-11 | II-26 | II-42 |
| Q1-1032 | I-3 | II-11 | II-32 | II-42 |
| Q1-1033 | I-3 | II-11 | II-37 | II-42 |
| Q1-1034 | I-3 | II-11 | II-39 | II-42 |
| Q1-1035 | I-3 | II-11 | II-50 | II-42 |
| Q1-1036 | I-3 | II-11 | II-62 | II-42 |
| Q1-1037 | I-3 | II-11 | II-76 | II-42 |
| Q1-1038 | I-3 | II-11 | II-78 | II-42 |
| Q1-1039 | I-3 | II-11 | II-84 | II-42 |
| Q1-1040 | I-3 | II-11 | II-86 | II-42 |
| Q1-1041 | I-3 | II-11 | II-92 | II-42 |
| Q1-1042 | I-3 | II-11 | II-1a | II-42 |
| Q1-1043 | I-3 | II-11 | II-2a | II-42 |
| Q1-1044 | I-3 | II-11 | II-3a | II-42 |
| Q1-1045 | I-3 | II-11 | II-4a | II-42 |
| Q1-1046 | I-3 | II-11 | II-5a | II-42 |
| Q1-1047 | I-3 | II-16 | II-21 | II-42 |
| Q1-1048 | I-3 | II-16 | II-26 | II-42 |
| Q1-1049 | I-3 | II-16 | II-32 | II-42 |
| Q1-1050 | I-3 | II-16 | II-37 | II-42 |
| Q1-1051 | I-3 | II-16 | II-39 | II-42 |
| Q1-1052 | I-3 | II-16 | II-50 | II-42 |
| Q1-1053 | I-3 | II-16 | II-62 | II-42 |
| Q1-1054 | I-3 | II-16 | II-76 | II-42 |
| Q1-1055 | I-3 | II-16 | II-78 | II-42 |
| Q1-1056 | I-3 | II-16 | II-84 | II-42 |
| Q1-1057 | I-3 | II-16 | II-86 | II-42 |
| Q1-1058 | I-3 | II-16 | II-92 | II-42 |
| Q1-1059 | I-3 | II-16 | II-1a | II-42 |
| Q1-1060 | I-3 | II-16 | II-2a | II-42 |
| Q1-1061 | I-3 | II-16 | II-3a | II-42 |
| Q1-1062 | I-3 | II-16 | II-4a | II-42 |
| Q1-1063 | I-3 | II-16 | II-5a | II-42 |
| Q1-1064 | I-3 | II-21 | II-26 | II-42 |
| Q1-1065 | I-3 | II-21 | II-32 | II-42 |
| Q1-1066 | I-3 | II-21 | II-37 | II-42 |
| Q1-1067 | I-3 | II-21 | II-39 | II-42 |
| Q1-1068 | I-3 | II-21 | II-50 | II-42 |
| Q1-1069 | I-3 | II-21 | II-62 | II-42 |
| Q1-1070 | I-3 | II-21 | II-76 | II-42 |
| Q1-1071 | I-3 | II-21 | II-78 | II-42 |
| Q1-1072 | I-3 | II-21 | II-84 | II-42 |
| Q1-1073 | I-3 | II-21 | II-86 | II-42 |
| Q1-1074 | I-3 | II-21 | II-92 | II-42 |
| Q1-1075 | I-3 | II-21 | II-1a | II-42 |
| Q1-1076 | I-3 | II-21 | II-2a | II-42 |
| Q1-1077 | I-3 | II-21 | II-3a | II-42 |
| Q1-1078 | I-3 | II-21 | II-4a | II-42 |
| Q1-1079 | I-3 | II-21 | II-5a | II-42 |
| Q1-1080 | I-3 | II-26 | II-32 | II-42 |
| Q1-1081 | I-3 | II-26 | II-37 | II-42 |
| Q1-1082 | I-3 | II-26 | II-39 | II-42 |
| Q1-1083 | I-3 | II-26 | II-50 | II-42 |
| Q1-1084 | I-3 | II-26 | II-62 | II-42 |
| Q1-1085 | I-3 | II-26 | II-76 | II-42 |
| Q1-1086 | I-3 | II-26 | II-78 | II-42 |
| Q1-1087 | I-3 | II-26 | II-84 | II-42 |
| Q1-1088 | I-3 | II-26 | II-86 | II-42 |
| Q1-1089 | I-3 | II-26 | II-92 | II-42 |
| Q1-1090 | I-3 | II-26 | II-1a | II-42 |
| Q1-1091 | I-3 | II-26 | II-2a | II-42 |
| Q1-1092 | I-3 | II-26 | II-3a | II-42 |
| Q1-1093 | I-3 | II-26 | II-4a | II-42 |
| Q1-1094 | I-3 | II-26 | II-5a | II-42 |
| Q1-1095 | I-3 | II-32 | II-37 | II-42 |
| Q1-1096 | I-3 | II-32 | II-39 | II-42 |
| Q1-1097 | I-3 | II-32 | II-50 | II-42 |
| Q1-1098 | I-3 | II-32 | II-62 | II-42 |
| Q1-1099 | I-3 | II-32 | II-76 | II-42 |
| Q1-1100 | I-3 | II-32 | II-78 | II-42 |
| Q1-1101 | I-3 | II-32 | II-84 | II-42 |
| Q1-1102 | I-3 | II-32 | II-86 | II-42 |
| Q1-1103 | I-3 | II-32 | II-92 | II-42 |
| Q1-1104 | I-3 | II-32 | II-1a | II-42 |
| Q1-1105 | I-3 | II-32 | II-2a | II-42 |
| Q1-1106 | I-3 | II-32 | II-3a | II-42 |
| Q1-1107 | I-3 | II-32 | II-4a | II-42 |
| Q1-1108 | I-3 | II-32 | II-5a | II-42 |
| Q1-1109 | I-3 | II-37 | II-39 | II-42 |
| Q1-1110 | I-3 | II-37 | II-50 | II-42 |

TABLE Q1-continued

Four-component compositions comprising a component I, a fungicide or growth regulator as component II and III and a fungicidal component IV.

| composition | I | II | III | IV |
|---|---|---|---|---|
| Q1-1111 | I-3 | II-37 | II-62 | II-42 |
| Q1-1112 | I-3 | II-37 | II-76 | II-42 |
| Q1-1113 | I-3 | II-37 | II-78 | II-42 |
| Q1-1114 | I-3 | II-37 | II-84 | II-42 |
| Q1-1115 | I-3 | II-37 | II-86 | II-42 |
| Q1-1116 | I-3 | II-37 | II-92 | II-42 |
| Q1-1117 | I-3 | II-37 | II-1a | II-42 |
| Q1-1118 | I-3 | II-37 | II-2a | II-42 |
| Q1-1119 | I-3 | II-37 | II-3a | II-42 |
| Q1-1120 | I-3 | II-37 | II-4a | II-42 |
| Q1-1121 | I-3 | II-37 | II-5a | II-42 |
| Q1-1122 | I-3 | II-39 | II-50 | II-42 |
| Q1-1123 | I-3 | II-39 | II-62 | II-42 |
| Q1-1124 | I-3 | II-39 | II-76 | II-42 |
| Q1-1125 | I-3 | II-39 | II-78 | II-42 |
| Q1-1126 | I-3 | II-39 | II-84 | II-42 |
| Q1-1127 | I-3 | II-39 | II-86 | II-42 |
| Q1-1128 | I-3 | II-39 | II-92 | II-42 |
| Q1-1129 | I-3 | II-39 | II-1a | II-42 |
| Q1-1130 | I-3 | II-39 | II-2a | II-42 |
| Q1-1131 | I-3 | II-39 | II-3a | II-42 |
| Q1-1132 | I-3 | II-39 | II-4a | II-42 |
| Q1-1133 | I-3 | II-39 | II-5a | II-42 |
| Q1-1134 | I-3 | II-50 | II-62 | II-42 |
| Q1-1135 | I-3 | II-50 | II-76 | II-42 |
| Q1-1136 | I-3 | II-50 | II-78 | II-42 |
| Q1-1137 | I-3 | II-50 | II-84 | II-42 |
| Q1-1138 | I-3 | II-50 | II-86 | II-42 |
| Q1-1139 | I-3 | II-50 | II-92 | II-42 |
| Q1-1140 | I-3 | II-50 | II-1a | II-42 |
| Q1-1141 | I-3 | II-50 | II-2a | II-42 |
| Q1-1142 | I-3 | II-50 | II-3a | II-42 |
| Q1-1143 | I-3 | II-50 | II-4a | II-42 |
| Q1-1144 | I-3 | II-50 | II-5a | II-42 |
| Q1-1145 | I-3 | II-62 | II-76 | II-42 |
| Q1-1146 | I-3 | II-62 | II-78 | II-42 |
| Q1-1147 | I-3 | II-62 | II-84 | II-42 |
| Q1-1148 | I-3 | II-62 | II-86 | II-42 |
| Q1-1149 | I-3 | II-62 | II-92 | II-42 |
| Q1-1150 | I-3 | II-62 | II-1a | II-42 |
| Q1-1151 | I-3 | II-62 | II-2a | II-42 |
| Q1-1152 | I-3 | II-62 | II-3a | II-42 |
| Q1-1153 | I-3 | II-62 | II-4a | II-42 |
| Q1-1154 | I-3 | II-62 | II-5a | II-42 |
| Q1-1155 | I-3 | II-76 | II-78 | II-42 |
| Q1-1156 | I-3 | II-76 | II-84 | II-42 |
| Q1-1157 | I-3 | II-76 | II-86 | II-42 |
| Q1-1158 | I-3 | II-76 | II-92 | II-42 |
| Q1-1159 | I-3 | II-76 | II-1a | II-42 |
| Q1-1160 | I-3 | II-76 | II-2a | II-42 |
| Q1-1161 | I-3 | II-76 | II-3a | II-42 |
| Q1-1162 | I-3 | II-76 | II-4a | II-42 |
| Q1-1163 | I-3 | II-76 | II-5a | II-42 |
| Q1-1164 | I-3 | II-78 | II-84 | II-42 |
| Q1-1165 | I-3 | II-78 | II-86 | II-42 |
| Q1-1166 | I-3 | II-78 | II-92 | II-42 |
| Q1-1167 | I-3 | II-78 | II-1a | II-42 |
| Q1-1168 | I-3 | II-78 | II-2a | II-42 |
| Q1-1169 | I-3 | II-78 | II-3a | II-42 |
| Q1-1170 | I-3 | II-78 | II-4a | II-42 |
| Q1-1171 | I-3 | II-78 | II-5a | II-42 |
| Q1-1172 | I-3 | II-84 | II-86 | II-42 |
| Q1-1173 | I-3 | II-84 | II-92 | II-42 |
| Q1-1174 | I-3 | II-84 | II-1a | II-42 |
| Q1-1175 | I-3 | II-84 | II-2a | II-42 |
| Q1-1176 | I-3 | II-84 | II-3a | II-42 |
| Q1-1177 | I-3 | II-84 | II-4a | II-42 |
| Q1-1178 | I-3 | II-84 | II-5a | II-42 |
| Q1-1179 | I-3 | II-86 | II-92 | II-42 |
| Q1-1180 | I-3 | II-86 | II-1a | II-42 |
| Q1-1181 | I-3 | II-86 | II-2a | II-42 |
| Q1-1182 | I-3 | II-86 | II-3a | II-42 |
| Q1-1183 | I-3 | II-86 | II-4a | II-42 |
| Q1-1184 | I-3 | II-86 | II-5a | II-42 |
| Q1-1185 | I-3 | II-92 | II-1a | II-42 |
| Q1-1186 | I-3 | II-92 | II-2a | II-42 |
| Q1-1187 | I-3 | II-92 | II-3a | II-42 |
| Q1-1188 | I-3 | II-92 | II-4a | II-42 |
| Q1-1189 | I-3 | II-92 | II-5a | II-42 |
| Q1-1190 | I-3 | II-1a | II-2a | II-42 |
| Q1-1191 | I-3 | II-1a | II-3a | II-42 |
| Q1-1192 | I-3 | II-1a | II-4a | II-42 |
| Q1-1193 | I-3 | II-1a | II-5a | II-42 |
| Q1-1194 | I-3 | II-2a | II-3a | II-42 |
| Q1-1195 | I-3 | II-2a | II-4a | II-42 |
| Q1-1196 | I-3 | II-2a | II-5a | II-42 |
| Q1-1197 | I-3 | II-3a | II-4a | II-42 |
| Q1-1198 | I-3 | II-3a | II-5a | II-42 |
| Q1-1199 | I-3 | II-4a | II-5a | II-42 |
| Q1-1200 | I-3 | II-3 | II-6 | II-66 |
| Q1-1201 | I-3 | II-3 | II-8 | II-66 |
| Q1-1202 | I-3 | II-3 | II-11 | II-66 |
| Q1-1203 | I-3 | II-3 | II-16 | II-66 |
| Q1-1204 | I-3 | II-3 | II-21 | II-66 |
| Q1-1205 | I-3 | II-3 | II-26 | II-66 |
| Q1-1206 | I-3 | II-3 | II-32 | II-66 |
| Q1-1207 | I-3 | II-3 | II-37 | II-66 |
| Q1-1208 | I-3 | II-3 | II-39 | II-66 |
| Q1-1209 | I-3 | II-3 | II-42 | II-66 |
| Q1-1210 | I-3 | II-3 | II-50 | II-66 |
| Q1-1211 | I-3 | II-3 | II-62 | II-66 |
| Q1-1212 | I-3 | II-3 | II-76 | II-66 |
| Q1-1213 | I-3 | II-3 | II-78 | II-66 |
| Q1-1214 | I-3 | II-3 | II-84 | II-66 |
| Q1-1215 | I-3 | II-3 | II-86 | II-66 |
| Q1-1216 | I-3 | II-3 | II-92 | II-66 |
| Q1-1217 | I-3 | II-3 | II-1a | II-66 |
| Q1-1218 | I-3 | II-3 | II-2a | II-66 |
| Q1-1219 | I-3 | II-3 | II-3a | II-66 |
| Q1-1220 | I-3 | II-3 | II-4a | II-66 |
| Q1-1221 | I-3 | II-3 | II-5a | II-66 |
| Q1-1222 | I-3 | II-6 | II-8 | II-66 |
| Q1-1223 | I-3 | II-6 | II-11 | II-66 |
| Q1-1224 | I-3 | II-6 | II-16 | II-66 |
| Q1-1225 | I-3 | II-6 | II-21 | II-66 |
| Q1-1226 | I-3 | II-6 | II-26 | II-66 |
| Q1-1227 | I-3 | II-6 | II-32 | II-66 |
| Q1-1228 | I-3 | II-6 | II-37 | II-66 |
| Q1-1229 | I-3 | II-6 | II-39 | II-66 |
| Q1-1230 | I-3 | II-6 | II-42 | II-66 |
| Q1-1231 | I-3 | II-6 | II-50 | II-66 |
| Q1-1232 | I-3 | II-6 | II-62 | II-66 |
| Q1-1233 | I-3 | II-6 | II-76 | II-66 |
| Q1-1234 | I-3 | II-6 | II-78 | II-66 |
| Q1-1235 | I-3 | II-6 | II-84 | II-66 |
| Q1-1236 | I-3 | II-6 | II-86 | II-66 |
| Q1-1237 | I-3 | II-6 | II-92 | II-66 |
| Q1-1238 | I-3 | II-6 | II-1a | II-66 |
| Q1-1239 | I-3 | II-6 | II-2a | II-66 |
| Q1-1240 | I-3 | II-6 | II-3a | II-66 |
| Q1-1241 | I-3 | II-6 | II-4a | II-66 |
| Q1-1242 | I-3 | II-6 | II-5a | II-66 |
| Q1-1243 | I-3 | II-8 | II-11 | II-66 |
| Q1-1244 | I-3 | II-8 | II-16 | II-66 |
| Q1-1245 | I-3 | II-8 | II-21 | II-66 |
| Q1-1246 | I-3 | II-8 | II-26 | II-66 |
| Q1-1247 | I-3 | II-8 | II-32 | II-66 |
| Q1-1248 | I-3 | II-8 | II-37 | II-66 |
| Q1-1249 | I-3 | II-8 | II-39 | II-66 |
| Q1-1250 | I-3 | II-8 | II-42 | II-66 |
| Q1-1251 | I-3 | II-8 | II-50 | II-66 |
| Q1-1252 | I-3 | II-8 | II-62 | II-66 |
| Q1-1253 | I-3 | II-8 | II-76 | II-66 |
| Q1-1254 | I-3 | II-8 | II-78 | II-66 |
| Q1-1255 | I-3 | II-8 | II-84 | II-66 |
| Q1-1256 | I-3 | II-8 | II-86 | II-66 |
| Q1-1257 | I-3 | II-8 | II-92 | II-66 |
| Q1-1258 | I-3 | II-8 | II-1a | II-66 |

TABLE Q1-continued

Four-component compositions comprising a component I, a fungicide or growth regulator as component II and III and a fungicidal component IV.

| composition | I | II | III | IV |
|---|---|---|---|---|
| Q1-1259 | I-3 | II-8 | II-2a | II-66 |
| Q1-1260 | I-3 | II-8 | II-3a | II-66 |
| Q1-1261 | I-3 | II-8 | II-4a | II-66 |
| Q1-1262 | I-3 | II-8 | II-5a | II-66 |
| Q1-1263 | I-3 | II-11 | II-16 | II-66 |
| Q1-1264 | I-3 | II-11 | II-21 | II-66 |
| Q1-1265 | I-3 | II-11 | II-26 | II-66 |
| Q1-1266 | I-3 | II-11 | II-32 | II-66 |
| Q1-1267 | I-3 | II-11 | II-37 | II-66 |
| Q1-1268 | I-3 | II-11 | II-39 | II-66 |
| Q1-1269 | I-3 | II-11 | II-42 | II-66 |
| Q1-1270 | I-3 | II-11 | II-50 | II-66 |
| Q1-1271 | I-3 | II-11 | II-62 | II-66 |
| Q1-1272 | I-3 | II-11 | II-76 | II-66 |
| Q1-1273 | I-3 | II-11 | II-78 | II-66 |
| Q1-1274 | I-3 | II-11 | II-84 | II-66 |
| Q1-1275 | I-3 | II-11 | II-86 | II-66 |
| Q1-1276 | I-3 | II-11 | II-92 | II-66 |
| Q1-1277 | I-3 | II-11 | II-1a | II-66 |
| Q1-1278 | I-3 | II-11 | II-2a | II-66 |
| Q1-1279 | I-3 | II-11 | II-3a | II-66 |
| Q1-1280 | I-3 | II-11 | II-4a | II-66 |
| Q1-1281 | I-3 | II-11 | II-5a | II-66 |
| Q1-1282 | I-3 | II-16 | II-21 | II-66 |
| Q1-1283 | I-3 | II-16 | II-26 | II-66 |
| Q1-1284 | I-3 | II-16 | II-32 | II-66 |
| Q1-1285 | I-3 | II-16 | II-37 | II-66 |
| Q1-1286 | I-3 | II-16 | II-39 | II-66 |
| Q1-1287 | I-3 | II-16 | II-42 | II-66 |
| Q1-1288 | I-3 | II-16 | II-50 | II-66 |
| Q1-1289 | I-3 | II-16 | II-62 | II-66 |
| Q1-1290 | I-3 | II-16 | II-76 | II-66 |
| Q1-1291 | I-3 | II-16 | II-78 | II-66 |
| Q1-1292 | I-3 | II-16 | II-84 | II-66 |
| Q1-1293 | I-3 | II-16 | II-86 | II-66 |
| Q1-1294 | I-3 | II-16 | II-92 | II-66 |
| Q1-1295 | I-3 | II-16 | II-1a | II-66 |
| Q1-1296 | I-3 | II-16 | II-2a | II-66 |
| Q1-1297 | I-3 | II-16 | II-3a | II-66 |
| Q1-1298 | I-3 | II-16 | II-4a | II-66 |
| Q1-1299 | I-3 | II-16 | II-5a | II-66 |
| Q1-1300 | I-3 | II-21 | II-26 | II-66 |
| Q1-1301 | I-3 | II-21 | II-32 | II-66 |
| Q1-1302 | I-3 | II-21 | II-37 | II-66 |
| Q1-1303 | I-3 | II-21 | II-39 | II-66 |
| Q1-1304 | I-3 | II-21 | II-42 | II-66 |
| Q1-1305 | I-3 | II-21 | II-50 | II-66 |
| Q1-1306 | I-3 | II-21 | II-62 | II-66 |
| Q1-1307 | I-3 | II-21 | II-76 | II-66 |
| Q1-1308 | I-3 | II-21 | II-78 | II-66 |
| Q1-1309 | I-3 | II-21 | II-84 | II-66 |
| Q1-1310 | I-3 | II-21 | II-86 | II-66 |
| Q1-1311 | I-3 | II-21 | II-92 | II-66 |
| Q1-1312 | I-3 | II-21 | II-1a | II-66 |
| Q1-1313 | I-3 | II-21 | II-2a | II-66 |
| Q1-1314 | I-3 | II-21 | II-3a | II-66 |
| Q1-1315 | I-3 | II-21 | II-4a | II-66 |
| Q1-1316 | I-3 | II-21 | II-5a | II-66 |
| Q1-1317 | I-3 | II-26 | II-32 | II-66 |
| Q1-1318 | I-3 | II-26 | II-37 | II-66 |
| Q1-1319 | I-3 | II-26 | II-39 | II-66 |
| Q1-1320 | I-3 | II-26 | II-42 | II-66 |
| Q1-1321 | I-3 | II-26 | II-50 | II-66 |
| Q1-1322 | I-3 | II-26 | II-62 | II-66 |
| Q1-1323 | I-3 | II-26 | II-76 | II-66 |
| Q1-1324 | I-3 | II-26 | II-78 | II-66 |
| Q1-1325 | I-3 | II-26 | II-84 | II-66 |
| Q1-1326 | I-3 | II-26 | II-86 | II-66 |
| Q1-1327 | I-3 | II-26 | II-92 | II-66 |
| Q1-1328 | I-3 | II-26 | II-1a | II-66 |
| Q1-1329 | I-3 | II-26 | II-2a | II-66 |
| Q1-1330 | I-3 | II-26 | II-3a | II-66 |
| Q1-1331 | I-3 | II-26 | II-4a | II-66 |
| Q1-1332 | I-3 | II-26 | II-5a | II-66 |
| Q1-1333 | I-3 | II-32 | II-37 | II-66 |
| Q1-1334 | I-3 | II-32 | II-39 | II-66 |
| Q1-1335 | I-3 | II-32 | II-42 | II-66 |
| Q1-1336 | I-3 | II-32 | II-50 | II-66 |
| Q1-1337 | I-3 | II-32 | II-62 | II-66 |
| Q1-1338 | I-3 | II-32 | II-76 | II-66 |
| Q1-1339 | I-3 | II-32 | II-78 | II-66 |
| Q1-1340 | I-3 | II-32 | II-84 | II-66 |
| Q1-1341 | I-3 | II-32 | II-86 | II-66 |
| Q1-1342 | I-3 | II-32 | II-92 | II-66 |
| Q1-1343 | I-3 | II-32 | II-1a | II-66 |
| Q1-1344 | I-3 | II-32 | II-2a | II-66 |
| Q1-1345 | I-3 | II-32 | II-3a | II-66 |
| Q1-1346 | I-3 | II-32 | II-4a | II-66 |
| Q1-1347 | I-3 | II-32 | II-5a | II-66 |
| Q1-1348 | I-3 | II-37 | II-39 | II-66 |
| Q1-1349 | I-3 | II-37 | II-42 | II-66 |
| Q1-1350 | I-3 | II-37 | II-50 | II-66 |
| Q1-1351 | I-3 | II-37 | II-62 | II-66 |
| Q1-1352 | I-3 | II-37 | II-76 | II-66 |
| Q1-1353 | I-3 | II-37 | II-78 | II-66 |
| Q1-1354 | I-3 | II-37 | II-84 | II-66 |
| Q1-1355 | I-3 | II-37 | II-86 | II-66 |
| Q1-1356 | I-3 | II-37 | II-92 | II-66 |
| Q1-1357 | I-3 | II-37 | II-1a | II-66 |
| Q1-1358 | I-3 | II-37 | II-2a | II-66 |
| Q1-1359 | I-3 | II-37 | II-3a | II-66 |
| Q1-1360 | I-3 | II-37 | II-4a | II-66 |
| Q1-1361 | I-3 | II-37 | II-5a | II-66 |
| Q1-1362 | I-3 | II-39 | II-42 | II-66 |
| Q1-1363 | I-3 | II-39 | II-50 | II-66 |
| Q1-1364 | I-3 | II-39 | II-62 | II-66 |
| Q1-1365 | I-3 | II-39 | II-76 | II-66 |
| Q1-1366 | I-3 | II-39 | II-78 | II-66 |
| Q1-1367 | I-3 | II-39 | II-84 | II-66 |
| Q1-1368 | I-3 | II-39 | II-86 | II-66 |
| Q1-1369 | I-3 | II-39 | II-92 | II-66 |
| Q1-1370 | I-3 | II-39 | II-1a | II-66 |
| Q1-1371 | I-3 | II-39 | II-2a | II-66 |
| Q1-1372 | I-3 | II-39 | II-3a | II-66 |
| Q1-1373 | I-3 | II-39 | II-4a | II-66 |
| Q1-1374 | I-3 | II-39 | II-5a | II-66 |
| Q1-1375 | I-3 | II-42 | II-50 | II-66 |
| Q1-1376 | I-3 | II-42 | II-62 | II-66 |
| Q1-1377 | I-3 | II-42 | II-76 | II-66 |
| Q1-1378 | I-3 | II-42 | II-78 | II-66 |
| Q1-1379 | I-3 | II-42 | II-84 | II-66 |
| Q1-1380 | I-3 | II-42 | II-86 | II-66 |
| Q1-1381 | I-3 | II-42 | II-92 | II-66 |
| Q1-1382 | I-3 | II-42 | II-1a | II-66 |
| Q1-1383 | I-3 | II-42 | II-2a | II-66 |
| Q1-1384 | I-3 | II-42 | II-3a | II-66 |
| Q1-1385 | I-3 | II-42 | II-4a | II-66 |
| Q1-1386 | I-3 | II-42 | II-5a | II-66 |
| Q1-1387 | I-3 | II-50 | II-62 | II-66 |
| Q1-1388 | I-3 | II-50 | II-76 | II-66 |
| Q1-1389 | I-3 | II-50 | II-78 | II-66 |
| Q1-1390 | I-3 | II-50 | II-84 | II-66 |
| Q1-1391 | I-3 | II-50 | II-86 | II-66 |
| Q1-1392 | I-3 | II-50 | II-92 | II-66 |
| Q1-1393 | I-3 | II-50 | II-1a | II-66 |
| Q1-1394 | I-3 | II-50 | II-2a | II-66 |
| Q1-1395 | I-3 | II-50 | II-3a | II-66 |
| Q1-1396 | I-3 | II-50 | II-4a | II-66 |
| Q1-1397 | I-3 | II-50 | II-5a | II-66 |
| Q1-1398 | I-3 | II-62 | II-76 | II-66 |
| Q1-1399 | I-3 | II-62 | II-78 | II-66 |
| Q1-1400 | I-3 | II-62 | II-84 | II-66 |
| Q1-1401 | I-3 | II-62 | II-86 | II-66 |
| Q1-1402 | I-3 | II-62 | II-92 | II-66 |
| Q1-1403 | I-3 | II-62 | II-1a | II-66 |
| Q1-1404 | I-3 | II-62 | II-2a | II-66 |
| Q1-1405 | I-3 | II-62 | II-3a | II-66 |
| Q1-1406 | I-3 | II-62 | II-4a | II-66 |

TABLE Q1-continued

Four-component compositions comprising a component I, a fungicide or growth regulator as component II and III and a fungicidal component IV.

| composition | I | II | III | IV |
|---|---|---|---|---|
| Q1-1407 | I-3 | II-62 | II-5a | II-66 |
| Q1-1408 | I-3 | II-76 | II-78 | II-66 |
| Q1-1409 | I-3 | II-76 | II-84 | II-66 |
| Q1-1410 | I-3 | II-76 | II-86 | II-66 |
| Q1-1411 | I-3 | II-76 | II-92 | II-66 |
| Q1-1412 | I-3 | II-76 | II-1a | II-66 |
| Q1-1413 | I-3 | II-76 | II-2a | II-66 |
| Q1-1414 | I-3 | II-76 | II-3a | II-66 |
| Q1-1415 | I-3 | II-76 | II-4a | II-66 |
| Q1-1416 | I-3 | II-76 | II-5a | II-66 |
| Q1-1417 | I-3 | II-78 | II-84 | II-66 |
| Q1-1418 | I-3 | II-78 | II-86 | II-66 |
| Q1-1419 | I-3 | II-78 | II-92 | II-66 |
| Q1-1420 | I-3 | II-78 | II-1a | II-66 |
| Q1-1421 | I-3 | II-78 | II-2a | II-66 |
| Q1-1422 | I-3 | II-78 | II-3a | II-66 |
| Q1-1423 | I-3 | II-78 | II-4a | II-66 |
| Q1-1424 | I-3 | II-78 | II-5a | II-66 |
| Q1-1425 | I-3 | II-84 | II-86 | II-66 |
| Q1-1426 | I-3 | II-84 | II-92 | II-66 |
| Q1-1427 | I-3 | II-84 | II-1a | II-66 |
| Q1-1428 | I-3 | II-84 | II-2a | II-66 |
| Q1-1429 | I-3 | II-84 | II-3a | II-66 |
| Q1-1430 | I-3 | II-84 | II-4a | II-66 |
| Q1-1431 | I-3 | II-84 | II-5a | II-66 |
| Q1-1432 | I-3 | II-86 | II-92 | II-66 |
| Q1-1433 | I-3 | II-86 | II-1a | II-66 |
| Q1-1434 | I-3 | II-86 | II-2a | II-66 |
| Q1-1435 | I-3 | II-86 | II-3a | II-66 |
| Q1-1436 | I-3 | II-86 | II-4a | II-66 |
| Q1-1437 | I-3 | II-86 | II-5a | II-66 |
| Q1-1438 | I-3 | II-92 | II-1a | II-66 |
| Q1-1439 | I-3 | II-92 | II-2a | II-66 |
| Q1-1440 | I-3 | II-92 | II-3a | II-66 |
| Q1-1441 | I-3 | II-92 | II-4a | II-66 |
| Q1-1442 | I-3 | II-92 | II-5a | II-66 |
| Q1-1443 | I-3 | II-1a | II-2a | II-66 |
| Q1-1444 | I-3 | II-1a | II-3a | II-66 |
| Q1-1445 | I-3 | II-1a | II-4a | II-66 |
| Q1-1446 | I-3 | II-1a | II-5a | II-66 |
| Q1-1447 | I-3 | II-2a | II-3a | II-66 |
| Q1-1448 | I-3 | II-2a | II-4a | II-66 |
| Q1-1449 | I-3 | II-2a | II-5a | II-66 |
| Q1-1450 | I-3 | II-3a | II-4a | II-66 |
| Q1-1451 | I-3 | II-3a | II-5a | II-66 |
| Q1-1452 | I-3 | II-4a | II-5a | II-66 |
| Q1-1453 | I-4 | II-3 | II-6 | II-42 |
| Q1-1454 | I-4 | II-3 | II-8 | II-42 |
| Q1-1455 | I-4 | II-3 | II-11 | II-42 |
| Q1-1456 | I-4 | II-3 | II-16 | II-42 |
| Q1-1457 | I-4 | II-3 | II-21 | II-42 |
| Q1-1458 | I-4 | II-3 | II-26 | II-42 |
| Q1-1459 | I-4 | II-3 | II-32 | II-42 |
| Q1-1460 | I-4 | II-3 | II-37 | II-42 |
| Q1-1461 | I-4 | II-3 | II-39 | II-42 |
| Q1-1462 | I-4 | II-3 | II-50 | II-42 |
| Q1-1463 | I-4 | II-3 | II-62 | II-42 |
| Q1-1464 | I-4 | II-3 | II-76 | II-42 |
| Q1-1465 | I-4 | II-3 | II-78 | II-42 |
| Q1-1466 | I-4 | II-3 | II-84 | II-42 |
| Q1-1467 | I-4 | II-3 | II-86 | II-42 |
| Q1-1468 | I-4 | II-3 | II-92 | II-42 |
| Q1-1469 | I-4 | II-3 | II-1a | II-42 |
| Q1-1470 | I-4 | II-3 | II-2a | II-42 |
| Q1-1471 | I-4 | II-3 | II-3a | II-42 |
| Q1-1472 | I-4 | II-3 | II-4a | II-42 |
| Q1-1473 | I-4 | II-3 | II-5a | II-42 |
| Q1-1474 | I-4 | II-6 | II-8 | II-42 |
| Q1-1475 | I-4 | II-6 | II-11 | II-42 |
| Q1-1476 | I-4 | II-6 | II-16 | II-42 |
| Q1-1477 | I-4 | II-6 | II-21 | II-42 |
| Q1-1478 | I-4 | II-6 | II-26 | II-42 |
| Q1-1479 | I-4 | II-6 | II-32 | II-42 |
| Q1-1480 | I-4 | II-6 | II-37 | II-42 |
| Q1-1481 | I-4 | II-6 | II-39 | II-42 |
| Q1-1482 | I-4 | II-6 | II-50 | II-42 |
| Q1-1483 | I-4 | II-6 | II-62 | II-42 |
| Q1-1484 | I-4 | II-6 | II-76 | II-42 |
| Q1-1485 | I-4 | II-6 | II-78 | II-42 |
| Q1-1486 | I-4 | II-6 | II-84 | II-42 |
| Q1-1487 | I-4 | II-6 | II-86 | II-42 |
| Q1-1488 | I-4 | II-6 | II-92 | II-42 |
| Q1-1489 | I-4 | II-6 | II-1a | II-42 |
| Q1-1490 | I-4 | II-6 | II-2a | II-42 |
| Q1-1491 | I-4 | II-6 | II-3a | II-42 |
| Q1-1492 | I-4 | II-6 | II-4a | II-42 |
| Q1-1493 | I-4 | II-6 | II-5a | II-42 |
| Q1-1494 | I-4 | II-8 | II-11 | II-42 |
| Q1-1495 | I-4 | II-8 | II-16 | II-42 |
| Q1-1496 | I-4 | II-8 | II-21 | II-42 |
| Q1-1497 | I-4 | II-8 | II-26 | II-42 |
| Q1-1498 | I-4 | II-8 | II-32 | II-42 |
| Q1-1499 | I-4 | II-8 | II-37 | II-42 |
| Q1-1500 | I-4 | II-8 | II-39 | II-42 |
| Q1-1501 | I-4 | II-8 | II-50 | II-42 |
| Q1-1502 | I-4 | II-8 | II-62 | II-42 |
| Q1-1503 | I-4 | II-8 | II-76 | II-42 |
| Q1-1504 | I-4 | II-8 | II-78 | II-42 |
| Q1-1505 | I-4 | II-8 | II-84 | II-42 |
| Q1-1506 | I-4 | II-8 | II-86 | II-42 |
| Q1-1507 | I-4 | II-8 | II-92 | II-42 |
| Q1-1508 | I-4 | II-8 | II-1a | II-42 |
| Q1-1509 | I-4 | II-8 | II-2a | II-42 |
| Q1-1510 | I-4 | II-8 | II-3a | II-42 |
| Q1-1511 | I-4 | II-8 | II-4a | II-42 |
| Q1-1512 | I-4 | II-8 | II-5a | II-42 |
| Q1-1513 | I-4 | II-11 | II-16 | II-42 |
| Q1-1514 | I-4 | II-11 | II-21 | II-42 |
| Q1-1515 | I-4 | II-11 | II-26 | II-42 |
| Q1-1516 | I-4 | II-11 | II-32 | II-42 |
| Q1-1517 | I-4 | II-11 | II-37 | II-42 |
| Q1-1518 | I-4 | II-11 | II-39 | II-42 |
| Q1-1519 | I-4 | II-11 | II-50 | II-42 |
| Q1-1520 | I-4 | II-11 | II-62 | II-42 |
| Q1-1521 | I-4 | II-11 | II-76 | II-42 |
| Q1-1522 | I-4 | II-11 | II-78 | II-42 |
| Q1-1523 | I-4 | II-11 | II-84 | II-42 |
| Q1-1524 | I-4 | II-11 | II-86 | II-42 |
| Q1-1525 | I-4 | II-11 | II-92 | II-42 |
| Q1-1526 | I-4 | II-11 | II-1a | II-42 |
| Q1-1527 | I-4 | II-11 | II-2a | II-42 |
| Q1-1528 | I-4 | II-11 | II-3a | II-42 |
| Q1-1529 | I-4 | II-11 | II-4a | II-42 |
| Q1-1530 | I-4 | II-11 | II-5a | II-42 |
| Q1-1531 | I-4 | II-16 | II-21 | II-42 |
| Q1-1532 | I-4 | II-16 | II-26 | II-42 |
| Q1-1533 | I-4 | II-16 | II-32 | II-42 |
| Q1-1534 | I-4 | II-16 | II-37 | II-42 |
| Q1-1535 | I-4 | II-16 | II-39 | II-42 |
| Q1-1536 | I-4 | II-16 | II-50 | II-42 |
| Q1-1537 | I-4 | II-16 | II-62 | II-42 |
| Q1-1538 | I-4 | II-16 | II-76 | II-42 |
| Q1-1539 | I-4 | II-16 | II-78 | II-42 |
| Q1-1540 | I-4 | II-16 | II-84 | II-42 |
| Q1-1541 | I-4 | II-16 | II-86 | II-42 |
| Q1-1542 | I-4 | II-16 | II-92 | II-42 |
| Q1-1543 | I-4 | II-16 | II-1a | II-42 |
| Q1-1544 | I-4 | II-16 | II-2a | II-42 |
| Q1-1545 | I-4 | II-16 | II-3a | II-42 |
| Q1-1546 | I-4 | II-16 | II-4a | II-42 |
| Q1-1547 | I-4 | II-16 | II-5a | II-42 |
| Q1-1548 | I-4 | II-21 | II-26 | II-42 |
| Q1-1549 | I-4 | II-21 | II-32 | II-42 |
| Q1-1550 | I-4 | II-21 | II-37 | II-42 |
| Q1-1551 | I-4 | II-21 | II-39 | II-42 |
| Q1-1552 | I-4 | II-21 | II-50 | II-42 |
| Q1-1553 | I-4 | II-21 | II-62 | II-42 |
| Q1-1554 | I-4 | II-21 | II-76 | II-42 |

TABLE Q1-continued

Four-component compositions comprising a component I, a fungicide or growth regulator as component II and III and a fungicidal component IV.

| composition | I | II | III | IV |
|---|---|---|---|---|
| Q1-1555 | I-4 | II-21 | II-78 | II-42 |
| Q1-1556 | I-4 | II-21 | II-84 | II-42 |
| Q1-1557 | I-4 | II-21 | II-86 | II-42 |
| Q1-1558 | I-4 | II-21 | II-92 | II-42 |
| Q1-1559 | I-4 | II-21 | II-1a | II-42 |
| Q1-1560 | I-4 | II-21 | II-2a | II-42 |
| Q1-1561 | I-4 | II-21 | II-3a | II-42 |
| Q1-1562 | I-4 | II-21 | II-4a | II-42 |
| Q1-1563 | I-4 | II-21 | II-5a | II-42 |
| Q1-1564 | I-4 | II-26 | II-32 | II-42 |
| Q1-1565 | I-4 | II-26 | II-37 | II-42 |
| Q1-1566 | I-4 | II-26 | II-39 | II-42 |
| Q1-1567 | I-4 | II-26 | II-50 | II-42 |
| Q1-1568 | I-4 | II-26 | II-62 | II-42 |
| Q1-1569 | I-4 | II-26 | II-76 | II-42 |
| Q1-1570 | I-4 | II-26 | II-78 | II-42 |
| Q1-1571 | I-4 | II-26 | II-84 | II-42 |
| Q1-1572 | I-4 | II-26 | II-86 | II-42 |
| Q1-1573 | I-4 | II-26 | II-92 | II-42 |
| Q1-1574 | I-4 | II-26 | II-1a | II-42 |
| Q1-1575 | I-4 | II-26 | II-2a | II-42 |
| Q1-1576 | I-4 | II-26 | II-3a | II-42 |
| Q1-1577 | I-4 | II-26 | II-4a | II-42 |
| Q1-1578 | I-4 | II-26 | II-5a | II-42 |
| Q1-1579 | I-4 | II-32 | II-37 | II-42 |
| Q1-1580 | I-4 | II-32 | II-39 | II-42 |
| Q1-1581 | I-4 | II-32 | II-50 | II-42 |
| Q1-1582 | I-4 | II-32 | II-62 | II-42 |
| Q1-1583 | I-4 | II-32 | II-76 | II-42 |
| Q1-1584 | I-4 | II-32 | II-78 | II-42 |
| Q1-1585 | I-4 | II-32 | II-84 | II-42 |
| Q1-1586 | I-4 | II-32 | II-86 | II-42 |
| Q1-1587 | I-4 | II-32 | II-92 | II-42 |
| Q1-1588 | I-4 | II-32 | II-1a | II-42 |
| Q1-1589 | I-4 | II-32 | II-2a | II-42 |
| Q1-1590 | I-4 | II-32 | II-3a | II-42 |
| Q1-1591 | I-4 | II-32 | II-4a | II-42 |
| Q1-1592 | I-4 | II-32 | II-5a | II-42 |
| Q1-1593 | I-4 | II-37 | II-39 | II-42 |
| Q1-1594 | I-4 | II-37 | II-50 | II-42 |
| Q1-1595 | I-4 | II-37 | II-62 | II-42 |
| Q1-1596 | I-4 | II-37 | II-76 | II-42 |
| Q1-1597 | I-4 | II-37 | II-78 | II-42 |
| Q1-1598 | I-4 | II-37 | II-84 | II-42 |
| Q1-1599 | I-4 | II-37 | II-86 | II-42 |
| Q1-1600 | I-4 | II-37 | II-92 | II-42 |
| Q1-1601 | I-4 | II-37 | II-1a | II-42 |
| Q1-1602 | I-4 | II-37 | II-2a | II-42 |
| Q1-1603 | I-4 | II-37 | II-3a | II-42 |
| Q1-1604 | I-4 | II-37 | II-4a | II-42 |
| Q1-1605 | I-4 | II-37 | II-5a | II-42 |
| Q1-1606 | I-4 | II-39 | II-50 | II-42 |
| Q1-1607 | I-4 | II-39 | II-62 | II-42 |
| Q1-1608 | I-4 | II-39 | II-76 | II-42 |
| Q1-1609 | I-4 | II-39 | II-78 | II-42 |
| Q1-1610 | I-4 | II-39 | II-84 | II-42 |
| Q1-1611 | I-4 | II-39 | II-86 | II-42 |
| Q1-1612 | I-4 | II-39 | II-92 | II-42 |
| Q1-1613 | I-4 | II-39 | II-1a | II-42 |
| Q1-1614 | I-4 | II-39 | II-2a | II-42 |
| Q1-1615 | I-4 | II-39 | II-3a | II-42 |
| Q1-1616 | I-4 | II-39 | II-4a | II-42 |
| Q1-1617 | I-4 | II-39 | II-5a | II-42 |
| Q1-1618 | I-4 | II-50 | II-62 | II-42 |
| Q1-1619 | I-4 | II-50 | II-76 | II-42 |
| Q1-1620 | I-4 | II-50 | II-78 | II-42 |
| Q1-1621 | I-4 | II-50 | II-84 | II-42 |
| Q1-1622 | I-4 | II-50 | II-86 | II-42 |
| Q1-1623 | I-4 | II-50 | II-92 | II-42 |
| Q1-1624 | I-4 | II-50 | II-1a | II-42 |
| Q1-1625 | I-4 | II-50 | II-2a | II-42 |
| Q1-1626 | I-4 | II-50 | II-3a | II-42 |
| Q1-1627 | I-4 | II-50 | II-4a | II-42 |
| Q1-1628 | I-4 | II-50 | II-5a | II-42 |
| Q1-1629 | I-4 | II-62 | II-76 | II-42 |
| Q1-1630 | I-4 | II-62 | II-78 | II-42 |
| Q1-1631 | I-4 | II-62 | II-84 | II-42 |
| Q1-1632 | I-4 | II-62 | II-86 | II-42 |
| Q1-1633 | I-4 | II-62 | II-92 | II-42 |
| Q1-1634 | I-4 | II-62 | II-1a | II-42 |
| Q1-1635 | I-4 | II-62 | II-2a | II-42 |
| Q1-1636 | I-4 | II-62 | II-3a | II-42 |
| Q1-1637 | I-4 | II-62 | II-4a | II-42 |
| Q1-1638 | I-4 | II-62 | II-5a | II-42 |
| Q1-1639 | I-4 | II-76 | II-78 | II-42 |
| Q1-1640 | I-4 | II-76 | II-84 | II-42 |
| Q1-1641 | I-4 | II-76 | II-86 | II-42 |
| Q1-1642 | I-4 | II-76 | II-92 | II-42 |
| Q1-1643 | I-4 | II-76 | II-1a | II-42 |
| Q1-1644 | I-4 | II-76 | II-2a | II-42 |
| Q1-1645 | I-4 | II-76 | II-3a | II-42 |
| Q1-1646 | I-4 | II-76 | II-4a | II-42 |
| Q1-1647 | I-4 | II-76 | II-5a | II-42 |
| Q1-1648 | I-4 | II-78 | II-84 | II-42 |
| Q1-1649 | I-4 | II-78 | II-86 | II-42 |
| Q1-1650 | I-4 | II-78 | II-92 | II-42 |
| Q1-1651 | I-4 | II-78 | II-1a | II-42 |
| Q1-1652 | I-4 | II-78 | II-2a | II-42 |
| Q1-1653 | I-4 | II-78 | II-3a | II-42 |
| Q1-1654 | I-4 | II-78 | II-4a | II-42 |
| Q1-1655 | I-4 | II-78 | II-5a | II-42 |
| Q1-1656 | I-4 | II-84 | II-86 | II-42 |
| Q1-1657 | I-4 | II-84 | II-92 | II-42 |
| Q1-1658 | I-4 | II-84 | II-1a | II-42 |
| Q1-1659 | I-4 | II-84 | II-2a | II-42 |
| Q1-1660 | I-4 | II-84 | II-3a | II-42 |
| Q1-1661 | I-4 | II-84 | II-4a | II-42 |
| Q1-1662 | I-4 | II-84 | II-5a | II-42 |
| Q1-1663 | I-4 | II-86 | II-92 | II-42 |
| Q1-1664 | I-4 | II-86 | II-1a | II-42 |
| Q1-1665 | I-4 | II-86 | II-2a | II-42 |
| Q1-1666 | I-4 | II-86 | II-3a | II-42 |
| Q1-1667 | I-4 | II-86 | II-4a | II-42 |
| Q1-1668 | I-4 | II-86 | II-5a | II-42 |
| Q1-1669 | I-4 | II-92 | II-1a | II-42 |
| Q1-1670 | I-4 | II-92 | II-2a | II-42 |
| Q1-1671 | I-4 | II-92 | II-3a | II-42 |
| Q1-1672 | I-4 | II-92 | II-4a | II-42 |
| Q1-1673 | I-4 | II-92 | II-5a | II-42 |
| Q1-1674 | I-4 | II-1a | II-2a | II-42 |
| Q1-1675 | I-4 | II-1a | II-3a | II-42 |
| Q1-1676 | I-4 | II-1a | II-4a | II-42 |
| Q1-1677 | I-4 | II-1a | II-5a | II-42 |
| Q1-1678 | I-4 | II-2a | II-3a | II-42 |
| Q1-1679 | I-4 | II-2a | II-4a | II-42 |
| Q1-1680 | I-4 | II-2a | II-5a | II-42 |
| Q1-1681 | I-4 | II-3a | II-4a | II-42 |
| Q1-1682 | I-4 | II-3a | II-5a | II-42 |
| Q1-1683 | I-4 | II-4a | II-5a | II-42 |
| Q1-1684 | I-4 | II-3 | II-6 | II-66 |
| Q1-1685 | I-4 | II-3 | II-8 | II-66 |
| Q1-1686 | I-4 | II-3 | II-11 | II-66 |
| Q1-1687 | I-4 | II-3 | II-16 | II-66 |
| Q1-1688 | I-4 | II-3 | II-21 | II-66 |
| Q1-1689 | I-4 | II-3 | II-26 | II-66 |
| Q1-1690 | I-4 | II-3 | II-32 | II-66 |
| Q1-1691 | I-4 | II-3 | II-37 | II-66 |
| Q1-1692 | I-4 | II-3 | II-39 | II-66 |
| Q1-1693 | I-4 | II-3 | II-42 | II-66 |
| Q1-1694 | I-4 | II-3 | II-50 | II-66 |
| Q1-1695 | I-4 | II-3 | II-62 | II-66 |
| Q1-1696 | I-4 | II-3 | II-76 | II-66 |
| Q1-1697 | I-4 | II-3 | II-78 | II-66 |
| Q1-1698 | I-4 | II-3 | II-84 | II-66 |
| Q1-1699 | I-4 | II-3 | II-86 | II-66 |
| Q1-1700 | I-4 | II-3 | II-92 | II-66 |
| Q1-1701 | I-4 | II-3 | II-1a | II-66 |
| Q1-1702 | I-4 | II-3 | II-2a | II-66 |

TABLE Q1-continued

Four-component compositions comprising a component I, a fungicide or growth regulator as component II and III and a fungicidal component IV.

| composition | I | II | III | IV |
|---|---|---|---|---|
| Q1-1703 | I-4 | II-3 | II-3a | II-66 |
| Q1-1704 | I-4 | II-3 | II-4a | II-66 |
| Q1-1705 | I-4 | II-3 | II-5a | II-66 |
| Q1-1706 | I-4 | II-6 | II-8 | II-66 |
| Q1-1707 | I-4 | II-6 | II-11 | II-66 |
| Q1-1708 | I-4 | II-6 | II-16 | II-66 |
| Q1-1709 | I-4 | II-6 | II-21 | II-66 |
| Q1-1710 | I-4 | II-6 | II-26 | II-66 |
| Q1-1711 | I-4 | II-6 | II-32 | II-66 |
| Q1-1712 | I-4 | II-6 | II-37 | II-66 |
| Q1-1713 | I-4 | II-6 | II-39 | II-66 |
| Q1-1714 | I-4 | II-6 | II-42 | II-66 |
| Q1-1715 | I-4 | II-6 | II-50 | II-66 |
| Q1-1716 | I-4 | II-6 | II-62 | II-66 |
| Q1-1717 | I-4 | II-6 | II-76 | II-66 |
| Q1-1718 | I-4 | II-6 | II-78 | II-66 |
| Q1-1719 | I-4 | II-6 | II-84 | II-66 |
| Q1-1720 | I-4 | II-6 | II-86 | II-66 |
| Q1-1721 | I-4 | II-6 | II-92 | II-66 |
| Q1-1722 | I-4 | II-6 | II-1a | II-66 |
| Q1-1723 | I-4 | II-6 | II-2a | II-66 |
| Q1-1724 | I-4 | II-6 | II-3a | II-66 |
| Q1-1725 | I-4 | II-6 | II-4a | II-66 |
| Q1-1726 | I-4 | II-6 | II-5a | II-66 |
| Q1-1727 | I-4 | II-8 | II-11 | II-66 |
| Q1-1728 | I-4 | II-8 | II-16 | II-66 |
| Q1-1729 | I-4 | II-8 | II-21 | II-66 |
| Q1-1730 | I-4 | II-8 | II-26 | II-66 |
| Q1-1731 | I-4 | II-8 | II-32 | II-66 |
| Q1-1732 | I-4 | II-8 | II-37 | II-66 |
| Q1-1733 | I-4 | II-8 | II-39 | II-66 |
| Q1-1734 | I-4 | II-8 | II-42 | II-66 |
| Q1-1735 | I-4 | II-8 | II-50 | II-66 |
| Q1-1736 | I-4 | II-8 | II-62 | II-66 |
| Q1-1737 | I-4 | II-8 | II-76 | II-66 |
| Q1-1738 | I-4 | II-8 | II-78 | II-66 |
| Q1-1739 | I-4 | II-8 | II-84 | II-66 |
| Q1-1740 | I-4 | II-8 | II-86 | II-66 |
| Q1-1741 | I-4 | II-8 | II-92 | II-66 |
| Q1-1742 | I-4 | II-8 | II-1a | II-66 |
| Q1-1743 | I-4 | II-8 | II-2a | II-66 |
| Q1-1744 | I-4 | II-8 | II-3a | II-66 |
| Q1-1745 | I-4 | II-8 | II-4a | II-66 |
| Q1-1746 | I-4 | II-8 | II-5a | II-66 |
| Q1-1747 | I-4 | II-11 | II-16 | II-66 |
| Q1-1748 | I-4 | II-11 | II-21 | II-66 |
| Q1-1749 | I-4 | II-11 | II-26 | II-66 |
| Q1-1750 | I-4 | II-11 | II-32 | II-66 |
| Q1-1751 | I-4 | II-11 | II-37 | II-66 |
| Q1-1752 | I-4 | II-11 | II-39 | II-66 |
| Q1-1753 | I-4 | II-11 | II-42 | II-66 |
| Q1-1754 | I-4 | II-11 | II-50 | II-66 |
| Q1-1755 | I-4 | II-11 | II-62 | II-66 |
| Q1-1756 | I-4 | II-11 | II-76 | II-66 |
| Q1-1757 | I-4 | II-11 | II-78 | II-66 |
| Q1-1758 | I-4 | II-11 | II-84 | II-66 |
| Q1-1759 | I-4 | II-11 | II-86 | II-66 |
| Q1-1760 | I-4 | II-11 | II-92 | II-66 |
| Q1-1761 | I-4 | II-11 | II-1a | II-66 |
| Q1-1762 | I-4 | II-11 | II-2a | II-66 |
| Q1-1763 | I-4 | II-11 | II-3a | II-66 |
| Q1-1764 | I-4 | II-11 | II-4a | II-66 |
| Q1-1765 | I-4 | II-11 | II-5a | II-66 |
| Q1-1766 | I-4 | II-16 | II-21 | II-66 |
| Q1-1767 | I-4 | II-16 | II-26 | II-66 |
| Q1-1768 | I-4 | II-16 | II-32 | II-66 |
| Q1-1769 | I-4 | II-16 | II-37 | II-66 |
| Q1-1770 | I-4 | II-16 | II-39 | II-66 |
| Q1-1771 | I-4 | II-16 | II-42 | II-66 |
| Q1-1772 | I-4 | II-16 | II-50 | II-66 |
| Q1-1773 | I-4 | II-16 | II-62 | II-66 |
| Q1-1774 | I-4 | II-16 | II-76 | II-66 |
| Q1-1775 | I-4 | II-16 | II-78 | II-66 |
| Q1-1776 | I-4 | II-16 | II-84 | II-66 |
| Q1-1777 | I-4 | II-16 | II-86 | II-66 |
| Q1-1778 | I-4 | II-16 | II-92 | II-66 |
| Q1-1779 | I-4 | II-16 | II-1a | II-66 |
| Q1-1780 | I-4 | II-16 | II-2a | II-66 |
| Q1-1781 | I-4 | II-16 | II-3a | II-66 |
| Q1-1782 | I-4 | II-16 | II-4a | II-66 |
| Q1-1783 | I-4 | II-16 | II-5a | II-66 |
| Q1-1784 | I-4 | II-21 | II-26 | II-66 |
| Q1-1785 | I-4 | II-21 | II-32 | II-66 |
| Q1-1786 | I-4 | II-21 | II-37 | II-66 |
| Q1-1787 | I-4 | II-21 | II-39 | II-66 |
| Q1-1788 | I-4 | II-21 | II-42 | II-66 |
| Q1-1789 | I-4 | II-21 | II-50 | II-66 |
| Q1-1790 | I-4 | II-21 | II-62 | II-66 |
| Q1-1791 | I-4 | II-21 | II-76 | II-66 |
| Q1-1792 | I-4 | II-21 | II-78 | II-66 |
| Q1-1793 | I-4 | II-21 | II-84 | II-66 |
| Q1-1794 | I-4 | II-21 | II-86 | II-66 |
| Q1-1795 | I-4 | II-21 | II-92 | II-66 |
| Q1-1796 | I-4 | II-21 | II-1a | II-66 |
| Q1-1797 | I-4 | II-21 | II-2a | II-66 |
| Q1-1798 | I-4 | II-21 | II-3a | II-66 |
| Q1-1799 | I-4 | II-21 | II-4a | II-66 |
| Q1-1800 | I-4 | II-21 | II-5a | II-66 |
| Q1-1801 | I-4 | II-26 | II-32 | II-66 |
| Q1-1802 | I-4 | II-26 | II-37 | II-66 |
| Q1-1803 | I-4 | II-26 | II-39 | II-66 |
| Q1-1804 | I-4 | II-26 | II-42 | II-66 |
| Q1-1805 | I-4 | II-26 | II-50 | II-66 |
| Q1-1806 | I-4 | II-26 | II-62 | II-66 |
| Q1-1807 | I-4 | II-26 | II-76 | II-66 |
| Q1-1808 | I-4 | II-26 | II-78 | II-66 |
| Q1-1809 | I-4 | II-26 | II-84 | II-66 |
| Q1-1810 | I-4 | II-26 | II-86 | II-66 |
| Q1-1811 | I-4 | II-26 | II-92 | II-66 |
| Q1-1812 | I-4 | II-26 | II-1a | II-66 |
| Q1-1813 | I-4 | II-26 | II-2a | II-66 |
| Q1-1814 | I-4 | II-26 | II-3a | II-66 |
| Q1-1815 | I-4 | II-26 | II-4a | II-66 |
| Q1-1816 | I-4 | II-26 | II-5a | II-66 |
| Q1-1817 | I-4 | II-32 | II-37 | II-66 |
| Q1-1818 | I-4 | II-32 | II-39 | II-66 |
| Q1-1819 | I-4 | II-32 | II-42 | II-66 |
| Q1-1820 | I-4 | II-32 | II-50 | II-66 |
| Q1-1821 | I-4 | II-32 | II-62 | II-66 |
| Q1-1822 | I-4 | II-32 | II-76 | II-66 |
| Q1-1823 | I-4 | II-32 | II-78 | II-66 |
| Q1-1824 | I-4 | II-32 | II-84 | II-66 |
| Q1-1825 | I-4 | II-32 | II-86 | II-66 |
| Q1-1826 | I-4 | II-32 | II-92 | II-66 |
| Q1-1827 | I-4 | II-32 | II-1a | II-66 |
| Q1-1828 | I-4 | II-32 | II-2a | II-66 |
| Q1-1829 | I-4 | II-32 | II-3a | II-66 |
| Q1-1830 | I-4 | II-32 | II-4a | II-66 |
| Q1-1831 | I-4 | II-32 | II-5a | II-66 |
| Q1-1832 | I-4 | II-37 | II-39 | II-66 |
| Q1-1833 | I-4 | II-37 | II-42 | II-66 |
| Q1-1834 | I-4 | II-37 | II-50 | II-66 |
| Q1-1835 | I-4 | II-37 | II-62 | II-66 |
| Q1-1836 | I-4 | II-37 | II-76 | II-66 |
| Q1-1837 | I-4 | II-37 | II-78 | II-66 |
| Q1-1838 | I-4 | II-37 | II-84 | II-66 |
| Q1-1839 | I-4 | II-37 | II-86 | II-66 |
| Q1-1840 | I-4 | II-37 | II-92 | II-66 |
| Q1-1841 | I-4 | II-37 | II-1a | II-66 |
| Q1-1842 | I-4 | II-37 | II-2a | II-66 |
| Q1-1843 | I-4 | II-37 | II-3a | II-66 |
| Q1-1844 | I-4 | II-37 | II-4a | II-66 |
| Q1-1845 | I-4 | II-37 | II-5a | II-66 |
| Q1-1846 | I-4 | II-39 | II-42 | II-66 |
| Q1-1847 | I-4 | II-39 | II-50 | II-66 |
| Q1-1848 | I-4 | II-39 | II-62 | II-66 |
| Q1-1849 | I-4 | II-39 | II-76 | II-66 |
| Q1-1850 | I-4 | II-39 | II-78 | II-66 |

TABLE Q1-continued

Four-component compositions comprising a component I, a fungicide or growth regulator as component II and III and a fungicidal component IV.

| composition | I | II | III | IV |
|---|---|---|---|---|
| Q1-1851 | I-4 | II-39 | II-84 | II-66 |
| Q1-1852 | I-4 | II-39 | II-86 | II-66 |
| Q1-1853 | I-4 | II-39 | II-92 | II-66 |
| Q1-1854 | I-4 | II-39 | II-1a | II-66 |
| Q1-1855 | I-4 | II-39 | II-2a | II-66 |
| Q1-1856 | I-4 | II-39 | II-3a | II-66 |
| Q1-1857 | I-4 | II-39 | II-4a | II-66 |
| Q1-1858 | I-4 | II-39 | II-5a | II-66 |
| Q1-1859 | I-4 | II-42 | II-50 | II-66 |
| Q1-1860 | I-4 | II-42 | II-62 | II-66 |
| Q1-1861 | I-4 | II-42 | II-76 | II-66 |
| Q1-1862 | I-4 | II-42 | II-78 | II-66 |
| Q1-1863 | I-4 | II-42 | II-84 | II-66 |
| Q1-1864 | I-4 | II-42 | II-86 | II-66 |
| Q1-1865 | I-4 | II-42 | II-92 | II-66 |
| Q1-1866 | I-4 | II-42 | II-1a | II-66 |
| Q1-1867 | I-4 | II-42 | II-2a | II-66 |
| Q1-1868 | I-4 | II-42 | II-3a | II-66 |
| Q1-1869 | I-4 | II-42 | II-4a | II-66 |
| Q1-1870 | I-4 | II-42 | II-5a | II-66 |
| Q1-1871 | I-4 | II-50 | II-62 | II-66 |
| Q1-1872 | I-4 | II-50 | II-76 | II-66 |
| Q1-1873 | I-4 | II-50 | II-78 | II-66 |
| Q1-1874 | I-4 | II-50 | II-84 | II-66 |
| Q1-1875 | I-4 | II-50 | II-86 | II-66 |
| Q1-1876 | I-4 | II-50 | II-92 | II-66 |
| Q1-1877 | I-4 | II-50 | II-1a | II-66 |
| Q1-1878 | I-4 | II-50 | II-2a | II-66 |
| Q1-1879 | I-4 | II-50 | II-3a | II-66 |
| Q1-1880 | I-4 | II-50 | II-4a | II-66 |
| Q1-1881 | I-4 | II-50 | II-5a | II-66 |
| Q1-1882 | I-4 | II-62 | II-76 | II-66 |
| Q1-1883 | I-4 | II-62 | II-78 | II-66 |
| Q1-1884 | I-4 | II-62 | II-84 | II-66 |
| Q1-1885 | I-4 | II-62 | II-86 | II-66 |
| Q1-1886 | I-4 | II-62 | II-92 | II-66 |
| Q1-1887 | I-4 | II-62 | II-1a | II-66 |
| Q1-1888 | I-4 | II-62 | II-2a | II-66 |
| Q1-1889 | I-4 | II-62 | II-3a | II-66 |
| Q1-1890 | I-4 | II-62 | II-4a | II-66 |
| Q1-1891 | I-4 | II-62 | II-5a | II-66 |
| Q1-1892 | I-4 | II-76 | II-78 | II-66 |
| Q1-1893 | I-4 | II-76 | II-84 | II-66 |
| Q1-1894 | I-4 | II-76 | II-86 | II-66 |
| Q1-1895 | I-4 | II-76 | II-92 | II-66 |
| Q1-1896 | I-4 | II-76 | II-1a | II-66 |
| Q1-1897 | I-4 | II-76 | II-2a | II-66 |
| Q1-1898 | I-4 | II-76 | II-3a | II-66 |
| Q1-1899 | I-4 | II-76 | II-4a | II-66 |
| Q1-1900 | I-4 | II-76 | II-5a | II-66 |
| Q1-1901 | I-4 | II-78 | II-84 | II-66 |
| Q1-1902 | I-4 | II-78 | II-86 | II-66 |
| Q1-1903 | I-4 | II-78 | II-92 | II-66 |
| Q1-1904 | I-4 | II-78 | II-1a | II-66 |
| Q1-1905 | I-4 | II-78 | II-2a | II-66 |
| Q1-1906 | I-4 | II-78 | II-3a | II-66 |
| Q1-1907 | I-4 | II-78 | II-4a | II-66 |
| Q1-1908 | I-4 | II-78 | II-5a | II-66 |
| Q1-1909 | I-4 | II-84 | II-86 | II-66 |
| Q1-1910 | I-4 | II-84 | II-92 | II-66 |
| Q1-1911 | I-4 | II-84 | II-1a | II-66 |
| Q1-1912 | I-4 | II-84 | II-2a | II-66 |
| Q1-1913 | I-4 | II-84 | II-3a | II-66 |
| Q1-1914 | I-4 | II-84 | II-4a | II-66 |
| Q1-1915 | I-4 | II-84 | II-5a | II-66 |
| Q1-1916 | I-4 | II-86 | II-92 | II-66 |
| Q1-1917 | I-4 | II-86 | II-1a | II-66 |
| Q1-1918 | I-4 | II-86 | II-2a | II-66 |
| Q1-1919 | I-4 | II-86 | II-3a | II-66 |
| Q1-1920 | I-4 | II-86 | II-4a | II-66 |
| Q1-1921 | I-4 | II-86 | II-5a | II-66 |
| Q1-1922 | I-4 | II-92 | II-1a | II-66 |
| Q1-1923 | I-4 | II-92 | II-2a | II-66 |
| Q1-1924 | I-4 | II-92 | II-3a | II-66 |
| Q1-1925 | I-4 | II-92 | II-4a | II-66 |
| Q1-1926 | I-4 | II-92 | II-5a | II-66 |
| Q1-1927 | I-4 | II-1a | II-2a | II-66 |
| Q1-1928 | I-4 | II-1a | II-3a | II-66 |
| Q1-1929 | I-4 | II-1a | II-4a | II-66 |
| Q1-1930 | I-4 | II-1a | II-5a | II-66 |
| Q1-1931 | I-4 | II-2a | II-3a | II-66 |
| Q1-1932 | I-4 | II-2a | II-4a | II-66 |
| Q1-1933 | I-4 | II-2a | II-5a | II-66 |
| Q1-1934 | I-4 | II-3a | II-4a | II-66 |
| Q1-1935 | I-4 | II-3a | II-5a | II-66 |
| Q1-1936 | I-4 | II-4a | II-5a | II-66 |
| Q1-1937 | I-5 | II-3 | II-6 | II-42 |
| Q1-1938 | I-5 | II-3 | II-8 | II-42 |
| Q1-1939 | I-5 | II-3 | II-11 | II-42 |
| Q1-1940 | I-5 | II-3 | II-16 | II-42 |
| Q1-1941 | I-5 | II-3 | II-21 | II-42 |
| Q1-1942 | I-5 | II-3 | II-26 | II-42 |
| Q1-1943 | I-5 | II-3 | II-32 | II-42 |
| Q1-1944 | I-5 | II-3 | II-37 | II-42 |
| Q1-1945 | I-5 | II-3 | II-39 | II-42 |
| Q1-1946 | I-5 | II-3 | II-50 | II-42 |
| Q1-1947 | I-5 | II-3 | II-62 | II-42 |
| Q1-1948 | I-5 | II-3 | II-76 | II-42 |
| Q1-1949 | I-5 | II-3 | II-78 | II-42 |
| Q1-1950 | I-5 | II-3 | II-84 | II-42 |
| Q1-1951 | I-5 | II-3 | II-86 | II-42 |
| Q1-1952 | I-5 | II-3 | II-92 | II-42 |
| Q1-1953 | I-5 | II-3 | II-1a | II-42 |
| Q1-1954 | I-5 | II-3 | II-2a | II-42 |
| Q1-1955 | I-5 | II-3 | II-3a | II-42 |
| Q1-1956 | I-5 | II-3 | II-4a | II-42 |
| Q1-1957 | I-5 | II-3 | II-5a | II-42 |
| Q1-1958 | I-5 | II-6 | II-8 | II-42 |
| Q1-1959 | I-5 | II-6 | II-11 | II-42 |
| Q1-1960 | I-5 | II-6 | II-16 | II-42 |
| Q1-1961 | I-5 | II-6 | II-21 | II-42 |
| Q1-1962 | I-5 | II-6 | II-26 | II-42 |
| Q1-1963 | I-5 | II-6 | II-32 | II-42 |
| Q1-1964 | I-5 | II-6 | II-37 | II-42 |
| Q1-1965 | I-5 | II-6 | II-39 | II-42 |
| Q1-1966 | I-5 | II-6 | II-50 | II-42 |
| Q1-1967 | I-5 | II-6 | II-62 | II-42 |
| Q1-1968 | I-5 | II-6 | II-76 | II-42 |
| Q1-1969 | I-5 | II-6 | II-78 | II-42 |
| Q1-1970 | I-5 | II-6 | II-84 | II-42 |
| Q1-1971 | I-5 | II-6 | II-86 | II-42 |
| Q1-1972 | I-5 | II-6 | II-92 | II-42 |
| Q1-1973 | I-5 | II-6 | II-1a | II-42 |
| Q1-1974 | I-5 | II-6 | II-2a | II-42 |
| Q1-1975 | I-5 | II-6 | II-3a | II-42 |
| Q1-1976 | I-5 | II-6 | II-4a | II-42 |
| Q1-1977 | I-5 | II-6 | II-5a | II-42 |
| Q1-1978 | I-5 | II-8 | II-11 | II-42 |
| Q1-1979 | I-5 | II-8 | II-16 | II-42 |
| Q1-1980 | I-5 | II-8 | II-21 | II-42 |
| Q1-1981 | I-5 | II-8 | II-26 | II-42 |
| Q1-1982 | I-5 | II-8 | II-32 | II-42 |
| Q1-1983 | I-5 | II-8 | II-37 | II-42 |
| Q1-1984 | I-5 | II-8 | II-39 | II-42 |
| Q1-1985 | I-5 | II-8 | II-50 | II-42 |
| Q1-1986 | I-5 | II-8 | II-62 | II-42 |
| Q1-1987 | I-5 | II-8 | II-76 | II-42 |
| Q1-1988 | I-5 | II-8 | II-78 | II-42 |
| Q1-1989 | I-5 | II-8 | II-84 | II-42 |
| Q1-1990 | I-5 | II-8 | II-86 | II-42 |
| Q1-1991 | I-5 | II-8 | II-92 | II-42 |
| Q1-1992 | I-5 | II-8 | II-1a | II-42 |
| Q1-1993 | I-5 | II-8 | II-2a | II-42 |
| Q1-1994 | I-5 | II-8 | II-3a | II-42 |
| Q1-1995 | I-5 | II-8 | II-4a | II-42 |
| Q1-1996 | I-5 | II-8 | II-5a | II-42 |
| Q1-1997 | I-5 | II-11 | II-16 | II-42 |
| Q1-1998 | I-5 | II-11 | II-21 | II-42 |

TABLE Q1-continued

Four-component compositions comprising a component I, a fungicide or growth regulator as component II and III and a fungicidal component IV.

| composition | I | II | III | IV |
|---|---|---|---|---|
| Q1-1999 | I-5 | II-11 | II-26 | II-42 |
| Q1-2000 | I-5 | II-11 | II-32 | II-42 |
| Q1-2001 | I-5 | II-11 | II-37 | II-42 |
| Q1-2002 | I-5 | II-11 | II-39 | II-42 |
| Q1-2003 | I-5 | II-11 | II-50 | II-42 |
| Q1-2004 | I-5 | II-11 | II-62 | II-42 |
| Q1-2005 | I-5 | II-11 | II-76 | II-42 |
| Q1-2006 | I-5 | II-11 | II-78 | II-42 |
| Q1-2007 | I-5 | II-11 | II-84 | II-42 |
| Q1-2008 | I-5 | II-11 | II-86 | II-42 |
| Q1-2009 | I-5 | II-11 | II-92 | II-42 |
| Q1-2010 | I-5 | II-11 | II-1a | II-42 |
| Q1-2011 | I-5 | II-11 | II-2a | II-42 |
| Q1-2012 | I-5 | II-11 | II-3a | II-42 |
| Q1-2013 | I-5 | II-11 | II-4a | II-42 |
| Q1-2014 | I-5 | II-11 | II-5a | II-42 |
| Q1-2015 | I-5 | II-16 | II-21 | II-42 |
| Q1-2016 | I-5 | II-16 | II-26 | II-42 |
| Q1-2017 | I-5 | II-16 | II-32 | II-42 |
| Q1-2018 | I-5 | II-16 | II-37 | II-42 |
| Q1-2019 | I-5 | II-16 | II-39 | II-42 |
| Q1-2020 | I-5 | II-16 | II-50 | II-42 |
| Q1-2021 | I-5 | II-16 | II-62 | II-42 |
| Q1-2022 | I-5 | II-16 | II-76 | II-42 |
| Q1-2023 | I-5 | II-16 | II-78 | II-42 |
| Q1-2024 | I-5 | II-16 | II-84 | II-42 |
| Q1-2025 | I-5 | II-16 | II-86 | II-42 |
| Q1-2026 | I-5 | II-16 | II-92 | II-42 |
| Q1-2027 | I-5 | II-16 | II-1a | II-42 |
| Q1-2028 | I-5 | II-16 | II-2a | II-42 |
| Q1-2029 | I-5 | II-16 | II-3a | II-42 |
| Q1-2030 | I-5 | II-16 | II-4a | II-42 |
| Q1-2031 | I-5 | II-16 | II-5a | II-42 |
| Q1-2032 | I-5 | II-21 | II-26 | II-42 |
| Q1-2033 | I-5 | II-21 | II-32 | II-42 |
| Q1-2034 | I-5 | II-21 | II-37 | II-42 |
| Q1-2035 | I-5 | II-21 | II-39 | II-42 |
| Q1-2036 | I-5 | II-21 | II-50 | II-42 |
| Q1-2037 | I-5 | II-21 | II-62 | II-42 |
| Q1-2038 | I-5 | II-21 | II-76 | II-42 |
| Q1-2039 | I-5 | II-21 | II-78 | II-42 |
| Q1-2040 | I-5 | II-21 | II-84 | II-42 |
| Q1-2041 | I-5 | II-21 | II-86 | II-42 |
| Q1-2042 | I-5 | II-21 | II-92 | II-42 |
| Q1-2043 | I-5 | II-21 | II-1a | II-42 |
| Q1-2044 | I-5 | II-21 | II-2a | II-42 |
| Q1-2045 | I-5 | II-21 | II-3a | II-42 |
| Q1-2046 | I-5 | II-21 | II-4a | II-42 |
| Q1-2047 | I-5 | II-21 | II-5a | II-42 |
| Q1-2048 | I-5 | II-26 | II-32 | II-42 |
| Q1-2049 | I-5 | II-26 | II-37 | II-42 |
| Q1-2050 | I-5 | II-26 | II-39 | II-42 |
| Q1-2051 | I-5 | II-26 | II-50 | II-42 |
| Q1-2052 | I-5 | II-26 | II-62 | II-42 |
| Q1-2053 | I-5 | II-26 | II-76 | II-42 |
| Q1-2054 | I-5 | II-26 | II-78 | II-42 |
| Q1-2055 | I-5 | II-26 | II-84 | II-42 |
| Q1-2056 | I-5 | II-26 | II-86 | II-42 |
| Q1-2057 | I-5 | II-26 | II-92 | II-42 |
| Q1-2058 | I-5 | II-26 | II-1a | II-42 |
| Q1-2059 | I-5 | II-26 | II-2a | II-42 |
| Q1-2060 | I-5 | II-26 | II-3a | II-42 |
| Q1-2061 | I-5 | II-26 | II-4a | II-42 |
| Q1-2062 | I-5 | II-26 | II-5a | II-42 |
| Q1-2063 | I-5 | II-32 | II-37 | II-42 |
| Q1-2064 | I-5 | II-32 | II-39 | II-42 |
| Q1-2065 | I-5 | II-32 | II-50 | II-42 |
| Q1-2066 | I-5 | II-32 | II-62 | II-42 |
| Q1-2067 | I-5 | II-32 | II-76 | II-42 |
| Q1-2068 | I-5 | II-32 | II-78 | II-42 |
| Q1-2069 | I-5 | II-32 | II-84 | II-42 |
| Q1-2070 | I-5 | II-32 | II-86 | II-42 |
| Q1-2071 | I-5 | II-32 | II-92 | II-42 |
| Q1-2072 | I-5 | II-32 | II-1a | II-42 |
| Q1-2073 | I-5 | II-32 | II-2a | II-42 |
| Q1-2074 | I-5 | II-32 | II-3a | II-42 |
| Q1-2075 | I-5 | II-32 | II-4a | II-42 |
| Q1-2076 | I-5 | II-32 | II-5a | II-42 |
| Q1-2077 | I-5 | II-37 | II-39 | II-42 |
| Q1-2078 | I-5 | II-37 | II-50 | II-42 |
| Q1-2079 | I-5 | II-37 | II-62 | II-42 |
| Q1-2080 | I-5 | II-37 | II-76 | II-42 |
| Q1-2081 | I-5 | II-37 | II-78 | II-42 |
| Q1-2082 | I-5 | II-37 | II-84 | II-42 |
| Q1-2083 | I-5 | II-37 | II-86 | II-42 |
| Q1-2084 | I-5 | II-37 | II-92 | II-42 |
| Q1-2085 | I-5 | II-37 | II-1a | II-42 |
| Q1-2086 | I-5 | II-37 | II-2a | II-42 |
| Q1-2087 | I-5 | II-37 | II-3a | II-42 |
| Q1-2088 | I-5 | II-37 | II-4a | II-42 |
| Q1-2089 | I-5 | II-37 | II-5a | II-42 |
| Q1-2090 | I-5 | II-39 | II-50 | II-42 |
| Q1-2091 | I-5 | II-39 | II-62 | II-42 |
| Q1-2092 | I-5 | II-39 | II-76 | II-42 |
| Q1-2093 | I-5 | II-39 | II-78 | II-42 |
| Q1-2094 | I-5 | II-39 | II-84 | II-42 |
| Q1-2095 | I-5 | II-39 | II-86 | II-42 |
| Q1-2096 | I-5 | II-39 | II-92 | II-42 |
| Q1-2097 | I-5 | II-39 | II-1a | II-42 |
| Q1-2098 | I-5 | II-39 | II-2a | II-42 |
| Q1-2099 | I-5 | II-39 | II-3a | II-42 |
| Q1-2100 | I-5 | II-39 | II-4a | II-42 |
| Q1-2101 | I-5 | II-39 | II-5a | II-42 |
| Q1-2102 | I-5 | II-50 | II-62 | II-42 |
| Q1-2103 | I-5 | II-50 | II-76 | II-42 |
| Q1-2104 | I-5 | II-50 | II-78 | II-42 |
| Q1-2105 | I-5 | II-50 | II-84 | II-42 |
| Q1-2106 | I-5 | II-50 | II-86 | II-42 |
| Q1-2107 | I-5 | II-50 | II-92 | II-42 |
| Q1-2108 | I-5 | II-50 | II-1a | II-42 |
| Q1-2109 | I-5 | II-50 | II-2a | II-42 |
| Q1-2110 | I-5 | II-50 | II-3a | II-42 |
| Q1-2111 | I-5 | II-50 | II-4a | II-42 |
| Q1-2112 | I-5 | II-50 | II-5a | II-42 |
| Q1-2113 | I-5 | II-62 | II-76 | II-42 |
| Q1-2114 | I-5 | II-62 | II-78 | II-42 |
| Q1-2115 | I-5 | II-62 | II-84 | II-42 |
| Q1-2116 | I-5 | II-62 | II-86 | II-42 |
| Q1-2117 | I-5 | II-62 | II-92 | II-42 |
| Q1-2118 | I-5 | II-62 | II-1a | II-42 |
| Q1-2119 | I-5 | II-62 | II-2a | II-42 |
| Q1-2120 | I-5 | II-62 | II-3a | II-42 |
| Q1-2121 | I-5 | II-62 | II-4a | II-42 |
| Q1-2122 | I-5 | II-62 | II-5a | II-42 |
| Q1-2123 | I-5 | II-76 | II-78 | II-42 |
| Q1-2124 | I-5 | II-76 | II-84 | II-42 |
| Q1-2125 | I-5 | II-76 | II-86 | II-42 |
| Q1-2126 | I-5 | II-76 | II-92 | II-42 |
| Q1-2127 | I-5 | II-76 | II-1a | II-42 |
| Q1-2128 | I-5 | II-76 | II-2a | II-42 |
| Q1-2129 | I-5 | II-76 | II-3a | II-42 |
| Q1-2130 | I-5 | II-76 | II-4a | II-42 |
| Q1-2131 | I-5 | II-76 | II-5a | II-42 |
| Q1-2132 | I-5 | II-78 | II-84 | II-42 |
| Q1-2133 | I-5 | II-78 | II-86 | II-42 |
| Q1-2134 | I-5 | II-78 | II-92 | II-42 |
| Q1-2135 | I-5 | II-78 | II-1a | II-42 |
| Q1-2136 | I-5 | II-78 | II-2a | II-42 |
| Q1-2137 | I-5 | II-78 | II-3a | II-42 |
| Q1-2138 | I-5 | II-78 | II-4a | II-42 |
| Q1-2139 | I-5 | II-78 | II-5a | II-42 |
| Q1-2140 | I-5 | II-84 | II-86 | II-42 |
| Q1-2141 | I-5 | II-84 | II-92 | II-42 |
| Q1-2142 | I-5 | II-84 | II-1a | II-42 |
| Q1-2143 | I-5 | II-84 | II-2a | II-42 |
| Q1-2144 | I-5 | II-84 | II-3a | II-42 |
| Q1-2145 | I-5 | II-84 | II-4a | II-42 |
| Q1-2146 | I-5 | II-84 | II-5a | II-42 |

TABLE Q1-continued

Four-component compositions comprising a component I, a fungicide or growth regulator as component II and III and a fungicidal component IV.

| composition | I | II | III | IV |
|---|---|---|---|---|
| Q1-2147 | I-5 | II-86 | II-92 | II-42 |
| Q1-2148 | I-5 | II-86 | II-1a | II-42 |
| Q1-2149 | I-5 | II-86 | II-2a | II-42 |
| Q1-2150 | I-5 | II-86 | II-3a | II-42 |
| Q1-2151 | I-5 | II-86 | II-4a | II-42 |
| Q1-2152 | I-5 | II-86 | II-5a | II-42 |
| Q1-2153 | I-5 | II-92 | II-1a | II-42 |
| Q1-2154 | I-5 | II-92 | II-2a | II-42 |
| Q1-2155 | I-5 | II-92 | II-3a | II-42 |
| Q1-2156 | I-5 | II-92 | II-4a | II-42 |
| Q1-2157 | I-5 | II-92 | II-5a | II-42 |
| Q1-2158 | I-5 | II-1a | II-2a | II-42 |
| Q1-2159 | I-5 | II-1a | II-3a | II-42 |
| Q1-2160 | I-5 | II-1a | II-4a | II-42 |
| Q1-2161 | I-5 | II-1a | II-5a | II-42 |
| Q1-2162 | I-5 | II-2a | II-3a | II-42 |
| Q1-2163 | I-5 | II-2a | II-4a | II-42 |
| Q1-2164 | I-5 | II-2a | II-5a | II-42 |
| Q1-2165 | I-5 | II-3a | II-4a | II-42 |
| Q1-2166 | I-5 | II-3a | II-5a | II-42 |
| Q1-2167 | I-5 | II-4a | II-5a | II-42 |
| Q1-2168 | I-5 | II-3 | II-6 | II-66 |
| Q1-2169 | I-5 | II-3 | II-8 | II-66 |
| Q1-2170 | I-5 | II-3 | II-11 | II-66 |
| Q1-2171 | I-5 | II-3 | II-16 | II-66 |
| Q1-2172 | I-5 | II-3 | II-21 | II-66 |
| Q1-2173 | I-5 | II-3 | II-26 | II-66 |
| Q1-2174 | I-5 | II-3 | II-32 | II-66 |
| Q1-2175 | I-5 | II-3 | II-37 | II-66 |
| Q1-2176 | I-5 | II-3 | II-39 | II-66 |
| Q1-2177 | I-5 | II-3 | II-42 | II-66 |
| Q1-2178 | I-5 | II-3 | II-50 | II-66 |
| Q1-2179 | I-5 | II-3 | II-62 | II-66 |
| Q1-2180 | I-5 | II-3 | II-76 | II-66 |
| Q1-2181 | I-5 | II-3 | II-78 | II-66 |
| Q1-2182 | I-5 | II-3 | II-84 | II-66 |
| Q1-2183 | I-5 | II-3 | II-86 | II-66 |
| Q1-2184 | I-5 | II-3 | II-92 | II-66 |
| Q1-2185 | I-5 | II-3 | II-1a | II-66 |
| Q1-2186 | I-5 | II-3 | II-2a | II-66 |
| Q1-2187 | I-5 | II-3 | II-3a | II-66 |
| Q1-2188 | I-5 | II-3 | II-4a | II-66 |
| Q1-2189 | I-5 | II-3 | II-5a | II-66 |
| Q1-2190 | I-5 | II-6 | II-8 | II-66 |
| Q1-2191 | I-5 | II-6 | II-11 | II-66 |
| Q1-2192 | I-5 | II-6 | II-16 | II-66 |
| Q1-2193 | I-5 | II-6 | II-21 | II-66 |
| Q1-2194 | I-5 | II-6 | II-26 | II-66 |
| Q1-2195 | I-5 | II-6 | II-32 | II-66 |
| Q1-2196 | I-5 | II-6 | II-37 | II-66 |
| Q1-2197 | I-5 | II-6 | II-39 | II-66 |
| Q1-2198 | I-5 | II-6 | II-42 | II-66 |
| Q1-2199 | I-5 | II-6 | II-50 | II-66 |
| Q1-2200 | I-5 | II-6 | II-62 | II-66 |
| Q1-2201 | I-5 | II-6 | II-76 | II-66 |
| Q1-2202 | I-5 | II-6 | II-78 | II-66 |
| Q1-2203 | I-5 | II-6 | II-84 | II-66 |
| Q1-2204 | I-5 | II-6 | II-86 | II-66 |
| Q1-2205 | I-5 | II-6 | II-92 | II-66 |
| Q1-2206 | I-5 | II-6 | II-1a | II-66 |
| Q1-2207 | I-5 | II-6 | II-2a | II-66 |
| Q1-2208 | I-5 | II-6 | II-3a | II-66 |
| Q1-2209 | I-5 | II-6 | II-4a | II-66 |
| Q1-2210 | I-5 | II-6 | II-5a | II-66 |
| Q1-2211 | I-5 | II-8 | II-11 | II-66 |
| Q1-2212 | I-5 | II-8 | II-16 | II-66 |
| Q1-2213 | I-5 | II-8 | II-21 | II-66 |
| Q1-2214 | I-5 | II-8 | II-26 | II-66 |
| Q1-2215 | I-5 | II-8 | II-32 | II-66 |
| Q1-2216 | I-5 | II-8 | II-37 | II-66 |
| Q1-2217 | I-5 | II-8 | II-39 | II-66 |
| Q1-2218 | I-5 | II-8 | II-42 | II-66 |
| Q1-2219 | I-5 | II-8 | II-50 | II-66 |
| Q1-2220 | I-5 | II-8 | II-62 | II-66 |
| Q1-2221 | I-5 | II-8 | II-76 | II-66 |
| Q1-2222 | I-5 | II-8 | II-78 | II-66 |
| Q1-2223 | I-5 | II-8 | II-84 | II-66 |
| Q1-2224 | I-5 | II-8 | II-86 | II-66 |
| Q1-2225 | I-5 | II-8 | II-92 | II-66 |
| Q1-2226 | I-5 | II-8 | II-1a | II-66 |
| Q1-2227 | I-5 | II-8 | II-2a | II-66 |
| Q1-2228 | I-5 | II-8 | II-3a | II-66 |
| Q1-2229 | I-5 | II-8 | II-4a | II-66 |
| Q1-2230 | I-5 | II-8 | II-5a | II-66 |
| Q1-2231 | I-5 | II-11 | II-16 | II-66 |
| Q1-2232 | I-5 | II-11 | II-21 | II-66 |
| Q1-2233 | I-5 | II-11 | II-26 | II-66 |
| Q1-2234 | I-5 | II-11 | II-32 | II-66 |
| Q1-2235 | I-5 | II-11 | II-37 | II-66 |
| Q1-2236 | I-5 | II-11 | II-39 | II-66 |
| Q1-2237 | I-5 | II-11 | II-42 | II-66 |
| Q1-2238 | I-5 | II-11 | II-50 | II-66 |
| Q1-2239 | I-5 | II-11 | II-62 | II-66 |
| Q1-2240 | I-5 | II-11 | II-76 | II-66 |
| Q1-2241 | I-5 | II-11 | II-78 | II-66 |
| Q1-2242 | I-5 | II-11 | II-84 | II-66 |
| Q1-2243 | I-5 | II-11 | II-86 | II-66 |
| Q1-2244 | I-5 | II-11 | II-92 | II-66 |
| Q1-2245 | I-5 | II-11 | II-1a | II-66 |
| Q1-2246 | I-5 | II-11 | II-2a | II-66 |
| Q1-2247 | I-5 | II-11 | II-3a | II-66 |
| Q1-2248 | I-5 | II-11 | II-4a | II-66 |
| Q1-2249 | I-5 | II-11 | II-5a | II-66 |
| Q1-2250 | I-5 | II-16 | II-21 | II-66 |
| Q1-2251 | I-5 | II-16 | II-26 | II-66 |
| Q1-2252 | I-5 | II-16 | II-32 | II-66 |
| Q1-2253 | I-5 | II-16 | II-37 | II-66 |
| Q1-2254 | I-5 | II-16 | II-39 | II-66 |
| Q1-2255 | I-5 | II-16 | II-42 | II-66 |
| Q1-2256 | I-5 | II-16 | II-50 | II-66 |
| Q1-2257 | I-5 | II-16 | II-62 | II-66 |
| Q1-2258 | I-5 | II-16 | II-76 | II-66 |
| Q1-2259 | I-5 | II-16 | II-78 | II-66 |
| Q1-2260 | I-5 | II-16 | II-84 | II-66 |
| Q1-2261 | I-5 | II-16 | II-86 | II-66 |
| Q1-2262 | I-5 | II-16 | II-92 | II-66 |
| Q1-2263 | I-5 | II-16 | II-1a | II-66 |
| Q1-2264 | I-5 | II-16 | II-2a | II-66 |
| Q1-2265 | I-5 | II-16 | II-3a | II-66 |
| Q1-2266 | I-5 | II-16 | II-4a | II-66 |
| Q1-2267 | I-5 | II-16 | II-5a | II-66 |
| Q1-2268 | I-5 | II-21 | II-26 | II-66 |
| Q1-2269 | I-5 | II-21 | II-32 | II-66 |
| Q1-2270 | I-5 | II-21 | II-37 | II-66 |
| Q1-2271 | I-5 | II-21 | II-39 | II-66 |
| Q1-2272 | I-5 | II-21 | II-42 | II-66 |
| Q1-2273 | I-5 | II-21 | II-50 | II-66 |
| Q1-2274 | I-5 | II-21 | II-62 | II-66 |
| Q1-2275 | I-5 | II-21 | II-76 | II-66 |
| Q1-2276 | I-5 | II-21 | II-78 | II-66 |
| Q1-2277 | I-5 | II-21 | II-84 | II-66 |
| Q1-2278 | I-5 | II-21 | II-86 | II-66 |
| Q1-2279 | I-5 | II-21 | II-92 | II-66 |
| Q1-2280 | I-5 | II-21 | II-1a | II-66 |
| Q1-2281 | I-5 | II-21 | II-2a | II-66 |
| Q1-2282 | I-5 | II-21 | II-3a | II-66 |
| Q1-2283 | I-5 | II-21 | II-4a | II-66 |
| Q1-2284 | I-5 | II-21 | II-5a | II-66 |
| Q1-2285 | I-5 | II-26 | II-32 | II-66 |
| Q1-2286 | I-5 | II-26 | II-37 | II-66 |
| Q1-2287 | I-5 | II-26 | II-39 | II-66 |
| Q1-2288 | I-5 | II-26 | II-42 | II-66 |
| Q1-2289 | I-5 | II-26 | II-50 | II-66 |
| Q1-2290 | I-5 | II-26 | II-62 | II-66 |
| Q1-2291 | I-5 | II-26 | II-76 | II-66 |
| Q1-2292 | I-5 | II-26 | II-78 | II-66 |
| Q1-2293 | I-5 | II-26 | II-84 | II-66 |
| Q1-2294 | I-5 | II-26 | II-86 | II-66 |

TABLE Q1-continued

Four-component compositions comprising a component I, a fungicide or growth regulator as component II and III and a fungicidal component IV.

| composition | I | II | III | IV |
|---|---|---|---|---|
| Q1-2295 | I-5 | II-26 | II-92 | II-66 |
| Q1-2296 | I-5 | II-26 | II-1a | II-66 |
| Q1-2297 | I-5 | II-26 | II-2a | II-66 |
| Q1-2298 | I-5 | II-26 | II-3a | II-66 |
| Q1-2299 | I-5 | II-26 | II-4a | II-66 |
| Q1-2300 | I-5 | II-26 | II-5a | II-66 |
| Q1-2301 | I-5 | II-32 | II-37 | II-66 |
| Q1-2302 | I-5 | II-32 | II-39 | II-66 |
| Q1-2303 | I-5 | II-32 | II-42 | II-66 |
| Q1-2304 | I-5 | II-32 | II-50 | II-66 |
| Q1-2305 | I-5 | II-32 | II-62 | II-66 |
| Q1-2306 | I-5 | II-32 | II-76 | II-66 |
| Q1-2307 | I-5 | II-32 | II-78 | II-66 |
| Q1-2308 | I-5 | II-32 | II-84 | II-66 |
| Q1-2309 | I-5 | II-32 | II-86 | II-66 |
| Q1-2310 | I-5 | II-32 | II-92 | II-66 |
| Q1-2311 | I-5 | II-32 | II-1a | II-66 |
| Q1-2312 | I-5 | II-32 | II-2a | II-66 |
| Q1-2313 | I-5 | II-32 | II-3a | II-66 |
| Q1-2314 | I-5 | II-32 | II-4a | II-66 |
| Q1-2315 | I-5 | II-32 | II-5a | II-66 |
| Q1-2316 | I-5 | II-37 | II-39 | II-66 |
| Q1-2317 | I-5 | II-37 | II-42 | II-66 |
| Q1-2318 | I-5 | II-37 | II-50 | II-66 |
| Q1-2319 | I-5 | II-37 | II-62 | II-66 |
| Q1-2320 | I-5 | II-37 | II-76 | II-66 |
| Q1-2321 | I-5 | II-37 | II-78 | II-66 |
| Q1-2322 | I-5 | II-37 | II-84 | II-66 |
| Q1-2323 | I-5 | II-37 | II-86 | II-66 |
| Q1-2324 | I-5 | II-37 | II-92 | II-66 |
| Q1-2325 | I-5 | II-37 | II-1a | II-66 |
| Q1-2326 | I-5 | II-37 | II-2a | II-66 |
| Q1-2327 | I-5 | II-37 | II-3a | II-66 |
| Q1-2328 | I-5 | II-37 | II-4a | II-66 |
| Q1-2329 | I-5 | II-37 | II-5a | II-66 |
| Q1-2330 | I-5 | II-39 | II-42 | II-66 |
| Q1-2331 | I-5 | II-39 | II-50 | II-66 |
| Q1-2332 | I-5 | II-39 | II-62 | II-66 |
| Q1-2333 | I-5 | II-39 | II-76 | II-66 |
| Q1-2334 | I-5 | II-39 | II-78 | II-66 |
| Q1-2335 | I-5 | II-39 | II-84 | II-66 |
| Q1-2336 | I-5 | II-39 | II-86 | II-66 |
| Q1-2337 | I-5 | II-39 | II-92 | II-66 |
| Q1-2338 | I-5 | II-39 | II-1a | II-66 |
| Q1-2339 | I-5 | II-39 | II-2a | II-66 |
| Q1-2340 | I-5 | II-39 | II-3a | II-66 |
| Q1-2341 | I-5 | II-39 | II-4a | II-66 |
| Q1-2342 | I-5 | II-39 | II-5a | II-66 |
| Q1-2343 | I-5 | II-42 | II-50 | II-66 |
| Q1-2344 | I-5 | II-42 | II-62 | II-66 |
| Q1-2345 | I-5 | II-42 | II-76 | II-66 |
| Q1-2346 | I-5 | II-42 | II-78 | II-66 |
| Q1-2347 | I-5 | II-42 | II-84 | II-66 |
| Q1-2348 | I-5 | II-42 | II-86 | II-66 |
| Q1-2349 | I-5 | II-42 | II-92 | II-66 |
| Q1-2350 | I-5 | II-42 | II-1a | II-66 |
| Q1-2351 | I-5 | II-42 | II-2a | II-66 |
| Q1-2352 | I-5 | II-42 | II-3a | II-66 |
| Q1-2353 | I-5 | II-42 | II-4a | II-66 |
| Q1-2354 | I-5 | II-42 | II-5a | II-66 |
| Q1-2355 | I-5 | II-50 | II-62 | II-66 |
| Q1-2356 | I-5 | II-50 | II-76 | II-66 |
| Q1-2357 | I-5 | II-50 | II-78 | II-66 |
| Q1-2358 | I-5 | II-50 | II-84 | II-66 |
| Q1-2359 | I-5 | II-50 | II-86 | II-66 |
| Q1-2360 | I-5 | II-50 | II-92 | II-66 |
| Q1-2361 | I-5 | II-50 | II-1a | II-66 |
| Q1-2362 | I-5 | II-50 | II-2a | II-66 |
| Q1-2363 | I-5 | II-50 | II-3a | II-66 |
| Q1-2364 | I-5 | II-50 | II-4a | II-66 |
| Q1-2365 | I-5 | II-50 | II-5a | II-66 |
| Q1-2366 | I-5 | II-62 | II-76 | II-66 |
| Q1-2367 | I-5 | II-62 | II-78 | II-66 |
| Q1-2368 | I-5 | II-62 | II-84 | II-66 |
| Q1-2369 | I-5 | II-62 | II-86 | II-66 |
| Q1-2370 | I-5 | II-62 | II-92 | II-66 |
| Q1-2371 | I-5 | II-62 | II-1a | II-66 |
| Q1-2372 | I-5 | II-62 | II-2a | II-66 |
| Q1-2373 | I-5 | II-62 | II-3a | II-66 |
| Q1-2374 | I-5 | II-62 | II-4a | II-66 |
| Q1-2375 | I-5 | II-62 | II-5a | II-66 |
| Q1-2376 | I-5 | II-76 | II-78 | II-66 |
| Q1-2377 | I-5 | II-76 | II-84 | II-66 |
| Q1-2378 | I-5 | II-76 | II-86 | II-66 |
| Q1-2379 | I-5 | II-76 | II-92 | II-66 |
| Q1-2380 | I-5 | II-76 | II-1a | II-66 |
| Q1-2381 | I-5 | II-76 | II-2a | II-66 |
| Q1-2382 | I-5 | II-76 | II-3a | II-66 |
| Q1-2383 | I-5 | II-76 | II-4a | II-66 |
| Q1-2384 | I-5 | II-76 | II-5a | II-66 |
| Q1-2385 | I-5 | II-78 | II-84 | II-66 |
| Q1-2386 | I-5 | II-78 | II-86 | II-66 |
| Q1-2387 | I-5 | II-78 | II-92 | II-66 |
| Q1-2388 | I-5 | II-78 | II-1a | II-66 |
| Q1-2389 | I-5 | II-78 | II-2a | II-66 |
| Q1-2390 | I-5 | II-78 | II-3a | II-66 |
| Q1-2391 | I-5 | II-78 | II-4a | II-66 |
| Q1-2392 | I-5 | II-78 | II-5a | II-66 |
| Q1-2393 | I-5 | II-84 | II-86 | II-66 |
| Q1-2394 | I-5 | II-84 | II-92 | II-66 |
| Q1-2395 | I-5 | II-84 | II-1a | II-66 |
| Q1-2396 | I-5 | II-84 | II-2a | II-66 |
| Q1-2397 | I-5 | II-84 | II-3a | II-66 |
| Q1-2398 | I-5 | II-84 | II-4a | II-66 |
| Q1-2399 | I-5 | II-84 | II-5a | II-66 |
| Q1-2400 | I-5 | II-86 | II-92 | II-66 |
| Q1-2401 | I-5 | II-86 | II-1a | II-66 |
| Q1-2402 | I-5 | II-86 | II-2a | II-66 |
| Q1-2403 | I-5 | II-86 | II-3a | II-66 |
| Q1-2404 | I-5 | II-86 | II-4a | II-66 |
| Q1-2405 | I-5 | II-86 | II-5a | II-66 |
| Q1-2406 | I-5 | II-92 | II-1a | II-66 |
| Q1-2407 | I-5 | II-92 | II-2a | II-66 |
| Q1-2408 | I-5 | II-92 | II-3a | II-66 |
| Q1-2409 | I-5 | II-92 | II-4a | II-66 |
| Q1-2410 | I-5 | II-92 | II-5a | II-66 |
| Q1-2411 | I-5 | II-1a | II-2a | II-66 |
| Q1-2412 | I-5 | II-1a | II-3a | II-66 |
| Q1-2413 | I-5 | II-1a | II-4a | II-66 |
| Q1-2414 | I-5 | II-1a | II-5a | II-66 |
| Q1-2415 | I-5 | II-2a | II-3a | II-66 |
| Q1-2416 | I-5 | II-2a | II-4a | II-66 |
| Q1-2417 | I-5 | II-2a | II-5a | II-66 |
| Q1-2418 | I-5 | II-3a | II-4a | II-66 |
| Q1-2419 | I-5 | II-3a | II-5a | II-66 |
| Q1-2420 | I-5 | II-4a | II-5a | II-66 |

Four-component compositions comprising another compound I as component I, a fungicide or growth regulator as component II and III and a fungicidal component IV.

| composition | I | II | III | IV |
|---|---|---|---|---|
| Q1-2421 | I-13 | II-3 | II-6 | II-42 |
| Q1-2422 | I-13 | II-3 | II-8 | II-42 |
| Q1-2423 | I-13 | II-3 | II-11 | II-42 |
| Q1-2424 | I-13 | II-3 | II-16 | II-42 |
| Q1-2425 | I-13 | II-3 | II-21 | II-42 |
| Q1-2426 | I-13 | II-3 | II-26 | II-42 |
| Q1-2427 | I-13 | II-3 | II-32 | II-42 |
| Q1-2428 | I-13 | II-3 | II-37 | II-42 |
| Q1-2429 | I-13 | II-3 | II-39 | II-42 |
| Q1-2430 | I-13 | II-3 | II-50 | II-42 |
| Q1-2431 | I-13 | II-3 | II-62 | II-42 |
| Q1-2432 | I-13 | II-3 | II-76 | II-42 |
| Q1-2433 | I-13 | II-3 | II-78 | II-42 |
| Q1-2434 | I-13 | II-3 | II-84 | II-42 |
| Q1-2435 | I-13 | II-3 | II-86 | II-42 |
| Q1-2436 | I-13 | II-3 | II-92 | II-42 |
| Q1-2437 | I-13 | II-3 | II-1a | II-42 |
| Q1-2438 | I-13 | II-3 | II-2a | II-42 |

TABLE Q1-continued

Four-component compositions comprising a component I, a fungicide or growth regulator as component II and III and a fungicidal component IV.

| composition | I | II | III | IV |
|---|---|---|---|---|
| Q1-2439 | I-13 | II-3 | II-3a | II-42 |
| Q1-2440 | I-13 | II-3 | II-4a | II-42 |
| Q1-2441 | I-13 | II-3 | II-5a | II-42 |
| Q1-2442 | I-13 | II-6 | II-8 | II-42 |
| Q1-2443 | I-13 | II-6 | II-11 | II-42 |
| Q1-2444 | I-13 | II-6 | II-16 | II-42 |
| Q1-2445 | I-13 | II-6 | II-21 | II-42 |
| Q1-2446 | I-13 | II-6 | II-26 | II-42 |
| Q1-2447 | I-13 | II-6 | II-32 | II-42 |
| Q1-2448 | I-13 | II-6 | II-37 | II-42 |
| Q1-2449 | I-13 | II-6 | II-39 | II-42 |
| Q1-2450 | I-13 | II-6 | II-50 | II-42 |
| Q1-2451 | I-13 | II-6 | II-62 | II-42 |
| Q1-2452 | I-13 | II-6 | II-76 | II-42 |
| Q1-2453 | I-13 | II-6 | II-78 | II-42 |
| Q1-2454 | I-13 | II-6 | II-84 | II-42 |
| Q1-2455 | I-13 | II-6 | II-86 | II-42 |
| Q1-2456 | I-13 | II-6 | II-92 | II-42 |
| Q1-2457 | I-13 | II-6 | II-1a | II-42 |
| Q1-2458 | I-13 | II-6 | II-2a | II-42 |
| Q1-2459 | I-13 | II-6 | II-3a | II-42 |
| Q1-2460 | I-13 | II-6 | II-4a | II-42 |
| Q1-2461 | I-13 | II-6 | II-5a | II-42 |
| Q1-2462 | I-13 | II-8 | II-11 | II-42 |
| Q1-2463 | I-13 | II-8 | II-16 | II-42 |
| Q1-2464 | I-13 | II-8 | II-21 | II-42 |
| Q1-2465 | I-13 | II-8 | II-26 | II-42 |
| Q1-2466 | I-13 | II-8 | II-32 | II-42 |
| Q1-2467 | I-13 | II-8 | II-37 | II-42 |
| Q1-2468 | I-13 | II-8 | II-39 | II-42 |
| Q1-2469 | I-13 | II-8 | II-50 | II-42 |
| Q1-2470 | I-13 | II-8 | II-62 | II-42 |
| Q1-2471 | I-13 | II-8 | II-76 | II-42 |
| Q1-2472 | I-13 | II-8 | II-78 | II-42 |
| Q1-2473 | I-13 | II-8 | II-84 | II-42 |
| Q1-2474 | I-13 | II-8 | II-86 | II-42 |
| Q1-2475 | I-13 | II-8 | II-92 | II-42 |
| Q1-2476 | I-13 | II-8 | II-1a | II-42 |
| Q1-2477 | I-13 | II-8 | II-2a | II-42 |
| Q1-2478 | I-13 | II-8 | II-3a | II-42 |
| Q1-2479 | I-13 | II-8 | II-4a | II-42 |
| Q1-2480 | I-13 | II-8 | II-5a | II-42 |
| Q1-2481 | I-13 | II-11 | II-16 | II-42 |
| Q1-2482 | I-13 | II-11 | II-21 | II-42 |
| Q1-2483 | I-13 | II-11 | II-26 | II-42 |
| Q1-2484 | I-13 | II-11 | II-32 | II-42 |
| Q1-2485 | I-13 | II-11 | II-37 | II-42 |
| Q1-2486 | I-13 | II-11 | II-39 | II-42 |
| Q1-2487 | I-13 | II-11 | II-50 | II-42 |
| Q1-2488 | I-13 | II-11 | II-62 | II-42 |
| Q1-2489 | I-13 | II-11 | II-76 | II-42 |
| Q1-2490 | I-13 | II-11 | II-78 | II-42 |
| Q1-2491 | I-13 | II-11 | II-84 | II-42 |
| Q1-2492 | I-13 | II-11 | II-86 | II-42 |
| Q1-2493 | I-13 | II-11 | II-92 | II-42 |
| Q1-2494 | I-13 | II-11 | II-1a | II-42 |
| Q1-2495 | I-13 | II-11 | II-2a | II-42 |
| Q1-2496 | I-13 | II-11 | II-3a | II-42 |
| Q1-2497 | I-13 | II-11 | II-4a | II-42 |
| Q1-2498 | I-13 | II-11 | II-5a | II-42 |
| Q1-2499 | I-13 | II-16 | II-21 | II-42 |
| Q1-2500 | I-13 | II-16 | II-26 | II-42 |
| Q1-2501 | I-13 | II-16 | II-32 | II-42 |
| Q1-2502 | I-13 | II-16 | II-37 | II-42 |
| Q1-2503 | I-13 | II-16 | II-39 | II-42 |
| Q1-2504 | I-13 | II-16 | II-50 | II-42 |
| Q1-2505 | I-13 | II-16 | II-62 | II-42 |
| Q1-2506 | I-13 | II-16 | II-76 | II-42 |
| Q1-2507 | I-13 | II-16 | II-78 | II-42 |
| Q1-2508 | I-13 | II-16 | II-84 | II-42 |
| Q1-2509 | I-13 | II-16 | II-86 | II-42 |
| Q1-2510 | I-13 | II-16 | II-92 | II-42 |
| Q1-2511 | I-13 | II-16 | II-1a | II-42 |
| Q1-2512 | I-13 | II-16 | II-2a | II-42 |
| Q1-2513 | I-13 | II-16 | II-3a | II-42 |
| Q1-2514 | I-13 | II-16 | II-4a | II-42 |
| Q1-2515 | I-13 | II-16 | II-5a | II-42 |
| Q1-2516 | I-13 | II-21 | II-26 | II-42 |
| Q1-2517 | I-13 | II-21 | II-32 | II-42 |
| Q1-2518 | I-13 | II-21 | II-37 | II-42 |
| Q1-2519 | I-13 | II-21 | II-39 | II-42 |
| Q1-2520 | I-13 | II-21 | II-50 | II-42 |
| Q1-2521 | I-13 | II-21 | II-62 | II-42 |
| Q1-2522 | I-13 | II-21 | II-76 | II-42 |
| Q1-2523 | I-13 | II-21 | II-78 | II-42 |
| Q1-2524 | I-13 | II-21 | II-84 | II-42 |
| Q1-2525 | I-13 | II-21 | II-86 | II-42 |
| Q1-2526 | I-13 | II-21 | II-92 | II-42 |
| Q1-2527 | I-13 | II-21 | II-1a | II-42 |
| Q1-2528 | I-13 | II-21 | II-2a | II-42 |
| Q1-2529 | I-13 | II-21 | II-3a | II-42 |
| Q1-2530 | I-13 | II-21 | II-4a | II-42 |
| Q1-2531 | I-13 | II-21 | II-5a | II-42 |
| Q1-2532 | I-13 | II-26 | II-32 | II-42 |
| Q1-2533 | I-13 | II-26 | II-37 | II-42 |
| Q1-2534 | I-13 | II-26 | II-39 | II-42 |
| Q1-2535 | I-13 | II-26 | II-50 | II-42 |
| Q1-2536 | I-13 | II-26 | II-62 | II-42 |
| Q1-2537 | I-13 | II-26 | II-76 | II-42 |
| Q1-2538 | I-13 | II-26 | II-78 | II-42 |
| Q1-2539 | I-13 | II-26 | II-84 | II-42 |
| Q1-2540 | I-13 | II-26 | II-86 | II-42 |
| Q1-2541 | I-13 | II-26 | II-92 | II-42 |
| Q1-2542 | I-13 | II-26 | II-1a | II-42 |
| Q1-2543 | I-13 | II-26 | II-2a | II-42 |
| Q1-2544 | I-13 | II-26 | II-3a | II-42 |
| Q1-2545 | I-13 | II-26 | II-4a | II-42 |
| Q1-2546 | I-13 | II-26 | II-5a | II-42 |
| Q1-2547 | I-13 | II-32 | II-37 | II-42 |
| Q1-2548 | I-13 | II-32 | II-39 | II-42 |
| Q1-2549 | I-13 | II-32 | II-50 | II-42 |
| Q1-2550 | I-13 | II-32 | II-62 | II-42 |
| Q1-2551 | I-13 | II-32 | II-76 | II-42 |
| Q1-2552 | I-13 | II-32 | II-78 | II-42 |
| Q1-2553 | I-13 | II-32 | II-84 | II-42 |
| Q1-2554 | I-13 | II-32 | II-86 | II-42 |
| Q1-2555 | I-13 | II-32 | II-92 | II-42 |
| Q1-2556 | I-13 | II-32 | II-1a | II-42 |
| Q1-2557 | I-13 | II-32 | II-2a | II-42 |
| Q1-2558 | I-13 | II-32 | II-3a | II-42 |
| Q1-2559 | I-13 | II-32 | II-4a | II-42 |
| Q1-2560 | I-13 | II-32 | II-5a | II-42 |
| Q1-2561 | I-13 | II-37 | II-39 | II-42 |
| Q1-2562 | I-13 | II-37 | II-50 | II-42 |
| Q1-2563 | I-13 | II-37 | II-62 | II-42 |
| Q1-2564 | I-13 | II-37 | II-76 | II-42 |
| Q1-2565 | I-13 | II-37 | II-78 | II-42 |
| Q1-2566 | I-13 | II-37 | II-84 | II-42 |
| Q1-2567 | I-13 | II-37 | II-86 | II-42 |
| Q1-2568 | I-13 | II-37 | II-92 | II-42 |
| Q1-2569 | I-13 | II-37 | II-1a | II-42 |
| Q1-2570 | I-13 | II-37 | II-2a | II-42 |
| Q1-2571 | I-13 | II-37 | II-3a | II-42 |
| Q1-2572 | I-13 | II-37 | II-4a | II-42 |
| Q1-2573 | I-13 | II-37 | II-5a | II-42 |
| Q1-2574 | I-13 | II-39 | II-50 | II-42 |
| Q1-2575 | I-13 | II-39 | II-62 | II-42 |
| Q1-2576 | I-13 | II-39 | II-76 | II-42 |
| Q1-2577 | I-13 | II-39 | II-78 | II-42 |
| Q1-2578 | I-13 | II-39 | II-84 | II-42 |
| Q1-2579 | I-13 | II-39 | II-86 | II-42 |
| Q1-2580 | I-13 | II-39 | II-92 | II-42 |
| Q1-2581 | I-13 | II-39 | II-1a | II-42 |
| Q1-2582 | I-13 | II-39 | II-2a | II-42 |
| Q1-2583 | I-13 | II-39 | II-3a | II-42 |
| Q1-2584 | I-13 | II-39 | II-4a | II-42 |
| Q1-2585 | I-13 | II-39 | II-5a | II-42 |
| Q1-2586 | I-13 | II-50 | II-62 | II-42 |

TABLE Q1-continued

Four-component compositions comprising a component I, a fungicide or growth regulator as component II and III and a fungicidal component IV.

| composition | I | II | III | IV |
|---|---|---|---|---|
| Q1-2587 | I-13 | II-50 | II-76 | II-42 |
| Q1-2588 | I-13 | II-50 | II-78 | II-42 |
| Q1-2589 | I-13 | II-50 | II-84 | II-42 |
| Q1-2590 | I-13 | II-50 | II-86 | II-42 |
| Q1-2591 | I-13 | II-50 | II-92 | II-42 |
| Q1-2592 | I-13 | II-50 | II-1a | II-42 |
| Q1-2593 | I-13 | II-50 | II-2a | II-42 |
| Q1-2594 | I-13 | II-50 | II-3a | II-42 |
| Q1-2595 | I-13 | II-50 | II-4a | II-42 |
| Q1-2596 | I-13 | II-50 | II-5a | II-42 |
| Q1-2597 | I-13 | II-62 | II-76 | II-42 |
| Q1-2598 | I-13 | II-62 | II-78 | II-42 |
| Q1-2599 | I-13 | II-62 | II-84 | II-42 |
| Q1-2600 | I-13 | II-62 | II-86 | II-42 |
| Q1-2601 | I-13 | II-62 | II-92 | II-42 |
| Q1-2602 | I-13 | II-62 | II-1a | II-42 |
| Q1-2603 | I-13 | II-62 | II-2a | II-42 |
| Q1-2604 | I-13 | II-62 | II-3a | II-42 |
| Q1-2605 | I-13 | II-62 | II-4a | II-42 |
| Q1-2606 | I-13 | II-62 | II-5a | II-42 |
| Q1-2607 | I-13 | II-76 | II-78 | II-42 |
| Q1-2608 | I-13 | II-76 | II-84 | II-42 |
| Q1-2609 | I-13 | II-76 | II-86 | II-42 |
| Q1-2610 | I-13 | II-76 | II-92 | II-42 |
| Q1-2611 | I-13 | II-76 | II-1a | II-42 |
| Q1-2612 | I-13 | II-76 | II-2a | II-42 |
| Q1-2613 | I-13 | II-76 | II-3a | II-42 |
| Q1-2614 | I-13 | II-76 | II-4a | II-42 |
| Q1-2615 | I-13 | II-76 | II-5a | II-42 |
| Q1-2616 | I-13 | II-78 | II-84 | II-42 |
| Q1-2617 | I-13 | II-78 | II-86 | II-42 |
| Q1-2618 | I-13 | II-78 | II-92 | II-42 |
| Q1-2619 | I-13 | II-78 | II-1a | II-42 |
| Q1-2620 | I-13 | II-78 | II-2a | II-42 |
| Q1-2621 | I-13 | II-78 | II-3a | II-42 |
| Q1-2622 | I-13 | II-78 | II-4a | II-42 |
| Q1-2623 | I-13 | II-78 | II-5a | II-42 |
| Q1-2624 | I-13 | II-84 | II-86 | II-42 |
| Q1-2625 | I-13 | II-84 | II-92 | II-42 |
| Q1-2626 | I-13 | II-84 | II-1a | II-42 |
| Q1-2627 | I-13 | II-84 | II-2a | II-42 |
| Q1-2628 | I-13 | II-84 | II-3a | II-42 |
| Q1-2629 | I-13 | II-84 | II-4a | II-42 |
| Q1-2630 | I-13 | II-84 | II-5a | II-42 |
| Q1-2631 | I-13 | II-86 | II-92 | II-42 |
| Q1-2632 | I-13 | II-86 | II-1a | II-42 |
| Q1-2633 | I-13 | II-86 | II-2a | II-42 |
| Q1-2634 | I-13 | II-86 | II-3a | II-42 |
| Q1-2635 | I-13 | II-86 | II-4a | II-42 |
| Q1-2636 | I-13 | II-86 | II-5a | II-42 |
| Q1-2637 | I-13 | II-92 | II-1a | II-42 |
| Q1-2638 | I-13 | II-92 | II-2a | II-42 |
| Q1-2639 | I-13 | II-92 | II-3a | II-42 |
| Q1-2640 | I-13 | II-92 | II-4a | II-42 |
| Q1-2641 | I-13 | II-92 | II-5a | II-42 |
| Q1-2642 | I-13 | II-1a | II-2a | II-42 |
| Q1-2643 | I-13 | II-1a | II-3a | II-42 |
| Q1-2644 | I-13 | II-1a | II-4a | II-42 |
| Q1-2645 | I-13 | II-1a | II-5a | II-42 |
| Q1-2646 | I-13 | II-2a | II-3a | II-42 |
| Q1-2647 | I-13 | II-2a | II-4a | II-42 |
| Q1-2648 | I-13 | II-2a | II-5a | II-42 |
| Q1-2649 | I-13 | II-3a | II-4a | II-42 |
| Q1-2650 | I-13 | II-3a | II-5a | II-42 |
| Q1-2651 | I-13 | II-4a | II-5a | II-42 |
| Q1-2652 | I-13 | II-3 | II-6 | II-66 |
| Q1-2653 | I-13 | II-3 | II-8 | II-66 |
| Q1-2654 | I-13 | II-3 | II-11 | II-66 |
| Q1-2655 | I-13 | II-3 | II-16 | II-66 |
| Q1-2656 | I-13 | II-3 | II-21 | II-66 |
| Q1-2657 | I-13 | II-3 | II-26 | II-66 |
| Q1-2658 | I-13 | II-3 | II-32 | II-66 |
| Q1-2659 | I-13 | II-3 | II-37 | II-66 |
| Q1-2660 | I-13 | II-3 | II-39 | II-66 |
| Q1-2661 | I-13 | II-3 | II-42 | II-66 |
| Q1-2662 | I-13 | II-3 | II-50 | II-66 |
| Q1-2663 | I-13 | II-3 | II-62 | II-66 |
| Q1-2664 | I-13 | II-3 | II-76 | II-66 |
| Q1-2665 | I-13 | II-3 | II-78 | II-66 |
| Q1-2666 | I-13 | II-3 | II-84 | II-66 |
| Q1-2667 | I-13 | II-3 | II-86 | II-66 |
| Q1-2668 | I-13 | II-3 | II-92 | II-66 |
| Q1-2669 | I-13 | II-3 | II-1a | II-66 |
| Q1-2670 | I-13 | II-3 | II-2a | II-66 |
| Q1-2671 | I-13 | II-3 | II-3a | II-66 |
| Q1-2672 | I-13 | II-3 | II-4a | II-66 |
| Q1-2673 | I-13 | II-3 | II-5a | II-66 |
| Q1-2674 | I-13 | II-6 | II-8 | II-66 |
| Q1-2675 | I-13 | II-6 | II-11 | II-66 |
| Q1-2676 | I-13 | II-6 | II-16 | II-66 |
| Q1-2677 | I-13 | II-6 | II-21 | II-66 |
| Q1-2678 | I-13 | II-6 | II-26 | II-66 |
| Q1-2679 | I-13 | II-6 | II-32 | II-66 |
| Q1-2680 | I-13 | II-6 | II-37 | II-66 |
| Q1-2681 | I-13 | II-6 | II-39 | II-66 |
| Q1-2682 | I-13 | II-6 | II-42 | II-66 |
| Q1-2683 | I-13 | II-6 | II-50 | II-66 |
| Q1-2684 | I-13 | II-6 | II-62 | II-66 |
| Q1-2685 | I-13 | II-6 | II-76 | II-66 |
| Q1-2686 | I-13 | II-6 | II-78 | II-66 |
| Q1-2687 | I-13 | II-6 | II-84 | II-66 |
| Q1-2688 | I-13 | II-6 | II-86 | II-66 |
| Q1-2689 | I-13 | II-6 | II-92 | II-66 |
| Q1-2690 | I-13 | II-6 | II-1a | II-66 |
| Q1-2691 | I-13 | II-6 | II-2a | II-66 |
| Q1-2692 | I-13 | II-6 | II-3a | II-66 |
| Q1-2693 | I-13 | II-6 | II-4a | II-66 |
| Q1-2694 | I-13 | II-6 | II-5a | II-66 |
| Q1-2695 | I-13 | II-8 | II-11 | II-66 |
| Q1-2696 | I-13 | II-8 | II-16 | II-66 |
| Q1-2697 | I-13 | II-8 | II-21 | II-66 |
| Q1-2698 | I-13 | II-8 | II-26 | II-66 |
| Q1-2699 | I-13 | II-8 | II-32 | II-66 |
| Q1-2700 | I-13 | II-8 | II-37 | II-66 |
| Q1-2701 | I-13 | II-8 | II-39 | II-66 |
| Q1-2702 | I-13 | II-8 | II-42 | II-66 |
| Q1-2703 | I-13 | II-8 | II-50 | II-66 |
| Q1-2704 | I-13 | II-8 | II-62 | II-66 |
| Q1-2705 | I-13 | II-8 | II-76 | II-66 |
| Q1-2706 | I-13 | II-8 | II-78 | II-66 |
| Q1-2707 | I-13 | II-8 | II-84 | II-66 |
| Q1-2708 | I-13 | II-8 | II-86 | II-66 |
| Q1-2709 | I-13 | II-8 | II-92 | II-66 |
| Q1-2710 | I-13 | II-8 | II-1a | II-66 |
| Q1-2711 | I-13 | II-8 | II-2a | II-66 |
| Q1-2712 | I-13 | II-8 | II-3a | II-66 |
| Q1-2713 | I-13 | II-8 | II-4a | II-66 |
| Q1-2714 | I-13 | II-8 | II-5a | II-66 |
| Q1-2715 | I-13 | II-11 | II-16 | II-66 |
| Q1-2716 | I-13 | II-11 | II-21 | II-66 |
| Q1-2717 | I-13 | II-11 | II-26 | II-66 |
| Q1-2718 | I-13 | II-11 | II-32 | II-66 |
| Q1-2719 | I-13 | II-11 | II-37 | II-66 |
| Q1-2720 | I-13 | II-11 | II-39 | II-66 |
| Q1-2721 | I-13 | II-11 | II-42 | II-66 |
| Q1-2722 | I-13 | II-11 | II-50 | II-66 |
| Q1-2723 | I-13 | II-11 | II-62 | II-66 |
| Q1-2724 | I-13 | II-11 | II-76 | II-66 |
| Q1-2725 | I-13 | II-11 | II-78 | II-66 |
| Q1-2726 | I-13 | II-11 | II-84 | II-66 |
| Q1-2727 | I-13 | II-11 | II-86 | II-66 |
| Q1-2728 | I-13 | II-11 | II-92 | II-66 |
| Q1-2729 | I-13 | II-11 | II-1a | II-66 |
| Q1-2730 | I-13 | II-11 | II-2a | II-66 |
| Q1-2731 | I-13 | II-11 | II-3a | II-66 |
| Q1-2732 | I-13 | II-11 | II-4a | II-66 |
| Q1-2733 | I-13 | II-11 | II-5a | II-66 |
| Q1-2734 | I-13 | II-16 | II-21 | II-66 |

TABLE Q1-continued

Four-component compositions comprising a component I, a fungicide or growth regulator as component II and III and a fungicidal component IV.

| composition | I | II | III | IV |
|---|---|---|---|---|
| Q1-2735 | I-13 | II-16 | II-26 | II-66 |
| Q1-2736 | I-13 | II-16 | II-32 | II-66 |
| Q1-2737 | I-13 | II-16 | II-37 | II-66 |
| Q1-2738 | I-13 | II-16 | II-39 | II-66 |
| Q1-2739 | I-13 | II-16 | II-42 | II-66 |
| Q1-2740 | I-13 | II-16 | II-50 | II-66 |
| Q1-2741 | I-13 | II-16 | II-62 | II-66 |
| Q1-2742 | I-13 | II-16 | II-76 | II-66 |
| Q1-2743 | I-13 | II-16 | II-78 | II-66 |
| Q1-2744 | I-13 | II-16 | II-84 | II-66 |
| Q1-2745 | I-13 | II-16 | II-86 | II-66 |
| Q1-2746 | I-13 | II-16 | II-92 | II-66 |
| Q1-2747 | I-13 | II-16 | II-1a | II-66 |
| Q1-2748 | I-13 | II-16 | II-2a | II-66 |
| Q1-2749 | I-13 | II-16 | II-3a | II-66 |
| Q1-2750 | I-13 | II-16 | II-4a | II-66 |
| Q1-2751 | I-13 | II-16 | II-5a | II-66 |
| Q1-2752 | I-13 | II-21 | II-26 | II-66 |
| Q1-2753 | I-13 | II-21 | II-32 | II-66 |
| Q1-2754 | I-13 | II-21 | II-37 | II-66 |
| Q1-2755 | I-13 | II-21 | II-39 | II-66 |
| Q1-2756 | I-13 | II-21 | II-42 | II-66 |
| Q1-2757 | I-13 | II-21 | II-50 | II-66 |
| Q1-2758 | I-13 | II-21 | II-62 | II-66 |
| Q1-2759 | I-13 | II-21 | II-76 | II-66 |
| Q1-2760 | I-13 | II-21 | II-78 | II-66 |
| Q1-2761 | I-13 | II-21 | II-84 | II-66 |
| Q1-2762 | I-13 | II-21 | II-86 | II-66 |
| Q1-2763 | I-13 | II-21 | II-92 | II-66 |
| Q1-2764 | I-13 | II-21 | II-1a | II-66 |
| Q1-2765 | I-13 | II-21 | II-2a | II-66 |
| Q1-2766 | I-13 | II-21 | II-3a | II-66 |
| Q1-2767 | I-13 | II-21 | II-4a | II-66 |
| Q1-2768 | I-13 | II-21 | II-5a | II-66 |
| Q1-2769 | I-13 | II-26 | II-32 | II-66 |
| Q1-2770 | I-13 | II-26 | II-37 | II-66 |
| Q1-2771 | I-13 | II-26 | II-39 | II-66 |
| Q1-2772 | I-13 | II-26 | II-42 | II-66 |
| Q1-2773 | I-13 | II-26 | II-50 | II-66 |
| Q1-2774 | I-13 | II-26 | II-62 | II-66 |
| Q1-2775 | I-13 | II-26 | II-76 | II-66 |
| Q1-2776 | I-13 | II-26 | II-78 | II-66 |
| Q1-2777 | I-13 | II-26 | II-84 | II-66 |
| Q1-2778 | I-13 | II-26 | II-86 | II-66 |
| Q1-2779 | I-13 | II-26 | II-92 | II-66 |
| Q1-2780 | I-13 | II-26 | II-1a | II-66 |
| Q1-2781 | I-13 | II-26 | II-2a | II-66 |
| Q1-2782 | I-13 | II-26 | II-3a | II-66 |
| Q1-2783 | I-13 | II-26 | II-4a | II-66 |
| Q1-2784 | I-13 | II-26 | II-5a | II-66 |
| Q1-2785 | I-13 | II-32 | II-37 | II-66 |
| Q1-2786 | I-13 | II-32 | II-39 | II-66 |
| Q1-2787 | I-13 | II-32 | II-42 | II-66 |
| Q1-2788 | I-13 | II-32 | II-50 | II-66 |
| Q1-2789 | I-13 | II-32 | II-62 | II-66 |
| Q1-2790 | I-13 | II-32 | II-76 | II-66 |
| Q1-2791 | I-13 | II-32 | II-78 | II-66 |
| Q1-2792 | I-13 | II-32 | II-84 | II-66 |
| Q1-2793 | I-13 | II-32 | II-86 | II-66 |
| Q1-2794 | I-13 | II-32 | II-92 | II-66 |
| Q1-2795 | I-13 | II-32 | II-1a | II-66 |
| Q1-2796 | I-13 | II-32 | II-2a | II-66 |
| Q1-2797 | I-13 | II-32 | II-3a | II-66 |
| Q1-2798 | I-13 | II-32 | II-4a | II-66 |
| Q1-2799 | I-13 | II-32 | II-5a | II-66 |
| Q1-2800 | I-13 | II-37 | II-39 | II-66 |
| Q1-2801 | I-13 | II-37 | II-42 | II-66 |
| Q1-2802 | I-13 | II-37 | II-50 | II-66 |
| Q1-2803 | I-13 | II-37 | II-62 | II-66 |
| Q1-2804 | I-13 | II-37 | II-76 | II-66 |
| Q1-2805 | I-13 | II-37 | II-78 | II-66 |
| Q1-2806 | I-13 | II-37 | II-84 | II-66 |
| Q1-2807 | I-13 | II-37 | II-86 | II-66 |
| Q1-2808 | I-13 | II-37 | II-92 | II-66 |
| Q1-2809 | I-13 | II-37 | II-1a | II-66 |
| Q1-2810 | I-13 | II-37 | II-2a | II-66 |
| Q1-2811 | I-13 | II-37 | II-3a | II-66 |
| Q1-2812 | I-13 | II-37 | II-4a | II-66 |
| Q1-2813 | I-13 | II-37 | II-5a | II-66 |
| Q1-2814 | I-13 | II-39 | II-42 | II-66 |
| Q1-2815 | I-13 | II-39 | II-50 | II-66 |
| Q1-2816 | I-13 | II-39 | II-62 | II-66 |
| Q1-2817 | I-13 | II-39 | II-76 | II-66 |
| Q1-2818 | I-13 | II-39 | II-78 | II-66 |
| Q1-2819 | I-13 | II-39 | II-84 | II-66 |
| Q1-2820 | I-13 | II-39 | II-86 | II-66 |
| Q1-2821 | I-13 | II-39 | II-92 | II-66 |
| Q1-2822 | I-13 | II-39 | II-1a | II-66 |
| Q1-2823 | I-13 | II-39 | II-2a | II-66 |
| Q1-2824 | I-13 | II-39 | II-3a | II-66 |
| Q1-2825 | I-13 | II-39 | II-4a | II-66 |
| Q1-2826 | I-13 | II-39 | II-5a | II-66 |
| Q1-2827 | I-13 | II-42 | II-50 | II-66 |
| Q1-2828 | I-13 | II-42 | II-62 | II-66 |
| Q1-2829 | I-13 | II-42 | II-76 | II-66 |
| Q1-2830 | I-13 | II-42 | II-78 | II-66 |
| Q1-2831 | I-13 | II-42 | II-84 | II-66 |
| Q1-2832 | I-13 | II-42 | II-86 | II-66 |
| Q1-2833 | I-13 | II-42 | II-92 | II-66 |
| Q1-2834 | I-13 | II-42 | II-1a | II-66 |
| Q1-2835 | I-13 | II-42 | II-2a | II-66 |
| Q1-2836 | I-13 | II-42 | II-3a | II-66 |
| Q1-2837 | I-13 | II-42 | II-4a | II-66 |
| Q1-2838 | I-13 | II-42 | II-5a | II-66 |
| Q1-2839 | I-13 | II-50 | II-62 | II-66 |
| Q1-2840 | I-13 | II-50 | II-76 | II-66 |
| Q1-2841 | I-13 | II-50 | II-78 | II-66 |
| Q1-2842 | I-13 | II-50 | II-84 | II-66 |
| Q1-2843 | I-13 | II-50 | II-86 | II-66 |
| Q1-2844 | I-13 | II-50 | II-92 | II-66 |
| Q1-2845 | I-13 | II-50 | II-1a | II-66 |
| Q1-2846 | I-13 | II-50 | II-2a | II-66 |
| Q1-2847 | I-13 | II-50 | II-3a | II-66 |
| Q1-2848 | I-13 | II-50 | II-4a | II-66 |
| Q1-2849 | I-13 | II-50 | II-5a | II-66 |
| Q1-2850 | I-13 | II-62 | II-76 | II-66 |
| Q1-2851 | I-13 | II-62 | II-78 | II-66 |
| Q1-2852 | I-13 | II-62 | II-84 | II-66 |
| Q1-2853 | I-13 | II-62 | II-86 | II-66 |
| Q1-2854 | I-13 | II-62 | II-92 | II-66 |
| Q1-2855 | I-13 | II-62 | II-1a | II-66 |
| Q1-2856 | I-13 | II-62 | II-2a | II-66 |
| Q1-2857 | I-13 | II-62 | II-3a | II-66 |
| Q1-2858 | I-13 | II-62 | II-4a | II-66 |
| Q1-2859 | I-13 | II-62 | II-5a | II-66 |
| Q1-2860 | I-13 | II-76 | II-78 | II-66 |
| Q1-2861 | I-13 | II-76 | II-84 | II-66 |
| Q1-2862 | I-13 | II-76 | II-86 | II-66 |
| Q1-2863 | I-13 | II-76 | II-92 | II-66 |
| Q1-2864 | I-13 | II-76 | II-1a | II-66 |
| Q1-2865 | I-13 | II-76 | II-2a | II-66 |
| Q1-2866 | I-13 | II-76 | II-3a | II-66 |
| Q1-2867 | I-13 | II-76 | II-4a | II-66 |
| Q1-2868 | I-13 | II-76 | II-5a | II-66 |
| Q1-2869 | I-13 | II-78 | II-84 | II-66 |
| Q1-2870 | I-13 | II-78 | II-86 | II-66 |
| Q1-2871 | I-13 | II-78 | II-92 | II-66 |
| Q1-2872 | I-13 | II-78 | II-1a | II-66 |
| Q1-2873 | I-13 | II-78 | II-2a | II-66 |
| Q1-2874 | I-13 | II-78 | II-3a | II-66 |
| Q1-2875 | I-13 | II-78 | II-4a | II-66 |
| Q1-2876 | I-13 | II-78 | II-5a | II-66 |
| Q1-2877 | I-13 | II-84 | II-86 | II-66 |
| Q1-2878 | I-13 | II-84 | II-92 | II-66 |
| Q1-2879 | I-13 | II-84 | II-1a | II-66 |
| Q1-2880 | I-13 | II-84 | II-2a | II-66 |
| Q1-2881 | I-13 | II-84 | II-3a | II-66 |
| Q1-2882 | I-13 | II-84 | II-4a | II-66 |

TABLE Q1-continued

Four-component compositions comprising a component I, a fungicide or growth regulator as component II and III and a fungicidal component IV.

| composition | I | II | III | IV |
|---|---|---|---|---|
| Q1-2883 | I-13 | II-84 | II-5a | II-66 |
| Q1-2884 | I-13 | II-86 | II-92 | II-66 |
| Q1-2885 | I-13 | II-86 | II-1a | II-66 |
| Q1-2886 | I-13 | II-86 | II-2a | II-66 |
| Q1-2887 | I-13 | II-86 | II-3a | II-66 |
| Q1-2888 | I-13 | II-86 | II-4a | II-66 |
| Q1-2889 | I-13 | II-86 | II-5a | II-66 |
| Q1-2890 | I-13 | II-92 | II-1a | II-66 |
| Q1-2891 | I-13 | II-92 | II-2a | II-66 |
| Q1-2892 | I-13 | II-92 | II-3a | II-66 |
| Q1-2893 | I-13 | II-92 | II-4a | II-66 |
| Q1-2894 | I-13 | II-92 | II-5a | II-66 |
| Q1-2895 | I-13 | II-1a | II-2a | II-66 |
| Q1-2896 | I-13 | II-1a | II-3a | II-66 |
| Q1-2897 | I-13 | II-1a | II-4a | II-66 |
| Q1-2898 | I-13 | II-1a | II-5a | II-66 |
| Q1-2899 | I-13 | II-2a | II-3a | II-66 |
| Q1-2900 | I-13 | II-2a | II-4a | II-66 |
| Q1-2901 | I-13 | II-2a | II-5a | II-66 |
| Q1-2902 | I-13 | II-3a | II-4a | II-66 |
| Q1-2903 | I-13 | II-3a | II-5a | II-66 |
| Q1-2904 | I-13 | II-4a | II-5a | II-66 |

TABLE Q1a

Four-component compositions comprising a component I, a fungicide as component II and III and a fungicidal component IV.

| composition | I | II | III | IV |
|---|---|---|---|---|
| Q1a-1 | I-1 | II-34 | II-93 | II-42 |
| Q1a-2 | I-2 | II-34 | II-93 | II-42 |
| Q1a-3 | I-3 | II-34 | II-93 | II-42 |
| Q1a-4 | I-4 | II-34 | II-93 | II-42 |
| Q1a-5 | I-5 | II-34 | II-93 | II-42 |
| Q1a-6 | I-13 | II-34 | II-93 | II-42 |

In table Q1, according to particular embodiments of the invention, the respective component I is present as (S) enantiomer, wherein each row corresponds to one embodiment of the compositions according to the invention, i.e. one specific individualized composition. According to one specific aspect, these are ternary compositions which each only contain these two components as active compounds. Furthermore, also every combination of the compositions individualized in this table represent embodiments of the present invention (S) enantiomer.

In table Q1, according to a further particular embodiments of the invention, the respective component I is present as (R) enantiomer, wherein each row corresponds to one embodiment of the compositions according to the invention, i.e. one specific individualized composition. According to one specific aspect, these are ternary compositions which each only contain these two components as active compounds. Furthermore, also every combination of the compositions individualized in this table represent embodiments of the present invention (R) enantiomer.

One further aspect of the present invention are novel three-component compositions comprising the component II, component III and the component IV as listed the above Table Q1, i.e. the compositions given in the following Table TQ1, as far as they are novel.

TABLE TQ1

Three-component compositions comprising a fungicidal component II, a component III and IV. Each line of line TQ1-1 to TQ1-484 corresponds to one particular individualized composition. Furthermore, also every combination of the compositions individualized in this table represent embodiments of the present invention.

| composition | II | III | IV |
|---|---|---|---|
| TQ1-1 | II-3 | II-6 | II-42 |
| TQ1-2 | II-3 | II-8 | II-42 |
| TQ1-3 | II-3 | II-11 | II-42 |
| TQ1-4 | II-3 | II-16 | II-42 |
| TQ1-5 | II-3 | II-21 | II-42 |
| TQ1-6 | II-3 | II-26 | II-42 |
| TQ1-7 | II-3 | II-32 | II-42 |
| TQ1-8 | II-3 | II-37 | II-42 |
| TQ1-9 | II-3 | II-39 | II-42 |
| TQ1-10 | II-3 | II-50 | II-42 |
| TQ1-11 | II-3 | II-62 | II-42 |
| TQ1-12 | II-3 | II-76 | II-42 |
| TQ1-13 | II-3 | II-78 | II-42 |
| TQ1-14 | II-3 | II-84 | II-42 |
| TQ1-15 | II-3 | II-86 | II-42 |
| TQ1-16 | II-3 | II-92 | II-42 |
| TQ1-17 | II-3 | II-1a | II-42 |
| TQ1-18 | II-3 | II-2a | II-42 |
| TQ1-19 | II-3 | II-3a | II-42 |
| TQ1-20 | II-3 | II-4a | II-42 |
| TQ1-21 | II-3 | II-5a | II-42 |
| TQ1-22 | II-6 | II-8 | II-42 |
| TQ1-23 | II-6 | II-11 | II-42 |
| TQ1-24 | II-6 | II-16 | II-42 |
| TQ1-25 | II-6 | II-21 | II-42 |
| TQ1-26 | II-6 | II-26 | II-42 |
| TQ1-27 | II-6 | II-32 | II-42 |
| TQ1-28 | II-6 | II-37 | II-42 |
| TQ1-29 | II-6 | II-39 | II-42 |
| TQ1-30 | II-6 | II-50 | II-42 |
| TQ1-31 | II-6 | II-62 | II-42 |
| TQ1-32 | II-6 | II-76 | II-42 |
| TQ1-33 | II-6 | II-78 | II-42 |
| TQ1-34 | II-6 | II-84 | II-42 |
| TQ1-35 | II-6 | II-86 | II-42 |
| TQ1-36 | II-6 | II-92 | II-42 |
| TQ1-37 | II-6 | II-1a | II-42 |
| TQ1-38 | II-6 | II-2a | II-42 |
| TQ1-39 | II-6 | II-3a | II-42 |
| TQ1-40 | II-6 | II-4a | II-42 |
| TQ1-41 | II-6 | II-5a | II-42 |
| TQ1-42 | II-8 | II-11 | II-42 |
| TQ1-43 | II-8 | II-16 | II-42 |
| TQ1-44 | II-8 | II-21 | II-42 |
| TQ1-45 | II-8 | II-26 | II-42 |
| TQ1-46 | II-8 | II-32 | II-42 |
| TQ1-47 | II-8 | II-37 | II-42 |
| TQ1-48 | II-8 | II-39 | II-42 |
| TQ1-49 | II-8 | II-50 | II-42 |
| TQ1-50 | II-8 | II-62 | II-42 |
| TQ1-51 | II-8 | II-76 | II-42 |
| TQ1-52 | II-8 | II-78 | II-42 |
| TQ1-53 | II-8 | II-84 | II-42 |
| TQ1-54 | II-8 | II-86 | II-42 |
| TQ1-55 | II-8 | II-92 | II-42 |
| TQ1-56 | II-8 | II-1a | II-42 |
| TQ1-57 | II-8 | II-2a | II-42 |
| TQ1-58 | II-8 | II-3a | II-42 |
| TQ1-59 | II-8 | II-4a | II-42 |
| TQ1-60 | II-8 | II-5a | II-42 |
| TQ1-61 | II-11 | II-16 | II-42 |
| TQ1-62 | II-11 | II-21 | II-42 |
| TQ1-63 | II-11 | II-26 | II-42 |
| TQ1-64 | II-11 | II-32 | II-42 |
| TQ1-65 | II-11 | II-37 | II-42 |
| TQ1-66 | II-11 | II-39 | II-42 |
| TQ1-67 | II-11 | II-50 | II-42 |
| TQ1-68 | II-11 | II-62 | II-42 |
| TQ1-69 | II-11 | II-76 | II-42 |
| TQ1-70 | II-11 | II-78 | II-42 |
| TQ1-71 | II-11 | II-84 | II-42 |

TABLE TQ1-continued

Three-component compositions comprising a fungicidal component II, a component III and IV. Each line of line TQ1-1 to TQ1-484 corresponds to one particular individualized composition. Furthermore, also every combination of the compositions individualized in this table represent embodiments of the present invention.

| composition | II | III | IV |
|---|---|---|---|
| TQ1-72 | II-11 | II-86 | II-42 |
| TQ1-73 | II-11 | II-92 | II-42 |
| TQ1-74 | II-11 | II-1a | II-42 |
| TQ1-75 | II-11 | II-2a | II-42 |
| TQ1-76 | II-11 | II-3a | II-42 |
| TQ1-77 | II-11 | II-4a | II-42 |
| TQ1-78 | II-11 | II-5a | II-42 |
| TQ1-79 | II-16 | II-21 | II-42 |
| TQ1-80 | II-16 | II-26 | II-42 |
| TQ1-81 | II-16 | II-32 | II-42 |
| TQ1-82 | II-16 | II-37 | II-42 |
| TQ1-83 | II-16 | II-39 | II-42 |
| TQ1-84 | II-16 | II-50 | II-42 |
| TQ1-85 | II-16 | II-62 | II-42 |
| TQ1-86 | II-16 | II-76 | II-42 |
| TQ1-87 | II-16 | II-78 | II-42 |
| TQ1-88 | II-16 | II-84 | II-42 |
| TQ1-89 | II-16 | II-86 | II-42 |
| TQ1-90 | II-16 | II-92 | II-42 |
| TQ1-91 | II-16 | II-1a | II-42 |
| TQ1-92 | II-16 | II-2a | II-42 |
| TQ1-93 | II-16 | II-3a | II-42 |
| TQ1-94 | II-16 | II-4a | II-42 |
| TQ1-95 | II-16 | II-5a | II-42 |
| TQ1-96 | II-21 | II-26 | II-42 |
| TQ1-97 | II-21 | II-32 | II-42 |
| TQ1-98 | II-21 | II-37 | II-42 |
| TQ1-99 | II-21 | II-39 | II-42 |
| TQ1-100 | II-21 | II-50 | II-42 |
| TQ1-101 | II-21 | II-62 | II-42 |
| TQ1-102 | II-21 | II-76 | II-42 |
| TQ1-103 | II-21 | II-78 | II-42 |
| TQ1-104 | II-21 | II-84 | II-42 |
| TQ1-105 | II-21 | II-86 | II-42 |
| TQ1-106 | II-21 | II-92 | II-42 |
| TQ1-107 | II-21 | II-1a | II-42 |
| TQ1-108 | II-21 | II-2a | II-42 |
| TQ1-109 | II-21 | II-3a | II-42 |
| TQ1-110 | II-21 | II-4a | II-42 |
| TQ1-111 | II-21 | II-5a | II-42 |
| TQ1-112 | II-26 | II-32 | II-42 |
| TQ1-113 | II-26 | II-37 | II-42 |
| TQ1-114 | II-26 | II-39 | II-42 |
| TQ1-115 | II-26 | II-50 | II-42 |
| TQ1-116 | II-26 | II-62 | II-42 |
| TQ1-117 | II-26 | II-76 | II-42 |
| TQ1-118 | II-26 | II-78 | II-42 |
| TQ1-119 | II-26 | II-84 | II-42 |
| TQ1-120 | II-26 | II-86 | II-42 |
| TQ1-121 | II-26 | II-92 | II-42 |
| TQ1-122 | II-26 | II-1a | II-42 |
| TQ1-123 | II-26 | II-2a | II-42 |
| TQ1-124 | II-26 | II-3a | II-42 |
| TQ1-125 | II-26 | II-4a | II-42 |
| TQ1-126 | II-26 | II-5a | II-42 |
| TQ1-127 | II-32 | II-37 | II-42 |
| TQ1-128 | II-32 | II-39 | II-42 |
| TQ1-129 | II-32 | II-50 | II-42 |
| TQ1-130 | II-32 | II-62 | II-42 |
| TQ1-131 | II-32 | II-76 | II-42 |
| TQ1-132 | II-32 | II-78 | II-42 |
| TQ1-133 | II-32 | II-84 | II-42 |
| TQ1-134 | II-32 | II-86 | II-42 |
| TQ1-135 | II-32 | II-92 | II-42 |
| TQ1-136 | II-32 | II-1a | II-42 |
| TQ1-137 | II-32 | II-2a | II-42 |
| TQ1-138 | II-32 | II-3a | II-42 |
| TQ1-139 | II-32 | II-4a | II-42 |
| TQ1-140 | II-32 | II-5a | II-42 |
| TQ1-141 | II-37 | II-39 | II-42 |
| TQ1-142 | II-37 | II-50 | II-42 |
| TQ1-143 | II-37 | II-62 | II-42 |
| TQ1-144 | II-37 | II-76 | II-42 |
| TQ1-145 | II-37 | II-78 | II-42 |
| TQ1-146 | II-37 | II-84 | II-42 |
| TQ1-147 | II-37 | II-86 | II-42 |
| TQ1-148 | II-37 | II-92 | II-42 |
| TQ1-149 | II-37 | II-1a | II-42 |
| TQ1-150 | II-37 | II-2a | II-42 |
| TQ1-151 | II-37 | II-3a | II-42 |
| TQ1-152 | II-37 | II-4a | II-42 |
| TQ1-153 | II-37 | II-5a | II-42 |
| TQ1-154 | II-39 | II-50 | II-42 |
| TQ1-155 | II-39 | II-62 | II-42 |
| TQ1-156 | II-39 | II-76 | II-42 |
| TQ1-157 | II-39 | II-78 | II-42 |
| TQ1-158 | II-39 | II-84 | II-42 |
| TQ1-159 | II-39 | II-86 | II-42 |
| TQ1-160 | II-39 | II-92 | II-42 |
| TQ1-161 | II-39 | II-1a | II-42 |
| TQ1-162 | II-39 | II-2a | II-42 |
| TQ1-163 | II-39 | II-3a | II-42 |
| TQ1-164 | II-39 | II-4a | II-42 |
| TQ1-165 | II-39 | II-5a | II-42 |
| TQ1-166 | II-50 | II-62 | II-42 |
| TQ1-167 | II-50 | II-76 | II-42 |
| TQ1-168 | II-50 | II-78 | II-42 |
| TQ1-169 | II-50 | II-84 | II-42 |
| TQ1-170 | II-50 | II-86 | II-42 |
| TQ1-171 | II-50 | II-92 | II-42 |
| TQ1-172 | II-50 | II-1a | II-42 |
| TQ1-173 | II-50 | II-2a | II-42 |
| TQ1-174 | II-50 | II-3a | II-42 |
| TQ1-175 | II-50 | II-4a | II-42 |
| TQ1-176 | II-50 | II-5a | II-42 |
| TQ1-177 | II-62 | II-76 | II-42 |
| TQ1-178 | II-62 | II-78 | II-42 |
| TQ1-179 | II-62 | II-84 | II-42 |
| TQ1-180 | II-62 | II-86 | II-42 |
| TQ1-181 | II-62 | II-92 | II-42 |
| TQ1-182 | II-62 | II-1a | II-42 |
| TQ1-183 | II-62 | II-2a | II-42 |
| TQ1-184 | II-62 | II-3a | II-42 |
| TQ1-185 | II-62 | II-4a | II-42 |
| TQ1-186 | II-62 | II-5a | II-42 |
| TQ1-187 | II-76 | II-78 | II-42 |
| TQ1-188 | II-76 | II-84 | II-42 |
| TQ1-189 | II-76 | II-86 | II-42 |
| TQ1-190 | II-76 | II-92 | II-42 |
| TQ1-191 | II-76 | II-1a | II-42 |
| TQ1-192 | II-76 | II-2a | II-42 |
| TQ1-193 | II-76 | II-3a | II-42 |
| TQ1-194 | II-76 | II-4a | II-42 |
| TQ1-195 | II-76 | II-5a | II-42 |
| TQ1-196 | II-78 | II-84 | II-42 |
| TQ1-197 | II-78 | II-86 | II-42 |
| TQ1-198 | II-78 | II-92 | II-42 |
| TQ1-199 | II-78 | II-1a | II-42 |
| TQ1-200 | II-78 | II-2a | II-42 |
| TQ1-201 | II-78 | II-3a | II-42 |
| TQ1-202 | II-78 | II-4a | II-42 |
| TQ1-203 | II-78 | II-5a | II-42 |
| TQ1-204 | II-84 | II-86 | II-42 |
| TQ1-205 | II-84 | II-92 | II-42 |
| TQ1-206 | II-84 | II-1a | II-42 |
| TQ1-207 | II-84 | II-2a | II-42 |
| TQ1-208 | II-84 | II-3a | II-42 |
| TQ1-209 | II-84 | II-4a | II-42 |
| TQ1-210 | II-84 | II-5a | II-42 |
| TQ1-211 | II-86 | II-92 | II-42 |
| TQ1-212 | II-86 | II-1a | II-42 |
| TQ1-213 | II-86 | II-2a | II-42 |

TABLE TQ1-continued

Three-component compositions comprising a fungicidal component II, a component III and IV. Each line of line TQ1-1 to TQ1-484 corresponds to one particular individualized composition. Furthermore, also every combination of the compositions individualized in this table represent embodiments of the present invention.

| composition | II | III | IV |
|---|---|---|---|
| TQ1-214 | II-86 | II-3a | II-42 |
| TQ1-215 | II-86 | II-4a | II-42 |
| TQ1-216 | II-86 | II-5a | II-42 |
| TQ1-217 | II-92 | II-1a | II-42 |
| TQ1-218 | II-92 | II-2a | II-42 |
| TQ1-219 | II-92 | II-3a | II-42 |
| TQ1-220 | II-92 | II-4a | II-42 |
| TQ1-221 | II-92 | II-5a | II-42 |
| TQ1-222 | II-1a | II-2a | II-42 |
| TQ1-223 | II-1a | II-3a | II-42 |
| TQ1-224 | II-1a | II-4a | II-42 |
| TQ1-225 | II-1a | II-5a | II-42 |
| TQ1-226 | II-2a | II-3a | II-42 |
| TQ1-227 | II-2a | II-4a | II-42 |
| TQ1-228 | II-2a | II-5a | II-42 |
| TQ1-229 | II-3a | II-4a | II-42 |
| TQ1-230 | II-3a | II-5a | II-42 |
| TQ1-231 | II-4a | II-5a | II-42 |
| TQ1-232 | II-3 | II-6 | II-66 |
| TQ1-233 | II-3 | II-8 | II-66 |
| TQ1-234 | II-3 | II-11 | II-66 |
| TQ1-235 | II-3 | II-16 | II-66 |
| TQ1-236 | II-3 | II-21 | II-66 |
| TQ1-237 | II-3 | II-26 | II-66 |
| TQ1-238 | II-3 | II-32 | II-66 |
| TQ1-239 | II-3 | II-37 | II-66 |
| TQ1-240 | II-3 | II-39 | II-66 |
| TQ1-241 | II-3 | II-42 | II-66 |
| TQ1-242 | II-3 | II-50 | II-66 |
| TQ1-243 | II-3 | II-62 | II-66 |
| TQ1-244 | II-3 | II-76 | II-66 |
| TQ1-245 | II-3 | II-78 | II-66 |
| TQ1-246 | II-3 | II-84 | II-66 |
| TQ1-247 | II-3 | II-86 | II-66 |
| TQ1-248 | II-3 | II-92 | II-66 |
| TQ1-249 | II-3 | II-1a | II-66 |
| TQ1-250 | II-3 | II-2a | II-66 |
| TQ1-251 | II-3 | II-3a | II-66 |
| TQ1-252 | II-3 | II-4a | II-66 |
| TQ1-253 | II-3 | II-5a | II-66 |
| TQ1-254 | II-6 | II-8 | II-66 |
| TQ1-255 | II-6 | II-11 | II-66 |
| TQ1-256 | II-6 | II-16 | II-66 |
| TQ1-257 | II-6 | II-21 | II-66 |
| TQ1-258 | II-6 | II-26 | II-66 |
| TQ1-259 | II-6 | II-32 | II-66 |
| TQ1-260 | II-6 | II-37 | II-66 |
| TQ1-261 | II-6 | II-39 | II-66 |
| TQ1-262 | II-6 | II-42 | II-66 |
| TQ1-263 | II-6 | II-50 | II-66 |
| TQ1-264 | II-6 | II-62 | II-66 |
| TQ1-265 | II-6 | II-76 | II-66 |
| TQ1-266 | II-6 | II-78 | II-66 |
| TQ1-267 | II-6 | II-84 | II-66 |
| TQ1-268 | II-6 | II-86 | II-66 |
| TQ1-269 | II-6 | II-92 | II-66 |
| TQ1-270 | II-6 | II-1a | II-66 |
| TQ1-271 | II-6 | II-2a | II-66 |
| TQ1-272 | II-6 | II-3a | II-66 |
| TQ1-273 | II-6 | II-4a | II-66 |
| TQ1-274 | II-6 | II-5a | II-66 |
| TQ1-275 | II-8 | II-11 | II-66 |
| TQ1-276 | II-8 | II-16 | II-66 |
| TQ1-277 | II-8 | II-21 | II-66 |
| TQ1-278 | II-8 | II-26 | II-66 |
| TQ1-279 | II-8 | II-32 | II-66 |
| TQ1-280 | II-8 | II-37 | II-66 |
| TQ1-281 | II-8 | II-39 | II-66 |
| TQ1-282 | II-8 | II-42 | II-66 |
| TQ1-283 | II-8 | II-50 | II-66 |
| TQ1-284 | II-8 | II-62 | II-66 |
| TQ1-285 | II-8 | II-76 | II-66 |
| TQ1-286 | II-8 | II-78 | II-66 |
| TQ1-287 | II-8 | II-84 | II-66 |
| TQ1-288 | II-8 | II-86 | II-66 |
| TQ1-289 | II-8 | II-92 | II-66 |
| TQ1-290 | II-8 | II-1a | II-66 |
| TQ1-291 | II-8 | II-2a | II-66 |
| TQ1-292 | II-8 | II-3a | II-66 |
| TQ1-293 | II-8 | II-4a | II-66 |
| TQ1-294 | II-8 | II-5a | II-66 |
| TQ1-295 | II-11 | II-16 | II-66 |
| TQ1-296 | II-11 | II-21 | II-66 |
| TQ1-297 | II-11 | II-26 | II-66 |
| TQ1-298 | II-11 | II-32 | II-66 |
| TQ1-299 | II-11 | II-37 | II-66 |
| TQ1-300 | II-11 | II-39 | II-66 |
| TQ1-301 | II-11 | II-42 | II-66 |
| TQ1-302 | II-11 | II-50 | II-66 |
| TQ1-303 | II-11 | II-62 | II-66 |
| TQ1-304 | II-11 | II-76 | II-66 |
| TQ1-305 | II-11 | II-78 | II-66 |
| TQ1-306 | II-11 | II-84 | II-66 |
| TQ1-307 | II-11 | II-86 | II-66 |
| TQ1-308 | II-11 | II-92 | II-66 |
| TQ1-309 | II-11 | II-1a | II-66 |
| TQ1-310 | II-11 | II-2a | II-66 |
| TQ1-311 | II-11 | II-3a | II-66 |
| TQ1-312 | II-11 | II-4a | II-66 |
| TQ1-313 | II-11 | II-5a | II-66 |
| TQ1-314 | II-16 | II-21 | II-66 |
| TQ1-315 | II-16 | II-26 | II-66 |
| TQ1-316 | II-16 | II-32 | II-66 |
| TQ1-317 | II-16 | II-37 | II-66 |
| TQ1-318 | II-16 | II-39 | II-66 |
| TQ1-319 | II-16 | II-42 | II-66 |
| TQ1-320 | II-16 | II-50 | II-66 |
| TQ1-321 | II-16 | II-62 | II-66 |
| TQ1-322 | II-16 | II-76 | II-66 |
| TQ1-323 | II-16 | II-78 | II-66 |
| TQ1-324 | II-16 | II-84 | II-66 |
| TQ1-325 | II-16 | II-86 | II-66 |
| TQ1-326 | II-16 | II-92 | II-66 |
| TQ1-327 | II-16 | II-1a | II-66 |
| TQ1-328 | II-16 | II-2a | II-66 |
| TQ1-329 | II-16 | II-3a | II-66 |
| TQ1-330 | II-16 | II-4a | II-66 |
| TQ1-331 | II-16 | II-5a | II-66 |
| TQ1-332 | II-21 | II-26 | II-66 |
| TQ1-333 | II-21 | II-32 | II-66 |
| TQ1-334 | II-21 | II-37 | II-66 |
| TQ1-335 | II-21 | II-39 | II-66 |
| TQ1-336 | II-21 | II-42 | II-66 |
| TQ1-337 | II-21 | II-50 | II-66 |
| TQ1-338 | II-21 | II-62 | II-66 |
| TQ1-339 | II-21 | II-76 | II-66 |
| TQ1-340 | II-21 | II-78 | II-66 |
| TQ1-341 | II-21 | II-84 | II-66 |
| TQ1-342 | II-21 | II-86 | II-66 |
| TQ1-343 | II-21 | II-92 | II-66 |
| TQ1-344 | II-21 | II-1a | II-66 |
| TQ1-345 | II-21 | II-2a | II-66 |
| TQ1-346 | II-21 | II-3a | II-66 |
| TQ1-347 | II-21 | II-4a | II-66 |
| TQ1-348 | II-21 | II-5a | II-66 |
| TQ1-349 | II-26 | II-32 | II-66 |
| TQ1-350 | II-26 | II-37 | II-66 |
| TQ1-351 | II-26 | II-39 | II-66 |
| TQ1-352 | II-26 | II-42 | II-66 |
| TQ1-353 | II-26 | II-50 | II-66 |
| TQ1-354 | II-26 | II-62 | II-66 |
| TQ1-355 | II-26 | II-76 | II-66 |

TABLE TQ1-continued

Three-component compositions comprising a fungicidal component II, a component III and IV. Each line of line TQ1-1 to TQ1-484 corresponds to one particular individualized composition. Furthermore, also every combination of the compositions individualized in this table represent embodiments of the present invention.

| composition | II | III | IV |
|---|---|---|---|
| TQ1-356 | II-26 | II-78 | II-66 |
| TQ1-357 | II-26 | II-84 | II-66 |
| TQ1-358 | II-26 | II-86 | II-66 |
| TQ1-359 | II-26 | II-92 | II-66 |
| TQ1-360 | II-26 | II-1a | II-66 |
| TQ1-361 | II-26 | II-2a | II-66 |
| TQ1-362 | II-26 | II-3a | II-66 |
| TQ1-363 | II-26 | II-4a | II-66 |
| TQ1-364 | II-26 | II-5a | II-66 |
| TQ1-365 | II-32 | II-37 | II-66 |
| TQ1-366 | II-32 | II-39 | II-66 |
| TQ1-367 | II-32 | II-42 | II-66 |
| TQ1-368 | II-32 | II-50 | II-66 |
| TQ1-369 | II-32 | II-62 | II-66 |
| TQ1-370 | II-32 | II-76 | II-66 |
| TQ1-371 | II-32 | II-78 | II-66 |
| TQ1-372 | II-32 | II-84 | II-66 |
| TQ1-373 | II-32 | II-86 | II-66 |
| TQ1-374 | II-32 | II-92 | II-66 |
| TQ1-375 | II-32 | II-1a | II-66 |
| TQ1-376 | II-32 | II-2a | II-66 |
| TQ1-377 | II-32 | II-3a | II-66 |
| TQ1-378 | II-32 | II-4a | II-66 |
| TQ1-379 | II-32 | II-5a | II-66 |
| TQ1-380 | II-37 | II-39 | II-66 |
| TQ1-381 | II-37 | II-42 | II-66 |
| TQ1-382 | II-37 | II-50 | II-66 |
| TQ1-383 | II-37 | II-62 | II-66 |
| TQ1-384 | II-37 | II-76 | II-66 |
| TQ1-385 | II-37 | II-78 | II-66 |
| TQ1-386 | II-37 | II-84 | II-66 |
| TQ1-387 | II-37 | II-86 | II-66 |
| TQ1-388 | II-37 | II-92 | II-66 |
| TQ1-389 | II-37 | II-1a | II-66 |
| TQ1-390 | II-37 | II-2a | II-66 |
| TQ1-391 | II-37 | II-3a | II-66 |
| TQ1-392 | II-37 | II-4a | II-66 |
| TQ1-393 | II-37 | II-5a | II-66 |
| TQ1-394 | II-39 | II-42 | II-66 |
| TQ1-395 | II-39 | II-50 | II-66 |
| TQ1-396 | II-39 | II-62 | II-66 |
| TQ1-397 | II-39 | II-76 | II-66 |
| TQ1-398 | II-39 | II-78 | II-66 |
| TQ1-399 | II-39 | II-84 | II-66 |
| TQ1-400 | II-39 | II-86 | II-66 |
| TQ1-401 | II-39 | II-92 | II-66 |
| TQ1-402 | II-39 | II-1a | II-66 |
| TQ1-403 | II-39 | II-2a | II-66 |
| TQ1-404 | II-39 | II-3a | II-66 |
| TQ1-405 | II-39 | II-4a | II-66 |
| TQ1-406 | II-39 | II-5a | II-66 |
| TQ1-407 | II-42 | II-50 | II-66 |
| TQ1-408 | II-42 | II-62 | II-66 |
| TQ1-409 | II-42 | II-76 | II-66 |
| TQ1-410 | II-42 | II-78 | II-66 |
| TQ1-411 | II-42 | II-84 | II-66 |
| TQ1-412 | II-42 | II-86 | II-66 |
| TQ1-413 | II-42 | II-92 | II-66 |
| TQ1-414 | II-42 | II-1a | II-66 |
| TQ1-415 | II-42 | II-2a | II-66 |
| TQ1-416 | II-42 | II-3a | II-66 |
| TQ1-417 | II-42 | II-4a | II-66 |
| TQ1-418 | II-42 | II-5a | II-66 |
| TQ1-419 | II-50 | II-62 | II-66 |
| TQ1-420 | II-50 | II-76 | II-66 |
| TQ1-421 | II-50 | II-78 | II-66 |
| TQ1-422 | II-50 | II-84 | II-66 |
| TQ1-423 | II-50 | II-86 | II-66 |
| TQ1-424 | II-50 | II-92 | II-66 |
| TQ1-425 | II-50 | II-1a | II-66 |
| TQ1-426 | II-50 | II-2a | II-66 |
| TQ1-427 | II-50 | II-3a | II-66 |
| TQ1-428 | II-50 | II-4a | II-66 |
| TQ1-429 | II-50 | II-5a | II-66 |
| TQ1-430 | II-62 | II-76 | II-66 |
| TQ1-431 | II-62 | II-78 | II-66 |
| TQ1-432 | II-62 | II-84 | II-66 |
| TQ1-433 | II-62 | II-86 | II-66 |
| TQ1-434 | II-62 | II-92 | II-66 |
| TQ1-435 | II-62 | II-1a | II-66 |
| TQ1-436 | II-62 | II-2a | II-66 |
| TQ1-437 | II-62 | II-3a | II-66 |
| TQ1-438 | II-62 | II-4a | II-66 |
| TQ1-439 | II-62 | II-5a | II-66 |
| TQ1-440 | II-76 | II-78 | II-66 |
| TQ1-441 | II-76 | II-84 | II-66 |
| TQ1-442 | II-76 | II-86 | II-66 |
| TQ1-443 | II-76 | II-92 | II-66 |
| TQ1-444 | II-76 | II-1a | II-66 |
| TQ1-445 | II-76 | II-2a | II-66 |
| TQ1-446 | II-76 | II-3a | II-66 |
| TQ1-447 | II-76 | II-4a | II-66 |
| TQ1-448 | II-76 | II-5a | II-66 |
| TQ1-449 | II-78 | II-84 | II-66 |
| TQ1-450 | II-78 | II-86 | II-66 |
| TQ1-451 | II-78 | II-92 | II-66 |
| TQ1-452 | II-78 | II-1a | II-66 |
| TQ1-453 | II-78 | II-2a | II-66 |
| TQ1-454 | II-78 | II-3a | II-66 |
| TQ1-455 | II-78 | II-4a | II-66 |
| TQ1-456 | II-78 | II-5a | II-66 |
| TQ1-457 | II-84 | II-86 | II-66 |
| TQ1-458 | II-84 | II-92 | II-66 |
| TQ1-459 | II-84 | II-1a | II-66 |
| TQ1-460 | II-84 | II-2a | II-66 |
| TQ1-461 | II-84 | II-3a | II-66 |
| TQ1-462 | II-84 | II-4a | II-66 |
| TQ1-463 | II-84 | II-5a | II-66 |
| TQ1-464 | II-86 | II-92 | II-66 |
| TQ1-465 | II-86 | II-1a | II-66 |
| TQ1-466 | II-86 | II-2a | II-66 |
| TQ1-467 | II-86 | II-3a | II-66 |
| TQ1-468 | II-86 | II-4a | II-66 |
| TQ1-469 | II-86 | II-5a | II-66 |
| TQ1-470 | II-92 | II-1a | II-66 |
| TQ1-471 | II-92 | II-2a | II-66 |
| TQ1-472 | II-92 | II-3a | II-66 |
| TQ1-473 | II-92 | II-4a | II-66 |
| TQ1-474 | II-92 | II-5a | II-66 |
| TQ1-475 | II-1a | II-2a | II-66 |
| TQ1-476 | II-1a | II-3a | II-66 |
| TQ1-477 | II-1a | II-4a | II-66 |
| TQ1-478 | II-1a | II-5a | II-66 |
| TQ1-479 | II-2a | II-3a | II-66 |
| TQ1-480 | II-2a | II-4a | II-66 |
| TQ1-481 | II-2a | II-5a | II-66 |
| TQ1-482 | II-3a | II-4a | II-66 |
| TQ1-483 | II-3a | II-5a | II-66 |
| TQ1-484 | II-4a | II-5a | II-66 |

Further particularly preferred compositions are the four-component compositions, wherein component I is as defined above, i.e. a compound I, in particular a compound selected from compounds I-1, I-2, I-3, I-4, I-5, I-6, I-7, I-8, I-9, I-11, I-13, I-14, I-15 and I-16 or any group of compounds I detailed above, and components II, III and IV are selected from the following fungicides

| | |
|---|---|
| II-6 | bixafen |
| II-11 | chlorothalonil |
| II-15 | cyproconazole |
| II-26 | epoxiconazole |
| II-32 | fenpropimorph |
| II-62 | metrafenone |
| II-76 | propiconazole |
| II-78 | prothioconazole |
| II-84 | spiroxamine |
| II-86 | tebuconazole | wherein components II, III and IV are different active compounds.

Specifically preferred embodiments of these compositions are compiled in Table Q2, where each row corresponds to one embodiment of the compositions according to the invention, i.e. one specific individualized four-component composition. According to one specific aspect, these are quarternary compositions which each only contain these four components as the active compound. Furthermore, also every combination of the compositions individualized in this table represent embodiments of the present invention.

TABLE Q2

Four-component compositions comprising a component I and fungicidal compounds as components II, III and IV.

| composition | I | II | III | IV |
|---|---|---|---|---|
| Q2-1 | I-1 | II-6 | II-11 | II-15 |
| Q2-2 | I-1 | II-6 | II-11 | II-26 |
| Q2-3 | I-1 | II-6 | II-11 | II-32 |
| Q2-4 | I-1 | II-6 | II-11 | II-62 |
| Q2-5 | I-1 | II-6 | II-11 | II-76 |
| Q2-6 | I-1 | II-6 | II-11 | II-78 |
| Q2-7 | I-1 | II-6 | II-11 | II-84 |
| Q2-8 | I-1 | II-6 | II-11 | II-86 |
| Q2-9 | I-1 | II-6 | II-15 | II-26 |
| Q2-10 | I-1 | II-6 | II-15 | II-32 |
| Q2-11 | I-1 | II-6 | II-15 | II-62 |
| Q2-12 | I-1 | II-6 | II-15 | II-76 |
| Q2-13 | I-1 | II-6 | II-15 | II-78 |
| Q2-14 | I-1 | II-6 | II-15 | II-84 |
| Q2-15 | I-1 | II-6 | II-15 | II-86 |
| Q2-16 | I-1 | II-6 | II-26 | II-32 |
| Q2-17 | I-1 | II-6 | II-26 | II-62 |
| Q2-18 | I-1 | II-6 | II-26 | II-76 |
| Q2-19 | I-1 | II-6 | II-26 | II-78 |
| Q2-20 | I-1 | II-6 | II-26 | II-84 |
| Q2-21 | I-1 | II-6 | II-26 | II-86 |
| Q2-22 | I-1 | II-6 | II-32 | II-62 |
| Q2-23 | I-1 | II-6 | II-32 | II-76 |
| Q2-24 | I-1 | II-6 | II-32 | II-78 |
| Q2-25 | I-1 | II-6 | II-32 | II-84 |
| Q2-26 | I-1 | II-6 | II-32 | II-86 |
| Q2-27 | I-1 | II-6 | II-62 | II-76 |
| Q2-28 | I-1 | II-6 | II-62 | II-78 |
| Q2-29 | I-1 | II-6 | II-62 | II-84 |
| Q2-30 | I-1 | II-6 | II-62 | II-86 |
| Q2-31 | I-1 | II-6 | II-76 | II-78 |
| Q2-32 | I-1 | II-6 | II-76 | II-84 |
| Q2-33 | I-1 | II-6 | II-76 | II-86 |
| Q2-34 | I-1 | II-6 | II-78 | II-84 |
| Q2-35 | I-1 | II-6 | II-78 | II-86 |
| Q2-36 | I-1 | II-6 | II-84 | II-86 |
| Q2-37 | I-1 | II-11 | II-15 | II-26 |
| Q2-38 | I-1 | II-11 | II-15 | II-32 |
| Q2-39 | I-1 | II-11 | II-15 | II-62 |
| Q2-40 | I-1 | II-11 | II-15 | II-76 |
| Q2-41 | I-1 | II-11 | II-15 | II-78 |
| Q2-42 | I-1 | II-11 | II-15 | II-84 |
| Q2-43 | I-1 | II-11 | II-15 | II-86 |
| Q2-44 | I-1 | II-11 | II-26 | II-32 |
| Q2-45 | I-1 | II-11 | II-26 | II-62 |
| Q2-46 | I-1 | II-11 | II-26 | II-76 |
| Q2-47 | I-1 | II-11 | II-26 | II-78 |
| Q2-48 | I-1 | II-11 | II-26 | II-84 |
| Q2-49 | I-1 | II-11 | II-26 | II-86 |
| Q2-50 | I-1 | II-11 | II-32 | II-62 |
| Q2-51 | I-1 | II-11 | II-32 | II-76 |
| Q2-52 | I-1 | II-11 | II-32 | II-78 |
| Q2-53 | I-1 | II-11 | II-32 | II-84 |
| Q2-54 | I-1 | II-11 | II-32 | II-86 |
| Q2-55 | I-1 | II-11 | II-62 | II-76 |
| Q2-56 | I-1 | II-11 | II-62 | II-78 |
| Q2-57 | I-1 | II-11 | II-62 | II-84 |
| Q2-58 | I-1 | II-11 | II-62 | II-86 |
| Q2-59 | I-1 | II-11 | II-76 | II-78 |
| Q2-60 | I-1 | II-11 | II-76 | II-84 |
| Q2-61 | I-1 | II-11 | II-76 | II-86 |
| Q2-62 | I-1 | II-11 | II-78 | II-84 |
| Q2-63 | I-1 | II-11 | II-78 | II-86 |
| Q2-64 | I-1 | II-11 | II-84 | II-86 |
| Q2-65 | I-1 | II-15 | II-26 | II-32 |
| Q2-66 | I-1 | II-15 | II-26 | II-62 |
| Q2-67 | I-1 | II-15 | II-26 | II-76 |
| Q2-68 | I-1 | II-15 | II-26 | II-78 |
| Q2-69 | I-1 | II-15 | II-26 | II-84 |
| Q2-70 | I-1 | II-15 | II-26 | II-86 |
| Q2-71 | I-1 | II-15 | II-32 | II-62 |
| Q2-72 | I-1 | II-15 | II-32 | II-76 |
| Q2-73 | I-1 | II-15 | II-32 | II-78 |
| Q2-74 | I-1 | II-15 | II-32 | II-84 |
| Q2-75 | I-1 | II-15 | II-32 | II-86 |
| Q2-76 | I-1 | II-15 | II-62 | II-76 |
| Q2-77 | I-1 | II-15 | II-62 | II-78 |
| Q2-78 | I-1 | II-15 | II-62 | II-84 |
| Q2-79 | I-1 | II-15 | II-62 | II-86 |
| Q2-80 | I-1 | II-15 | II-76 | II-78 |
| Q2-81 | I-1 | II-15 | II-76 | II-84 |
| Q2-82 | I-1 | II-15 | II-76 | II-86 |
| Q2-83 | I-1 | II-15 | II-78 | II-84 |
| Q2-84 | I-1 | II-15 | II-78 | II-86 |
| Q2-85 | I-1 | II-15 | II-84 | II-86 |
| Q2-86 | I-1 | II-26 | II-32 | II-62 |
| Q2-87 | I-1 | II-26 | II-32 | II-76 |
| Q2-88 | I-1 | II-26 | II-32 | II-78 |
| Q2-89 | I-1 | II-26 | II-32 | II-84 |
| Q2-90 | I-1 | II-26 | II-32 | II-86 |
| Q2-91 | I-1 | II-26 | II-62 | II-76 |
| Q2-92 | I-1 | II-26 | II-62 | II-78 |
| Q2-93 | I-1 | II-26 | II-62 | II-84 |
| Q2-94 | I-1 | II-26 | II-62 | II-86 |
| Q2-95 | I-1 | II-26 | II-76 | II-78 |
| Q2-96 | I-1 | II-26 | II-76 | II-84 |
| Q2-97 | I-1 | II-26 | II-76 | II-86 |
| Q2-98 | I-1 | II-26 | II-78 | II-84 |
| Q2-99 | I-1 | II-26 | II-78 | II-86 |
| Q2-100 | I-1 | II-26 | II-84 | II-86 |
| Q2-101 | I-1 | II-32 | II-62 | II-76 |
| Q2-102 | I-1 | II-32 | II-62 | II-78 |
| Q2-103 | I-1 | II-32 | II-62 | II-84 |
| Q2-104 | I-1 | II-32 | II-62 | II-86 |
| Q2-105 | I-1 | II-32 | II-76 | II-78 |
| Q2-106 | I-1 | II-32 | II-76 | II-84 |
| Q2-107 | I-1 | II-32 | II-76 | II-86 |
| Q2-108 | I-1 | II-32 | II-78 | II-84 |
| Q2-109 | I-1 | II-32 | II-78 | II-86 |
| Q2-110 | I-1 | II-32 | II-84 | II-86 |
| Q2-111 | I-1 | II-62 | II-76 | II-78 |
| Q2-112 | I-1 | II-62 | II-76 | II-84 |
| Q2-113 | I-1 | II-62 | II-76 | II-86 |
| Q2-114 | I-1 | II-62 | II-78 | II-84 |
| Q2-115 | I-1 | II-62 | II-78 | II-86 |
| Q2-116 | I-1 | II-62 | II-84 | II-86 |
| Q2-117 | I-1 | II-76 | II-78 | II-84 |
| Q2-118 | I-1 | II-76 | II-78 | II-86 |
| Q2-119 | I-1 | II-76 | II-84 | II-86 |
| Q2-120 | I-1 | II-78 | II-84 | II-86 |
| Q2-121 | I-5 | II-6 | II-11 | II-15 |
| Q2-122 | I-5 | II-6 | II-11 | II-26 |
| Q2-123 | I-5 | II-6 | II-11 | II-32 |
| Q2-124 | I-5 | II-6 | II-11 | II-62 |
| Q2-125 | I-5 | II-6 | II-11 | II-76 |
| Q2-126 | I-5 | II-6 | II-11 | II-78 |

TABLE Q2-continued

| | | | | | | | | |
|---|---|---|---|---|---|---|---|---|
| Q2-127 | I-5 | II-6 | II-11 | II-84 | Q2-207 | I-5 | II-26 | II-32 | II-76 |
| Q2-128 | I-5 | II-6 | II-11 | II-86 | Q2-208 | I-5 | II-26 | II-32 | II-78 |
| Q2-129 | I-5 | II-6 | II-15 | II-26 | Q2-209 | I-5 | II-26 | II-32 | II-84 |
| Q2-130 | I-5 | II-6 | II-15 | II-32 | Q2-210 | I-5 | II-26 | II-32 | II-86 |
| Q2-131 | I-5 | II-6 | II-15 | II-62 | Q2-211 | I-5 | II-26 | II-62 | II-76 |
| Q2-132 | I-5 | II-6 | II-15 | II-76 | Q2-212 | I-5 | II-26 | II-62 | II-78 |
| Q2-133 | I-5 | II-6 | II-15 | II-78 | Q2-213 | I-5 | II-26 | II-62 | II-84 |
| Q2-134 | I-5 | II-6 | II-15 | II-84 | Q2-214 | I-5 | II-26 | II-62 | II-86 |
| Q2-135 | I-5 | II-6 | II-15 | II-86 | Q2-215 | I-5 | II-26 | II-76 | II-78 |
| Q2-136 | I-5 | II-6 | II-26 | II-32 | Q2-216 | I-5 | II-26 | II-76 | II-84 |
| Q2-137 | I-5 | II-6 | II-26 | II-62 | Q2-217 | I-5 | II-26 | II-76 | II-86 |
| Q2-138 | I-5 | II-6 | II-26 | II-76 | Q2-218 | I-5 | II-26 | II-78 | II-84 |
| Q2-139 | I-5 | II-6 | II-26 | II-78 | Q2-219 | I-5 | II-26 | II-78 | II-86 |
| Q2-140 | I-5 | II-6 | II-26 | II-84 | Q2-220 | I-5 | II-26 | II-84 | II-86 |
| Q2-141 | I-5 | II-6 | II-26 | II-86 | Q2-221 | I-5 | II-32 | II-62 | II-76 |
| Q2-142 | I-5 | II-6 | II-32 | II-62 | Q2-222 | I-5 | II-32 | II-62 | II-78 |
| Q2-143 | I-5 | II-6 | II-32 | II-76 | Q2-223 | I-5 | II-32 | II-62 | II-84 |
| Q2-144 | I-5 | II-6 | II-32 | II-78 | Q2-224 | I-5 | II-32 | II-62 | II-86 |
| Q2-145 | I-5 | II-6 | II-32 | II-84 | Q2-225 | I-5 | II-32 | II-76 | II-78 |
| Q2-146 | I-5 | II-6 | II-32 | II-86 | Q2-226 | I-5 | II-32 | II-76 | II-84 |
| Q2-147 | I-5 | II-6 | II-62 | II-76 | Q2-227 | I-5 | II-32 | II-76 | II-86 |
| Q2-148 | I-5 | II-6 | II-62 | II-78 | Q2-228 | I-5 | II-32 | II-78 | II-84 |
| Q2-149 | I-5 | II-6 | II-62 | II-84 | Q2-229 | I-5 | II-32 | II-78 | II-86 |
| Q2-150 | I-5 | II-6 | II-62 | II-86 | Q2-230 | I-5 | II-32 | II-84 | II-86 |
| Q2-151 | I-5 | II-6 | II-76 | II-78 | Q2-231 | I-5 | II-62 | II-76 | II-78 |
| Q2-152 | I-5 | II-6 | II-76 | II-84 | Q2-232 | I-5 | II-62 | II-76 | II-84 |
| Q2-153 | I-5 | II-6 | II-76 | II-86 | Q2-233 | I-5 | II-62 | II-76 | II-86 |
| Q2-154 | I-5 | II-6 | II-78 | II-84 | Q2-234 | I-5 | II-62 | II-78 | II-84 |
| Q2-155 | I-5 | II-6 | II-78 | II-86 | Q2-235 | I-5 | II-62 | II-78 | II-86 |
| Q2-156 | I-5 | II-6 | II-84 | II-86 | Q2-236 | I-5 | II-62 | II-84 | II-86 |
| Q2-157 | I-5 | II-11 | II-15 | II-26 | Q2-237 | I-5 | II-76 | II-78 | II-84 |
| Q2-158 | I-5 | II-11 | II-15 | II-32 | Q2-238 | I-5 | II-76 | II-78 | II-86 |
| Q2-159 | I-5 | II-11 | II-15 | II-62 | Q2-239 | I-5 | II-76 | II-84 | II-86 |
| Q2-160 | I-5 | II-11 | II-15 | II-76 | Q2-240 | I-5 | II-78 | II-84 | II-86 |
| Q2-161 | I-5 | II-11 | II-15 | II-78 | Q2-241 | I-2 | II-6 | II-11 | II-15 |
| Q2-162 | I-5 | II-11 | II-15 | II-84 | Q2-242 | I-2 | II-6 | II-11 | II-26 |
| Q2-163 | I-5 | II-11 | II-15 | II-86 | Q2-243 | I-2 | II-6 | II-11 | II-32 |
| Q2-164 | I-5 | II-11 | II-26 | II-32 | Q2-244 | I-2 | II-6 | II-11 | II-62 |
| Q2-165 | I-5 | II-11 | II-26 | II-62 | Q2-245 | I-2 | II-6 | II-11 | II-76 |
| Q2-166 | I-5 | II-11 | II-26 | II-76 | Q2-246 | I-2 | II-6 | II-11 | II-78 |
| Q2-167 | I-5 | II-11 | II-26 | II-78 | Q2-247 | I-2 | II-6 | II-11 | II-84 |
| Q2-168 | I-5 | II-11 | II-26 | II-84 | Q2-248 | I-2 | II-6 | II-11 | II-86 |
| Q2-169 | I-5 | II-11 | II-26 | II-86 | Q2-249 | I-2 | II-6 | II-15 | II-26 |
| Q2-170 | I-5 | II-11 | II-32 | II-62 | Q2-250 | I-2 | II-6 | II-15 | II-32 |
| Q2-171 | I-5 | II-11 | II-32 | II-76 | Q2-251 | I-2 | II-6 | II-15 | II-62 |
| Q2-172 | I-5 | II-11 | II-32 | II-78 | Q2-252 | I-2 | II-6 | II-15 | II-76 |
| Q2-173 | I-5 | II-11 | II-32 | II-84 | Q2-253 | I-2 | II-6 | II-15 | II-78 |
| Q2-174 | I-5 | II-11 | II-32 | II-86 | Q2-254 | I-2 | II-6 | II-15 | II-84 |
| Q2-175 | I-5 | II-11 | II-62 | II-76 | Q2-255 | I-2 | II-6 | II-15 | II-86 |
| Q2-176 | I-5 | II-11 | II-62 | II-78 | Q2-256 | I-2 | II-6 | II-26 | II-32 |
| Q2-177 | I-5 | II-11 | II-62 | II-84 | Q2-257 | I-2 | II-6 | II-26 | II-62 |
| Q2-178 | I-5 | II-11 | II-62 | II-86 | Q2-258 | I-2 | II-6 | II-26 | II-76 |
| Q2-179 | I-5 | II-11 | II-76 | II-78 | Q2-259 | I-2 | II-6 | II-26 | II-78 |
| Q2-180 | I-5 | II-11 | II-76 | II-84 | Q2-260 | I-2 | II-6 | II-26 | II-84 |
| Q2-181 | I-5 | II-11 | II-76 | II-86 | Q2-261 | I-2 | II-6 | II-26 | II-86 |
| Q2-182 | I-5 | II-11 | II-78 | II-84 | Q2-262 | I-2 | II-6 | II-32 | II-62 |
| Q2-183 | I-5 | II-11 | II-78 | II-86 | Q2-263 | I-2 | II-6 | II-32 | II-76 |
| Q2-184 | I-5 | II-11 | II-84 | II-86 | Q2-264 | I-2 | II-6 | II-32 | II-78 |
| Q2-185 | I-5 | II-15 | II-26 | II-32 | Q2-265 | I-2 | II-6 | II-32 | II-84 |
| Q2-186 | I-5 | II-15 | II-26 | II-62 | Q2-266 | I-2 | II-6 | II-32 | II-86 |
| Q2-187 | I-5 | II-15 | II-26 | II-76 | Q2-267 | I-2 | II-6 | II-62 | II-76 |
| Q2-188 | I-5 | II-15 | II-26 | II-78 | Q2-268 | I-2 | II-6 | II-62 | II-78 |
| Q2-189 | I-5 | II-15 | II-26 | II-84 | Q2-269 | I-2 | II-6 | II-62 | II-84 |
| Q2-190 | I-5 | II-15 | II-26 | II-86 | Q2-270 | I-2 | II-6 | II-62 | II-86 |
| Q2-191 | I-5 | II-15 | II-32 | II-62 | Q2-271 | I-2 | II-6 | II-76 | II-78 |
| Q2-192 | I-5 | II-15 | II-32 | II-76 | Q2-272 | I-2 | II-6 | II-76 | II-84 |
| Q2-193 | I-5 | II-15 | II-32 | II-78 | Q2-273 | I-2 | II-6 | II-76 | II-86 |
| Q2-194 | I-5 | II-15 | II-32 | II-84 | Q2-274 | I-2 | II-6 | II-78 | II-84 |
| Q2-195 | I-5 | II-15 | II-32 | II-86 | Q2-275 | I-2 | II-6 | II-78 | II-86 |
| Q2-196 | I-5 | II-15 | II-62 | II-76 | Q2-276 | I-2 | II-6 | II-84 | II-86 |
| Q2-197 | I-5 | II-15 | II-62 | II-78 | Q2-277 | I-2 | II-11 | II-15 | II-26 |
| Q2-198 | I-5 | II-15 | II-62 | II-84 | Q2-278 | I-2 | II-11 | II-15 | II-32 |
| Q2-199 | I-5 | II-15 | II-62 | II-86 | Q2-279 | I-2 | II-11 | II-15 | II-62 |
| Q2-200 | I-5 | II-15 | II-76 | II-78 | Q2-280 | I-2 | II-11 | II-15 | II-76 |
| Q2-201 | I-5 | II-15 | II-76 | II-84 | Q2-281 | I-2 | II-11 | II-15 | II-78 |
| Q2-202 | I-5 | II-15 | II-76 | II-86 | Q2-282 | I-2 | II-11 | II-15 | II-84 |
| Q2-203 | I-5 | II-15 | II-78 | II-84 | Q2-283 | I-2 | II-11 | II-15 | II-86 |
| Q2-204 | I-5 | II-15 | II-78 | II-86 | Q2-284 | I-2 | II-11 | II-26 | II-32 |
| Q2-205 | I-5 | II-15 | II-84 | II-86 | Q2-285 | I-2 | II-11 | II-26 | II-62 |
| Q2-206 | I-5 | II-26 | II-32 | II-62 | Q2-286 | I-2 | II-11 | II-26 | II-76 |

TABLE Q2-continued

| | | | |
|---|---|---|---|
| Q2-287 | I-2 | II-11 | II-26 | II-78 |
| Q2-288 | I-2 | II-11 | II-26 | II-84 |
| Q2-289 | I-2 | II-11 | II-26 | II-86 |
| Q2-290 | I-2 | II-11 | II-32 | II-62 |
| Q2-291 | I-2 | II-11 | II-32 | II-76 |
| Q2-292 | I-2 | II-11 | II-32 | II-78 |
| Q2-293 | I-2 | II-11 | II-32 | II-84 |
| Q2-294 | I-2 | II-11 | II-32 | II-86 |
| Q2-295 | I-2 | II-11 | II-62 | II-76 |
| Q2-296 | I-2 | II-11 | II-62 | II-78 |
| Q2-297 | I-2 | II-11 | II-62 | II-84 |
| Q2-298 | I-2 | II-11 | II-62 | II-86 |
| Q2-299 | I-2 | II-11 | II-76 | II-78 |
| Q2-300 | I-2 | II-11 | II-76 | II-84 |
| Q2-301 | I-2 | II-11 | II-76 | II-86 |
| Q2-302 | I-2 | II-11 | II-78 | II-84 |
| Q2-303 | I-2 | II-11 | II-78 | II-86 |
| Q2-304 | I-2 | II-11 | II-84 | II-86 |
| Q2-305 | I-2 | II-15 | II-26 | II-32 |
| Q2-306 | I-2 | II-15 | II-26 | II-62 |
| Q2-307 | I-2 | II-15 | II-26 | II-76 |
| Q2-308 | I-2 | II-15 | II-26 | II-78 |
| Q2-309 | I-2 | II-15 | II-26 | II-84 |
| Q2-310 | I-2 | II-15 | II-26 | II-86 |
| Q2-311 | I-2 | II-15 | II-32 | II-62 |
| Q2-312 | I-2 | II-15 | II-32 | II-76 |
| Q2-313 | I-2 | II-15 | II-32 | II-78 |
| Q2-314 | I-2 | II-15 | II-32 | II-84 |
| Q2-315 | I-2 | II-15 | II-32 | II-86 |
| Q2-316 | I-2 | II-15 | II-62 | II-76 |
| Q2-317 | I-2 | II-15 | II-62 | II-78 |
| Q2-318 | I-2 | II-15 | II-62 | II-84 |
| Q2-319 | I-2 | II-15 | II-62 | II-86 |
| Q2-320 | I-2 | II-15 | II-76 | II-78 |
| Q2-321 | I-2 | II-15 | II-76 | II-84 |
| Q2-322 | I-2 | II-15 | II-76 | II-86 |
| Q2-323 | I-2 | II-15 | II-78 | II-84 |
| Q2-324 | I-2 | II-15 | II-78 | II-86 |
| Q2-325 | I-2 | II-15 | II-84 | II-86 |
| Q2-326 | I-2 | II-26 | II-32 | II-62 |
| Q2-327 | I-2 | II-26 | II-32 | II-76 |
| Q2-328 | I-2 | II-26 | II-32 | II-78 |
| Q2-329 | I-2 | II-26 | II-32 | II-84 |
| Q2-330 | I-2 | II-26 | II-32 | II-86 |
| Q2-331 | I-2 | II-26 | II-62 | II-76 |
| Q2-332 | I-2 | II-26 | II-62 | II-78 |
| Q2-333 | I-2 | II-26 | II-62 | II-84 |
| Q2-334 | I-2 | II-26 | II-62 | II-86 |
| Q2-335 | I-2 | II-26 | II-76 | II-78 |
| Q2-336 | I-2 | II-26 | II-76 | II-84 |
| Q2-337 | I-2 | II-26 | II-76 | II-86 |
| Q2-338 | I-2 | II-26 | II-78 | II-84 |
| Q2-339 | I-2 | II-26 | II-78 | II-86 |
| Q2-340 | I-2 | II-26 | II-84 | II-86 |
| Q2-341 | I-2 | II-32 | II-62 | II-76 |
| Q2-342 | I-2 | II-32 | II-62 | II-78 |
| Q2-343 | I-2 | II-32 | II-62 | II-84 |
| Q2-344 | I-2 | II-32 | II-62 | II-86 |
| Q2-345 | I-2 | II-32 | II-76 | II-78 |
| Q2-346 | I-2 | II-32 | II-76 | II-84 |
| Q2-347 | I-2 | II-32 | II-76 | II-86 |
| Q2-348 | I-2 | II-32 | II-78 | II-84 |
| Q2-349 | I-2 | II-32 | II-78 | II-86 |
| Q2-350 | I-2 | II-32 | II-84 | II-86 |
| Q2-351 | I-2 | II-62 | II-76 | II-78 |
| Q2-352 | I-2 | II-62 | II-76 | II-84 |
| Q2-353 | I-2 | II-62 | II-76 | II-86 |
| Q2-354 | I-2 | II-62 | II-78 | II-84 |
| Q2-355 | I-2 | II-62 | II-78 | II-86 |
| Q2-356 | I-2 | II-62 | II-84 | II-86 |
| Q2-357 | I-2 | II-76 | II-78 | II-84 |
| Q2-358 | I-2 | II-76 | II-78 | II-86 |
| Q2-359 | I-2 | II-76 | II-84 | II-86 |
| Q2-360 | I-2 | II-78 | II-84 | II-86 |
| Q2-361 | I-3 | II-6 | II-11 | II-15 |
| Q2-362 | I-3 | II-6 | II-11 | II-26 |
| Q2-363 | I-3 | II-6 | II-11 | II-32 |
| Q2-364 | I-3 | II-6 | II-11 | II-62 |
| Q2-365 | I-3 | II-6 | II-11 | II-76 |
| Q2-366 | I-3 | II-6 | II-11 | II-78 |
| Q2-367 | I-3 | II-6 | II-11 | II-84 |
| Q2-368 | I-3 | II-6 | II-11 | II-86 |
| Q2-369 | I-3 | II-6 | II-15 | II-26 |
| Q2-370 | I-3 | II-6 | II-15 | II-32 |
| Q2-371 | I-3 | II-6 | II-15 | II-62 |
| Q2-372 | I-3 | II-6 | II-15 | II-76 |
| Q2-373 | I-3 | II-6 | II-15 | II-78 |
| Q2-374 | I-3 | II-6 | II-15 | II-84 |
| Q2-375 | I-3 | II-6 | II-15 | II-86 |
| Q2-376 | I-3 | II-6 | II-26 | II-32 |
| Q2-377 | I-3 | II-6 | II-26 | II-62 |
| Q2-378 | I-3 | II-6 | II-26 | II-76 |
| Q2-379 | I-3 | II-6 | II-26 | II-78 |
| Q2-380 | I-3 | II-6 | II-26 | II-84 |
| Q2-381 | I-3 | II-6 | II-26 | II-86 |
| Q2-382 | I-3 | II-6 | II-32 | II-62 |
| Q2-383 | I-3 | II-6 | II-32 | II-76 |
| Q2-384 | I-3 | II-6 | II-32 | II-78 |
| Q2-385 | I-3 | II-6 | II-32 | II-84 |
| Q2-386 | I-3 | II-6 | II-32 | II-86 |
| Q2-387 | I-3 | II-6 | II-62 | II-76 |
| Q2-388 | I-3 | II-6 | II-62 | II-78 |
| Q2-389 | I-3 | II-6 | II-62 | II-84 |
| Q2-390 | I-3 | II-6 | II-62 | II-86 |
| Q2-391 | I-3 | II-6 | II-76 | II-78 |
| Q2-392 | I-3 | II-6 | II-76 | II-84 |
| Q2-393 | I-3 | II-6 | II-76 | II-86 |
| Q2-394 | I-3 | II-6 | II-78 | II-84 |
| Q2-395 | I-3 | II-6 | II-78 | II-86 |
| Q2-396 | I-3 | II-6 | II-84 | II-86 |
| Q2-397 | I-3 | II-11 | II-15 | II-26 |
| Q2-398 | I-3 | II-11 | II-15 | II-32 |
| Q2-399 | I-3 | II-11 | II-15 | II-62 |
| Q2-400 | I-3 | II-11 | II-15 | II-76 |
| Q2-401 | I-3 | II-11 | II-15 | II-78 |
| Q2-402 | I-3 | II-11 | II-15 | II-84 |
| Q2-403 | I-3 | II-11 | II-15 | II-86 |
| Q2-404 | I-3 | II-11 | II-26 | II-32 |
| Q2-405 | I-3 | II-11 | II-26 | II-62 |
| Q2-406 | I-3 | II-11 | II-26 | II-76 |
| Q2-407 | I-3 | II-11 | II-26 | II-78 |
| Q2-408 | I-3 | II-11 | II-26 | II-84 |
| Q2-409 | I-3 | II-11 | II-26 | II-86 |
| Q2-410 | I-3 | II-11 | II-32 | II-62 |
| Q2-411 | I-3 | II-11 | II-32 | II-76 |
| Q2-412 | I-3 | II-11 | II-32 | II-78 |
| Q2-413 | I-3 | II-11 | II-32 | II-84 |
| Q2-414 | I-3 | II-11 | II-32 | II-86 |
| Q2-415 | I-3 | II-11 | II-62 | II-76 |
| Q2-416 | I-3 | II-11 | II-62 | II-78 |
| Q2-417 | I-3 | II-11 | II-62 | II-84 |
| Q2-418 | I-3 | II-11 | II-62 | II-86 |
| Q2-419 | I-3 | II-11 | II-76 | II-78 |
| Q2-420 | I-3 | II-11 | II-76 | II-84 |
| Q2-421 | I-3 | II-11 | II-76 | II-86 |
| Q2-422 | I-3 | II-11 | II-78 | II-84 |
| Q2-423 | I-3 | II-11 | II-78 | II-86 |
| Q2-424 | I-3 | II-11 | II-84 | II-86 |
| Q2-425 | I-3 | II-15 | II-26 | II-32 |
| Q2-426 | I-3 | II-15 | II-26 | II-62 |
| Q2-427 | I-3 | II-15 | II-26 | II-76 |
| Q2-428 | I-3 | II-15 | II-26 | II-78 |
| Q2-429 | I-3 | II-15 | II-26 | II-84 |
| Q2-430 | I-3 | II-15 | II-26 | II-86 |
| Q2-431 | I-3 | II-15 | II-32 | II-62 |
| Q2-432 | I-3 | II-15 | II-32 | II-76 |
| Q2-433 | I-3 | II-15 | II-32 | II-78 |
| Q2-434 | I-3 | II-15 | II-32 | II-84 |
| Q2-435 | I-3 | II-15 | II-32 | II-86 |
| Q2-436 | I-3 | II-15 | II-62 | II-76 |
| Q2-437 | I-3 | II-15 | II-62 | II-78 |
| Q2-438 | I-3 | II-15 | II-62 | II-84 |
| Q2-439 | I-3 | II-15 | II-62 | II-86 |
| Q2-440 | I-3 | II-15 | II-76 | II-78 |
| Q2-441 | I-3 | II-15 | II-76 | II-84 |
| Q2-442 | I-3 | II-15 | II-76 | II-86 |
| Q2-443 | I-3 | II-15 | II-78 | II-84 |
| Q2-444 | I-3 | II-15 | II-78 | II-86 |
| Q2-445 | I-3 | II-15 | II-84 | II-86 |
| Q2-446 | I-3 | II-26 | II-32 | II-62 |

TABLE Q2-continued

| | | | | |
|---|---|---|---|---|
| Q2-447 | I-3 | II-26 | II-32 | II-76 |
| Q2-448 | I-3 | II-26 | II-32 | II-78 |
| Q2-449 | I-3 | II-26 | II-32 | II-84 |
| Q2-450 | I-3 | II-26 | II-32 | II-86 |
| Q2-451 | I-3 | II-26 | II-62 | II-76 |
| Q2-452 | I-3 | II-26 | II-62 | II-78 |
| Q2-453 | I-3 | II-26 | II-62 | II-84 |
| Q2-454 | I-3 | II-26 | II-62 | II-86 |
| Q2-455 | I-3 | II-26 | II-76 | II-78 |
| Q2-456 | I-3 | II-26 | II-76 | II-84 |
| Q2-457 | I-3 | II-26 | II-76 | II-86 |
| Q2-458 | I-3 | II-26 | II-78 | II-84 |
| Q2-459 | I-3 | II-26 | II-78 | II-86 |
| Q2-460 | I-3 | II-26 | II-84 | II-86 |
| Q2-461 | I-3 | II-32 | II-62 | II-76 |
| Q2-462 | I-3 | II-32 | II-62 | II-78 |
| Q2-463 | I-3 | II-32 | II-62 | II-84 |
| Q2-464 | I-3 | II-32 | II-62 | II-86 |
| Q2-465 | I-3 | II-32 | II-76 | II-78 |
| Q2-466 | I-3 | II-32 | II-76 | II-84 |
| Q2-467 | I-3 | II-32 | II-76 | II-86 |
| Q2-468 | I-3 | II-32 | II-78 | II-84 |
| Q2-469 | I-3 | II-32 | II-78 | II-86 |
| Q2-470 | I-3 | II-32 | II-84 | II-86 |
| Q2-471 | I-3 | II-62 | II-76 | II-78 |
| Q2-472 | I-3 | II-62 | II-76 | II-84 |
| Q2-473 | I-3 | II-62 | II-76 | II-86 |
| Q2-474 | I-3 | II-62 | II-78 | II-84 |
| Q2-475 | I-3 | II-62 | II-78 | II-86 |
| Q2-476 | I-3 | II-62 | II-84 | II-86 |
| Q2-477 | I-3 | II-76 | II-78 | II-84 |
| Q2-478 | I-3 | II-76 | II-78 | II-86 |
| Q2-479 | I-3 | II-76 | II-84 | II-86 |
| Q2-480 | I-3 | II-78 | II-84 | II-86 |
| Q2-481 | I-4 | II-6 | II-11 | II-15 |
| Q2-482 | I-4 | II-6 | II-11 | II-26 |
| Q2-483 | I-4 | II-6 | II-11 | II-32 |
| Q2-484 | I-4 | II-6 | II-11 | II-62 |
| Q2-485 | I-4 | II-6 | II-11 | II-76 |
| Q2-486 | I-4 | II-6 | II-11 | II-78 |
| Q2-487 | I-4 | II-6 | II-11 | II-84 |
| Q2-488 | I-4 | II-6 | II-11 | II-86 |
| Q2-489 | I-4 | II-6 | II-15 | II-26 |
| Q2-490 | I-4 | II-6 | II-15 | II-32 |
| Q2-491 | I-4 | II-6 | II-15 | II-62 |
| Q2-492 | I-4 | II-6 | II-15 | II-76 |
| Q2-493 | I-4 | II-6 | II-15 | II-78 |
| Q2-494 | I-4 | II-6 | II-15 | II-84 |
| Q2-495 | I-4 | II-6 | II-15 | II-86 |
| Q2-496 | I-4 | II-6 | II-26 | II-32 |
| Q2-497 | I-4 | II-6 | II-26 | II-62 |
| Q2-498 | I-4 | II-6 | II-26 | II-76 |
| Q2-499 | I-4 | II-6 | II-26 | II-78 |
| Q2-500 | I-4 | II-6 | II-26 | II-84 |
| Q2-501 | I-4 | II-6 | II-26 | II-86 |
| Q2-502 | I-4 | II-6 | II-32 | II-62 |
| Q2-503 | I-4 | II-6 | II-32 | II-76 |
| Q2-504 | I-4 | II-6 | II-32 | II-78 |
| Q2-505 | I-4 | II-6 | II-32 | II-84 |
| Q2-506 | I-4 | II-6 | II-32 | II-86 |
| Q2-507 | I-4 | II-6 | II-62 | II-76 |
| Q2-508 | I-4 | II-6 | II-62 | II-78 |
| Q2-509 | I-4 | II-6 | II-62 | II-84 |
| Q2-510 | I-4 | II-6 | II-62 | II-86 |
| Q2-511 | I-4 | II-6 | II-76 | II-78 |
| Q2-512 | I-4 | II-6 | II-76 | II-84 |
| Q2-513 | I-4 | II-6 | II-76 | II-86 |
| Q2-514 | I-4 | II-6 | II-78 | II-84 |
| Q2-515 | I-4 | II-6 | II-78 | II-86 |
| Q2-516 | I-4 | II-6 | II-84 | II-86 |
| Q2-517 | I-4 | II-11 | II-15 | II-26 |
| Q2-518 | I-4 | II-11 | II-15 | II-32 |
| Q2-519 | I-4 | II-11 | II-15 | II-62 |
| Q2-520 | I-4 | II-11 | II-15 | II-76 |
| Q2-521 | I-4 | II-11 | II-15 | II-78 |
| Q2-522 | I-4 | II-11 | II-15 | II-84 |
| Q2-523 | I-4 | II-11 | II-15 | II-86 |
| Q2-524 | I-4 | II-11 | II-26 | II-32 |
| Q2-525 | I-4 | II-11 | II-26 | II-62 |
| Q2-526 | I-4 | II-11 | II-26 | II-76 |
| Q2-527 | I-4 | II-11 | II-26 | II-78 |
| Q2-528 | I-4 | II-11 | II-26 | II-84 |
| Q2-529 | I-4 | II-11 | II-26 | II-86 |
| Q2-530 | I-4 | II-11 | II-32 | II-62 |
| Q2-531 | I-4 | II-11 | II-32 | II-76 |
| Q2-532 | I-4 | II-11 | II-32 | II-78 |
| Q2-533 | I-4 | II-11 | II-32 | II-84 |
| Q2-534 | I-4 | II-11 | II-32 | II-86 |
| Q2-535 | I-4 | II-11 | II-62 | II-76 |
| Q2-536 | I-4 | II-11 | II-62 | II-78 |
| Q2-537 | I-4 | II-11 | II-62 | II-84 |
| Q2-538 | I-4 | II-11 | II-62 | II-86 |
| Q2-539 | I-4 | II-11 | II-76 | II-78 |
| Q2-540 | I-4 | II-11 | II-76 | II-84 |
| Q2-541 | I-4 | II-11 | II-76 | II-86 |
| Q2-542 | I-4 | II-11 | II-78 | II-84 |
| Q2-543 | I-4 | II-11 | II-78 | II-86 |
| Q2-544 | I-4 | II-11 | II-84 | II-86 |
| Q2-545 | I-4 | II-15 | II-26 | II-32 |
| Q2-546 | I-4 | II-15 | II-26 | II-62 |
| Q2-547 | I-4 | II-15 | II-26 | II-76 |
| Q2-548 | I-4 | II-15 | II-26 | II-78 |
| Q2-549 | I-4 | II-15 | II-26 | II-84 |
| Q2-550 | I-4 | II-15 | II-26 | II-86 |
| Q2-551 | I-4 | II-15 | II-32 | II-62 |
| Q2-552 | I-4 | II-15 | II-32 | II-76 |
| Q2-553 | I-4 | II-15 | II-32 | II-78 |
| Q2-554 | I-4 | II-15 | II-32 | II-84 |
| Q2-555 | I-4 | II-15 | II-32 | II-86 |
| Q2-556 | I-4 | II-15 | II-62 | II-76 |
| Q2-557 | I-4 | II-15 | II-62 | II-78 |
| Q2-558 | I-4 | II-15 | II-62 | II-84 |
| Q2-559 | I-4 | II-15 | II-62 | II-86 |
| Q2-560 | I-4 | II-15 | II-76 | II-78 |
| Q2-561 | I-4 | II-15 | II-76 | II-84 |
| Q2-562 | I-4 | II-15 | II-76 | II-86 |
| Q2-563 | I-4 | II-15 | II-78 | II-84 |
| Q2-564 | I-4 | II-15 | II-78 | II-86 |
| Q2-565 | I-4 | II-15 | II-84 | II-86 |
| Q2-566 | I-4 | II-26 | II-32 | II-62 |
| Q2-567 | I-4 | II-26 | II-32 | II-76 |
| Q2-568 | I-4 | II-26 | II-32 | II-78 |
| Q2-569 | I-4 | II-26 | II-32 | II-84 |
| Q2-570 | I-4 | II-26 | II-32 | II-86 |
| Q2-571 | I-4 | II-26 | II-62 | II-76 |
| Q2-572 | I-4 | II-26 | II-62 | II-78 |
| Q2-573 | I-4 | II-26 | II-62 | II-84 |
| Q2-574 | I-4 | II-26 | II-62 | II-86 |
| Q2-575 | I-4 | II-26 | II-76 | II-78 |
| Q2-576 | I-4 | II-26 | II-76 | II-84 |
| Q2-577 | I-4 | II-26 | II-76 | II-86 |
| Q2-578 | I-4 | II-26 | II-78 | II-84 |
| Q2-579 | I-4 | II-26 | II-78 | II-86 |
| Q2-580 | I-4 | II-26 | II-84 | II-86 |
| Q2-581 | I-4 | II-32 | II-62 | II-76 |
| Q2-582 | I-4 | II-32 | II-62 | II-78 |
| Q2-583 | I-4 | II-32 | II-62 | II-84 |
| Q2-584 | I-4 | II-32 | II-62 | II-86 |
| Q2-585 | I-4 | II-32 | II-76 | II-78 |
| Q2-586 | I-4 | II-32 | II-76 | II-84 |
| Q2-587 | I-4 | II-32 | II-76 | II-86 |
| Q2-588 | I-4 | II-32 | II-78 | II-84 |
| Q2-589 | I-4 | II-32 | II-78 | II-86 |
| Q2-590 | I-4 | II-32 | II-84 | II-86 |
| Q2-591 | I-4 | II-62 | II-76 | II-78 |
| Q2-592 | I-4 | II-62 | II-76 | II-84 |
| Q2-593 | I-4 | II-62 | II-76 | II-86 |
| Q2-594 | I-4 | II-62 | II-78 | II-84 |
| Q2-595 | I-4 | II-62 | II-78 | II-86 |
| Q2-596 | I-4 | II-62 | II-84 | II-86 |

TABLE Q2-continued

| | | | | |
|---|---|---|---|---|
| Q2-597 | I-4 | II-76 | II-78 | II-84 |
| Q2-598 | I-4 | II-76 | II-78 | II-86 |
| Q2-599 | I-4 | II-76 | II-84 | II-86 |
| Q2-600 | I-4 | II-78 | II-84 | II-86 |

Four-component compositions comprising another compound I as component I and fungicidal compounds as components II, III and IV.

| composition | I | II | III | IV |
|---|---|---|---|---|
| Q2-601 | I-13 | II-6 | II-11 | II-15 |
| Q2-602 | I-13 | II-6 | II-11 | II-26 |
| Q2-603 | I-13 | II-6 | II-11 | II-32 |
| Q2-604 | I-13 | II-6 | II-11 | II-62 |
| Q2-605 | I-13 | II-6 | II-11 | II-76 |
| Q2-606 | I-13 | II-6 | II-11 | II-78 |
| Q2-607 | I-13 | II-6 | II-11 | II-84 |
| Q2-608 | I-13 | II-6 | II-11 | II-86 |
| Q2-609 | I-13 | II-6 | II-15 | II-26 |
| Q2-610 | I-13 | II-6 | II-15 | II-32 |
| Q2-611 | I-13 | II-6 | II-15 | II-62 |
| Q2-612 | I-13 | II-6 | II-15 | II-76 |
| Q2-613 | I-13 | II-6 | II-15 | II-78 |
| Q2-614 | I-13 | II-6 | II-15 | II-84 |
| Q2-615 | I-13 | II-6 | II-15 | II-86 |
| Q2-616 | I-13 | II-6 | II-26 | II-32 |
| Q2-617 | I-13 | II-6 | II-26 | II-62 |
| Q2-618 | I-13 | II-6 | II-26 | II-76 |
| Q2-619 | I-13 | II-6 | II-26 | II-78 |
| Q2-620 | I-13 | II-6 | II-26 | II-84 |
| Q2-621 | I-13 | II-6 | II-26 | II-86 |
| Q2-622 | I-13 | II-6 | II-32 | II-62 |
| Q2-623 | I-13 | II-6 | II-32 | II-76 |
| Q2-624 | I-13 | II-6 | II-32 | II-78 |
| Q2-625 | I-13 | II-6 | II-32 | II-84 |
| Q2-626 | I-13 | II-6 | II-32 | II-86 |
| Q2-627 | I-13 | II-6 | II-62 | II-76 |
| Q2-628 | I-13 | II-6 | II-62 | II-78 |
| Q2-629 | I-13 | II-6 | II-62 | II-84 |
| Q2-630 | I-13 | II-6 | II-62 | II-86 |
| Q2-631 | I-13 | II-6 | II-76 | II-78 |
| Q2-632 | I-13 | II-6 | II-76 | II-84 |
| Q2-633 | I-13 | II-6 | II-76 | II-86 |
| Q2-634 | I-13 | II-6 | II-78 | II-84 |
| Q2-635 | I-13 | II-6 | II-78 | II-86 |
| Q2-636 | I-13 | II-6 | II-84 | II-86 |
| Q2-637 | I-13 | II-11 | II-15 | II-26 |
| Q2-638 | I-13 | II-11 | II-15 | II-32 |
| Q2-639 | I-13 | II-11 | II-15 | II-62 |
| Q2-640 | I-13 | II-11 | II-15 | II-76 |
| Q2-641 | I-13 | II-11 | II-15 | II-78 |
| Q2-642 | I-13 | II-11 | II-15 | II-84 |
| Q2-643 | I-13 | II-11 | II-15 | II-86 |
| Q2-644 | I-13 | II-11 | II-26 | II-32 |
| Q2-645 | I-13 | II-11 | II-26 | II-62 |
| Q2-646 | I-13 | II-11 | II-26 | II-76 |
| Q2-647 | I-13 | II-11 | II-26 | II-78 |
| Q2-648 | I-13 | II-11 | II-26 | II-84 |
| Q2-649 | I-13 | II-11 | II-26 | II-86 |
| Q2-650 | I-13 | II-11 | II-32 | II-62 |
| Q2-651 | I-13 | II-11 | II-32 | II-76 |
| Q2-652 | I-13 | II-11 | II-32 | II-78 |
| Q2-653 | I-13 | II-11 | II-32 | II-84 |
| Q2-654 | I-13 | II-11 | II-32 | II-86 |
| Q2-655 | I-13 | II-11 | II-62 | II-76 |
| Q2-656 | I-13 | II-11 | II-62 | II-78 |
| Q2-657 | I-13 | II-11 | II-62 | II-84 |
| Q2-658 | I-13 | II-11 | II-62 | II-86 |
| Q2-659 | I-13 | II-11 | II-76 | II-78 |
| Q2-660 | I-13 | II-11 | II-76 | II-84 |
| Q2-661 | I-13 | II-11 | II-76 | II-86 |
| Q2-662 | I-13 | II-11 | II-78 | II-84 |
| Q2-663 | I-13 | II-11 | II-78 | II-86 |
| Q2-664 | I-13 | II-11 | II-84 | II-86 |
| Q2-665 | I-13 | II-15 | II-26 | II-32 |
| Q2-666 | I-13 | II-15 | II-26 | II-62 |
| Q2-667 | I-13 | II-15 | II-26 | II-76 |
| Q2-668 | I-13 | II-15 | II-26 | II-78 |
| Q2-669 | I-13 | II-15 | II-26 | II-84 |
| Q2-670 | I-13 | II-15 | II-26 | II-86 |
| Q2-671 | I-13 | II-15 | II-32 | II-62 |
| Q2-672 | I-13 | II-15 | II-32 | II-76 |
| Q2-673 | I-13 | II-15 | II-32 | II-78 |
| Q2-674 | I-13 | II-15 | II-32 | II-84 |
| Q2-675 | I-13 | II-15 | II-32 | II-86 |
| Q2-676 | I-13 | II-15 | II-62 | II-76 |
| Q2-677 | I-13 | II-15 | II-62 | II-78 |
| Q2-678 | I-13 | II-15 | II-62 | II-84 |
| Q2-679 | I-13 | II-15 | II-62 | II-86 |
| Q2-680 | I-13 | II-15 | II-76 | II-78 |
| Q2-681 | I-13 | II-15 | II-76 | II-84 |
| Q2-682 | I-13 | II-15 | II-76 | II-86 |
| Q2-683 | I-13 | II-15 | II-78 | II-84 |
| Q2-684 | I-13 | II-15 | II-78 | II-86 |
| Q2-685 | I-13 | II-15 | II-84 | II-86 |
| Q2-686 | I-13 | II-26 | II-32 | II-62 |
| Q2-687 | I-13 | II-26 | II-32 | II-76 |
| Q2-688 | I-13 | II-26 | II-32 | II-78 |
| Q2-689 | I-13 | II-26 | II-32 | II-84 |
| Q2-690 | I-13 | II-26 | II-32 | II-86 |
| Q2-691 | I-13 | II-26 | II-62 | II-76 |
| Q2-692 | I-13 | II-26 | II-62 | II-78 |
| Q2-693 | I-13 | II-26 | II-62 | II-84 |
| Q2-694 | I-13 | II-26 | II-62 | II-86 |
| Q2-695 | I-13 | II-26 | II-76 | II-78 |
| Q2-696 | I-13 | II-26 | II-76 | II-84 |
| Q2-697 | I-13 | II-26 | II-76 | II-86 |
| Q2-698 | I-13 | II-26 | II-78 | II-84 |
| Q2-699 | I-13 | II-26 | II-78 | II-86 |
| Q2-700 | I-13 | II-26 | II-84 | II-86 |
| Q2-701 | I-13 | II-32 | II-62 | II-76 |
| Q2-702 | I-13 | II-32 | II-62 | II-78 |
| Q2-703 | I-13 | II-32 | II-62 | II-84 |
| Q2-704 | I-13 | II-32 | II-62 | II-86 |
| Q2-705 | I-13 | II-32 | II-76 | II-78 |
| Q2-706 | I-13 | II-32 | II-76 | II-84 |
| Q2-707 | I-13 | II-32 | II-76 | II-86 |
| Q2-708 | I-13 | II-32 | II-78 | II-84 |
| Q2-709 | I-13 | II-32 | II-78 | II-86 |
| Q2-710 | I-13 | II-32 | II-84 | II-86 |
| Q2-711 | I-13 | II-62 | II-76 | II-78 |
| Q2-712 | I-13 | II-62 | II-76 | II-84 |
| Q2-713 | I-13 | II-62 | II-76 | II-86 |
| Q2-714 | I-13 | II-62 | II-78 | II-84 |
| Q2-715 | I-13 | II-62 | II-78 | II-86 |
| Q2-716 | I-13 | II-62 | II-84 | II-86 |
| Q2-717 | I-13 | II-76 | II-78 | II-84 |
| Q2-718 | I-13 | II-76 | II-78 | II-86 |
| Q2-719 | I-13 | II-76 | II-84 | II-86 |
| Q2-720 | I-13 | II-78 | II-84 | II-86 |

In table Q2, according to particular embodiments of the invention, the respective component I is present as (S) enantiomer, wherein each row corresponds to one embodiment of the compositions according to the invention, i.e. one specific individualized composition. According to one specific aspect, these are ternary compositions which each only contain these two components as active compounds. Furthermore, also every combination of the compositions individualized in this table represent embodiments of the present invention (S) enantiomer.

In table Q2, according to a further particular embodiments of the invention, the respective component I is present as (R) enantiomer, wherein each row corresponds to one embodiment of the compositions according to the invention, i.e. one specific individualized composition. According to one specific aspect, these are ternary compositions which each only contain these two components as active compounds. Furthermore, also every combination of the compositions individualized in this table represent embodiments of the present invention (R) enantiomer.

One further aspect of the present invention are novel three-component compositions comprising the component II, component III and the component IV as listed the above Table Q2, i.e. the compositions given in the following Table TQ2, as far as they are novel.

TABLE TQ2

Three-component compositions comprising a fungicidal components II, III and IV. Each line of line TQ2-1 to TQ2-120 corresponds to one particular individualized composition. Furthermore, also every combination of the compositions individualized in this table represent embodiments of the present invention.

| composition | II | III | IV |
|---|---|---|---|
| TQ2-1 | II-6 | II-11 | II-15 |
| TQ2-2 | II-6 | II-11 | II-26 |
| TQ2-3 | II-6 | II-11 | II-32 |
| TQ2-4 | II-6 | II-11 | II-62 |
| TQ2-5 | II-6 | II-11 | II-76 |
| TQ2-6 | II-6 | II-11 | II-78 |
| TQ2-7 | II-6 | II-11 | II-84 |
| TQ2-8 | II-6 | II-11 | II-86 |
| TQ2-9 | II-6 | II-15 | II-26 |
| TQ2-10 | II-6 | II-15 | II-32 |
| TQ2-11 | II-6 | II-15 | II-62 |
| TQ2-12 | II-6 | II-15 | II-76 |
| TQ2-13 | II-6 | II-15 | II-78 |
| TQ2-14 | II-6 | II-15 | II-84 |
| TQ2-15 | II-6 | II-15 | II-86 |
| TQ2-16 | II-6 | II-26 | II-32 |
| TQ2-17 | II-6 | II-26 | II-62 |
| TQ2-18 | II-6 | II-26 | II-76 |
| TQ2-19 | II-6 | II-26 | II-78 |
| TQ2-20 | II-6 | II-26 | II-84 |
| TQ2-21 | II-6 | II-26 | II-86 |
| TQ2-22 | II-6 | II-32 | II-62 |
| TQ2-23 | II-6 | II-32 | II-76 |
| TQ2-24 | II-6 | II-32 | II-78 |
| TQ2-25 | II-6 | II-32 | II-84 |
| TQ2-26 | II-6 | II-32 | II-86 |
| TQ2-27 | II-6 | II-62 | II-76 |
| TQ2-28 | II-6 | II-62 | II-78 |
| TQ2-29 | II-6 | II-62 | II-84 |
| TQ2-30 | II-6 | II-62 | II-86 |
| TQ2-31 | II-6 | II-76 | II-78 |
| TQ2-32 | II-6 | II-76 | II-84 |
| TQ2-33 | II-6 | II-76 | II-86 |
| TQ2-34 | II-6 | II-78 | II-84 |
| TQ2-35 | II-6 | II-78 | II-86 |
| TQ2-36 | II-6 | II-84 | II-86 |
| TQ2-37 | II-11 | II-15 | II-26 |
| TQ2-38 | II-11 | II-15 | II-32 |
| TQ2-39 | II-11 | II-15 | II-62 |
| TQ2-40 | II-11 | II-15 | II-76 |
| TQ2-41 | II-11 | II-15 | II-78 |
| TQ2-42 | II-11 | II-15 | II-84 |
| TQ2-43 | II-11 | II-15 | II-86 |
| TQ2-44 | II-11 | II-26 | II-32 |
| TQ2-45 | II-11 | II-26 | II-62 |
| TQ2-46 | II-11 | II-26 | II-76 |
| TQ2-47 | II-11 | II-26 | II-78 |
| TQ2-48 | II-11 | II-26 | II-84 |
| TQ2-49 | II-11 | II-26 | II-86 |
| TQ2-50 | II-11 | II-32 | II-62 |
| TQ2-51 | II-11 | II-32 | II-76 |
| TQ2-52 | II-11 | II-32 | II-78 |
| TQ2-53 | II-11 | II-32 | II-84 |
| TQ2-54 | II-11 | II-32 | II-86 |
| TQ2-55 | II-11 | II-62 | II-76 |
| TQ2-56 | II-11 | II-62 | II-78 |
| TQ2-57 | II-11 | II-62 | II-84 |
| TQ2-58 | II-11 | II-62 | II-86 |
| TQ2-59 | II-11 | II-76 | II-78 |
| TQ2-60 | II-11 | II-76 | II-84 |
| TQ2-61 | II-11 | II-76 | II-86 |
| TQ2-62 | II-11 | II-78 | II-84 |
| TQ2-63 | II-11 | II-78 | II-86 |
| TQ2-64 | II-11 | II-84 | II-86 |
| TQ2-65 | II-15 | II-26 | II-32 |
| TQ2-66 | II-15 | II-26 | II-62 |
| TQ2-67 | II-15 | II-26 | II-76 |
| TQ2-68 | II-15 | II-26 | II-78 |
| TQ2-69 | II-15 | II-26 | II-84 |
| TQ2-70 | II-15 | II-26 | II-86 |
| TQ2-71 | II-15 | II-32 | II-62 |
| TQ2-72 | II-15 | II-32 | II-76 |
| TQ2-73 | II-15 | II-32 | II-78 |
| TQ2-74 | II-15 | II-32 | II-84 |
| TQ2-75 | II-15 | II-32 | II-86 |
| TQ2-76 | II-15 | II-62 | II-76 |
| TQ2-77 | II-15 | II-62 | II-78 |
| TQ2-78 | II-15 | II-62 | II-84 |
| TQ2-79 | II-15 | II-62 | II-86 |
| TQ2-80 | II-15 | II-76 | II-78 |
| TQ2-81 | II-15 | II-76 | II-84 |
| TQ2-82 | II-15 | II-76 | II-86 |
| TQ2-83 | II-15 | II-78 | II-84 |
| TQ2-84 | II-15 | II-78 | II-86 |
| TQ2-85 | II-15 | II-84 | II-86 |
| TQ2-86 | II-26 | II-32 | II-62 |
| TQ2-87 | II-26 | II-32 | II-76 |
| TQ2-88 | II-26 | II-32 | II-78 |
| TQ2-89 | II-26 | II-32 | II-84 |
| TQ2-90 | II-26 | II-32 | II-86 |
| TQ2-91 | II-26 | II-62 | II-76 |
| TQ2-92 | II-26 | II-62 | II-78 |
| TQ2-93 | II-26 | II-62 | II-84 |
| TQ2-94 | II-26 | II-62 | II-86 |
| TQ2-95 | II-26 | II-76 | II-78 |
| TQ2-96 | II-26 | II-76 | II-84 |
| TQ2-97 | II-26 | II-76 | II-86 |
| TQ2-98 | II-26 | II-78 | II-84 |
| TQ2-99 | II-26 | II-78 | II-86 |
| TQ2-100 | II-26 | II-84 | II-86 |
| TQ2-101 | II-32 | II-62 | II-76 |
| TQ2-102 | II-32 | II-62 | II-78 |
| TQ2-103 | II-32 | II-62 | II-84 |
| TQ2-104 | II-32 | II-62 | II-86 |
| TQ2-105 | II-32 | II-76 | II-78 |
| TQ2-106 | II-32 | II-76 | II-84 |
| TQ2-107 | II-32 | II-76 | II-86 |
| TQ2-108 | II-32 | II-78 | II-84 |
| TQ2-109 | II-32 | II-78 | II-86 |
| TQ2-110 | II-32 | II-84 | II-86 |
| TQ2-111 | II-62 | II-76 | II-78 |
| TQ2-112 | II-62 | II-76 | II-84 |
| TQ2-113 | II-62 | II-76 | II-86 |
| TQ2-114 | II-62 | II-78 | II-84 |
| TQ2-115 | II-62 | II-78 | II-86 |
| TQ2-116 | II-62 | II-84 | II-86 |
| TQ2-117 | II-76 | II-78 | II-84 |
| TQ2-118 | II-76 | II-78 | II-86 |
| TQ2-119 | II-76 | II-84 | II-86 |
| TQ2-120 | II-78 | II-84 | II-86 |

Further particularly preferred compositions are the four-component compositions, wherein component I is as defined above, i.e. a compound I, in particular a compound selected from compounds I-1, I-2, I-3, I-4, I-5, I-6, I-7, I-8, I-9, I-11, I-13, I-14, I-15 and I-16 or any group of compounds I detailed above, and components II, III and IV are selected from the following growth regulators

| | |
|---|---|
| II-1a | mepiquat chloride |
| II-2a | chlormequat chloride |
| II-3a | trinexapac-ethyl |
| II-4a | prohexadione-calcium |
| II-5a | ethophon | wherein components II, III and IV are different active compounds.

Specifically preferred embodiments of these compositions are compiled in Table Q3, where each row corresponds to one embodiment of the compositions according to the invention, i.e. one specific individualized four-component composition. According to one specific aspect, these are quaternary compositions which each only contain these four components as the active compound. Furthermore, also every combination of the compositions individualized in this table represent embodiments of the present invention.

TABLE Q3

Four-component compositions comprising a component I and growth regulators as components II, III and IV.

| composition | I | II | III | IV |
|---|---|---|---|---|
| Q3-1 | I-1 | II-1a | II-2a | II-3a |
| Q3-2 | I-1 | II-1a | II-2a | II-4a |
| Q3-3 | I-1 | II-1a | II-2a | II-5a |
| Q3-4 | I-1 | II-1a | II-3a | II-4a |
| Q3-5 | I-1 | II-1a | II-3a | II-5a |
| Q3-6 | I-1 | II-1a | II-4a | II-5a |
| Q3-7 | I-1 | II-2a | II-3a | II-4a |
| Q3-8 | I-1 | II-2a | II-3a | II-5a |
| Q3-9 | I-1 | II-2a | II-4a | II-5a |
| Q3-10 | I-1 | II-3a | II-4a | II-5a |
| Q3-11 | I-5 | II-1a | II-2a | II-3a |
| Q3-12 | I-5 | II-1a | II-2a | II-4a |
| Q3-13 | I-5 | II-1a | II-2a | II-5a |
| Q3-14 | I-5 | II-1a | II-3a | II-4a |
| Q3-15 | I-5 | II-1a | II-3a | II-5a |
| Q3-16 | I-5 | II-1a | II-4a | II-5a |
| Q3-17 | I-5 | II-2a | II-3a | II-4a |
| Q3-18 | I-5 | II-2a | II-3a | II-5a |
| Q3-19 | I-5 | II-2a | II-4a | II-5a |
| Q3-20 | I-5 | II-3a | II-4a | II-5a |
| Q3-21 | I-2 | II-1a | II-2a | II-3a |
| Q3-22 | I-2 | II-1a | II-2a | II-4a |
| Q3-23 | I-2 | II-1a | II-2a | II-5a |
| Q3-24 | I-2 | II-1a | II-3a | II-4a |
| Q3-25 | I-2 | II-1a | II-3a | II-5a |
| Q3-26 | I-2 | II-1a | II-4a | II-5a |
| Q3-27 | I-2 | II-2a | II-3a | II-4a |
| Q3-28 | I-2 | II-2a | II-3a | II-5a |
| Q3-29 | I-2 | II-2a | II-4a | II-5a |
| Q3-30 | I-2 | II-3a | II-4a | II-5a |
| Q3-31 | I-3 | II-1a | II-2a | II-3a |
| Q3-32 | I-3 | II-1a | II-2a | II-4a |
| Q3-33 | I-3 | II-1a | II-2a | II-5a |
| Q3-34 | I-3 | II-1a | II-3a | II-4a |
| Q3-35 | I-3 | II-1a | II-3a | II-5a |
| Q3-36 | I-3 | II-1a | II-4a | II-5a |
| Q3-37 | I-3 | II-2a | II-3a | II-4a |
| Q3-38 | I-3 | II-2a | II-3a | II-5a |
| Q3-39 | I-3 | II-2a | II-4a | II-5a |
| Q3-40 | I-3 | II-3a | II-4a | II-5a |
| Q3-41 | I-4 | II-1a | II-2a | II-3a |
| Q3-42 | I-4 | II-1a | II-2a | II-4a |
| Q3-43 | I-4 | II-1a | II-2a | II-5a |
| Q3-44 | I-4 | II-1a | II-3a | II-4a |
| Q3-45 | I-4 | II-1a | II-3a | II-5a |
| Q3-46 | I-4 | II-1a | II-4a | II-5a |
| Q3-47 | I-4 | II-2a | II-3a | II-4a |
| Q3-48 | I-4 | II-2a | II-3a | II-5a |
| Q3-49 | I-4 | II-2a | II-4a | II-5a |
| Q3-50 | I-4 | II-3a | II-4a | II-5a |

Four-component compositions comprising another compound I as component I and growth regulators as components II, III and IV.

| composition | I | II | III | IV |
|---|---|---|---|---|
| Q3-51 | I-13 | II-1a | II-2a | II-3a |
| Q3-52 | I-13 | II-1a | II-2a | II-4a |
| Q3-53 | I-13 | II-1a | II-2a | II-5a |
| Q3-54 | I-13 | II-1a | II-3a | II-4a |
| Q3-55 | I-13 | II-1a | II-3a | II-5a |
| Q3-56 | I-13 | II-1a | II-4a | II-5a |
| Q3-57 | I-13 | II-2a | II-3a | II-4a |
| Q3-58 | I-13 | II-2a | II-3a | II-5a |
| Q3-59 | I-13 | II-2a | II-4a | II-5a |
| Q3-60 | I-13 | II-3a | II-4a | II-5a |

In table Q3, according to particular embodiments of the invention, the respective component I is present as (S) enantiomer, wherein each row corresponds to one embodiment of the compositions according to the invention, i.e. one specific individualized composition. According to one specific aspect, these are ternary compositions which each only contain these two components as active compounds. Furthermore, also every combination of the compositions individualized in this table represent embodiments of the present invention (S) enantiomer.

In table Q3, according to a further particular embodiments of the invention, the respective component I is present as (R) enantiomer, wherein each row corresponds to one embodiment of the compositions according to the invention, i.e. one specific individualized composition. According to one specific aspect, these are ternary compositions which each only contain these two components as active compounds. Furthermore, also every combination of the compositions individualized in this table represent embodiments of the present invention (R) enantiomer.

Further particularly preferred compositions are the four-component compositions, wherein component I is as defined above, i.e. a compound I, in particular a compound selected from compounds I-1, I-2, I-3, I-4, I-5, I-6, I-7, I-8, I-9, I-11, I-13, I-14, I-15 and I-16 or any group of compounds I detailed above, components II is selected from the following fungicides

| II-3 | azoxystrobin |
|---|---|
| II-42 | fluxapyroxad |
| II-53 | kresoxim-methyl |
| II-66 | pyraclostrobin |
| II-72 | penthiopyrad |
| II-92 | trifloxystrobin | and component II selected from the group of the following compounds:

| II-11c | clothianidin |
|---|---|
| II-24c | imidacloprid |
| II-42c | thiamethoxam, | and component IV is fipronil (compound II-20c).

Specifically preferred embodiments of these compositions are compiled in Table Q4, where each row corresponds to one embodiment of the compositions according to the invention, i.e. one specific individualized four-component composition. According to one specific aspect, these are quaternary compositions which each only contain these four components as the active compound. Furthermore, also every combination of the compositions individualized in this table represent embodiments of the present invention.

TABLE Q4

Four-component compositions comprising a component I, a particular fungicide as component II and specific insecticides as components III and IV.

| composition | I | II | III | IV |
|---|---|---|---|---|
| Q4-1 | I-1 | II-3 | II-11c | II-20c |
| Q4-2 | I-1 | II-3 | II-24c | II-20c |
| Q4-3 | I-1 | II-3 | II-42c | II-20c |
| Q4-4 | I-1 | II-42 | II-11c | II-20c |
| Q4-5 | I-1 | II-42 | II-24c | II-20c |
| Q4-6 | I-1 | II-42 | II-42c | II-20c |
| Q4-7 | I-1 | II-53 | II-11c | II-20c |
| Q4-8 | I-1 | II-53 | II-24c | II-20c |
| Q4-9 | I-1 | II-53 | II-42c | II-20c |
| Q4-10 | I-1 | II-66 | II-11c | II-20c |
| Q4-11 | I-1 | II-66 | II-24c | II-20c |
| Q4-12 | I-1 | II-66 | II-42c | II-20c |
| Q4-13 | I-1 | II-72 | II-11c | II-20c |
| Q4-14 | I-1 | II-72 | II-24c | II-20c |
| Q4-15 | I-1 | II-72 | II-42c | II-20c |
| Q4-16 | I-1 | II-92 | II-11c | II-20c |
| Q4-17 | I-1 | II-92 | II-24c | II-20c |
| Q4-18 | I-1 | II-92 | II-42c | II-20c |
| Q4-19 | I-5 | II-3 | II-11c | II-20c |
| Q4-20 | I-5 | II-3 | II-24c | II-20c |
| Q4-21 | I-5 | II-3 | II-42c | II-20c |
| Q4-22 | I-5 | II-42 | II-11c | II-20c |
| Q4-23 | I-5 | II-42 | II-24c | II-20c |
| Q4-24 | I-5 | II-42 | II-42c | II-20c |
| Q4-25 | I-5 | II-53 | II-11c | II-20c |
| Q4-26 | I-5 | II-53 | II-24c | II-20c |
| Q4-27 | I-5 | II-53 | II-42c | II-20c |
| Q4-28 | I-5 | II-66 | II-11c | II-20c |
| Q4-29 | I-5 | II-66 | II-24c | II-20c |
| Q4-30 | I-5 | II-66 | II-42c | II-20c |
| Q4-31 | I-5 | II-72 | II-11c | II-20c |
| Q4-32 | I-5 | II-72 | II-24c | II-20c |
| Q4-33 | I-5 | II-72 | II-42c | II-20c |
| Q4-34 | I-5 | II-92 | II-11c | II-20c |
| Q4-35 | I-5 | II-92 | II-24c | II-20c |
| Q4-36 | I-5 | II-92 | II-42c | II-20c |
| Q4-37 | I-2 | II-3 | II-11c | II-20c |
| Q4-38 | I-2 | II-3 | II-24c | II-20c |
| Q4-39 | I-2 | II-3 | II-42c | II-20c |
| Q4-40 | I-2 | II-42 | II-11c | II-20c |
| Q4-41 | I-2 | II-42 | II-24c | II-20c |
| Q4-42 | I-2 | II-42 | II-42c | II-20c |
| Q4-43 | I-2 | II-53 | II-11c | II-20c |
| Q4-44 | I-2 | II-53 | II-24c | II-20c |
| Q4-45 | I-2 | II-53 | II-42c | II-20c |
| Q4-46 | I-2 | II-66 | II-11c | II-20c |
| Q4-47 | I-2 | II-66 | II-24c | II-20c |
| Q4-48 | I-2 | II-66 | II-42c | II-20c |
| Q4-49 | I-2 | II-72 | II-11c | II-20c |
| Q4-50 | I-2 | II-72 | II-24c | II-20c |
| Q4-51 | I-2 | II-72 | II-42c | II-20c |
| Q4-52 | I-2 | II-92 | II-11c | II-20c |
| Q4-53 | I-2 | II-92 | II-24c | II-20c |
| Q4-54 | I-2 | II-92 | II-42c | II-20c |
| Q4-55 | I-3 | II-3 | II-11c | II-20c |
| Q4-56 | I-3 | II-3 | II-24c | II-20c |
| Q4-57 | I-3 | II-3 | II-42c | II-20c |
| Q4-58 | I-3 | II-42 | II-11c | II-20c |
| Q4-59 | I-3 | II-42 | II-24c | II-20c |
| Q4-60 | I-3 | II-42 | II-42c | II-20c |
| Q4-61 | I-3 | II-53 | II-11c | II-20c |
| Q4-62 | I-3 | II-53 | II-24c | II-20c |
| Q4-63 | I-3 | II-53 | II-42c | II-20c |
| Q4-64 | I-3 | II-66 | II-11c | II-20c |
| Q4-65 | I-3 | II-66 | II-24c | II-20c |
| Q4-66 | I-3 | II-66 | II-42c | II-20c |
| Q4-67 | I-3 | II-72 | II-11c | II-20c |
| Q4-68 | I-3 | II-72 | II-24c | II-20c |
| Q4-69 | I-3 | II-72 | II-42c | II-20c |
| Q4-70 | I-3 | II-92 | II-11c | II-20c |
| Q4-71 | I-3 | II-92 | II-24c | II-20c |
| Q4-72 | I-3 | II-92 | II-42c | II-20c |
| Q4-73 | I-4 | II-3 | II-11c | II-20c |
| Q4-74 | I-4 | II-3 | II-24c | II-20c |
| Q4-75 | I-4 | II-3 | II-42c | II-20c |
| Q4-76 | I-4 | II-42 | II-11c | II-20c |
| Q4-77 | I-4 | II-42 | II-24c | II-20c |
| Q4-78 | I-4 | II-42 | II-42c | II-20c |
| Q4-79 | I-4 | II-53 | II-11c | II-20c |
| Q4-80 | I-4 | II-53 | II-24c | II-20c |
| Q4-81 | I-4 | II-53 | II-42c | II-20c |
| Q4-82 | I-4 | II-66 | II-11c | II-20c |
| Q4-83 | I-4 | II-66 | II-24c | II-20c |
| Q4-84 | I-4 | II-66 | II-42c | II-20c |
| Q4-85 | I-4 | II-72 | II-11c | II-20c |
| Q4-86 | I-4 | II-72 | II-24c | II-20c |
| Q4-87 | I-4 | II-72 | II-42c | II-20c |
| Q4-88 | I-4 | II-92 | II-11c | II-20c |
| Q4-89 | I-4 | II-92 | II-24c | II-20c |
| Q4-90 | I-4 | II-92 | II-42c | II-20c |

Four-component compositions comprising another compound I as component I, a particular fungicide as component II and specific insecticides as components III and IV.

| composition | I | II | III | IV |
|---|---|---|---|---|
| Q4-91 | I-13 | II-3 | II-11c | II-20c |
| Q4-92 | I-13 | II-3 | II-24c | II-20c |
| Q4-93 | I-13 | II-3 | II-42c | II-20c |
| Q4-94 | I-13 | II-42 | II-11c | II-20c |
| Q4-95 | I-13 | II-42 | II-24c | II-20c |
| Q4-96 | I-13 | II-42 | II-42c | II-20c |
| Q4-97 | I-13 | II-53 | II-11c | II-20c |
| Q4-98 | I-13 | II-53 | II-24c | II-20c |
| Q4-99 | I-13 | II-53 | II-42c | II-20c |
| Q4-100 | I-13 | II-66 | II-11c | II-20c |
| Q4-101 | I-13 | II-66 | II-24c | II-20c |
| Q4-102 | I-13 | II-66 | II-42c | II-20c |
| Q4-103 | I-13 | II-72 | II-11c | II-20c |
| Q4-104 | I-13 | II-72 | II-24c | II-20c |
| Q4-105 | I-13 | II-72 | II-42c | II-20c |
| Q4-106 | I-13 | II-92 | II-11c | II-20c |
| Q4-107 | I-13 | II-92 | II-24c | II-20c |
| Q4-108 | I-13 | II-92 | II-42c | II-20c |

In table Q4, according to particular embodiments of the invention, the respective component I is present as (S) enantiomer, wherein each row corresponds to one embodiment of the compositions according to the invention, i.e. one specific individualized composition. According to one specific aspect, these are ternary compositions which each only contain these two components as active compounds. Furthermore, also every combination of the compositions individualized in this table represent embodiments of the present invention (S) enantiomer.

In table Q4, according to a further particular embodiments of the invention, the respective component I is present as (R) enantiomer, wherein each row corresponds to one embodiment of the compositions according to the invention, i.e. one specific individualized composition. According to one specific aspect, these are ternary compositions which each only contain these two components as active compounds. Furthermore, also every combination of the compositions individualized in this table represent embodiments of the present invention (R) enantiomer.

A further aspect of the invention are compositions comprising more than four active ingredients, such as, in particular five-component-compositions. In addition to the four components I, II, III and IV as detailed above, these inventive compositions comprise a component V. Component V is selected from any one of groups A) to O). Any further active components, such as component V, is, if desired, added in a ratio of from 20:1 to 1:20, in particular 10:1 to 1:10, more particularly 3:1 to 1:3, to the compound I.

According to one embodiment of the five-component compositions, the component I, II, III and IV are as defined and preferably defined above, and component V is selected from any one of groups A) to K).

One specific embodiment relates to five-component compositions, wherein component I is as defined above, in particular selected from compounds I-1, I-2, I-3, I-4, I-5, I-6, I-7, I-8, I-9, I-11, I-13, I-14, I-15 and I-16 or any group of compounds I detailed above, components II, III and IV are as defined above and preferably defined above, and component V is selected from group A) of the respiration inhibitors. According to one embodiment thereof, component V is selected from the group of inhibitors of complex III at $Q_o$ site, in e.g. the strobilurins. Specifically, component V is selected from the group consisting of azoxystrobin, dimoxystrobin, fluoxastrobin, kresoxim-methyl, orysastrobin, picoxystrobin, pyraclostrobin, trifloxystrobin, famoxadone and fenamidone.

According to a further embodiment thereof, component V is selected from the group of inhibitors of complex II, e.g. carboxamides. Specifically, component V is selected from the group consisting of benzovindiflupyr, bixafen, boscalid, fluopyram, fluxapyroxad, isopyrazam, penflufen, penthiopyrad and sedaxane. According to a further embodiment, component V is selected from the group of ametotradin, cyazofamid, fluazinam, fentin salts such as fentin acetate.

One specific embodiment relates to five-component compositions, wherein component I is as defined above, in particular selected from compounds I-1, I-2, I-3, I-4, I-5, I-6, I-7, I-8, I-9, I-11, I-13, I-14, I-15 and I-16 or any group of compounds I detailed above, components II, III and IV are as defined above and preferably defined above, and component V is selected from group B) of the sterol biosynthesis inhibitors (SBI fungicides). According to one embodiment thereof, component V is selected from the group of the C14 demethylase inhibitors (DMI fungicides), selected from cyproconazole, difenoconazole, epoxiconazole, fluquinconazole, flusilazole, flutriafol, metconazole, myclobutanil, penconazole, propiconazole, prothioconazole, triadimefon, triadimenol, tebuconazole, tetraconazole, triticonazole, prochloraz, fenarimol and triforine. According to a further embodiment thereof, component V is selected from the group of the delta14-reductase inhibitors, in particular dodemorph, fenpropimorph, tridemorph, fenpropidin and spiroxamine. According to a further embodiment thereof, component V is selected from the group of Inhibitors of 3-keto reductase such as fenhexamid.

According to a further embodiment of the five-component compositions, component I is as defined above, in particular selected from compounds I-1, I-2, I-3, I-4, I-5, I-6, I-7, I-8, I-9, I-11, I-13, I-14, I-15 and I-16 or any group of compounds I detailed above, components II, III and IV are as defined above and preferably defined above, and component V is selected from group C) of the Nucleic acid synthesis inhibitors and particularly selected from metalaxyl, (metalaxyl-M) mefenoxam, ofurace.

According to a further embodiment of the five-component compositions, component I is as defined above, in particular selected from compounds I-1, I-2, I-3, I-4, I-5, I-6, I-7, I-8, I-9, I-11, I-13, I-14, I-15 and I-16 or any group of compounds I detailed above, components II, III and IV are as defined above and preferably defined above, and component V selected from group D) of the inhibitors of cell division and cytoskeleton, such as benomyl, carbendazim, thiophanate-methyl, ethaboxam, fluopicolide, zoxamide, metrafenone, pyriofenone, in particular ethaboxam, zoxamide and metrafenone.

According to a further embodiment of the five-component compositions, component I is as defined above, in particular selected from compounds I-1, I-2, I-3, I-4, I-5, I-6, I-7, I-8, I-9, I-11, I-13, I-14, I-15 and I-16 or any group of compounds I detailed above, components II, III and IV are as defined above and preferably defined above, and component V is selected from group E) of the inhibitors of amino acid and protein synthesis, in particular selected from cyprodinil, mepanipyrim and pyrimethanil.

According to a further embodiment of the five-component compositions, component I is as defined above, in particular selected from compounds I-1, I-2, I-3, I-4, I-5, I-6, I-7, I-8, I-9, I-11, I-13, I-14, I-15 and I-16 or any group of compounds I detailed above, components II, III and IV are as defined above and preferably defined above, and component V is selected from group F) of the signal transduction inhibitors, in particular selected from iprodione, fludioxonil, vinclozolin and quinoxyfen.

According to a further embodiment of the five-component compositions, component I is as defined above, in particular selected from compounds I-1, I-2, I-3, I-4, I-5, I-6, I-7, I-8, I-9, I-11, I-13, I-14, I-15 and I-16 or any group of compounds I detailed above, components II, III and IV are as defined above and preferably defined above, and component V is selected from group G) of the lipid and membrane synthesis inhibitors, such as dimethomorph, flumorph, iprovalicarb, benthiavalicarb, mandipropamid and propamocarb.

According to a further embodiment of the five-component compositions, component I is as defined above, in particular selected from compounds I-1, I-2, I-3, I-4, I-5, I-6, I-7, I-8, I-9, I-11, I-13, I-14, I-15 and I-16 or any group of compounds I detailed above, components II, III and IV are as defined above and preferably defined above, and component V is selected from group H) of the inhibitors with Multi Site Action, in particular selected from copper acetate, (tri)basic copper sulfate, copper oxychloride, copper sulfate, sulfur, mancozeb, metiram, propineb, thiram, captafol, folpet, chlorothalonil, dichlofluanid and dithianon.

According to a further embodiment of the five-component compositions, component I is as defined above, in particular selected from compounds I-1, I-2, I-3, I-4, I-5, I-6, I-7, I-8, I-9, I-11, I-13, I-14, I-15 and I-16 or any group of compounds I detailed above, components II, III and IV are as defined above and preferably defined above, and component V is selected from group I) of the cell wall synthesis inhibitors, in particular selected from carpropamid and fenoxanil.

According to a further embodiment of the five-component compositions, component I is as defined above, in particular selected from compounds I-1, I-2, I-3, I-4, I-5, I-6, I-7, I-8, I-9, I-11, I-13, I-14, I-15 and I-16 or any group of compounds I detailed above, components II, III and IV are as defined above and preferably defined above, and component V is selected from group J) of the plant defence inducers, in particular selected from acibenzolar-S-methyl, probenazole, tiadinil, fosetyl, fosetyl-aluminium, phosphorous acid and salts thereof such as potassium salt of phosphorous acid, sodium salt of phosphorous acid, calcium salt of phosphorous acid, lithium salt of phosphorous acid and aluminium salt of phosphorous acid.

According to a further embodiment of the five-component compositions, component I is as defined above, in particular selected from compounds I-1, I-2, I-3, I-4, I-5, I-6, I-7, I-8, I-9, I-11, I-13, I-14, I-15 and I-16 or any group of compounds I detailed above, components II, III and IV are as defined above and preferably defined above, and component V s selected from group K), in particular selected from cymoxanil, proquinazid and N-methyl-2-{1-[(5-methyl-3-trifluoromethyl-1H-pyrazol-1-yl)-acetyl]-piperidin-4-yl}-N-[(1R)-1,2,3,4-tetrahydronaphthalen-1-yl]-4-thiazolecarboxamide.

According to a further embodiment of the five-component compositions, component I is as defined above, in particular selected from compounds I-1, I-2, I-3, I-4, I-5, I-6, I-7, I-8, I-9, I-11, I-13, I-14, I-15 and I-16 or any group of compounds I detailed above, components II, III and IV are as defined above and preferably defined above, and component V is selected from any one of group L) (antifungal biocontrol agents and plant bioactivators), in particular selected from *Bacillus subtilis* strain NRRL No. B-21661, *Bacillus pumllus* strain NRRL No. B-30087 and *Ulocladium oudemansii*.

According to a further embodiment of the five-component compositions, component I is as defined above, in particular selected from compounds I-1, I-2, I-3, I-4, I-5, I-6, I-7, I-8, I-9, I-11, I-13, I-14, I-15 and I-16 or any group of compounds I detailed above, components II, III and IV are as defined above and preferably defined above, and component V is selected from any one of group M) (growth regulators). According to one specific embodiment, the growth regulator is selected from chlormequat (chlormequat chloride), mepiquat (mepiquat chloride), paclobutrazole, prohexadione (prohexadione-calcium), trinexapac-ethyl and uniconazole.

According to a further embodiment of the five-component compositions, component I is as defined above, in particular selected from compounds I-1, I-2, I-3, I-4, I-5, I-6, I-7, I-8, I-9, I-11, I-13, I-14, I-15 and I-16 or any group of compounds I detailed above, and component II component I is as defined above, in particular selected from compounds I-1, I-2, I-3, I-4, I-5, I-6, I-7, I-8, I-9, I-11, I-13, I-14, I-15 and I-16 or any group of compounds I detailed above, components II, III and IV are as defined above and preferably defined above, and component V is selected from any one of group N) (herbicides).

According to a further embodiment of the five-component compositions, component I is as defined above, in particular selected from compounds I-1, I-2, I-3, I-4, I-5, I-6, I-7, I-8, I-9, I-11, I-13, I-14, I-15 and I-16 or any group of compounds I detailed above, components II, III and IV are as defined above and preferably defined above, and component V is selected from any one of group O) (insecticides). According to one specific embodiment, the insecticide is selected from the group of the organo(thio)phosphates, in particular selected from the group consisting of acephate, chlorpyrifos, diazinon, dichlorvos, dimethoate, fenitrothion, methamidophos, methidathion, methyl-parathion, monocrotophos, phorate, profenofos and terbufos. According to a further specific embodiment, the insecticide is selected from the group of the carbamates, in particular selected from the group consisting of aldicarb, carbaryl, carbofuran, carbosulfan, methomyl and thiodicarb. According to a further specific embodiment, the insecticide is selected from the group of the pyrethroids, in particular selected from the group consisting of: bifenthrin, cyfluthrin, cypermethrin, alpha-cypermethrin, zeta-cypermethrin, deltamethrin, esfenvalerate, lambda-cyhalothrin and tefluthrin. According to still a further specific embodiment, the insecticide is selected from the group of insect growth regulators, in particular selected from the group consisting of lufenuron and spirotetramat. According to still a further specific embodiment, the insecticide is selected from the group of the nicotine receptor agonists/antagonists, in particular selected from the group consisting of: clothianidin, imidacloprid, thiamethoxam and thiacloprid. According to a further specific embodiment, the insecticide is selected from the group of the GABA antagonists, in particular selected from the group consisting of: endosulfan and fipronil. According to a further specific embodiment, the insecticide is selected from the group of the macrocyclic lactones, in particular selected from the group consisting of: abamectin, emamectin, spinosad and spinetoram. According to a further specific embodiment, the insecticide is hydramethylnon. According to a further specific embodiment, the insecticide is fenbutatin oxide. According to a further specific embodiment, the insecticide is selected from the group consisting of chlorfenapyr, indoxacarb, metaflumizone, flonicamid, flubendiamide, cyazypyr (HGW86) and cyflumetofen.

The compositions according to the invention are suitable as fungicides. They are distinguished by an outstanding effectiveness against a broad spectrum of phytopathogenic fungi, including soil-borne fungi, which derive especially from the classes of the Plasmodiophoromycetes, Peronosporomycetes (syn. Oomycetes), Chytridiomycetes, Zygomycetes, Ascomycetes, Basidiomycetes and Deuteromycetes (syn. *Fungi imperfecti*). Some are systemically effective and they can be used in crop protection as foliar fungicides, fungicides for seed dressing and soil fungicides. Moreover, they are suitable for controlling harmful fungi, which inter alia occur in wood or roots of plants.

Some compositions of the invention are particularly suitable for seed treatment. For example, an inventive three-component composition, wherein component I is as defined above, component II is selected from the sterol biosynthesis inhibitors (SBI fungicides), in particular from the C14 demethylase inhibitors (DMI fungicides), and component III is selected from the Signal transduction inhibitors, is useful for seed treatment, wherein, in a specific embodiment, component II is triticonazole and component III is fludioxonil.

Furthermore, also some inventive four-component compositions are specifically useful for seed treatment. For example compositions, wherein component I is as defined above, component II is selected from the sterol biosynthesis inhibitors (SBI fungicides), in particular from the C14 demethylase inhibitors (DMI fungicides), component III is selected from the Signal transduction inhibitors and component IV is selected from the group of the carboxamides, in particular selected from benodanil, benzovindiflupyr, bixafen, boscalid, carboxin, fenfuram, fluopyram, flutolanil, fluxapyroxad, furametpyr, isopyrazam, mepronil, oxycarboxin, penflufen, penthiopyrad, sedaxane, tecloftalam, thifluzamide, N-(4'-trifluoromethylthiobiphenyl-2-yl)-3-difluoromethyl-1-methyl-1H-pyrazole-4-carboxamide, N-(2-(1,3,3-trimethyl-butyl)-phenyl)-1,3-dimethyl-5-fluoro-1H-pyrazole-4-carboxamide, 3-(difluoromethyl)-1-methyl-N-(1,1,3-trimethylindan-4-yl)pyrazole-4-carboxamide, 3-(trifluoromethyl)-1-methyl-N-(1,1,3-trimethylindan-4-yl) pyrazole-4-carboxamide, 1,3-dimethyl-N-(1,1,3-trimethyl-indan-4-yl)pyrazole-4-carboxamide, 3-(trifluoromethyl)-1,5-dimethyl-N-(1,1,3-trimethylindan-4-yl)pyrazole-4-carboxamide, 3-(difluoromethyl)-1,5-dimethyl-N-(1,1,3-trimethylindan-4-yl)pyrazole-4-carboxamide and 1,3,5-trimethyl-N-(1,1,3-trimethylindan-4-yl)pyrazole-4-carboxamide, in particular selected from benzovindiflupyr, bixafen, boscalid, fluopyram, fluxapyroxad, isopyrazam, penflufen, penthiopyrad and sedaxane. In a specific embodiment for seed treatment, component II is triticonazole, component III is fludioxonil and component IV is fluxapyroxad.

The compositions according to the invention are particularly important in the control of a multitude of phytopathogenic fungi on various cultivated plants, such as cereals, e.g. wheat, rye, barley, triticale, oats or rice; beet, e.g. sugar beet or fodder beet; fruits, such as pomes, stone fruits or soft fruits, e.g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; sweet leaf (also called *Stevia*); natural rubber plants or ornamental and forestry plants, such as flowers, shrubs, broad-leaved trees or evergreens, e.g. conifers; and on the plant propagation material, such as seeds, and the crop material of these plants.

Preferably, the inventive compositions are used for controlling a multitude of fungi on field crops, such as potatoes sugar beets, tobacco, wheat, rye, barley, oats, rice, corn, cotton, soybeans, rape, legumes, sunflowers, coffee or sugar cane; fruits; vines; ornamentals; or vegetables, such as cucumbers, tomatoes, beans or squashes.

The term "plant propagation material" is to be understood to denote all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil. These young plants may also be protected before transplantation by a total or partial treatment by immersion or pouring.

Preferably, treatment of plant propagation materials with the components of the inventive compositions and the inventive compositions, respectively, is used for controlling a multitude of fungi on cereals, such as wheat, rye, barley and oats; rice, corn, cotton and soybeans.

The term "cultivated plants" is to be understood as including plants which have been modified by breeding, mutagenesis or genetic engineering including but not limiting to agricultural biotech products on the market or in development (cf. http://cera-gmc.org/, see GM crop database therein). Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-translational modification of protein (s), oligo- or polypeptides e.g. by glycosylation or polymer additions such as prenylated, acetylated or farnesylated moieties or PEG moieties.

Plants that have been modified by breeding, mutagenesis or genetic engineering, e.g. have been rendered tolerant to applications of specific classes of herbicides, such as auxin herbicides such as dicamba or 2,4-D; bleacher herbicides such as hydroxylphenylpyruvate dioxygenase (HPPD) inhibitors or phytoene desaturase (PDS) inhibitors; acetolactate synthase (ALS) inhibitors such as sulfonyl ureas or imidazolinones; enolpyruvylshikimate-3-phosphate synthase (EPSPS) inhibitors, such as glyphosate; glutamine synthetase (GS) inhibitors such as glufosinate; protoporphyrinogen-IX oxidase inhibitors; lipid biosynthesis inhibitors such as acetyl CoA carboxylase (ACCase) inhibitors; or oxynil (i. e. bromoxynil or ioxynil) herbicides as a result of conventional methods of breeding or genetic engineering. Furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors. These herbicide resistance technologies are e.g. described in Pest Managem. Sci. 61, 2005, 246; 61, 2005, 258; 61, 2005, 277; 61, 2005, 269; 61, 2005, 286; 64, 2008, 326; 64, 2008, 332; Weed Sci. 57, 2009, 108; Austral. J. Agricult. Res. 58, 2007, 708; Science 316, 2007, 1185; and references quoted therein. Several cultivated plants have been rendered tolerant to herbicides by conventional methods of breeding (mutagenesis), e.g. Clearfield® summer rape (Canola, BASF SE, Germany) being tolerant to imidazolinones, e.g. imazamox, or ExpressSun® sunflowers (DuPont, USA) being tolerant to sulfonyl ureas, e.g. tribenuron. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.), Cultivance® (imidazolinone tolerant, BASF SE, Germany) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as 5-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, e.g. *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e.g. WO 02/015701). Further examples of such toxins or genetically modified plants capable of synthesizing such toxins are disclosed, e.g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e.g. in the publications mentioned above. These insecticidal proteins contained in the genetically modified plants impart to the plants producing these proteins tolerance to harmful pests from all taxonomic groups of athropods, especially to beetles (Coeloptera), two-winged insects (Diptera), and moths (Lepidoptera) and to nematodes (Nematoda). Genetically modified plants capable to synthesize one or more insecticidal proteins are, e.g., described in the publications mentioned above, and some of which are commercially available such as YieldGard® (corn cultivars producing the CryIAb toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e.g. Agrisure® CB) and Bt176 from Syngenta Seeds SAS, France, (corn cultivars producing the Cry1Ab toxin and PAT enzyme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the CryIF toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e.g. EP-A 392 225), plant disease resistance genes (e.g. potato cultivars, which express resistance genes acting against *Phytophthora infestans* derived from the mexican wild potato *Solanum bulbocastanum*) or T4-lysozym (e.g. potato cultivars capable of synthesizing these proteins with increased resistance against bacteria such as Erwin/a amylvora). The methods for producing such genetically modified plants are generally known to the person skilled in the art and are described, e.g. in the publications mentioned above.

Furthermore, plants are also covered that are by the use of recombinant DNA techniques capable to synthesize one or more proteins to increase the productivity (e.g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e.g. oil crops that produce health-promoting long-chain omega-3 fatty acids or unsaturated omega-9 fatty acids (e.g. Nexera® rape, DOW Agro Sciences, Canada).

Furthermore, plants are also covered that contain by the use of recombinant DNA techniques a modified amount of substances of content or new substances of content, specifically to improve raw material production, e.g. potatoes that produce increased amounts of amylopectin (e.g. Amflora® potato, BASF SE, Germany).

The compositions are particularly suitable for controlling the following plant diseases:

*Albugo* spp. (white rust) on ornamentals, vegetables (e.g. *A. candida*) and sunflowers (e.g. *A. tragopogonis*); *Alternaria* spp. (*Alternaria* leaf spot) on vegetables, rape (*A. brassicola* or *brassicae*), sugar beets (*A. tenuis*), fruits, rice, soybeans, potatoes (e.g. *A. solani* or *A. alternata*), tomatoes (e.g. *A. solani* or *A. alternata*) and wheat; *Aphanomyces* spp. on sugar beets and vegetables; *Ascochyta* spp. on cereals and vegetables, e.g. *A. tritici* (anthracnose) on wheat and *A. hordei* on barley; *Bipolaris* and *Drechslera* spp. (teleomorph: *Cochliobolus* spp.), e.g. Southern leaf blight (*D. maydis*) or Northern leaf blight (*B. zeicola*) on corn, e.g. spot blotch (*B. sorokiniana*) on cereals and e.g. *B. oryzae* on rice and turfs; *Blumeria* (formerly *Erysiphe*) *graminis* (powdery mildew) on cereals (e.g. on wheat or barley); *Botrytis cinerea* (teleomorph: *Botryotinia fuckeliana*: grey mold) on fruits and berries (e.g. strawberries), vegetables (e.g. lettuce, carrots, celery and cabbages), rape, flowers, vines, forestry plants and wheat; *Bremia lactucae* (downy mildew) on lettuce; *Ceratocystis* (syn. *Ophiostoma*) spp. (rot or wilt) on broad-leaved trees and evergreens, e.g. *C. ulmi* (Dutch elm disease) on elms; *Cercospora* spp. (*Cercospora* leaf spots) on corn (e.g. Gray leaf spot: *C. zeae-maydis*), rice, sugar beets (e.g. *C. beticola*), sugar cane, vegetables, coffee, soybeans (e.g. *C. sojina* or *C. kikuchii*) and rice; *Cladosporium* spp. on tomatoes (e.g. *C. fulvum*: leaf mold) and cereals, e.g. *C. herbarum* (black ear) on wheat; *Claviceps purpurea* (ergot) on cereals; *Cochloiobolus* (anamorph: *Helminthosporium* of *Bipolaris*) spp. (leaf spots) on corn (*C. carbonum*), cereals (e.g. *C. sativus*, anamorph: *B. sorokiniana*) and rice (e.g. *C. miyabeanus*, anamorph: *H. oryzae*); *Colletotrichum* (teleomorph: *Glomerella*) spp. (anthracnose) on cotton (e.g. *C. gossypii*), corn (e.g. *C. gramihicola*: Anthracnose stalk rot), soft fruits, potatoes (e.g. *C. coccodes*: black dot), beans (e.g. *C. lindemuthianum*) and soybeans (e.g. *C. truncatum* or *C. gloeosporioides*); *Corticium* spp., e.g. *C. sasakii* (sheath blight) on rice; *Corynespora cassiicola* (leaf spots) on soybeans and ornamentals; *Cycloconium* spp., e.g. *C. oleaginum* on olive trees; *Cylindrocarpon* spp. (e.g. fruit tree canker or young vine decline, teleomorph: *Nectria* or *Neonectria* spp.) on fruit trees, vines (e.g. *C. liriodendri*, teleomorph: *Neonectria liriodendri*: Black Foot Disease) and ornamentals; *Dematophora* (teleomorph: *Rosellimia*) *necatrix* (root and stem rot) on soybeans; *Diaporthe* spp., e.g. *D. phaseolorum* (damping off) on soybeans; *Drechslera* (syn. *Helminthosporium*, teleomorph: *Pyrenophora*) spp. on corn, cereals, such as barley (e.g. *D. teres*, net blotch) and wheat (e.g. *D. tritici-repentis*: tan spot), rice and turf; Esca (dieback, apoplexy) on vines, caused by *Formitiporia* (syn. *Phellinus*) *punctata*, *F. mediterranea*, *Phaeomoniella chlamydospora* (earlier *Phaeoacremonium chlamydosporum*), *Phaeoacremonium aleophilum* and/or *Botryosphaeria obtusa*; *Elsinoe* spp. on pome fruits (*E. pyre*), soft fruits (*E. veneta*: anthracnose) and vines (*E. ampelina*: anthracnose); *Entyloma oryzae* (leaf smut) on rice; *Epicoccum* spp. (black mold) on wheat; *Erysiphe* spp. (powdery mildew) on sugar beets (*E. betae*), vegetables (e.g. *E. pisi*), such as cucurbits (e.g. *E. cichoracearum*), cabbages, rape (e.g. *E. cruciferarum*); *Eutypa lata* (*Eutypa* canker or dieback, anamorph: *Cytosporina lata*, syn. *Libertella blepharis*) on fruit trees, vines and ornamental woods; *Exserohllum* (syn. *Helminthosporium*) spp. on corn (e.g. *E. turcicum*); *Fusarium* (teleomorph: *Gibberella*) spp. (wilt, root or stem rot) on various plants, such as *F. graminearum* or *F. culmorum* (root rot, scab or head blight) on cereals (e.g. wheat or barley), *F. oxysporum* on tomatoes, *F. solani* (f. sp.

glycines now syn. *F. virguliforme*) and *F. tucumaniae* and *F. brasiliense* each causing sudden death syndrome on soybeans and F verticilliodes on corn; *Gaeumannomyces graminis* (take-all) on cereals (e.g. wheat or barley) and corn; *Gibberella* spp. on cereals (e.g. *G. zeae*) and rice (e.g. *G. fujikuroi*: Bakanae disease); *Glomerella angulata* on vines, pome fruits and other plants and *G. gossypii* on cotton; Grainstaining complex on rice; *Guignardia bidwellii* (black rot) on vines; *Gymnosporangium* spp. on rosaceous plants and junipers, e.g. *G. sabinae* (rust) on pears; *Helminthosporium* spp. (syn. *Drechslera*, teleomorph: *Cochliobolus*) on corn, cereals and rice; *Hemileia* spp., e.g. *H. vastatriX* (coffee leaf rust) on coffee; *Isariopsis clavispora* (syn. *Cladosporium vitis*) on vines; *Macrophomina phaseolina* (syn. *phaseoli*) (root and stem rot) on soybeans and cotton; *Microdochium* (syn. *Fusarium*) *nivale* (pink snow mold) on cereals (e.g. wheat or barley); *Microsphaera diffusa* (powdery mildew) on soybeans; *Monilinia* spp., e.g. *M. taxa, M. fructicola* and *M. fructigena* (bloom and twig blight, brown rot) on stone fruits and other rosaceous plants; *Mycosphaerella* spp. on cereals, bananas, soft fruits and ground nuts, such as e.g. *M. graminicola* (anamorph: *Septoria tritici, Septoria* blotch) on wheat or *M. fijiensis* (black Sigatoka disease) on bananas; *Peronospora* spp. (downy mildew) on cabbage (e.g. *P. brassicae*), rape (e.g. *P. parasitica*), onions (e.g. *P. destructor*), tobacco (*P. tabacina*) and soybeans (e.g. *P. manshurica*); *Phakopsora pachyrhizi* and *P. meibomiae* (soybean rust) on soybeans; *Phialophora* spp. e.g. on vines (e.g. *P. tracheiphila* and *P. tetraspora*) and soybeans (e.g. *P. gregata*: stem rot); *Phoma lingam* (root and stem rot) on rape and cabbage and *P. betae* (root rot, leaf spot and damping-off) on sugar beets; *Phomopsis* spp. on sunflowers, vines (e.g. *P. viticola*: can and leaf spot) and soybeans (e.g. stem rot: *P. phaseoli*, teleomorph: *Diaporthe phaseolorum*); *Physoderma maydis* (brown spots) on corn; *Phytophthora* spp. (wilt, root, leaf, fruit and stem root) on various plants, such as paprika and cucurbits (e.g. *P. capsici*), soybeans (e.g. *P. megasperma*, syn. *P. sojae*), potatoes and tomatoes (e.g. *P. infestans* late blight) and broad-leaved trees (e.g. *P. ramorum*: sudden oak death); *Plasmodiophora brassicae* (club root) on cabbage, rape, radish and other plants; *Plasmopara* spp., e.g. *P. viticola* (grapevine downy mildew) on vines and *P. halstedii* on sunflowers; *Podosphaera* spp. (powdery mildew) on rosaceous plants, hop, pome and soft fruits, e.g. *P. leucotricha* on apples; *Polymyxa* spp., e.g. on cereals, such as barley and wheat (*P. graminis*) and sugar beets (*P. betae*) and thereby transmitted viral diseases; *Pseudocercosporella herpotrichoides* (eyespot, teleomorph: *Tapesia yallundae*) on cereals, e.g. wheat or barley; *Pseudoperonospora* (downy mildew) on various plants, e.g. *P. cubensis* on cucurbits or *P. humili* on hop; *Pseudopezicula tracheiphila* (red fire disease or 'rotbrenner', anamorph: *Phialophora*) on vines; *Puccinia* spp. (rusts) on various plants, e.g. *P. triticina* (brown or leaf rust), *P. striiformis* (stripe or yellow rust), *P. hordei* (dwarf rust), *P. graminis* (stem or black rust) or *P. recondita* (brown or leaf rust) on cereals, such as e.g. wheat, barley or rye, *P. kuehnii* (orange rust) on sugar cane and *P. asparagi* on asparagus; *Pyrenophora* (anamorph: *Drechslera*) *tritici-repentis* (tan spot) on wheat or *P. teres* (net blotch) on barley; *Pyricularia* spp., e.g. *P. oryzae* (teleomorph: *Magnaporthe grisea*, rice blast) on rice and *P. grisea* on turf and cereals; *Pythium* spp. (damping-off) on turf, rice, corn, wheat, cotton, rape, sunflowers, soybeans, sugar beets, vegetables and various other plants (e.g. *P. ultimum* or *P. aphanidermatum*); *Ramularia* spp., e.g. *R. collo-cygni* (*Ramularia* leaf spots, Physiological leaf spots) on barley and *R. beticola* on sugar beets; *Rhizoctonia* spp. on cotton, rice, potatoes, turf, corn, rape, potatoes, sugar beets, vegetables and various other plants, e.g. *R. solani* (root and stem rot) on soybeans, *R. solani* (sheath blight) on rice or *R. cerealis* (*Rhizoctonia* spring blight) on wheat or barley; *Rhizopus stolonifer* (black mold, soft rot) on strawberries, carrots, cabbage, vines and tomatoes; *Rhynchosporium secalis* (scald) on barley, rye and triticale; *Sarocladium oryzae* and *S. attenuatum* (sheath rot) on rice; *Sclerotinia* spp. (stem rot or white mold) on vegetables and field crops, such as rape, sunflowers (e.g. *S. sclerotiorum*) and soybeans (e.g. *S. rolfsii* or *S. sclerotiorum*); *Septona* spp. on various plants, e.g. *S. glycines* (brown spot) on soybeans, *S. tritici* (*Septoria* blotch) on wheat and *S.* (syn. *Stagonospora*) *nodorum* (*Stagonospora* blotch) on cereals; *Uncinula* (syn. *Erysiphe*) *necator* (powdery mildew, anamorph: *Oidium tuckeri*) on vines; *Setospaeria* spp. (leaf blight) on corn (e.g. *S. turcicum,* syn. *Helminthosporium turcicum*) and turf; *Sphacelotheca* spp. (smut) on corn, (e.g. *S. reiliana*: head smut), sorghum and sugar cane; *Sphaerotheca fuliginea* (powdery mildew) on cucurbits; *Spongospora subterranea* (powdery scab) on potatoes and thereby transmitted viral diseases; *Stagonospora* spp. on cereals, e.g. *S. nodorum* (*Stagonospora* blotch, teleomorph: *Leptosphaeria* [syn. *Phaeosphaeria*] *nodorum*) on wheat; *Synchytrium endobioticum* on potatoes (potato wart disease); *Taphrina* spp., e.g. *T. deformans* (leaf curl disease) on peaches and *T. pruni* (plum pocket) on plums; *Thielaviopsis* spp. (black root rot) on tobacco, pome fruits, vegetables, soybeans and cotton, e.g. *T. basicola* (syn. *Chalara elegans*); *Tilletia* spp. (common bunt or stinking smut) on cereals, such as e.g. *T. tritici* (syn. *T. caries*, wheat bunt) and *T. controversa* (dwarf bunt) on wheat; *Typhula incarnata* (grey snow mold) on barley or wheat; *Urocystis* spp., e.g. *U. occulta* (stem smut) on rye; *Uromyces* spp. (rust) on vegetables, such as beans (e.g. *U. appendiculatus*, syn. *U. phaseoli*) and sugar beets (e.g. *U. betae*); *Ustiliago* spp. (loose smut) on cereals (e.g. *U. nuda* and *U. avaenae*), corn (e.g. *U. maydis*: corn smut) and sugar cane; *Venturia* spp. (scab) on apples (e.g. *V. inaequalis*) and pears; and *Verticillium* spp. (wilt) on various plants, such as fruits and ornamentals, vines, soft fruits, vegetables and field crops, e.g. *V. dahliae* on strawberries, rape, potatoes and tomatoes.

The compositions are also suitable for controlling harmful fungi in the protection of stored products or harvest and in the protection of materials. The term "protection of materials" is to be understood to denote the protection of technical and non-living materials, such as adhesives, glues, wood, paper and paperboard, textiles, leather, paint dispersions, plastics, coiling lubricants, fiber or fabrics, against the infestation and destruction by harmful microorganisms, such as fungi and bacteria. As to the protection of wood and other materials, the particular attention is paid to the following harmful fungi: Ascomycetes such as *Ophiostoma* spp., *Ceratocystis* spp., *Aureobasidium pullulans, Scierophoma* spp., *Chaetomium* spp., *Humicola* spp., *Petriella* spp., *Trichurus* spp.; Basidiomycetes such as *Coniophora* spp., *Coriolus* spp., *Gloeophyllum* spp., *Lentinus* spp., *Pleurotus* spp., *Poria* spp., *Serpula* spp. and *Tyromyces* spp., Deuteromycetes such as *Aspergillus* spp., *Cladosporium* spp., *Penicillium* spp., *Trichorma* spp., *Alternaria* spp., *Paecilomyces* spp. and Zygomycetes such as *Mucor* spp., and in addition in the protection of stored products and harvest the following yeast fungi are worthy of note: *Candida* spp. and *Saccharomyces cerevisae*.

The method of treatment according to the invention can also be used in the field of protecting stored products or harvest against attack of fungi and microorganisms. According to the present invention, the term "stored products" is understood to denote natural substances of plant or animal origin and their processed forms, which have been taken from the natural life cycle and for which long-term protection is desired. Stored products of crop plant origin, such as plants or parts thereof, for example stalks, leafs, tubers, seeds, fruits or grains, can be protected in the freshly harvested state or in processed form, such as pre-dried, moistened, comminuted, ground, pressed or roasted, which process is also known as post-harvest treatment. Also falling under the definition of stored products is timber, whether in the form of crude timber, such as construction timber, electricity pylons and barriers, or in the form of finished articles, such as furniture or objects made from wood. Stored products of animal origin are hides, leather, furs, hairs and the like. The combinations according the present invention can prevent disadvantageous effects such as decay, discoloration or mold. Preferably "stored products" is understood to denote natural substances of plant origin and their processed forms, more preferably fruits and their processed forms, such as pomes, stone fruits, soft fruits and citrus fruits and their processed forms.

The compositions may be used for improving the health of a plant. The invention also relates to a method for improving plant health by treating a plant, its propagation material and/or the locus where the plant is growing or is to grow with an effective amount of the components of the inventive compositions or the inventive compositions, respectively.

The term "plant health" is to be understood to denote a condition of the plant and/or its products which is determined by several indicators alone or in combination with each other such as yield (e.g. increased biomass and/or increased content of valuable ingredients), plant vigor (e.g. improved plant growth and/or greener leaves ("greening effect")), quality (e.g. improved content or composition of certain ingredients) and tolerance to abiotic and/or biotic stress. The above identified indicators for the health condition of a plant may be interdependent or may result from each other.

The compounds of formula I can be present in different crystal modifications whose biological activity may differ. Compositions comprising such modifications of compounds I are likewise subject matter of the present invention.

The compositions are used by treating the fungi or the plants, plant propagation materials, such as seeds, soil, surfaces, materials or rooms to be protected from fungal attack with a fungicidally effective amount of the active substances. The application can be carried out both before and after the infection of the plants, plant propagation materials, such as seeds, soil, surfaces, materials or rooms by the fungi.

Plant propagation materials may be treated with the components of the inventive compositions and the inventive compositions, respectively, prophylactically either at or before planting or transplanting.

The invention also relates to agrochemical compositions comprising an auxiliary and the components of the respective inventive composition or the inventive composition, respectively.

An agrochemical composition comprises a fungicidally effective amount of the components of the inventive compositions or the inventive composition, respectively. The term "effective amount" denotes an amount of the composition or of the components, which is sufficient for controlling harmful fungi on cultivated plants or in the protection of materials and which does not result in a substantial damage to the treated plants. Such an amount can vary in a broad range and is dependent on various factors, such as the fungal species to be controlled, the treated cultivated plant or material, the climatic conditions and the specific compound I used.

The components of the inventive compositions or the inventive compositions, respectively, their N-oxides and salts can be converted into customary types of agrochemical compositions, e.g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Monograph No. 2, $6^{th}$ Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e.g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharides, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emusifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B—C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compound I on the target. Examples are surfactants, mineral or vegetable oils, and other auxilaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkyliso-thiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for composition types and their preparation are (wherein active substances denote the respective components (=active ingredients) of the inventive composition):

i) Water-Soluble Concentrates (SL, LS)
10-60 wt % active substances and 5-15 wt % wetting agent (e.g. alcohol alkoxylates) are dissolved in water and/or in a water-soluble solvent (e.g. alcohols) ad 100 wt %. The active substance dissolves upon dilution with water.

ii) Dispersible Concentrates (DC)
5-25 wt % active substances and 1-10 wt % dispersant (e.g. polyvinylpyrrolidone) are dissolved in organic solvent (e.g. cyclohexanone) ad 100 wt %. Dilution with water gives a dispersion.

iii) Emulsifiable Concentrates (EC)
15-70 wt % active substances and 5-10 wt % emulsifiers (e.g. calcium dodecylben-zenesulfonate and castor oil ethoxylate) are dissolved in water-insoluble organic solvent (e.g. aromatic hydrocarbon) ad 100 wt %. Dilution with water gives an emulsion.

iv) Emulsions (EW, EO, ES)
5-40 wt % active substances and 1-10 wt % emulsifiers (e.g. calcium dodecylben-zenesulfonate and castor oil ethoxylate) are dissolved in 20-40 wt % water-insoluble organic solvent (e.g. aromatic hydrocarbon). This mixture is introduced into water ad 100 wt % by means of an emulsifying machine and made into a homogeneous emulsion. Dilution with water gives an emulsion.

v) Suspensions (SC, OD, FS)
In an agitated ball mill, 20-60 wt % active substances are comminuted with addition of 2-10 wt % dispersants and wetting agents (e.g. sodium lignosulfonate and alcohol ethoxylate), 0.1-2 wt % thickener (e.g. xanthan gum) and ad water ad 100 wt % to give a fine active substance suspension. Dilution with water gives a stable suspension of the active substance. For FS type composition up to 40 wt % binder (e.g. polyvinylalcohol) is added.

vi) Water-Dispersible Granules and Water-Soluble Granules (WG, SG)
50-80 wt % active substances are ground finely with addition of dispersants and wetting agents (e.g. sodium lignosulfonate and alcohol ethoxylate) ad 100 wt % and prepared as water-dispersible or water-soluble granules by means of technical appliances (e.g. extrusion, spray tower, fluidized bed). Dilution with water gives a stable dispersion or solution of the active substance.

vii) Water-Dispersible Powders and Water-Soluble Powders (WP, SP, WS)
50-80 wt % active substances are ground in a rotor-stator mill with addition of 1-5 wt % dispersants (e.g. sodium lignosulfonate), 1-3 wt % wetting agents (e.g. alcohol ethoxylate) and solid carrier (e.g. silica gel) ad 100 wt %. Dilution with water gives a stable dispersion or solution of the active substance.

viii) Gel (GW, GF)
In an agitated ball mill, 5-25 wt % active substances are comminuted with addition of 3-10 wt % dispersants (e.g. sodium lignosulfonate), 1-5 wt % thickener (e.g. carboxymethylcellulose) and water ad 100 wt % to give a fine suspension of the active substance. Dilution with water gives a stable suspension of the active substance.

iv) Microemulsion (ME)
5-20 wt % active substances are added to 5-30 wt % organic solvent blend (e.g. fatty acid dimethylamide and cyclohexanone), 10-25 wt % surfactant blend (e.g. alcohol ethoxylate and arylphenol ethoxylate), and water ad 100 wt %. This mixture is stirred for 1 h to produce spontaneously a thermodynamically stable microemulsion.

iv) Microcapsules (CS)
An oil phase comprising 5-50 wt % active substances, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of a compound I according to the invention, 0-40 wt % water insoluble organic solvent (e.g. aromatic hydrocarbon), and an isocyanate monomer (e.g. diphenylmethene-4,4'-diisocyanatae) are dispersed into an aqueous solution of a protective colloid (e.g. polyvinyl alcohol). The addition of a polyamine (e.g. hexamethylenediamine) results in the formation of polyurea microcapsules. The monomers amount to 1-10 wt %. The wt % relate to the total CS composition.

ix) Dustable powders (DP, DS)

1-10 wt % active substances are ground finely and mixed intimately with solid carrier (e.g. finely divided kaolin) ad 100 wt %.

x) Granules (GR, FG)

0.5-30 wt % active substances are ground finely and associated with solid carrier (e.g. silicate) ad 100 wt %. Granulation is achieved by extrusion, spray-drying or fluidized bed.

xi) Ultra-low volume liquids (UL)

1-50 wt % active substances are dissolved in organic solvent (e.g. aromatic hydrocarbon) ad 100 wt %.

The compositions types i) to xi) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, and in particular between 0.5 and 75%, by weight of active substance. The active substances are employed in a purity of from 90% to 100%, preferably from 95% to 100% (according to NMR spectrum).

Solutions for seed treatment (LS), Suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. The compositions in question give, after two-to-tenfold dilution, active substance concentrations of from 0.01 to 60% by weight, preferably from 0.1 to 40%, in the ready-to-use preparations. Application can be carried out before or during sowing. Methods for applying compound I and compositions thereof, respectively, on to plant propagation material, especially seeds include dressing, coating, pelleting, dusting, soaking and in-furrow application methods of the propagation material. Preferably, compound I or the compositions thereof, respectively, are applied on to the plant propagation material by a method such that germination is not induced, e.g. by seed dressing, pelleting, coating and dusting.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, and in particular from 0.1 to 0.75 kg per ha. from 0.1 to 10 kg active ingredients per 100 kg of seed In treatment of plant propagation materials such as seeds, e.g. by dusting, coating or drenching seed, amounts of active substance of from 0.1 to 10 kg active substances per 100 kg of seed, in particular from 0.1 to 1000 g, preferably from 1 to 1000 g, more preferably from 1 to 100 g and most preferably from 5 to 100 g, per 100 kilogram of plant propagation material (preferably seeds) are generally required.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizer, or micronutrients, and further pesticides (e.g. herbicides, insecticides, fungicides, growth regulators, safeners) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of composition may be mixed by the user himself in a spray tank and further auxiliaries may be added, if appropriate.

In the compositions, the ratios of the components are sometimes advantageously chosen so as to produce a synergistic effect.

The term "synergstic effect" is understood to refer in particular to that defined by Colby's formula (Colby, S. R., "Calculating synergistic and antagonistic responses of herbicide combinations", Weeds, 15, pp. 20-22, 1967).

The term "synergistic effect" is also understood to refer to that defined by application of the Tammes method, (Tammes, P. M. L., "Isoboles, a graphic representation of synergism in pesticides", Netherl. J. Plant Pathol. 70, 1964).

The components can be used individually or already partially or completely mixed with one another to prepare the composition according to the invention. It is also possible for them to be packaged and used as combination such as a kit of parts.

The fungicidal action of the compositions according to the invention can be shown by the tests described below.

The active compounds, separately or jointly, are prepared as a stock solution comprising 25 mg of active compound which is made up to 10 ml using a mixture of acetone and/or DMSO and the emulsifier Uniperol® EL (wetting agent having an emulsifying and dispersing action based on ethoxylated alkylphenols) in a ratio by volume of solvent/emulsifier of 99:1. The mixture is then made up to 100 ml with water. This stock solution is diluted with the solvent/emulsifier/water mixture described to give the concentration of active compound stated below.

The visually determined percentages of infected leaf areas are converted into efficacies in % of the untreated control.

The efficacy (E) is calculated as follows using Abbot's formula:

$$E=(1-\alpha/\beta) \cdot 100$$

α corresponds to the fungicidal infection of the treated plants in % and
β corresponds to the fungicidal infection of the untreated (control) plants in %

An efficacy of 0 means that the infection level of the treated plants corresponds to that of the untreated control plants; an efficacy of 100 means that the treated plants were not infected.

The expected efficacies of active compound combinations were determined using Colby's formula (Colby, S. R. "Calculating synergistic and antagonistic responses of herbicide combinations", Weeds, 15, pp. 20-22, 1967) and compared with the observed efficacies.

Colby's formula: $E = x + y - x \cdot y/100$

E expected efficacy, expressed in % of the untreated control, when using the mixture of the active compounds A and B at the concentrations a and b
x efficacy, expressed in % of the untreated control, when using the active compound A at the concentration a
y efficacy, expressed in % of the untreated control, when using the active compound B at the concentration b.

Microtests

The active compounds were formulated separately as a stock solution having a concentration of 10000 ppm in dimethyl sulfoxide.

The product orysastrobin was used as commercial finished formulation and diluted with water to the stated concentration of the active compound.

The stock solutions were mixed according to the ratio, pipetted onto a micro titer plate (MTP) and diluted with water to the stated concentrations. A spore suspension of the respective pathogen in the respective nutrient medium was then added. The plates were placed in a water vapor-saturated chamber at a temperature of 18° C. Using an absorption photometer, the MTPs were measured at 405 nm 7 days after the inoculation.

The measured parameters were compared to the growth of the active compound-free control variant (100%) and the fungus-free and active compound-free blank value to determine the relative growth in % of the pathogens in the respective active compounds. These percentages were converted into efficacies.

The expected efficacies of active compound mixtures were determined using Colby's formula [R. S. Colby, "Calculating synergistic and antagonistic responses of herbicide combinations", Weeds 15, 20-22 (1967)] and compared with the observed efficacies.

I. Synthesis of Components I:

With due modification of the starting compounds, the procedures shown in the synthesis examples below were used to obtain further compounds I.

EXAMPLE 1

Preparation of 2-[4-(4-chloro-phenoxy)-2-trifluoromethyl-phenyl]-1-[1,2,4]triazol-1-yl-propan-2-ol (compound I-3)

Step 1: 4-Fluoro-2-(trifluoromethyl)-acetophenone (35 g, 170 mmol), 4-chlorophenol (21.8 g, 170 mmol), potassium carbonate (28.1 g, 203 mmol) and DMF (284 g, 300 ml) were stirred together at about 115° C. for about five hours. After cooling, the mixture was added to a brine solution and extracted three times with MTBE. The organic phases were combined, washed twice with 10% aqueous LiCl solution and dried. Evaporation of the solvents gave the intermediate 1-[4-(4-chloro-phenoxy)-2-trifluoromethyl-phenyl]-ethanone (51.4 g, 87%; HPLC $R_t$=3.721 min*(conditions A see below)).

Step 2: DMSO (154 g, 140 ml, 1.97 mol) was added to a mixture of sodium hydride (0.831 g, 33 mmol) in THF (53 g, 6 0 ml) and cooled to about 5° C. Trimethylsulf(ox)onium iodide (6.42 g, 31.5 mmol) in DMSO (80 ml) was then added dropwise and the mixture was stirred at about 5° C. for a further hour. The intermediate 1-[4-(4-chloro-phenoxy)-2-trifluoromethyl-phenyl]-ethanone (5.0 g, 14.3 mol) in DMSO (40 ml) was then added dropwise over a period of about five minutes. The mixture was then stirred for 15 min, quenched with saturated ammonium chloride solution (150 ml) and extracted three times with MTBE. The organic phases were combined, washed with water and dried. Evaporation of the solvent gave 2-[4-(4-chloro-phenoxy)-2-trifluoromethyl-phenyl]-2-methyl-oxirane as a yellow oil (4.4 g, 89%, HPLC $R_t$=3.839 min*(conditions A see below)).

Step 3: A mixture of 2-[4-(4-chloro-phenoxy)-2-trifluoromethyl-phenyl]-2-methyl-oxirane (1.92 g, 4.96 mmol), 1,2,4-triazole (1.715 g, 24.8 mmol), NaOH (0.496 g, 12.41 mmol) and N-methyl pyrrolidone (48 ml) was stirred at about 110° C. for about one hour, followed by further four hours at about 130° C. After cooling to room temperature, saturated ammonium chloride solution was added and the organic phases extracted three times with MTBE. The organic phases were combined, washed twice with 10% LiCl solution and dried. Evaporation of the solvents followed by precipitation from diisopropyl ether gave the final product 2-[4-(4-chloro-phenoxy)-2-trifluoromethyl-phenyl]-1-[1,2,4]triazol-1-yl-propan-2-ol as a white solid (1.55 g, 75%, m.p. 121-122° C., HPLC $R_t$=3.196 min*(conditions A see below)).

EXAMPLE 2

Preparation of 2-[4-(4-chloro-phenoxy)-2-trifluoromethyl-phenyl]-1-[1,2,4]triazol-1-yl-butan-2-ol (compound I-7)

Step 1: Bromine (29.6 g, 185 mmol) was added dropwise over three minutes to a solution of the 1-[4-(4-chloro-phenoxy)-2-trifluoromethyl-phenyl]ethanone intermediate of step 1 of example 1, (61.4 g, 185 mmol), in diethyl ether (700 ml). The mixture was stirred at room temperature for about 90 min, after which a mixture of ice-cold water (1 l) and saturated sodium bicarbonate solution (300 ml) was added slowly under stirring until pH 7 to 8 was reached. The organic phases were extracted twice with MTBE and washed with LiCl solution. Drying and evaporation of the solvents gave the intermediate 2-bromo-1-[4-(4-chloro-phenoxy)-2-trifluoromethyl-phenyl]-ethanone as a brown oil (76 g, 83%, HPLC $R_t$=3.196 min*(conditions A see below)).

Step 2: 1,2,4-Triazole (3.76 g, 53 mmol) was added slowly and portionwise to a mixture of sodium hydride (1.28 g, 53 mmol) in THF (150 ml), and the mixture stirred at room temperature for about 30 min. To this mixture the intermediate 2-bromo-1-[4-(4-chloro-phenoxy)-2-trifluoromethyl-phenyl]-ethanone (20.0 g, 40.7 mmol) in THF (100 ml) was added dropwise and stirred at room temperature for about 150 min. The reaction mixture was cooled to about 10° C. and added slowly to a mixture of ice-cold water and saturated ammonium chloride solution, and the organic components extracted three times with ethyl acetate. The organic phases were combined, dried and the solvents evaporated. Recrystallisation from diisopropyl ether gave the intermediate 1-[4-(4-chloro-phenoxy)-2-trifluoromethyl-phenyl]-2-[1,2,4]triazol-1-yl-ethanone as a white solid (14.5 g, 84%; HPLC R$_t$=3.225 min*(conditions A see below)).

Step 3: Magnesium bromide diethyl etherate (2.65 g, 10.3 mmol) was added to a solution of 1-[4-(4-chloro-phenoxy)-2-trifluoromethyl-phenyl]-2-[1,2,4]triazol-1-yl-ethanone (2.0 g, 5.1 mmol) in dichloromethane (DCM, 20 ml) and the mixture stirred at room temperature for 90 min. This mixture was then cooled to about –10° C. and ethylmagnesium bromide (10.3 ml of a 1M solution in THF, 10.3 mmol) was added dropwise. After stirring for about two hours, the mixture was allowed to warm to room temperature and was then quenched by addition of a saturated ammonium chloride solution. The organic components were extracted three times with DCM, the organic phases combined, washed again with saturated ammonium chloride solution, dried and the solvents evaporated. Addition of diisopropyl ether resulted in precipitation of the unreacted starting material, which was filtered off. The filtrate was then purified using reverse phase chromatography, to give the final product 2-[4-(4-chloro-phenoxy)-2-trifluoromethyl-phenyl]-1-[1,2,4]triazol-1-yl-butan-2-ol as a light brown coloured solid (130 mg, 5.8%; HPLC R$_t$=3.366 min*(conditions A see below); HPLC Rt=1.21 min, masse=412 **(conditions B see below).

EXAMPLE 3

Preparation of 1-[2-[4-(4-chlorophenoxy)-2-(trifluoromethyl)phenyl]-2-methoxy-propyl]-1,2,4-triazole (compound I-9)

To a solution of 2-[4-(4-chlorophenoxy)-2-(trifluoromethyl)phenyl]-1-(1,2,4-triazol-1-yl)propan-2-01(33.35 g, 83 mmol) in 400 mL of THF was added sodium hydride (2.54 g, 100.5 mmol) at room temperature. The reaction mixture was then stirred for 30 min followed by the addition of methyliodide (14.24 g, 100.3 mmol) and stirred at 90° C. for 2 hours. After addition of an aq. solution of sodium chloride, the mixture was extracted with dichloromethane, dried, evaporated. The crude residue was purified by recrystallization in heptane/ethyl acetate (1:2) to give the title compound as a colorless solid (34.0 g, 98%; HPLC-MS R$_t$=1.26 min; masse=412 **(conditions B see below)).

EXAMPLE 4

Preparation of 2-[4-(4-chlorophenoxy)-2-(trifluoromethyl)phenyl]-1-(1,2,4-triazol-1-yl)pent-3-yn-2-ol (compound I-14)

Step 1:
1-Bromo-4-fluoro-2-(trifluoromethyl)benzene (2.04 g, 15.9 mmol) was mixed with potassium carbonate (4.18 g) in dimethylformamide and the reaction mixture heated to 110° C. Then 4-chloro-phenol (3.68 g, 15.14 mmol) was added and the resulting mixture was stirred for 5 hours at 110° C. After cooling and a water/DCM extraction, the organic layers were washed with an aqueous solution of lithium chloride and then sodium hydroxide, dried, filtrated and evaporated to give 3.14 g of 1-bromo-4-(4-chlorophenoxy)-2-(trifluoromethyl)benzene as an oil. $^1$H-NMR (CDCl$_3$; 400 MHz) . . . (pμm)=6.80 (d, 1H); 6.95 (d, 2H); 7.35 (d, 2H); 7.55 (d, 1H); 7.80 (s, 1H).

Step 2:
To a solution of 1-bromo-4-(4-chlorophenoxy)-2-(trifluoromethyl)benzene (100.0 g, 0.28 mol, 1.0 eq.) in 500 mL of THF was added dropwise isopropyl magnesium chloride lithium chloride complex (284 mL, 1.3 M in THF) at room temperature and stirred for 2 hours. This mixture was then added dropwise to a solution of acetyl chloride (29.0 g, 0.37 mmol) in 500 mL of THF at room temperature. The resulting reaction mixture was then stirred for 150 min and quenched with a sat. solution of ammonium chloride. After a water/MTBE extraction, the organic solvents were dried and evaporated to give 96.6 g of 1-[4-(4-chlorophenoxy)-2-(trifluoromethyl)-phenyl]ethanone as yellowish oil. $^1$H-NMR (CDCl$_3$; 400 MHz) •• (pμm)=2.6 (s, 3H); 7.0 (d, 2H); 7.10 (d, 1H); 7.30 (s, 1H); 7.37 (d, 2H); 7.50 (d, 1H).

Step 3:
Bromine (29.6 g, 185 mmol) was added dropwise over three minutes to a solution of 1-[4-(4-chloro-phenoxy)-2-trifluoromethyl-phenyl]-ethanone (61.4 g, 185 mmol), in diethyl ether (700 ml). The mixture was stirred at room temperature for about 90 min, after which a mixture of ice-cold water (1 L) and saturated sodium bicarbonate solution (300 ml) was added slowly under stirring until pH 7 to 8 was reached. The organic phases were extracted twice with MTBE and washed with LiCl solution. Drying and evaporation of the solvents gave the intermediate 2-bromo-1 [4-(4-chloro-phenoxy)-2-trifluoromethyl-phenyl]-ethanone as a brown oil (76 g, 83%). $^1$H-NMR (CDCl$_3$; 400 MHz) •• (pμm)=4.35 (s, 2H); 7.0 (d, 2H); 7.12 (d, 1H); 7.34 (s, 1H); 7.38 (d, 2H); 7.55 (d, 1H).

Step 4:
1,2,4-Triazole (3.76 g, 53 mmol) was added slowly and portionwise to a mixture of sodium hydride (1.28 g, 53 mmol) in THF (150 ml), and the mixture stirred at room temperature for about 30 min. To this mixture 2-bromo-1-[4-(4-chloro-phenoxy)-2-trifluoromethyl-phenyl]-ethanone (20.0 g, 40.7 mmol) in THF (100 ml) was added dropwise and stirred at room temperature for about 150 min. The reaction mixture was cooled to about 10° C. and added slowly to a mixture of ice-cold water and saturated ammonium chloride solution, and the organic components extracted three times with ethyl acetate. The organic phases were combined, dried and the solvents evaporated. Recrystallization from diisopropyl ether gave the intermediate 1-[4-(4-chloro-phenoxy)-2-trifluoromethyl-phenyl]-2-[1,2,4]triazol-1-yl-ethanone as a white solid (14.5 g, 84%). $^1$H-NMR (CDCl$_3$; 400 MHz) •δ• (pμm)=5.42 (s, 2H); 7.05 (d, 2H); 7.15 (d, 1H); 7.38 (s, 1H); 7.42 (d, 2H); 7.60 (d, 1H); 8.0 (s, 1H); 8.25 (s, 1H).

Step 5:
1-[4-(4-chlorophenoxy)-2-(trifluoromethyl)phenyl]-2-(1,2,4-triazol-1-yl)ethanone (0.5 g, 1.31 mmol) was dissolved in THF (5.0 mL) with a solution of LaCl$_3$.2LiCl (2.4 mL, 0.6M in THF) and stirred for 30 min at room temperature. The resulting solution was added dropwise to 1-propynyl-magnesium bromide (1.5 mL, 0.5M in THF) at room temperature. After 30 min at room temperature, the resulting mixture was quenched with a 10% aqueous solution of HCl and extracted with MTBE. The organic phase was washed with brine, dried and evaporated to give after purification on reverse phase chromatography 2-[4-(4-chlorophenoxy)-2-(trifluoromethyl)phenyl]-1-(1,2,4-triazol-1-yl)pent-3-yn-2-ol as solid (25 mg, HPLC-MS R$_t$=1.21 min, masse= 422 **(conditions B see below), m.p=137° C.).

EXAMPLE 5

Preparation of 1-[2-[4-(4-chlorophenoxy)-2-(trifluoromethyl)phenyl]-2-methoxy-butyl]-1,2,4-triazole (compound I-13)

To a solution of 2-[4-(4-chlorophenoxy)-2-(trifluoromethyl)phenyl]-1-(1,2,4-triazol-1-yl)butan-2-ol(4.0 g, 9.71 mmol) in 20 mL of THF was added sodium hydride (294 mg, 11.64 mmol) at room temperature. The reaction mixture was then stirred for 30 min followed by the addition of methyliodide (1.67 g, 11.78 mmol) and stirred at room temperature for 10 hours. After addition of an aq. solution of sodium chloride, the mixture was extracted with dichloromethane, dried, evaporated. The crude residue was purified by flash chromatography on silica gel to give the title compound as a colorless oil (2.42 g, 54%; HPLC-MS $R_t$=1.32 min; masse=426 **(conditions B see below)).

EXAMPLE 6

Preparation of 2-[4-(4-chlorophenoxy)-2-(trifluoromethyl)phenyl]-3-methyl-1-(1,2,4-triazol-1-yl)butan-2-ol (compound I-5)

Step 1:
To a solution of 1-bromo-4-(4-chlorophenoxy)-2-(trifluoromethyl)benzene (450.0 g, 1.15 mol) in 500 mL of THF was added dropwise to isopropyl magnesium chloride lithium chloride complex (1.152 L, 1.3 M in THF) at room temperature and stirred for 1 hour. The reaction mixture was then added dropwise over 1.5 hours at 10° C. to a solution of isopropyl carbonyl chloride (187.9 g, 1.73 mol), LiCl (3.30 g, 0.08 mol), AlCl$_3$ (4.61 g, 0.03 mol), CuCl (3.42 g, 0.03 mol) in THF (4 L). After 1 hour at room temperature, the resulting mixture was quenched with an aqueous solution of ammonium chloride at 10° C. and extracted with MTBE. The organic phase was washed with an aqueous solution of ammoniac then ammonium chloride, dried and evaporated to give after distillation (b.p.=150-155° C., P=0.25 mbar) 1-[4-(4-chlorophenoxy)-2-(trifluoromethyl)phenyl]-2-methyl-propan-1-one as yellowish oil (227.0 g, 52%). $^1$H-NMR (CDCl$_3$; 400 MHz) •δ• (pµm)=1.20 (d, 6H); 3.20 (m, 1H); 7.0 (d, 2H); 7.10 (d, 1H); 7.34 (s, 1H); 7.38 (d, 2H); 7.41 (d, 1H).

Step 2:
DMSO (120 ml) was added to a mixture of sodium hydride (4.43 g, 175.24 mmol) in THF (130 ml) and cooled to about 5° C. Trimethylsulfonium iodide (34.97 g, 167.9 mmol) in DMSO (12 ml) was then added dropwise and the mixture was stirred at about 5° C. for a further hour. The intermediate 1-[4-(4-chlorophenoxy)-2-(trifluoromethyl)phenyl]-2-methyl-propan-1-one (25.0 g, 72.9 mmol) in DMSO (60 ml) was then added dropwise over a period of about five minutes. The mixture was then stirred overnight at room temperature, then quenched with saturated ammonium chloride solution and extracted three times with MTBE. The organic phases were combined, washed with an aqueous solution of ammonium chloride, filtrated and dried. Evaporation of the solvent gave after purification on silica gel 2-[4-(4-chlorophenoxy)-2-(trifluoromethyl)phenyl]-2-isopropyl-oxirane as a yellowish oil (24.2 g, 84%, HPLC-MS: $R_t$=1.540 min; masse=356 **(conditions B see below)).

Step 3:
To 2-[4-(4-chlorophenoxy)-2-(trifluoromethyl)phenyl]-2-isopropyl-oxirane (173.0 g, 0.41 mol) dissolved in Mmethyl-2-pyrrolidon (1 L) was added sodium hydroxide (41.2 g, 1.03 mol) and triazole (145.2 g, 2.06 mol) at room temperature. The mixture was then stirred for 12 hours at 125° C. A solution of ammonium chloride and ice water was then added, the mixture extracted with MTBE and washed with an aqueous solution of lithium chloride. The crude residue was purified by recrystallization (Heptane/MTBE, 1:1) to give 2-[4-(4-chlorophenoxy)-2-(trifluoromethyl)phenyl]-3-methyl-1-(1,2,4-triazol-1-yl)butan-2-ol as a colorless solid (110 g, m.p.=114° C.; HPLC-MS $R_t$=1,27 min; masse=426 **(conditions B see below)).

EXAMPLE 7

Preparation of 1-[4-(4-chlorophenoxy)-2-(trifluoromethyl)phenyl]-1-cyclopropyl-2-(1,2,4-triazol-1-yl)ethanol (compound I-4)

Step 1:
To a solution of 1-bromo-4-(4-chlorophenoxy)-2-(trifluoromethyl)benzene (70.0 g, 199 mmol, 1.0 eq.) in 700 mL of THF was added dropwise isopropyl magnesium chloride lithium chloride complex (199.1 mL, 1.3 M in THF) at room temperature and stirred for 2 hours. The reaction mixture was then added dropwise to a solution of cyclopropane carbonyl chloride (27.05 g, 258 mmol), LiCl (0.5 g, 11.9 mmol), AlCl$_3$ (0.79 g, 5.9 mmol), CuCl (0.59 g, 5.9 mmol) in THF (700 mL). After 30 min at room temperature, the resulting mixture was quenched with an aqueous solution of ammonium chloride at 10° C. and extracted with MTBE. The organic phase was washed with an aqueous solution of ammoniac, dried and evaporated to give [4-(4-chlorophenoxy)-2-(trifluoromethyl)phenyl]-cyclopropyl-methanone as a brownish oil (66.8 g). $^1$H-NMR (CDCl$_3$; 400 MHz) •δ• (pµm)=1.10 (m, 2H); 1.30 (m, 2H); 2.32 (m, 1H); 7.0 (d, 2H); 7.15 (d, 1H); 7.32 (s, 1H); 7.37 (d, 2H); 7.60 (d, 1H).

Step 2:
To a solution of sodium hydride (10.77 g, 448 mmol) in THF (750 mL) and dry DMSO (250 mL) was added under argon drop wise at 5° C. a solution of trimethylsulfonium iodide (87.62 g, 429 mmol) in dry DMSO (800 mL). The mixture was stirred 1 hour at 5° C. followed by a dropwise addition of [4-(4-chlorophenoxy)-2-(trifluoromethyl)phenyl]-cyclopropyl-methanone (66.5 g, 195 mmol) in DMSO (500 mL). The resulting mixture was then warmed to room temperature overnight and quenched with an aqueous solution of ammonium chloride and iced water, and then extracted with MTBE. The organic solvents were washed with water, dried and evaporated to give 2-[4-(4-chlorophenoxy)-2-(trifluoromethyl)phenyl]-2-cyclopropyl-oxirane as an oil (66.0 g). $^1$H-NMR (CDCl$_3$; 400 MHz) •• (pµm)=0.38-0.50 (m, 4H); 1.40 (m, 1H); 2.90-3.0 (dd, 2H); 6.90 (d, 2H); 7.15 (d, 1H); 7.29 (s, 1H); 7.35 (d, 2H); 7.50 (d, 1H).

Step 3:
To 2-[4-(4-chlorophenoxy)-2-(trifluoromethyl)phenyl]-2-cyclopropyl-oxirane (866.0 g, 186 mmol) dissolved in N-methyl-2-pyrrolidon (820 mL) was added sodium hydroxide (18.6 g, 465 mmol) and 1,2,4-triazole (64.2 g, 930 mmol) at room temperature. The mixture was then stirred for 12 hours at 125° C. A solution of ammonium chloride and ice water was then added, the mixture extracted with MTBE and washed with an aqueous solution of lithium chloride. The crude residue was purified by flash chromatography on silica gel to give 1-[4-(4-chlorophenoxy)-2-(trifluoromethyl)phenyl]-1-cyclopropyl-2-(1,2,4-triazol-1-yl)ethanol as an oil (64.5 g, HPLC-MS Rt=1.24 min; masse=424 **(conditions B see below)).

The further compounds I, in particular the following, have been prepared in an analogous manner:

compound I-11 1-[2-[4-(4-chlorophenoxy)-2-(trifluoromethyl)phenyl]-2-cyclopropyl-2-methoxy-ethyl]-1,2,4-triazole; HPLC** $R_t$(min): 1.31

* (conditions A): HPLC column: RP-18 column (Chromolith Speed ROD from Merck KgaA, Germany), 50 mm×4.6 mm with Eluent: acetonitrile+0.1% trifluoroacetic acid (TFA)/water+0.1% TFA (gradient from 5:95 to 95:5 in 5 min at 40° C., flow of 1.8 ml/min)

** (conditions B): HPLC methode Data for continued Table I:

Mobile Phase: A: Water+0.1% TFA, B: acetonitrile; Gradient: 5% B to 100% B in 1.5 min; Temperature: 60° C.; MS method: ESI positive; mass area (m/z): 10-700; Flow: 0.8 ml/min to 1.0 ml/min in 1.5 min; Column: Kinetex XB C18 1.7µ 50×2.1 mm; Apparatus: Shimadzu Nexera LC-30 LCMS-2020

EXAMPLE 8

Preparation of 2-[2-chloro-4-(4-chlorophenoxyl) phenyl]-1-(1,2,4-triazol-1-yl)pent-3-yn-2-ol (compound I-1)

The intermediate 1-[2-chloro-4-(4-chloro-phenoxy)-phenyl]-2-[1,2,4]triazol-1-yl-ethanone was prepared as described in WO 2010/0146114.

To a solution of the above-mentioned ethanone (75.5 g, 216.8 mmol) dissolved in THF (450 mL) was added a solution of LaCl3.2LiCl (395.9 mL, 0.6 M in THF) at room temperature and stirred for 1 hour. The resulting solution was added dropwise to 1-propynylmagnesium bromide (650.5 mL, 0.5M in THF) at room temperature. After 1 hour at room temperature, the resulting mixture was quenched with a 10% aqueous solution of HCl and extracted with MTBE. The organic phase was washed with brine, dried and evaporated. The crude compound was stirred in a solution of MTBE/diisopropylether and filtrated to eliminate the starting material. The mother liquors were evaporated and purified on silica gel to give the title compound as a beige solid (31.1 g, HPLC-MS$^2$ $R_t$=1.15 min, masse=388, m.p=137° C.).

Compound I-2: 1-[2-chloro-4-(4-chlorophenoxyl)phenyl]-1-cyclopropyl-2-(1,2,4-triazol-1-yl)ethanol HPLC$^2$ $R_t$ (min): 1.24; melting point: 110° C.

Compound I-10: 2-[2-chloro-4-(4-chlorophenoxyl)phenyl]-3,3-dimethyl-1-(1,2,4-triazol-1-yl)butan-2-ol: HPLC$^1$ $R_t$ (min): 3.480; HPLC$^2$ $R_t$ (min): 1.38

HPLC$^1$ column: RP-18 column (Chromolith Speed ROD from Merck KgaA, Germany), 50 mm×4.6 mm with Eluent: acetonitrile+0.1% trifluoroacetic acid (TFA)/water+0.1% TFA (gradient from 5:95 to 95:5 in 5 min at 40° C., flow of 1.8 ml/min)

HPLC$^2$ column: column (Kinetex XB C18 1.7 µm), 50 mm×2.1 mm with Eluent: acetonitrile+0.1% trifluoroacetic acid (TFA)/water; (gradient from 5:95 to 95:5 in 1.5 min at 60° C., flow of 1.8 ml/min)

The enantiomers of compound I-3 were isolated by preparative chromatography using the racemic mixture as starting material.
Preparative Method:
Column: 250×30 mm CHIRALPAK AD-H 5 mm;
Mobil phase: Carbon dioxide/Ethanol 83/17
Flow rate: 100 mL/min
Detection: UV 240 nm
Outlet pressure: 130 bar
Temperature: 25° C.
Analytical Method:
Column: 250×4.6 mm CHIRALPAK IA 5 pm;
Mobil phase: Heptane/Isopropanol 90/10 (v/v)
Flow rate: 1 mL/min
Detection: DAD 250 nm
Temperature: 25 C The first eluting enantiomer (analytical method) had a retention time of 11.1 min ([α]=−27.8°, 0.100 g/5 mL THF at 20° C.) while the second enantiomer had a retention time of 12.7 min ([α]=+22.9, C=0.080 g/5 mL M, THF at 20° C.). The first eluting enantiomer is the (R)-enantiomer of I-3. The second eluting enantiomer is the (S)-enantiomer of I-3.

Examples showing the activity of the inventive compositions:

The fungicidal activity of the inventive compositions is demonstrated by the following biological examples.
Microtest The active compounds were formulated separately as a stock solution having a concentration of 10000 ppm in dimethyl sulfoxide.

1. Activity Against Early Blight Caused by *Alternaria solani* (Alteso)

The stock solutions were mixed according to the ratio, pipetted onto a micro titer plate (MTP) and diluted with water to the stated concentrations. A spore suspension of *Alternaria solani* in an aqueous biomalt or yeast-bactopeptone-glycerine solution was then added. The plates were placed in a water vapor-saturated chamber at a temperature of 18° C. Using an absorption photometer, the MTPs were measured at 405 nm 7 days after the inoculation.

2. Activity Against the Late Blight Pathogen *Phytophthora infestans* in the Microtiter Test (Phytin)

The stock solutions were mixed according to the ratio, pipetted onto a micro titer plate (MTP) and diluted with water to the stated concentrations. A spore suspension of *Phytophtora infestans* containing a pea juice-based aqueous nutrient medium or DDC medium was then added. The plates were placed in a water vapor-saturated chamber at a temperature of 18° C. Using an absorption photometer, the MTPs were measured at 405 nm 7 days after the inoculation.

3. Activity Against Rice Blast *Pyriculana Olyzae* in the Microtiterplate Test (Pyrior)

The stock solutions were mixed according to the ratio, pipetted onto a micro titer plate (MTP) and diluted with water to the stated concentrations. A spore suspension of *Pyricularia oryzae* in an aqueous biomalt or yeast-bacto-peptone-glycerine solution was then added. The plates were placed in a water vapor-saturated chamber at a temperature of 18° C. Using an absorption photometer, the MTPs were measured at 405 nm 7 days after the inoculation.

4. Activity Against Leaf Blotch on Wheat Caused by *Septoria tritici* (Septtr)

The stock solutions were mixed according to the ratio, pipetted onto a micro titer plate (MTP) and diluted with water to the stated concentrations. A spore suspension of *Septoria tritici* in an aqueous biomalt or yeast-bactopeptone-glycerine solution was then added. The plates were placed in a water vapor-saturated chamber at a temperature of 18° C. Using an absorption photometer, the MTPs were measured at 405 nm 7 days after the inoculation.

The measured parameters were compared to the growth of the active compound-free control variant (100%) and the fungus-free and active compound-free blank value to determine the relative growth in % of the pathogens in the respective active compounds. These percentages were converted into efficacies.

The expected efficacies of active compound mixtures were determined using Colby's formula [R. S. Colby, "Calculating synergistic and antagonistic responses of herbicide combinations", Weeds 15, 20-22 (1967)] and compared with the observed efficacies.

Alteso

| Active compound/ active mixture | Concentration (ppm) | Observed efficacy |
|---|---|---|
| Solo product A | | |
| I-1 | 0.00025 | 4 |
| I-3 | 0.000016 | 0 |
| I-4 | 0.00025 | 7 |
| Solo product B | | |
| Triticonazol | 0.063 | 1 |
| Fludioxonil | 0.016 | 13 |
| Fluxapyroxad | 0.001 | 4 |

Alteso Mixture

| Active compound/ active mixture | Concentration (ppm) | Observed efficacy | Calculated efficacy according to Colby (%) | Synergism (%) |
|---|---|---|---|---|
| I-1 | 0.00025 | 38 | 18 | 20 |
| Triticonazol | 0.063 | | | |
| Fludioxonil | 0.016 | | | |
| I-3 | 0.000016 | 33 | 15 | 18 |
| Triticonazol | 0.063 | | | |
| Fludioxonil | 0.016 | | | |
| I-4 | 0.00025 | 44 | 24 | 20 |
| Triticonazol | 0.063 | | | |
| Fludioxonil | 0.016 | | | |
| Fluxapyroxad | 0.001 | | | |

Phytin

| Active compound/ active mixture | Concentration (ppm) | Observed efficacy |
|---|---|---|
| Solo product A | | |
| I-5 | 63 | 45 |
| Solo product B | | |
| Fluquinconazol | 4 | 0 |
| Triticonazol | 16 | 0 |
| Fludioxonil | 1 | 0 |
| Pyraclostrobin | 0.016 | 9 |

Phytin Mixture

| Active compound/ active mixture | Concentration (ppm) | Observed efficacy | Calculated efficacy according to Colby (%) | Synergism (%) |
|---|---|---|---|---|
| I-5 | 63 | 71 | 45 | 26 |
| Triticonazol | 16 | | | |
| Fludioxonil | 1 | | | |

Pyrior

| Active compound/ active mixture | Concentration (ppm) | Observed efficacy |
|---|---|---|
| Solo product A | | |
| I-1 | 0.016 | 0 |
| I-3 | 0.25 | 10 |
| I-5 | 0.063 | 9 |
| I-4 | 0.25 | 23 |
| | 0.063 | 0 |
| Solo product B | | |
| Fluquinconazol | 1 | 1 |
| Triticonazol | 4 | 59 |
| | 1 | 1 |
| Fludioxonil | 0.016 | 36 |
| Pyraclostrobin | 0.001 | 5 |
| Fluxapyroxad | 0.25 | 1 |

Pyrior Mixture

| Active compound/ active mixture | Concentration (ppm) | Observed efficacy | Calculated efficacy according to Colby (%) | Synergism (%) |
|---|---|---|---|---|
| I-1 | 0.016 | 31 | 1 | 30 |
| Triticonazol | 1 | | | |
| I-1 | 0.016 | 98 | 36 | 62 |
| Fludioxonil | 0.016 | | | |
| I-1 | 0.016 | 31 | 3 | 28 |
| Fluquinconazol | 1 | | | |
| I-1 | 0.016 | 99 | 36 | 63 |
| Triticonazol | 1 | | | |
| Fludioxonil | 0.016 | | | |
| I-1 | 0.016 | 100 | 37 | 63 |
| Triticonazol | 1 | | | |
| Fludioxonil | 0.016 | | | |
| Fluxapyroxad | 0.25 | | | |
| I-1 | 0.016 | 44 | 6 | 38 |
| Fluquinconazol | 1 | | | |
| Pyraclostrobin | 0.001 | | | |
| I-3 | 0.25 | 84 | 63 | 21 |
| Triticonazol | 4 | | | |
| I-5 | 0.063 | 85 | 62 | 23 |
| Triticonazol | 4 | | | |
| I-4 | 0.25 | 96 | 68 | 28 |
| Triticonazol | 4 | | | |
| I-4 | 0.063 | 83 | 38 | 45 |
| Triticonazol | 1 | | | |
| Fludioxonil | 0.016 | | | |
| Fluxapyroxad | 0.25 | | | |

Septtr

| Active compound/ active mixture | Concentration (ppm) | Observed efficacy |
|---|---|---|
| Solo product A | | |
| I-1 | 0.000063 | 17 |
| I-5 | 0.000016 | 13 |
| I-4 | 0.001 | 0 |
| Solo product B | | |
| Fluquinconazol | 0.004 | 0 |
| Triticonazol | 0.25 | 0 |

Septtr Mixture

| Active compound/ active mixture | Concentration (ppm) | Observed efficacy | Calculated efficacy according to Colby (%) | Synergism (%) |
|---|---|---|---|---|
| I-1 Fluquinconazol | 0.000063 0.004 | 40 | 17 | 23 |
| I-5 Triticonazol | 0.000016 0.25 | 38 | 13 | 25 |
| I-4 Triticonazol | 0.001 0.25 | 57 | 0 | 57 |

Microtest

The active compounds were formulated separately as a stock solution having a concentration of 10000 ppm in dimethyl sulfoxide.

Activity Against Leaf Blotch on Wheat Caused by *Septoria tritici* (Septtr)

The stock solutions were mixed according to the ratio, pipetted onto a micro titer plate (MTP) and diluted with water to the stated concentrations. A spore suspension of *Septoria tritici* in an aqueous biomalt or yeast-bactopeptone-glycerine solution was then added. The plates were placed in a water vapor-saturated chamber at a temperature of 18° C. Using an absorption photometer, the MTPs were measured at 405 nm 7 days after the inoculation.

The measured parameters were compared to the growth of the active compound-free control variant (100%) and the fungus-free and active compound-free blank value to determine the relative growth in % of the pathogens in the respective active compounds. These percentages were converted into efficacies.

The expected efficacies of active compound mixtures were determined using Colby's formula [R. S. Colby, "Calculating synergistic and antagonistic responses of herbicide combinations", Weeds 15, 20-22 (1967)] and compared with the observed efficacies.

Solo Product a

| Active compound/ active mixture | Concentration (ppm) | Observed efficacy |
|---|---|---|
| I-1 | 0.00063 | 17 |
|  | 0.000004 | 11 |
| I-3 | 0.000016 | 16 |
|  | 0.000004 | 14 |
|  | 0.000001 | 5 |
|  | 0.00000025 | 8 |
| I-5 | 0.000016 | 13 |
|  | 0.000001 | 10 |
|  | 0.00000025 | 5 |
| I-4 | 0.001 | 0 |
|  | 0.000063 | 8 |
|  | 0.000016 | 3 |
| I-3a | 0.00025 | 0 |

Solo Product B

| Active compound/ active mixture | Concentration (ppm) | Observed efficacy |
|---|---|---|
| Azoxystrobin | 0.063 | 56 |
| Bixafen | 0.063 | 54 |
| Boscalid | 0.25 | 52 |
| Carbendazim | 16 | 16 |
| Cyazofamid | 16 | 40 |
| Difenoconazol | 0.016 | 26 |
| Epoxiconazol | 0.016 | 16 |
| Fluoxastrobin | 0.25 | 59 |
| Fluxapyroxad | 0.063 | 56 |
| Mepiquat-cl | 63 | 16 |
| Metconazol | 0.016 | 24 |
| Nitenpyram | 63 | 10 |
| Prohexadion-Ca | 63 | 15 |
| Prothioconazol | 0.063 | 58 |
|  | 0.016 | 17 |
| Pyraclostrobin | 0.004 | 37 |
| Tebuconazol | 0.063 | 15 |
| Thiamethoxam | 1 | 57 |
|  | 0.25 | 18 |
|  | 0.063 | 11 |
| Trinexapac-ethyl | 4 | 13 |

2-Way-Mixture

| Active compound/ active mixture | Concentration (ppm) | Observed efficacy | Calculated efficacy according to Colby (%) | Synergism (%) |
|---|---|---|---|---|
| I-1 Bixafen | 0.000004 0.063 | 76 | 59 | 17 |
| I-1 Difenoconazol | 0.000063 0.016 | 79 | 38 | 41 |
| I-1 Fluxapyroxad | 0.000004 0.063 | 80 | 61 | 19 |
| I-1 Prothioconazol | 0.000063 0.063 | 91 | 65 | 26 |
| I-1 Prothioconazol | 0.000063 0.016 | 48 | 31 | 17 |
| I-3 Bixafen | 0.000004 0.063 | 79 | 60 | 19 |
| I-3 Bixafen | 0.000001 0.063 | 100 | 56 | 44 |
| I-3 Boscalid | 0.000001 0.25 | 96 | 54 | 42 |
| I-3 Fluxapyroxad | 0.000004 0.063 | 94 | 62 | 32 |
| I-3 Fluxapyroxad | 0.000001 0.063 | 92 | 58 | 34 |
| I-3 Mepiquat-cl | 0.000004 63 | 97 | 27 | 70 |
| I-3 Mepiquat-cl | 0.000001 63 | 98 | 19 | 79 |
| I-3 Nitenpyram | 0.000001 63 | 82 | 14 | 68 |
| I-3 Nitenpyram | 0.000004 63 | 90 | 23 | 67 |
| I-3 Prohexadion-Ca | 0.000004 63 | 61 | 27 | 34 |
| I-3 Prohexadion-Ca | 0.000001 63 | 49 | 19 | 30 |
| I-3 Prothioconazol | 0.000016 0.063 | 92 | 64 | 28 |
| I-3 Prothioconazol | 0.00001 0.063 | 95 | 60 | 35 |
| I-3 Prothioconazol | 0.00000025 0.063 | 96 | 61 | 35 |
| I-5 | 0.000016 | 85 | 63 | 22 |

-continued

| Active compound/ active mixture | Concentration (ppm) | Observed efficacy | Calculated efficacy according to Colby (%) | Synergism (%) |
|---|---|---|---|---|
| Prothioconazol | 0.063 | | | |
| I-5 | 0.000001 | 46 | 26 | 20 |
| Thiamethoxam | 0.25 | | | |
| I-4 | 0.001 | 89 | 26 | 63 |
| Difenoconazol | 0.016 | | | |
| I-4 | 0.001 | 40 | 16 | 24 |
| Epoxiconazol | 0.016 | | | |
| I-4 | 0.001 | 49 | 24 | 25 |
| Metconazol | 0.016 | | | |
| I-4 | 0.001 | 98 | 58 | 40 |
| Prothioconazol | 0.063 | | | |
| I-4 | 0.001 | 79 | 17 | 62 |
| Prothioconazol | 0.016 | | | |
| I-4 | 0.000063 | 84 | 61 | 23 |
| Prothioconazol | 0.063 | | | |
| I-4 | 0.000016 | 95 | 59 | 36 |
| Prothioconazol | 0.063 | | | |
| I-4 | 0.001 | 38 | 16 | 22 |
| Tebuconazol | 0.063 | | | |
| I-4 | 0.001 | 37 | 12 | 25 |
| Thiamethoxam | 0.063 | | | |
| I-3a | 0.00025 | 97 | 40 | 57 |
| Cyazofamid | 0.016 | | | |
| I-3a | 0.00025 | 36 | 17 | 19 |
| Prothioconazol | 0.016 | | | |
| I-3a | 0.00025 | 100 | 58 | 42 |
| Prothioconazol | 0.063 | | | |

Microtest

The active compounds were formulated separately as a stock solution having a concentration of 10000 ppm in dimethyl sulfoxide.

Activity Against Leaf Blotch on Wheat Caused by *Septoria tritici* (Septtr)

The stock solutions were mixed according to the ratio, pipetted onto a micro titer plate (MTP) and diluted with water to the stated concentrations. A spore suspension of *Septoria tritici* in an aqueous biomalt or yeast-bactopeptone-glycerine solution was then added. The plates were placed in a water vapor-saturated chamber at a temperature of 18° C. Using an absorption photometer, the MTPs were measured at 405 nm 7 days after the inoculation.

The measured parameters were compared to the growth of the active compound-free control variant (100%) and the fungus-free and active compound-free blank value to determine the relative growth in % of the pathogens in the respective active compounds. These percentages were converted into efficacies.

The expected efficacies of active compound mixtures were determined using Colby's formula [R. S. Colby, "Calculating synergistic and antagonistic responses of herbicide combinations", Weeds 15, 20-22 (1967)] and compared with the observed efficacies.

Solo Product a

| Active compound/ active mixture | Concentration (ppm) | Observed efficacy |
|---|---|---|
| I-3 | 0.004 | 54 |
| | 0.000016 | 16 |
| I-5 | 0.000016 | 13 |
| I-4 | 0.016 | 18 |
| | 0.001 | 0 |

Solo Product B

| Active compound/ active mixture | Concentration (ppm) | Observed efficacy |
|---|---|---|
| Azoxystrobin | 0.001 | 12 |
| Bixafen | 0.063 | 54 |
| Difenoconazol | 0.016 | 26 |
| Fluoxastrobin | 0.063 | 23 |
| Prothioconazol | 0.063 | 58 |
| | 0.016 | 17 |
| Pyraclostrobin | 0.004 | 37 |
| | 0.001 | 12 |
| | 0.00025 | 8 |
| | 0.000063 | 7 |
| Tebuconazol | 0.016 | 5 |

Mixtures

| Active compound/ active mixture | Concentration (ppm) | Observed efficacy | Calculated efficacy according to Colby (%) | Synergism (%) |
|---|---|---|---|---|
| Pyraclostrobin | 0.004 | | | |
| I-4 | 0.001 | 99 | 71 | 28 |
| Bixafen | 0.063 | | | |
| Pyraclostrobin | 0.004 | | | |
| I-3 | 0.004 | 89 | 64 | 25 |
| Prothioconazol | 0.016 | | | |
| Tebuconazol | 0.016 | | | |
| I-3 | 0.004 | 88 | 67 | 21 |
| Pyraclostrobin | 0.00025 | | | |
| Prothioconazol | 0.016 | | | |
| Tebuconazol | 0.016 | | | |
| I-5 | 0.000016 | 99 | 75 | 24 |
| Bixafen | 0.063 | | | |
| Pyraclostrobin | 0.004 | | | |
| I-4 | 0.001 | 99 | 71 | 28 |
| Bixafen | 0.063 | | | |
| Pyraclostrobin | 0.004 | | | |
| I-4 | 0.016 | 70 | 46 | 24 |
| Pyraclostrobin | 0.001 | | | |
| Difenoconazol | 0.016 | | | |

Microtest

The active compounds were formulated separately as a stock solution having a concentration of 10000 ppm in dimethyl sulfoxide.

Activity Against Rice Blast *Pyricularia oryzae* in the Microtiterplate Test (Pyrior)

The stock solutions were mixed according to the ratio, pipetted onto a micro titer plate (MTP) and diluted with water to the stated concentrations. A spore suspension of *Pyricularia oryzae* in an aqueous biomalt or yeast-bactopeptone-glycerine solution was then added. The plates were placed in a water vapor-saturated chamber at a temperature of 18° C. Using an absorption photometer, the MTPs were measured at 405 nm 7 days after the inoculation.

The measured parameters were compared to the growth of the active compound-free control variant (100%) and the fungus-free and active compound-free blank value to determine the relative growth in % of the pathogens in the respective active compounds. These percentages were converted into efficacies.

The expected efficacies of active compound mixtures were determined using Colby's formula [R. S. Colby, "Calculating synergistic and antagonistic responses of herbicide combinations", Weeds 15, 20-22 (1967)] and compared with the observed efficacies.

Solo Product a

| Active compound/ active mixture | Concentration (ppm) | Observed efficacy |
|---|---|---|
| I-1 | 0.063 | 11 |
|  | 0.016 | 0 |
|  | 0.001 | 3 |
| I-3 | 0.25 | 10 |
|  | 0.004 | 0 |
| I-5 | 0.063 | 9 |
|  | 0.016 | 0 |
|  | 0.004 | 0 |
|  | 0.001 | 5 |
| I-4 | 0.25 | 23 |
| I-3a | 1 | 47 |
|  | 0.25 | 3 |
|  | 0.063 | 4 |
|  | 0.016 | 6 |

Solo Product B

| Active compound/ active mixture | Concentration (ppm) | Observed efficacy |
|---|---|---|
| Azoxystrobin | 0.004 | 1 |
| Boscalid | 16 | 2 |
| Cyazofamid | 4 | 9 |
| Difenoconazol | 1 | 11 |
|  | 0.25 | 1 |
| Epoxiconazol | 0.25 | 4 |
|  | 0.063 | 0 |
| Fipronil | 16 | 8 |
|  | 4 | 1 |
| Fluoxastrobin | 0.063 | 73 |
|  | 0.016 | 8 |
| Iprovalicarb | 4 | 0 |
| Mepiquat-cl | 16 | 4 |
| Metconazol | 0.25 | 7 |
| Nitenpyram | 63 | 3 |
|  | 16 | 0 |
|  | 4 | 1 |
| Prohexadion-Ca | 63 | 3 |
| Prothioconazol | 4 | 23 |
|  | 1 | 13 |
| Pyraclostrobin | 0.004 | 59 |
|  | 0.001 | 5 |
|  | 0.00025 | 2 |
| Tebuconazol | 0.25 | 3 |
|  | 0.063 | 0 |
| Thiamethoxam | 1 | 56 |
|  | 0.25 | 11 |
|  | 0.016 | 3 |
| Trifloxystrobin | 0.016 | 26 |
|  | 0.004 | 11 |
| Trinexapac-ethyl | 63 | 81 |
|  | 16 | 21 |
|  | 4 | 5 |

2-Way-Mixture

| Active compound/ active mixture | Concentration (ppm) | Observed efficacy | Calculated efficacy according to Colby (%) | Synergism (%) |
|---|---|---|---|---|
| I-1 Fluoxastrobin | 0.063 0.016 | 36 | 18 | 18 |
| I-1 Prothioconazol | 0.004 4 | 53 | 25 | 28 |
| I-1 Tebuconazol | 0.016 0.25 | 27 | 3 | 24 |
| I-3 Epoxiconazol | 0.25 0.25 | 32 | 14 | 18 |
| I-3 Prothioconazol | 0.25 4 | 58 | 31 | 27 |
| I-3 Prothioconazol | 0.004 4 | 59 | 23 | 36 |
| I-5 Epoxiconazol | 0.063 0.25 | 38 | 13 | 25 |
| I-5 Prothioconazol | 0.063 4 | 59 | 30 | 29 |
| I-5 Prothioconazol | 0.004 4 | 55 | 23 | 32 |
| I-5 Prothioconazol | 0.001 4 | 61 | 27 | 34 |
| I-5 Prothioconazol | 0.016 4 | 61 | 23 | 38 |
| I-4 Cyazofamid | 0.25 4 | 89 | 30 | 59 |
| I-4 Difenoconazol | 0.25 1 | 61 | 32 | 29 |
| I-4 Epoxiconazol | 0.25 0.25 | 72 | 26 | 46 |
| I-4 Fluoxastrobin | 0.25 0.016 | 46 | 29 | 17 |
| I-4 Iprovalicarb | 0.25 4 | 56 | 23 | 33 |
| I-4 Prothioconazol | 0.25 4 | 69 | 41 | 28 |
| I-4 Prothioconazol | 0.25 1 | 63 | 33 | 30 |
| I-4 Pyraclostrobin | 0.25 0.001 | 57 | 27 | 30 |
| I-4 Tebuconazol | 0.25 0.25 | 68 | 25 | 43 |
| I-4 Thiamethoxam | 0.25 1 | 83 | 66 | 17 |
| I-4 Trifloxystrobin | 0.25 0.016 | 63 | 43 | 20 |
| I-4 Trifloxystrobin | 0.25 0.004 | 51 | 31 | 20 |
| I-3a Cyazofamid | 0.063 4 | 32 | 12 | 20 |
| I-3a Cyazofamid | 1 4 | 97 | 51 | 46 |
| I-3a Difenoconazol | 0.016 1 | 33 | 16 | 17 |
| I-3a Epoxiconazol | 0.25 0.25 | 25 | 7 | 18 |
| I-3a Metconazol | 0.063 0.25 | 32 | 10 | 22 |
| I-3a Prothioconazol | 0.25 1 | 36 | 15 | 21 |
| I-3a Prothioconazol | 0.063 4 | 58 | 26 | 32 |
| I-3a Prothioconazol | 0.25 4 | 53 | 26 | 27 |
| I-3a Tebuconazol | 0.25 0.25 | 31 | 6 | 25 |

Microtest

The active compounds were formulated separately as a stock solution having a concentration of 10000 ppm in dimethyl sulfoxide.

Activity Against Rice Blast *Pyriculana oryzae* in the Microtiterplate Test placed in a water vapor-saturated chamber at a temperature of 18° C. Using an absorption photometer, the MTPs were measured at 405 nm 7 days after the inoculation.

The measured parameters were compared to the growth of the active compound-free control variant (100%) and the fungus-free and active compound-free blank value to determine the relative growth in % of the pathogens in the respective active compounds. These percentages were converted into efficacies.

The expected efficacies of active compound mixtures were determined using Colby's formula [R. S. Colby, "Calculating synergistic and antagonistic responses of herbicide combinations", Weeds 15, 20-22 (1967)] and Compared with the Observed Efficacies.

Solo Product A

| Active compound/ active mixture | Concentration (ppm) | Observed efficacy |
|---|---|---|
| I-1 | 0.25 | 8 |
| I-3 | 1 | 37 |
| I-5 | 1 | 67 |
| I-4 | 1 | 47 |

Solo Product B

| Active compound/ active mixture | Concentration (ppm) | Observed efficacy |
|---|---|---|
| Bixafen | 0.063 | 2 |
|  | 0.016 | 2 |
| Chlorothalonil | 0.063 | 7 |
| Difenoconazol | 1 | 11 |
|  | 0.25 | 1 |
| Epoxiconazol | 0.25 | 4 |
|  | 0.063 | 0 |
| Fluoxastrobin | 0.016 | 8 |
|  | 0.004 | 3 |
| Isopyrazam | 0.004 | 1 |
| Mepiquat-cl | 4 | 1 |
|  | 1 | 2 |
| Metconazol | 1 | 58 |
| Prohexadion-Ca | 16 | 2 |
|  | 4 | 2 |
| Prothioconazol | 4 | 23 |
|  | 1 | 13 |
| Pyraclostrobin | 0.001 | 5 |
|  | 0.00025 | 2 |
| Tebuconazol | 0.25 | 3 |
|  | 0.063 | 0 |
| Trifloxystrobin | 0.016 | 26 |
|  | 0.004 | 11 |
| Trinexapac-ethyl | 16 | 21 |
|  | 4 | 5 |

Mixtures

| Active compound/ active mixture | Concentration (ppm) | Observed efficacy | Calculated efficacy according to Colby (%) | Synergism (%) |
|---|---|---|---|---|
| I-1 Pyraclostrobin Prothioconazol | 0.25 0.00025 1 | 90 | 21 | 69 |
| I-1 Pyraclostrobin Difenoconazol | 0.25 0.00025 0.25 | 27 | 10 | 17 |
| I-1 Epoxiconazol Metconazol | 0.25 0.063 1 | 98 | 61 | 37 |
| I-1 Prothioconazol Tebuconazol | 0.25 1 0.063 | 77 | 20 | 57 |
| I-1 Bixafen Prothioconazol | 0.25 0.016 1 | 86 | 21 | 65 |
| I-1 Pyraclostrobin Fluoxastrobin Prothioconazol | 0.25 0.00025 0.004 1 | 91 | 23 | 68 |
| I-1 Pyraclostrobin Prothioconazol Tebuconazol | 0.25 0.00025 1 0.063 | 91 | 21 | 70 |
| I-1 Pyraclostrobin Trifloxystrobin Prothioconazol | 0.25 0.00025 0.004 1 | 90 | 29 | 61 |
| I-1 Pyraclostrobin Prohexadion Trinexapac-ethyl | 0.25 0.00025 4 4 | 37 | 16 | 21 |
| I-1 Bixafen Prothioconazol Tebuconazol | 0.25 0.016 1 0.063 | 92 | 21 | 71 |
| I-1 Bixafen Pyraclostrobin Prothioconazol | 0.25 0.016 0.00025 1 | 82 | 23 | 59 |
| I-3 Pyraclostrobin Epoxiconazol | 1 0.001 0.25 | 77 | 43 | 34 |
| I-3 Pyraclostrobin Fluoxastrobin | 1 0.001 0.016 | 69 | 46 | 23 |
| I-3 Pyraclostrobin Prothioconazol | 1 0.001 4 | 89 | 54 | 35 |
| I-3 Pyraclostrobin Trifloxystrobin | 1 0.001 0.016 | 82 | 56 | 26 |
| I-3 Pyraclostrobin Difenoconazol | 1 0.001 1 | 70 | 47 | 23 |
| I-3 Epoxiconazol Chlorothalonil | 1 0.25 0.063 | 72 | 44 | 28 |
| I-3 Isopyrazam Epoxiconazol | 1 0.004 0.25 | 70 | 41 | 29 |
| I-3 Prothioconazol Tebuconazol | 1 4 0.25 | 86 | 53 | 33 |
| I-3 Bixafen Prothioconazol | 1 0.063 4 | 78 | 53 | 25 |
| I-3 Pyraclostrobin Fluoxastrobin Prothioconazol | 1 0.001 0.016 4 | 93 | 58 | 35 |
| I-3 Pyraclostrobin Prothioconazol Tebuconazol | 1 0.001 4 0.25 | 92 | 56 | 36 |
| I-3 Pyraclostrobin Trifloxystrobin Prothioconazol | 1 0.001 0.016 4 | 99 | 66 | 33 |

| Active compound/ active mixture | Concentration (ppm) | Observed efficacy | Calculated efficacy according to Colby (%) | Synergism (%) |
|---|---|---|---|---|
| I-3 Pyraclostrobin Prohexadion Trinexapac-ethyl | 1 0.001 16 16 | 100 | 54 | 46 |
| I-3 Bixafen Prothioconazol Tebuconazol | 1 0.063 4 0.25 | 86 | 54 | 32 |
| I-3 Bixafen Pyraclostrobin Prothioconazol | 1 0.063 0.001 4 | 86 | 55 | 31 |
| I-3 Bixafen Pyraclostrobin Tebuconazol | 1 0.063 0.001 0.25 | 73 | 43 | 30 |
| I-5 Pyraclostrobin Difenoconazol | 1 0.001 1 | 93 | 72 | 21 |
| I-5 Isopyrazam Epoxiconazol | 1 0.004 0.25 | 89 | 69 | 20 |
| I-5 Prohexadion Mepiquat-cl | 1 16 4 | 90 | 68 | 22 |
| I-5 Bixafen Prothioconazol | 1 0.063 4 | 94 | 75 | 19 |
| I-5 Bixafen Pyraclostrobin | 1 0.063 0.001 | 97 | 69 | 28 |
| I-5 Pyraclostrobin Fluoxastrobin Prothioconazol | 1 0.001 0.016 4 | 100 | 78 | 22 |
| I-5 Pyraclostrobin Prothioconazol Tebuconazol | 1 0.001 4 0.25 | 100 | 77 | 23 |
| I-5 Pyraclostrobin Trifloxystrobin Prothioconazol | 1 0.001 0.016 4 | 100 | 82 | 18 |
| I-5 Pyraclostrobin Prohexadion Trinexapac-ethyl | 1 0.001 16 16 | 100 | 76 | 24 |
| I-5 Bixafen Pyraclostrobin Tebuconazol | 1 0.063 0.001 0.25 | 90 | 70 | 20 |
| I-4 Pyraclostrobin Epoxiconazol | 1 0.001 0.25 | 75 | 52 | 23 |
| I-4 Pyraclostrobin Prothioconazol | 1 0.001 4 | 96 | 61 | 35 |
| I-4 Pyraclostrobin Trifloxystrobin | 1 0.001 0.016 | 90 | 63 | 27 |
| I-4 Isopyrazam Epoxiconazol | 1 0.004 0.25 | 83 | 49 | 34 |
| I-4 Prothioconazol Tebuconazol | 1 4 0.25 | 96 | 60 | 36 |
| I-4 Bixafen Prothioconazol | 1 0.063 4 | 84 | 60 | 24 |
| I-4 Pyraclostrobin Fluoxastrobin Prothioconazol | 1 0.001 0.016 4 | 99 | 64 | 35 |
| I-4 Pyraclostrobin Prothioconazol Tebuconazol | 1 0.001 4 0.25 | 97 | 62 | 35 |
| I-4 Pyraclostrobin Trifloxystrobin Prothioconazol | 1 0.001 0.016 4 | 100 | 71 | 29 |
| I-4 Pyraclostrobin Prohexadion Trinexapac-ethyl | 1 0.001 16 16 | 100 | 61 | 39 |
| I-4 Bixafen Prothioconazol Tebuconazol | 1 0.063 4 0.25 | 89 | 61 | 28 |
| I-4 Bixafen Pyraclostrobin Prothioconazol | 1 0.063 0.001 4 | 97 | 62 | 35 |
| I-4 Bixafen Pyraclostrobin Tebuconazol | 1 0.063 0.001 0.25 | 86 | 52 | 34 |

Microtest

The active compounds were formulated separately as a stock solution having a concentration of 10000 ppm in dimethyl sulfoxide.

Activity Against the Late Blight Pathogen *Phytophthora infestans* in the Microtiter Test (Phytin)

The stock solutions were mixed according to the ratio, pipetted onto a micro titer plate (MTP) and diluted with water to the stated concentrations. A spore suspension of *Phytophtora infestans* containing a pea juice-based aqueous nutrient medium or DDC medium was then added. The plates were placed in a water vapor-saturated chamber at a temperature of 18° C. Using an absorption photometer, the MTPs were measured at 405 nm 7 days after the inoculation.

The measured parameters were compared to the growth of the active compound-free control variant (100%) and the fungus-free and active compound-free blank value to determine the relative growth in % of the pathogens in the respective active compounds. These percentages were converted into efficacies. The expected efficacies of active compound mixtures were determined using Colby's formula [R. S. Colby, "Calculating synergistic and antagonistic responses of herbicide combinations", Weeds 15, 20-22 (1967)] and compared with the observed efficacies.

Solo Product a

| Active compound/ active mixture | Concentration (ppm) | Observed efficacy |
|---|---|---|
| I-1 | 16 | 0 |
| I-3 | 16 | 4 |
|  | 4 | 4 |
| I-5 | 63 | 45 |
|  | 16 | 2 |

Solo Product B (continued)

| Active compound/ active mixture | Concentration (ppm) | Observed efficacy |
|---|---|---|
| I-4 | 16 | 9 |
|  | 4 | 3 |

Solo Product B

| Active compound/ active mixture | Concentration (ppm) | Observed efficacy |
|---|---|---|
| Ametoctradin | 1 | 75 |
|  | 0.25 | 19 |
|  | 0.063 | 2 |
| Azoxystrobin | 0.016 | 2 |
| Chlorothalonil | 0.016 | 2 |
| Cyazofamid | 0.004 | 8 |
| Epoxiconazol | 0.063 | 1 |
| Fipronil | 1 | 4 |
| Fluoxastrobin | 0.25 | 73 |
|  | 0.063 | 16 |
|  | 0.016 | 4 |
| Iprovalicarb | 0.25 | 19 |
| Isopyrazam | 16 | 23 |
| Mepiquat-cl | 4 | 5 |
| Metconazol | 0.004 | 2 |
| Prothioconazol | 16 | 35 |
|  | 4 | 12 |
|  | 1 | 4 |
|  | 0.25 | 2 |
| Pyraclostrobin | 0.063 | 34 |
| Tebuconazol | 0.016 | 1 |
| Thiamethoxam | 4 | 2 |
|  | 1 | 1 |
| Trifloxystrobin | 0.25 | 8 |
|  | 0.063 | 3 |

2-Way-Mixture

| Active compound/ active mixture | Concentration (ppm) | Observed efficacy | Calculated efficacy according to Colby (%) | Synergism (%) |
|---|---|---|---|---|
| I-1 Ametoctradin | 16 0.25 | 40 | 19 | 21 |
| I-1 Cyazofamid | 16 0.004 | 35 | 8 | 27 |
| I-1 Fipronil | 16 1 | 27 | 4 | 23 |
| I-1 Isopyrazam | 16 16 | 44 | 23 | 21 |
| I-1 Prothioconazol | 16 4 | 54 | 12 | 42 |
| I-1 Prothioconazol | 16 16 | 68 | 35 | 33 |

| Active compound/ active mixture | Concentration (ppm) | Mixture | Observed efficacy | Calculated efficacy according to Colby (%) | Synergism (%) |
|---|---|---|---|---|---|
| I-3 Iprovalicarb | 16 0.25 | 63:1 | 70 | 22 | 48 |
| I-3 Iprovalicarb | 4 0.25 | 16:1 | 42 | 22 | 20 |

| Active compound/ active mixture | Concentration (ppm) | Observed efficacy | Calculated efficacy according to Colby (%) | Synergism (%) |
|---|---|---|---|---|
| I-5 Ametoctradin | 63 0.25 | 81 | 55 | 26 |
| I-5 Ametoctradin | 16 1 | 97 | 76 | 21 |
| I-5 Ametoctradin | 16 0.25 | 99 | 21 | 78 |
| I-5 Azoxystrobin | 16 0.016 | 32 | 4 | 28 |
| I-5 Chlorothalonil | 16 0.016 | 21 | 4 | 17 |
| I-5 Cyazofamid | 16 0.004 | 37 | 10 | 27 |
| I-5 Epoxiconazol | 16 0.063 | 21 | 3 | 18 |
| I-5 Fipronil | 16 1 | 26 | 5 | 21 |
| I-5 Fluoxastrobin | 16 0.063 | 42 | 17 | 25 |
| I-5 Fluoxastrobin | 16 0.016 | 34 | 6 | 28 |
| I-5 Iprovalicarb | 16 0.25 | 45 | 21 | 24 |
| I-5 Iprovalicarb | 63 0.25 | 96 | 55 | 41 |
| I-5 Mepiquat-cl | 16 4 | 26 | 6 | 20 |
| I-5 Metconazol | 16 0.004 | 21 | 4 | 17 |
| I-5 Prothioconazol | 16 1 | 27 | 6 | 21 |
| I-5 Prothioconazol | 16 0.25 | 22 | 4 | 18 |
| I-5 Tebuconazol | 16 0.016 | 22 | 3 | 19 |
| I-5 Thiamethoxam | 16 1 | 31 | 3 | 28 |
| I-5 Thiamethoxam | 16 4 | 24 | 4 | 20 |
| I-5 Trifloxystrobin | 16 0.063 | 31 | 5 | 26 |
| I-5 Trifloxystrobin | 16 0.25 | 33 | 10 | 23 |
| I-4 Ametoctradin | 16 0.25 | 98 | 26 | 72 |
| I-4 Ametoctradin | 16 1 | 99 | 77 | 22 |
| I-4 Fluoxastrobin | 16 0.25 | 96 | 75 | 21 |
| I-4 Iprovalicarb | 16 0.25 | 63 | 26 | 37 |
| I-4 Prothioconazol | 16 16 | 94 | 40 | 54 |
| I-4 Prothioconazol | 4 16 | 66 | 37 | 29 |
| I-4 Pyraclostrobin | 16 0.063 | 85 | 40 | 45 |

Microtest

The active compounds were formulated separately as a stock solution having a concentration of 10000 ppm in dimethyl sulfoxide.

Activity Against the Late Blight Pathogen *Phytophthora infestans* in the Microtiter Test (Phytin)

The stock solutions were mixed according to the ratio, pipetted onto a micro titer plate (MTP) and diluted with water to the stated concentrations. A spore suspension of *Phytophtora infestans* containing a pea juice-based aqueous nutrient medium or DDC medium was then added. The plates were placed in a water vapor-saturated chamber at a temperature of 18° C. Using an absorption photometer, the MTPs were measured at 405 nm 7 days after the inoculation.

The measured parameters were compared to the growth of the active compound-free control variant (100%) and the fungus-free and active compound-free blank value to determine the relative growth in % of the pathogens in the respective active compounds.

These percentages were converted into efficacies. The expected efficacies of active compound mixtures were determined using Colby's formula [R. S. Colby, "Calculating synergistic and antagonistic responses of herbicide combinations", Weeds 15, 20-22 (1967)] and compared with the observed efficacies.

Solo Product A

| Active compound/ active mixture | Concentration (ppm) | Observed efficacy |
|---|---|---|
| I-4 | 16 | 9 |

Solo Product B

| Active compound/ active mixture | Concentration (ppm) | Observed efficacy |
|---|---|---|
| Bixafen | 1 | 25 |
| Carbendazim | 4 | 24 |
| Difenoconazol | 4 | 30 |
| Epoxiconazol | 4 | 27 |
| Prothioconazol | 16 | 35 |
| Pyraclostrobin | 0.063 | 34 |
| Tebuconazol | 1 | 25 |
| Trifloxystrobin | 1 | 37 |

Mixtures

| Active compound/ active mixture | Concentration (ppm) | Observed efficacy | Calculated efficacy according to Colby (%) | Synergism (%) |
|---|---|---|---|---|
| I-4 | 16 | 86 | 56 | 30 |
| Pyraclostrobin | 0.063 | | | |
| Epoxiconazol | 4 | | | |
| I-4 | 16 | 90 | 61 | 29 |
| Pyraclostrobin | 0.063 | | | |
| Prothioconazol | 16 | | | |
| I-4 | 16 | 94 | 62 | 32 |
| Pyraclostrobin | 0.063 | | | |
| Trifloxystrobin | 1 | | | |
| I-4 | 16 | 81 | 55 | 26 |
| Pyraclostrobin | 0.063 | | | |
| Carbendazim | 4 | | | |
| I-4 | 16 | 94 | 58 | 36 |
| Pyraclostrobin | 0.063 | | | |
| Difenoconazol | 4 | | | |
| I-4 | 16 | 95 | 56 | 39 |
| Prothioconazol | 16 | | | |
| Tebuconazol | 1 | | | |
| I-4 | 16 | 74 | 56 | 18 |
| Bixafen | 1 | | | |
| Prothioconazol | 16 | | | |
| I-4 | 16 | 78 | 55 | 23 |
| Bixafen | 1 | | | |
| Pyraclostrobin | 0.063 | | | |
| I-4 | 16 | 90 | 71 | 19 |
| Pyraclostrobin | 0.063 | | | |
| Prothioconazol | 16 | | | |
| Tebuconazol | 1 | | | |
| I-4 | 16 | 98 | 75 | 23 |
| Pyraclostrobin | 0.063 | | | |
| Trifloxystrobin | 1 | | | |
| Prothioconazol | 16 | | | |
| I-4 | 16 | 86 | 67 | 19 |
| Bixafen | 1 | | | |
| Prothioconazol | 16 | | | |
| Tebuconazol | 1 | | | |
| I-4 | 16 | 98 | 71 | 27 |
| Bixafen | 1 | | | |
| Pyraclostrobin | 0.063 | | | |
| Prothioconazol | 16 | | | |

Microtest

The active compounds were formulated separately as a stock solution having a concentration of 10000 ppm in dimethyl sulfoxide.

Activity Against Wheat Leaf Spots Caused by *Leptosphaeria nodorum* (Leptno)

The stock solutions were mixed according to the ratio, pipetted onto a micro titer plate (MTP) and diluted with water to the stated concentrations. A spore suspension of *Leptosphaeria nodorum* in an aqueous biomalt or yeast-bactopeptone-glycerine solution was then added. The plates were placed in a water vapor-saturated chamber at a temperature of 18° C. Using an absorption photometer, the MTPs were measured at 405 nm 7 days after the inoculation.

The measured parameters were compared to the growth of the active compound-free control variant (100%) and the fungus-free and active compound-free blank value to determine the relative growth in % of the pathogens in the respective active compounds.

These percentages were converted into efficacies. The expected efficacies of active compound mixtures were determined using Colby's formula [R. S. Colby, "Calculating synergistic and antagonistic responses of herbicide combinations", Weeds 15, 20-22 (1967)] and compared with the observed efficacies.

Solo Product A

| Active compound/ active mixture | Concentration (ppm) | Observed efficacy |
|---|---|---|
| I-1 | 0.000063 | 12 |
| I-3 | 0.000063 | 26 |
| I-5 | 0.063 | 20 |
|  | 0.001 | 9 |
| I-3a | 0.004 | 2 |
|  | 0.001 | 3 |

Solo Product B

| Active compound/ active mixture | Concentration (ppm) | Observed efficacy |
|---|---|---|
| Azoxystrobin | 0.063 | 42 |
| Bixafen | 0.25 | 19 |
| Boscalid | 4 | 23 |
| Chlorothalonil | 1 | 28 |
| Difenoconazol | 0.016 | 29 |

-continued

| Active compound/active mixture | Concentration (ppm) | Observed efficacy | Calculated efficacy according to Colby (%) | Synergism (%) |
|---|---|---|---|---|
| Epoxiconazol | 0.063 | 43 | | |
| Iprovalicarb | 16 | 19 | | |
| Mepiquat-cl | 63 | 28 | | |
| Metconazol | 0.063 | 53 | | |
| Nitenpyram | 63 | 23 | | |
| Prothioconazol | 1 | 43 | | |
| Pyraclostrobin | 0.016 | 24 | | |
| Tebuconazol | 0.25 | 43 | | |
| Thiamethoxam | 4 | 51 | | |
| | 1 | 22 | | |
| Trifloxystrobin | 0.063 | 39 | | |
| Trinexapac-ethyl | 63 | 17 | | |

| Active compound/active mixture | Concentration (ppm) | Observed efficacy | Calculated efficacy according to Colby (%) | Synergism (%) |
|---|---|---|---|---|
| I-1 Chlorothalonil | 0.000063 1 | 61 | 37 | 24 |
| I-3 Pyraclostrobin | 0.000063 0.016 | 68 | 44 | 24 |
| I-5 Chlorothalonil | 0.001 1 | 100 | 35 | 65 |
| I-5 Pyraclostrobin | 0.063 0.016 | 60 | 40 | 20 |
| I-3a Azoxystrobin | 0.004 0.063 | 63 | 42 | 21 |
| I-3a Bixafen | 0.004 0.25 | 45 | 20 | 25 |
| I-3a Boscalid | 0.004 4 | 53 | 24 | 29 |
| I-3a Difenoconazol | 0.004 0.016 | 58 | 30 | 28 |
| I-3a Epoxiconazol | 0.004 0.063 | 73 | 44 | 29 |
| I-3a Iprovalicarb | 0.004 16 | 39 | 20 | 19 |
| I-3a Mepiquat-cl | 0.004 63 | 46 | 29 | 17 |
| I-3a Metconazol | 0.004 0.063 | 93 | 53 | 40 |
| I-3a Nitenpyram | 0.004 63 | 57 | 24 | 33 |
| I-3a Prothioconazol | 0.004 1 | 96 | 44 | 52 |
| I-3a Tebuconazol | 0.004 0.25 | 86 | 44 | 42 |
| I-3a Thiamethoxam | 0.004 4 | 96 | 51 | 45 |
| I-3a Thiamethoxam | 0.004 1 | 50 | 24 | 26 |
| I-3a Trinexapac-ethyl | 0.004 63 | 100 | 18 | 82 |
| I-3a Trinexapac-ethyl | 0.001 63 | 100 | 19 | 81 |

Microtest

The active compounds were formulated separately as a stock solution having a concentration of 10000 ppm in dimethyl sulfoxide.

Activity Against Wheat Leaf Spots Caused by *Leptosphaeria nodorum* (Leptno)

The stock solutions were mixed according to the ratio, pipetted onto a micro titer plate (MTP) and diluted with water to the stated concentrations. A spore suspension of *Leptosphaeria nodorum* in an aqueous biomalt or yeast-bactopeptone-glycerine solution was then added. The plates were placed in a water vapor-saturated chamber at a temperature of 18° C. Using an absorption photometer, the MTPs were measured at 405 nm 7 days after the inoculation.

The measured parameters were compared to the growth of the active compound-free control variant (100%) and the fungus-free and active compound-free blank value to determine the relative growth in % of the pathogens in the respective active compounds.

These percentages were converted into efficacies.

The expected efficacies of active compound mixtures were determined using Colby's formula [R. S. Colby, "Calculating synergistic and antagonistic responses of herbicide combinations", Weeds 15, 20-22 (1967)] and compared with the observed efficacies.

Solo Product A

| Active compound/active mixture | Concentration (ppm) | Observed efficacy |
|---|---|---|
| I-1 | 0.063 | 19 |
| I-5 | 0.25 | 19 |
| | 0.063 | 20 |
| I-4 | 0.001 | 15 |

Solo Product B

| Active compound/active mixture | Concentration (ppm) | Observed efficacy |
|---|---|---|
| Bixafen | 0.25 | 19 |
| | 0.063 | 14 |
| Mepiquat-cl | 63 | 28 |
| | 0.25 | 30 |
| Pyraclostrobin | 0.016 | 24 |
| Tebuconazol | 0.25 | 43 |
| Prohexadion-Ca | 63 | 23 |
| Prothioconazol | 1 | 43 |
| | 0.063 | 24 |
| Trinexapac-ethyl | 63 | 17 |

Mixtures

| Active compound/active mixture | Concentration (ppm) | Observed efficacy | Calculated efficacy according to Colby (%) | Synergism (%) |
|---|---|---|---|---|
| I-1 Bixafen Prothioconazol | 0.063 0.063 0.25 | 76 | 52 | 24 |
| I-1 Bixafen Prothioconazol Tebuconazol | 0.063 0.063 0.25 0.063 | 83 | 63 | 20 |
| I-1 Bixafen Pyraclostrobin Prothioconazol | 0.063 0.063 0.016 0.25 | 81 | 63 | 18 |
| I-5 Prohexadion-Ca Trinexapac-ethyl | 0.063 63 63 | 99 | 49 | 50 |
| I-5 Prohexadion-Ca Trinexapac-ethyl Mepiquat-cl | 0.063 63 63 63 | 99 | 63 | 36 |
| I-5 Prothioconazol Tebuconazol | 0.25 1 0.25 | 94 | 74 | 20 |

| Active compound/ active mixture | Concentration (ppm) | Observed efficacy | Calculated efficacy according to Colby (%) | Synergism (%) |
|---|---|---|---|---|
| I-5 | 0.25 | 85 | 63 | 22 |
| Bixafen | 0.25 | | | |
| Prothioconazol | 1 | | | |
| I-4 | 0.001 | 99 | 46 | 53 |
| Prohexadion-Ca | 63 | | | |
| Trinexapac-ethyl | 63 | | | |
| I-4 | 0.001 | 99 | 61 | 38 |
| Prohexadion-Ca | 63 | | | |
| Trinexapac-ethyl | 63 | | | |
| Mepiquat-cl | 63 | | | |

Microtest

The active compounds were formulated separately as a stock solution having a concentration of 10000 ppm in dimethyl sulfoxide.

Activity Against the Grey Mold *Botrytis cinerea* in the Microtiterplate Test (Botrci)

The stock solutions were mixed according to the ratio, pipetted onto a micro titer plate (MTP) and diluted with water to the stated concentrations. A spore suspension of *Botrci cinerea* in an aqueous biomalt or yeast-bactopeptone-sodiumacetate solution was then added. The plates were placed in a water vapor-saturated chamber at a temperature of 18° C. Using an absorption photometer, the MTPs were measured at 405 nm 7 days after the inoculation.

The measured parameters were compared to the growth of the active compound-free control variant (100%) and the fungus-free and active compound-free blank value to determine the relative growth in % of the pathogens in the respective active compounds. These percentages were converted into efficacies.

The expected efficacies of active compound mixtures were determined using Colby's formula [R. S. Colby, "Calculating synergistic and antagonistic responses of herbicide combinations", Weeds 15, 20-22 (1967)] and compared with the observed efficacies.

Solo Product A

| Active compound/ active mixture | Concentration (ppm) | Observed efficacy |
|---|---|---|
| I-1 | 0.000063 | 0 |
| | 0.000016 | 1 |
| | 0.000004 | 0 |
| | 0.000001 | 4 |
| I-3 | 0.000063 | 0 |
| | 0.000016 | 5 |
| | 0.000004 | 0 |
| I-5 | 0.25 | 27 |
| | 0.063 | 14 |
| I-4 | 0.001 | 5 |
| | 0.00025 | 2 |
| | 0.000063 | 4 |

| Active compound/ active mixture | Concentration (ppm) | Observed efficacy |
|---|---|---|
| I-3a | 0.016 | 0 |
| | 0.001 | 0 |
| | 0.00025 | 0 |

Solo Product B

| Active compound/ active mixture | Concentration (ppm) | Observed efficacy |
|---|---|---|
| Ametoctradin | 63 | 4 |
| | 16 | 3 |
| Azoxystrobin | 4 | 14 |
| | 0.25 | 6 |
| Bixafen | 0.063 | 26 |
| Boscalid | 0.25 | 38 |
| Chlorothalonil | 4 | 41 |
| Cyazofamid | 16 | 24 |
| Difenoconazol | 0.25 | 19 |
| Fluoxastrobin | 16 | 23 |
| | 4 | 10 |
| | 1 | 5 |
| Iprovalicarb | 63 | 6 |
| | 16 | 3 |
| | 4 | 2 |
| Metconazol | 0.063 | 29 |
| Prohexadion-Ca | 63 | 4 |
| Prothioconazol | 4 | 72 |
| | 1 | 36 |
| | 0.25 | 23 |
| Pyraclostrobin | 16 | 66 |
| | 4 | 29 |
| Tebuconazol | 0.25 | 41 |
| Thiamethoxam | 63 | 8 |
| Trifloxystrobin | 16 | 6 |
| | 4 | 2 |
| Trinexapac-ethyl | 63 | 15 |
| | 16 | 5 |

2-Way-Mixture

| Active compound/ active mixture | Concentration (ppm) | Observed efficacy | Calculated efficacy according to Colby (%) | Synergism (%) |
|---|---|---|---|---|
| I-1 | 0.000063 | 55 | 38 | 17 |
| Boscalid | 0.25 | | | |
| I-1 | 0.000063 | 68 | 36 | 32 |
| Prothioconazol | 1 | | | |
| I-1 | 0.000004 | 89 | 72 | 17 |
| Prothioconazol | 4 | | | |
| I-1 | 0.000063 | 41 | 23 | 18 |
| Prothioconazol | 0.25 | | | |
| I-1 | 0.000016 | 92 | 72 | 20 |
| Prothioconazol | 4 | | | |
| I-1 | 0.000063 | 92 | 66 | 26 |
| Pyraclostrobin | 16 | | | |
| I-1 | 0.000063 | 59 | 29 | 30 |
| Pyraclostrobin | 4 | | | |
| I-1 | 0.000001 | 51 | 31 | 20 |
| Pyraclostrobin | 4 | | | |
| I-3 | 0.000063 | 45 | 26 | 19 |
| Bixafen | 0.063 | | | |
| I-3 | 0.000004 | 91 | 72 | 19 |
| Prothioconazol | 4 | | | |
| I-3 | 0.000016 | 63 | 39 | 24 |
| Prothioconazol | 1 | | | |

-continued

| Active compound/ active mixture | Concentration (ppm) | Observed efficacy | Calculated efficacy according to Colby (%) | Synergism (%) |
|---|---|---|---|---|
| I-3<br>Prothioconazol | 0.000063<br>1 | 78 | 36 | 42 |
| I-3<br>Prothioconazol | 0.000063<br>0.25 | 43 | 23 | 20 |
| I-3<br>Pyraclostrobin | 0.000063<br>4 | 56 | 29 | 27 |
| I-3<br>Trifloxystrobin | 0.000063<br>16 | 24 | 6 | 18 |
| I-5<br>Iprovalicarb | 0.25<br>16 | 53 | 29 | 24 |
| I-5<br>Iprovalicarb | 0.063<br>63 | 36 | 19 | 17 |
| I-5<br>Pyraclostrobin | 0.25<br>4 | 66 | 48 | 18 |
| I-4<br>Azoxystrobin | 0.001<br>4 | 36 | 18 | 18 |
| I-4<br>Bixafen | 0.001<br>0.063 | 53 | 30 | 23 |
| I-4<br>Boscalid | 0.001<br>0.25 | 61 | 41 | 20 |
| I-4<br>Chlorothalonil | 0.000063<br>4 | 62 | 43 | 19 |
| I-4<br>Prothioconazol | 0.001<br>1 | 61 | 39 | 22 |
| I-4<br>Pyraclostrobin | 0.001<br>16 | 86 | 68 | 18 |
| I-4<br>Pyraclostrobin | 0.001<br>4 | 79 | 32 | 47 |
| I-4<br>Thiamethoxam | 0.00025<br>63 | 28 | 10 | 18 |
| I-4<br>Trifloxystrobin | 0.001<br>16 | 30 | 11 | 19 |
| I-3a<br>Iprovalicarb | 0.016<br>63 | 77 | 6 | 71 |
| I-3a<br>Iprovalicarb | 0.016<br>16 | 26 | 3 | 23 |
| I-3a<br>Prothioconazol | 0.016<br>4 | 97 | 72 | 25 |
| I-3a<br>Prothioconazol | 0.016<br>1 | 99 | 36 | 63 |
| I-3a<br>Prothioconazol | 0.016<br>0.25 | 49 | 23 | 26 |
| I-3a<br>Prothioconazol | 0.001<br>1 | 84 | 36 | 48 |
| I-3a<br>Prothioconazol | 0.00025<br>1 | 86 | 36 | 50 |

Microtest

The active compounds were formulated separately as a stock solution having a concentration of 10000 ppm in dimethyl sulfoxide.

Activity Against the Grey Mold *Botrytis cinerea* in the Microtiterplate Test (Botrci)

The stock solutions were mixed according to the ratio, pipetted onto a micro titer plate (MTP) and diluted with water to the stated concentrations. A spore suspension of *Botrci cinerea* in an aqueous biomalt or yeast-bactopeptone-sodiumacetate solution was then added. The plates were placed in a water vapor-saturated chamber at a temperature of 18° C. Using an absorption photometer, the MTPs were measured at 405 nm 7 days after the inoculation.

The measured parameters were compared to the growth of the active compound-free control variant (100%) and the fungus-free and active compound-free blank value to determine the relative growth in % of the pathogens in the respective active compounds. These percentages were converted into efficacies.

The expected efficacies of active compound mixtures were determined using Colby's formula [R. S. Colby, "Calculating synergistic and antagonistic responses of herbicide combinations", Weeds 15, 20-22 (1967)] and compared with the observed efficacies.

Solo Product A

| Active compound/ active mixture | Concentration (ppm) | Observed efficacy |
|---|---|---|
| I-1 | 0.063 | 16 |
|  | 0.000063 | 0 |
|  | 0.000016 | 1 |
| I-3 | 0.063 | 23 |
|  | 0.000063 | 0 |
|  | 0.000016 | 5 |
| I-5 | 0.25 | 27 |
|  | 0.063 | 14 |
| I-4 | 0.25 | 17 |
|  | 0.063 | 4 |
|  | 0.001 | 5 |
|  | 0.00025 | 2 |

Solo Product B

| Active compound/ active mixture | Concentration (ppm) | Observed efficacy |
|---|---|---|
| Azoxystrobin | 16 | 23 |
|  | 4 | 14 |
| Bixafen | 0.063 | 26 |
|  | 0.016 | 8 |
| Carbendazim | 0.016 | 3 |
|  | 0.004 | 5 |
| Chlorothalonil | 4 | 41 |
|  | 1 | 23 |
| Difenoconazol | 0.25 | 19 |
|  | 0.063 | 10 |
| Epoxiconazol | 0.063 | 23 |
|  | 0.016 | 11 |
| Fluoxastrobin | 4 | 10 |
|  | 1 | 5 |
| Isopyrazam | 0.016 | 6 |
| Mepiquat-cl | 16 | 11 |
| Metconazol | 0.063 | 29 |
| Prohexadion-Ca | 16 | 5 |
|  | 4 | 10 |
| Prothioconazol | 1 | 36 |
|  | 0.25 | 23 |
| Pyraclostrobin | 16 | 66 |
|  | 4 | 29 |
| Tebuconazol | 0.063 | 12 |
|  | 0.016 | 9 |
| Trifloxystrobin | 16 | 6 |
|  | 4 | 2 |
| Trinexapac-ethyl | 16 | 5 |
|  | 4 | 7 |

Mixtures

| Active compound/ active mixture | Concentration (ppm) | Observed efficacy | Calculated efficacy according to Colby (%) | Synergism (%) |
|---|---|---|---|---|
| I-1<br>Pyraclostrobin<br>Chlorothalonil | 0.000016<br>16<br>1 | 100 | 74 | 26 |
| I-1<br>Azoxystrobin<br>Chlorothalonil | 0.000063<br>16<br>4 | 100 | 55 | 45 |
| I-1<br>Pyraclostrobin<br>Prothioconazol | 0.063<br>4<br>0.25 | 83 | 54 | 29 |

| Active compound/ active mixture | Concentration (ppm) | Observed efficacy | Calculated efficacy according to Colby (%) | Synergism (%) |
|---|---|---|---|---|
| I-1 | 0.063 | 62 | 45 | 17 |
| Bixafen | 0.016 | | | |
| Pyraclostrobin | 4 | | | |
| I-1 | 0.063 | 85 | 56 | 29 |
| Pyraclostrobin | 4 | | | |
| Fluoxastrobin | 1 | | | |
| Prothioconazol | 0.25 | | | |
| I-1 | 0.063 | 88 | 58 | 30 |
| Pyraclostrobin | 4 | | | |
| Prothioconazol | 0.25 | | | |
| Tebuconazol | 0.016 | | | |
| I-1 | 0.063 | 84 | 55 | 29 |
| Pyraclostrobin | 4 | | | |
| Trifloxystrobin | 4 | | | |
| Prothioconazol | 0.25 | | | |
| I-1 | 0.063 | 69 | 49 | 20 |
| Bixafen | 0.016 | | | |
| Pyraclostrobin | 4 | | | |
| Tebuconazol | 0.016 | | | |
| I-1 | 0.000016 | 100 | 78 | 22 |
| Pyraclostrobin | 16 | | | |
| Azoxystrobin | 4 | | | |
| Chlorothalonil | 1 | | | |
| I-3 | 0.000016 | 100 | 75 | 25 |
| Pyraclostrobin | 16 | | | |
| Chlorothalonil | 1 | | | |
| I-3 | 0.000063 | 99 | 55 | 44 |
| Azoxystrobin | 16 | | | |
| Chlorothalonil | 4 | | | |
| I-3 | 0.063 | 77 | 51 | 26 |
| Pyraclostrobin | 4 | | | |
| Epoxiconazol | 0.016 | | | |
| I-3 | 0.063 | 82 | 47 | 35 |
| Pyraclostrobin | 4 | | | |
| Fluoxastrobin | 1 | | | |
| I-3 | 0.063 | 92 | 58 | 34 |
| Pyraclostrobin | 4 | | | |
| Prothioconazol | 0.25 | | | |
| I-3 | 0.063 | 81 | 46 | 35 |
| Pyraclostrobin | 4 | | | |
| Trifloxystrobin | 4 | | | |
| I-3 | 0.063 | 75 | 48 | 27 |
| Pyraclostrobin | 4 | | | |
| Carbendazim | 0.004 | | | |
| I-3 | 0.063 | 79 | 51 | 28 |
| Pyraclostrobin | 4 | | | |
| Difenoconazol | 0.063 | | | |
| I-3 | 0.063 | 71 | 51 | 20 |
| Pyraclostrobin | 4 | | | |
| Prohexadion-Ca | 4 | | | |
| I-3 | 0.063 | 86 | 49 | 37 |
| Bixafen | 0.016 | | | |
| Pyraclostrobin | 4 | | | |
| I-3 | 0.063 | 91 | 60 | 31 |
| Pyraclostrobin | 4 | | | |
| Fluoxastrobin | 1 | | | |
| Prothioconazol | 0.25 | | | |
| I-3 | 0.063 | 92 | 62 | 30 |
| Pyraclostrobin | 4 | | | |
| Prothioconazol | 0.25 | | | |
| Tebuconazol | 0.016 | | | |
| I-3 | 0.063 | 87 | 59 | 28 |
| Pyraclostrobin | 4 | | | |
| Trifloxystrobin | 4 | | | |
| Prothioconazol | 0.25 | | | |
| I-3 | 0.063 | 90 | 61 | 29 |
| Bixafen | 0.016 | | | |
| Pyraclostrobin | 4 | | | |
| Prothioconazol | 0.25 | | | |
| I-3 | 0.063 | 69 | 54 | 15 |
| Bixafen | 0.016 | | | |
| Pyraclostrobin | 4 | | | |
| Tebuconazol | 0.016 | | | |
| I-3 | 0.000016 | 100 | 79 | 21 |
| Pyraclostrobin | 16 | | | |
| Azoxystrobin | 4 | | | |
| Chlorothalonil | 1 | | | |
| I-5 | 0.063 | 100 | 78 | 22 |
| Pyraclostrobin | 16 | | | |
| Chlorothalonil | 1 | | | |
| I-5 | 0.063 | 86 | 48 | 38 |
| Trifloxystrobin | 16 | | | |
| Prothioconazol | 1 | | | |
| I-5 | 0.25 | 96 | 67 | 29 |
| Azoxystrobin | 16 | | | |
| Chlorothalonil | 4 | | | |
| I-5 | 0.063 | 100 | 81 | 19 |
| Pyraclostrobin | 16 | | | |
| Azoxystrobin | 4 | | | |
| Chlorothalonil | 1 | | | |
| I-4 | 0.00025 | 100 | 75 | 25 |
| Pyraclostrobin | 16 | | | |
| Chlorothalonil | 1 | | | |
| I-4 | 0.001 | 100 | 57 | 43 |
| Azoxystrobin | 16 | | | |
| Chlorothalonil | 4 | | | |
| I-4 | 0.063 | 74 | 48 | 26 |
| Pyraclostrobin | 4 | | | |
| Prothioconazol | 0.25 | | | |
| I-4 | 0.25 | 84 | 53 | 31 |
| Pyraclostrobin | 1 | | | |
| Tebuconazol | 0.063 | | | |
| I-4 | 0.25 | 83 | 61 | 22 |
| Bixafen | 0.063 | | | |
| Prothioconazol | 1 | | | |
| I-4 | 0.063 | 58 | 37 | 21 |
| Bixafen | 0.016 | | | |
| Pyraclostrobin | 4 | | | |
| I-4 | 0.063 | 88 | 50 | 38 |
| Pyraclostrobin | 4 | | | |
| Fluoxastrobin | 1 | | | |
| Prothioconazol | 0.25 | | | |
| I-4 | 0.063 | 85 | 52 | 33 |
| Pyraclostrobin | 4 | | | |
| Prothioconazol | 0.25 | | | |
| Tebuconazol | 0.016 | | | |
| I-4 | 0.063 | 83 | 49 | 34 |
| Pyraclostrobin | 4 | | | |
| Trifloxystrobin | 4 | | | |
| Prothioconazol | 0.25 | | | |
| I-4 | 0.25 | 85 | 65 | 20 |
| Bixafen | 0.063 | | | |
| Prothioconazol | 1 | | | |
| Tebuconazol | 0.063 | | | |
| I-4 | 0.063 | 85 | 52 | 33 |
| Bixafen | 0.016 | | | |
| Pyraclostrobin | 4 | | | |
| Prothioconazol | 0.25 | | | |
| I-4 | 0.063 | 62 | 42 | 20 |
| Bixafen | 0.016 | | | |
| Pyraclostrobin | 4 | | | |
| Tebuconazol | 0.016 | | | |

Microtest

The active compounds were formulated separately as a stock solution having a concentration of 10000 ppm in dimethyl sulfoxide.

Activity Against Early Blight Caused by *Alternaria solani* (Alteso)

The stock solutions were mixed according to the ratio, pipetted onto a micro titer plate (MTP) and diluted with water to the stated concentrations. A spore suspension of *Alternaria solani* in an aqueous biomalt or yeast-bactopeptone-glycerine solution was then added. The plates were placed in a water vapor-saturated chamber at a temperature of 18° C. Using an absorption photometer, the MTPs were measured at 405 nm 7 days after the inoculation.

The measured parameters were compared to the growth of the active compound-free control variant (100%) and the fungus-free and active compound-free blank value to determine the relative growth in % of the pathogens in the respective active compounds.

These percentages were converted into efficacies.

The expected efficacies of active compound mixtures were determined using Colby's formula [R. S. Colby, "Calculating synergistic and antagonistic responses of herbicide combinations", Weeds 15, 20-22 (1967)] and compared with the observed efficacies.

Solo Product A

| Active compound/ active mixture | Concentration (ppm) | Observed efficacy |
|---|---|---|
| I-1 | 0.001 | 10 |
| I-3 | 0.000063 | 8 |
|  | 0.000004 | 5 |
| I-5 | 1 | 49 |
|  | 0.063 | 14 |
|  | 0.016 | 10 |
|  | 0.004 | 11 |
|  | 0.000004 | 8 |
| I-4 | 0.001 | 10 |
|  | 0.00025 | 7 |
|  | 0.000063 | 5 |
| I-3a | 0.016 | 36 |

Solo Product B

| Active compound/ active mixture | Concentration (ppm) | Observed efficacy |
|---|---|---|
| Ametoctradin | 63 | 6 |
|  | 16 | 2 |
|  | 4 | 5 |
| Azoxystrobin | 0.016 | 14 |
|  | 0.004 | 6 |
| Bixafen | 0.004 | 38 |
|  | 0.001 | 5 |
|  | 0.000025 | 6 |
| Boscalid | 0.004 | 6 |
|  | 0.001 | 5 |
| Carbendazim | 63 | 34 |
|  | 16 | 10 |
|  | 4 | 7 |
| Chlorothalonil | 0.25 | 2 |
|  | 0.063 | 4 |
| Cyazofamid | 16 | 35 |
|  | 4 | 14 |
| Difenoconazol | 0.063 | 18 |
|  | 0.016 | 5 |
|  | 0.004 | 5 |
| Epoxiconazol | 0.063 | 52 |
|  | 0.016 | 8 |
|  | 0.004 | 5 |
| Fipronil | 4 | 2 |
|  | 1 | 6 |
| Fluoxastrobin | 0.063 | 27 |
|  | 0.016 | 11 |
| Fluxapyroxad | 0.001 | 4 |
| Iprovalicarb | 63 | 1 |
|  | 16 | 2 |
|  | 4 | 1 |

| Active compound/ active mixture | Concentration (ppm) | Observed efficacy |
|---|---|---|
| Isopyrazam | 0.016 | 15 |
| Mepiquat-cl | 63 | 16 |
|  | 16 | 10 |
| Metconazol | 0.016 | 17 |
| Nitenpyram | 63 | 8 |
|  | 16 | 2 |
|  | 4 | 2 |
| Prohexadion-Ca | 16 | 2 |
|  | 4 | 6 |
| Prothioconazol | 1 | 66 |
|  | 0.25 | 15 |
|  | 0.063 | 8 |
| Pyraclostrobin | 0.016 | 18 |
|  | 0.004 | 8 |
| Tebuconazol | 0.016 | 8 |
| Thiamethoxam | 4 | 51 |
|  | 1 | 10 |
|  | 0.25 | 8 |
| Trifloxystrobin | 0.016 | 11 |
|  | 0.004 | 7 |
| Trinexapac-ethyl | 16 | 27 |
|  | 4 | 12 |

2-Way-Mixture

| Active compound/ active mixture | Concentration (ppm) | Observed efficacy | Calculated efficacy according to Colby (%) | Synergism (%) |
|---|---|---|---|---|
| I-1 Azoxystrobin | 0.001 0.016 | 43 | 23 | 20 |
| I-1 Fluoxastrobin | 0.001 0.063 | 57 | 34 | 23 |
| I-1 Isopyrazam | 0.001 0.016 | 42 | 23 | 19 |
| I-1 Isopyrazam | 0.000004 0.016 | 46 | 21 | 25 |
| I-3 Azoxystrobin | 0.000063 0.016 | 42 | 14 | 28 |
| I-3 Fluoxastrobin | 0.000063 0.063 | 54 | 27 | 27 |
| I-3 Isopyrazam | 0.000063 0.016 | 42 | 15 | 27 |
| I-3 Isopyrazam | 0.000004 0.016 | 57 | 19 | 38 |
| I-3 Pyraclostrobin | 0.000063 0.016 | 47 | 18 | 29 |
| I-3 Trifloxystrobin | 0.000063 0.016 | 32 | 11 | 21 |
| I-5 Ametoctradin | 1 4 | 82 | 52 | 30 |
| I-5 Ametoctradin | 1 16 | 82 | 50 | 32 |
| I-5 Azoxystrobin | 1 0.004 | 76 | 53 | 23 |
| I-5 Azoxystrobin | 1 0.016 | 83 | 57 | 26 |
| I-5 Bixafen | 1 0.00025 | 81 | 52 | 29 |
| I-5 Bixafen | 1 0.001 | 82 | 52 | 30 |
| I-5 Boscalid | 1 0.004 | 79 | 53 | 26 |
| I-5 Carbendazim | 1 16 | 81 | 54 | 27 |
| I-5 Chlorothalonil | 1 0.063 | 70 | 52 | 18 |
| I-5 Chlorothalonil | 1 0.25 | 75 | 50 | 25 |
| I-5 Cyazofamid | 1 4 | 79 | 56 | 23 |

| Active compound/ active mixture | Concentration (ppm) | Observed efficacy | Calculated efficacy according to Colby (%) | Synergism (%) |
|---|---|---|---|---|
| I-5 Difenoconazol | 1 0.016 | 88 | 52 | 36 |
| I-5 Difenoconazol | 1 0.063 | 89 | 59 | 30 |
| I-5 Difenoconazol | 1 0.004 | 75 | 52 | 23 |
| I-5 Epoxiconazol | 1 0.016 | 72 | 54 | 18 |
| I-5 Epoxiconazol | 1 0.004 | 76 | 52 | 24 |
| I-5 Fipronil | 1 1 | 72 | 52 | 20 |
| I-5 Fipronil | 1 4 | 78 | 50 | 28 |
| I-5 Fluoxastrobin | 1 0.063 | 85 | 63 | 22 |
| I-5 Fluoxastrobin | 1 0.016 | 85 | 55 | 30 |
| I-5 Fluxapyroxad | 1 0.001 | 82 | 51 | 31 |
| I-5 Iprovalicarb | 1 16 | 74 | 50 | 24 |
| I-5 Iprovalicarb | 1 63 | 76 | 50 | 26 |
| I-5 Iprovalicarb | 1 4 | 81 | 50 | 31 |
| I-5 Isopyrazam | 0.063 0.016 | 55 | 27 | 28 |
| I-5 Isopyrazam | 0.016 0.016 | 52 | 23 | 29 |
| I-5 Metconazol | 1 0.016 | 78 | 58 | 20 |
| I-5 Metconazol | 0.016 0.016 | 48 | 26 | 22 |
| I-5 Metconazol | 0.004 0.016 | 46 | 27 | 19 |
| I-5 Nitenpyram | 1 63 | 82 | 53 | 29 |
| I-5 Nitenpyram | 1 4 | 81 | 51 | 30 |
| I-5 Nitenpyram | 1 16 | 79 | 51 | 28 |
| I-5 Prohexadion-Ca | 1 16 | 76 | 50 | 26 |
| I-5 Prohexadion-Ca | 1 4 | 86 | 52 | 34 |
| I-5 Prothioconazol | 1 0.25 | 83 | 57 | 26 |
| I-5 Prothioconazol | 1 0.063 | 90 | 53 | 37 |
| I-5 Pyraclostrobin | 1 0.016 | 79 | 59 | 20 |
| I-5 Pyraclostrobin | 1 0.004 | 80 | 54 | 26 |
| I-5 Tebuconazol | 1 0.063 | 69 | 47 | 22 |
| I-5 Tebuconazol | 1 0.016 | 78 | 53 | 25 |
| I-5 Thiamethoxam | 1 1 | 85 | 55 | 30 |
| I-5 Thiamethoxam | 1 0.25 | 87 | 53 | 34 |
| I-5 Thiamethoxam | 0.25 1 | 72 | 48 | 24 |
| I-5 Trifloxystrobin | 1 0.016 | 84 | 55 | 29 |
| I-5 Trifloxystrobin | 1 0.004 | 85 | 53 | 32 |
| I-5 Trinexapac-ethyl | 1 4 | 79 | 56 | 23 |
| I-4 Azoxystrobin | 0.001 0.016 | 49 | 23 | 26 |
| I-4 Cyazofamid | 0.00025 16 | 58 | 39 | 19 |
| I-4 Difenoconazol | 0.001 0.063 | 46 | 26 | 20 |
| I-4 Metconazol | 0.001 0.016 | 44 | 26 | 18 |
| I-4 Fluoxastrobin | 0.001 0.063 | 78 | 34 | 44 |
| I-4 Prothioconazol | 0.001 0.25 | 70 | 23 | 47 |
| I-4 Prothioconazol | 0.000063 0.25 | 44 | 19 | 25 |
| I-4 Prothioconazol | 0.000063 1 | 88 | 68 | 20 |
| I-4 Pyraclostrobin | 0.001 0.004 | 43 | 18 | 25 |
| I-4 Pyraclostrobin | 0.001 0.016 | 88 | 26 | 62 |
| I-4 Trifloxystrobin | 0.001 0.016 | 41 | 21 | 20 |
| I-3a Azoxystrobin | 0.016 0.016 | 65 | 46 | 19 |
| I-3a Nitenpyram | 0.016 63 | 72 | 41 | 31 |
| I-3a Prothioconazol | 0.016 0.25 | 64 | 46 | 18 |

Microtest

The active compounds were formulated separately as a stock solution having a concentration of 10000 ppm in dimethyl sulfoxide.

Activity Against Early Blight Caused by *Alternaria solani* (Alteso)

The stock solutions were mixed according to the ratio, pipetted onto a micro titer plate (MTP) and diluted with water to the stated concentrations. A spore suspension of *Alternaria solani* in an aqueous biomalt or yeast-bactopeptone-glycerine solution was then added. The plates were placed in a water vapor-saturated chamber at a temperature of 18° C. Using an absorption photometer, the MTPs were measured at 405 nm 7 days after the inoculation.

The measured parameters were compared to the growth of the active compound-free control variant (100%) and the fungus-free and active compound-free blank value to determine the relative growth in % of the pathogens in the respective active compounds.

These percentages were converted into efficacies.

The expected efficacies of active compound mixtures were determined using Colby's formula

[R. S. Colby, "Calculating synergistic and antagonistic responses of herbicide combinations", Weeds 15, 20-22 (1967)] and compared with the observed efficacies.

| Active compound/ active mixture | Concentration (ppm) | Observed efficacy |
|---|---|---|
| Solo product A | | |
| I-1 | 0.00025 | 4 |
| I-5 | 1 | 49 |
| I-4 | 0.25 | 33 |

-continued

| Active compound/ active mixture | Concentration (ppm) | Observed efficacy |
|---|---|---|
| Solo product B | | |
| Bixafen | 0.001 | 5 |
| Difenoconazol | 0.063 | 5 |
| Mepiquat-cl | 63 | 16 |
| Prohexadion-Ca | 63 | 2 |
| | 16 | 2 |
| Prothioconazol | 0.25 | 15 |
| Pyraclostrobin | 0.016 | 18 |

Mixtures

| Active compound/ active mixture | Concentration (ppm) | Observed efficacy | Calculated efficacy according to Colby (%) | Synergism (%) |
|---|---|---|---|---|
| I-1 | 0.00025 | 57 | 23 | 34 |
| Bixafen | 0.001 | | | |
| Prothioconazol | 0.25 | | | |
| I-5 | 1 | 76 | 58 | 18 |
| Prohexadion-Ca | 63 | | | |
| Mepiquat-cl | 63 | | | |
| I-4 | 0.25 | 65 | 48 | 17 |
| Pyraclostrobin | 0.016 | | | |
| Difenoconazol | 0.063 | | | |
| I-4 | 0.25 | 66 | 46 | 20 |
| Pyraclostrobin | 0.016 | | | |
| Prohexadion-Ca | 16 | | | |
| I-4 | 0.25 | 71 | 46 | 25 |
| Bixafen | 0.001 | | | |
| Prothioconazol | 0.25 | | | |
| I-4 | 0.25 | 70 | 48 | 22 |
| Bixafen | 0.001 | | | |
| Pyraclostrobin | 0.016 | | | |

Structures of the Compounds I:

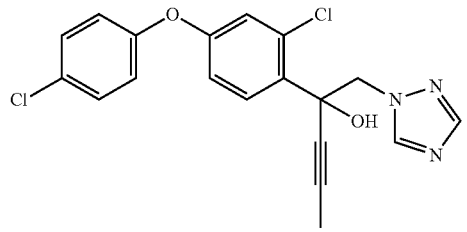

2-[2-chloro-4-(4-chlorophenoxy)phenyl]-1-(1,2,4-triazol-1-yl)pent-3-yn-2-ol

I-1

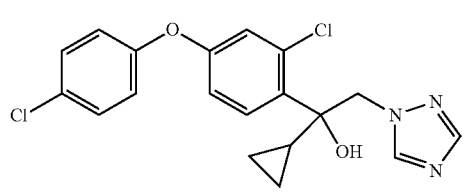

1-[2-chloro-4-(4-chlorophenoxy)phenyl]-1-cyclopropyl-2-(1,2,4-triazol-1-yl)ethanol

I-2

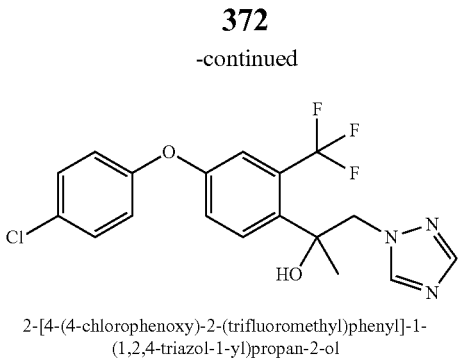

2-[4-(4-chlorophenoxy)-2-(trifluoromethyl)phenyl]-1-(1,2,4-triazol-1-yl)propan-2-ol

I-3

I-3a = (R)-I-3 = (R) enantiomer of I-3

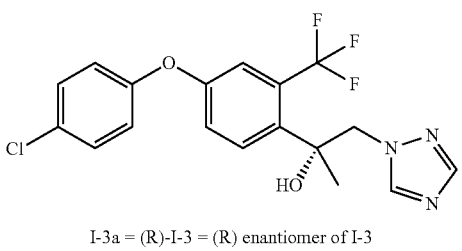

1-[4-(4-chlorophenoxy)-2-(trifluoromethyl)phenyl]-1-cyclopropyl-2-(1,2,4-triazol-1-yl)ethanol

I-4

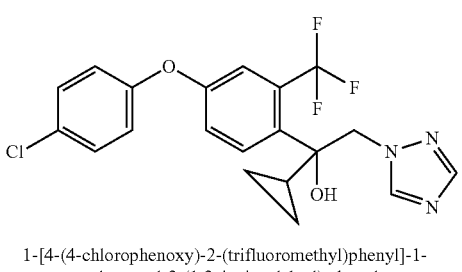

2-[4-(4-chlorophenoxy)-2-(trifluoromethyl)phenyl]-3-methyl-1-(1,2,4-triazol-1-yl)butan-2-ol

I-5

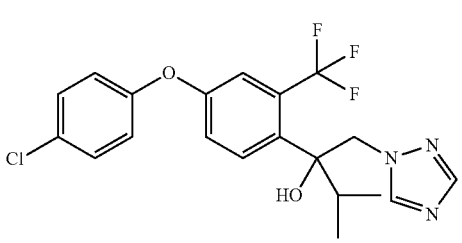

1-[2-[2-chloro-4-(4-chlorophenoxy)phenyl]-2-methoxy-pent-3-ynyl]-1,2,4-triazole

I-6

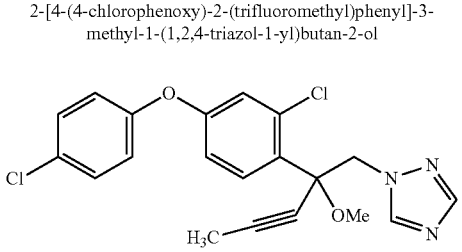

2-[4-(4-chlorophenoxy)-2-(trifluoromethyl)phenyl]-1-(1,2,4-triazol-1-yl)butan-2-ol

I-7

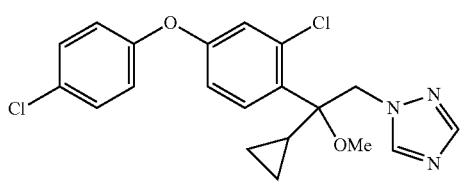

1-[2-[2-chloro-4-(4-chlorophenoxy)phenyl]-2-cyclopropyl-
2-methoxy-ethyl]-1,2,4-triazole

I-8

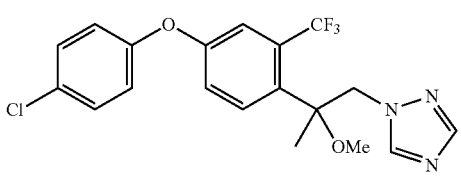

1-[2-[4-(4-chlorophenoxy)-2-(trifluoromethyl)phenyl]-2-
methoxy-propyl]-1,2,4-triazole

I-9

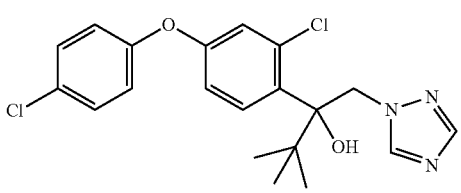

2-[2-chloro-4-(4-chlorophenoxy)phenyl]3,3-dimethyl-
1-(1,2,4-triazol-1-yl)butan-2-ol

I-10

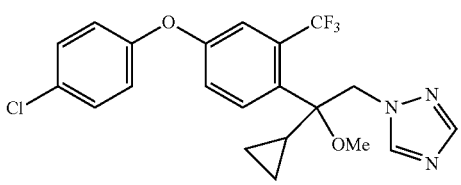

1-[2-[4-(4-chlorophenoxy)-2-(trifluoromethyl)phenyl]-2-
cyclopropyl-2-methoxy-ethyl]-1,2,4-triazole

I-11

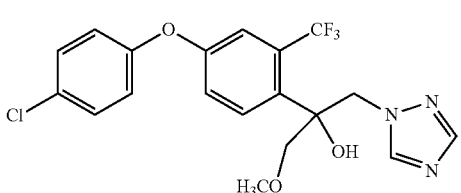

2-[2-trifluoromethyl-4-(4-chlorophenoxy)phenyl]-1-
methoxy-3-(1,2,4-triazol-1-yl)propan-2-ol

I-12

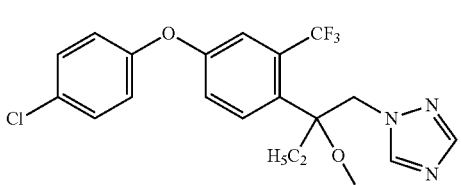

1-[2-[4-(4-chlorophenoxy)-2-(trifluoromethyl)phenyl]-
2-methoxy-butyl]1,2,4-triazole

I-13

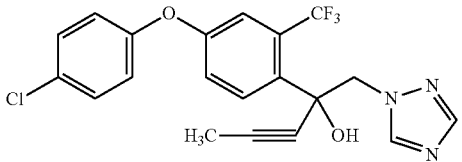

2-[4-(4-chlorophenoxy)-2-(trifluoromethyl)phenyl]-
1-(1,2,4-triazol-1-yl)pent-3-yn-2-ol

I-14

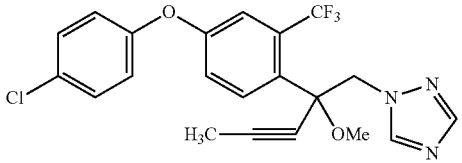

1-[2-[4-(4-chlorophenoxy)-2-(trifluoromethyl)phenyl]-
2-methoxy-pent-3-ynyl]-1,2,4-triazole

I-15

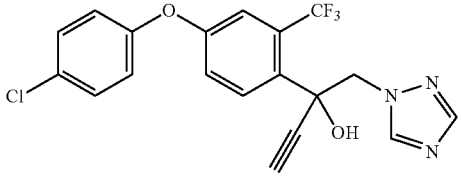

2-[4-(4-chlorophenoxy)-2-(trifluoromethyl)phenyl]-
1-(1,2,4-triazol-1-yl)but-3-yn-2-ol

I-16

The invention claimed is:

1. A composition comprising, a mixture of two components, the two components comprising
1) as component I
compound I-3 2-[4-(4-chlorophenoxy)-2-(trifluoromethyl)phenyl]-1-(1,2,4-triazol-1-yl)propan-2-ol;
and
2) as component II
an active ingredient in the form of a strobilurin fungicide selected from the group consisting of azoxystrobin, dimoxystrobin, fluoxastrobin, kresoxim-methyl, picoxystrobin, pyraclostrobin, and trifloxystrobin; or a carboxamide fungicide selected from the group consisting of, benzovindiflupyr, bixafen, boscalid, fluopyram, fluxapyroxad, isopyrazam, and sedaxane; or a DMI fungicide selected from the group consisting of, cyproconazole, difenoconazole, epoxiconazole, metconazole, propiconazole, prothioconazole, tebuconazole, tetraconazole, and triticonazole; or a delta14-reductase inhibitor selected from the group consisting of fenpropimorph and fenpropidin; or an acyl amino acid fungicide selected from the group consisting of metalaxyl and metalaxyl-M (mefenoxam) or a cell division inhibitor selected from metrafenone or a lipid and membrane synthesis inhibitor selected from iprovalicarb or an inhibitor with multi site action selected from the group consisting of copper oxychloride, sulfur, mancozeb, chlorothalonil, and dithianon; or a plant growth regulator selected from the group consisting of mepiquat (mepiquat chloride), prohexadione (prohexadione-calcium), and trinexapac-ethyl or an insect growth regulator selected from the group consisting of flupyradifurone, thiamethoxam, and nitenpyram; or another type of fungicide selected from the group consisting of cyazofamid, fluazinam, oxathiapiprolin, tricyclazole, and picarbutrazox,
wherein the weight ratio of component I to component II is from 20:1 to 1:20 with synergistic effects being exhibited by the composition.

2. The composition of claim 1, wherein component II is selected from the group consisting of azoxystrobin, fluoxastrobin, picoxystrobin, pyraclostrobin, trifloxystrobin, cyazofamid, benzovindiflupyr, bixafen, boscalid, fluxapyroxad, isopyrazam, difenoconazole, epoxiconazole, metconazole, propiconazole, prothioconazole, tebuconazole, triticonazole, fenpropimorph, iprovalicarb, sulfur, dithianon, and tricyclazole.

3. The composition of claim 1, wherein component II is selected from thiamethoxam and nitenpyram.

4. The composition of claim 1, wherein component II is selected from azoxystrobin, fluoxastrobin, picoxystrobin, pyraclostrobin, and trifloxystrobin.

5. The composition of claim 1, further comprising an agrochemical auxiliary.

6. The composition according to claim 1, comprising additionally a further active substance, component III.

7. A method for combating phytopathogenic fungi, comprising treating the fungi or materials, plants, soil or seeds to be protected against fungal attack with an effective amount of a composition as defined in claim 1.

8. Seed, coated with the components I and II of the composition as defined in claim 1, in an amount of from 0.1 to 10 kg active substances per 100 kg of seed.

9. The method of claim 7, wherein component II is selected from azoxystrobin, fluoxastrobin, picoxystrobin, pyraclostrobin, trifloxystrobin, benzovindiflupyr, bixafen, boscalid, fluxapyroxad, isopyrazam, difenoconazole, epoxiconazole, metconazole, propiconazole, prothioconazole, tebuconazole, triticonazole, fenpropimorph, iprovalicarb, sulfur, dithianon, and tricyclazole.

10. The method of claim 7, wherein component II is selected from thiamethoxam and nitenpyram.

11. The method of claim 7, wherein component II is selected from azoxystrobin, fluoxastrobin, picoxystrobin, pyraclostrobin, and trifloxystrobin.

* * * * *